US012364508B2

(12) United States Patent
Shah et al.

(10) Patent No.: US 12,364,508 B2
(45) Date of Patent: Jul. 22, 2025

(54) REUSABLE APPLICATORS FOR TRANSCUTANEOUS ANALYTE SENSORS, AND ASSOCIATED METHODS

(71) Applicant: DexCom, Inc., San Diego, CA (US)

(72) Inventors: Neel Shah, Carlsbad, CA (US); Joseph J. Baker, Escondido, CA (US)

(73) Assignee: DexCom, Inc., San Diego, CA (US)

(*) Notice: Subject to any disclaimer, the term of this patent is extended or adjusted under 35 U.S.C. 154(b) by 682 days.

(21) Appl. No.: 17/566,604

(22) Filed: Dec. 30, 2021

(65) Prior Publication Data

US 2022/0202448 A1 Jun. 30, 2022

Related U.S. Application Data

(63) Continuation of application No. 17/566,491, filed on Dec. 30, 2021.

(60) Provisional application No. 63/132,703, filed on Dec. 31, 2020.

(51) Int. Cl.
*A61B 17/34* (2006.01)
*A61B 5/00* (2006.01)
*A61B 5/145* (2006.01)

(52) U.S. Cl.
CPC ........ *A61B 17/3468* (2013.01); *A61B 5/0004* (2013.01); *A61B 5/14503* (2013.01); *A61B 5/14532* (2013.01); *A61B 5/6833* (2013.01); *A61B 17/3496* (2013.01); *A61B 2560/0443* (2013.01); *A61B 2560/063* (2013.01); *A61B 2562/164* (2013.01)

(58) Field of Classification Search
CPC ............ A61B 5/14503; A61B 5/14532; A61B 5/14546; A61B 5/6801; A61B 5/6833; A61B 5/6847; A61B 5/6848; A61B 17/3468; A61B 17/3496; A61B 2560/063; A61B 2562/164
See application file for complete search history.

(56) References Cited

U.S. PATENT DOCUMENTS

| | | | |
|---|---|---|---|
| 7,310,544 B2 | 12/2007 | Brister et al. | |
| 9,451,910 B2 | 9/2016 | Brister et al. | |
| 10,863,944 B2 | 12/2020 | Gray et al. | |
| 2004/0010207 A1 | 1/2004 | Flaherty et al. | |
| 2012/0265042 A1* | 10/2012 | Neinast | A61B 17/3468 600/347 |
| 2012/0303043 A1 | 11/2012 | Donnay | |
| 2013/0253289 A1* | 9/2013 | Hadvary | A61B 5/150664 600/309 |

(Continued)

FOREIGN PATENT DOCUMENTS

WO WO-2020231405 A1 11/2020

OTHER PUBLICATIONS

International Search Report and Written Opinion for Application No. PCT/US2021/065788, mailed May 4, 2022, 20 pages.

*Primary Examiner* — Daniel L Cerioni
*Assistant Examiner* — Abel Seifu Abegaz
(74) *Attorney, Agent, or Firm* — Snell & Wilmer LLP

(57) ABSTRACT

The present embodiments relate generally to systems and methods for measuring an analyte in a host. More particularly, the present embodiments provide sensor applicators and methods of use to insert the sensor into an individual's skin. Applicators are disclosed for inserting the sensor. Such applicators may be reusable applicators configured to implant multiple different sensors.

17 Claims, 163 Drawing Sheets

(56) References Cited

U.S. PATENT DOCUMENTS

| | | |
|---|---|---|
| 2014/0128839 A1 | 5/2014 | Diianni et al. |
| 2014/0187876 A1 | 7/2014 | Ohkoshi |
| 2015/0119666 A1 | 4/2015 | Brister et al. |
| 2017/0112534 A1 | 4/2017 | Schoonmaker et al. |
| 2017/0188910 A1 | 7/2017 | Halac et al. |
| 2017/0188912 A1* | 7/2017 | Halac ................. A61B 5/14532 |
| 2017/0290533 A1 | 10/2017 | Antonio et al. |
| 2018/0368771 A1 | 12/2018 | Gray et al. |
| 2018/0368772 A1 | 12/2018 | Gray et al. |
| 2020/0178899 A1 | 6/2020 | Chae et al. |
| 2021/0030344 A1 | 2/2021 | Huang |
| 2021/0259595 A1 | 8/2021 | Chae et al. |
| 2022/0117627 A1 | 4/2022 | Garai |

* cited by examiner

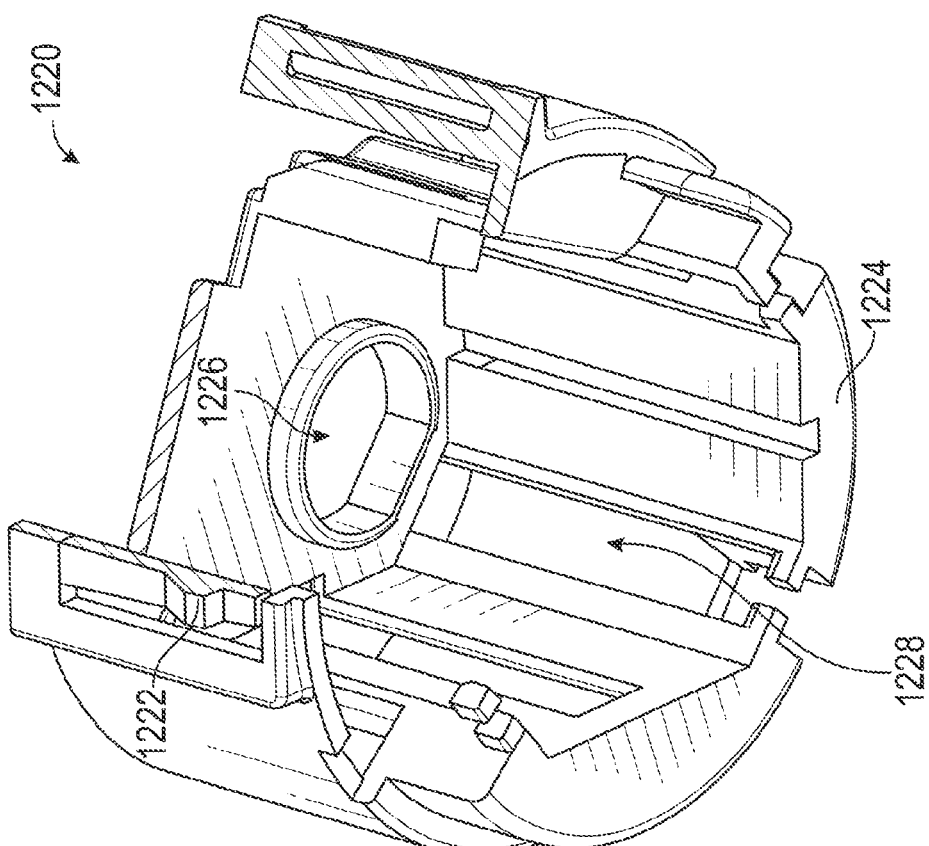
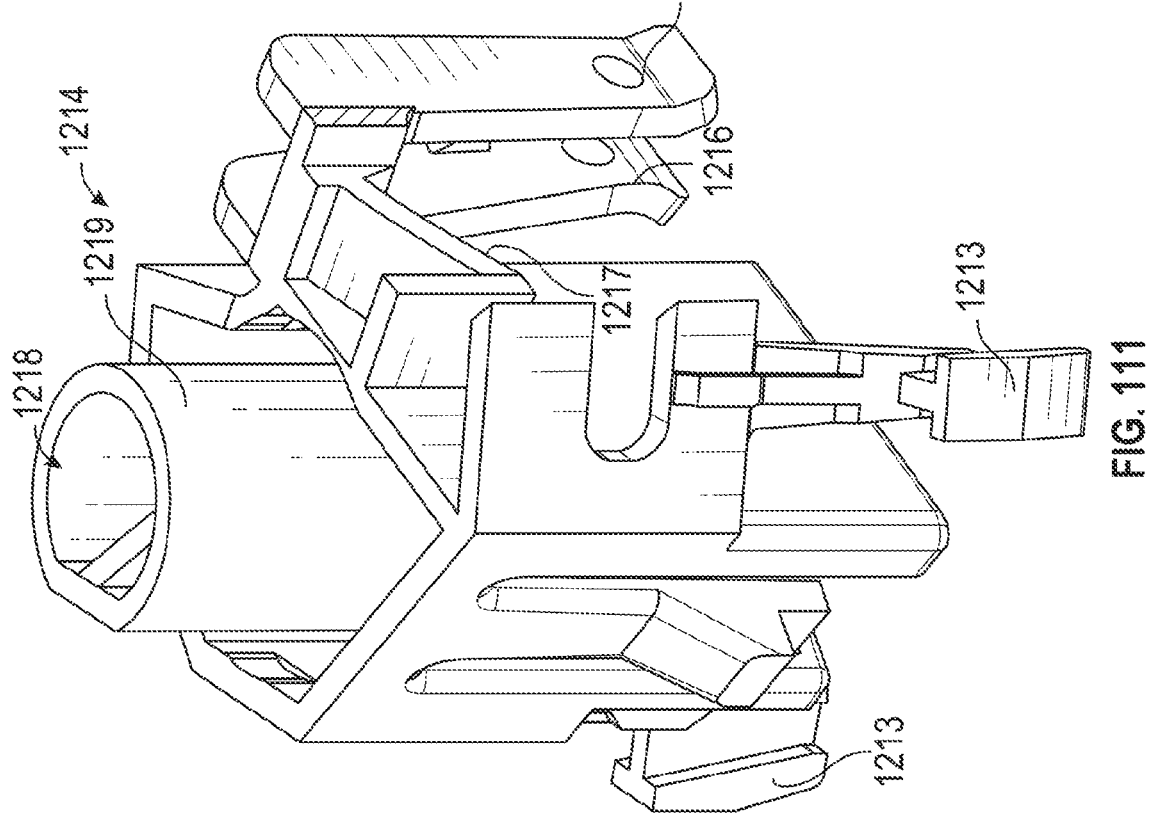

REUSABLE APPLICATORS FOR TRANSCUTANEOUS ANALYTE SENSORS, AND ASSOCIATED METHODS

CROSS REFERENCE TO RELATED APPLICATIONS

This application is a continuation of U.S. patent application Ser. No. 17/566,491, filed Dec. 30, 2021, which claims the benefit of U.S. Provisional Application No. 63/132,703, filed Dec. 31, 2020, the entire contents of each of which are incorporated by reference herein.

BACKGROUND OF THE INVENTION

Field of the Invention

Systems and methods for measuring an analyte in an individual are provided. More particularly, systems and methods are provided for applying a transcutaneous analyte sensor to an individual.

Description of the Related Technology

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which can cause an array of physiological derangements associated with the deterioration of small blood vessels, for example, kidney failure, skin ulcers, or bleeding into the vitreous of the eye. A hypoglycemic reaction (low blood sugar) can be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricking methods. Due to the lack of comfort and convenience, a person with diabetes normally only measures his or her glucose levels two to four times per day. Unfortunately, such time intervals are spread so far apart that the person with diabetes likely finds out too late of a hyperglycemic or hypoglycemic condition, sometimes incurring dangerous side effects. Glucose levels may be alternatively monitored continuously by a measurement system including an on-skin sensor assembly. The sensor assembly may have a wireless transmitter which transmits measurement data to a receiver which can process and display information based on the measurements.

The process of applying the sensor to the person is important for such a system to be effective and user friendly. The application process should result in the on-skin sensor assembly being attached to the person in a state where it is capable of sensing the analyte (e.g., glucose) level information, communicating the sensed data to the transmitter, and transmitting the analyte level information to the receiver.

Existing systems tend to utilize types of applicators for the sensor that were single-use and intended to be disposed after such use. The applicators may insert the sensor into the skin of the individual, and then be discarded. Another applicator may then be used to insert another sensor into the skin of the individual at a desired time.

Such systems may result in multiple single-use applicators produced and distributed for use on the individual. Production of multiple of such single-use applicators may be costly and may be considered to be wasteful. Reusable applicators may desirably reduce the costs and waste associated with applying sensors into the skin of the individual.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

The present systems and methods relate to systems and methods for measuring an analyte in a host, and for applying a transcutaneous analyte measurement system to a host. The various embodiments of the present systems and methods for applying the analyte measurement system have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description," one will understand how the features of the present embodiments provide the advantages described herein.

In a first aspect, a system for inserting a transcutaneous analyte sensor into an individual's skin may be provided, the system including an applicator housing configured to be gripped to apply the transcutaneous analyte sensor into the individual's skin. The system may include an actuator coupled to the applicator housing and configured to insert a needle into the individual's skin, wherein the needle is configured to guide the transcutaneous analyte sensor into the individual's skin. The system may include a releasable coupler configured retain the needle at least partially within the applicator housing following insertion of the transcutaneous analyte sensor into the individual's skin, and release the needle from within the applicator housing.

Implementations of the embodiments may include one or more of the following. The actuator may include a control device configured to be operated by the individual; and a driver configured to drive the needle into the individual's skin to guide the transcutaneous analyte sensor into the individual's skin. The actuator may further comprise a carriage configured to slide relative to the applicator housing and configured to be slid by the driver. The driver may include a spring. A release actuator may be configured to release the needle from the releasable coupler. The release actuator may include a control device configured to be operated by the individual to cause the needle to release from the releasable coupler. The control device may be configured to be operated in a first operation to activate the actuator configured to insert the needle into the individual's skin, and is configured to be operated in a second operation following the first operation to activate the release actuator. The first operation may include pressing the control device, and the second operation includes pressing the control device. The control device may be configured to protrude from the applicator housing to a different distance for the first operation than for the second operation. The release actuator may further comprise a pressing surface configured to apply a force to the releasable coupler to cause the needle to release from the releasable coupler. The releasable coupler may be configured to couple to a needle hub of the needle. A retraction actuator may be for retracting the needle from the individual's skin following insertion of the transcutaneous analyte sensor into the individual's skin. The retraction actuator may be configured to automatically operate upon the needle guiding the transcutaneous analyte sensor into the individual's skin. The retraction actuator may be configured to activate based on a force of contact with the individual's skin at a deployment site of the transcutaneous analyte sensor. A first carriage may be configured to displace relative to a second carriage based on contact with the individual's skin to operate the release actuator. A spring may bias the first carriage away from the second carriage. The retraction actuator may include a driver configured to drive the needle out of the individual's skin; and a carriage configured to slide relative to the applicator housing and configured to be slid by the driver of the retraction actuator. The releasable coupler may be coupled to the carriage of the retraction actuator. The carriage of the retraction actuator may be a first carriage and the driver of the retraction actuator is a first driver and the releasable coupler is a first releasable coupler, and the actuator configured to insert the needle into the individual's skin includes a second carriage configured to slide relative to the applicator housing and configured to be slid by a second driver, and further comprising a second releasable coupler for coupling the first carriage to the second carriage. The second releasable coupler may be configured to release the first carriage from the second carriage to allow the first driver to move the first carriage in a direction away from the second carriage. The second releasable coupler may be configured to automatically release upon contact with a coupler release. The retraction actuator may be configured to position the needle into a needle cover. The retraction actuator may be configured to rotate the needle into the needle cover. The releasable coupler configured to retain the needle is configured to release the needle positioned within the needle cover from within the applicator housing. The releasable coupler may be configured to rotate to hook onto or release from a needle hub of the needle. The applicator housing may include a top portion, a side portion, and a bottom portion including an opening for the transcutaneous analyte sensor to be deployed from to be guided into the individual's skin. The side portion may include an opening for receiving a cartridge retaining the transcutaneous analyte sensor. The system may further comprise a cartridge configured to be inserted into the applicator housing and to retain the transcutaneous analyte sensor. The cartridge may retain the needle and retains a wearable housing for the transcutaneous analyte sensor. The cartridge may retain a patch for the wearable housing that has a liner, and the cartridge is coupled to the patch such that withdrawal of the cartridge from the wearable housing removes the liner from the patch. The cartridge may be configured to be inserted into the applicator housing to provide energy to the actuator. The cartridge may be configured to be removed from the applicator housing prior to the needle being inserted into the individual's skin. The cartridge may include a needle coupler configured to engage a used needle that is retained within the applicator housing and retain the used needle when the cartridge is withdrawn from the applicator housing. The cartridge may include an upper surface and a lower surface facing opposite the upper surface, and a retainer is positioned on the upper surface for retaining the transcutaneous analyte sensor, and the needle coupler is positioned on the lower surface. The cartridge may include an upper surface and a lower surface facing opposite the upper surface, and a retainer is positioned on the upper surface for retaining the transcutaneous analyte sensor, and the needle coupler is positioned on the upper surface. The cartridge may be configured to remain in a receiver of the applicator housing during the needle being inserted into the individual's skin to guide the transcutaneous analyte sensor into the individual's skin. The cartridge may include a retraction actuator for retracting the needle from the individual's skin following insertion of the transcutaneous analyte sensor into the individual's skin. The cartridge may include a bottom surface with an opening for the transcutaneous analyte sensor to be deployed from and a patch for the transcutaneous analyte sensor coupled to the bottom surface and covering the opening. The transcutaneous analyte sensor may be configured to slide within the cartridge relative to the patch. The applicator housing may include a receiver for receiving the cartridge, and the cartridge includes a keyed portion configured to align the cartridge with the receiver in a single rotational orientation. The actuator may be a reloadable actuator configured to insert multiple different needles into the individual's skin. The applicator housing may include an opening at a bottom surface of the applicator housing for the transcutaneous analyte sensor to be deployed from, and the actuator includes a needle carriage configured to retain the needle after insertion into the individual's skin and rotate the needle about an axis that is vertical with respect to the opening. The system may include a pull tab configured to be pulled to release the needle from the releasable coupler. The pull tab may be configured to couple to a needle hub of the needle. The actuator may include a control device configured to be operated by the individual, and the applicator housing includes a roughened outer surface indicating a position of the control device.

In a second aspect, a system for inserting a transcutaneous analyte sensor into an individual's skin may be provided. The system may include an applicator housing configured to be gripped to apply the transcutaneous analyte sensor into the individual's skin and including a receiver configured to receive a cartridge retaining the transcutaneous analyte sensor. The system may include an actuator configured to insert a needle into the individual's skin to guide the transcutaneous analyte sensor into the individual's skin, the actuator configured such that insertion of the cartridge into the receiver provides energy to the actuator.

Implementations of the embodiments may include one or more of the following. The actuator may include a driver configured to drive the needle into the individual's skin to guide the transcutaneous analyte sensor into the individual's skin, the actuator configured such that insertion of the cartridge into the receiver provides energy to the driver. The driver may include a spring configured to drive the needle into the individual's skin to guide the transcutaneous analyte sensor into the individual's skin, and the actuator is configured such that insertion of the cartridge into the receiver compresses the spring. The actuator may be an insertion actuator, and further comprising a retraction actuator configured to retract the needle from the individual's skin, the retraction actuator configured to activate based on a force of contact with the individual's skin at a deployment site of the transcutaneous analyte sensor. A first carriage may be configured to displace relative to a second carriage based on contact with the individual's skin to operate the release actuator. A spring may bias the first carriage away from the second carriage. The actuator may be an insertion actuator, and further comprising a retraction actuator configured to retract the needle from the individual's skin, and the retraction actuator is configured such that insertion of the cartridge into the receiver provides energy to the retraction actuator. The retraction actuator may include a driver configured to retract the needle from the individual's skin, the retraction actuator being configured such that insertion of the cartridge into the receiver provides energy to the driver of the retraction actuator. The driver of the retraction actuator may include a spring configured to retract the needle from the individual's skin, and the actuator is configured such that insertion of the cartridge into the receiver compresses the spring of the retraction actuator. The retraction actuator may be configured to rotate the needle into a needle cover. The insertion actuator may include a carriage configured to be moved by a spring that is configured to drive the needle into the individual's skin to guide the transcutaneous analyte sensor into the individual's skin, and the retraction actuator includes a carriage configured to be moved by the spring of the retraction actuator in a direction away from the carriage of the insertion actuator. The system may include a releasable coupler for coupling the carriage of the insertion actuator to the carriage of the retraction actuator to resist a force of the spring of the retraction actuator. The system may include a releasable coupler coupled to the carriage of the retraction actuator and configured to retain the needle at least partially within the applicator housing following insertion of the transcutaneous analyte sensor into the individual's skin, and release the needle from within the applicator housing. The releasable coupler may be configured to rotate to hook onto or release from a needle hub of the needle. The system may include a pull tab configured to be pulled to release the needle from the releasable coupler. The pull tab may be configured to couple to a needle hub of the needle. The system may include a release actuator configured to release the needle from the releasable coupler. The system may include a control device configured to be operated in a first operation to activate the actuator configured to insert the needle into the individual's skin, and is configured to be operated in a second operation following the first operation to activate the release actuator. The first operation may include pressing the control device, and the second operation includes pressing the control device. The control device may be configured to protrude from the applicator housing to a different distance for the first operation than for the second operation. The applicator housing may include a top portion, a side portion, and a bottom portion including an opening for the transcutaneous analyte sensor to be deployed from to be guided into the individual's skin. The receiver may be configured to receive the cartridge through the opening. The side portion may include an opening, and the receiver is configured to receive the cartridge through the opening of the side portion. The actuator may be configured such that a force applied by the cartridge to the actuator provides energy to the actuator. The system may include a cartridge, and wherein the cartridge includes a pressing surface for pressing against the actuator for providing energy to the actuator. The cartridge may include a bottom surface with an opening for the transcutaneous analyte sensor to be deployed from and a patch for the transcutaneous analyte sensor coupled to the bottom surface and covering the opening. The cartridge may be configured to allow the transcutaneous analyte sensor to slide within the cartridge relative to the patch. The cartridge may retain a patch for a wearable housing for the transcutaneous analyte sensor, the patch having a liner, and the cartridge is coupled to the patch such that withdrawal of the cartridge from the wearable housing removes the liner from the patch. The cartridge may include a retraction actuator for retracting the needle from the individual's skin following insertion of the transcutaneous analyte sensor into the individual's skin. The cartridge may include a needle coupler configured to engage a used needle that is retained within the applicator housing and retain the used needle when the applicator housing is withdrawn from the applicator housing. The cartridge may include an upper surface and a lower surface facing opposite the upper surface, and a retainer is positioned on the upper surface for retaining the transcutaneous analyte sensor, and the needle coupler is positioned on the lower surface. The cartridge may include an upper surface and a lower surface facing opposite the upper surface, and a retainer is positioned on the upper surface for retaining the transcutaneous analyte sensor, and the needle coupler is positioned on the upper surface. The applicator housing may include an opening at a bottom surface of the applicator housing for the transcutaneous analyte sensor to be deployed from, and the actuator includes a needle carriage configured to retain the needle after insertion into the individual's skin and rotate the needle about an axis that is vertical with respect to the opening. The applicator housing may include a receiver for receiving the cartridge, and the cartridge includes a keyed portion configured to align the cartridge with the receiver in a single rotational orientation. The actuator may include a control device configured to be operated by the individual, and the applicator housing includes a roughened outer surface indicating a position of the control device.

In a third aspect, a system for inserting a transcutaneous analyte sensor into an individual's skin may be provided, the system including an applicator housing configured to be gripped to apply the transcutaneous analyte sensor into the individual's skin. The system may include an insertion actuator coupled to the applicator housing and configured to insert a needle into the individual's skin to guide the transcutaneous analyte sensor into the individual's skin. The system may include a releasable coupler configured to retain the needle at least partially within the applicator housing. The system may include a release actuator configured to release the needle from the releasable coupler.

Implementations of the embodiments may include one or more of the following. The release actuator may be configured to eject the needle from the applicator housing. The release actuator may include a pressing surface configured to apply force to the needle to eject the needle from the applicator housing. The release actuator may include a control device configured to be operated by the individual to cause the needle to release from the releasable coupler. The control device may include a button. The control device may be configured to activate the insertion actuator. The control device may be configured to be operated in a first operation to activate the insertion actuator, and is configured to be operated in a second operation following the first operation to activate the release actuator. The first operation may include pressing the control device, and the second operation includes pressing the control device. The control device may be configured to protrude from the applicator housing to a different distance for the first operation than for the second operation. The applicator housing may include a top portion, a side portion, and a bottom portion including an opening for the transcutaneous analyte sensor to be deployed from to be inserted into the individual's skin, the release actuator configured to release the needle from the releasable coupler to allow the needle to be passed through the opening. The applicator housing may include a receiver configured to receive a cartridge retaining the transcutaneous analyte sensor, and the release actuator is configured to be operated to allow the cartridge to be removed from the receiver. The release actuator may be configured to unlock the cartridge from the applicator housing. The system may include the cartridge, and wherein the cartridge includes a retraction actuator for retracting the needle from the individual's skin following insertion of the transcutaneous analyte sensor into the individual's skin. The system may include the cartridge, wherein the cartridge includes a bottom surface with an opening for the transcutaneous analyte sensor to be deployed from and a patch for the transcutaneous analyte sensor coupled to the bottom surface and covering the opening. The cartridge may be configured to allow the transcutaneous analyte sensor to slide within the cartridge relative to the patch. The cartridge may be configured to allow the needle to slide within the cartridge relative to the patch. The patch may be configured to be deployed to the individual's skin from the bottom surface of the cartridge. The system may include the cartridge, wherein the cartridge includes a keyed portion configured to align the cartridge with the receiver in a single rotational orientation. The release actuator may be configured to release a needle cover from the applicator housing. The system may include a cartridge retaining the transcutaneous analyte sensor, the needle, and a needle cover, and wherein the needle is configured to be moved relative to the needle cover to be positioned into the needle cover. The release actuator may be configured to release the needle covered by the needle cover from within the applicator housing. The needle and the needle cover may form a unit configured to be ejected from within the applicator housing by the release actuator. The releasable coupler may be configured to rotate to hook onto or release from a needle hub of the needle. The system may include a retraction actuator configured to retract the needle from the individual's skin, the retraction actuator configured to activate based on a force of contact with the individual's skin at a deployment site of the transcutaneous analyte sensor. The insertion actuator may include a control device configured to be operated by the individual, and the applicator housing includes a roughened outer surface indicating a position of the control device.

In a fourth aspect, a system for inserting a transcutaneous analyte sensor into an individual's skin may be provided, the system may include an applicator housing configured to be gripped to apply the transcutaneous analyte sensor into the individual's skin, the applicator housing including a top portion, a side portion, and a bottom portion, the side portion including an opening for the transcutaneous analyte sensor to be inserted into, and the bottom portion including an opening for the transcutaneous analyte sensor to be deployed from. The system may include an actuator coupled to the applicator housing and configured to insert a needle into the individual's skin from the opening of the bottom portion to guide the transcutaneous analyte sensor into the individual's skin.

Implementations of the embodiments may include one or more of the following. The opening of the bottom portion may be configured for the needle and the transcutaneous analyte sensor to pass through to guide the transcutaneous analyte sensor into the individual's skin. The applicator housing may include a receiver configured to receive the transcutaneous analyte sensor through the opening of the side portion. The receiver may include a cavity. The receiver may be configured to receive a cartridge retaining the transcutaneous analyte sensor through the opening of the side portion. The actuator may be configured such that insertion of the cartridge into the receiver provides energy to the actuator. The actuator may be configured such that insertion of the cartridge into the receiver compresses a spring of the actuator, the spring configured to drive the needle into the individual's skin to guide the transcutaneous analyte sensor into the individual's skin. The system may include a cocking device for providing energy to the actuator. The cocking device may include a lever for compressing a spring of the actuator, the spring configured to drive the needle into the individual's skin to guide the transcutaneous analyte sensor into the individual's skin. The system may include a cartridge retaining the transcutaneous analyte sensor and the needle. The cartridge may include an inner cartridge body and an outer cartridge body. The outer cartridge body may be configured to be separated from the inner cartridge body prior to the actuator inserting the needle into the individual's skin. The system may include a releasable coupler configured to retain the needle at least partially within the applicator housing following insertion of the transcutaneous analyte sensor into the individual's skin, and release the needle from within the applicator housing. The cartridge may be configured to be withdrawn from the receiver through the opening of the side portion to release the needle from the releasable coupler. The system may include a retraction actuator for retracting the needle from the individual's skin following insertion of the transcutaneous analyte sensor into the individual's skin.

In a fifth aspect, a system for inserting a transcutaneous analyte sensor into an individual's skin may be provided, the system including an applicator housing configured to be gripped to apply the transcutaneous analyte sensor into the individual's skin. The system may include an actuator coupled to the applicator housing and configured to insert a needle into the individual's skin to guide the transcutaneous analyte sensor into the individual's skin. The system may include a cocking device configured to be manually operated to cock the actuator for insertion of the needle into the individual's skin.

Implementations of the embodiments may include one or more of the following. The cocking device may include a lever configured to be manually pressed. The cocking device may be configured to be manually operated to provide energy to the actuator. The actuator may include a driver configured to drive the needle into the individual's skin to guide the transcutaneous analyte sensor into the individual's skin, and the cocking device is configured to provide energy to the driver. The driver may include a spring configured to drive the needle into the individual's skin to guide the transcutaneous analyte sensor into the individual's skin, and the cocking device is configured to compress the spring. The actuator may include a carriage configured to slide relative to the applicator housing and configured to be slid by the spring, and the cocking device is configured to move the carriage to compress the spring. The cocking device may be coupled to the carriage. The applicator housing may include a top portion, a side portion, and a bottom portion including an opening for the transcutaneous analyte sensor to be deployed from to be inserted into the individual's skin. The side portion may include an opening for receiving a cartridge retaining the transcutaneous analyte sensor. The cocking device may be configured to move at least a portion of the cartridge upon being manually operated. The actuator may include a control device configured to be manually operated to activate the actuator. The cocking device may be configured to be in an initial uncocked state and manually moved to a cocked state in which cocking device cocks the actuator, and the control device is configured such that operation of the control device returns the cocking device to an uncocked state. The cocking device may protrude from the applicator housing. A releasable coupler may be configured to retain the needle at least partially within the applicator housing following insertion of the transcutaneous analyte sensor into the individual's skin, and release the needle from within the applicator housing. The system may include retraction actuator for retracting the needle from the individual's skin following insertion of the transcutaneous analyte sensor into the individual's skin.

In a sixth aspect, a system for inserting a transcutaneous analyte sensor into an individual's skin may be provided. The system may include an applicator housing including a receiver configured to receive a cartridge retaining the transcutaneous analyte sensor and a needle for guiding the transcutaneous analyte sensor into skin of an individual, the receiver configured to release the cartridge from the applicator housing. The system may include an actuator coupled to the applicator housing and configured to insert the needle into the individual's skin with the cartridge positioned within the receiver to guide the transcutaneous analyte sensor into the individual's skin.

Implementations of the embodiments may include one or more of the following. The receiver may comprise a cavity within the applicator housing. The system may include a releasable coupler for retaining the needle at least partially within the applicator housing. The releasable coupler may be configured to release the cartridge from the applicator housing to release the needle from the applicator housing. The system may include a cartridge, and wherein the cartridge defines a cavity for receiving the transcutaneous analyte sensor. The cartridge may include a keyed portion configured to align the cartridge with the receiver in a single rotational orientation. The cartridge may include a retraction actuator for retracting the needle from the individual's skin following insertion of the transcutaneous analyte sensor into the individual's skin. The retraction actuator may be configured to activate based on a force of contact with the individual's skin at a deployment site of the transcutaneous analyte sensor. A first carriage may be configured to displace relative to a second carriage based on contact with the individual's skin to operate the release actuator. A spring may bias the first carriage away from the second carriage. The cartridge may include a bottom surface with an opening for the transcutaneous analyte sensor to be deployed from and a patch for the transcutaneous analyte sensor coupled to the bottom surface and covering the opening. The cartridge may be configured to allow the transcutaneous analyte sensor to slide within the cartridge relative to the patch. The cartridge may be configured to allow the needle to slide within the cartridge relative to the patch. The patch may be configured to be deployed to the individual's skin from the bottom surface of the cartridge. The system may include the cartridge, and wherein the cartridge includes a wall extending around the transcutaneous analyte sensor. The wall may be configured to extend around the needle. The wall may include an inner surface configured to face inward towards the transcutaneous analyte sensor, and includes an outer surface facing opposite the inner surface. The outer surface may comprise a mating surface for the receiver. The mating surface may be contoured to a shape of an inner surface of the receiver. The system may include a protrusion on the outer surface configured to align the cartridge with the receiver. The system may include the cartridge, and wherein the cartridge is configured to retain the needle after the cartridge has been separated from the receiver and the needle has been inserted into the individual's skin. The system may include the cartridge, and the transcutaneous analyte sensor and the needle coupled to the cartridge. The system may include a needle cover coupled to the cartridge. The cartridge may include a removable cover covering the transcutaneous analyte sensor and the needle within the cartridge. The actuator may include a control device configured to be operated by the individual, and the applicator housing includes a roughened outer surface indicating a position of the control device.

In a seventh aspect, a cartridge for coupling to an applicator housing of a transcutaneous analyte sensor applicator may be provided. The cartridge may include a transcutaneous analyte sensor. The cartridge may include a needle configured to guide the transcutaneous analyte sensor into skin of an individual. The cartridge may include a needle cover configured to cover at least a portion of the needle following the needle guiding the transcutaneous analyte sensor into the skin of the individual. The cartridge may include a body configured to be coupled to the applicator housing and including a retainer retaining the transcutaneous analyte sensor and including a wall extending around at least a portion of the transcutaneous analyte sensor.

Implementations of the embodiments may include one or more of the following. The body may include an upper opening. The cartridge may include a removable cover covering the upper opening. The removable cover may form a hermetic seal of the upper opening. The removable cover may comprise a flap. The removable cover may comprise a body having a height and width and covering the needle cover. The cartridge may include a wearable housing for the transcutaneous analyte sensor coupled to the transcutaneous analyte sensor, and wherein the needle cover is coupled to the wearable housing. The wearable housing may be configured to couple to an electronics unit. The needle cover may be configured to be separable from the wearable housing. The needle cover may comprise a sheath configured to extend over at least the portion of the needle. The needle cover may be configured to rotate relative to the needle to extend over at least the portion of the needle. The wall may extend around at least a portion of the needle cover. The wall may include an inner surface configured to face inward towards the transcutaneous analyte sensor, and includes an outer surface facing opposite the inner surface and configured to be positioned within the applicator housing. The outer surface may have an asymmetrical contour. The cartridge may include a protrusion on the outer surface configured to align the body with the applicator housing.

In an eighth aspect, a system for inserting a transcutaneous analyte sensor into an individual's skin may be provided. The system may include an applicator housing configured to be gripped to apply the transcutaneous analyte sensor into the individual's skin. The system may include an actuator coupled to the applicator housing and configured to insert a needle into the individual's skin to guide the transcutaneous analyte sensor into the individual's skin. The system may include a receiver configured to retain the transcutaneous analyte sensor within the applicator housing. The system may include a mounting base configured to retain an electronics unit for the transcutaneous analyte sensor and configured to apply the electronics unit to a coupler for the transcutaneous analyte sensor when the transcutaneous analyte sensor is retained by the receiver, to couple the electronics unit to the transcutaneous analyte sensor.

Implementations of the embodiments may include one or more of the following. The receiver may include a cavity configured to receive the mounting base. The receiver may be configured to retain the transcutaneous analyte sensor within the cavity. The applicator housing may include an opening for the mounting base to be passed through to enter the cavity. The opening may be positioned at a bottom portion of the applicator housing, and the receiver is positioned at an upper portion of the cavity. The receiver may include an inner surface extending between a lower portion of the receiver and an upper portion of the receiver and surrounding the cavity. The mounting base may include an upper surface configured to retain the electronics unit, a lower surface, and one or more side surfaces extending between the upper surface and the lower surface. The one or more side surfaces may be shaped to mate with the inner surface of the receiver. The system may include a protrusion on the one or more side surfaces configured to align the mounting base with the receiver. The receiver may be positioned on a carriage of an insertion actuator configured to insert the needle and the transcutaneous analyte sensor into the individual's skin. The receiver may form at least a portion of a cartridge configured for insertion into the applicator housing. The mounting base may be configured to be inserted into the cartridge to apply the electronics unit to the coupler for the transcutaneous analyte sensor. The mounting base may be configured to be removed from the cartridge prior to the needle guiding the transcutaneous analyte sensor into the individual's skin. The mounting base may be configured to be inserted into the applicator housing to apply the electronics unit to the coupler for the transcutaneous analyte sensor. The mounting base may be configured to be removed from the applicator housing prior to the needle guiding the transcutaneous analyte sensor into the individual's skin.

In a ninth aspect, a cartridge for coupling to an applicator housing of a transcutaneous analyte sensor applicator. The cartridge may include a body configured to be coupled to the applicator housing; a retainer configured to retain a transcutaneous analyte sensor to the body; a receiver configured to receive an unused needle that is coupled to the transcutaneous analyte sensor; and a needle coupler configured to engage a used needle that is retained within the applicator housing and retain the used needle when the body is withdrawn from the applicator housing.

Implementations of the embodiments may include one or more of the following. The body may include an upper surface and a lower surface facing opposite the upper surface, and the retainer is positioned on the upper surface and the needle coupler is positioned on the lower surface. The body may be configured to be inserted into a receiver of the applicator housing with the upper surface facing towards the applicator housing and alternatively with the lower surface facing towards the applicator housing. The body may include an upper surface and a lower surface facing opposite the upper surface, and the retainer is positioned on the upper surface and the needle coupler is positioned on the upper surface. The transcutaneous analyte sensor may be coupled to the retainer and the unused needle positioned within the receiver and coupled to the transcutaneous analyte sensor, and wherein the body includes a wall extending around at least a portion of the transcutaneous analyte sensor.

In a tenth aspect, a system for inserting a transcutaneous analyte sensor into an individual's skin, the system comprising: an applicator housing configured to be gripped to apply the transcutaneous analyte sensor into the individual's skin and including an opening at a bottom surface of the applicator housing for the transcutaneous analyte sensor to be deployed from; a driver for inserting a needle into the individual's skin to guide the transcutaneous analyte sensor into the individual's skin; and a needle carriage configured to retain the needle after insertion into the individual's skin and rotate the needle about an axis that is vertical with respect to the opening.

Implementations of the embodiments may include one or more of the following. The driver may be configured to drive the needle carriage towards the individual's skin to insert the needle into the individual's skin. A gear may be for rotating the needle carriage about the axis. A cartridge may include a needle coupler for engaging the needle to withdraw the needle from the needle carriage. The needle carriage may be configured to rotate the needle to align with the needle coupler.

In an eleventh aspect, a cartridge for coupling to an applicator housing of a transcutaneous analyte sensor applicator, the cartridge comprising: a transcutaneous analyte sensor; a body configured to be coupled to the applicator housing and including a bottom surface with an opening for the transcutaneous analyte sensor to be deployed from; a needle configured to guide the transcutaneous analyte sensor into skin of an individual; and a patch for the transcutaneous analyte sensor coupled to the bottom surface and covering the opening.

Implementations of the embodiments may include one or more of the following. A wearable housing for the transcutaneous analyte sensor, wherein the wearable housing is spaced from the patch. The wearable housing may be configured to slide relative to the patch. The needle may be configured to slide relative to the patch to guide the transcutaneous analyte sensor into the skin of the individual. A retraction actuator may be for retracting the needle from the skin of the individual.

In a twelfth aspect, a cartridge for coupling to an applicator housing of a transcutaneous analyte sensor applicator, the cartridge comprising: a transcutaneous analyte sensor; a needle configured to guide the transcutaneous analyte sensor into skin of an individual; and a first body retaining the transcutaneous analyte sensor and the needle and configured to be coupled to the applicator housing, the first body including a bottom cavity configured to receive a second body having a same shape as the first body to stack the first body upon the second body.

Implementations of the embodiments may include one or more of the following. A cover covering an upper opening of the first body. The first body may include an upper cavity retaining the transcutaneous analyte sensor and the needle. The first body may have a bottom surface that is wider than an upper surface of the first body. The first body may have a trapezoidal shape.

In a thirteenth aspect, a method of applying a transcutaneous analyte sensor into an individual's skin may be provided. The method may include utilizing an actuator coupled to an applicator housing to insert a needle into the individual's skin to guide the transcutaneous analyte sensor into the individual's skin, the needle positioned at least partially within the applicator housing. The method may include withdrawing the applicator housing from the individual's skin with the needle positioned at least partially within the applicator housing after the needle has guided the transcutaneous analyte sensor into the individual's skin. The method may include separating the needle from the applicator housing.

Implementations of the embodiments may include one or more of the following. The actuator may comprise a reusable actuator. The method may include discarding the needle after the needle has been separated from the applicator housing. The needle may be positioned in a needle cover after the needle has guided the transcutaneous analyte sensor into the individual's skin, and the method further comprises separating the needle cover from the applicator housing. The method may include ejecting the needle and the needle cover from the applicator housing with the needle positioned in the needle cover. The method may include discarding the needle and the needle cover as a unit. The method may include operating a retraction actuator to cover the needle with the needle cover. The method may include operating the retraction actuator to rotate the needle into the needle cover. The method may include operating a control device to release the needle from the applicator housing. The control device may be configured to be operated in a first operation to activate the actuator to insert the needle into the individual's skin, and is configured to be operated in a second operation following the first operation to activate a release actuator to release the needle from the applicator, and the control device protrudes from the applicator housing to a different distance for the first operation than for the second operation. The method may include releasing the needle from a releasable coupler that retains the needle at least partially within the applicator housing. The releasable coupler may retain the needle at least partially within the applicator housing while the applicator housing is withdrawn from the individual's skin. The releasable coupler may rotate to hook onto or release from a needle hub of the needle. The method may include pulling a pull tab to release the needle from the releasable coupler. The method may include providing energy to the actuator by inserting the transcutaneous analyte sensor into the applicator housing. The method may include providing energy to the actuator by inserting a cartridge retaining the transcutaneous analyte sensor into the applicator housing. The cartridge may retain a patch for a wearable housing that has a liner, and the method further comprises withdrawing the cartridge from the wearable housing to remove the liner from the patch. The cartridge may include a needle coupler configured to engage a used needle that is retained within the applicator housing and retain the used needle when the applicator housing is withdrawn from the applicator housing. The cartridge may include an upper surface and a lower surface facing opposite the upper surface, and a retainer is positioned on the upper surface for retaining the transcutaneous analyte sensor, and the needle coupler is positioned on the lower surface. The cartridge may include an upper surface and a lower surface facing opposite the upper surface, and a retainer is positioned on the upper surface for retaining the transcutaneous analyte sensor, and the needle coupler is positioned on the upper surface. Providing energy to the actuator may include compressing a spring of the actuator. The actuator may be an insertion actuator, and inserting the transcutaneous analyte sensor into the applicator housing compresses a spring of a retraction actuator for retracting the needle from the individual's skin. The method may include utilizing the actuator to insert multiple different transcutaneous analyte sensors into the individual's skin. The method may include deploying the transcutaneous analyte sensor from a cartridge that remains in a receiver of the applicator housing during the needle being inserted into the individual's skin to guide the transcutaneous analyte sensor into the individual's skin. The cartridge may include a retraction actuator for retracting the needle from the individual's skin following insertion of the transcutaneous analyte sensor into the individual's skin. The cartridge may include a bottom surface with an opening for the transcutaneous analyte sensor to be deployed from and a patch for the transcutaneous analyte sensor coupled to the bottom surface and covering the opening. The applicator housing may include an opening at a bottom surface of the applicator housing for the transcutaneous analyte sensor to be deployed from, and the actuator includes a needle carriage configured to retain the needle after insertion into the individual's skin and rotate the needle about an axis that is vertical with respect to the opening. A retraction actuator for retracting the needle from the individual's skin may activate based on a force of contact with the individual's skin at a deployment site of the transcutaneous analyte sensor. The actuator may include a control device configured to be operated by the individual, and the applicator housing includes a roughened outer surface indicating a position of the control device. The method may include deploying the transcutaneous analyte sensor from a cartridge that includes a keyed portion configured to align the cartridge with a receiver of the applicator housing in a single rotational orientation.

In a fourteenth aspect, a method of applying a transcutaneous analyte sensor into an individual's skin may be provided. The method may include inserting a transcutaneous analyte sensor into an opening in a side portion of an applicator housing, the applicator housing including a top portion and a bottom portion including an opening. The method may include inserting the transcutaneous analyte sensor into the individual's skin from the opening in the bottom portion of the applicator housing.

Implementations of the embodiments may include one or more of the following. The method may include inserting a needle into the individual's skin from the opening in the bottom portion of the applicator housing to guide the transcutaneous analyte sensor into the individual's skin. The method may include inserting a cartridge retaining the transcutaneous analyte sensor into the opening in the side portion of an applicator housing to insert the transcutaneous analyte sensor into the opening in the side portion of the applicator housing. Inserting the cartridge into the opening in the side portion of the applicator housing may include inserting the cartridge in a receiver of the applicator housing, and the method may further comprise leaving the cartridge in the receiver of the applicator housing while the transcutaneous analyte sensor is inserted into the individual's skin. Inserting the cartridge into the opening in the side portion of an applicator housing may provide energy to an actuator for inserting the transcutaneous analyte sensor into the individual's skin.

In a fifteenth aspect, a method of applying a transcutaneous analyte sensor into an individual's skin may be provided. The method may include manually cocking an insertion actuator of a reusable applicator for the transcutaneous analyte sensor. The method may include utilizing the insertion actuator to insert a needle into the individual's skin to guide the transcutaneous analyte sensor into the individual's skin.

Implementations of the embodiments may include one or more of the following. Manually cocking the insertion actuator may include manually operating a cocking device extending from a housing of the reusable applicator. The cocking device may include a lever configured to be manually pressed. Manually cocking the insertion actuator may include compressing a spring of the insertion actuator. Manually cocking the insertion actuator may include compressing a spring of a retraction actuator for retracting the needle from the individual's skin.

In a sixteenth aspect, a method of applying a transcutaneous analyte sensor into an individual's skin may be provided. The method may include coupling a cartridge retaining a transcutaneous analyte sensor and a needle to an applicator housing including an actuator. The method may include utilizing the actuator to insert the transcutaneous analyte sensor and the needle into the individual's skin with the cartridge remaining coupled to the applicator housing. The method may include separating the cartridge from the applicator housing after the needle has guided the transcutaneous analyte sensor into the individual's skin.

Implementations of the embodiments may include one or more of the following. The method may include coupling the cartridge to the applicator housing by inserting the cartridge into a receiver of the applicator housing. The cartridge may include a keyed portion configured to align the cartridge with the receiver in a single rotational orientation. The method may include inserting the cartridge into an opening of the applicator housing that the transcutaneous analyte sensor is inserted into the individual's skin from. The method may include separating the needle from the applicator housing by separating the cartridge from the applicator housing. The method may include operating a release actuator to release the needle from the applicator housing. The method may include operating the release actuator to release the cartridge from the applicator housing. The cartridge may include a retraction actuator for retracting the needle from the individual's skin following insertion of the transcutaneous analyte sensor into the individual's skin. The retraction actuator may be configured to activate based on a force of contact with the individual's skin at a deployment site of the transcutaneous analyte sensor. A first carriage may be configured to displace relative to a second carriage based on contact with the individual's skin to operate the release actuator. A spring may bias the first carriage away from the second carriage. The cartridge may include a bottom surface with an opening for the transcutaneous analyte sensor to be deployed from and a patch for the transcutaneous analyte sensor coupled to the bottom surface and covering the opening. The transcutaneous analyte sensor may be configured to slide within the cartridge relative to the patch. The method may comprise applying the patch from the bottom surface of the cartridge to the individual's skin. The actuator may include a control device configured to be operated by the individual, and the applicator housing includes a roughened outer surface indicating a position of the control device.

In a seventeenth aspect, a method of applying a transcutaneous analyte sensor into an individual's skin may be provided. The method may include coupling a cartridge to an applicator housing, the cartridge including: the transcutaneous analyte sensor, a needle configured to guide the transcutaneous analyte sensor into the skin of an individual, a needle cover configured to cover at least a portion of the needle after the needle guides the transcutaneous analyte sensor into the skin of the individual, and a body retaining the transcutaneous analyte sensor and having a wall extending around at least a portion of the transcutaneous analyte sensor. The method may include utilizing an actuator coupled to the applicator housing to insert the needle into the individual's skin to guide the transcutaneous analyte sensor into the individual's skin. The method may include covering the needle with the needle cover after the needle has guided the transcutaneous analyte sensor into the individual's skin.

Implementations of the embodiments may include one or more of the following. The method may include releasing the needle covered with the needle cover from the applicator housing. The method may include discarding the needle covered with the needle cover. The method may include coupling the cartridge to the applicator housing by inserting the cartridge into a receiver of the applicator housing. The method may include leaving the cartridge within the receiver while the actuator is utilized to insert the needle into the individual's skin to guide the transcutaneous analyte sensor into the individual's skin. The cartridge may include a keyed portion configured to align the cartridge with the receiver in a single rotational orientation. The actuator may include a control device configured to be operated by the individual, and the applicator housing includes a roughened outer surface indicating a position of the control device. The actuator may include a control device that is configured to be operated in a first operation to activate the actuator, and is configured to be operated in a second operation following the first operation to activate a release actuator configured to release the needle from a releasable coupler. The first operation may include pressing the control device, and the second operation includes pressing the control device. The control device may protrude from the applicator housing to a different distance for the first operation than for the second operation.

In an eighteenth aspect, a method of applying a transcutaneous analyte sensor into an individual's skin may be provided. The method may include providing an electronics unit for the transcutaneous analyte sensor on a mounting base. The method may include coupling the electronics unit to the transcutaneous analyte sensor. The method may include separating the mounting base from the electronics unit. The method may include inserting the transcutaneous analyte sensor into the individual's skin while the transcutaneous analyte sensor is coupled to the electronics unit.

Implementations of the embodiments may include one or more of the following. The electronics unit may include a communication device for the transcutaneous analyte sensor. The method may include inserting the mounting base into a receiver retaining the transcutaneous analyte sensor. The receiver may be positioned on a carriage of an insertion actuator configured to insert a needle and the transcutaneous analyte sensor into the individual's skin. The method may include coupling the electronics unit to a wearable housing to couple the electronics unit to the transcutaneous analyte sensor.

In a nineteenth aspect, a method comprising: coupling a cartridge to an applicator housing, the cartridge including: a transcutaneous analyte sensor, an unused needle configured to guide the transcutaneous analyte sensor into skin of an individual, and a needle coupler configured to engage a used needle that is retained within the applicator housing and retain the used needle when the cartridge is withdrawn from the applicator housing; withdrawing the cartridge from the applicator housing; and retaining the used needle to the cartridge with the needle coupler when the cartridge is withdrawn from the applicator housing.

Implementations of the embodiments may include one or more of the following. The cartridge may include an upper surface and a lower surface facing opposite the upper surface, and the transcutaneous analyte sensor is positioned on the upper surface and the needle coupler is positioned on the lower surface. The method may include inserting the cartridge into a receiver of the applicator housing with the lower surface facing the applicator housing; rotating the cartridge so that the upper surface faces the applicator housing; and inserting the cartridge into the receiver of the applicator housing with the upper surface facing the applicator housing. The method may include rotating a carriage within the applicator housing to position the used needle for alignment with the needle coupler. The method may include inserting the cartridge into a receiver of the applicator housing to engage the needle coupler with the used needle.

In a twentieth aspect, a cartridge for coupling to an applicator housing of a transcutaneous analyte sensor applicator, the cartridge comprising: a transcutaneous analyte sensor; a needle configured to guide the transcutaneous analyte sensor into skin of an individual; and a cartridge body configured to be coupled to the applicator housing and configured to retain the transcutaneous analyte sensor and the needle, and including a removable body configured to retain a used needle and to be removable from the cartridge body to separate the used needle from the cartridge body.

Implementations of the embodiments may include one or more of the following. The removable body may have a smaller volume than a portion of the cartridge body remaining after the removable body is removed from the cartridge body. A pull body may be coupled to the removable body and configured to be pulled to remove the removable body from the cartridge body. The removable body may comprise an insert positioned within the cartridge body. The cartridge body may be configured to be split apart to release the removable body from the cartridge body.

In a twenty-first aspect, a method comprising: coupling a cartridge to an applicator housing, the cartridge including: a transcutaneous analyte sensor, a needle configured to guide the transcutaneous analyte sensor into skin of an individual, and a cartridge body configured to be coupled to the applicator housing and configured to retain the transcutaneous analyte sensor and the needle, and including a removable body configured to retain a used needle and to be removable from the cartridge body to separate the used needle from the cartridge body.

Implementations of the embodiments may include one or more of the following. The removable body may have a smaller volume than a portion of the cartridge body remaining after the removable body is removed from the cartridge body. A pull body may be coupled to the removable body and configured to be pulled to remove the removable body from the cartridge body. The removable body may comprise an insert positioned within the cartridge body. The cartridge body may be configured to be split apart to release the removable body from the cartridge body.

In further aspects and embodiments, the above methods and features of the various aspects are formulated in terms of a system as in various aspects, having an applicator configured to carry out the method features. Any of the features of an embodiment of any of the aspects, including but not limited to any embodiments of any of the first through twenty-first aspects referred to above, is applicable to all other aspects and embodiments identified herein, including but not limited to any embodiments of any of the first through twenty-first aspects referred to above. Moreover, any of the features of an embodiment of the various aspects, including but not limited to any embodiments of any of the first through twenty-first aspects referred to above, is independently combinable, partly or wholly with other embodiments described herein in any way, e.g., one, two, or three or more embodiments may be combinable in whole or in part. Further, any of the features of an embodiment of the various aspects, including but not limited to any embodiments of any of the first through twenty-first aspects referred to above, may be made optional to other aspects or embodiments. Any aspect or embodiment of a method can be performed by a system or apparatus of another aspect or embodiment, and any aspect or embodiment of a system or apparatus can be configured to perform a method of another aspect or embodiment, including but not limited to any embodiments of any of the first through twenty-first aspects referred to above.

This Summary is provided to introduce a selection of concepts in a simplified form. The concepts are further described in the Detailed Description section. Elements or steps other than those described in this Summary are possible, and no element or step is necessarily required. This Summary is not intended to identify key features or essential features of the claimed subject matter, nor is it intended for use as an aid in determining the scope of the claimed subject matter. The claimed subject matter is not limited to implementations that solve any or all disadvantages noted in any part of this disclosure.

BRIEF DESCRIPTION OF THE DRAWINGS

These and other features, aspects, and advantages are described below with reference to the drawings, which are intended to illustrate, but not to limit, the disclosure. In the drawings, like reference characters denote corresponding features consistently throughout similar embodiments.

FIG. 111 illustrates a perspective view of a carriage shown in partial cross sectional view.

FIG. 112 illustrates a perspective view of a carriage shown in partial cross sectional view.

FIG. 119 illustrates a three quarters cross section perspective view of the applicator of FIG. 113.

FIG. 120 illustrates an exploded perspective view of a cartridge.

FIG. 121 illustrates a cross sectional view of the assembled cartridge along line XI-XI of FIG. 120.

FIG. 122 illustrates a top perspective view of the assembled cartridge of FIG. 120.

FIG. 123 illustrates an exploded view of an applicator.

FIG. 124 illustrates a perspective view of a carriage of the applicator shown in FIG. 123.

FIG. 125 illustrates a perspective view of a carriage of an applicator shown in FIG. 123.

FIG. 126 illustrates a rear perspective view of a control device of an applicator shown in FIG. 123.

FIG. 127 illustrates a cross sectional view of the applicator along line XII-XII shown in FIG. 123.

FIG. 128 illustrates a cross-sectional view of the applicator along line XIII-XIII shown in FIG. 123, which is orthogonal to line XII-XII.

FIG. 129 illustrates a perspective cross-sectional view of the applicator along line XIII-XIII shown in FIG. 123, which is orthogonal to line XII-XII.

FIG. 130 illustrates a cross sectional view of the applicator along line XII-XII shown in FIG. 123.

Figure 123:
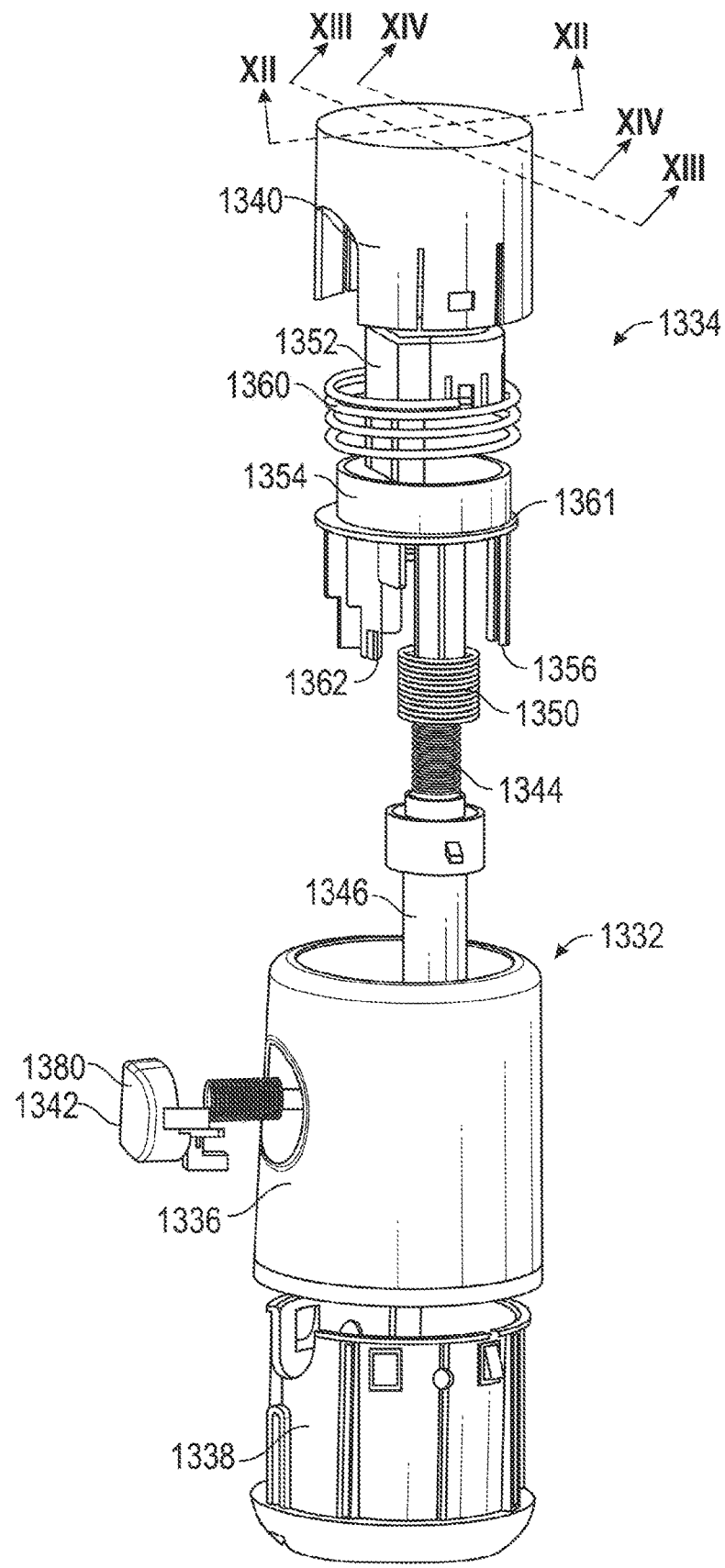
Figure 131:
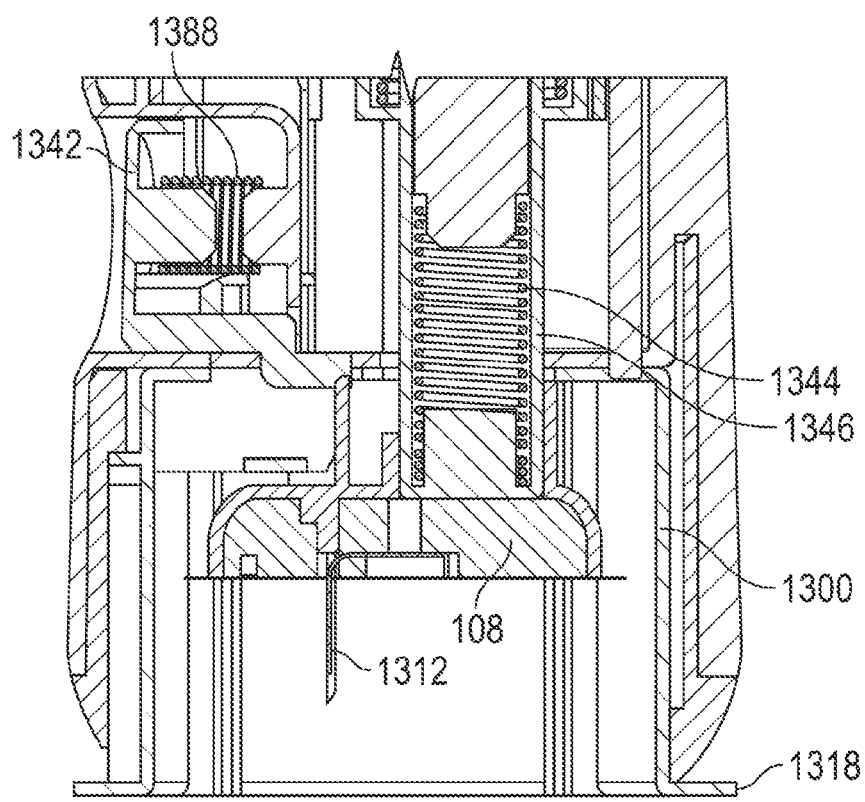

FIG. 131 illustrates a cross sectional view of the applicator along line XII-XII shown in FIG. 123.

Figure 132:
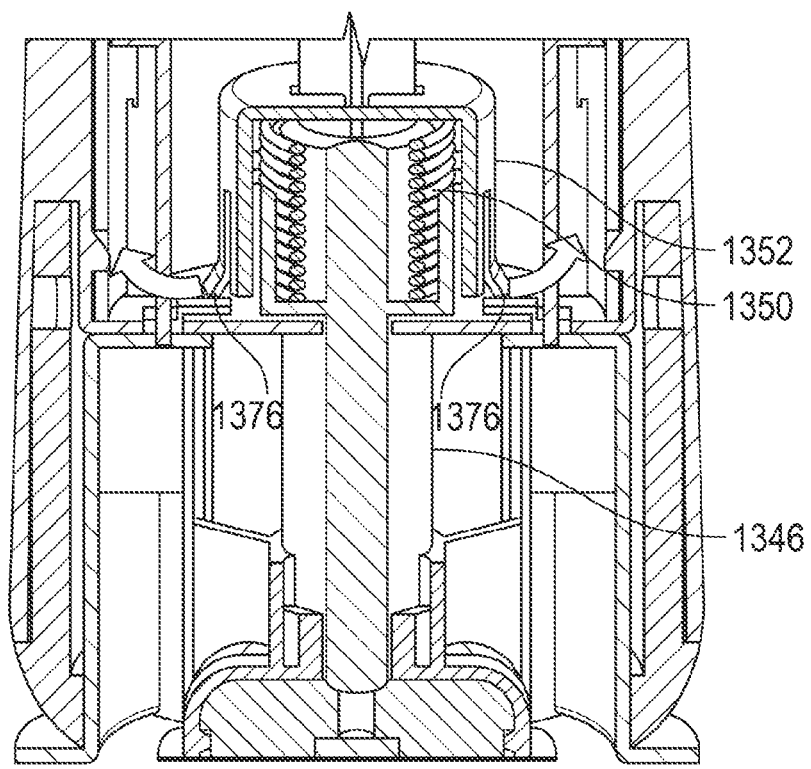

FIG. 132 illustrates a cross-sectional view of the applicator along line XIII-XIII shown in FIG. 123, which is orthogonal to line XII-XII.

Figure 133:
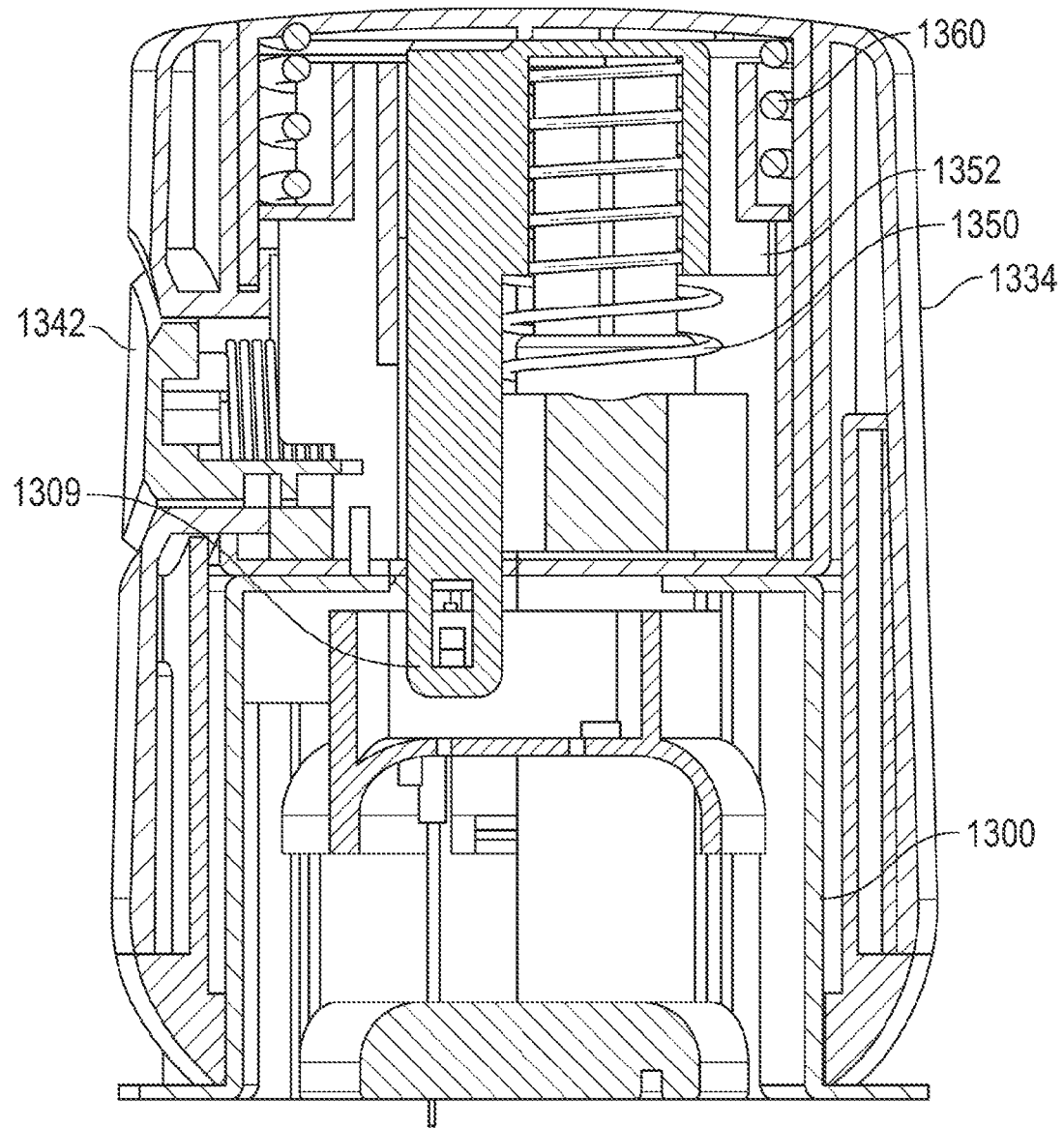

FIG. 133 illustrates a cross sectional view of the applicator along line XII-XII shown in FIG. 123.

Figure 134:
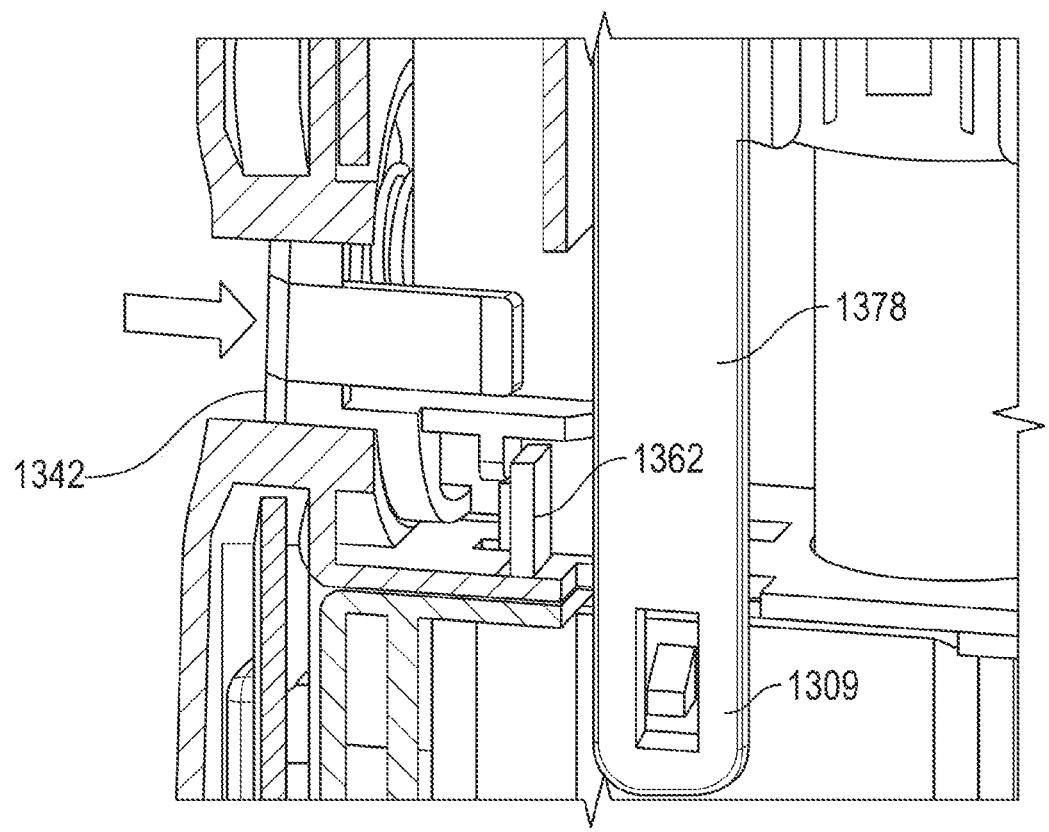

FIG. 134 illustrates a perspective cross sectional view of the applicator along line XII-XII shown in FIG. 123.

Figure 135:
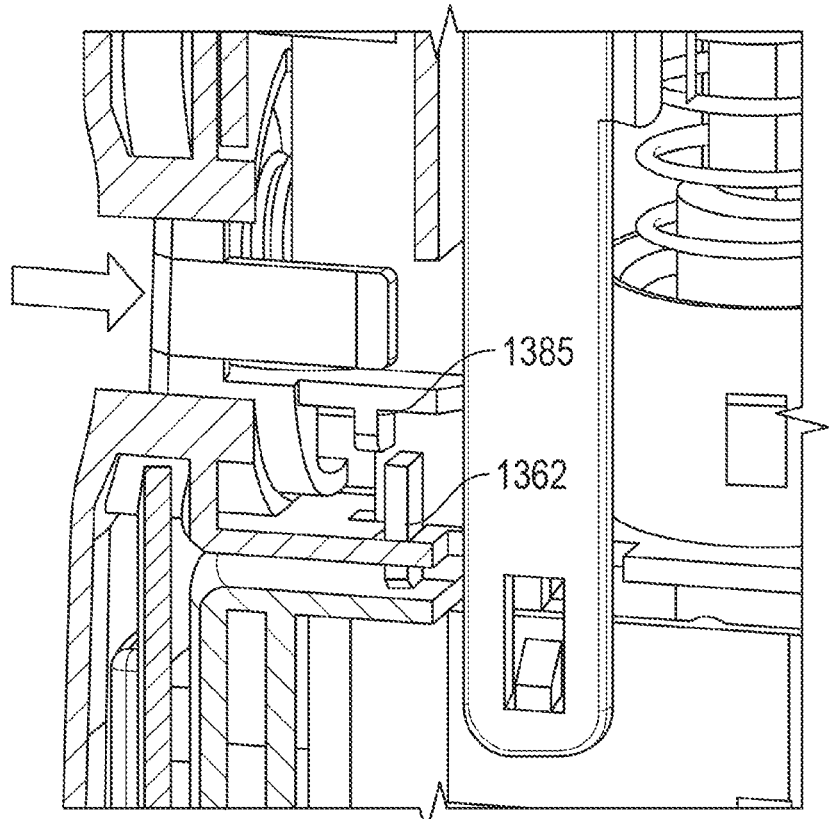

FIG. 135 illustrates a perspective cross sectional view of the applicator along line XII-XII shown in FIG. 123.

Figure 136:
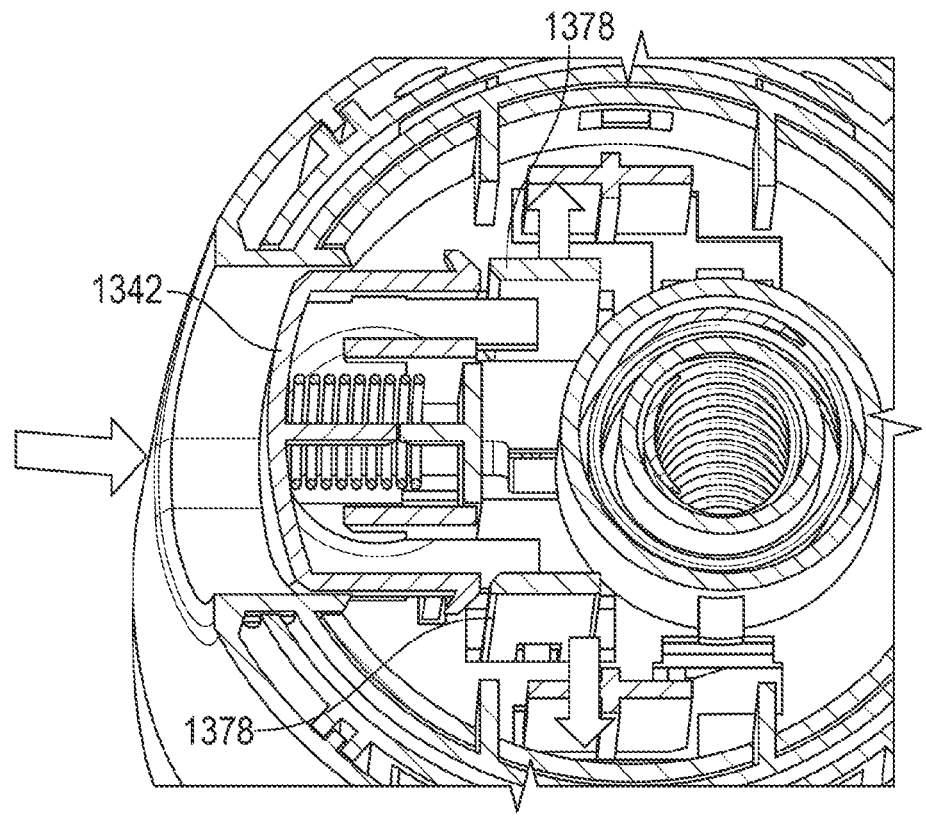

FIG. 136 illustrates a top down cross sectional view of the applicator shown in FIG. 123, along a mid line of the control device shown in FIG. 123.

Figure 137:
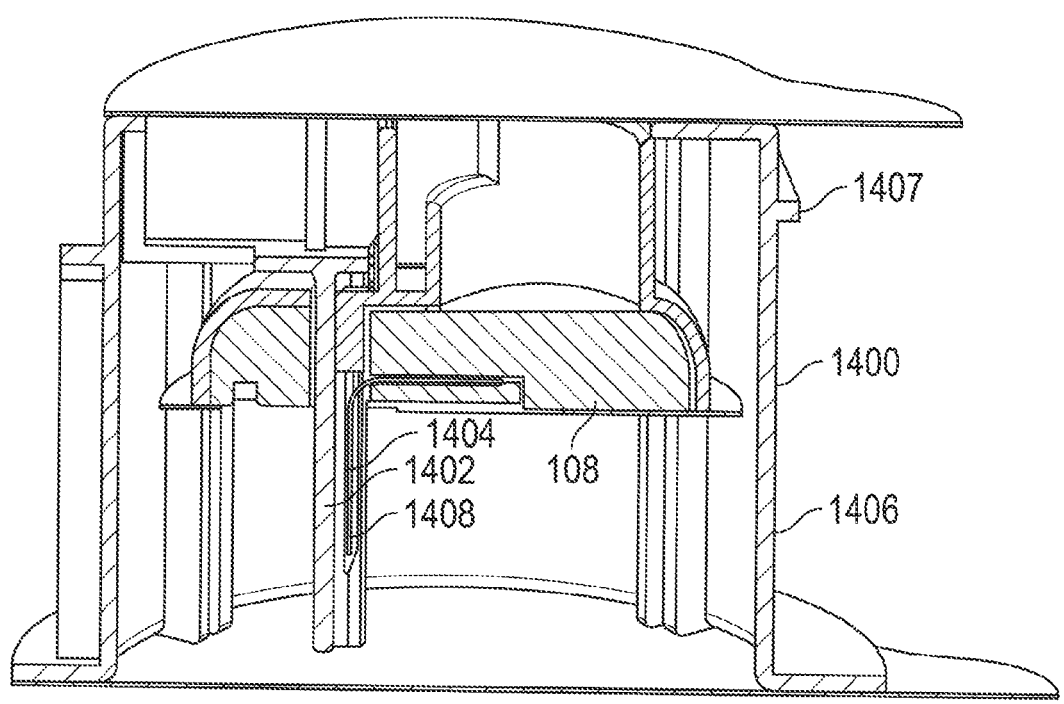

FIG. 137 illustrates a cross sectional view of a cartridge.

Figure 138:
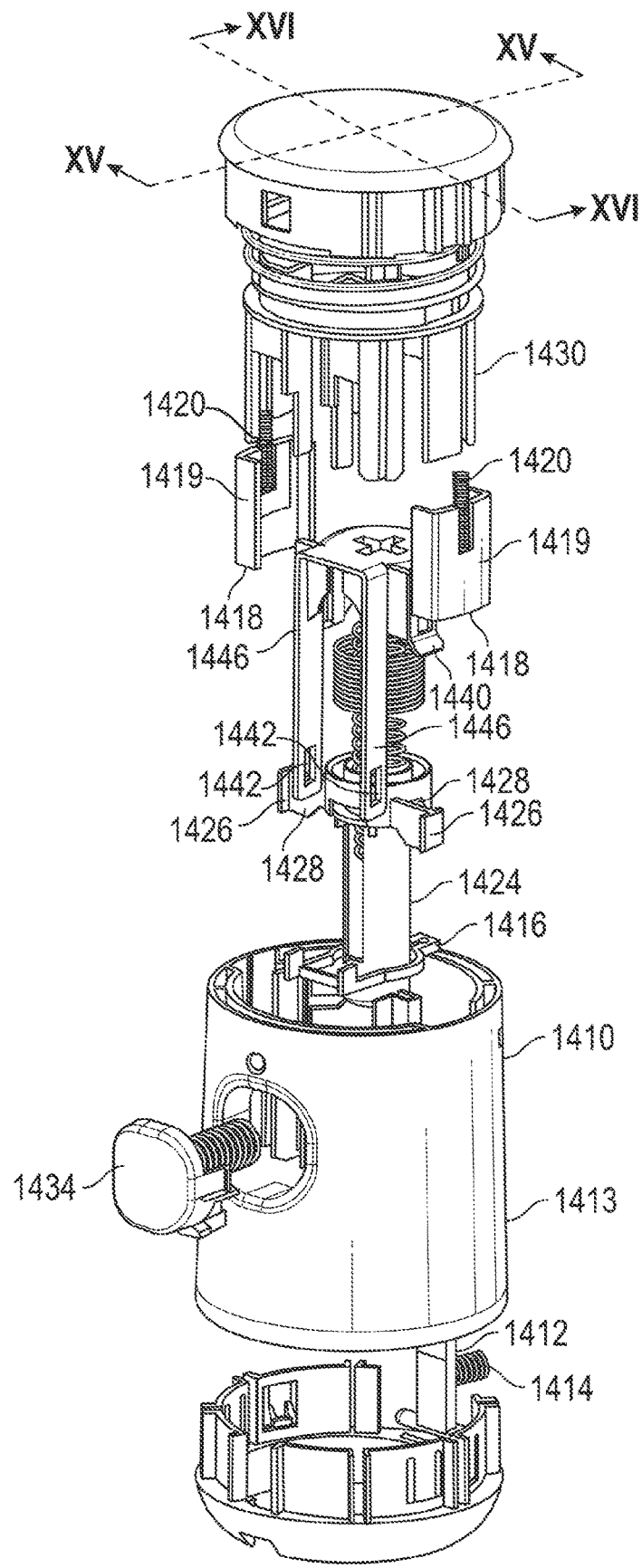

FIG. 138 illustrates an exploded perspective view of an applicator.

Figure 139:
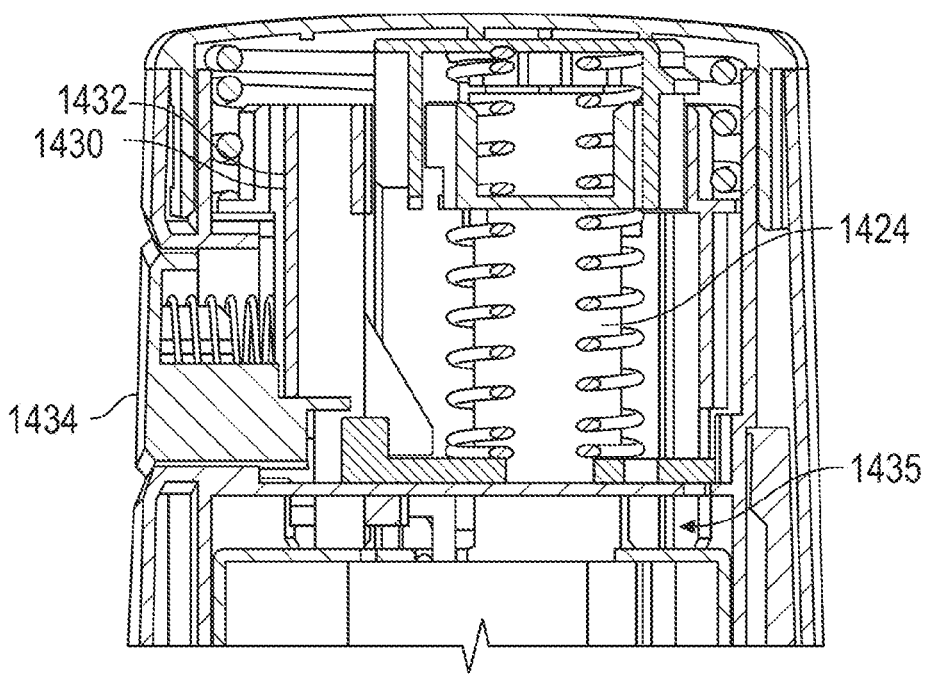

FIG. 139 illustrates a cross sectional view of the applicator along line XV-XV shown in FIG. 138.

Figure 140:
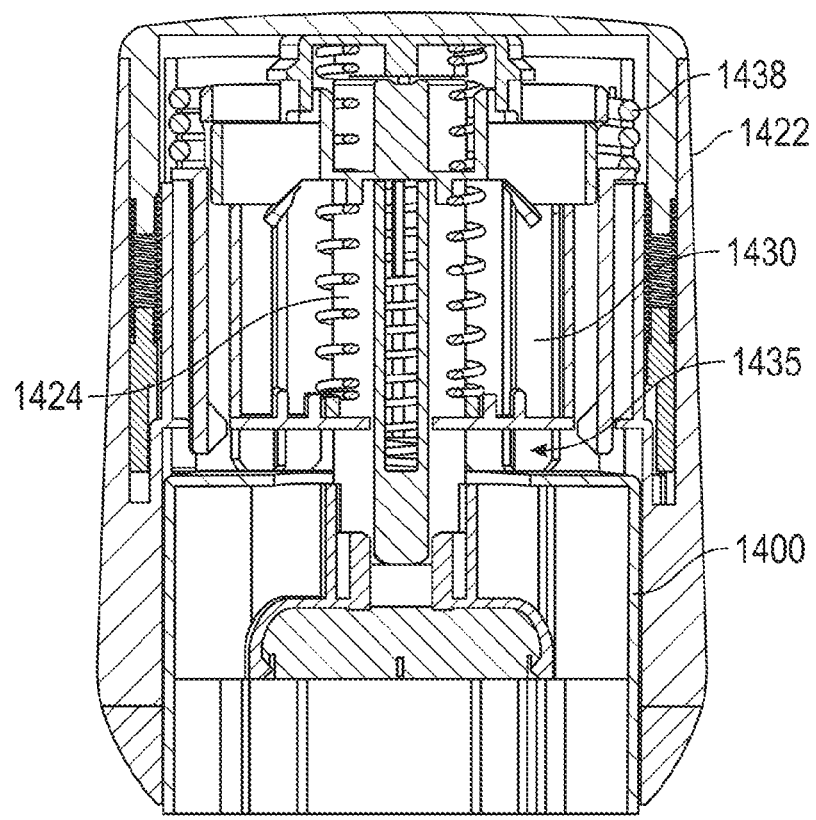

FIG. 140 illustrates a cross sectional view of the applicator along line XVI-XVI shown in FIG. 138.

Figure 141:
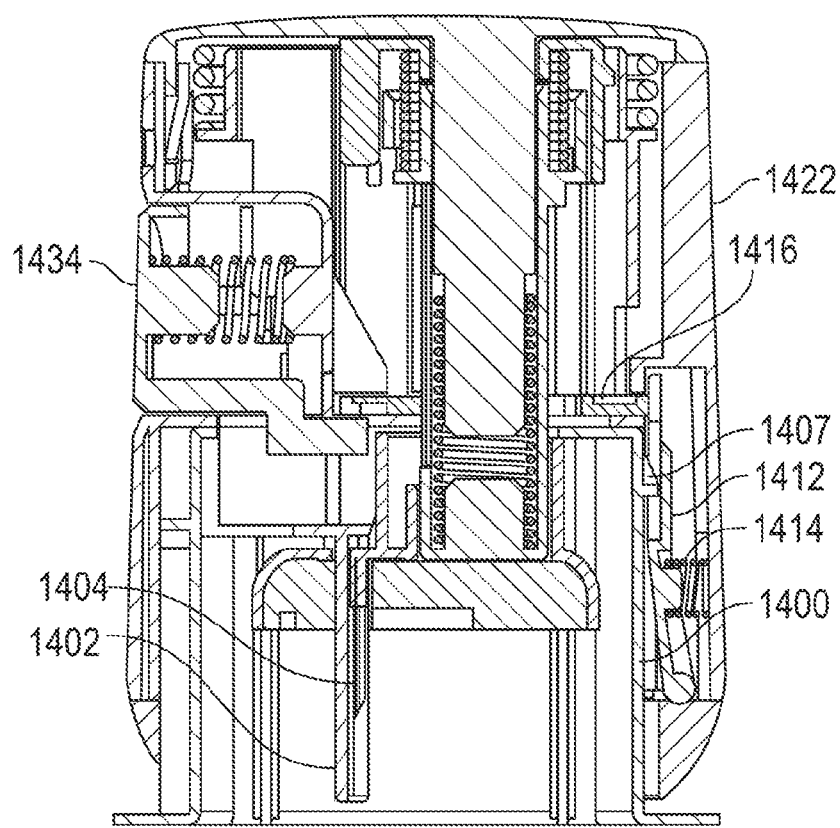

FIG. 141 illustrates a cross sectional view of the applicator along line XV-XV shown in FIG. 138.

Figure 142:
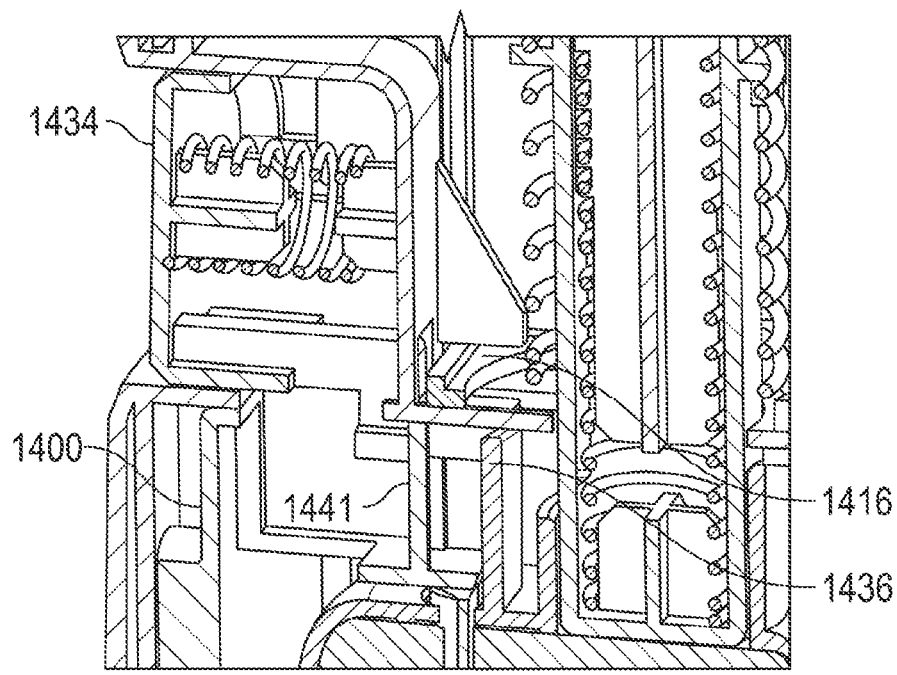

FIG. 142 illustrates a close up perspective cross sectional view of the applicator along line XV-XV shown in FIG. 138.

Figure 143:
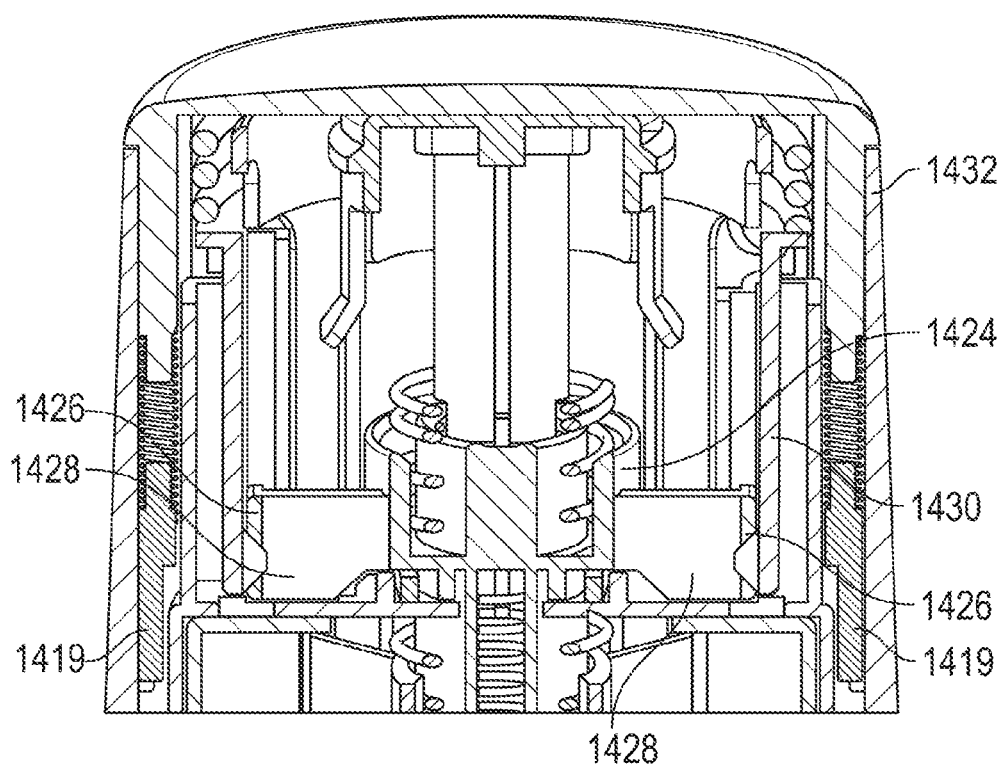

FIG. 143 illustrates a cross sectional view of the applicator along line XVI-XVI shown in FIG. 138.

Figure 144:
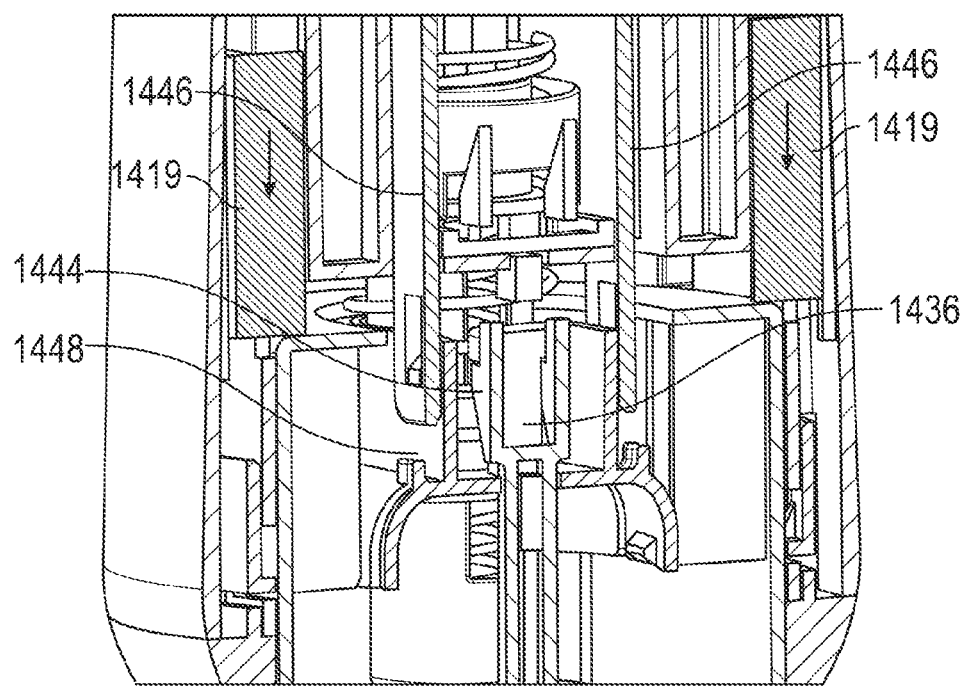

FIG. 144 illustrates a cross sectional view of the applicator along line XVI-XVI shown in FIG. 138.

Figure 145:
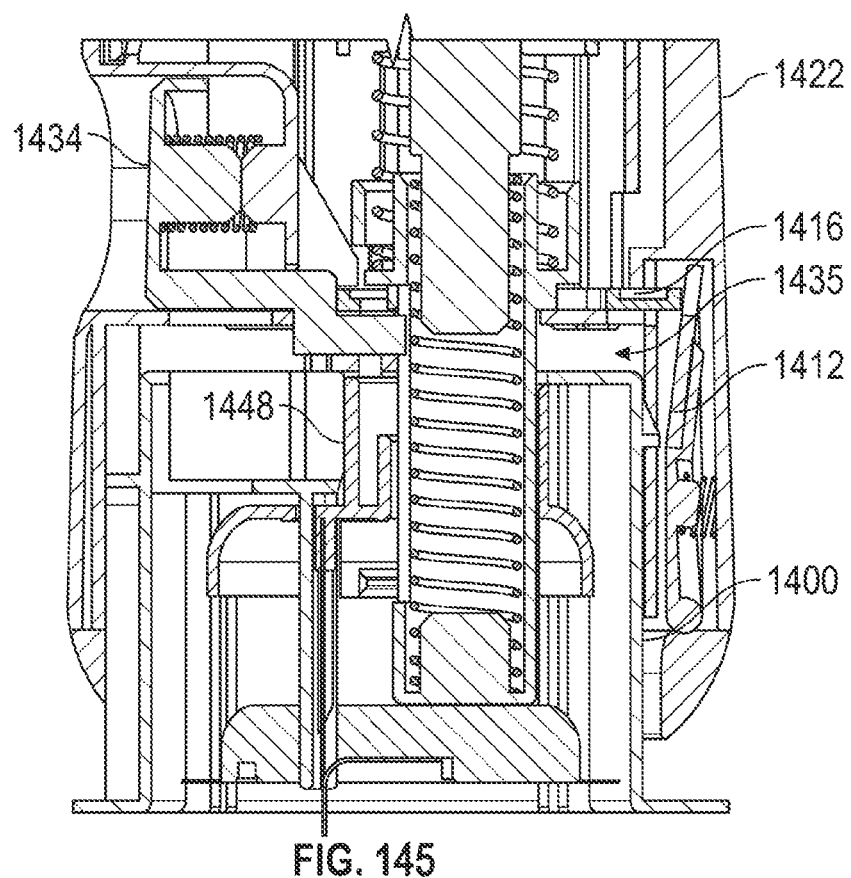

FIG. 145 illustrates a cross sectional view of the applicator along line XV-XV shown in FIG. 138.

Figure 146:
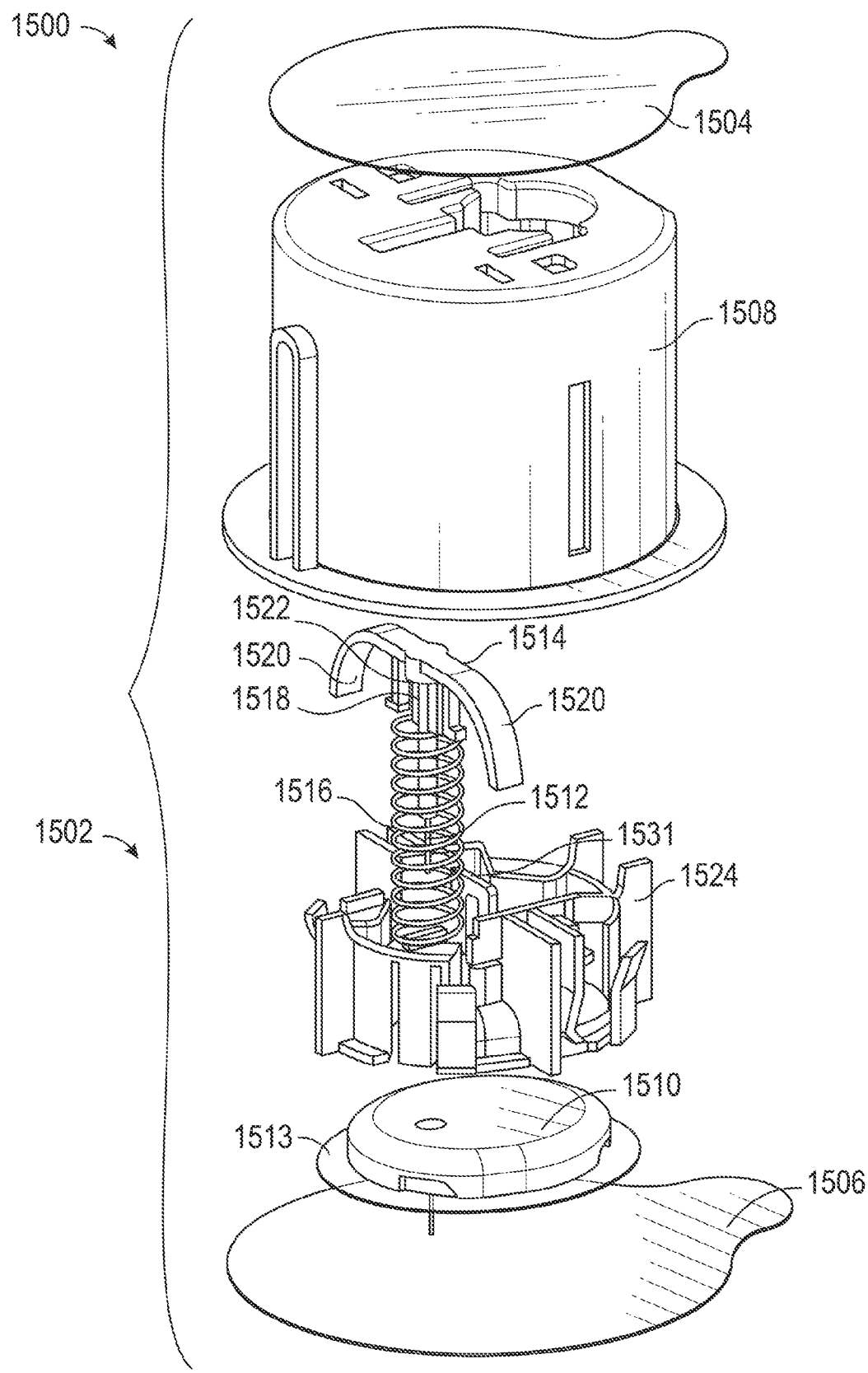

FIG. 146 illustrates an exploded view of a cartridge.

Figure 147:
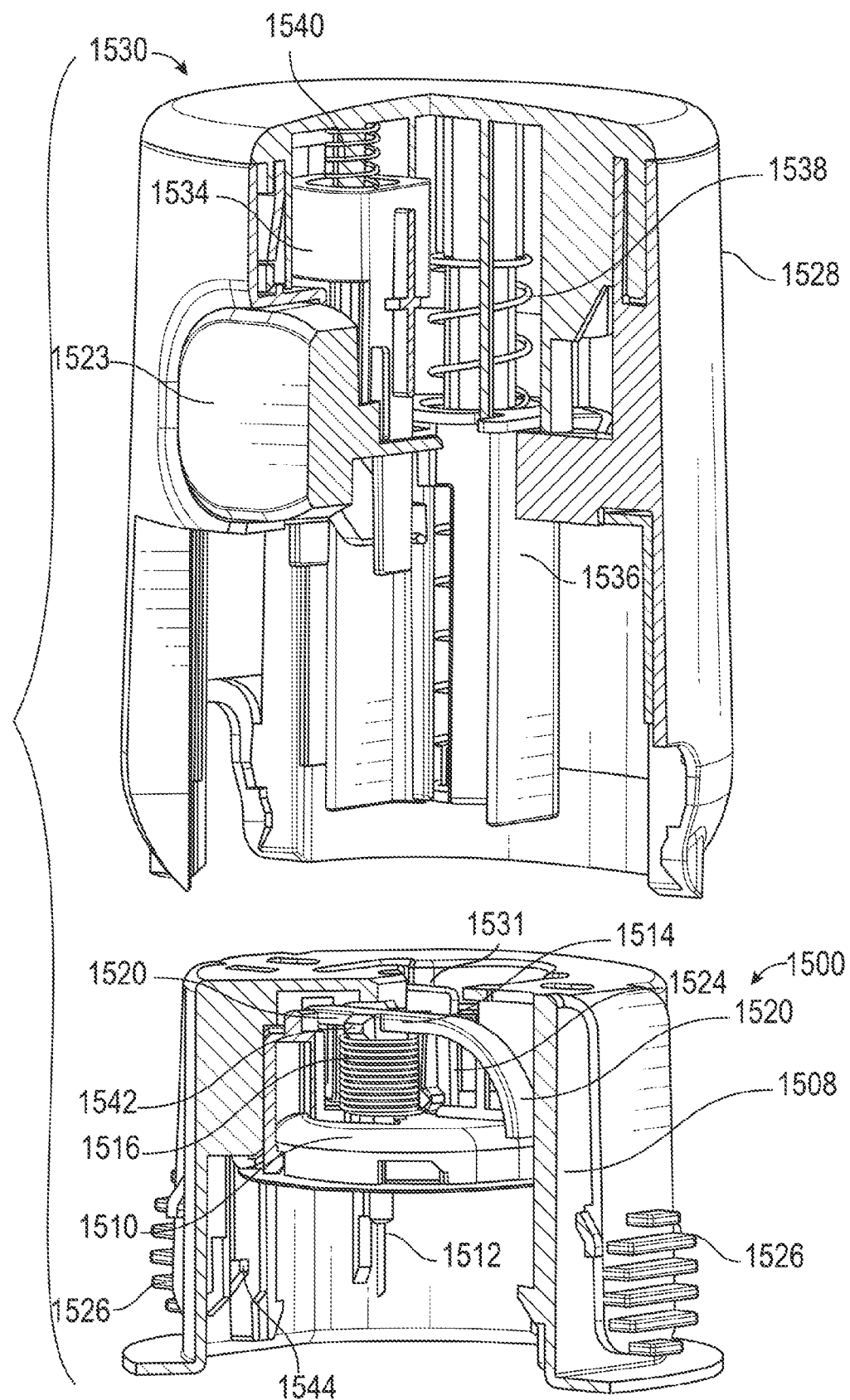

FIG. 147 illustrates a three quarters cross section perspective view of the cartridge of FIG. 146 and an applicator.

Figure 148:
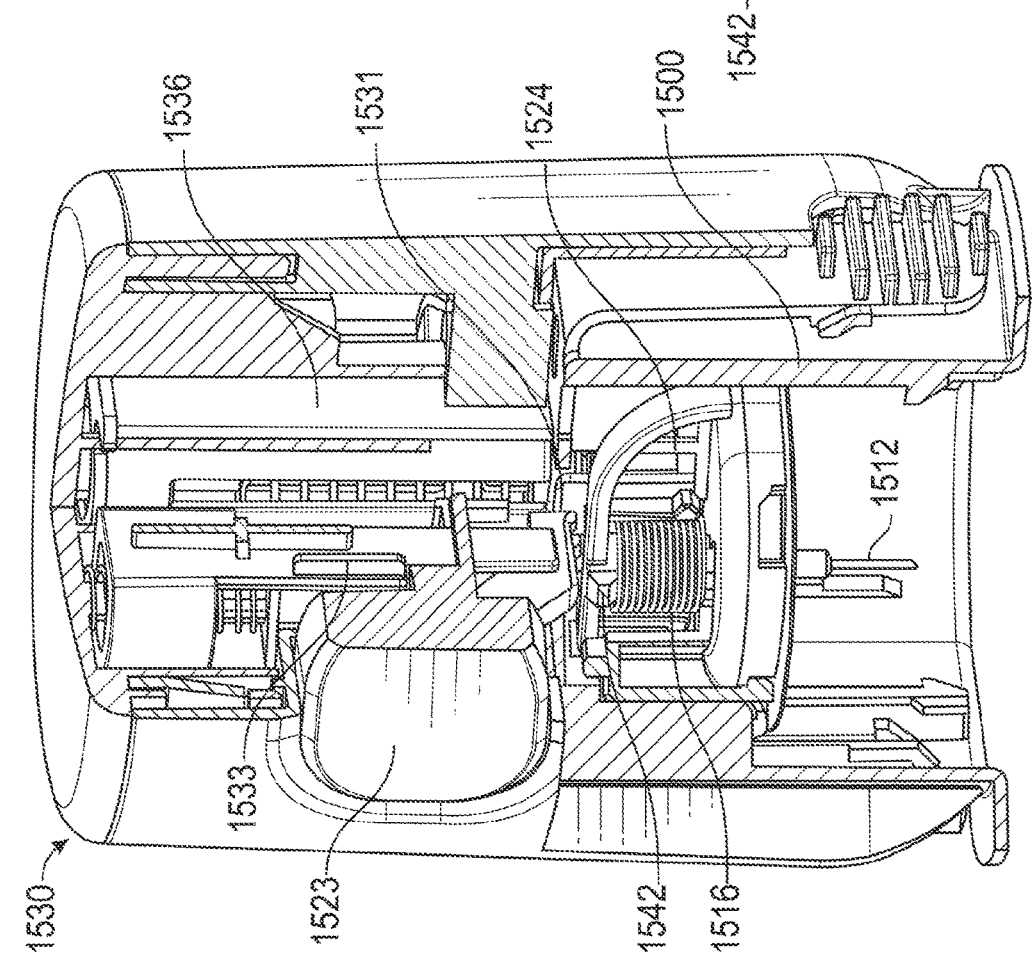

FIG. 148 illustrates a three quarters cross section perspective view of the cartridge of FIG. 146 and the applicator of FIG. 147.

Figure 149:
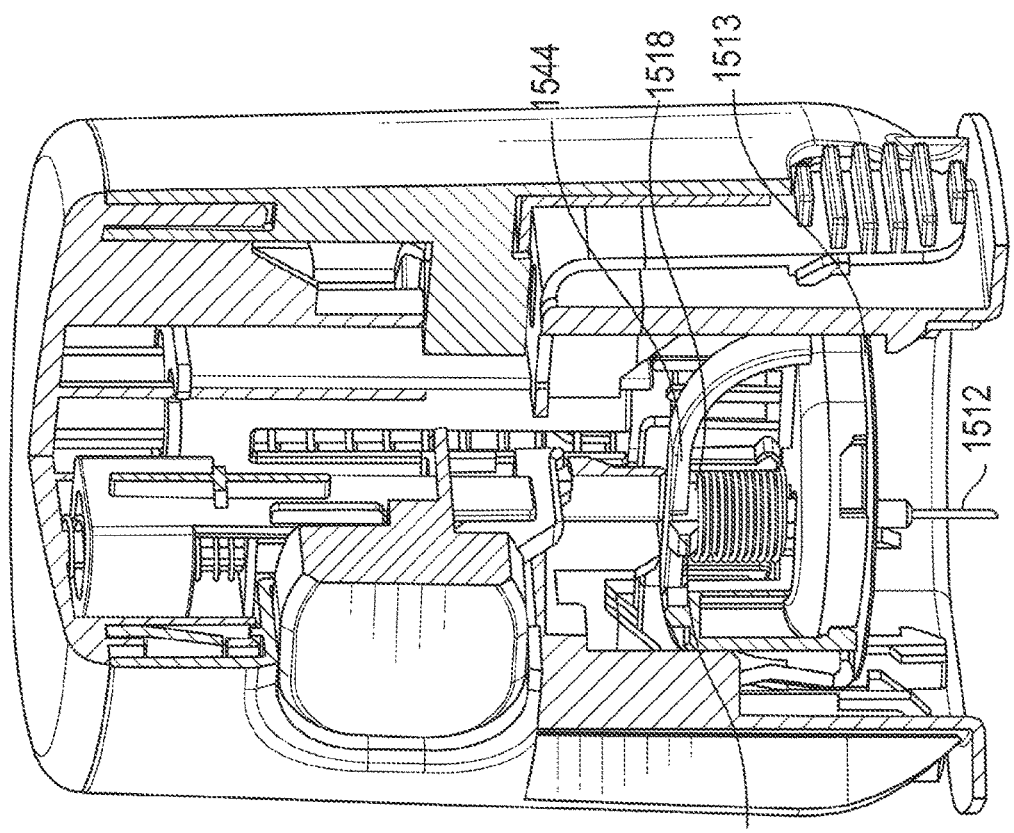

FIG. 149 illustrates a three quarters cross section perspective view of the cartridge of FIG. 146 and the applicator of FIG. 147.

Figure 150:
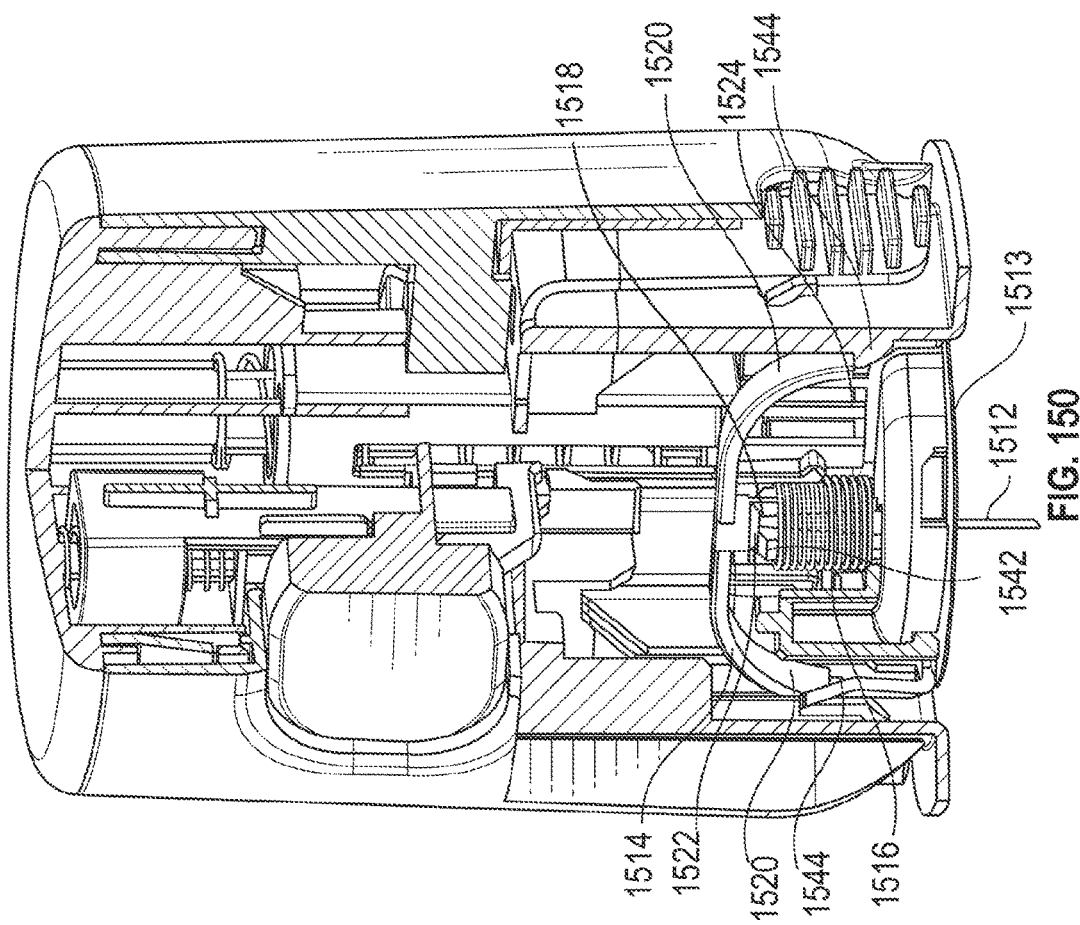

FIG. 150 illustrates a three quarters cross section perspective view of the cartridge of FIG. 146 and the applicator of FIG. 147.

Figure 151:
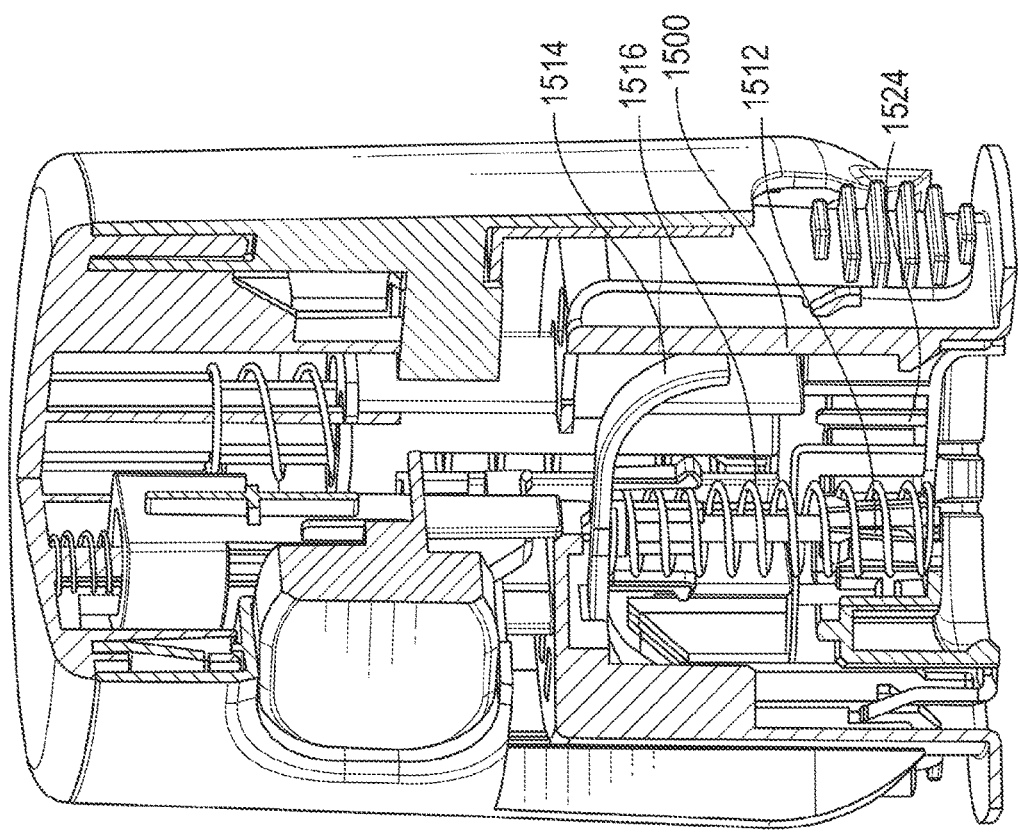

FIG. 151 illustrates a three quarters cross section perspective view of the cartridge of FIG. 146 and the applicator of FIG. 147.

Figure 152:
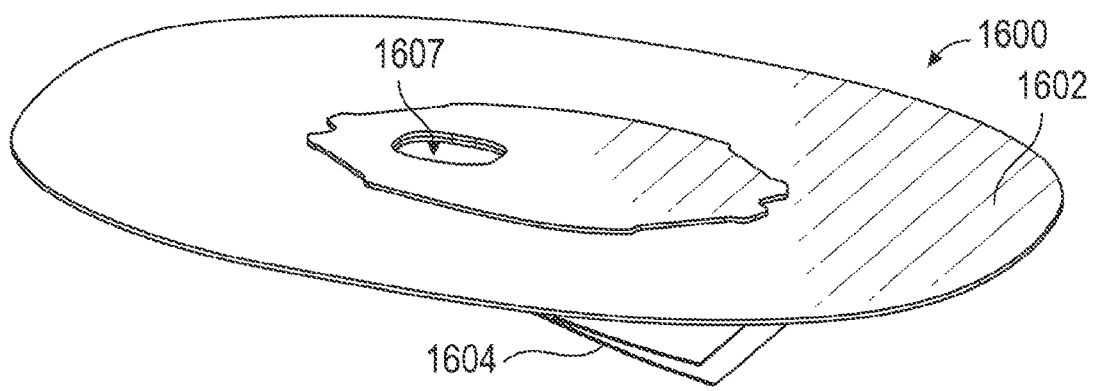

FIG. 152 illustrates a top perspective view of a patch.

Figure 153:
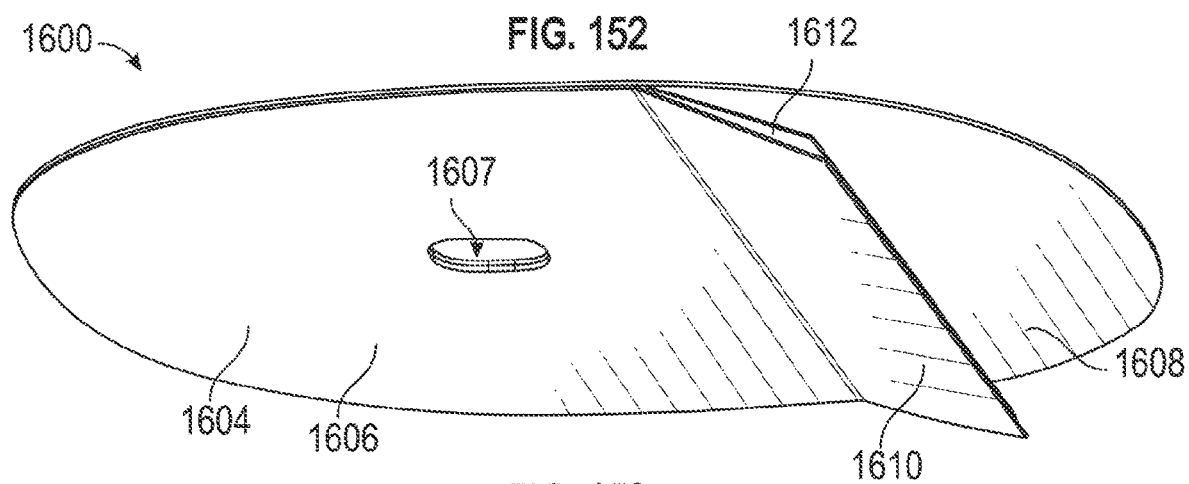

FIG. 153 illustrates a bottom perspective view of the patch of FIG. 152.

Figure 154:
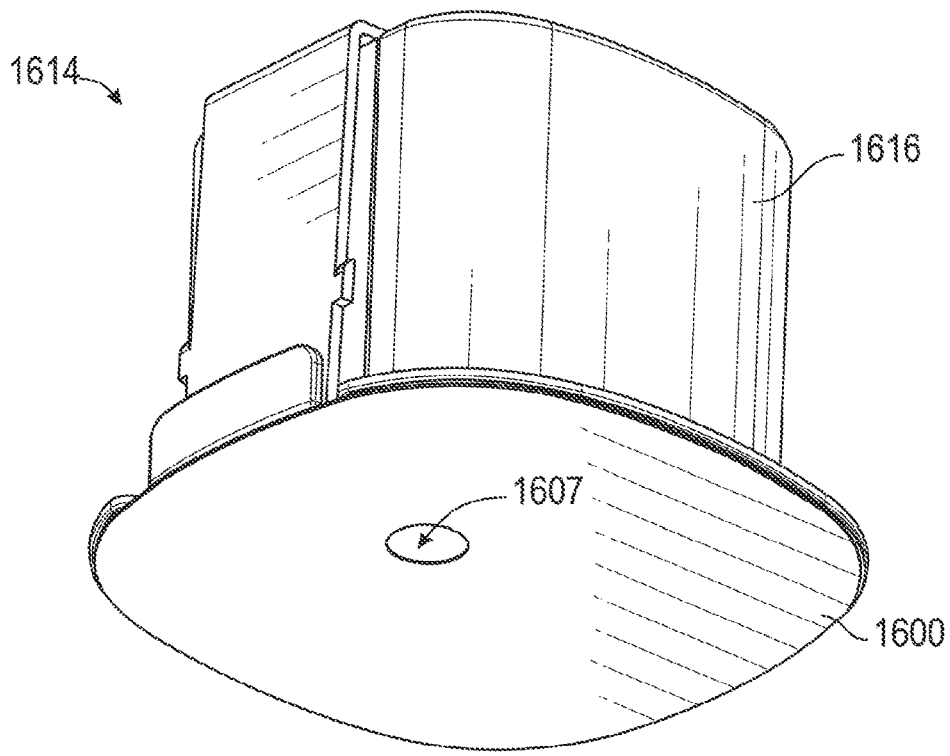

FIG. 154 illustrates a bottom perspective view of a cartridge.

Figure 155:
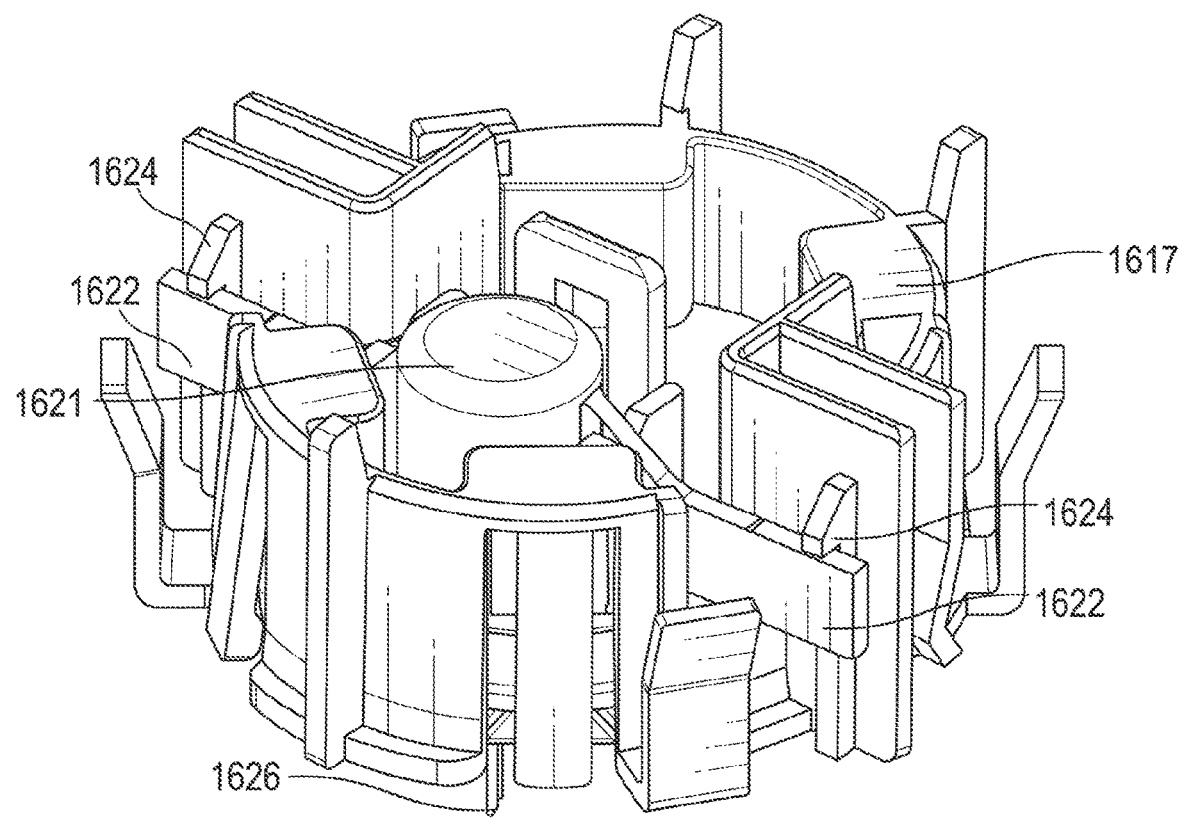

FIG. 155 illustrates a perspective view of a component of the cartridge shown in FIG. 154.

Figure 156:
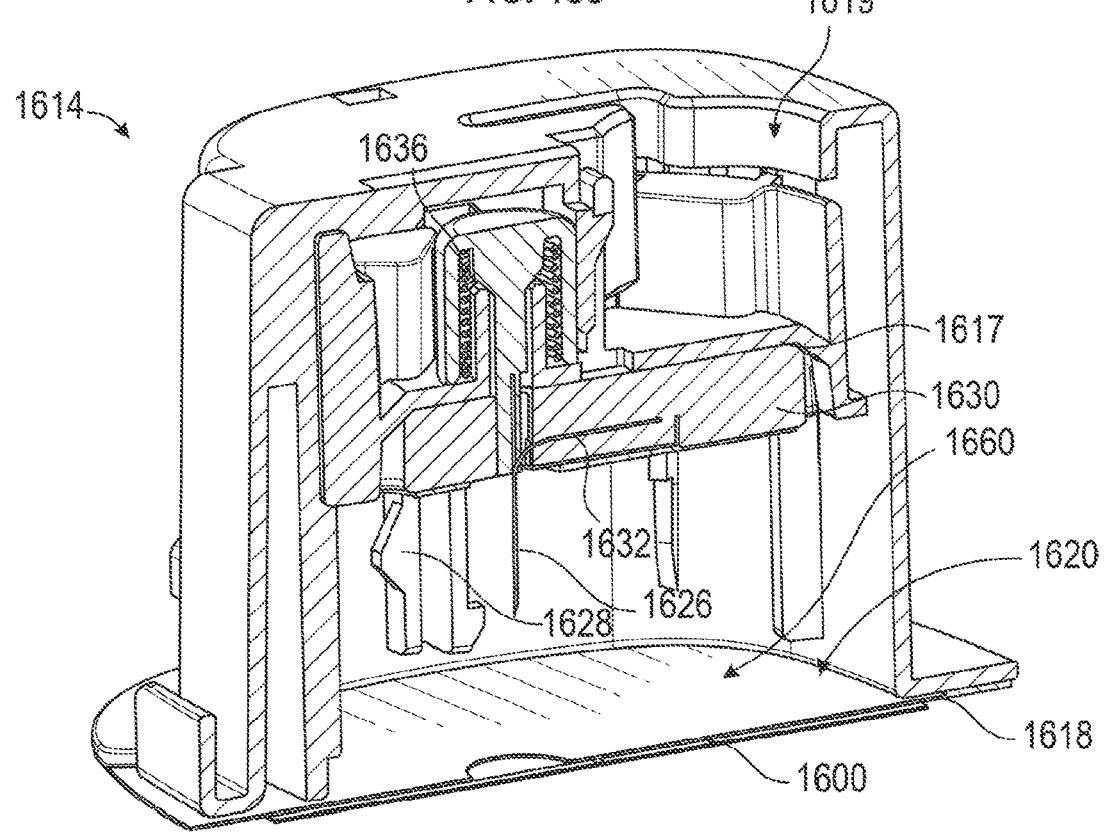

FIG. 156 illustrates a cross sectional view of a cartridge shown in FIG. 154.

Figure 157:
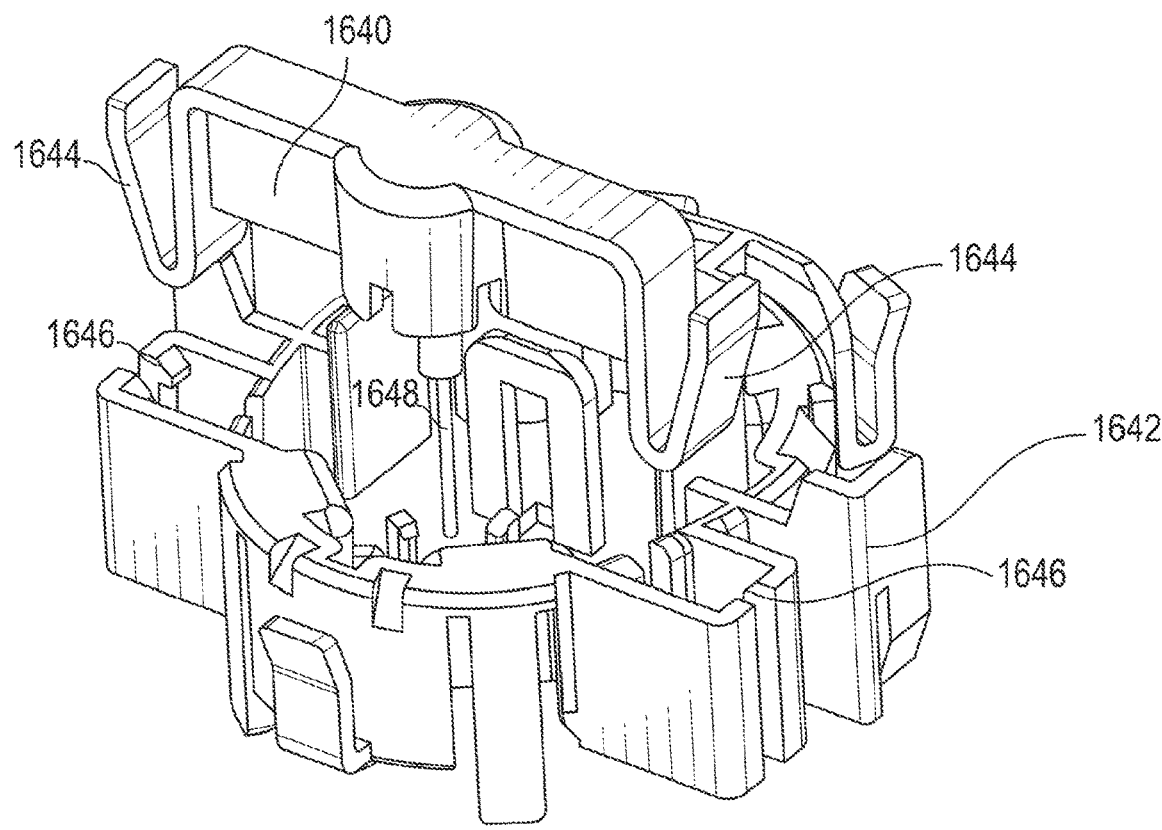

FIG. 157 illustrates a perspective view of a component of a cartridge.

Figure 158:
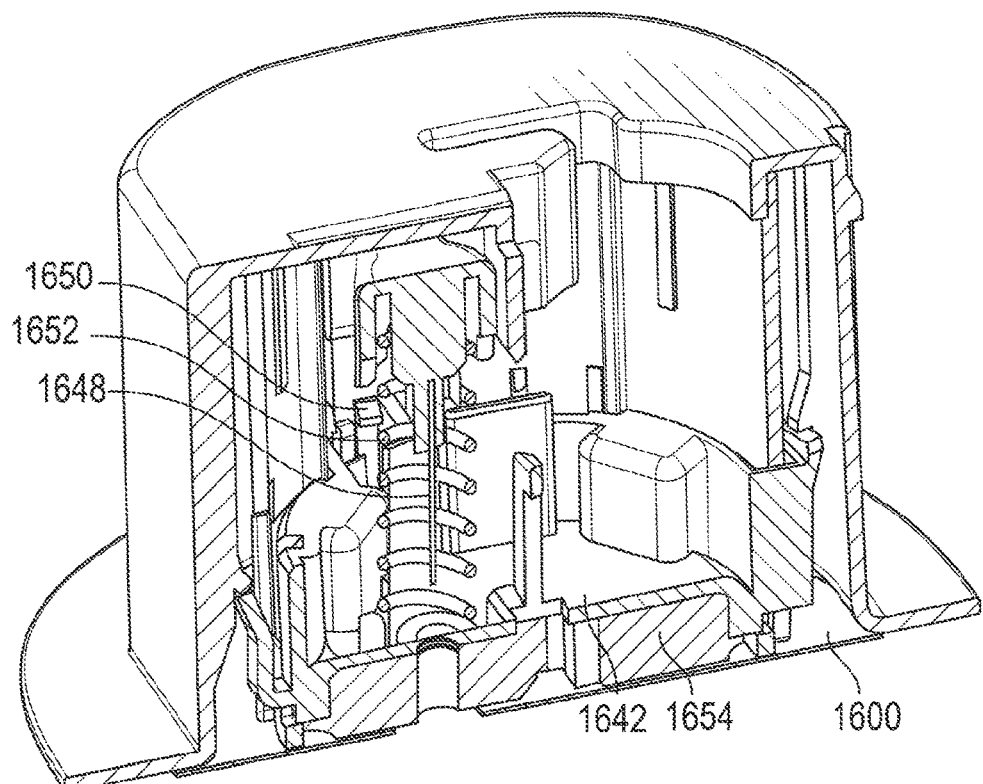

FIG. 158 illustrates a cross sectional view of a cartridge including the component shown in FIG. 157.

Figure 159:
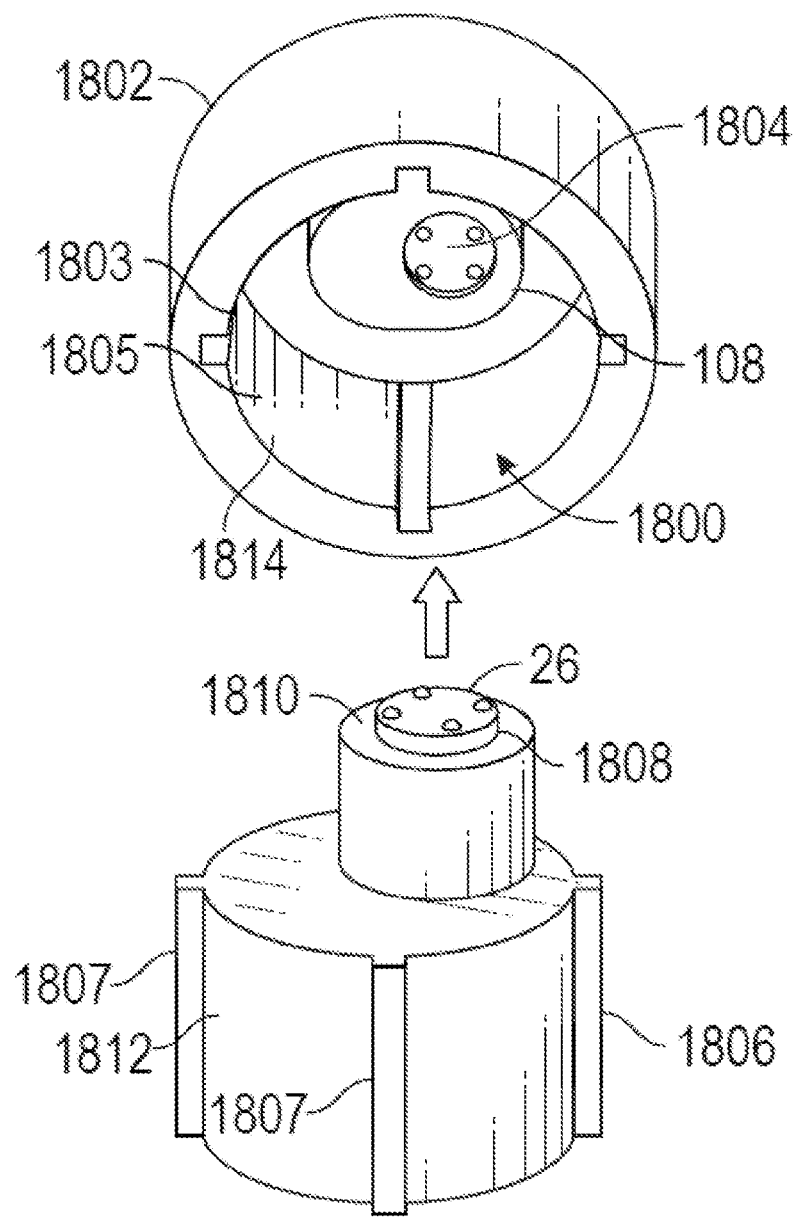

FIG. 159 illustrates a perspective assembly view of an applicator and a mounting base.

Figure 160:
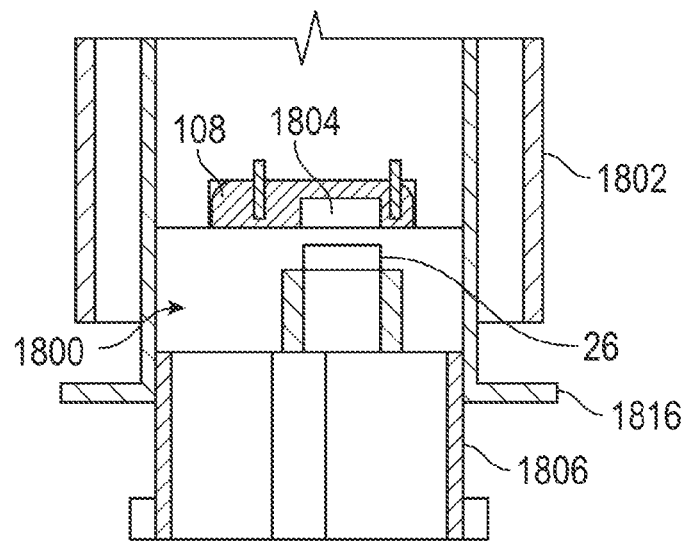

FIG. 160 illustrates a cross sectional view an applicator housing, a cartridge, and a mounting base.

Figure 161:
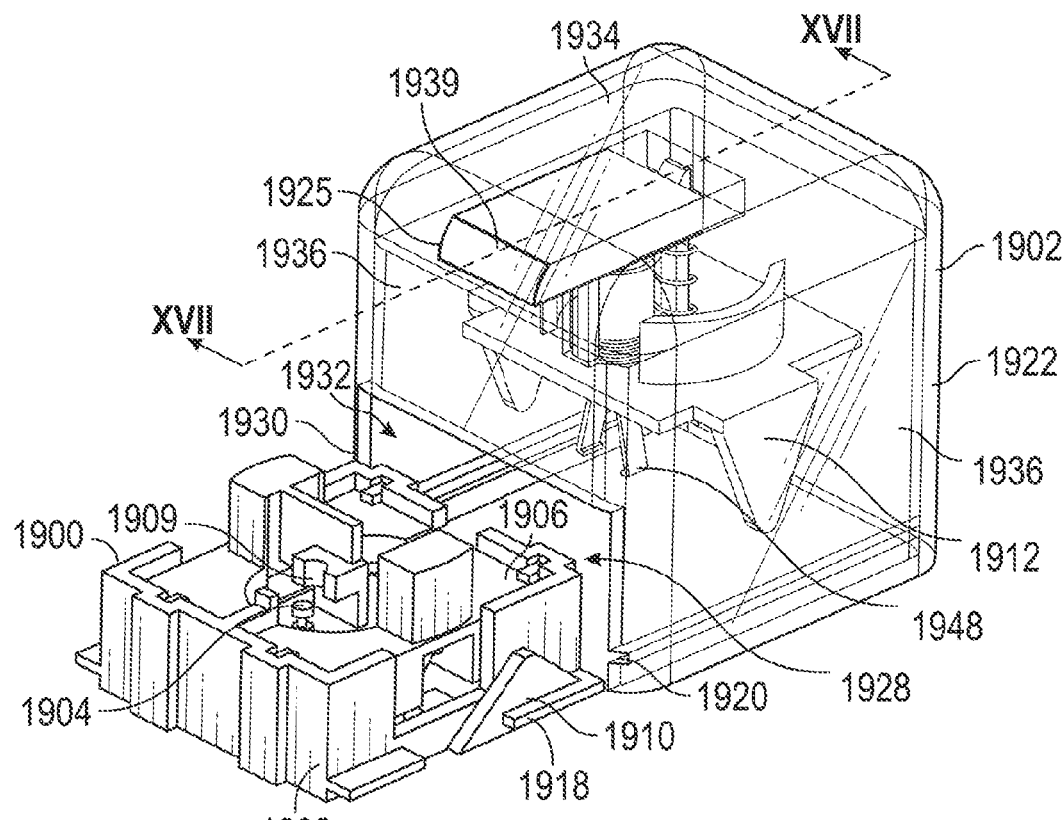

FIG. 161 illustrates a perspective view of an applicator and a cartridge.

Figure 162:
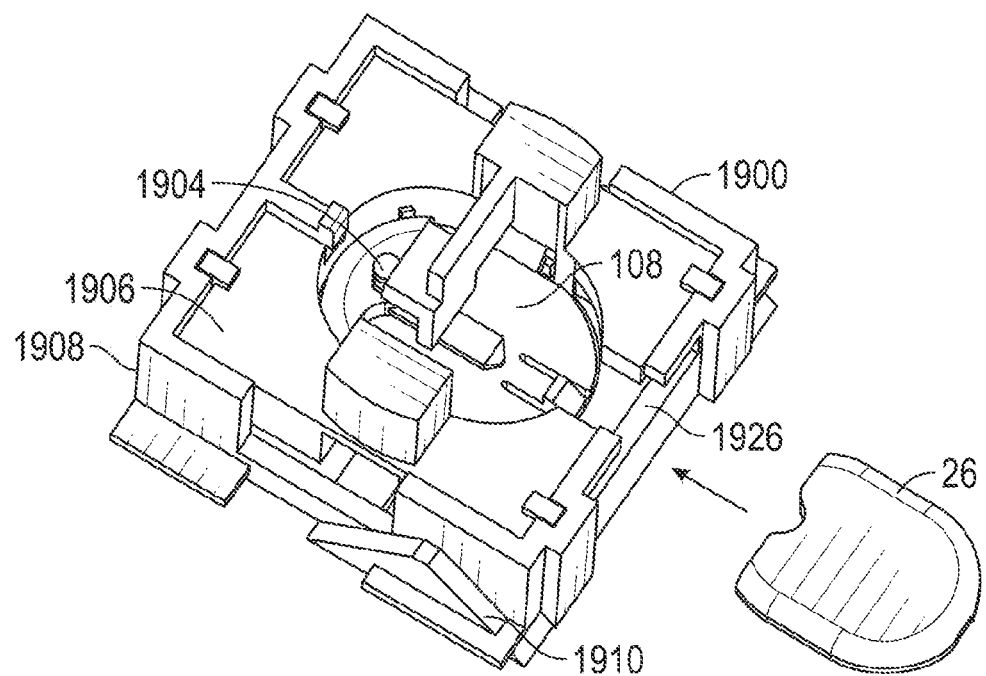

FIG. 162 illustrates a perspective top view of a cartridge shown in FIG. 161.

Figure 163:
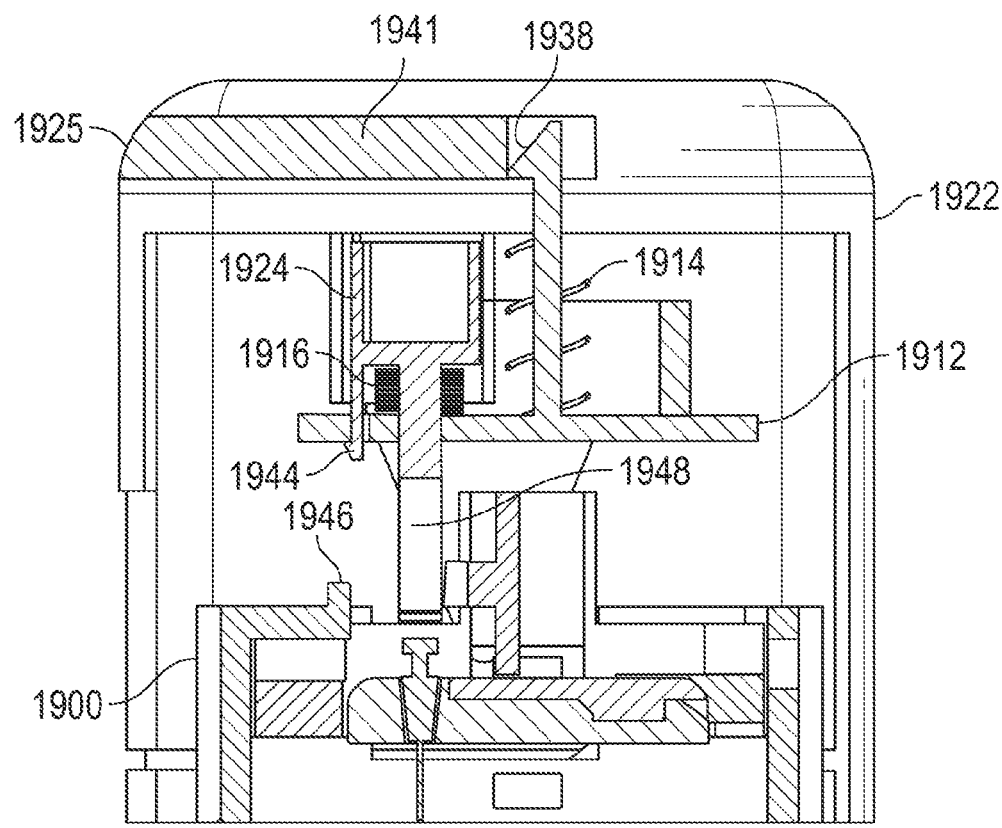

FIG. 163 illustrates a cross sectional view of an applicator and a cartridge along line XVII-XVII in FIG. 161.

Figure 164:
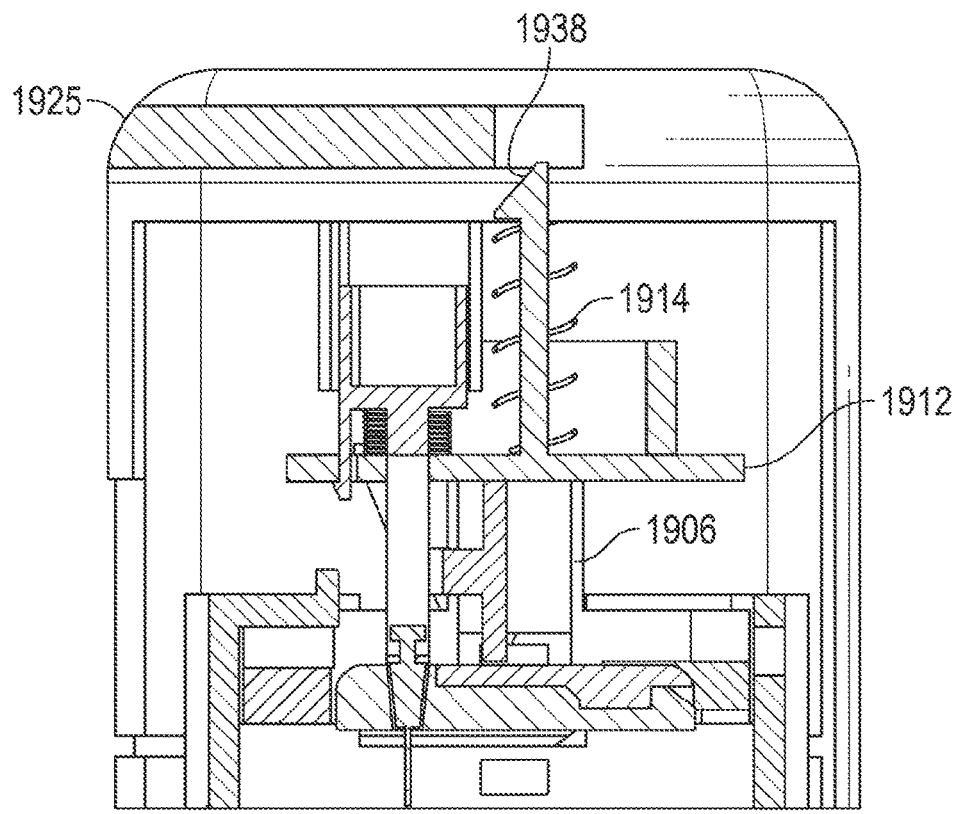

FIG. 164 illustrates a cross sectional view of an applicator and a cartridge along line XVII-XVII in FIG. 161.

Figure 165:
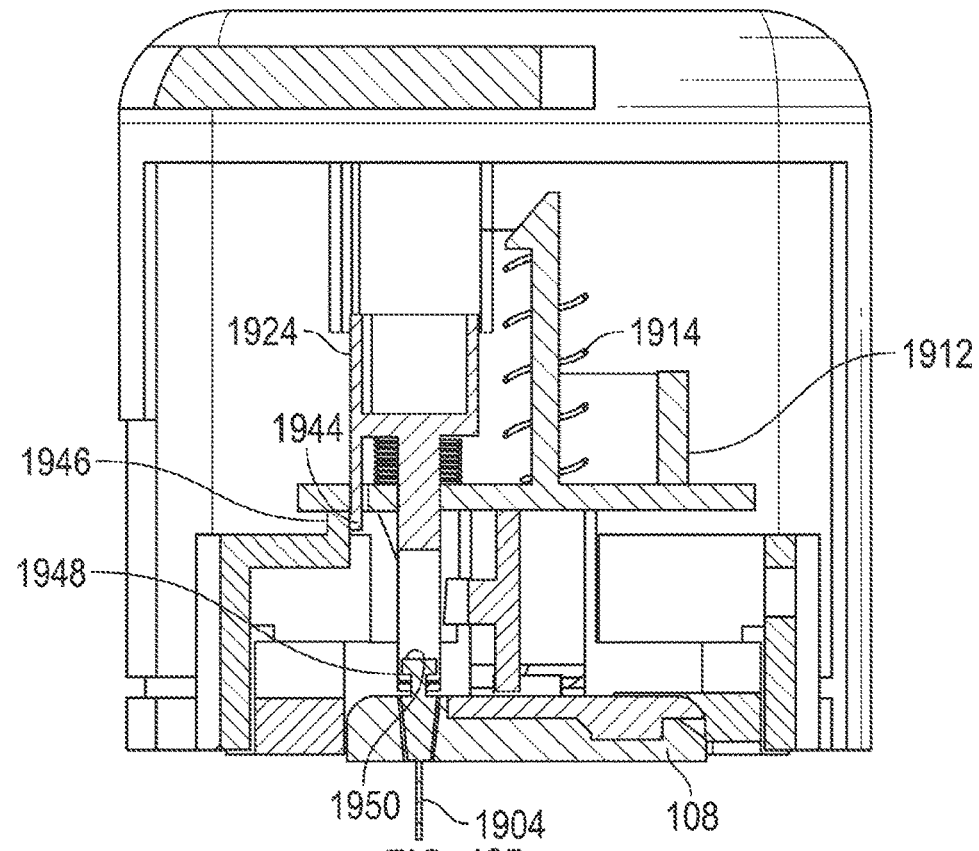

FIG. 165 illustrates a cross sectional view of an applicator and a cartridge along line XVII-XVII in FIG. 161.

Figure 166:
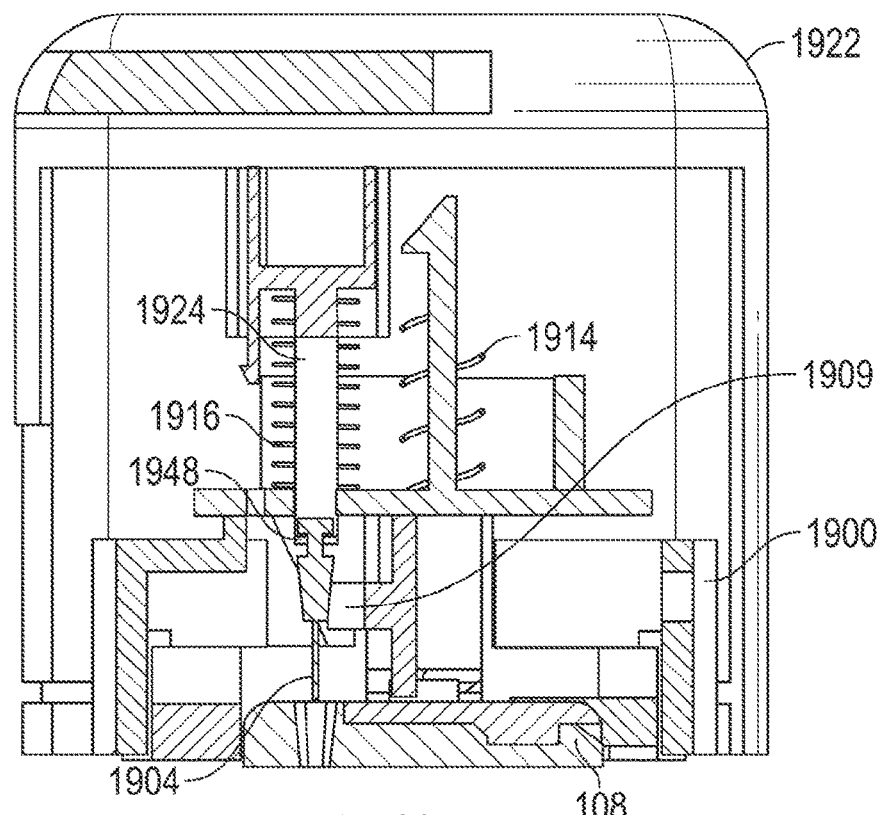

FIG. 166 illustrates a cross sectional view of an applicator and a cartridge along line XVII-XVII in FIG. 161.

Figure 167:
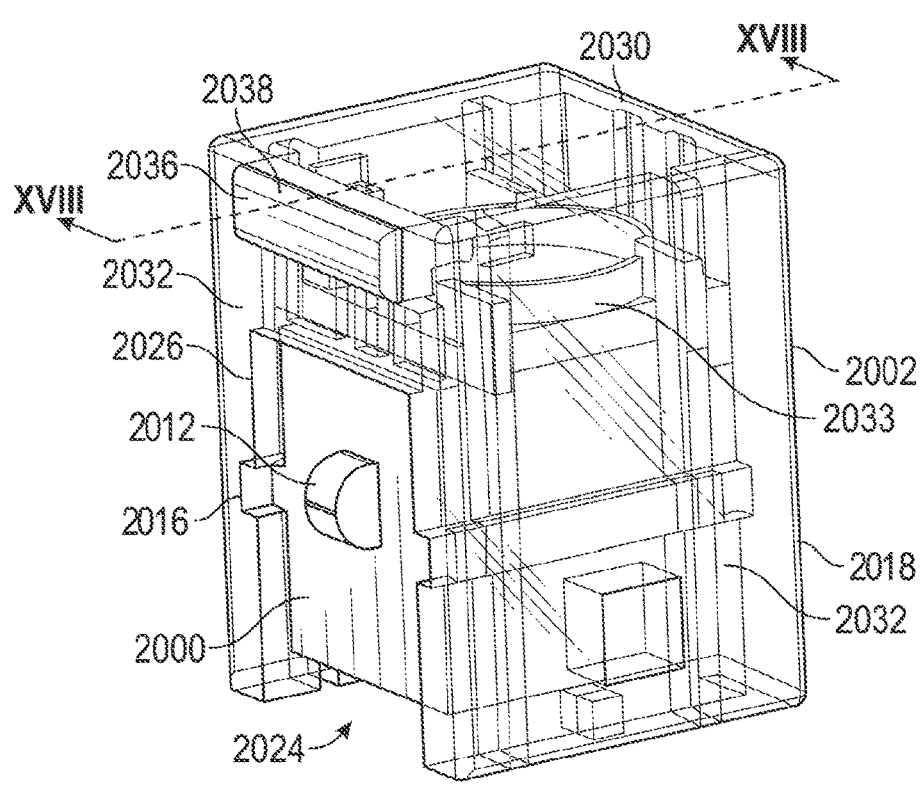

FIG. 167 illustrates a perspective view of an applicator and a cartridge.

Figure 168:
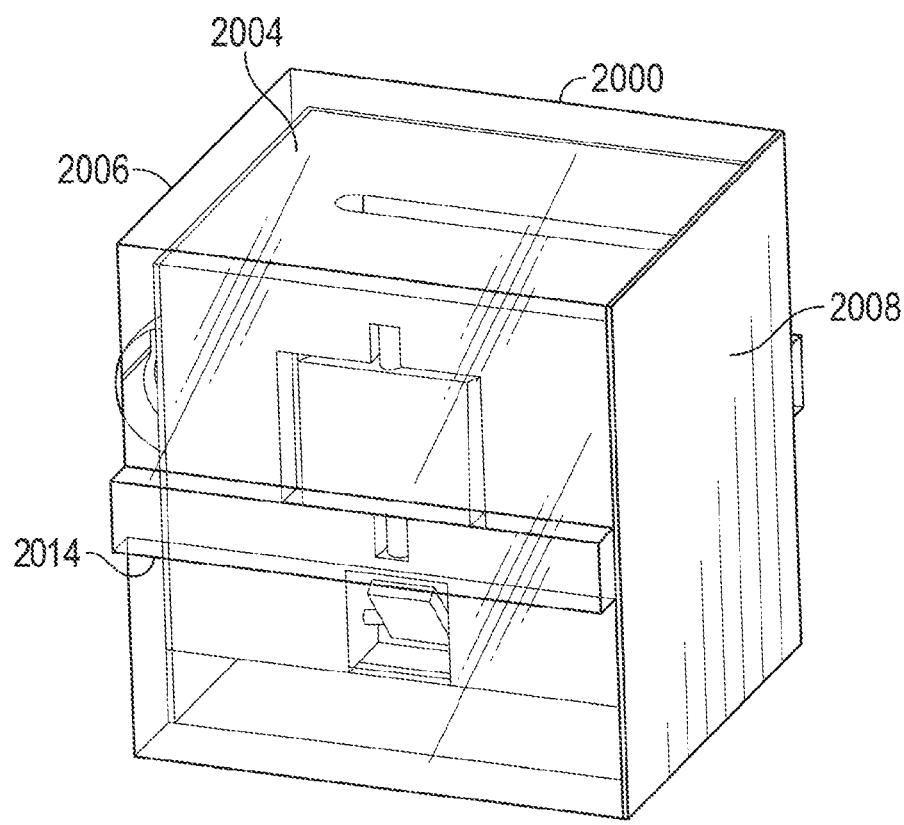

FIG. 168 illustrates a perspective view of the cartridge shown in FIG. 167.

Figure 169:
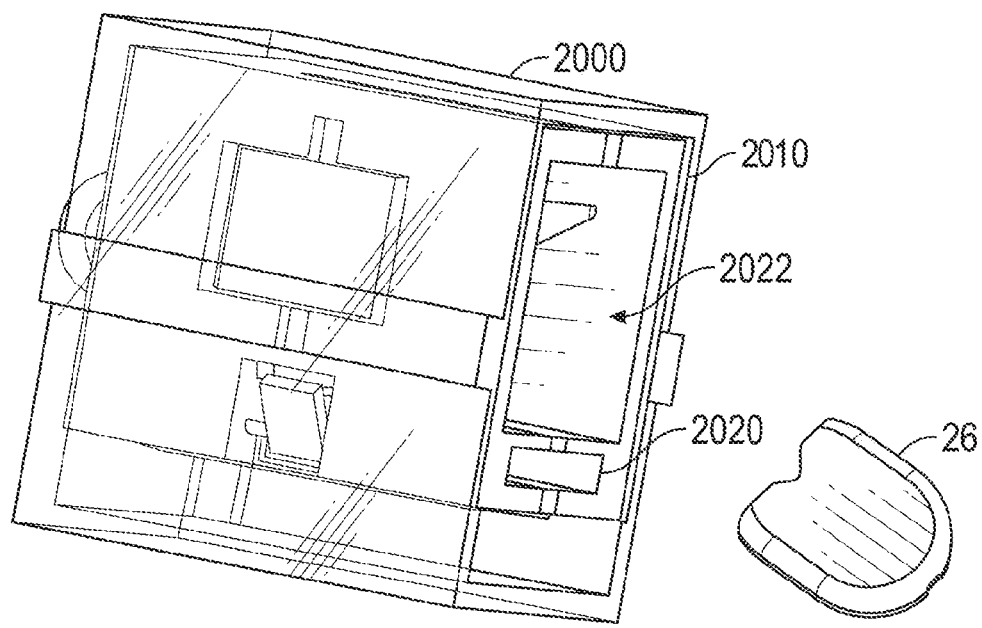

FIG. 169 illustrates an assembly view of the cartridge shown in FIG. 167.

Figure 170:
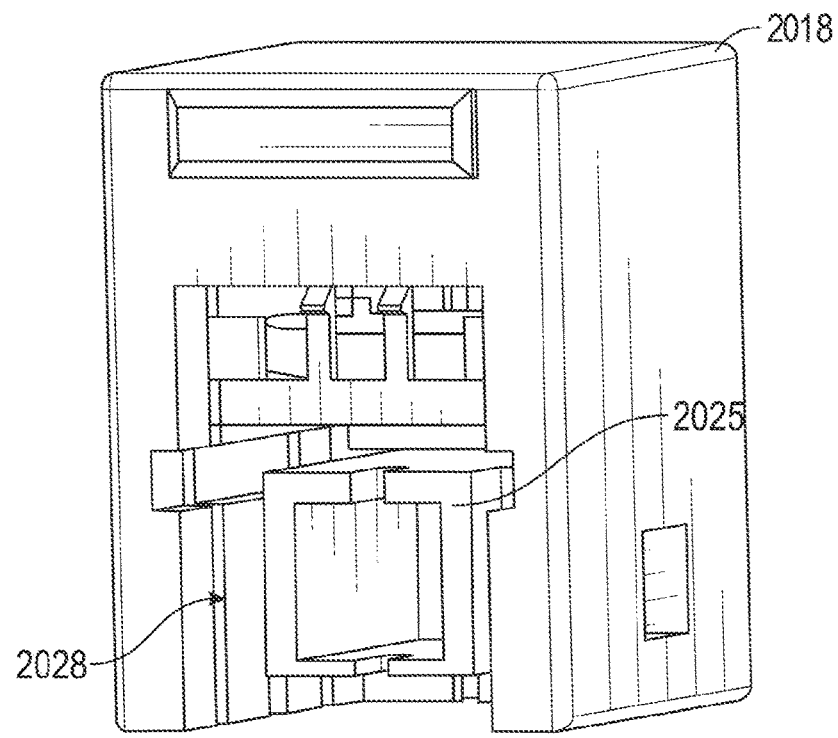

FIG. 170 illustrates a front perspective view of the applicator shown in FIG. 167.

Figure 171:
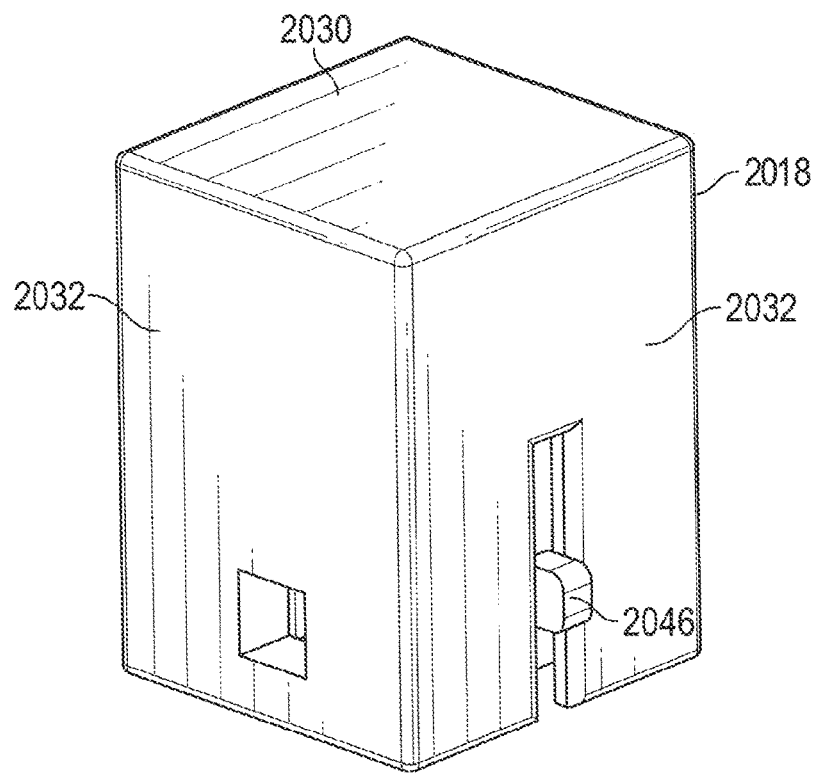

FIG. 171 illustrates a rear perspective view of the applicator shown in FIG. 167.

Figure 172:
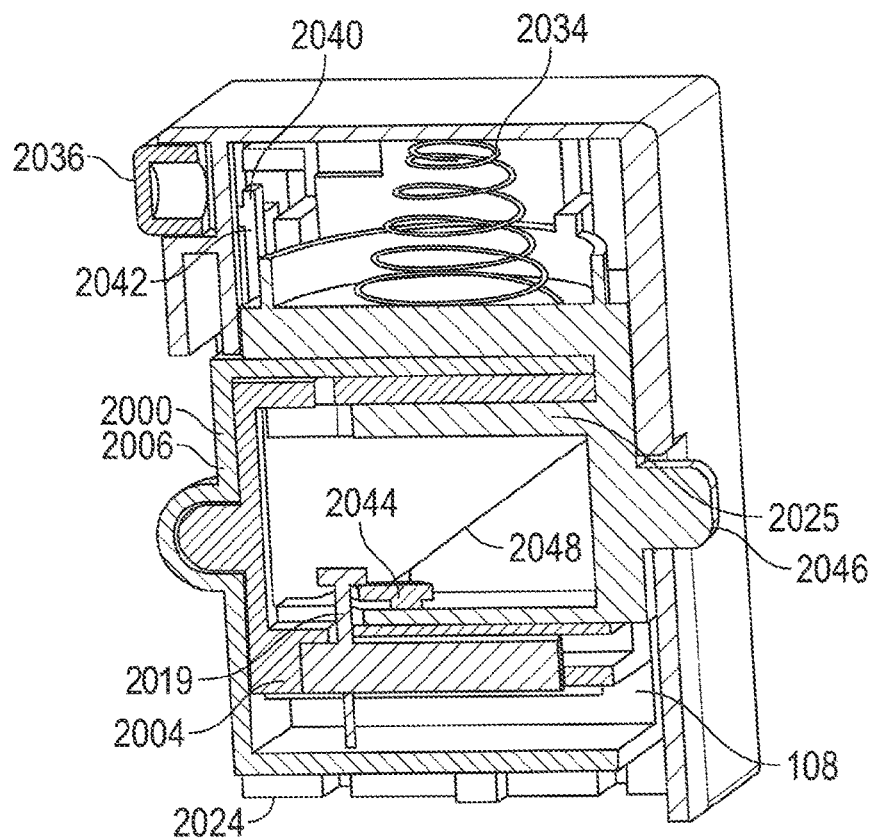

FIG. 172 illustrates a cross sectional view along line XVIII-XVIII of the applicator and the cartridge shown in FIG. 167.

Figure 173:
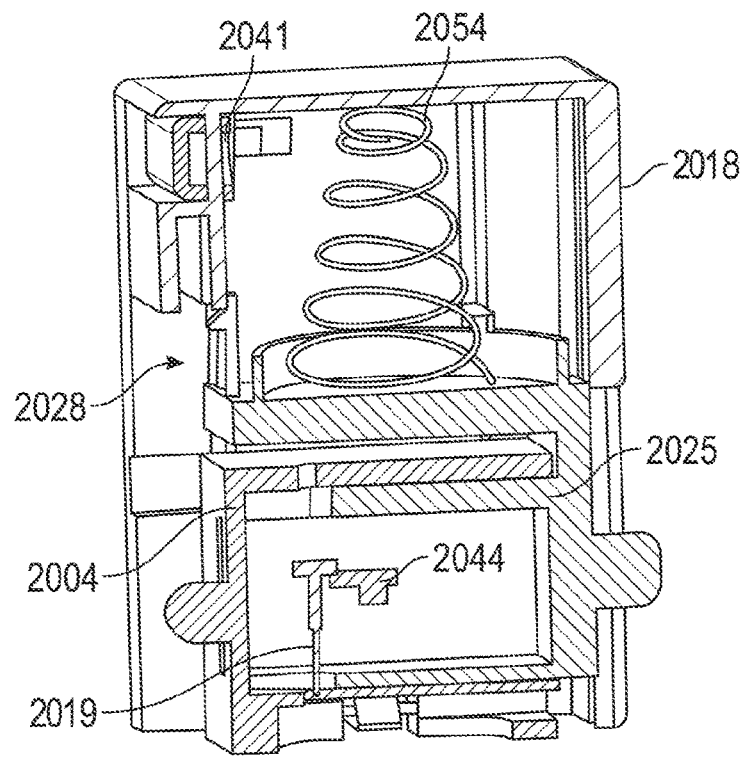

FIG. 173 illustrates a cross sectional view along line XVIII-XVIII of the applicator and the cartridge shown in FIG. 167.

Figure 174:
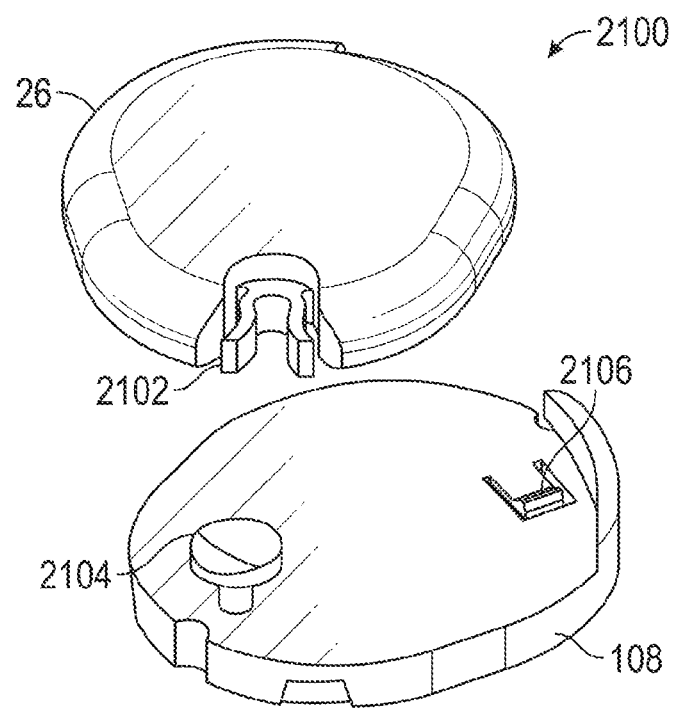

FIG. 174 illustrates an exploded view of an on-skin sensor assembly.

Figure 175:
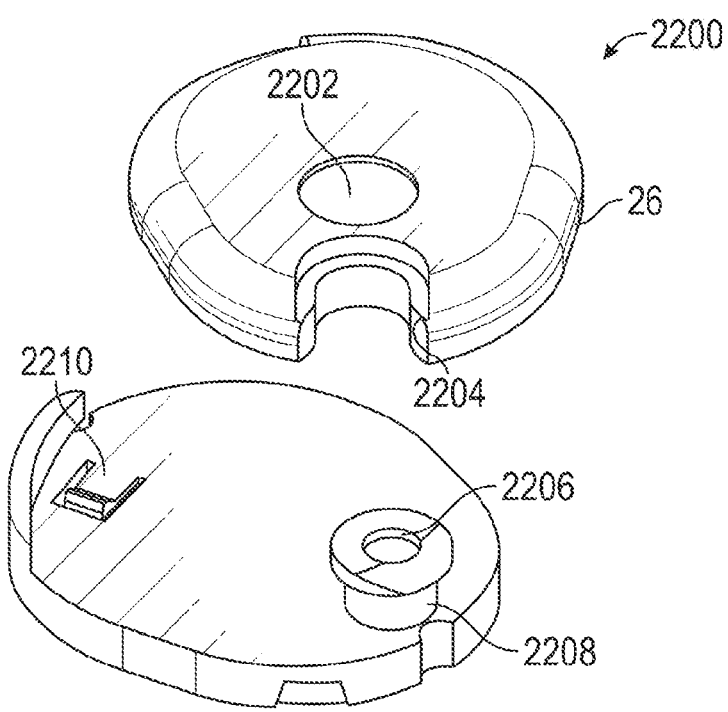

FIG. 175 illustrates an exploded view of an on-skin sensor assembly.

Figure 176:
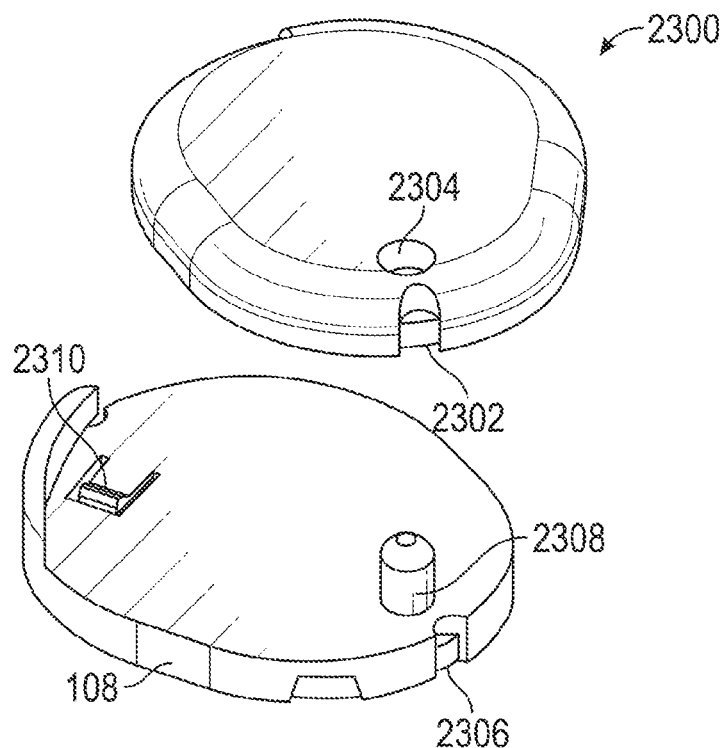

FIG. 176 illustrates an exploded view of an on-skin sensor assembly.

Figure 177:
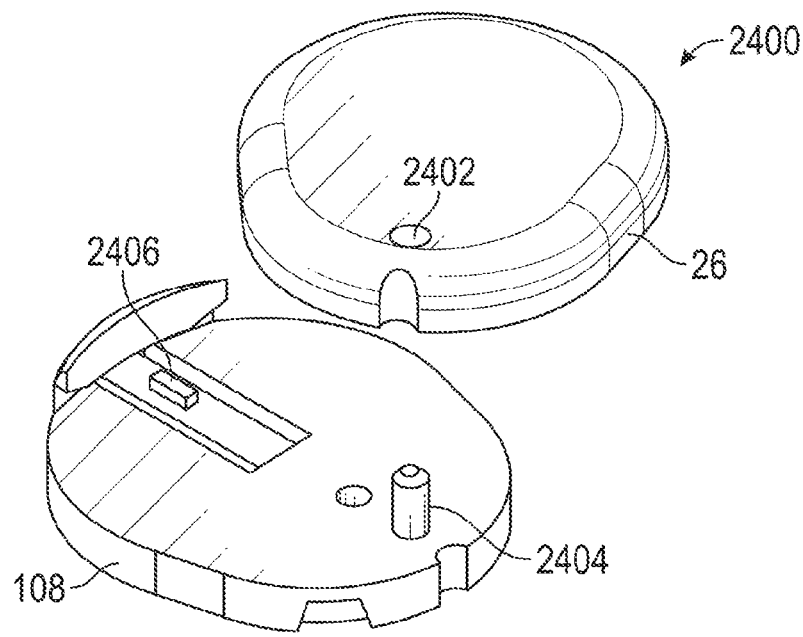

FIG. 177 illustrates an exploded view of an on-skin sensor assembly.

Figure 178:
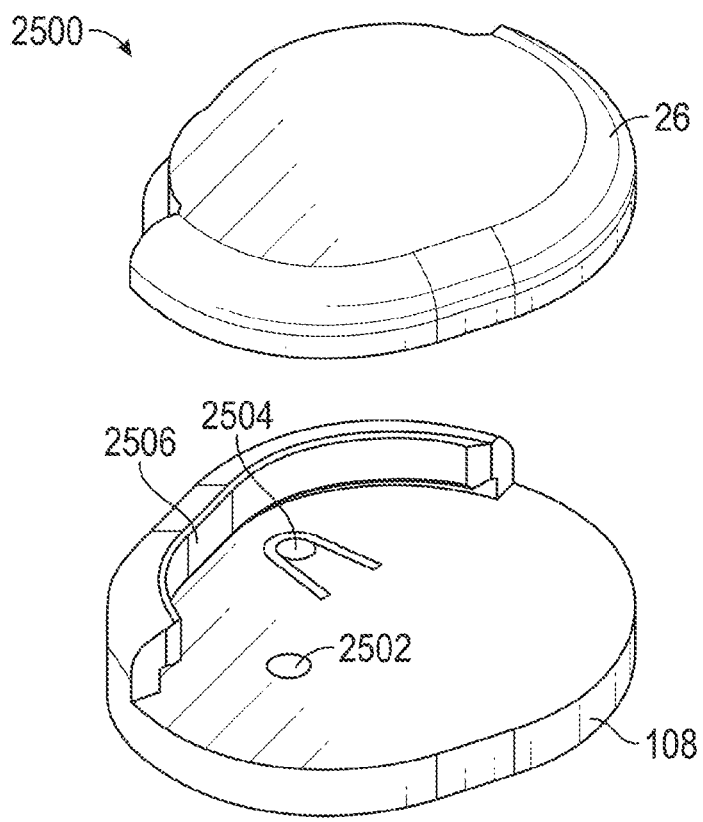

FIG. 178 illustrates an exploded view of an on-skin sensor assembly.

Figure 179:
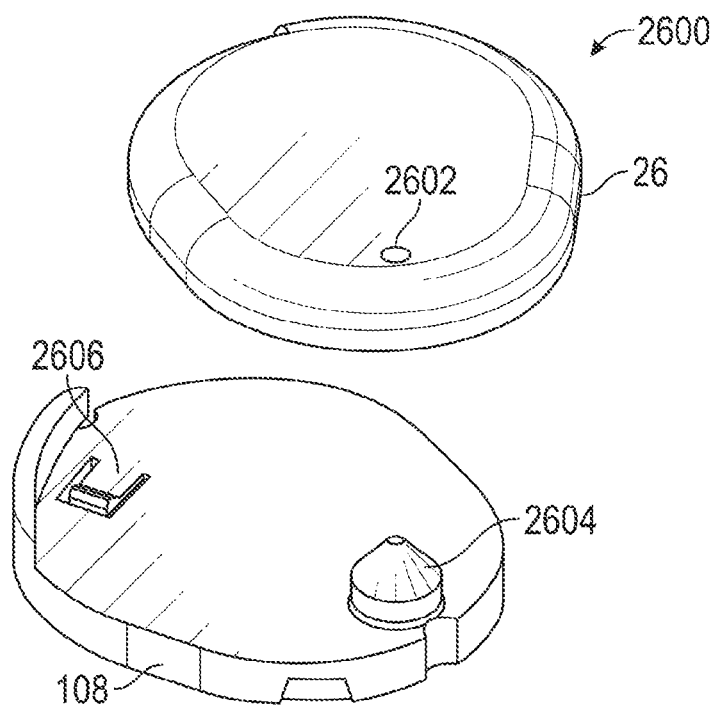

FIG. 179 illustrates an exploded view of an on-skin sensor assembly.

Figure 180:
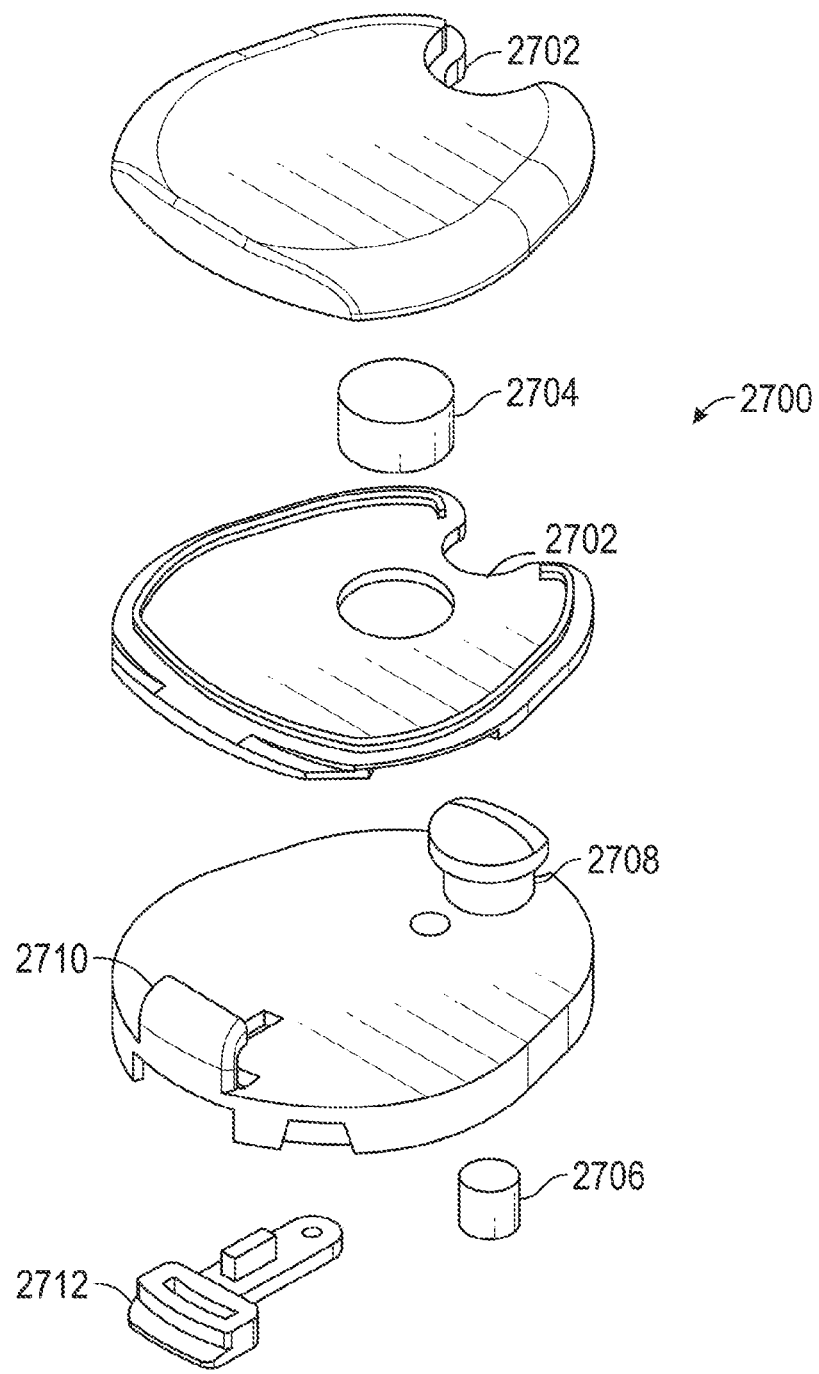

FIG. 180 illustrates an exploded view of an on-skin sensor assembly.

Figure 181:
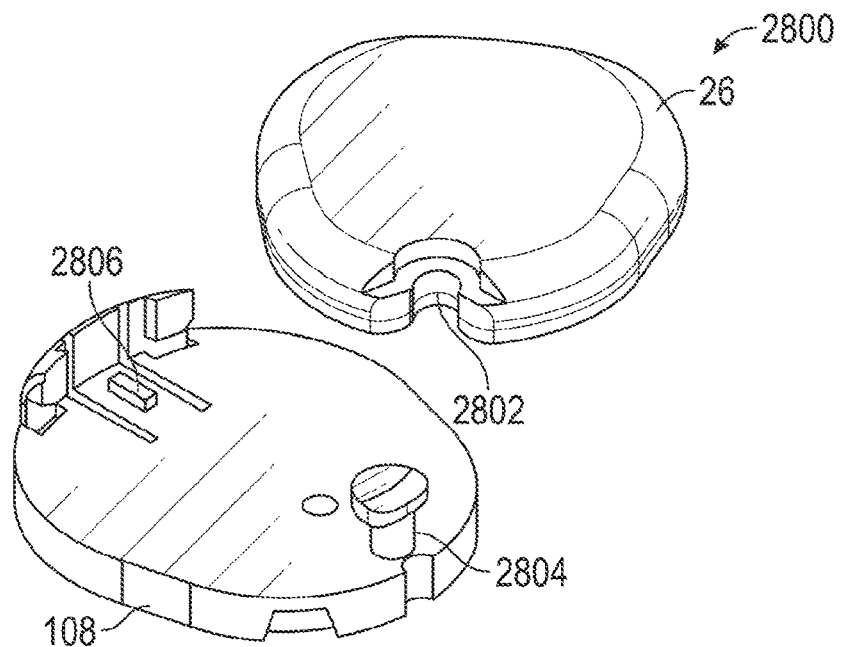

FIG. 181 illustrates an exploded view of an on-skin sensor assembly.

Figure 182:
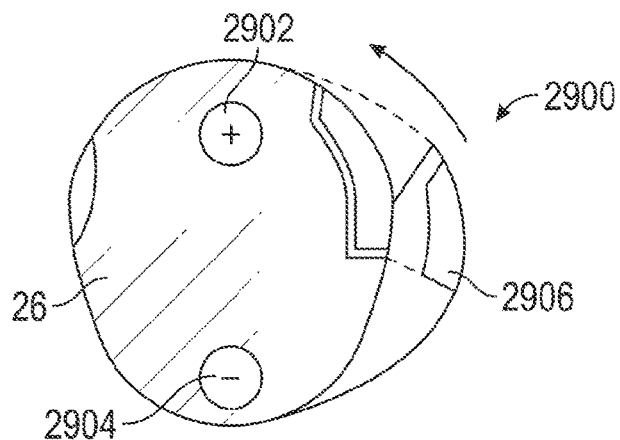

FIG. 182 illustrates a schematic view of an on-skin sensor assembly.

Figure 183:
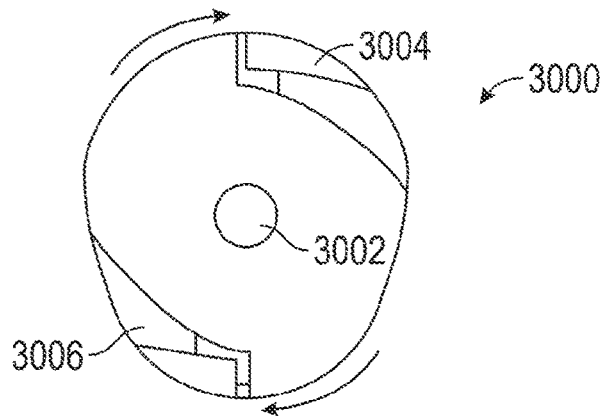

FIG. 183 illustrates a schematic view of an on-skin sensor assembly.

Figure 184:
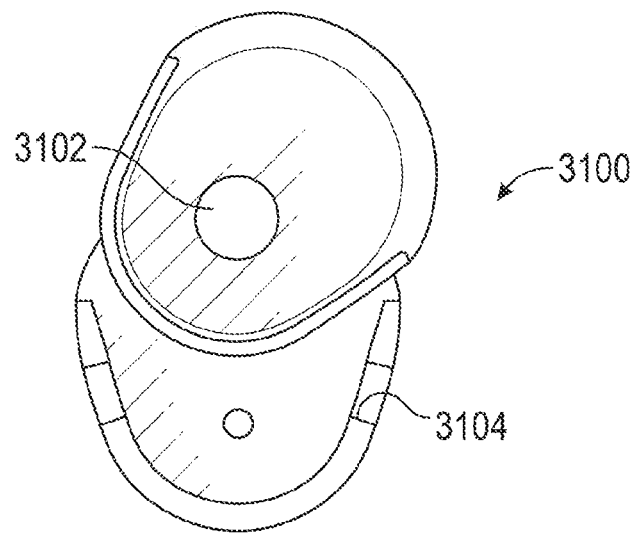

FIG. 184 illustrates a top view of an on-skin sensor assembly.

Figure 185:
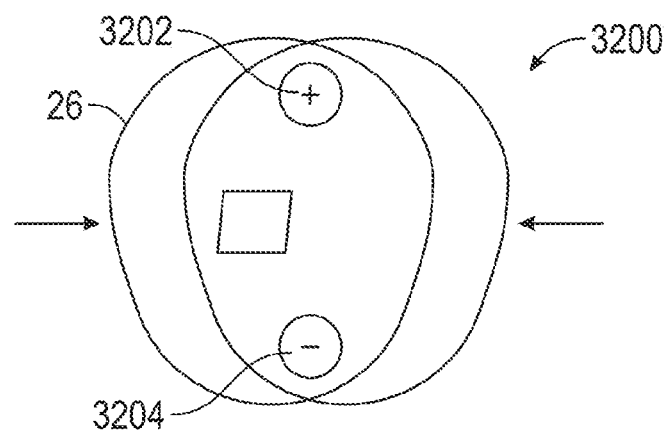

FIG. 185 illustrates a schematic view of an on-skin sensor assembly.

Figures 186, 187:
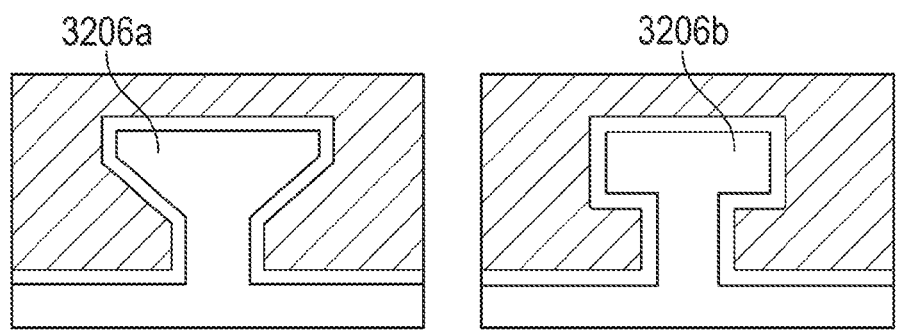

FIG. 186 illustrates a schematic view of a coupler for an on-skin sensor assembly.

FIG. 187 illustrates a schematic view of a coupler for an on-skin sensor assembly.

Figure 188:
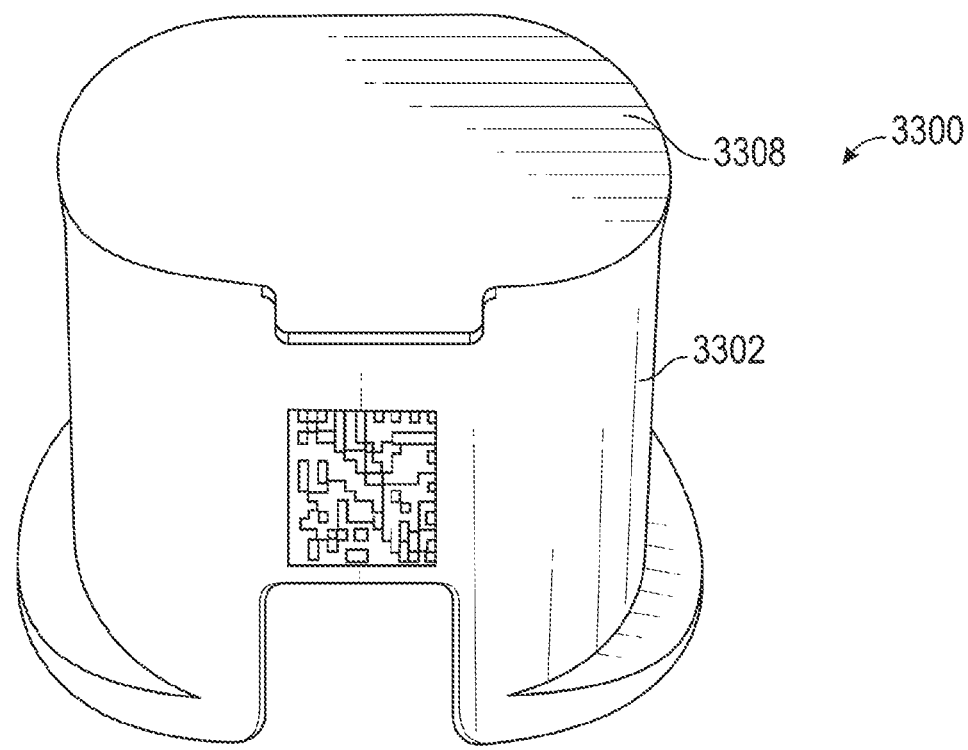

FIG. 188 illustrates a perspective view of a cartridge.

Figure 189:
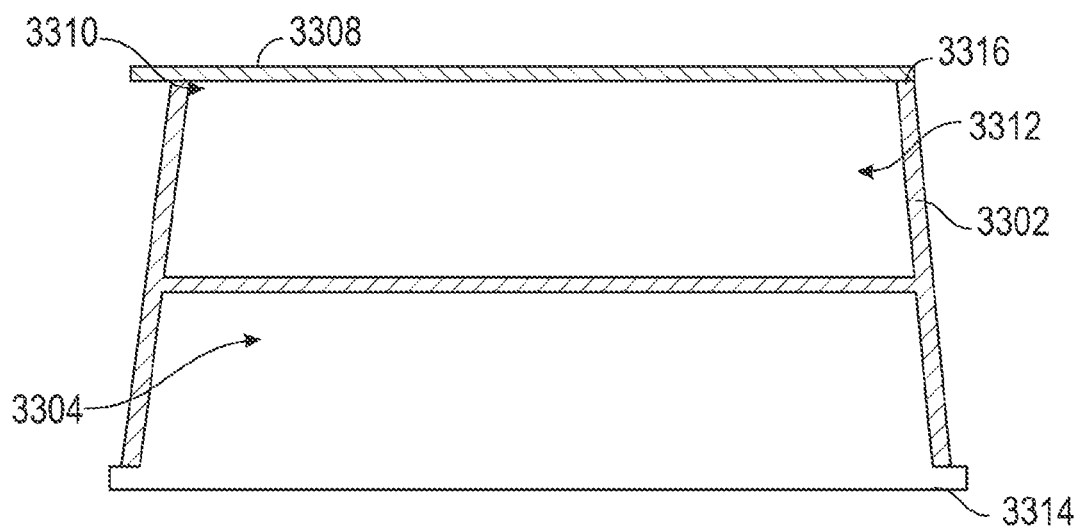

FIG. 189 illustrates a cross sectional schematic of the cartridge shown in FIG. 188.

Figure 190:
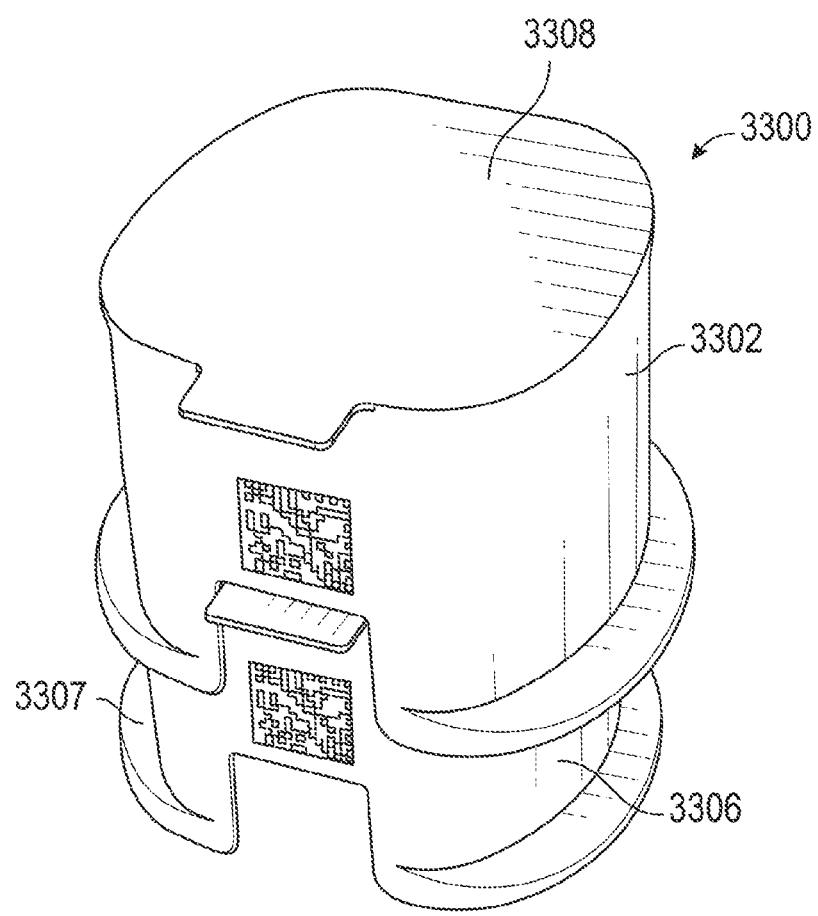

FIG. 190 illustrates a perspective view of cartridges stacked upon each other.

Figure 191:
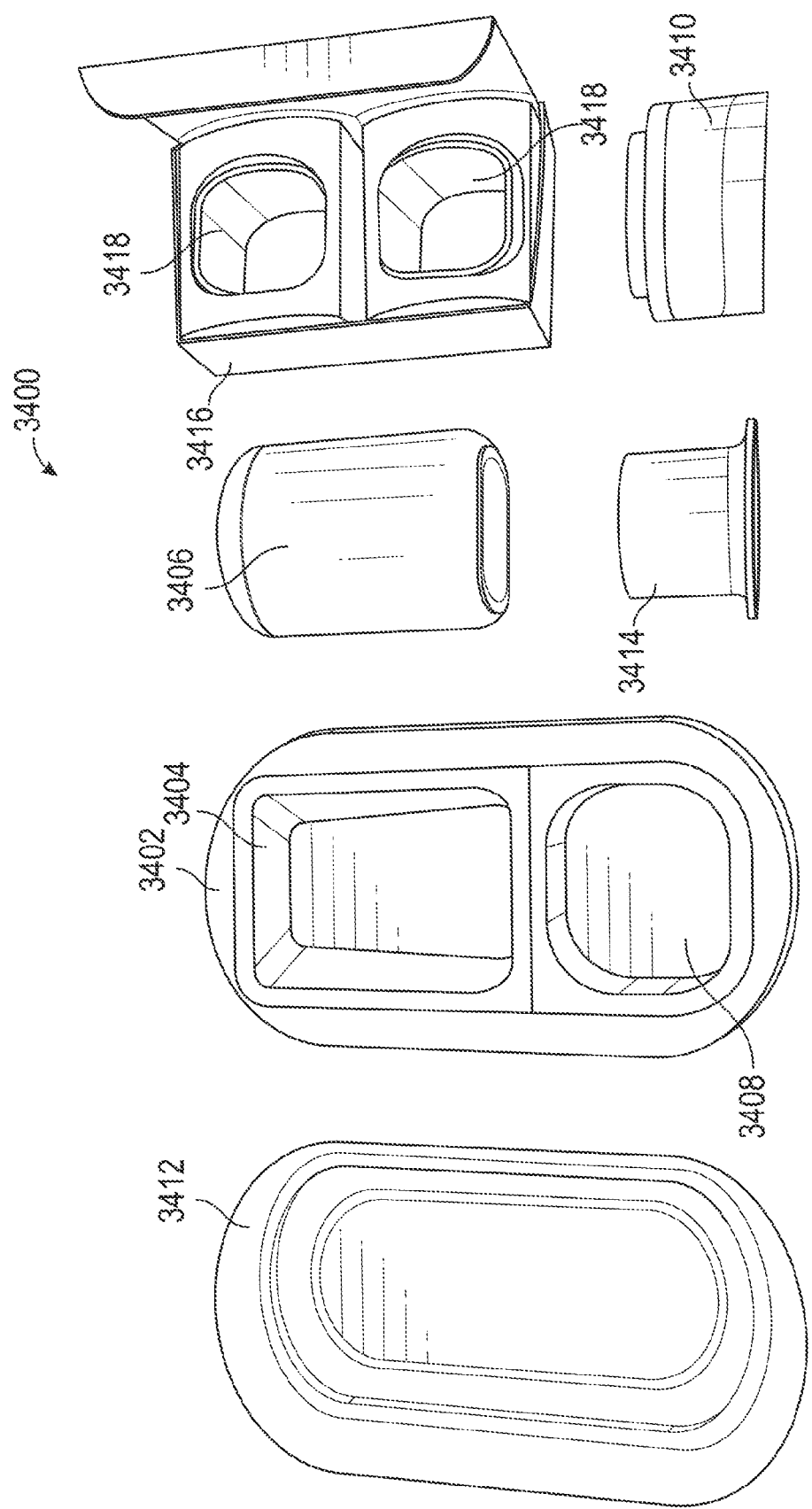

FIG. 191 illustrates a container system.

Figure 192:
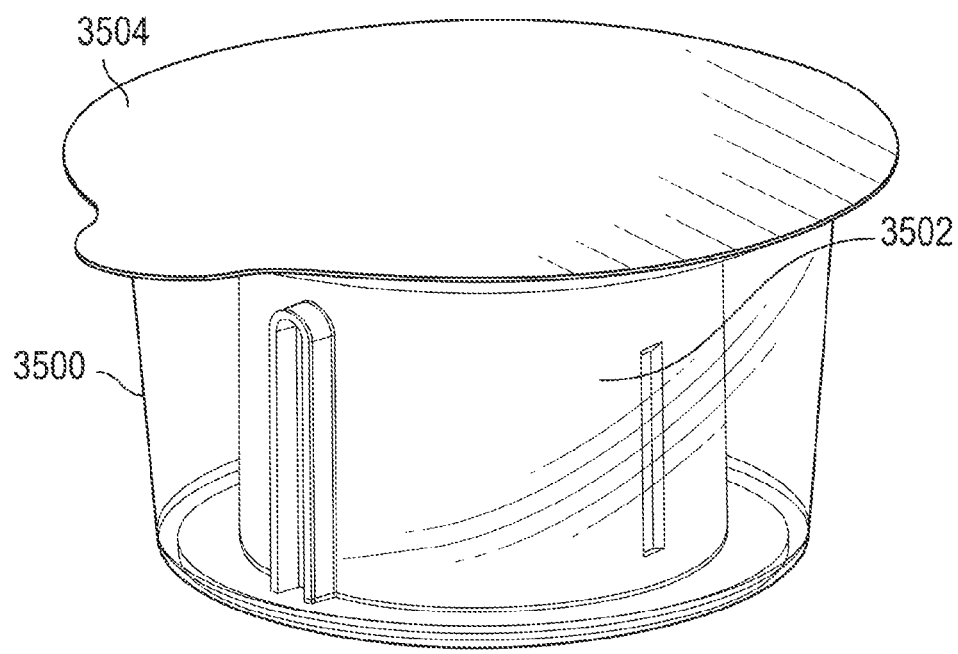

FIG. 192 illustrates a perspective view of a cartridge within a container having a seal.

Figure 193:
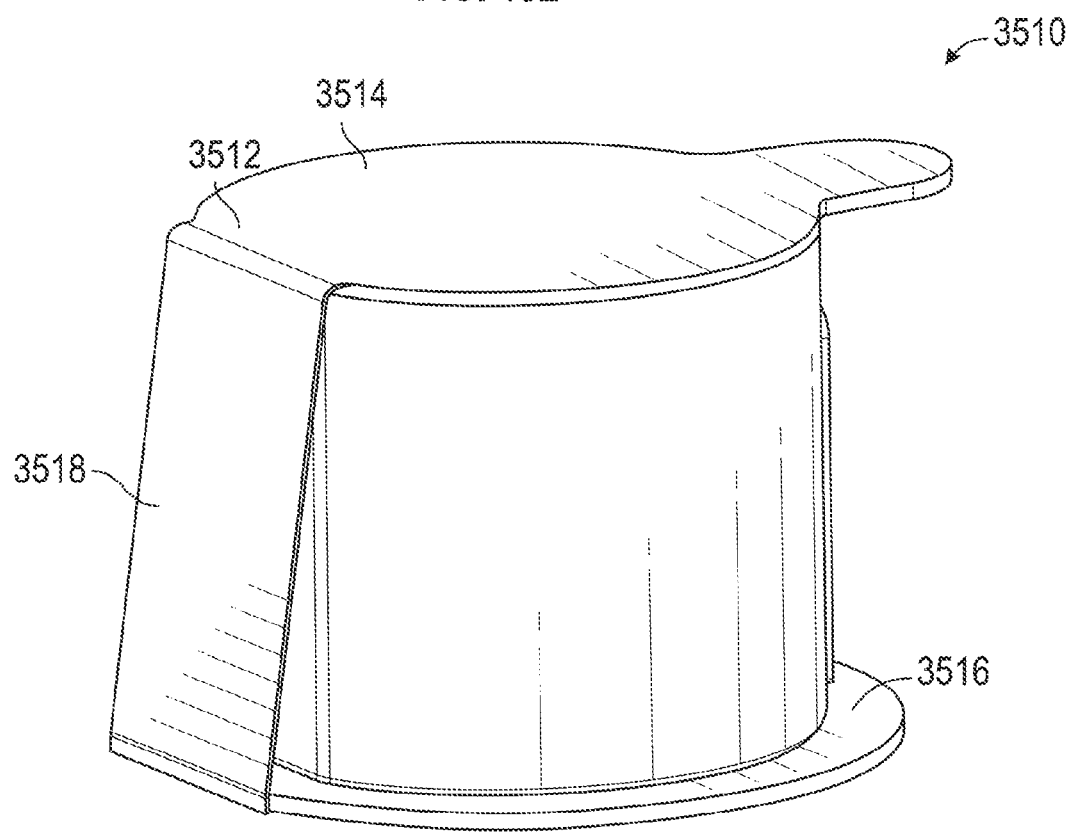

FIG. 193 illustrates a perspective view of a cartridge having a seal.

Figure 194:
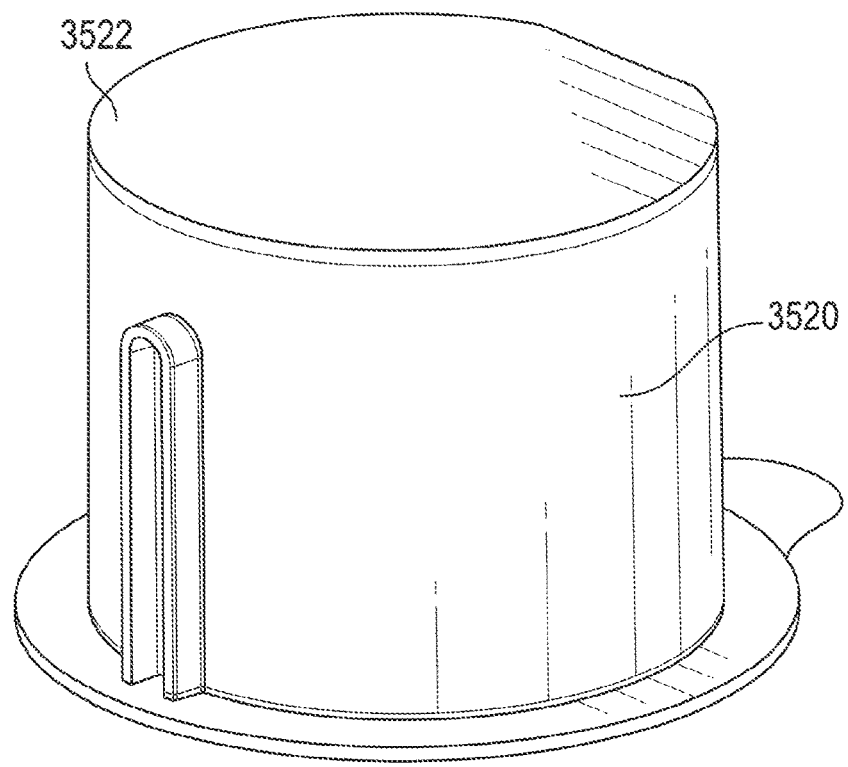

FIG. 194 illustrates a perspective view of a cartridge having a seal.

Figure 195:
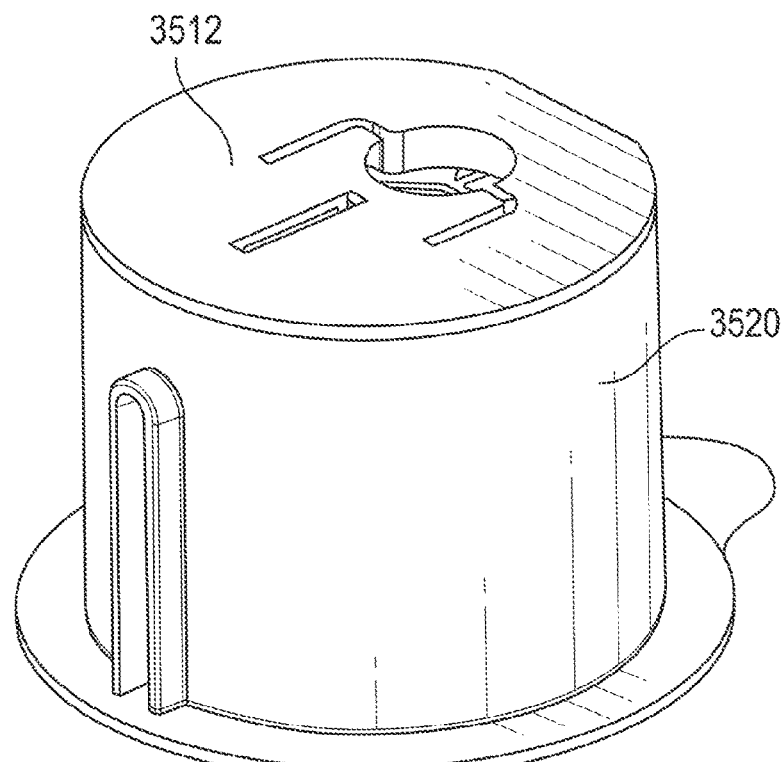

FIG. 195 illustrates a perspective view of the cartridge of FIG. 194 having the seal broken.

Figure 196:
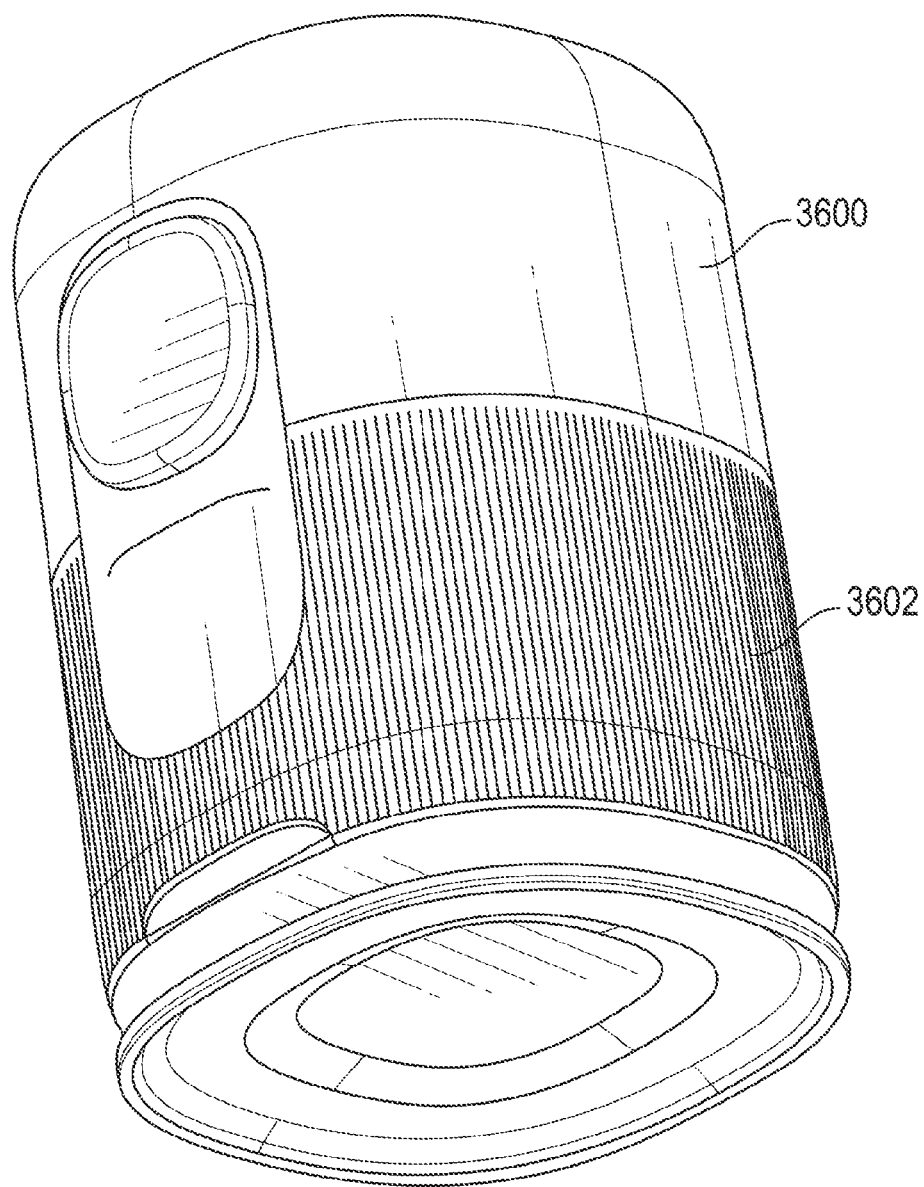

FIG. 196 illustrates a perspective view of an applicator having a bottom cover.

Figure 197:
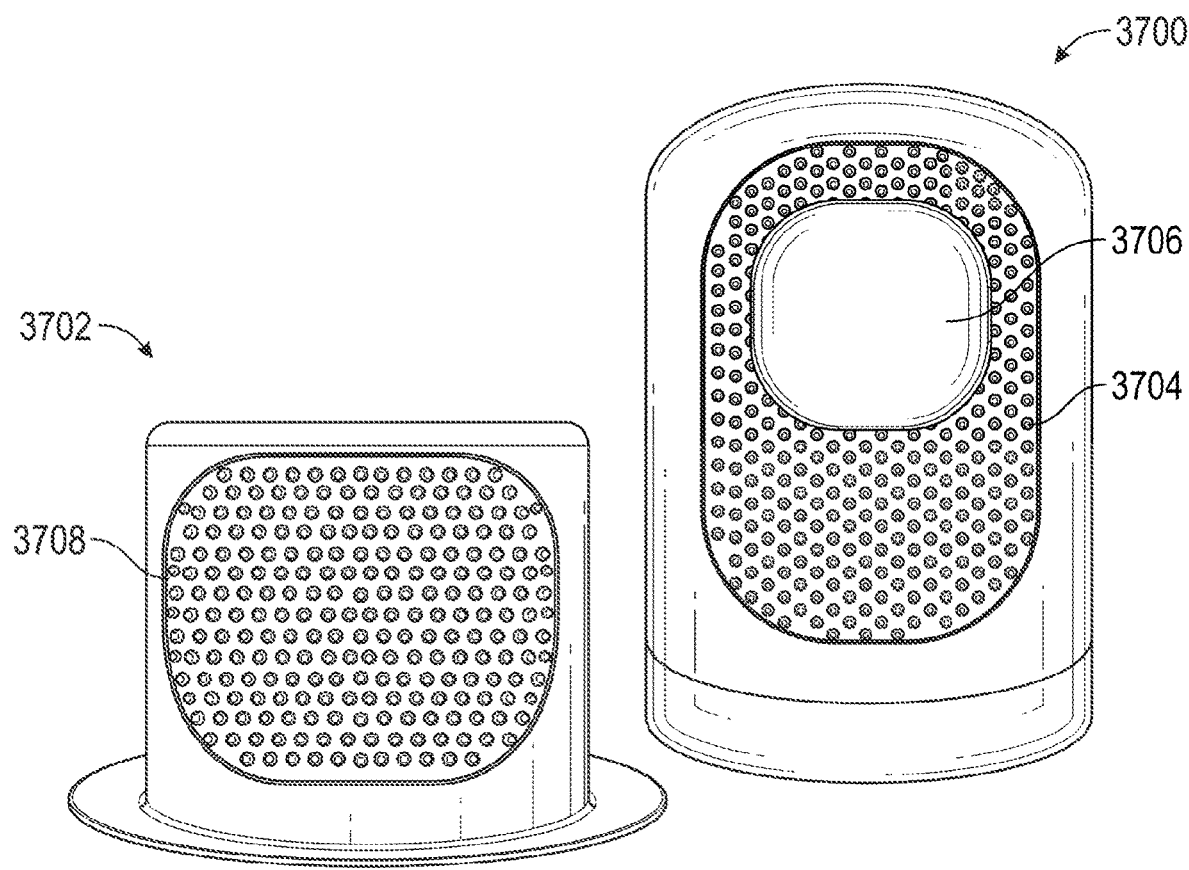

FIG. 197 illustrates a side view of an applicator and a cartridge.

Figure 198:
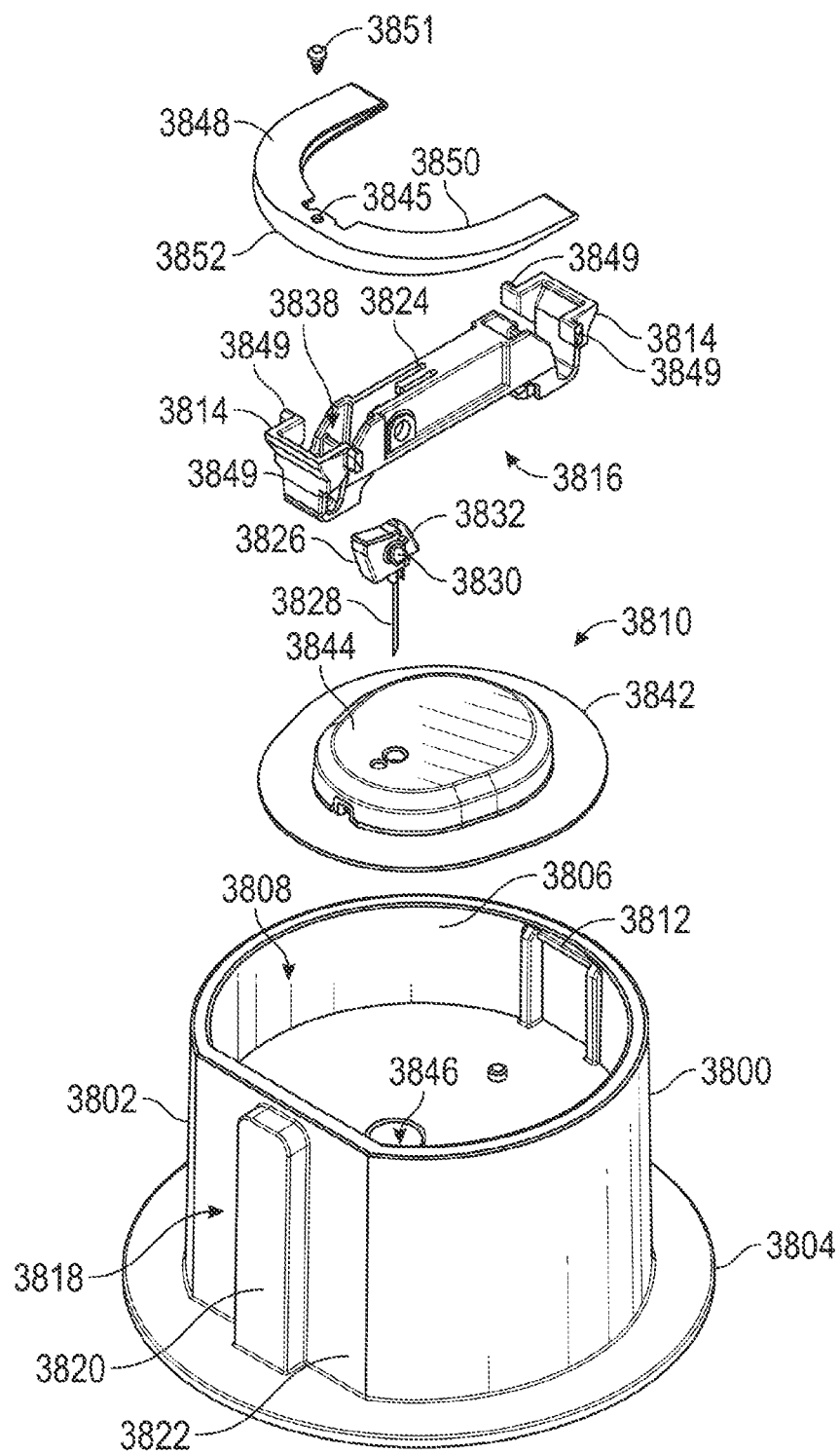

FIG. 198 illustrates an exploded view of components of a cartridge.

Figure 199:
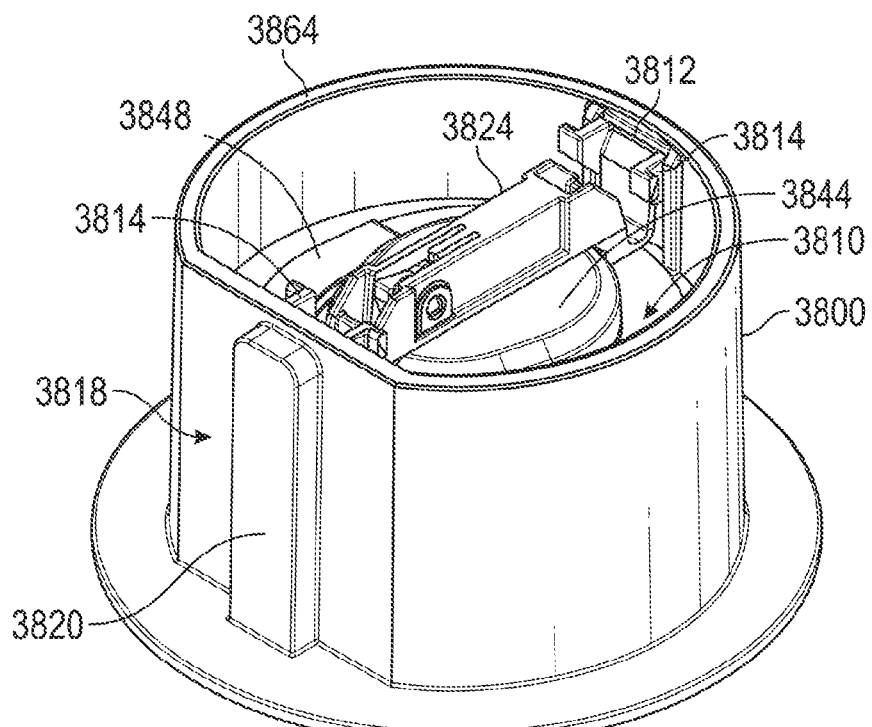

FIG. 199 illustrates a perspective view of the cartridge shown in FIG. 198.

Figure 200:
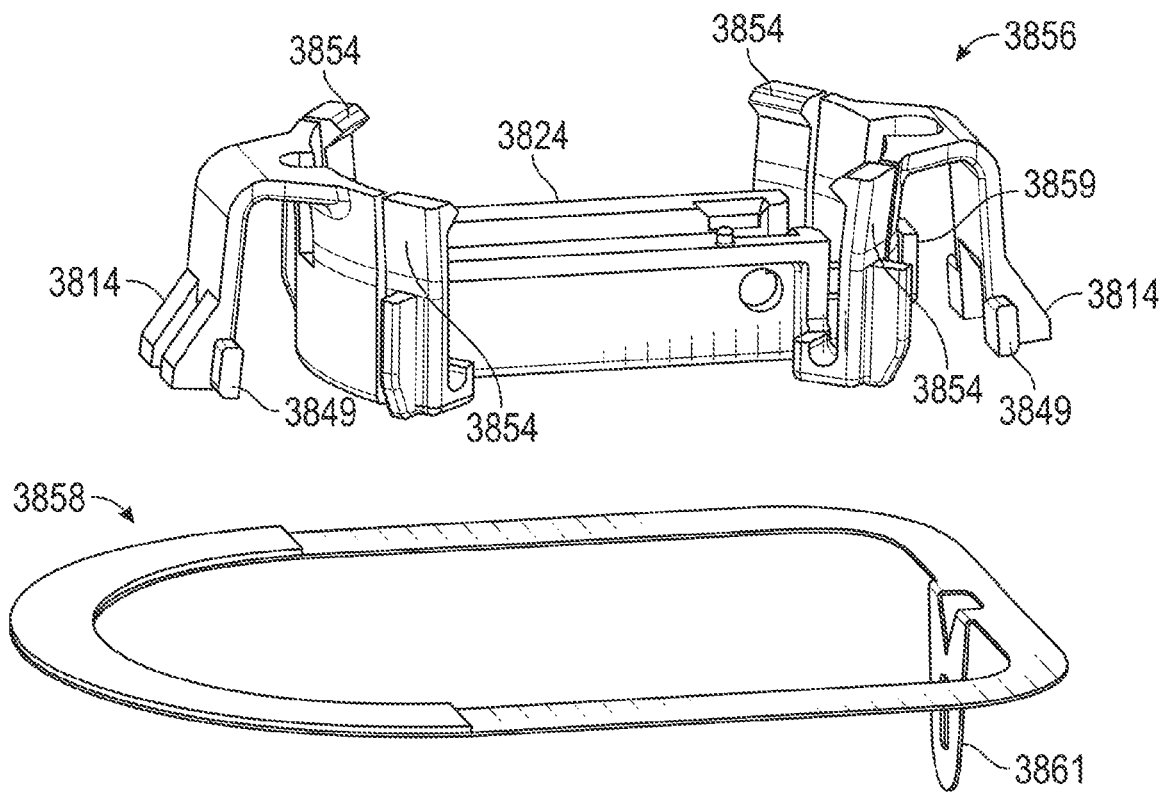

FIG. 200 illustrates a perspective view of components of a cartridge.

Figure 201:
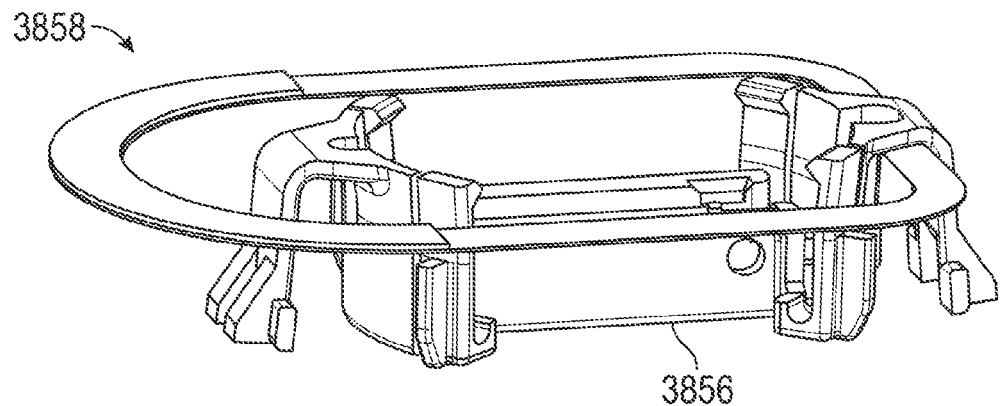

FIG. 201 illustrates a perspective view of components of a cartridge.

Figure 202:
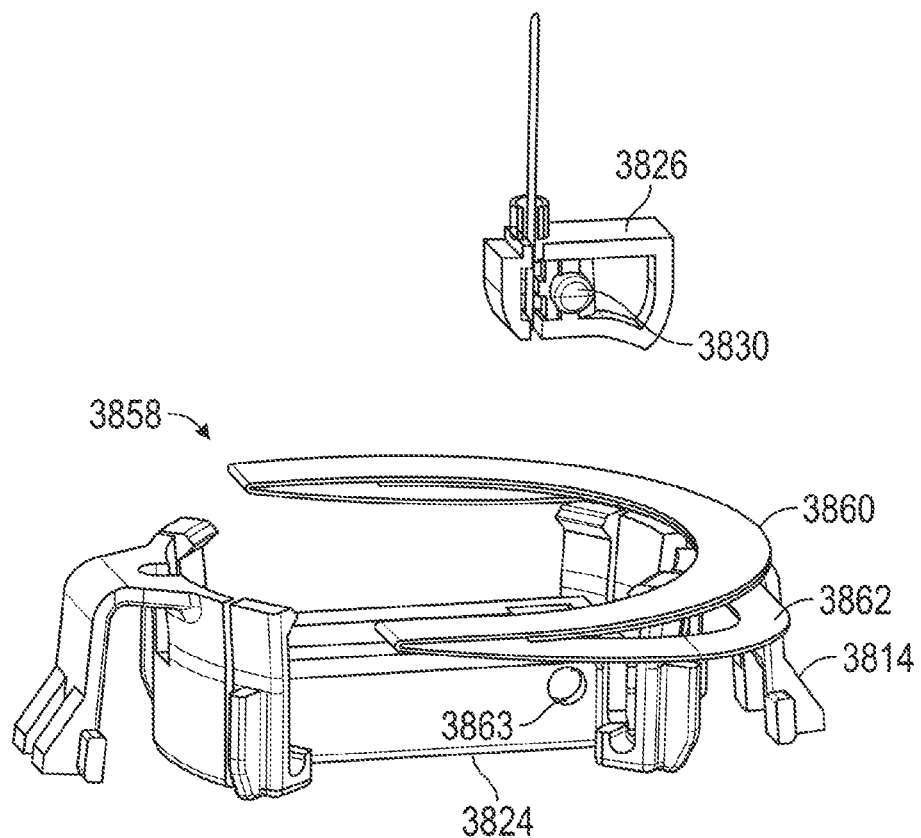

FIG. 202 illustrates a perspective view of components of a cartridge.

Figure 203:
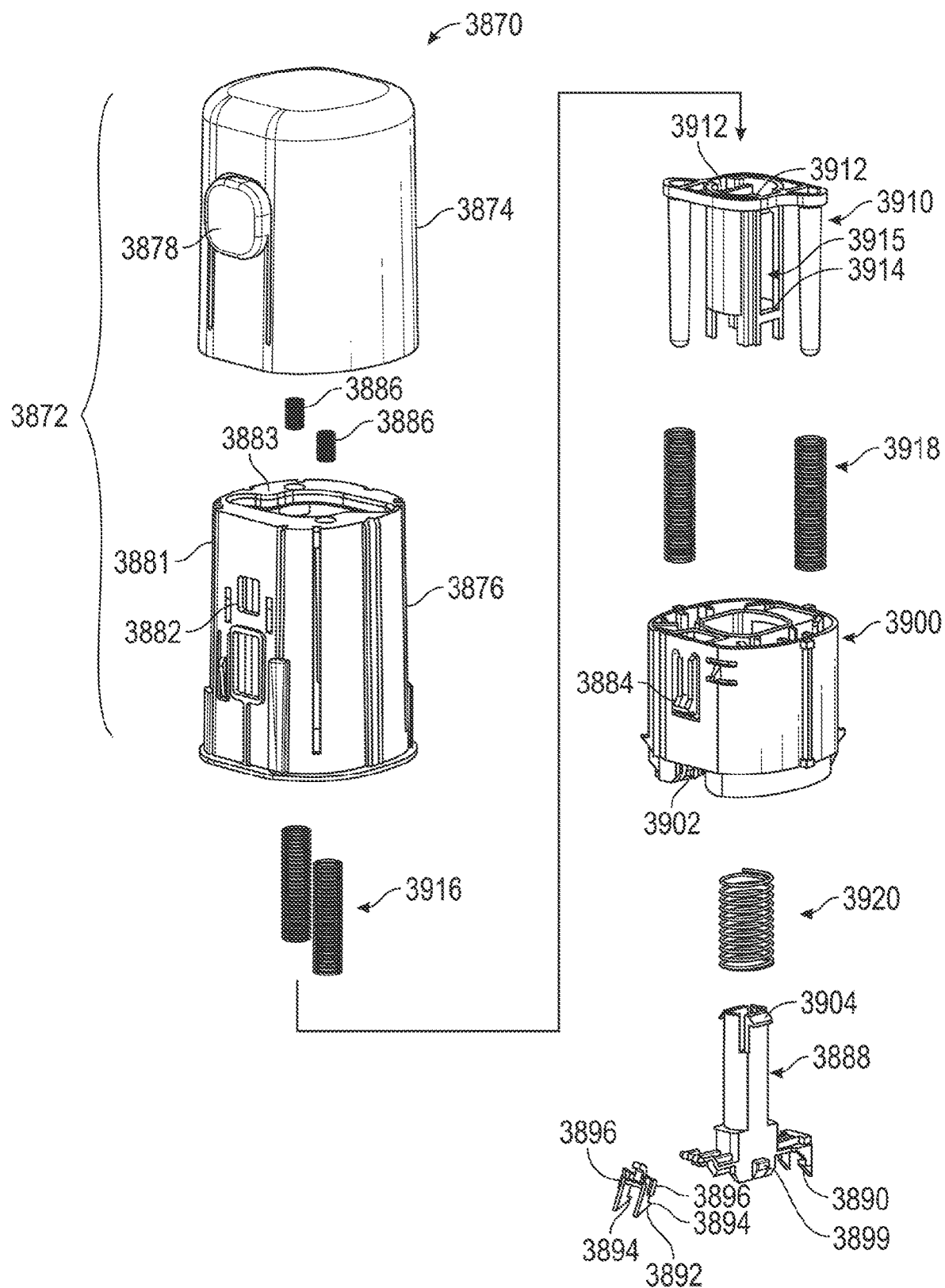

FIG. 203 illustrates an exploded perspective view of an applicator.

Figure 204:
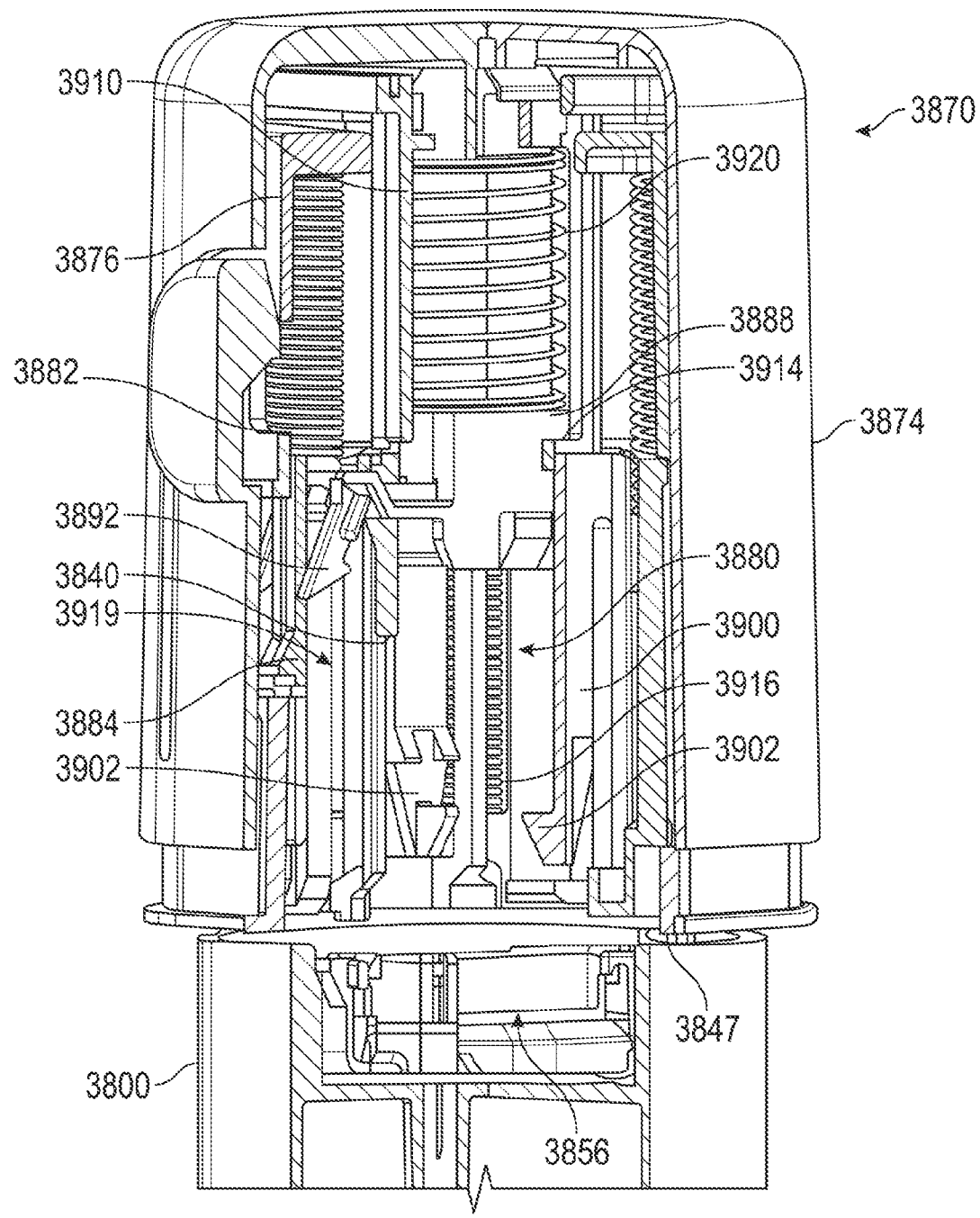

FIG. 204 illustrates a three quarters cross section perspective view of the applicator shown in FIG. 203 and a cartridge.

Figure 205:
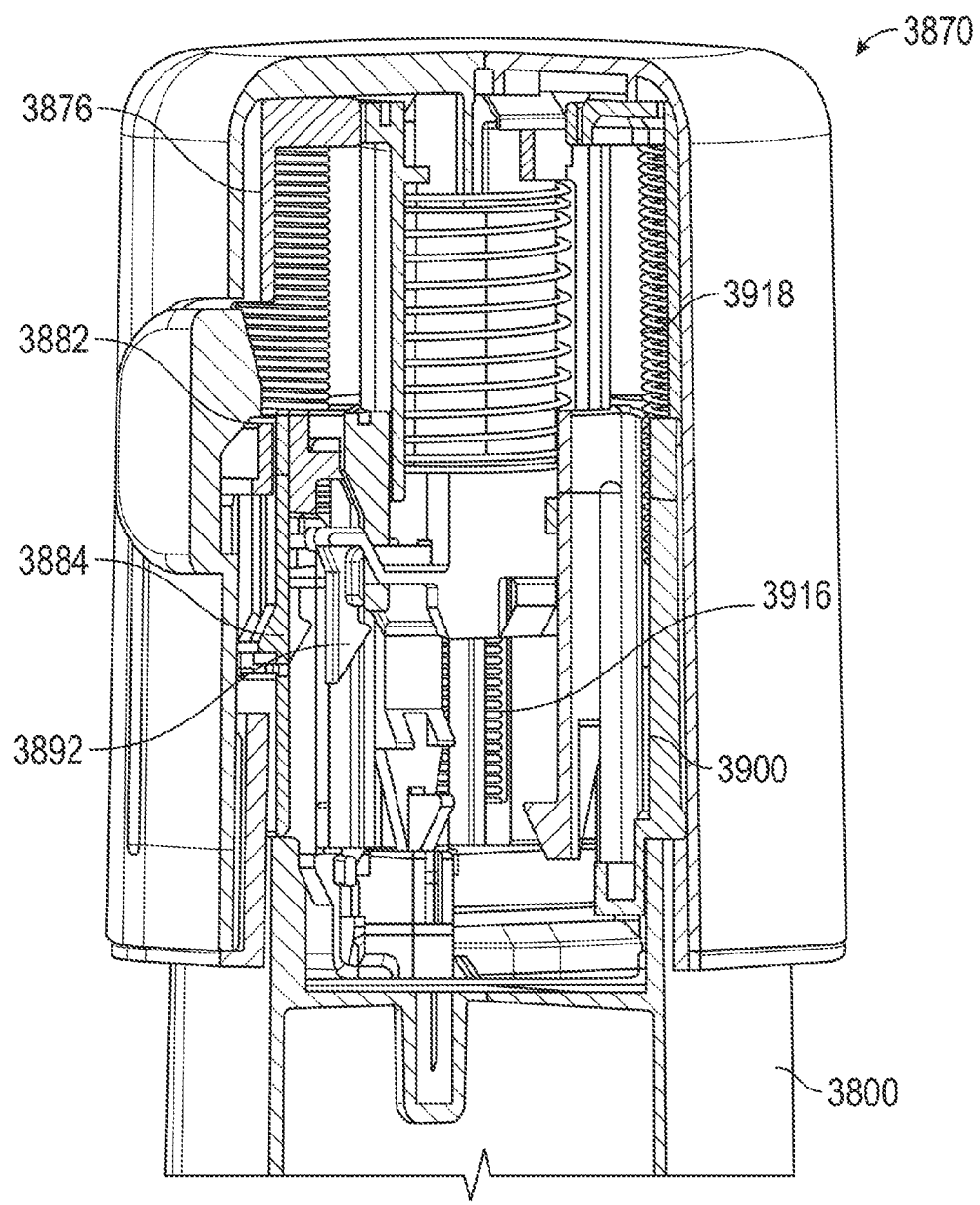

FIG. 205 illustrates a three quarters cross section perspective view of the applicator shown in FIG. 203 and a cartridge.

Figure 206:
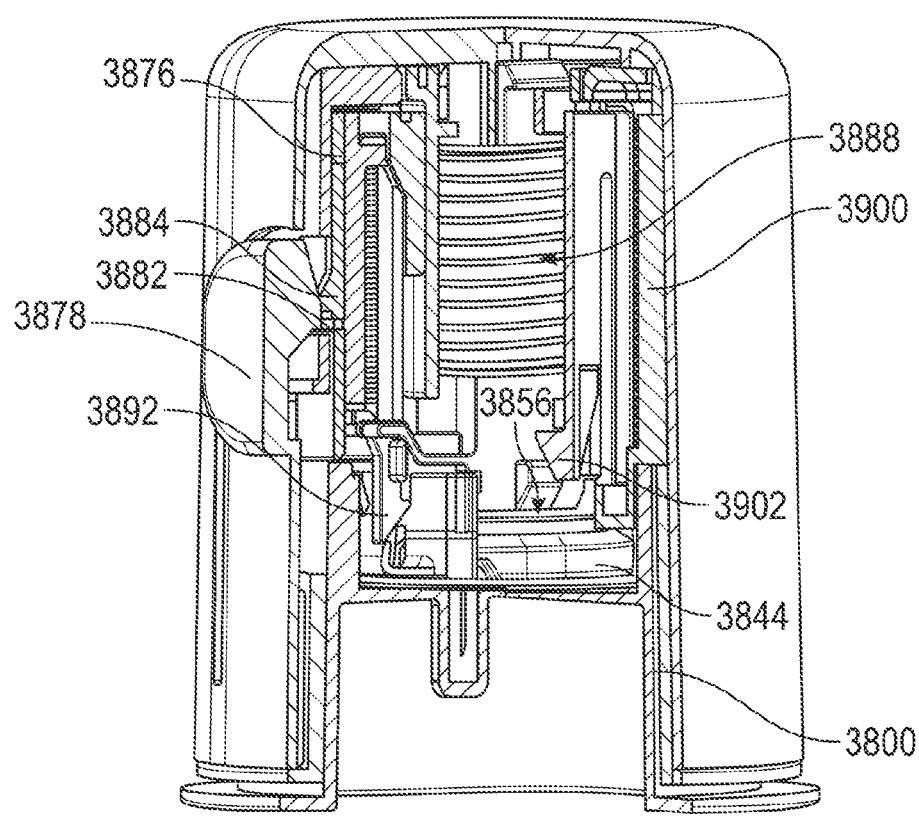

FIG. 206 illustrates a three quarters cross section perspective view of the applicator shown in FIG. 203 and a cartridge.

Figure 207:
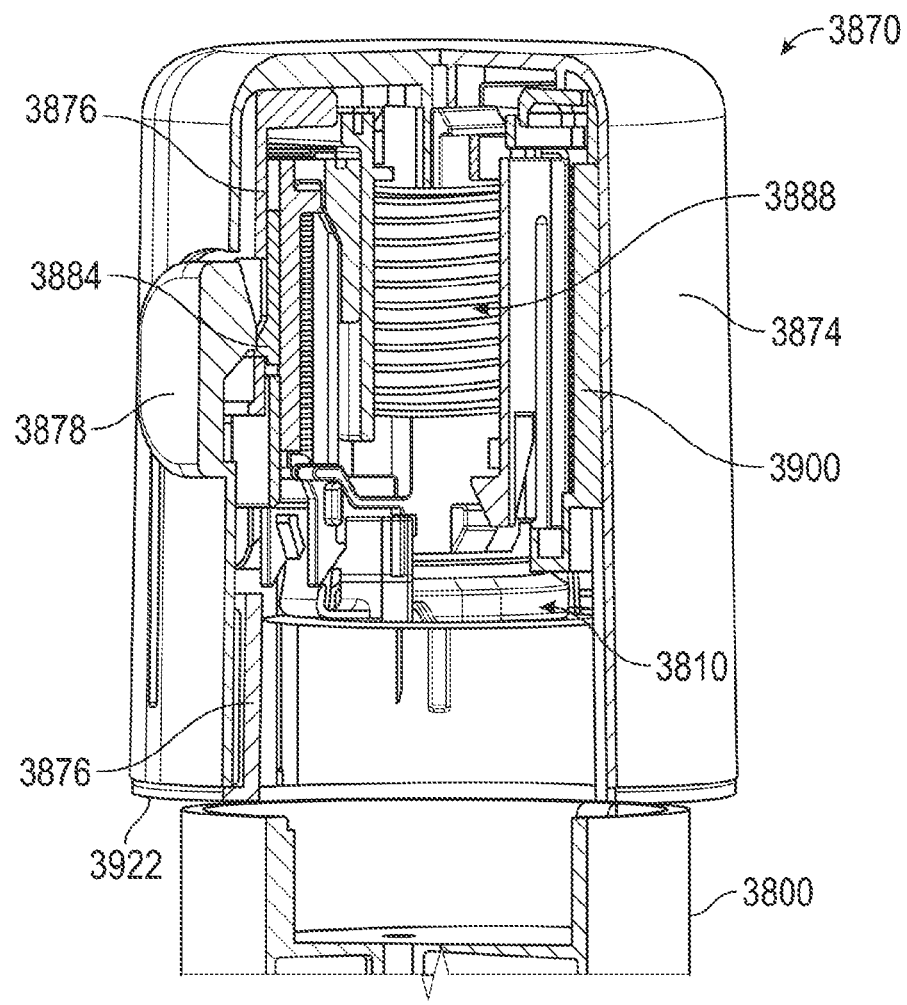

FIG. 207 illustrates a three quarters cross section perspective view of the applicator shown in FIG. 203 and a cartridge.

Figure 208:
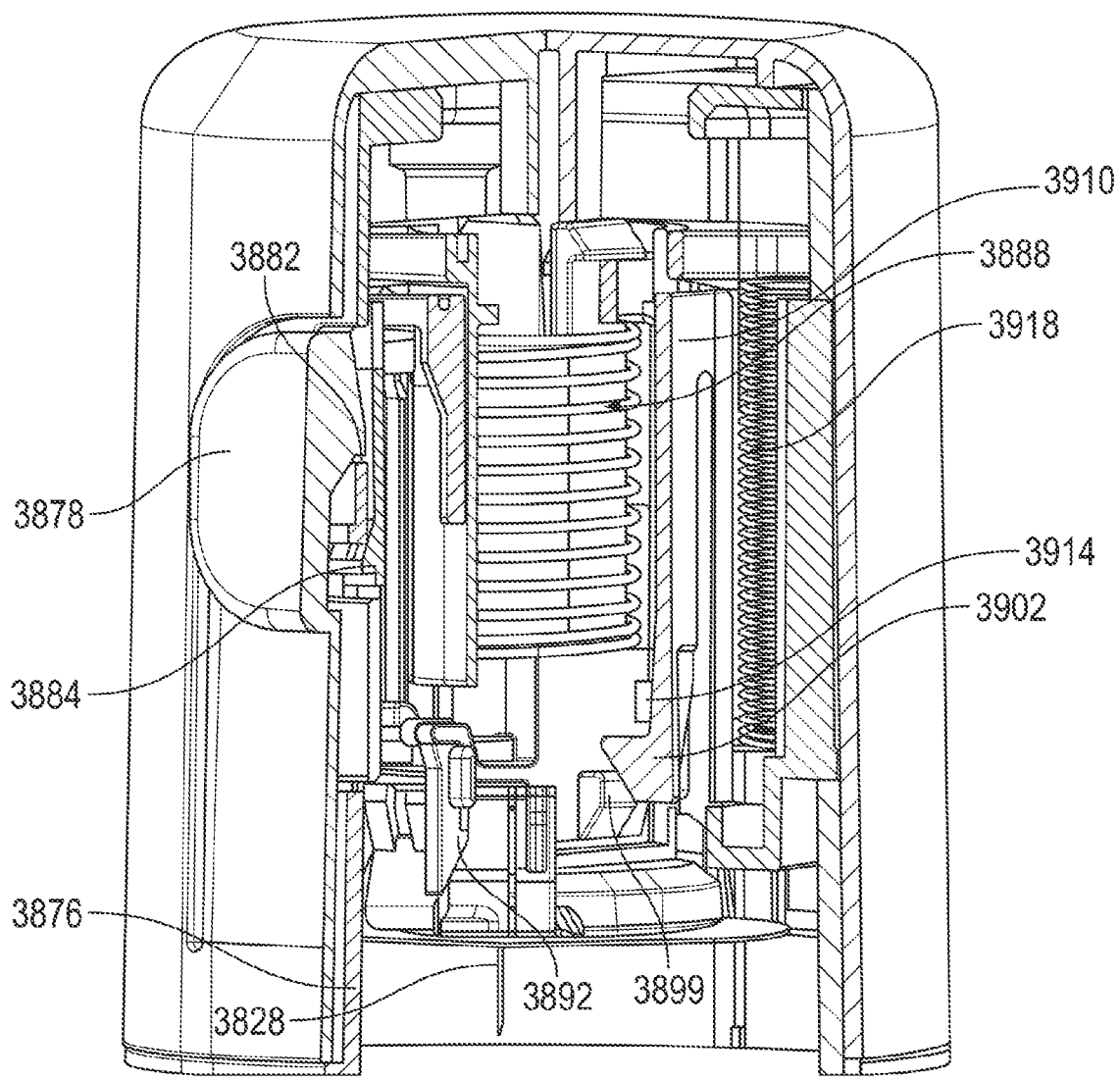

FIG. 208 illustrates a three quarters cross section perspective view of the applicator shown in FIG. 203.

Figure 209:
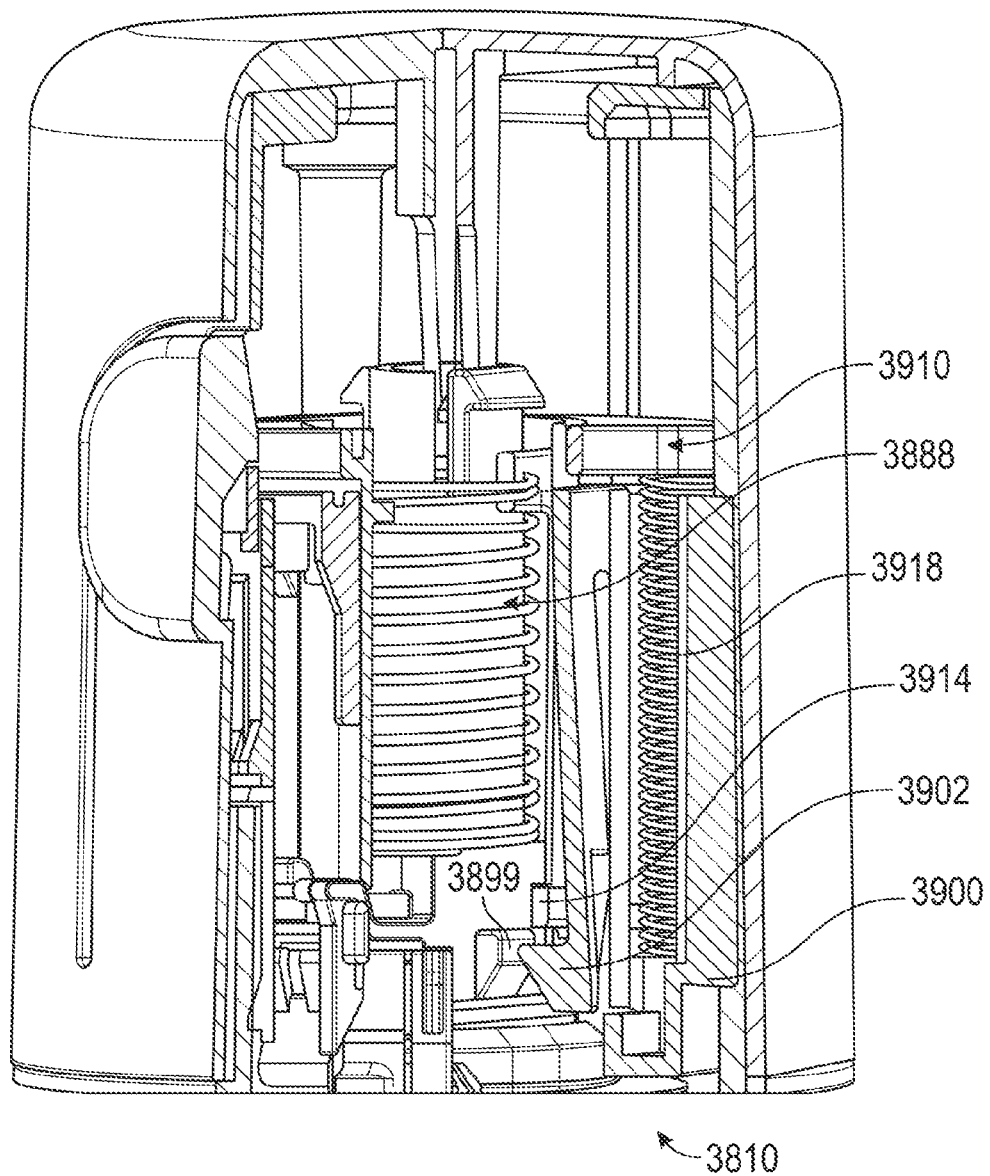

FIG. 209 illustrates a three quarters cross section perspective view of the applicator shown in FIG. 203.

Figure 210:
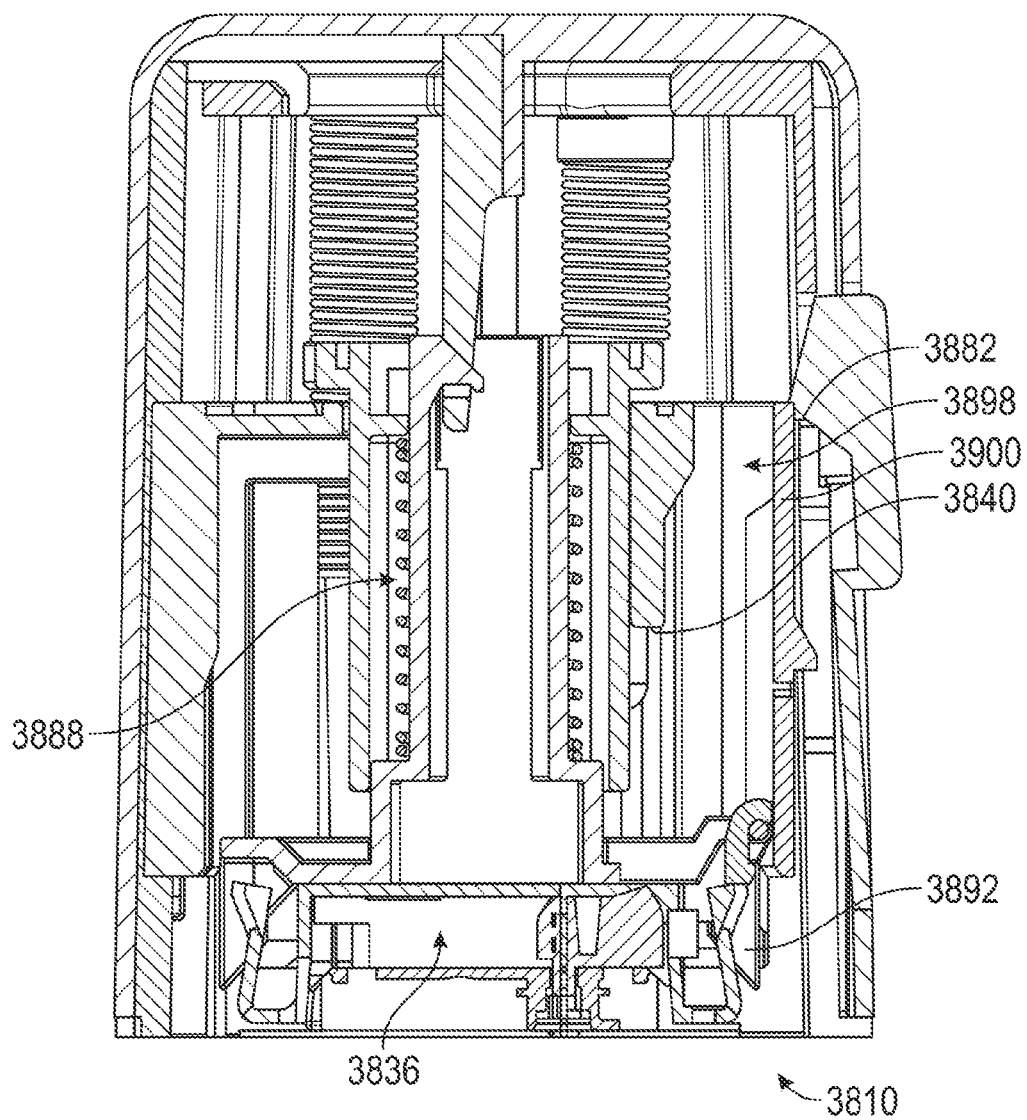

FIG. 210 illustrates a cross sectional view of the applicator shown in FIG. 203 along a mid line.

Figure 211:
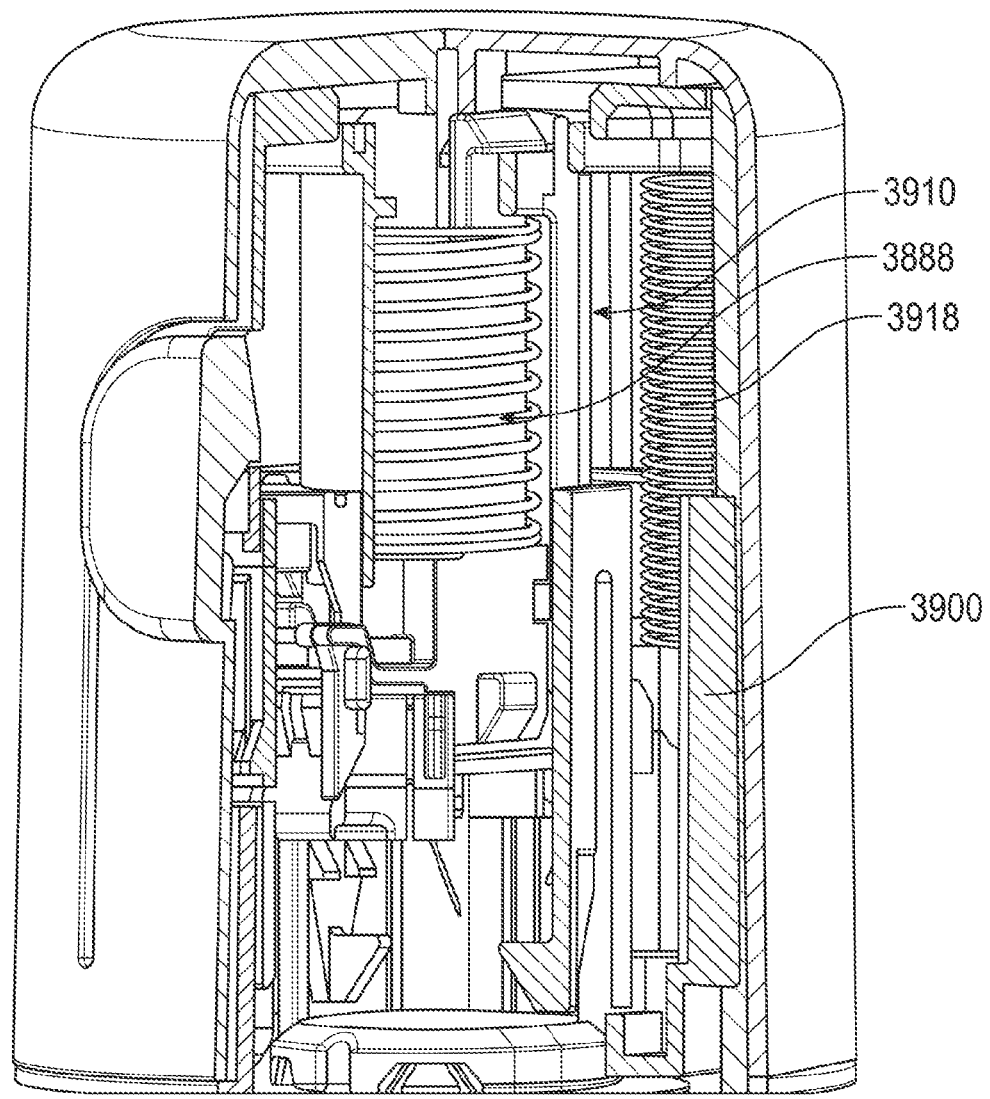

FIG. 211 illustrates a three quarters cross section perspective view of the applicator shown in FIG. 203.

Figure 212:
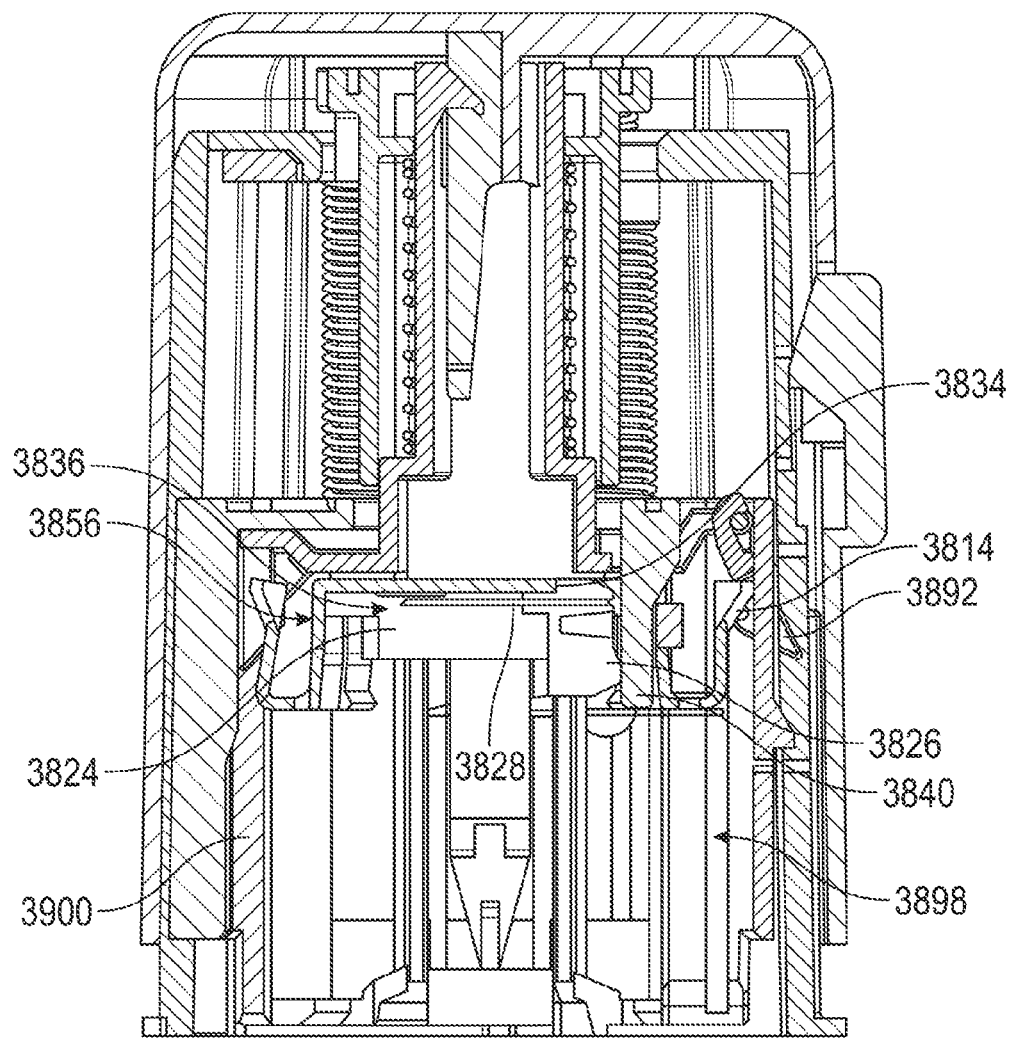

FIG. 212 illustrates a cross sectional view of the applicator shown in FIG. 203 along a mid line.

Figure 213:
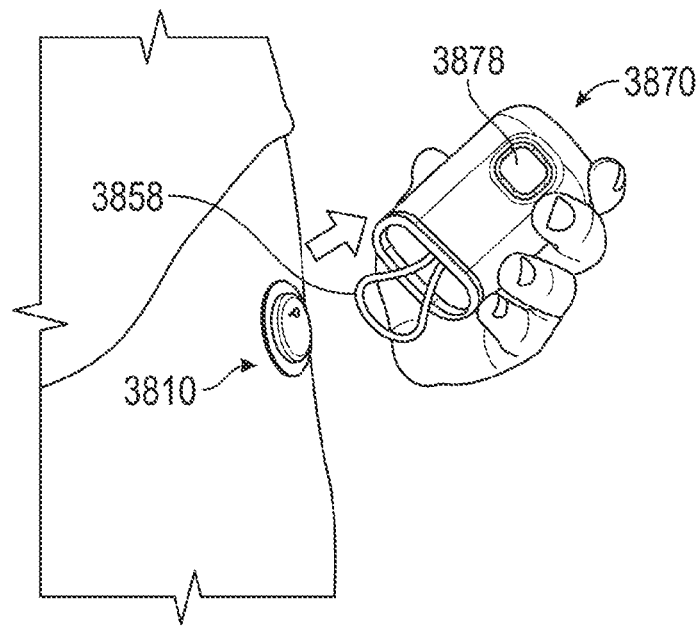

FIG. 213 illustrates a perspective view of an applicator housing being withdrawn from a deployment site.

Figure 214:
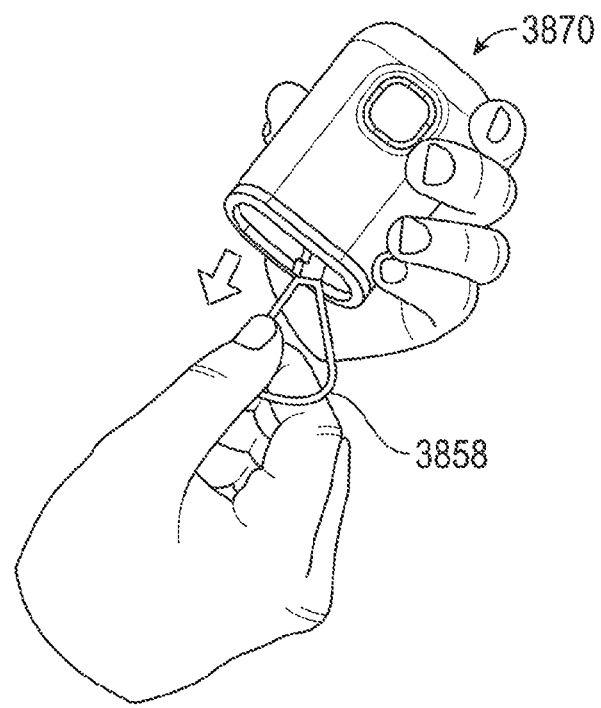

FIG. 214 illustrates a perspective view of a pull tab being pulled from an applicator housing.

Figure 215:
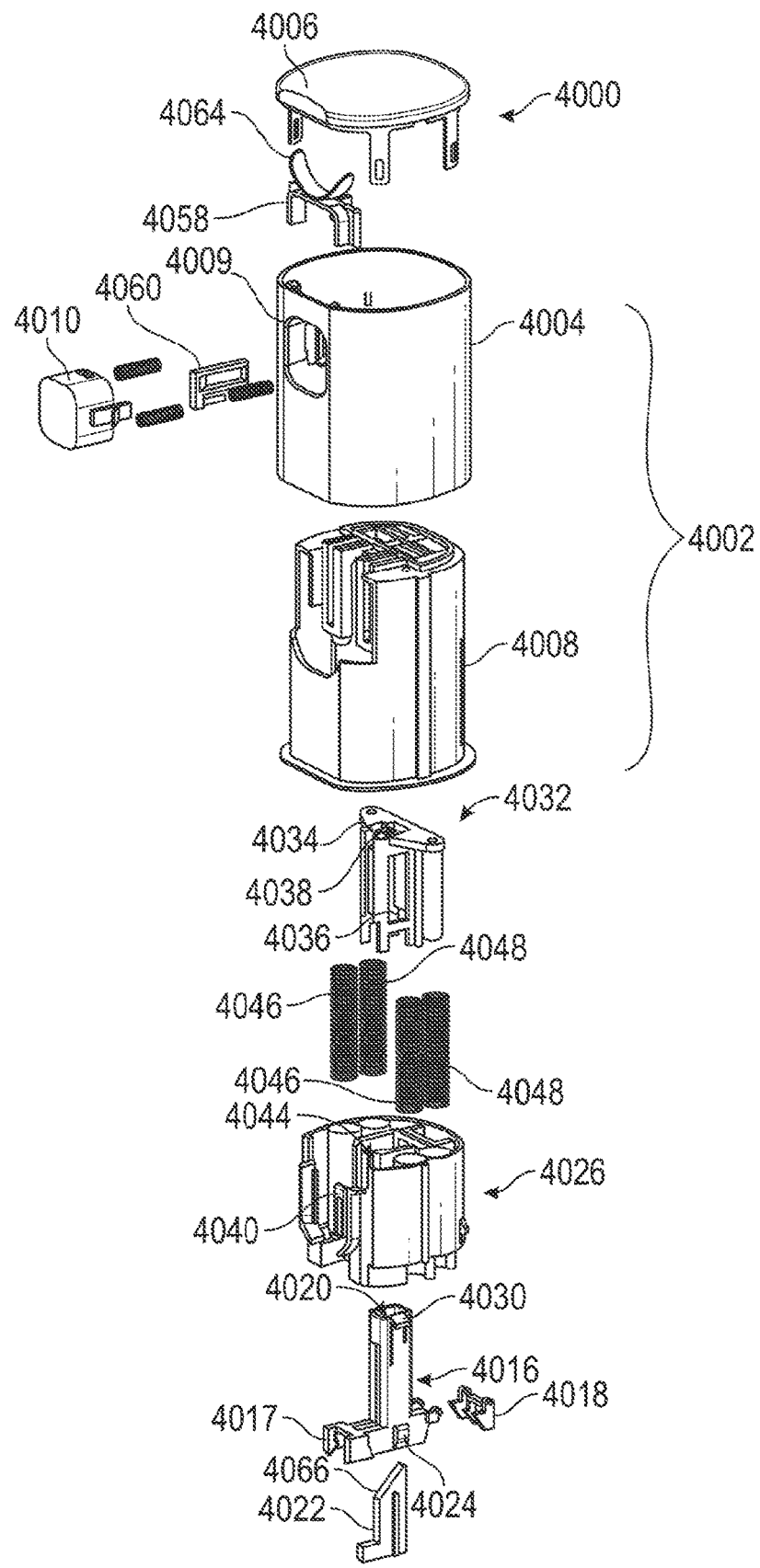

FIG. 215 illustrates an exploded perspective view of an applicator.

Figure 216:
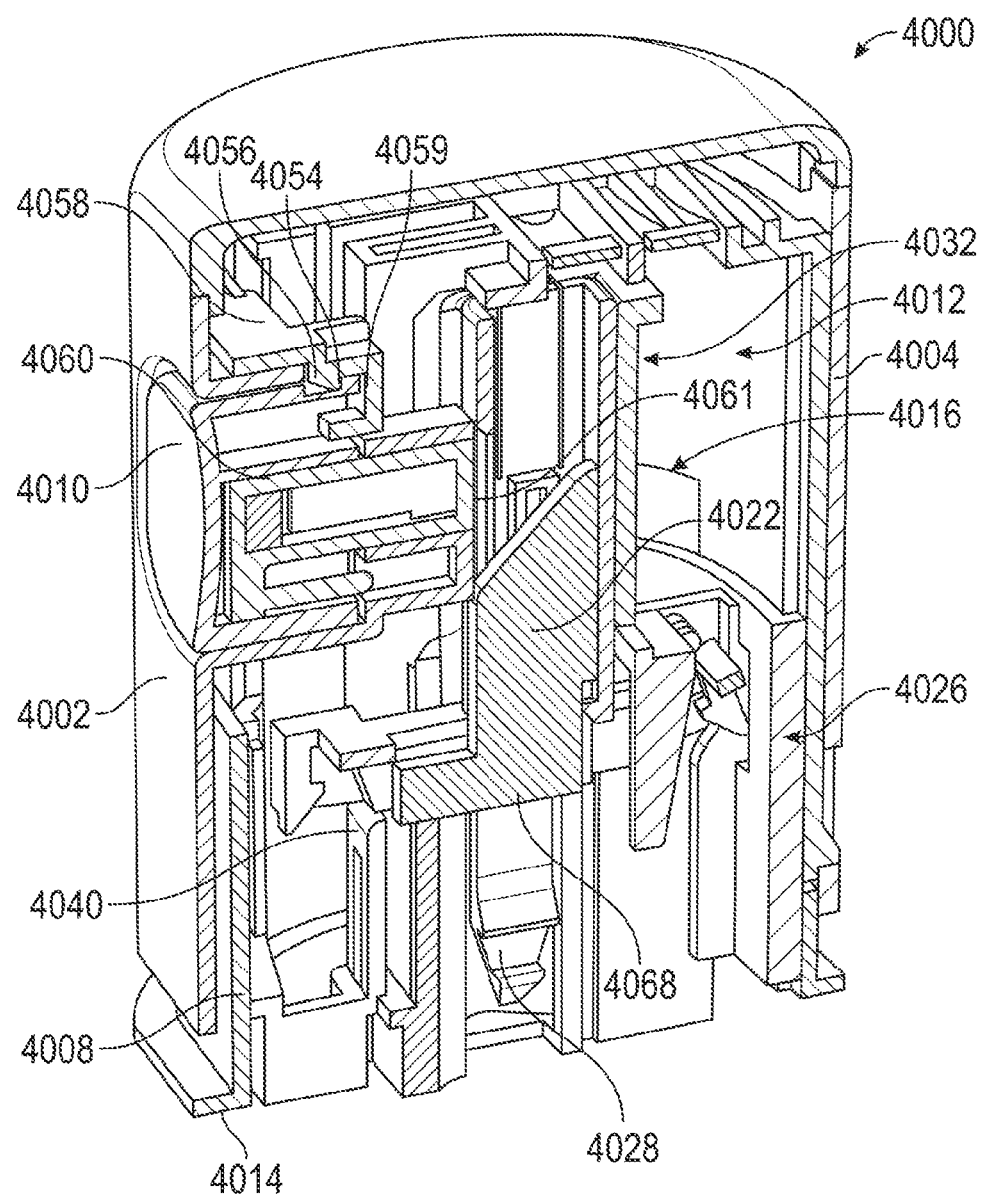

FIG. 216 illustrates a cross sectional view of the applicator shown in FIG. 215 along a mid line.

Figure 217:
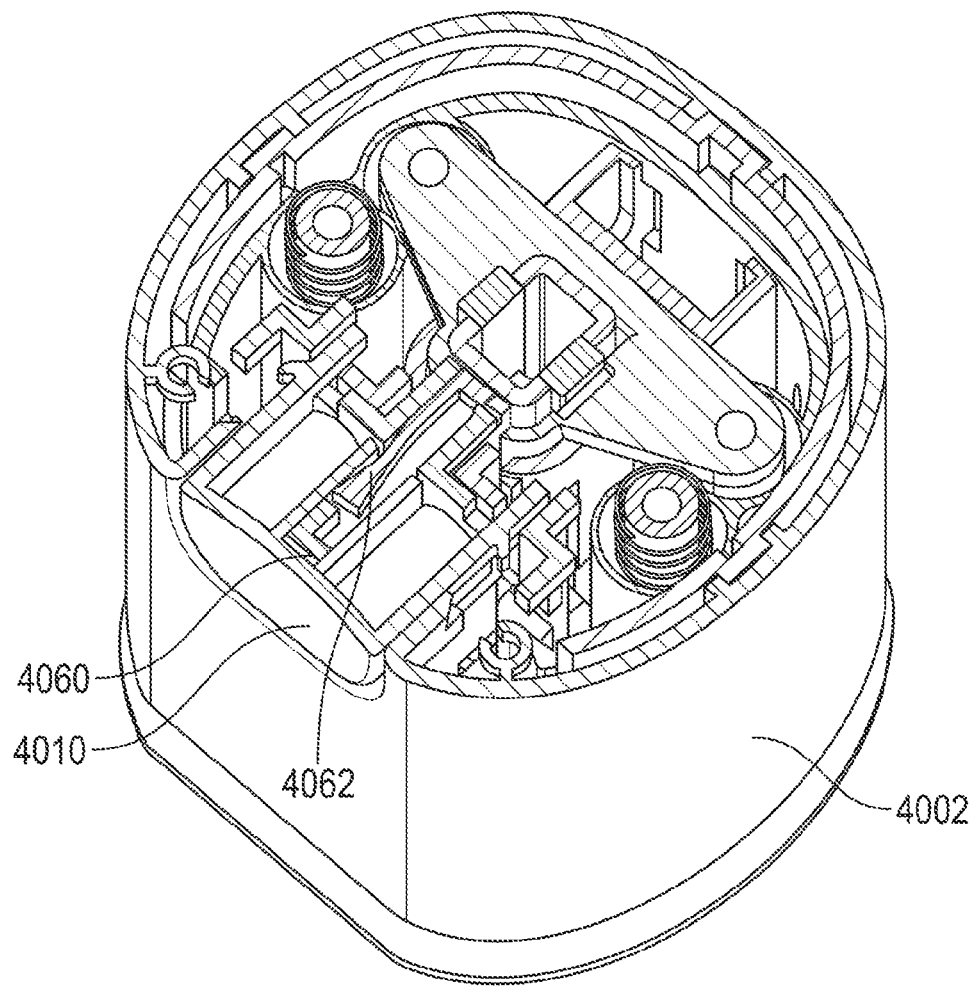

FIG. 217 illustrates a cross sectional view of the applicator shown in FIG. 215 along a transverse cross sectional plane.

Figure 218:
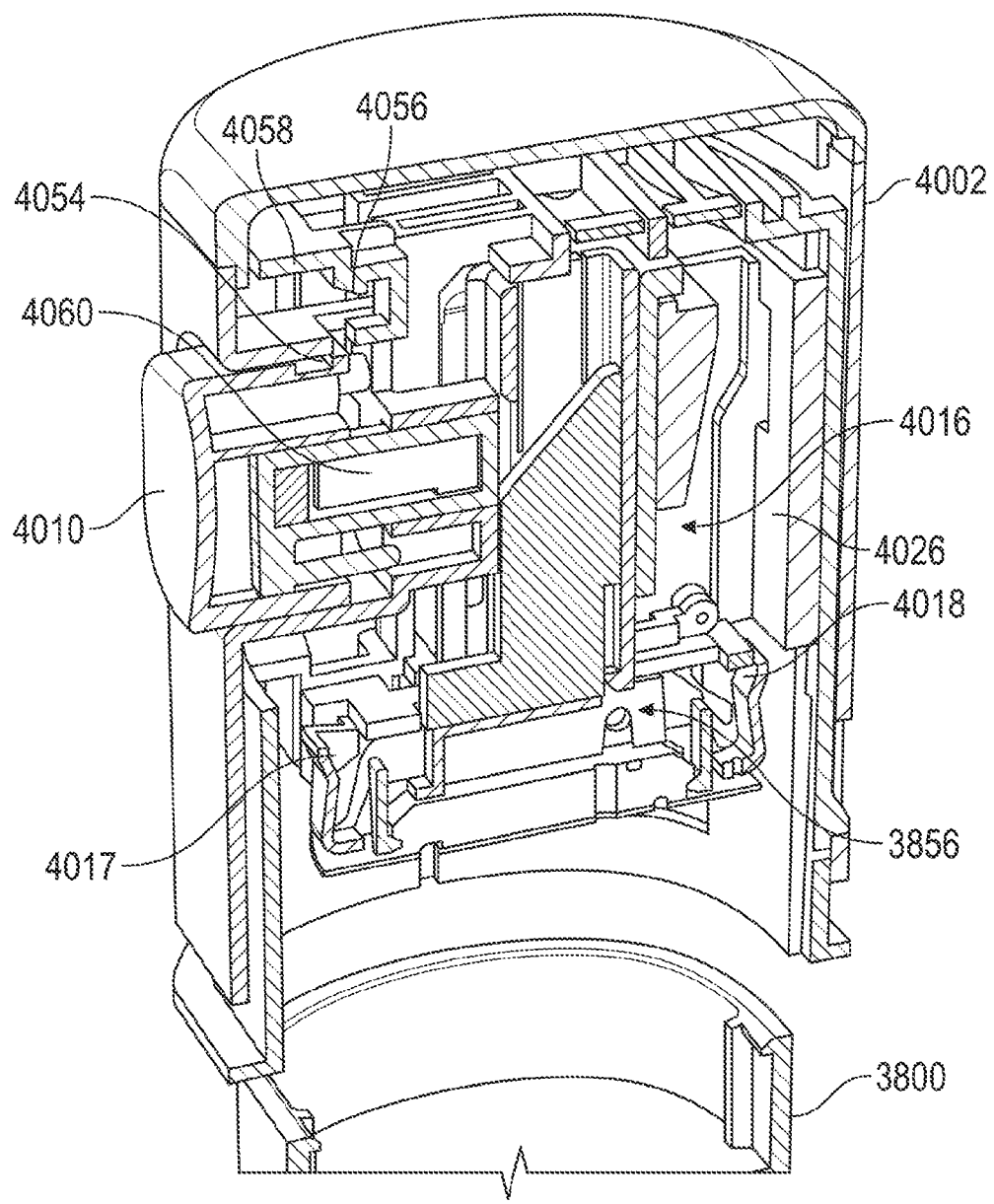

FIG. 218 illustrates a cross sectional view of the applicator shown in FIG. 215 along a mid line.

Figure 219:
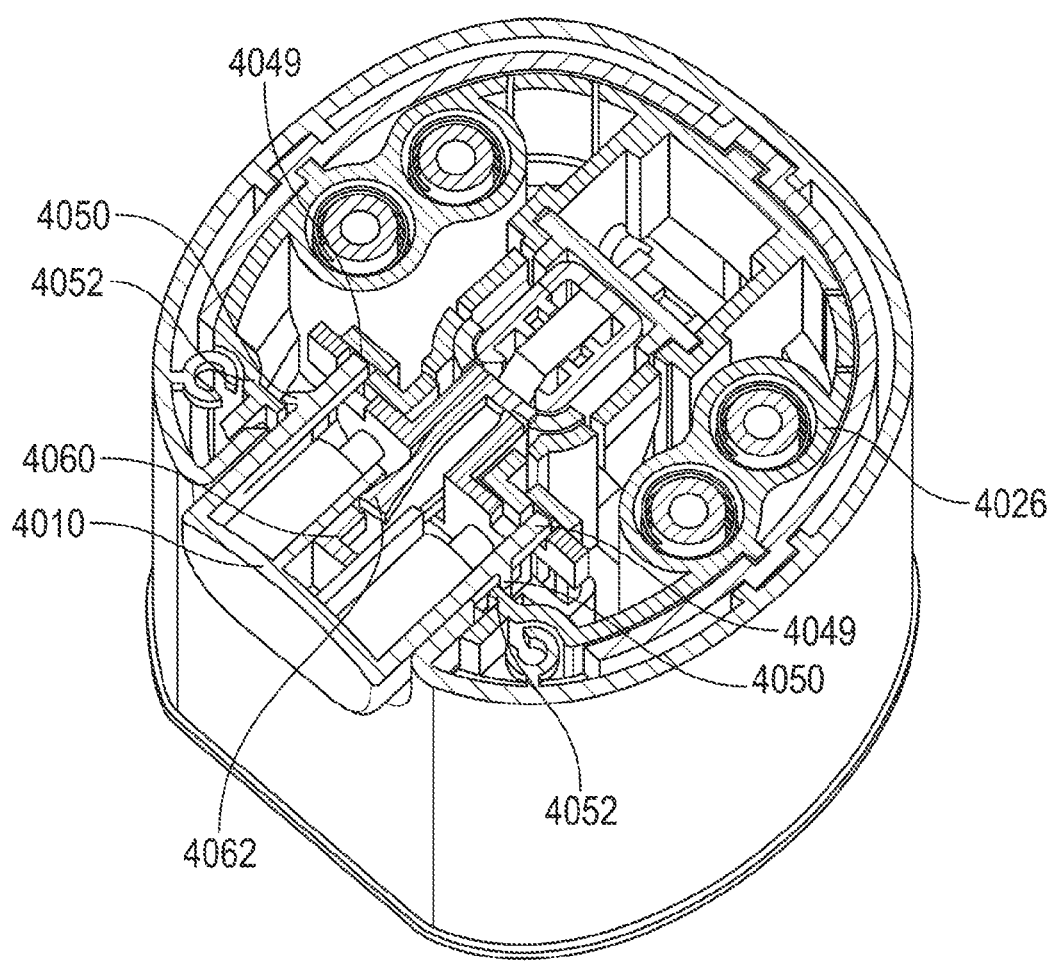

FIG. 219 illustrates a cross sectional view of the applicator shown in FIG. 215 along a transverse cross sectional plane.

Figure 220:
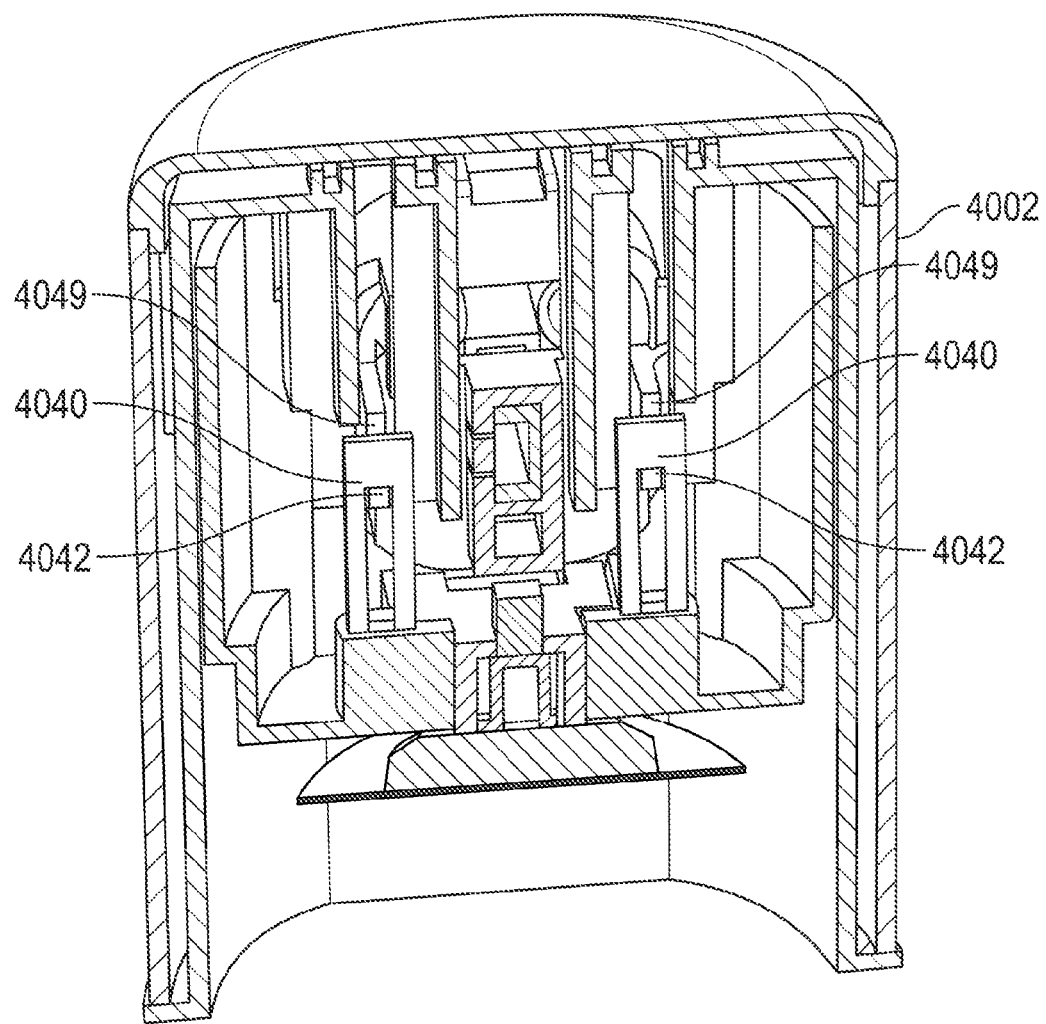

FIG. 220 illustrates a cross sectional view of the applicator shown in FIG. 215 along a vertical plane.

Figure 221:
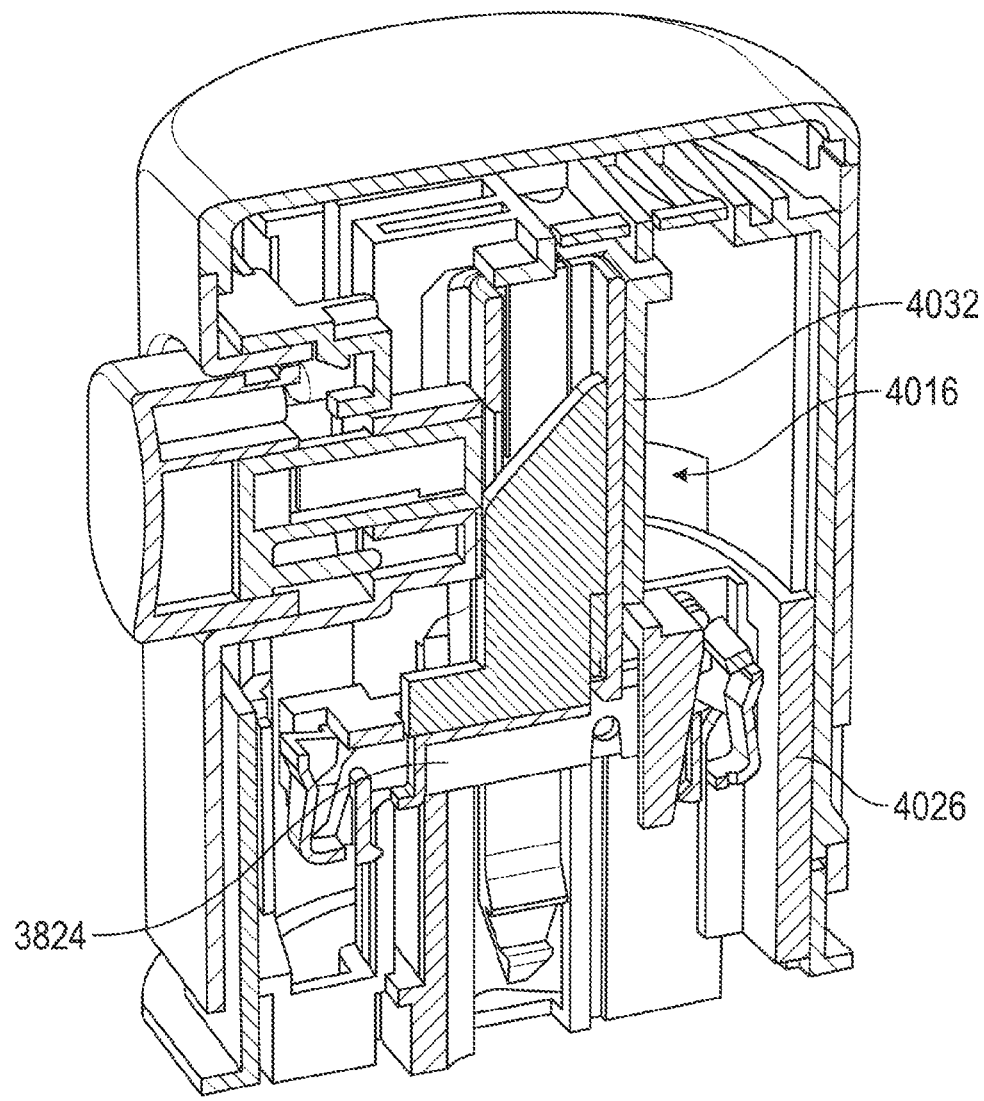

FIG. 221 illustrates a cross sectional view of the applicator shown in FIG. 215 along a mid line.

Figure 222:
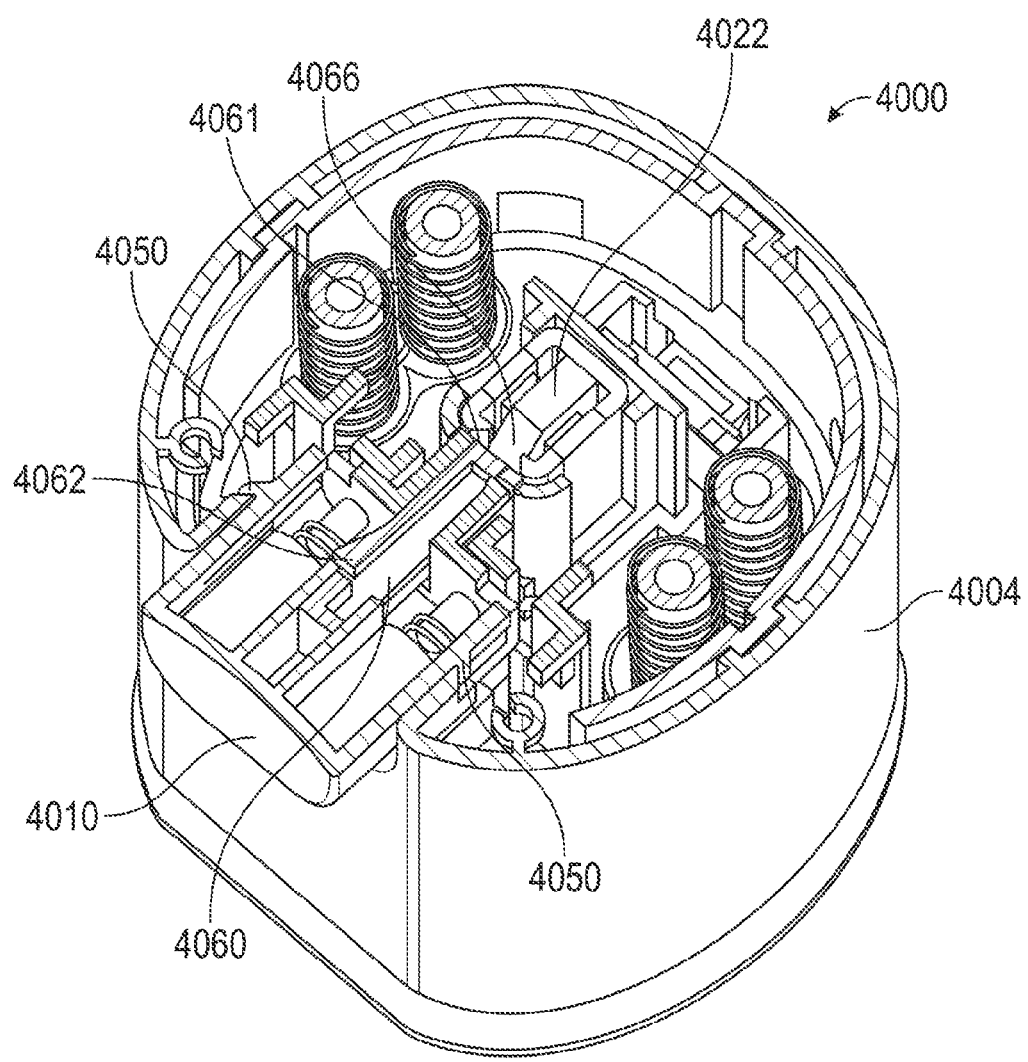

FIG. 222 illustrates a cross sectional view of the applicator shown in FIG. 215 along a transverse cross sectional plane.

Figure 223:
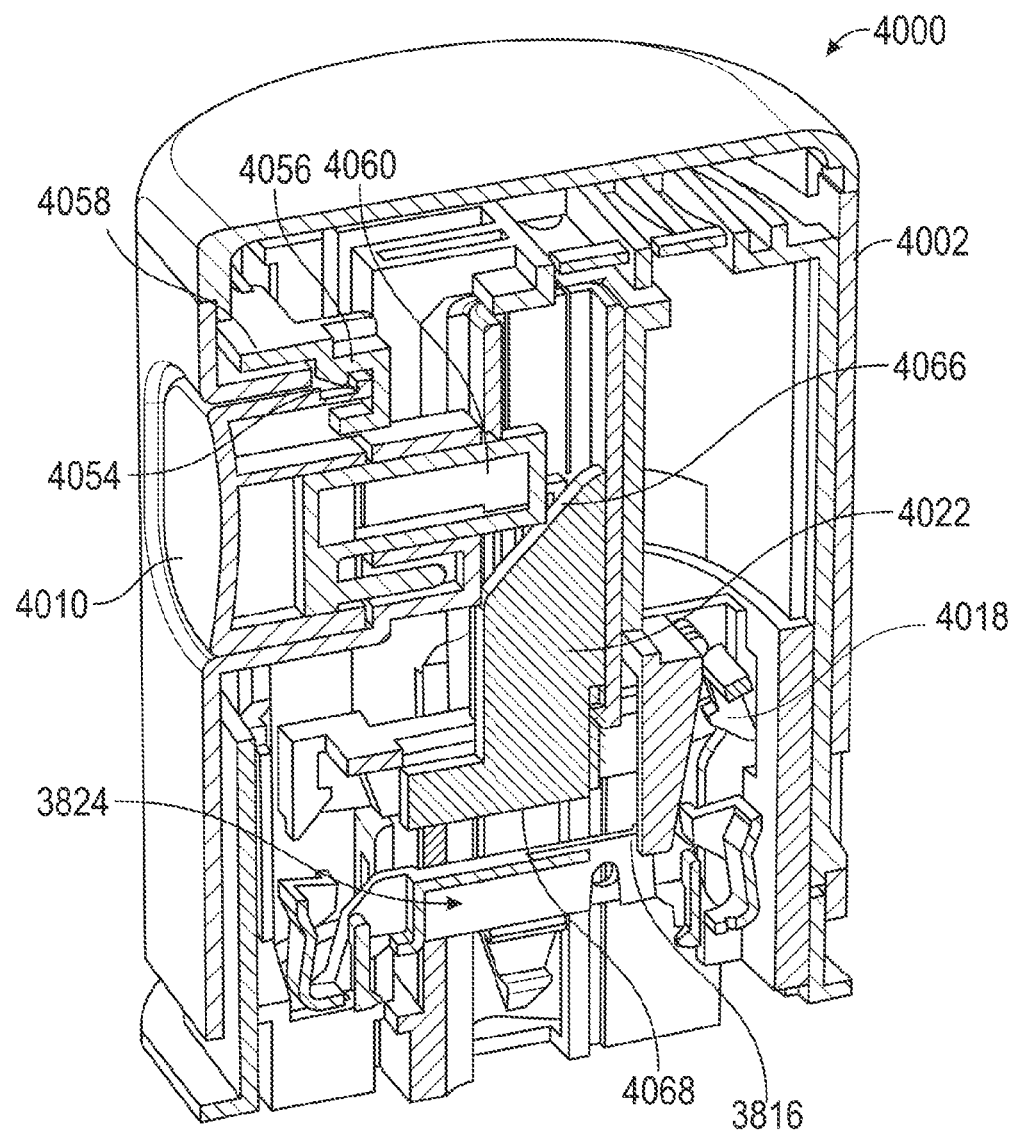

FIG. 223 illustrates a cross sectional view of the applicator shown in FIG. 215 along a mid line.

Figure 224:
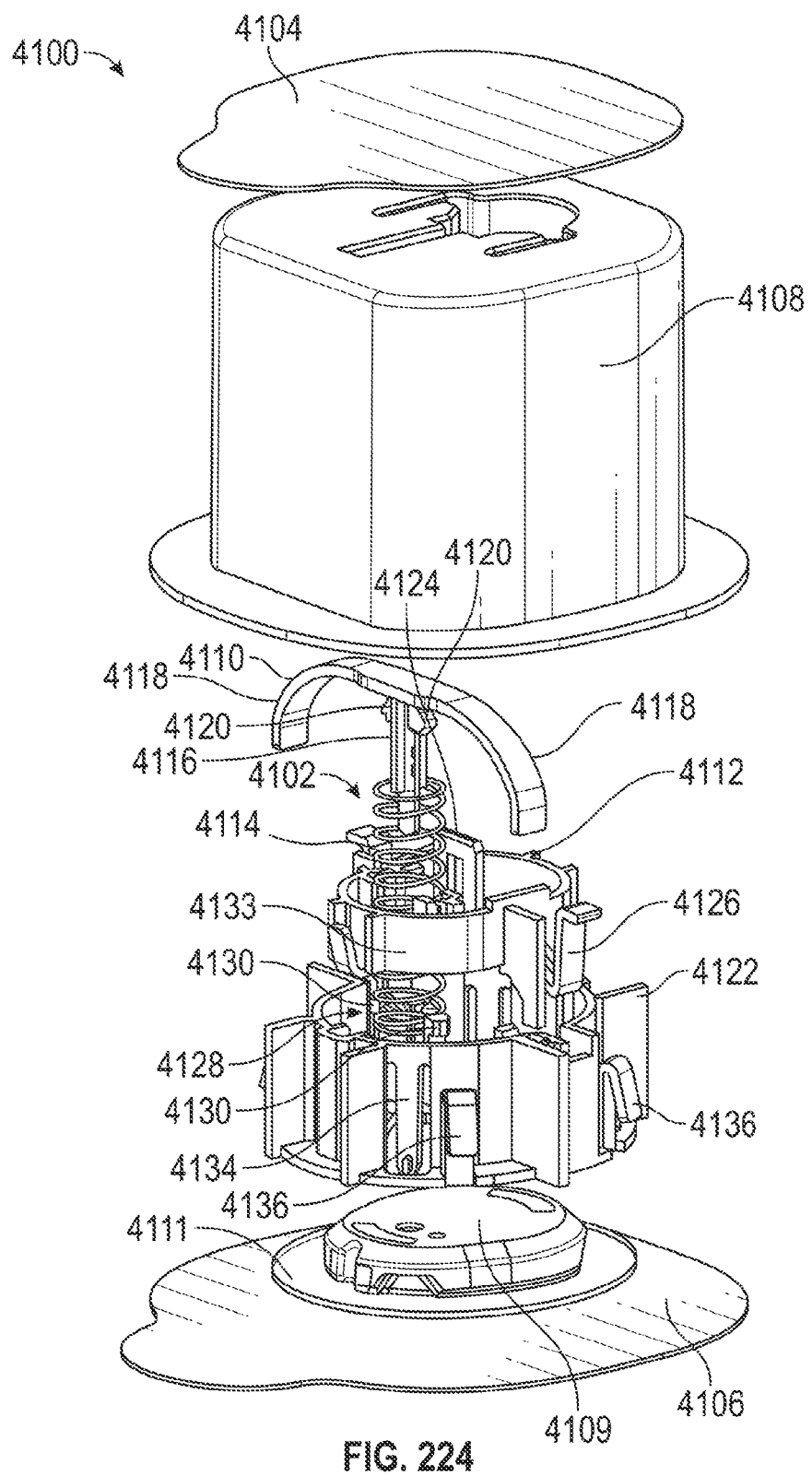

FIG. 224 illustrates an exploded perspective view of a cartridge.

Figure 225:
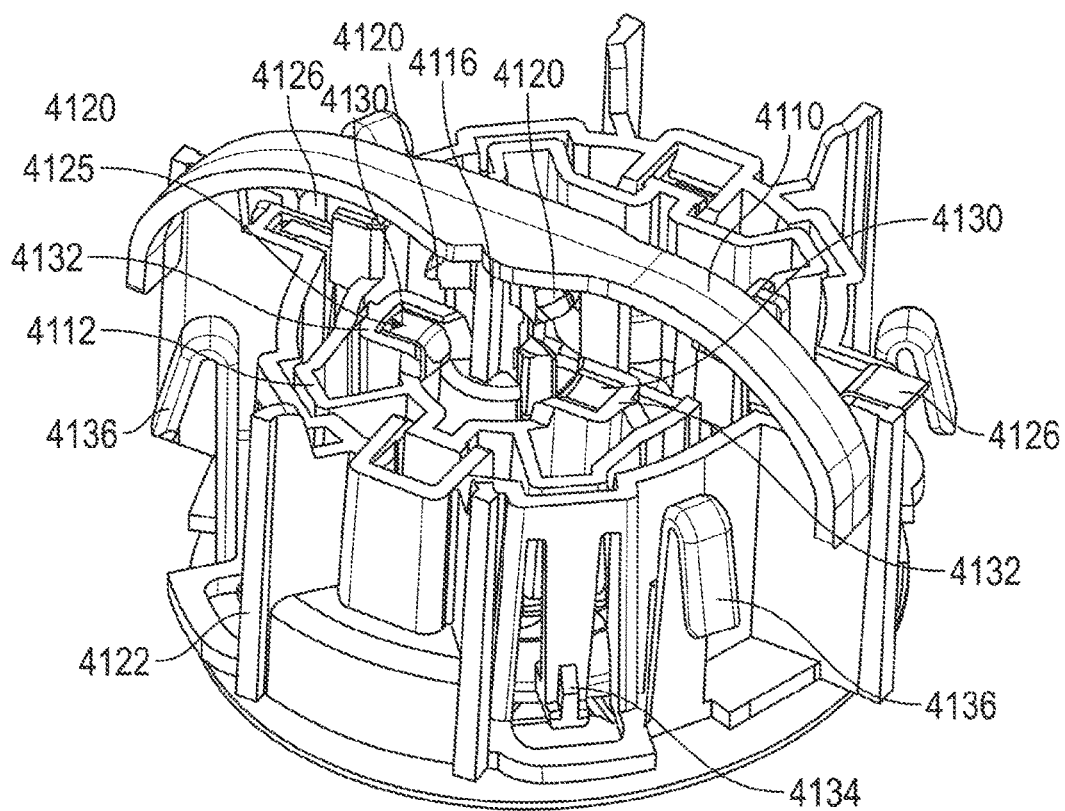

FIG. 225 illustrates a perspective view of components of a cartridge.

Figure 226:
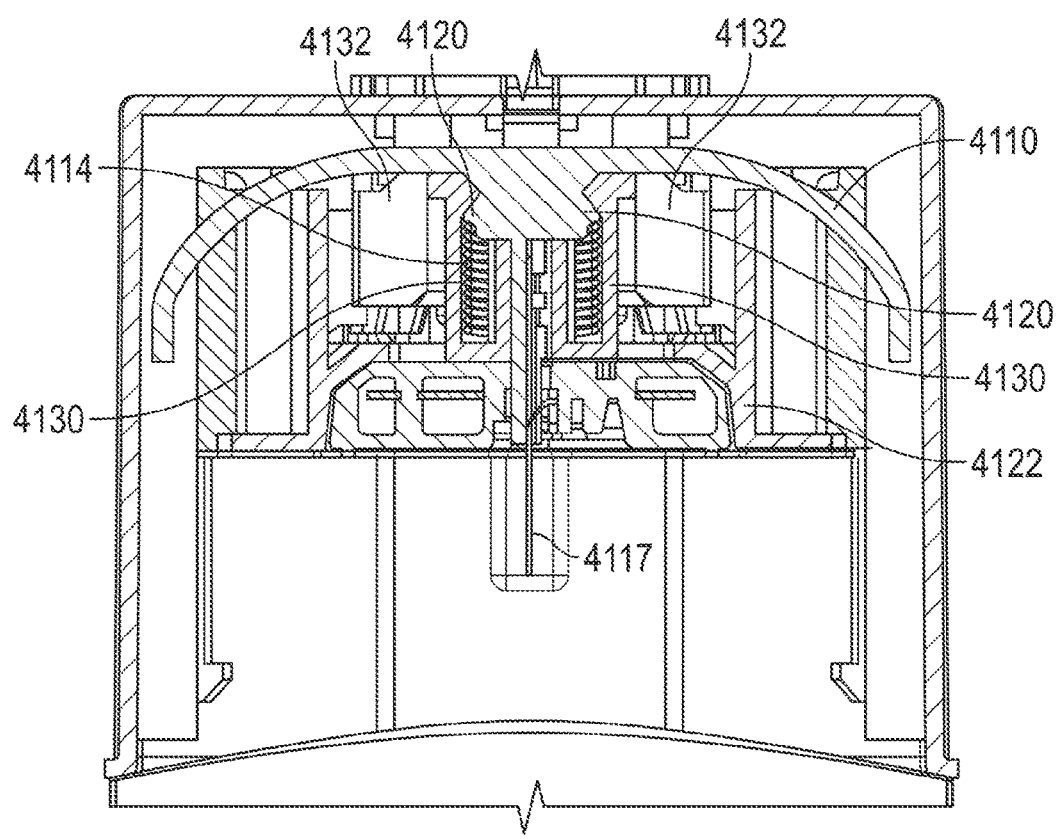

FIG. 226 illustrates a cross sectional view of a cartridge shown in FIG. 224.

Figure 227:
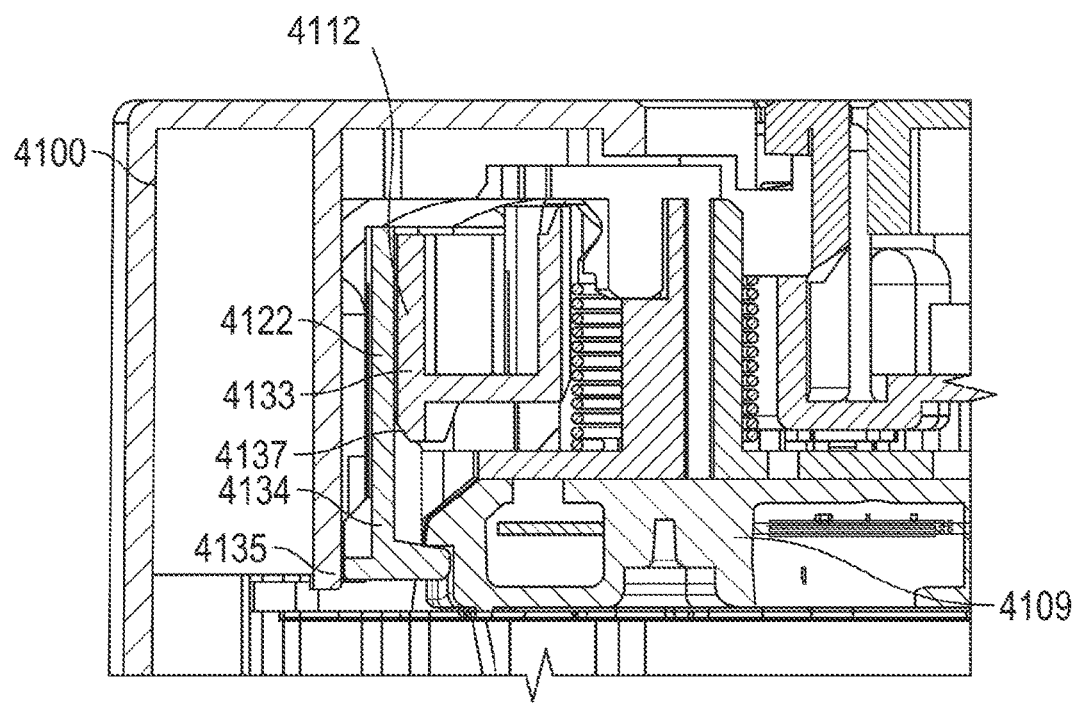

FIG. 227 illustrates a close up view of a portion of the cartridge shown in FIG. 224.

Figure 228:
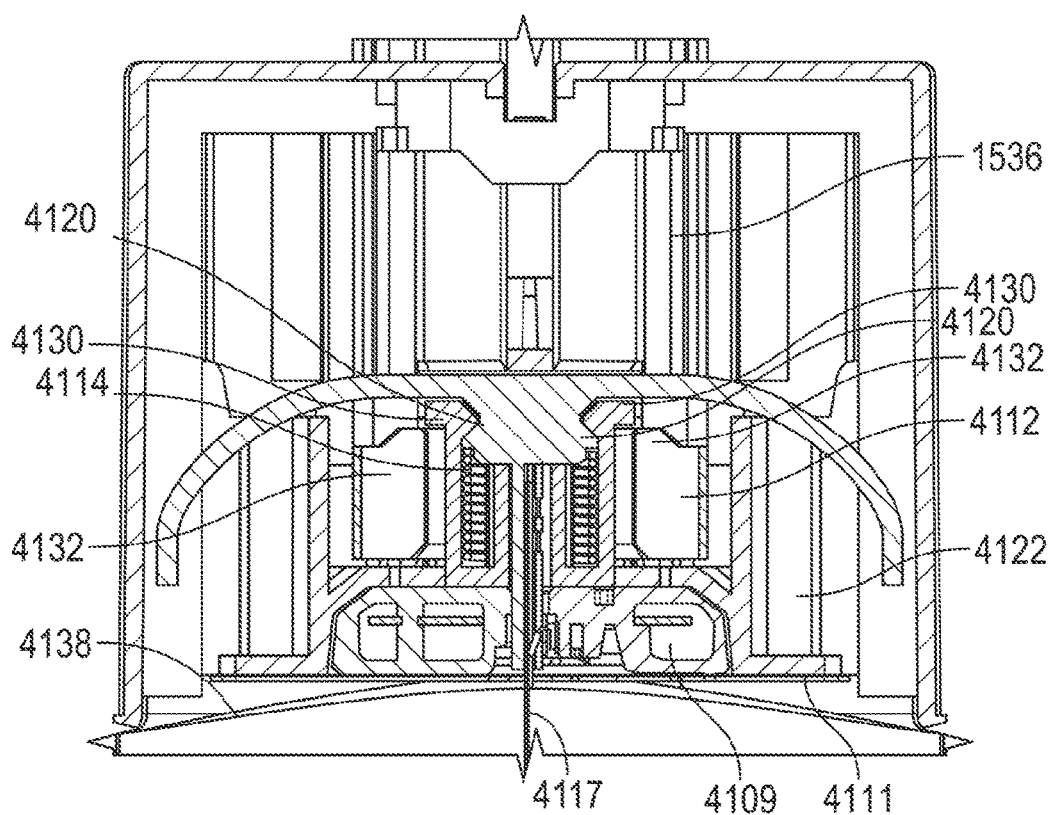

FIG. 228 illustrates a cross sectional view of a cartridge shown in FIG. 224.

Figure 229:
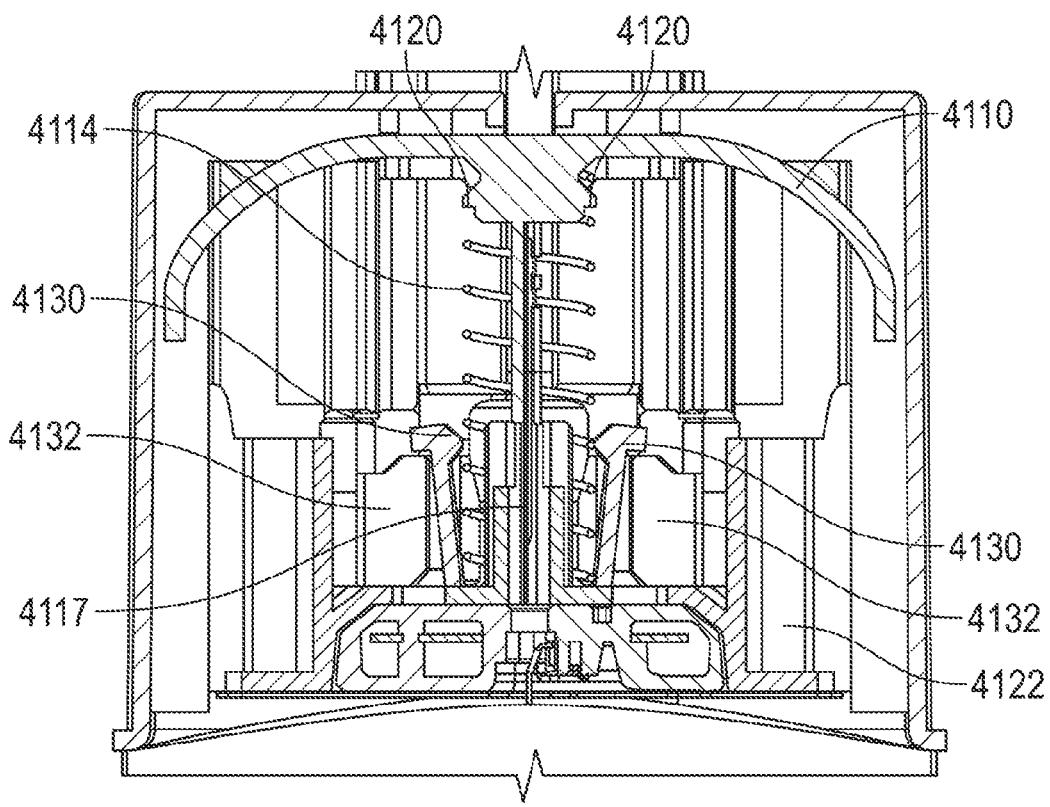

FIG. 229 illustrates a cross sectional view of a cartridge shown in FIG. 224.

Figure 230:
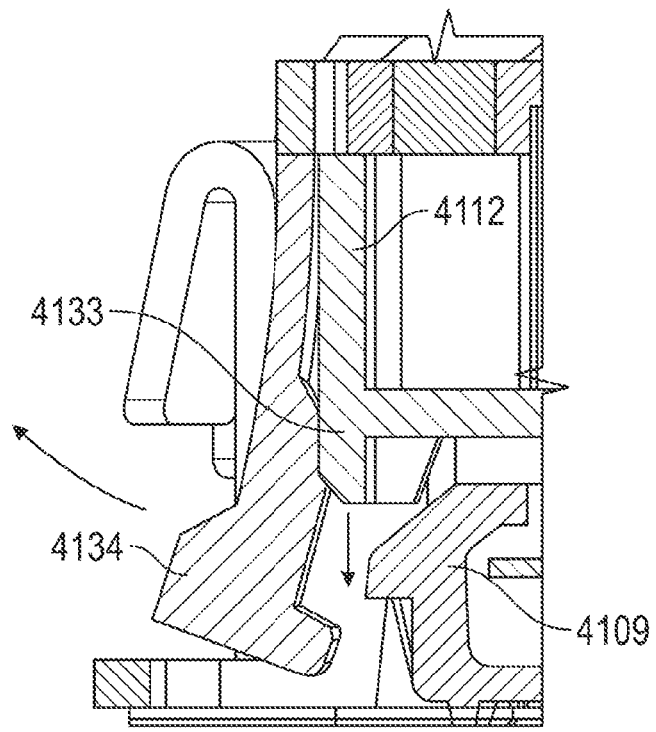

FIG. 230 illustrates a close up view of a portion of the cartridge shown in FIG. 224.

Figure 231:
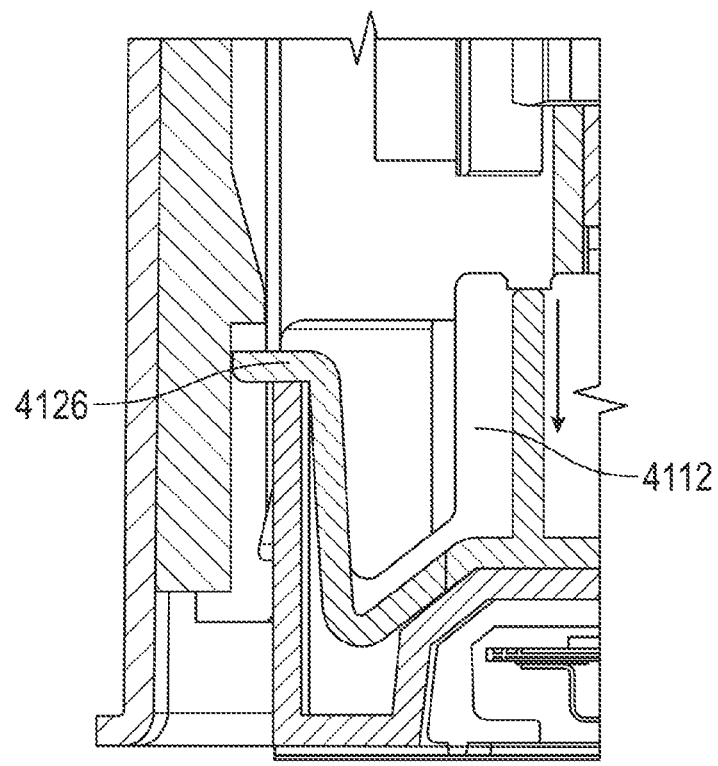

FIG. 231 illustrates a close up view of a portion of the cartridge shown in FIG. 224.

Figure 232:
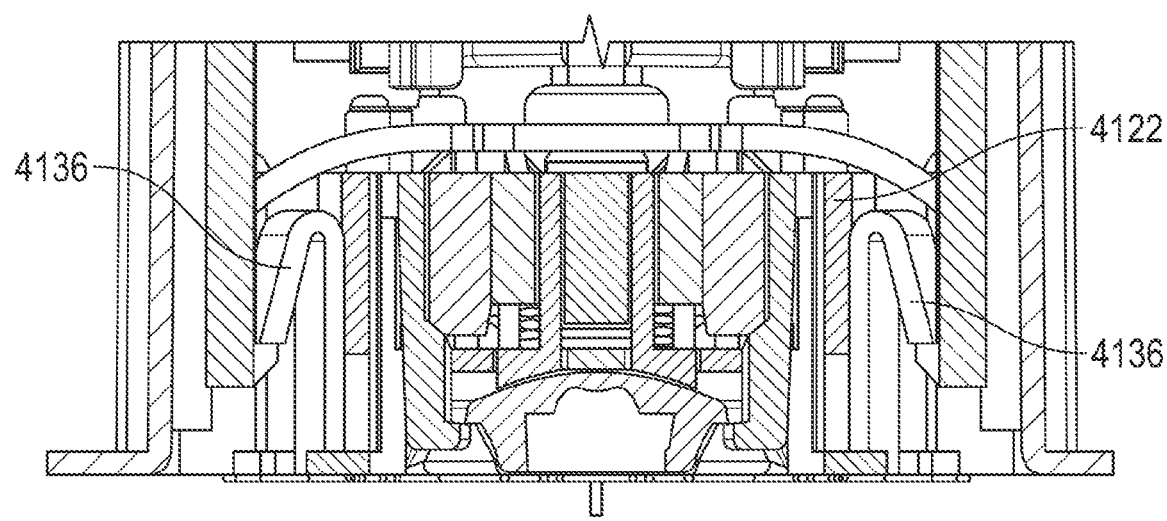

FIG. 232 illustrates a cross sectional view of a cartridge shown in FIG. 224.

Figure 233:
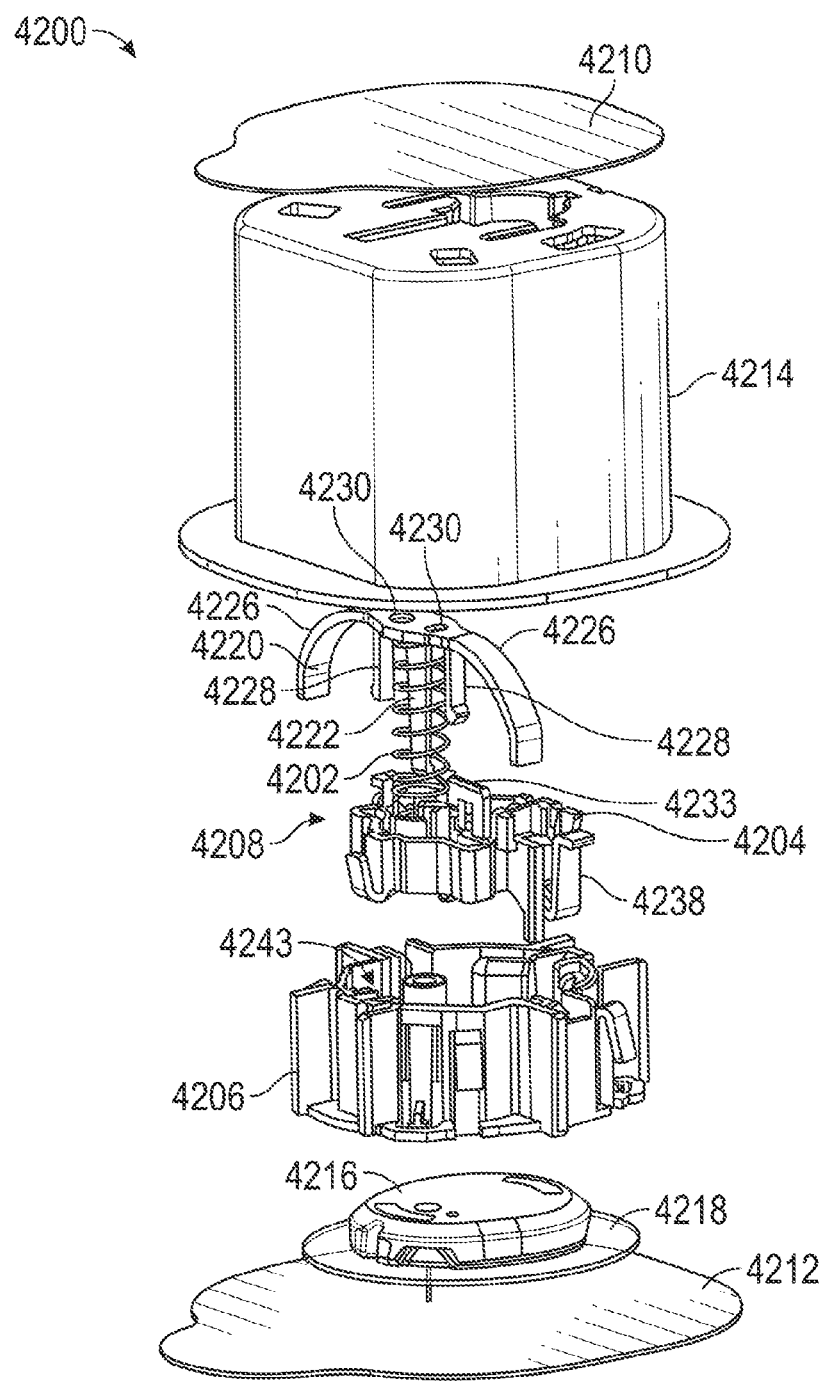

FIG. 233 illustrates an exploded perspective view of a cartridge.

Figure 234:
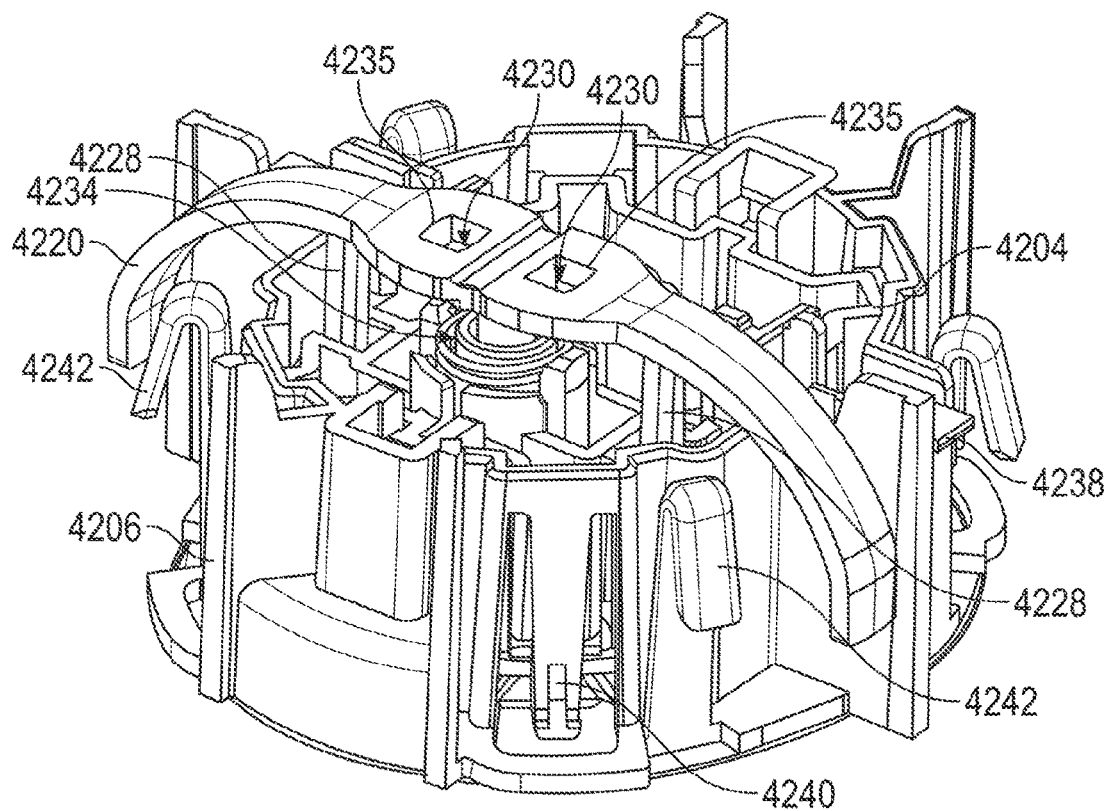

FIG. 234 illustrates a perspective view of components of a cartridge.

Figure 235:
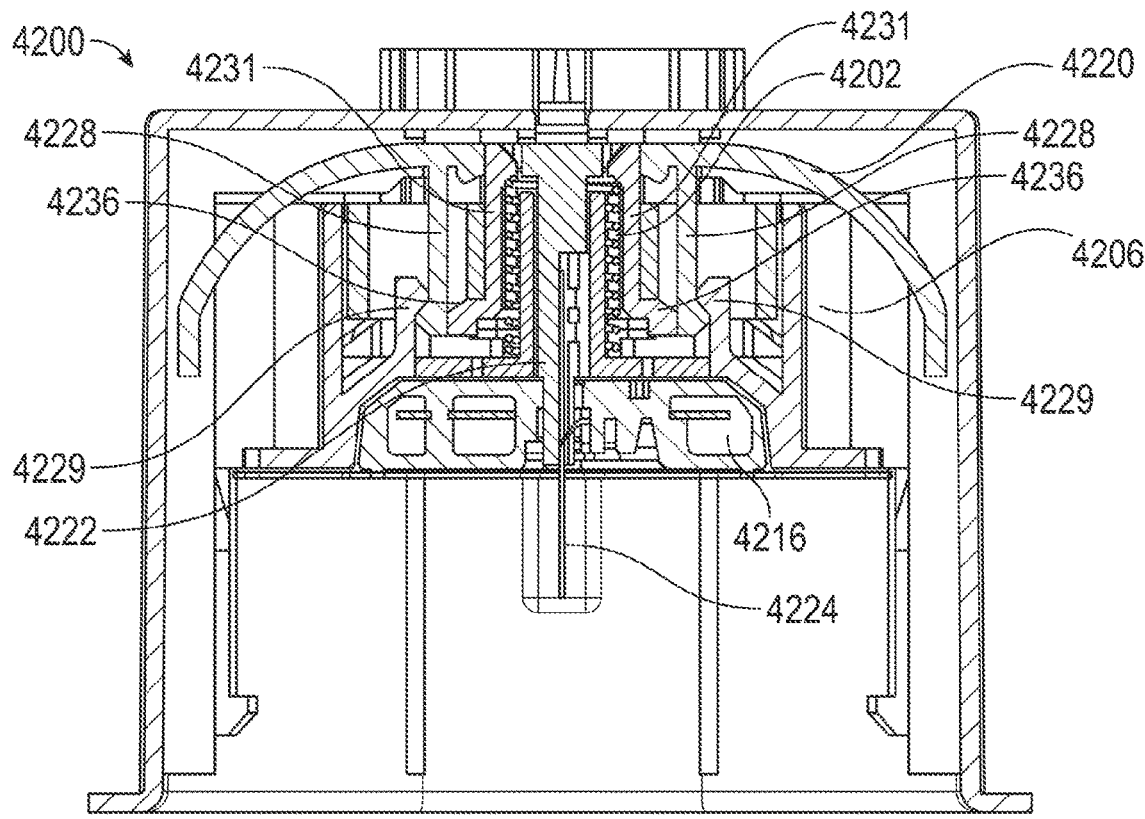

FIG. 235 illustrates a cross sectional view of a cartridge shown in FIG. 233.

Figure 236:
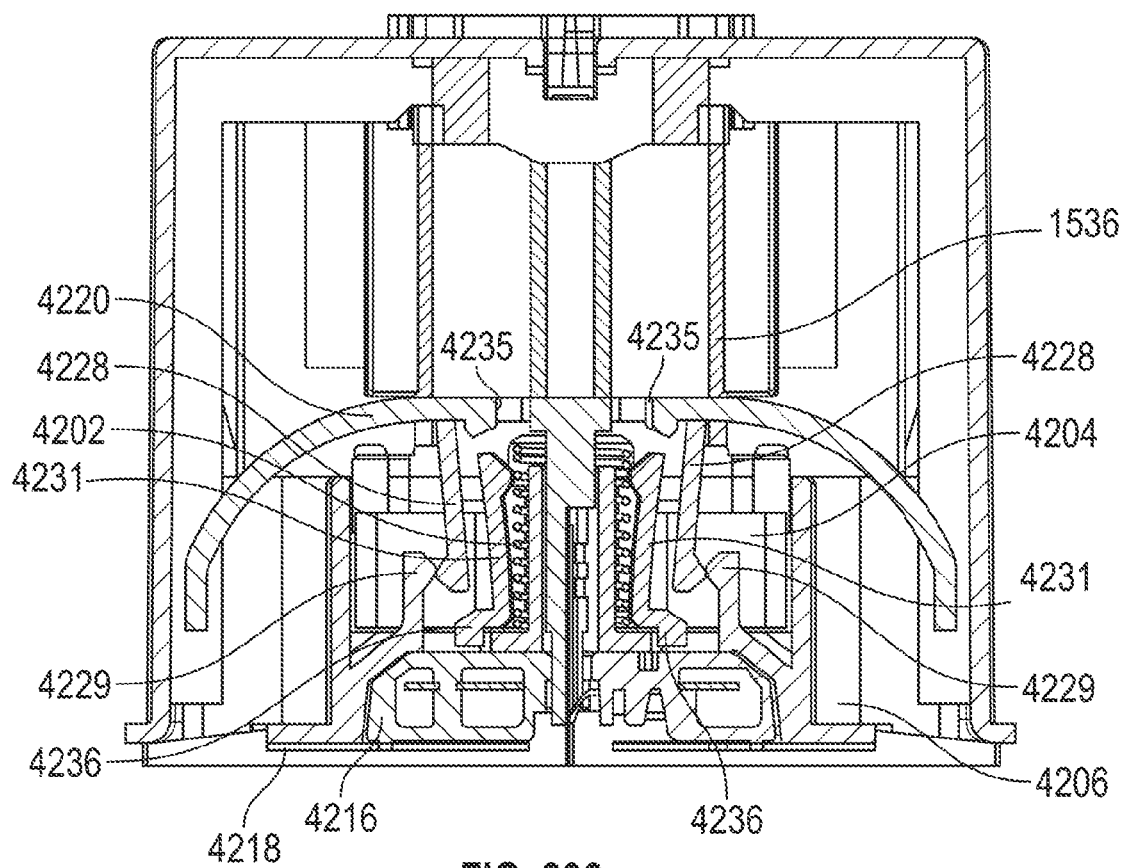

FIG. 236 illustrates a cross sectional view of a cartridge shown in FIG. 233.

Figure 237:
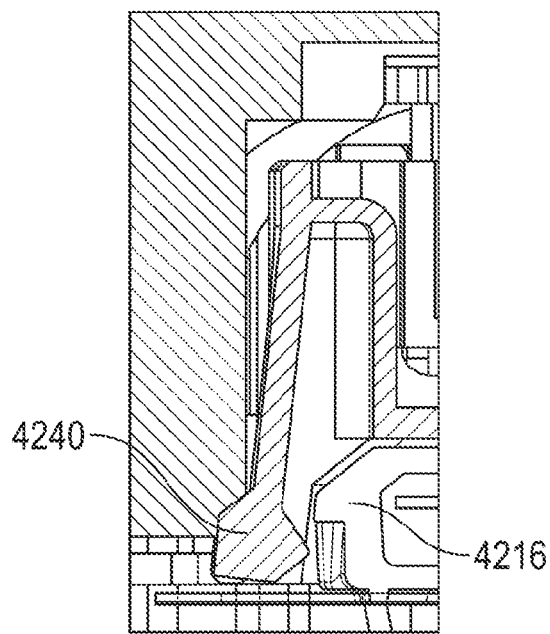

FIG. 237 illustrates a close up view of a portion of the cartridge shown in FIG. 233.

Figure 238:
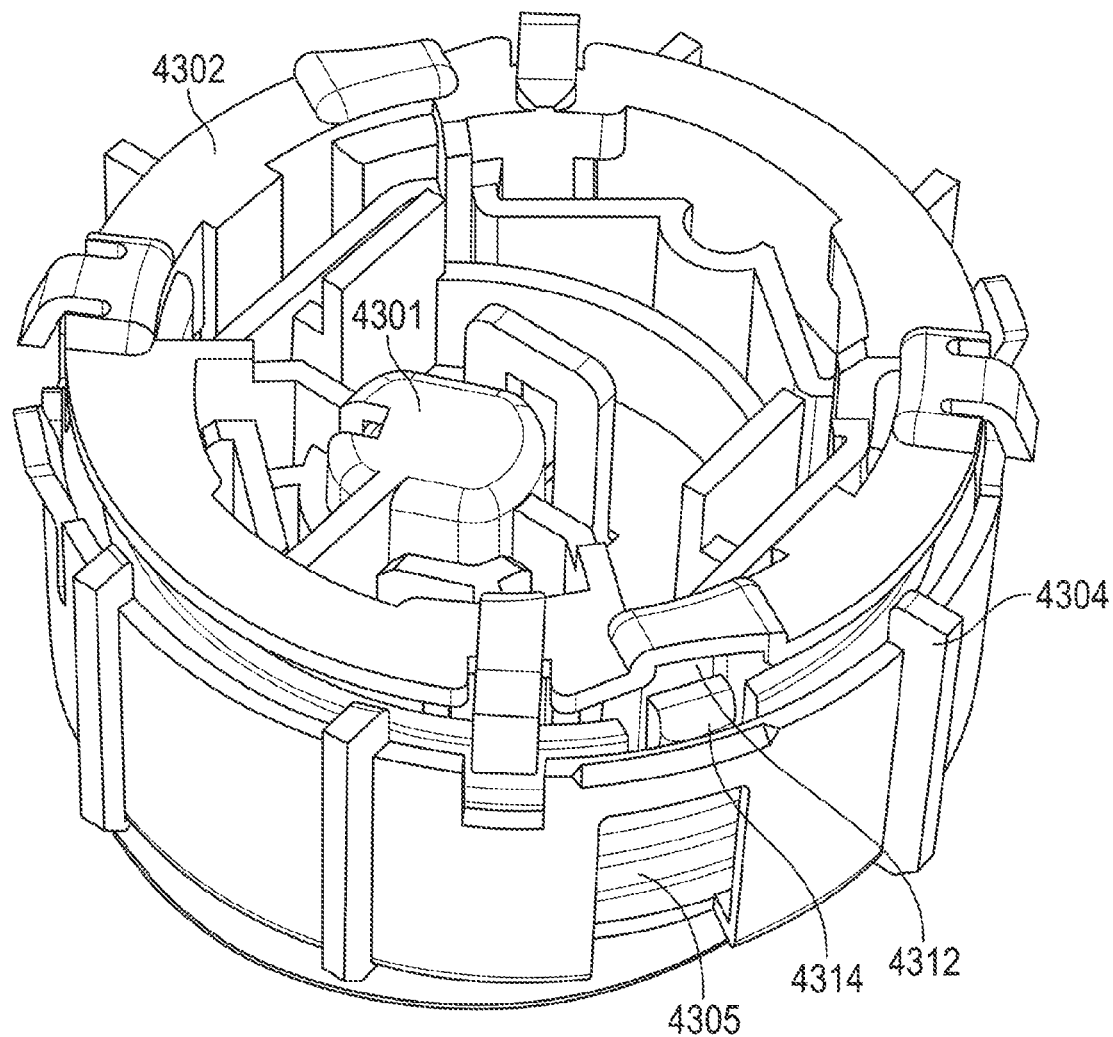

FIG. 238 illustrates a close up view of a portion of a cartridge.

Figure 239:
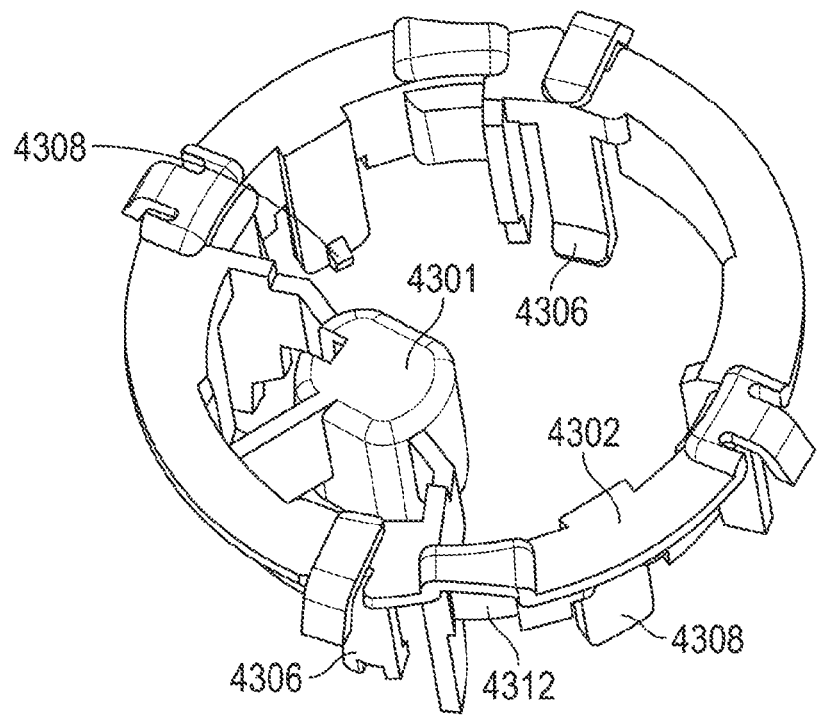

FIG. 239 illustrates a close up view of a portion of a cartridge.

Figure 240:
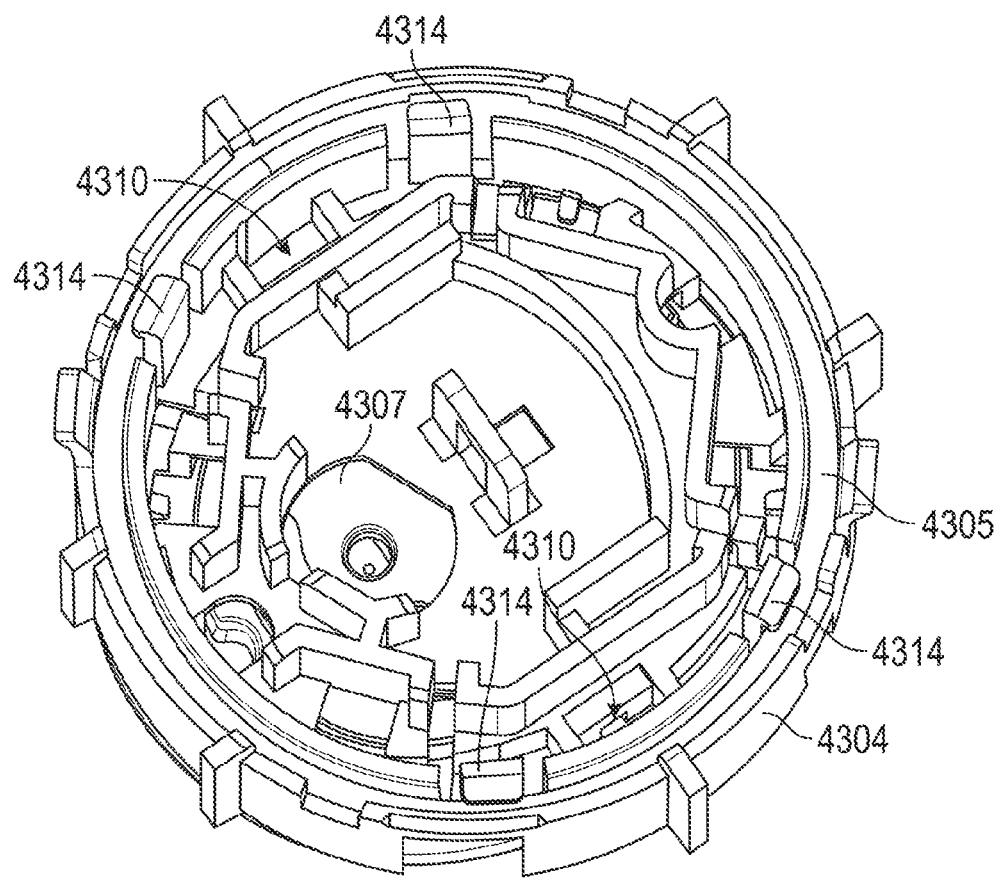

FIG. 240 illustrates a perspective view of components of a cartridge.

Figure 241:
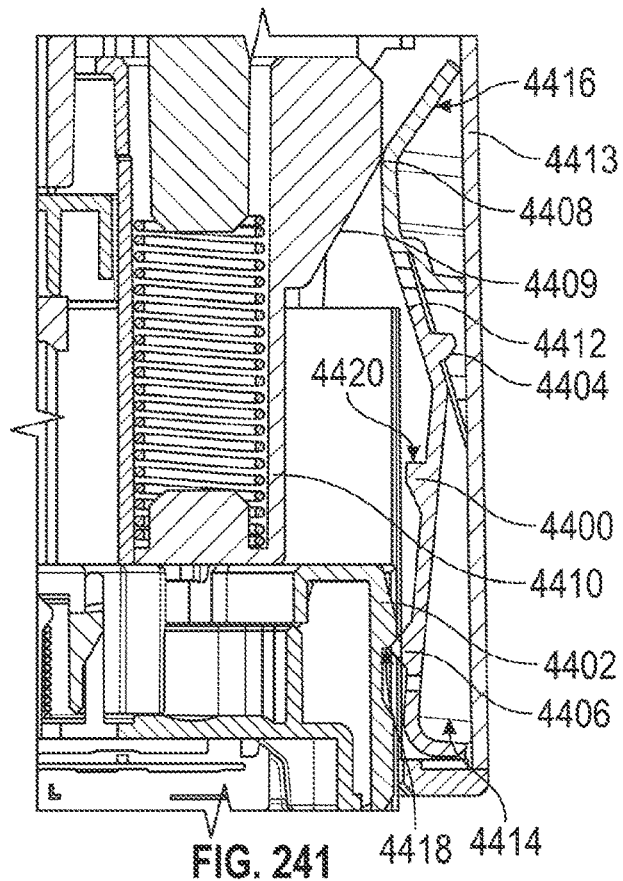

FIG. 241 illustrates a cross sectional view of a portion of an applicator including a releasable coupler.

Figure 242:
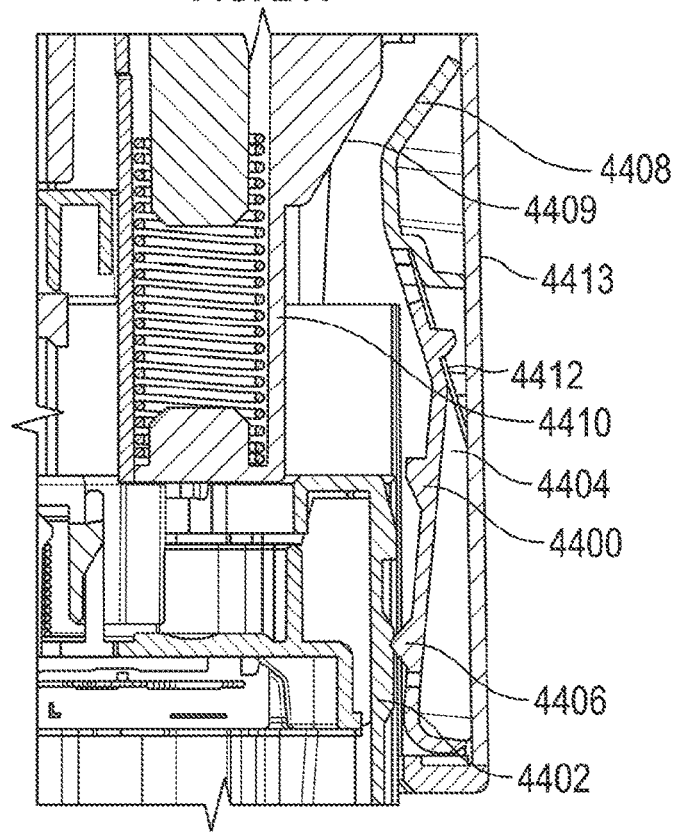

FIG. 242 illustrates a cross sectional view of the portion of the applicator shown in FIG. 241.

Figure 243:
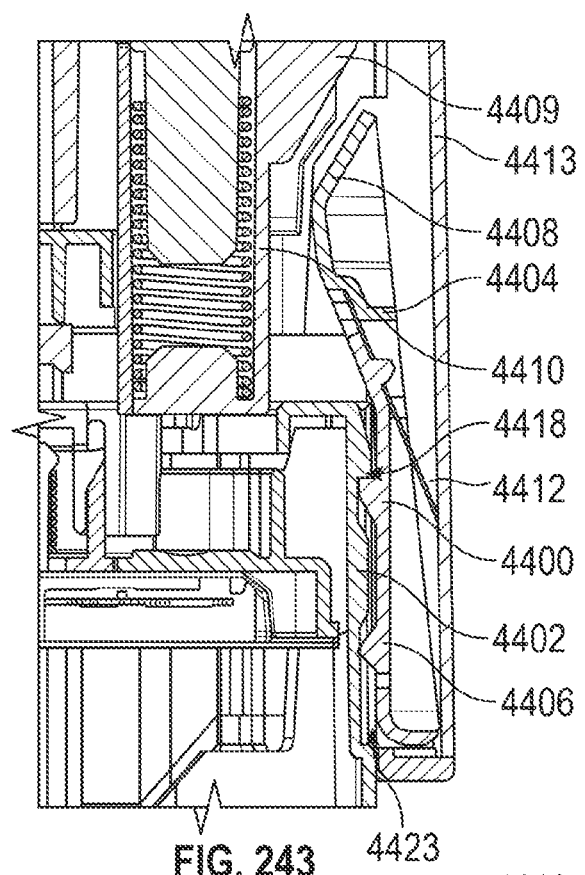

FIG. 243 illustrates a cross sectional view of the portion of the applicator shown in FIG. 241.

Figure 244:
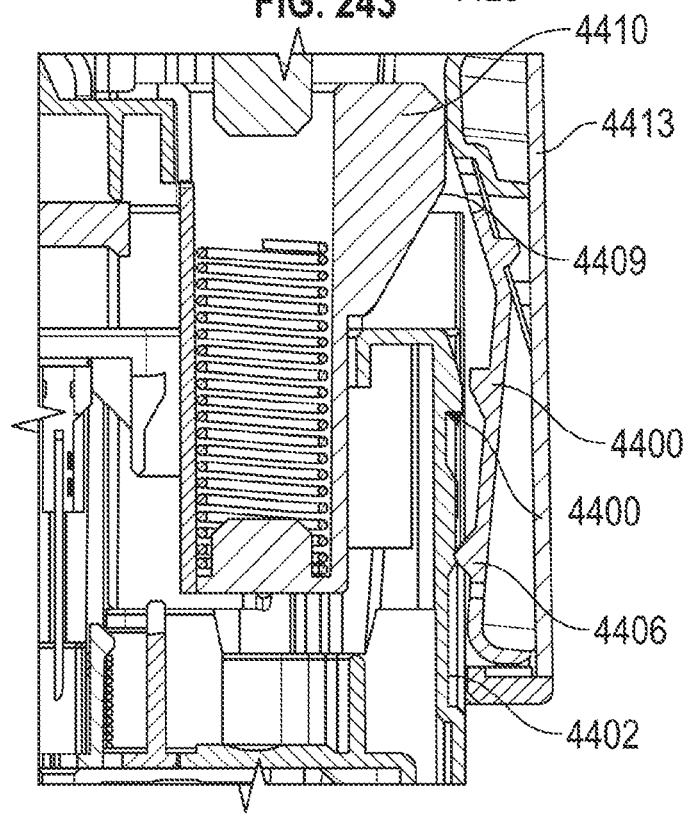

FIG. 244 illustrates a cross sectional view of the portion of the applicator shown in FIG. 241.

Figure 245:
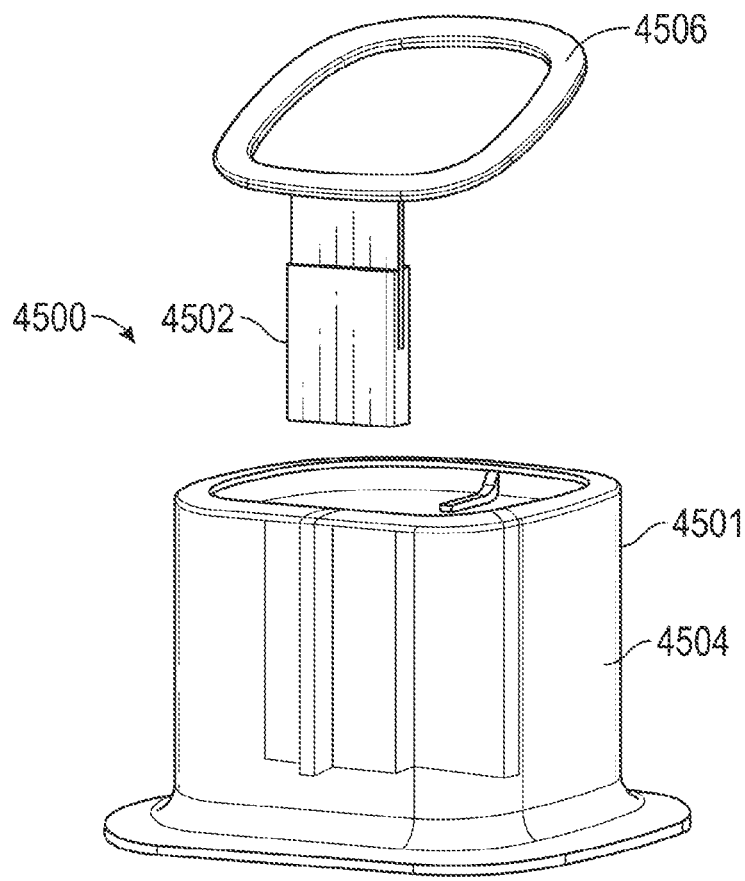

FIG. 245 illustrates a perspective view of a cartridge.

Figure 246A:
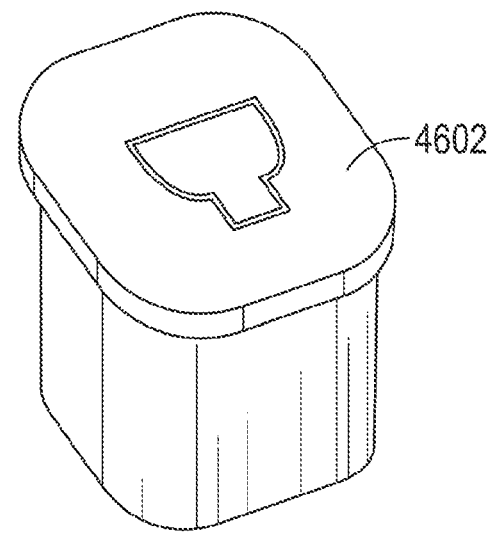

FIG. 246A illustrates a perspective view of a removable body of a cartridge.

Figure 246B:
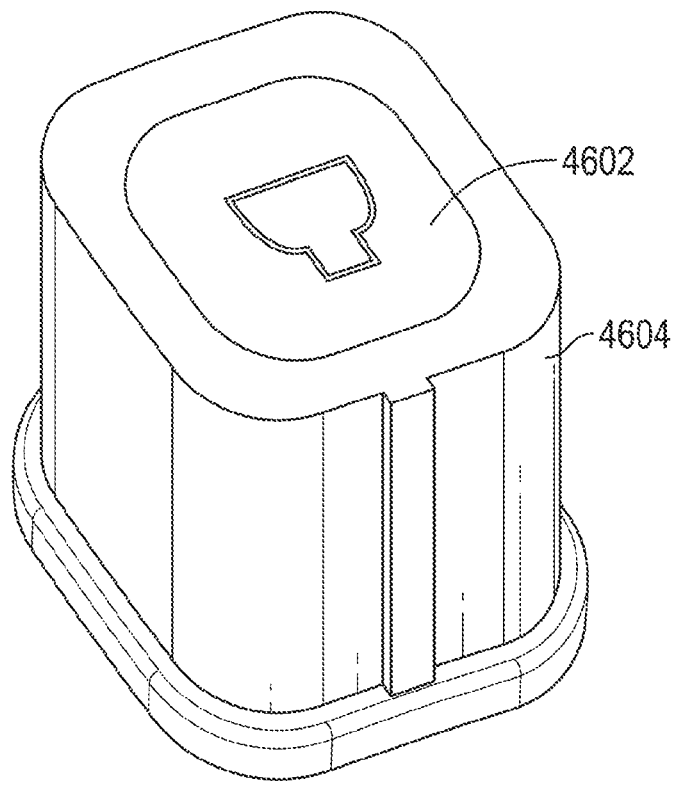

FIG. 246B illustrates a perspective view of the cartridge including the removable body shown in FIG. 246A.

Figure 247A:
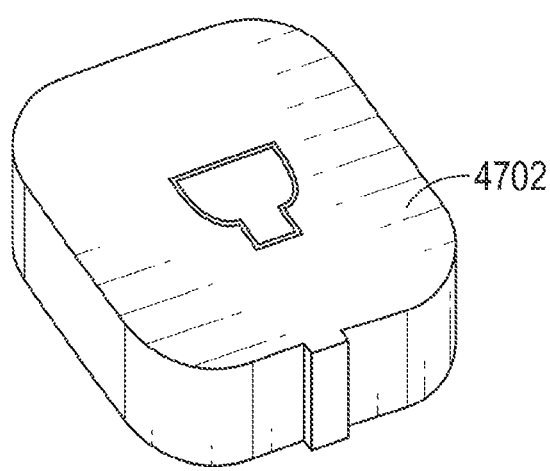

FIG. 247A illustrates a perspective view of a removable body of a cartridge.

Figure 247B:
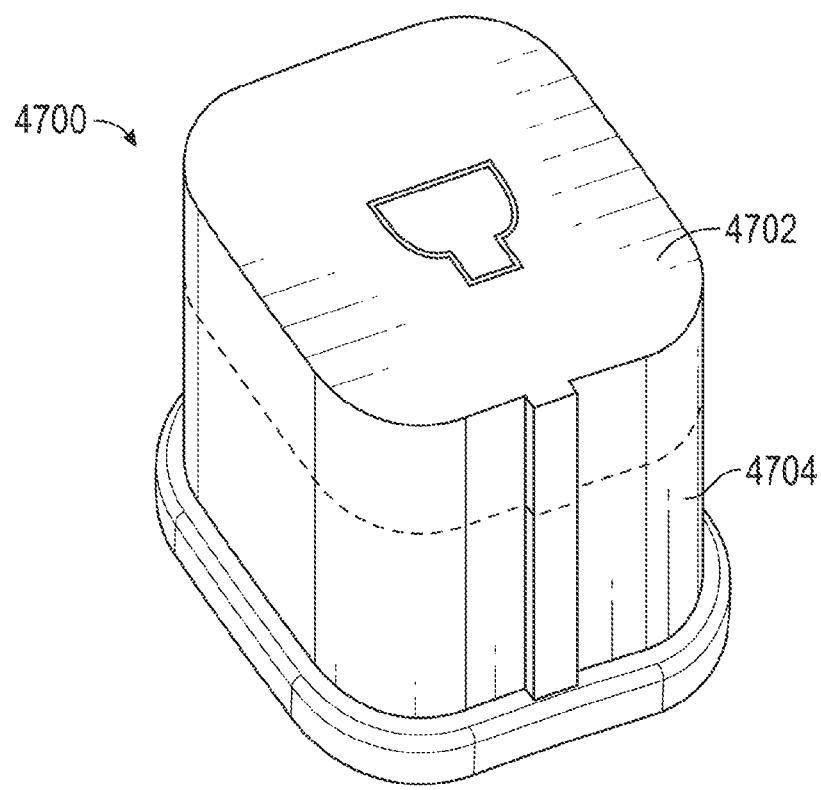

FIG. 247B illustrates a perspective view of a cartridge including the removable body shown in FIG. 247A.

Figure 248A:
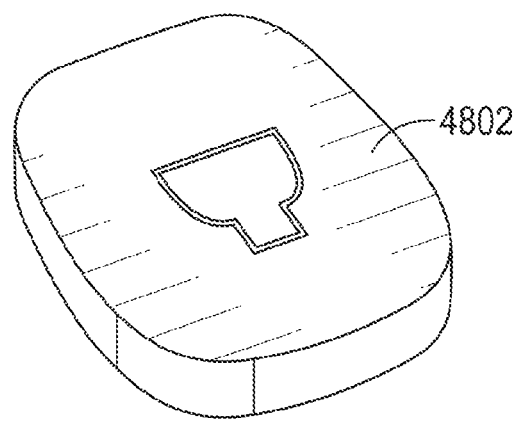

FIG. 248A illustrates a perspective view of a removable body of a cartridge.

Figure 248B:
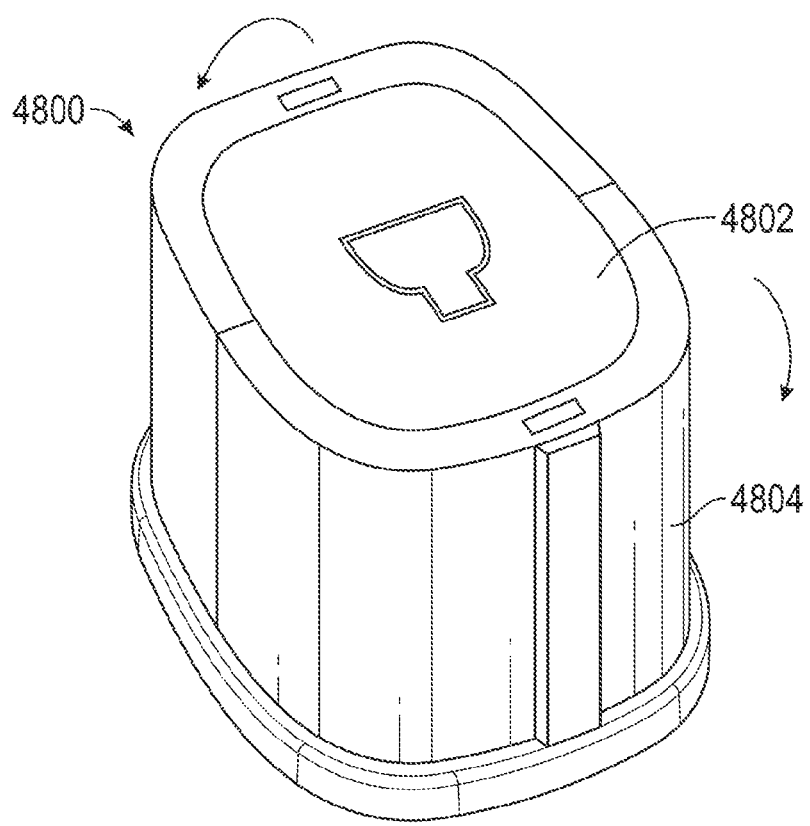

FIG. 248B illustrates a perspective view of a cartridge including the removable body shown in FIG. 248A.

DETAILED DESCRIPTION OF CERTAIN INVENTIVE EMBODIMENTS

The following description and examples illustrate some example embodiments of the disclosure in detail. Those of skill in the art will recognize that there are numerous variations and modifications of the disclosure that are encompassed by its scope. Accordingly, the description of a certain example embodiment should not be deemed to limit the scope of the present disclosure.

Figure 1:
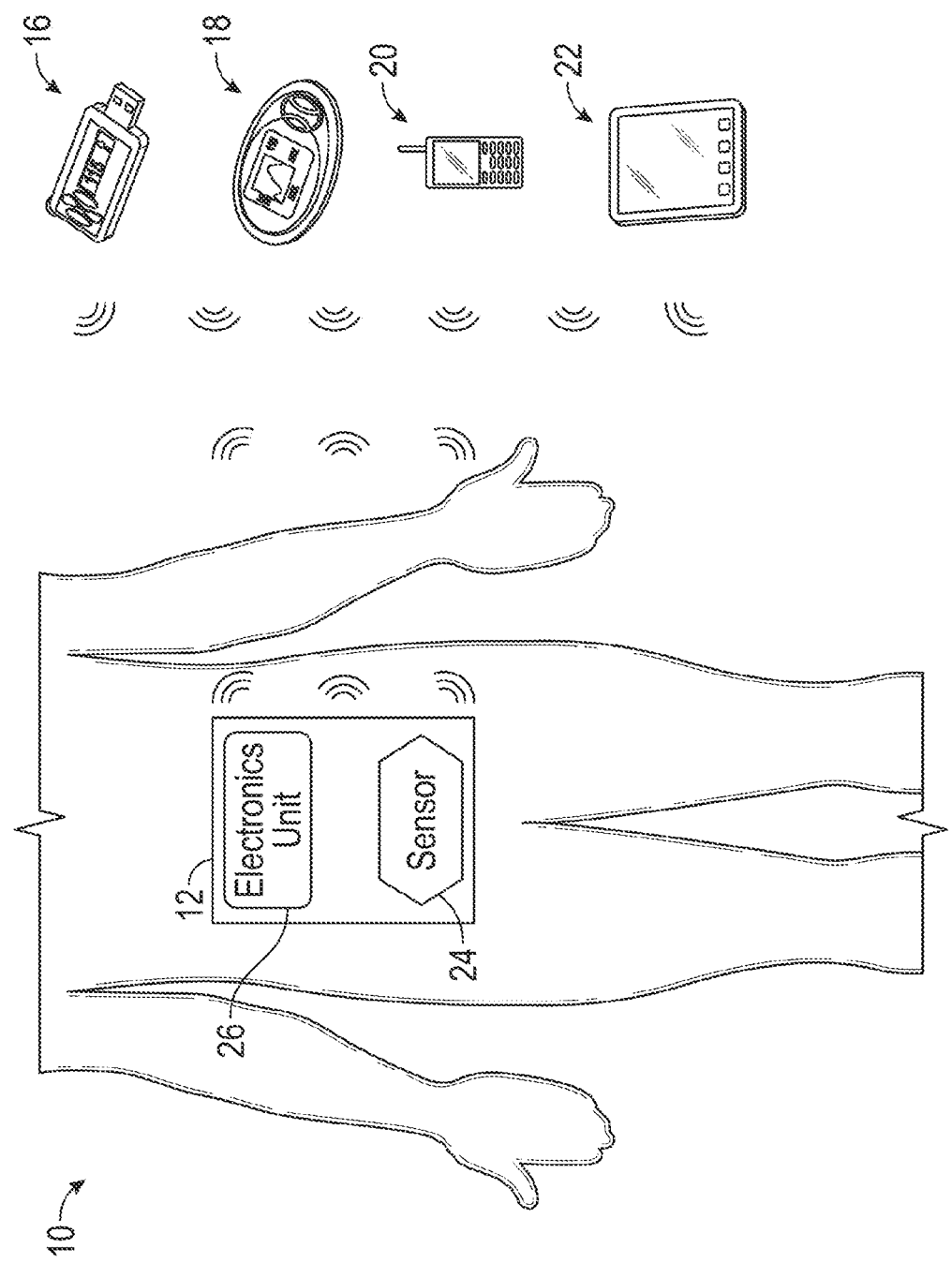
FIG. 1 is a schematic view of an on-skin sensor assembly positioned on an individual and communicating with other devices.

FIG. 1 illustrates a schematic view of a transcutaneous analyte measurement system 10. The transcutaneous analyte measurement system 10 may comprise a continuous analyte measurement system for continuously measuring an analyte of an individual. The transcutaneous analyte measurement system 10 may include a transcutaneous analyte sensor system, which may be in the form of a wearable or on-skin sensor assembly 12, which is shown fastened to the skin of an individual via a disposable housing (not shown). The on-skin sensor assembly 12 may be attached to the individual and be configured to communicate with one or more other example devices 16, 18, 20, 22 of the transcutaneous analyte measurement system 10. The on-skin sensor assembly 12 may include a transcutaneous analyte sensor 24 and an electronics unit 26 (which may be referred to interchangeably as "sensor electronics," "communications device," or "transmitter") for wirelessly transmitting analyte information to a receiver. During use, a sensing portion of the transcutaneous analyte sensor 24 is under the individual's skin and a contact portion of the transcutaneous analyte sensor 24 may be electrically connected to the electronics unit 26. The electronics unit 26 may be engaged with a housing that may be attached to an adhesive patch fastened to the skin of the individual.

The on-skin sensor assembly 12 may be attached to the individual with use of an applicator that may be adapted to provide convenient and secure application. Such an applicator may also be used for inserting the transcutaneous analyte sensor 24 through the individual's skin. Once the transcutaneous analyte sensor 24 has been inserted, the applicator may detach from the on-skin sensor assembly 12 and may be removed from the transcutaneous analyte sensor 24.

In general, the transcutaneous analyte measurement system 10 may include any sensor configuration that provides an output signal indicative of a concentration of an analyte. The output signal including (e.g., sensor data, such as a raw data stream, filtered data, smoothed data, and/or otherwise transformed sensor data) is sent to a receiver which may be e.g., a smart phone, smart watch, dedicated device and the like (marked as example devices 16, 18, 20, 22 in FIG. 1). In one embodiment, the transcutaneous analyte measurement system 10 includes a transcutaneous glucose sensor, such as is described in US Patent Publication No. US-2011-0027127-A1, the contents of which are hereby incorporated by reference in its entirety. In some embodiments, the transcutaneous analyte measurement system 10 includes a continuous glucose sensor and comprises a transcutaneous sensor such as described in U.S. Pat. No. 6,565,509 to Say et al., for example. In another embodiment, the transcutaneous analyte measurement system 10 includes a continuous glucose sensor and comprises a subcutaneous sensor such as described with reference to U.S. Pat. No. 6,579,690 to Bonnecaze et al. or U.S. Pat. No. 6,484,046 to Say et al., for example. In another embodiment, the transcutaneous analyte measurement system 10 includes a continuous glucose sensor and comprises a subcutaneous sensor such as described with reference to U.S. Pat. No. 6,512,939 to Colvin et al. In another embodiment, the transcutaneous analyte measurement system 10 includes a continuous glucose sensor and comprises an intravascular sensor such as described with reference to U.S. Pat. No. 6,477,395 to Schulman et al., for example. In another embodiment, the transcutaneous analyte measurement system 10 includes a continuous glucose sensor and comprises an intravascular sensor such as described with reference to U.S. Pat. No. 6,424,847 to Mastrototaro et al. Other signal processing techniques and glucose monitoring system embodiments suitable for use with the embodiments described herein are described in U.S. Patent Publication No. US-2005-0203360-A1 and U.S. Patent Publication No. US-2009-0192745-A1, the contents of which are hereby incorporated by reference in their entireties. The transcutaneous analyte sensor 24 may extend through a housing that may maintain the sensor on the skin and may provide for electrical connection of the transcutaneous analyte sensor 24 to sensor electronics, which may be provided in the electronics unit 26.

In still further embodiments, a system may be provided utilizing components disclosed herein for use in applying a drug delivery device, such as an infusion device, to the skin of an individual. In such embodiments, the system can include a catheter instead of, or in addition to, a transcutaneous analyte sensor 24, the catheter being connected to an infusion pump configured to deliver liquid medicines or other fluids into the patient's body. In embodiments, the catheter can be deployed into the skin in much the same manner as the transcutaneous analyte sensor 24 would be, for example as described herein.

In one embodiment, the transcutaneous analyte sensor 24 may be formed from a wire or is in a form of a wire. For example, the transcutaneous analyte sensor 24 may include an elongated conductive body, such as a bare elongated conductive core (e.g., a metal wire) or an elongated conductive core coated with one, two, three, four, five, or more layers of material, each of which may or may not be conductive. The elongated transcutaneous analyte sensor 24 may be long and thin, yet flexible and strong. For example, in some embodiments, the smallest dimension of the elongated conductive body of the transcutaneous analyte sensor 24 is less than about 0.1 inches, less than about 0.075 inches, less than about 0.05 inches, less than about 0.025 inches, less than about 0.01 inches, less than about 0.004 inches, or less than about 0.002 inches. The transcutaneous analyte sensor 24 may have a circular cross-section. In some embodiments, the cross-section of the elongated conductive body can be ovoid, rectangular, triangular, polyhedral, star-shaped, C-shaped, T-shaped, X-shaped, Y-Shaped, irregular, or the like. In one embodiment, a conductive wire electrode is employed as a core. To clad such an electrode, one or two additional conducting layers may be added (e.g., with intervening insulating layers provided for electrical isolation). The conductive layers can be comprised of any suitable material. In certain embodiments, it can be desirable to employ a conductive layer comprising conductive particles (i.e., particles of a conductive material) in a polymer or other binder.

In certain embodiments, the materials used to form an elongated conductive body of the transcutaneous analyte sensor 24 (e.g., stainless steel, titanium, tantalum, platinum, platinum-iridium, iridium, certain polymers, and/or the like) can be strong and hard, and therefore are resistant to breakage. For example, in some embodiments, the ultimate tensile strength of the elongated conductive body may be from about 80 kPsi to about 500 kPsi. In another example, in some embodiments, the Young's modulus of the elongated conductive body is from about 160 GPa to about 220 GPa. In still another example, in some embodiments, the yield strength of the elongated conductive body is from about 60 kPsi to about 2200 kPsi. In some embodiments, the transcutaneous analyte sensor 24 may have a small diameter that provides (e.g., imparts, enables) flexibility to these materials, and therefore to the transcutaneous analyte sensor 24 as a whole. Thus, the transcutaneous analyte sensor 24 can withstand repeated forces applied to it by surrounding tissue.

In addition to providing structural support, resiliency and flexibility, in some embodiments, the core (or a component thereof) of the transcutaneous analyte sensor 24 provides electrical conduction for an electrical signal from a working electrode to sensor electronics. In some embodiments, the core may comprise a conductive material, such as stainless steel, titanium, tantalum, a conductive polymer, and/or the like. However, in other embodiments, the core is formed from a non-conductive material, such as a non-conductive polymer. In yet other embodiments, the core may comprise a plurality of layers of materials. For example, in one embodiment the core includes an inner core and an outer core. In a further embodiment, the inner core is formed of a first conductive material and the outer core is formed of a second conductive material. For example, in some embodiments, the first conductive material is stainless steel, titanium, tantalum, a conductive polymer, an alloy, and/or the like, and the second conductive material is conductive material selected to provide electrical conduction between the core and the first layer, and/or to attach the first layer to the core (e.g., if the first layer is formed of a material that does not attach well to the core material). In another embodiment, the core is formed of a non-conductive material (e.g., a non-conductive metal and/or a non-conductive polymer) and the first layer is a conductive material, such as stainless steel, titanium, tantalum, a conductive polymer, and/or the like. The core and the first layer can be of a single (or same) material, e.g., platinum. One skilled in the art appreciates that additional configurations are possible.

In certain embodiments, the electronics unit 26 may be releasably coupled to the transcutaneous analyte sensor 24. The electronics unit 26 may include electronic circuitry associated with measuring and processing the continuous analyte sensor data and may be configured to perform algorithms associated with processing and calibration of data from the transcutaneous analyte sensor 24. For example, the electronics unit 26 may provide various aspects of the functionality of a sensor electronics module as described in U.S. Patent Publication No. 2009-0240120-A1 and U.S. Patent Publication No. 2012-0078071-A1 the contents of which are hereby incorporated by reference in their entireties. The electronics unit 26 may include hardware, firmware, and/or software that enable measurement of levels of the analyte via a glucose sensor, such as a transcutaneous analyte sensor 24. For example, the electronics unit 26 may include a potentiostat, a power source for providing power to the transcutaneous analyte sensor 24, other components useful for signal processing and data storage, and preferably a telemetry module for one- or two-way data communication between the electronics unit 26 and one or more receivers, repeaters, and/or display devices, such as devices 16, 18, 20, 22. Electronics can be affixed to a printed circuit board (PCB), or the like, and can take a variety of forms. For example, the electronics can take the form of an integrated circuit (IC), such as an Application-Specific Integrated Circuit (ASIC), a microcontroller, and/or a processor. The electronics unit 26 may include sensor electronics that are configured to process sensor information, such as storing data, analyzing data streams, calibrating analyte sensor data, estimating analyte values, comparing estimated analyte values with time corresponding measured analyte values, analyzing a variation of estimated analyte values, and the like. Examples of systems and methods for processing sensor analyte data are described in more detail herein and in U.S. Pat. Nos. 7,310,544, 6,931,327, U.S. Patent Publication No. 2005-0043598-A1, U.S. Patent Publication No. 2007-0032706-A1, U.S. Patent Publication No. 2007-0016381-A1, U.S. Patent Publication No. 2008-0033254-A1, U.S. Patent Publication No. 2005-0203360-A1, U.S. Patent Publication No. 2005-0154271-A1, U.S. Patent Publication No. 2005-0192557-A1, U.S. Patent Publication No. 2006-0222566-A1, U.S. Patent Publication No. 2007-0203966-A1 and U.S. Patent Publication No. 2007-0208245-A1, the contents of which are hereby incorporated by reference in their entireties.

One or more repeaters, receivers and/or display devices, such as key fob repeater 16, medical device receiver 18 (e.g., insulin delivery device and/or dedicated glucose sensor receiver), smart phone 20, portable computer 22, and the like are operatively linked to the electronics unit 26, which receive data from the electronics unit 26 and in some embodiments transmit data to the electronics unit 26. For example, the sensor data can be transmitted from the sensor electronics unit 26 to one or more of key fob repeater 16, medical device receiver 18, smart phone 20, portable computer 22, and the like. In one embodiment, a repeater, receiver and/or display device may include an input module with a quartz crystal operably connected to an RF transceiver (not shown) that together function to transmit, receive and synchronize data streams from the electronics unit 26. However, the input module can be configured in any manner that is capable of receiving data from the electronics unit 26. Once received, the input module sends the data stream to a processor that processes the data stream, such as described in more detail below. The processor is the central control unit that performs the processing, such as storing data, analyzing data streams, calibrating analyte sensor data, estimating analyte values, comparing estimated analyte values with time corresponding measured analyte values, analyzing a variation of estimated analyte values, downloading data, and controlling the user interface by providing analyte values, prompts, messages, warnings, alarms, and the like. The processor includes hardware that performs the processing described herein, for example read-only memory (ROM) provides permanent or semi-permanent storage of data, storing data such as sensor ID (sensor identity), receiver ID (receiver identity), and programming to process data streams (for example, programming for performing estimation and other algorithms described elsewhere herein) and random access memory (RAM) that stores the system's cache memory and is helpful in data processing. An output module, which may be integral with and/or operatively connected with the processor, includes programming for generating output based on the sensor data received from the electronics unit (and any processing that incurred in the processor).

In some embodiments, analyte values are displayed on a display device. In some embodiments, prompts or messages can be displayed on the display device to convey information to the user, such as reference outlier values, requests for reference analyte values, therapy recommendations, deviation of the measured analyte values from the estimated analyte values, or the like. Additionally, prompts can be displayed to guide the user through calibration or troubleshooting of the calibration.

Additionally, data output from the output module can provide wired or wireless, one- or two-way communication between the receiver and an external device. The external device can be any device that interfaces or communicates with the receiver. In some embodiments, the external device is a computer, and the receiver is able to download current or historical data for retrospective analysis by a physician, for example. In some embodiments, the external device is a modem, and the receiver is able to send alerts, warnings, emergency messages, or the like, via telecommunication lines to another party, such as a doctor or family member. In some embodiments, the external device is an insulin pen, and the receiver is able to communicate therapy recommendations, such as insulin amount and time, to the insulin pen. In some embodiments, the external device is an insulin pump, and the receiver is able to communicate therapy recommendations, such as insulin amount and time to the insulin pump. The external device can include other technology or medical devices, for example pacemakers, implanted analyte sensor patches, other infusion devices, telemetry devices, or the like. The receiver may communicate with the external device, and/or any number of additional devices, via any suitable communication protocol, including radio frequency, Bluetooth, universal serial bus, any of the wireless local area network (WLAN) communication standards, including the IEEE 802.11, 802.15, 802.20, 802.22 and other 802 communication protocols, ZigBee, wireless (e.g., cellular) telecommunication, paging network communication, magnetic induction, satellite data communication, GPRS, ANT, and/or a proprietary communication protocol.

The transcutaneous analyte measurement system 10 may be inserted into the skin of an individual by use of an applicator for the transcutaneous analyte sensor system. The transcutaneous analyte sensor system may be in form of an on-skin sensor assembly 12, as discussed in regard to FIG. 1.

Figure 2:
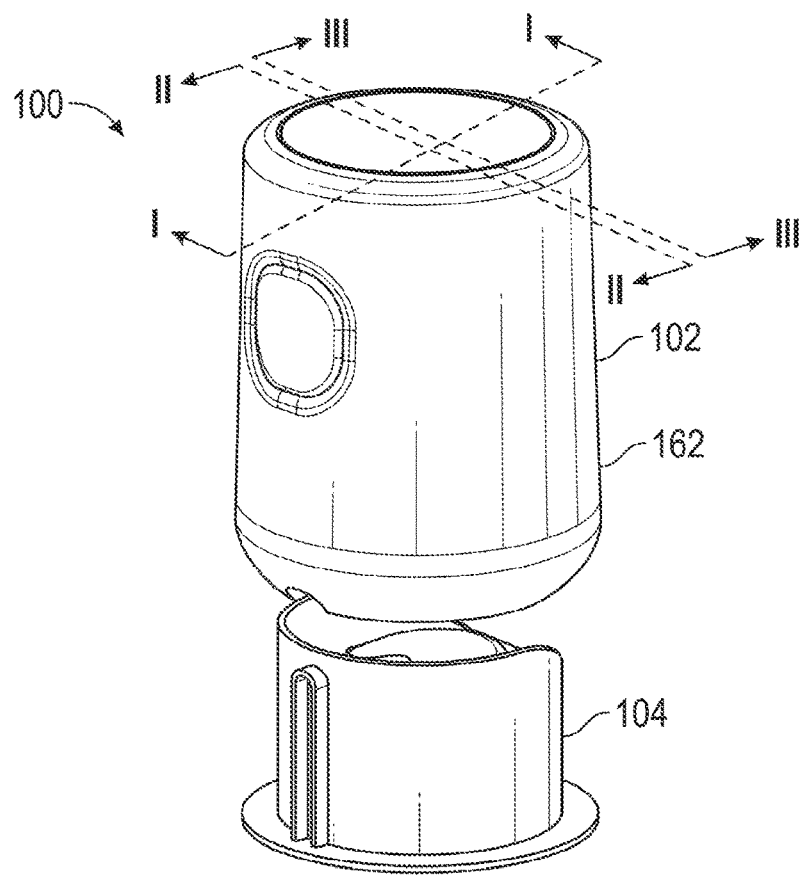
FIG. 2 illustrates a perspective view of a system.

FIG. 2 illustrates an embodiment of a system 100 for inserting a transcutaneous analyte sensor into an individual's skin. The system 100 may be configured to deploy an on-skin sensor assembly to the individual's skin. The system 100 may include an applicator 102 and may include a cartridge 104 configured to couple with the applicator 102. The cartridge 104 may be configured to retain all or a portion of the transcutaneous analyte sensor system (e.g., an on-skin sensor assembly 12) prior to deployment to the individual's skin.

Figure 3:
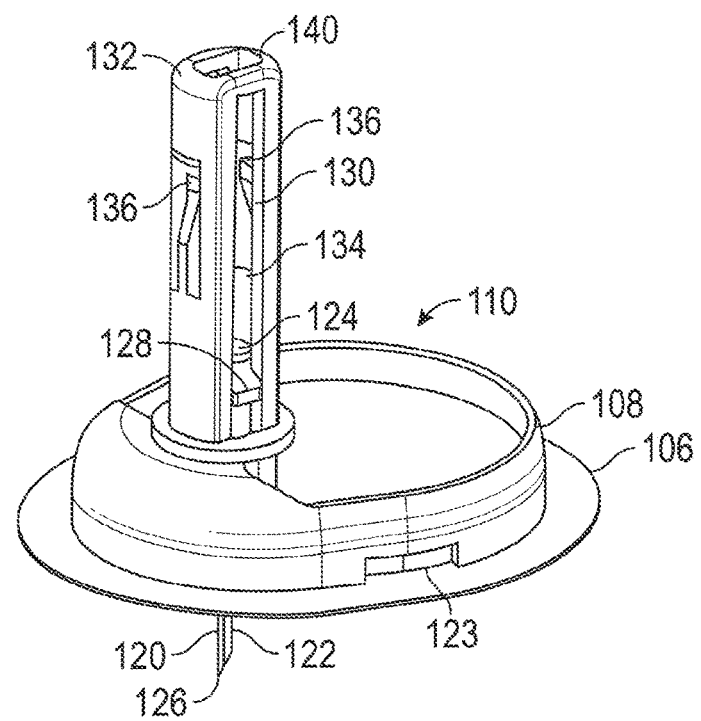
FIG. 3 illustrates a perspective view of components of an on-skin sensor assembly.

FIG. 3, for example, illustrates components of a transcutaneous analyte sensor system that may be retained by the cartridge 104. The components may include a patch 106 and a housing for the on-skin sensor assembly (a wearable housing 108). The patch 106 may comprise an adhesive patch that may be utilized to adhere the wearable housing 108 to the individual's skin. The patch 106 may extend radially outward from the wearable housing 108 and may surround the wearable housing 108. The patch 106 may have a disk shape, or other shapes as desired. The patch 106 may be made of a flexible material, such as a cloth, or a polymer material, or a combination thereof, among other types of flexible materials. The patch 106 may have an adhesive surface for being applied to the individual's skin. The wearable housing 108 may include a receiver 110 for coupling to an electronics unit 26, which may include a communications device such as a transmitter, and may include other electronics of the transcutaneous analyte sensor system. The electronics unit 26 may be coupled to the wearable housing 108 to couple the electronics unit 26 to the transcutaneous analyte sensor 24. The receiver 110 may comprise a cavity in the wearable housing 108 for receiving the electronics unit 26.

Figure 4:
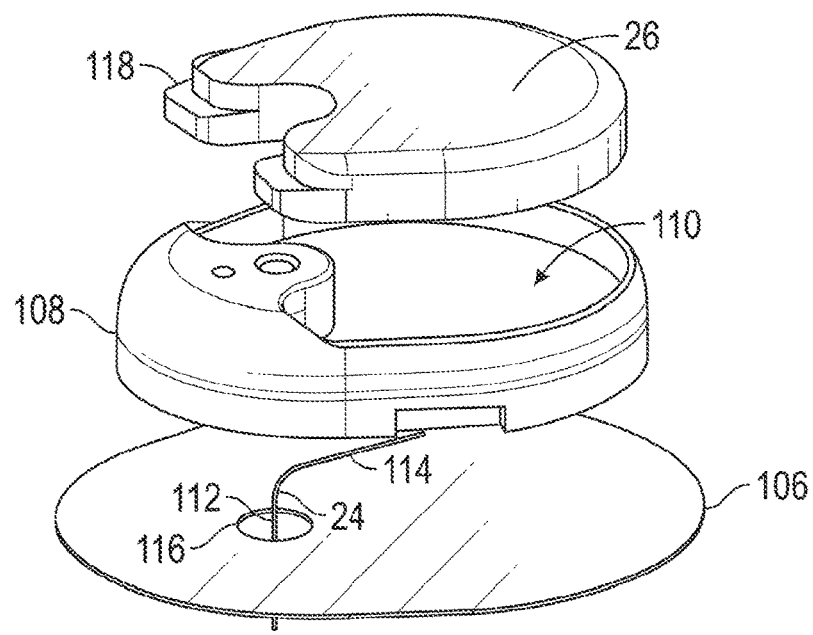
FIG. 4 illustrates an exploded view of components of an on-skin sensor assembly.

Other components of the transcutaneous analyte sensor system may include the transcutaneous analyte sensor 24 and the electronics unit 26. FIG. 4, for example, illustrates an exploded view of a transcutaneous analyte sensor system, in the form of an on-skin sensor assembly, showing the transcutaneous analyte sensor 24 and the electronics unit 26. The transcutaneous analyte sensor 24, as shown in FIG. 4, may comprise a wire, and may have a sensing portion 112 and a contact portion 114. The sensing portion 112 may be configured to be under the individual's skin for sensing the analyte and the contact portion 114 of the transcutaneous analyte sensor 24 may be configured to be electrically connected to the electronics unit 26. The transcutaneous analyte sensor 24 may be configured to be positioned between the patch 106 and the wearable housing 108. The sensing portion 112 may extend downward, transverse to the plane that the wearable housing 108 extends in, and may extend through an opening 116 in the patch 106. The contact portion 114 may extend parallel to the plane that the wearable housing 108 extends in, and may be configured to engage a coupler that allows electrical signals from the contact portion 114 to be provided to the electronics unit 26.

The electronics unit 26 may operate as disclosed herein and may be configured to be inserted into the receiver 110 of the wearable housing 108. The electronics unit 26 may be configured to include a coupler 118 in the form of a tab (as shown in FIG. 4), or in another form as desired for coupling to the wearable housing 108. The tab may slide into a cavity of the wearable housing 108 having a corresponding shape. The electronics unit 26 may be configured to receive electrical signals from the contact portion 114 of the transcutaneous analyte sensor 24.

The electronics unit 26 may be configured to be separable from the wearable housing 108, such that the wearable housing 108 may be applied to the skin of the individual and the transcutaneous analyte sensor 24 may be inserted into the skin of the individual without the electronics unit 26 being coupled to the wearable housing 108. The electronics unit 26 may later be coupled to the wearable housing 108 after the wearable housing 108 is applied to the skin of the individual and the transcutaneous analyte sensor is inserted into the skin of the individual. The coupler 118 may be utilized to couple the electronics unit 26 to the housing 108. In embodiments, the wearable housing 108 may be applied to the skin of the individual and the transcutaneous analyte sensor 24 may be inserted into the skin of the individual with the electronics unit 26 coupled to the wearable housing 108.

The electronics unit 26 may be removably coupled to the wearable housing 108 such that the electronics unit 26 may be removed from the wearable housing 108 when the wearable housing 108 is to be replaced. For example, after a certain period of wear of the transcutaneous analyte sensor system, the transcutaneous analyte sensor 24, the patch 106, and the wearable housing 108 may be removed from the individual's body in order to be discarded. The transcutaneous analyte sensor 24, the patch 106, and the wearable housing 108 accordingly may be disposable and may be intended for a single implantation. The electronics unit 26 accordingly may be removed from the wearable housing 108 at a time for disposal of the wearable housing 108, such that the electronics unit 26 may be used again with a different wearable housing. The electronics unit 26 as such may be for repeated use and the transcutaneous analyte sensor 24, the patch 106, and the wearable housing 108 may be for single use. The electronics unit 26 may be removable from the wearable housing 108 for a variety of other reasons, including recharge of a battery contained in the electronics unit 26, replacement of a battery contained in the electronics unit 26, download of data from the electronics unit 26 to an external device, or another reason as desired. In embodiments, the electronics unit 26 may be integral with the wearable housing 108 and may be configured to comprise a disposable or single use electronics unit 26 that is disposed along with the transcutaneous analyte sensor 24, the patch 106, and the wearable housing 108. In embodiments, the electronics unit 26 may be releasably coupled with the housing 108 yet may be configured to comprise a disposable or single use electronics unit 26 that is disposed along with the transcutaneous analyte sensor 24, the patch 106, and the wearable housing 108. For example, the electronics unit 26 may be separated from the wearable housing 108 during implantation of the transcutaneous analyte sensor 24, and then coupled to the wearable housing 108 following implantation of the transcutaneous analyte sensor 24. The electronics unit 26 though may be discarded along with the transcutaneous analyte sensor 24, the patch 106, and the wearable housing 108.

Referring back to FIG. 3, further components of the system 100 may be retained by the cartridge 104. Such components may include a needle 120, which may include a needle shaft 122 and a needle hub 124. The needle shaft 122 may include a penetrating tip 126 at a distal end of the needle shaft 122 and may have the needle hub 124 positioned at a proximal end of the needle shaft 122. The needle hub 124 may include coupling members 128 that may be configured to engage a releasable coupler. The coupling members 128 as shown in FIG. 3 may comprise protrusions extending from the needle hub 124. The protrusions may extend into a guide channel 130 of a needle cover 132, to guide the movement of the needle 120 within a slide channel 134 of the needle cover 132. For example, the protrusions may prevent undesired axial rotation of the needle 120 within the slide channel 134. In other embodiments, the coupling members 128 may have a different form, for example, the coupling members 128 may comprise cavities in the needle hub 124, or other shapes of protrusions, or even magnetically coupling structures in an embodiment in which a magnetic coupler is utilized. A variety of forms of coupling members 128 may be utilized.

A needle cover 132 may be retained by the cartridge 104. The needle cover 132 may have a distal end coupled to a portion of the wearable housing 108 and a proximal end extending away from the wearable housing 108 in a direction transverse to a plane that the wearable housing 108 extends in. The needle cover 132 may be configured to be separable from the wearable housing 108. The needle cover 132 may extend upward from the wearable housing 108 and have a column shape as shown in FIG. 3. The needle cover 132 may comprise a body forming a sheath configured to extend over at least a portion of the needle 120 when the needle 120 is retracted into the needle cover 132 as disclosed herein. The needle 120 may be configured to be moved relative to the needle cover 132 to be positioned into the needle cover 132. The needle cover 132 may include a slide channel 134 positioned centrally in the cover body and configured for the needle 120 to slide in, particularly in a proximal direction. The needle cover 132 may be configured to cover at least a portion of the needle 120 following the needle 120 guiding the transcutaneous analyte sensor into the skin of the individual.

The needle cover 132 may include one or more guide channels 130 (a similar guide channel 130 is located on the opposite side of the cover 132) for the coupling members 128 of the needle hub 124 to slide along. The needle cover 132 may include locks 136 that may be part of the body of the needle cover 132 and may extend inward towards the slide channel 134. The locks 136 may be configured to lock to and engage locking members 138 (marked in FIG. 26) of the needle hub 124. The engagement of the lock 136 with the locking members 138 may hold the needle 120 in position within the slide channel 134 when the needle 120 is retracted within the slide channel 134. The lock 136 may hold the needle 120 within the slide channel 134 such that the needle cover 132 covers the penetrating tip 126, such that an individual cannot contact the penetrating tip 126 upon retraction of the needle 120 into the slide channel 134. The locking members 138 may comprise contoured surfaces of the needle hub 124 or may have another configuration as desired.

The proximal end of the needle cover 132 may include an opening 140 that is configured to receive a release actuator configured to release the needle 120 and the needle cover 132 from a releasable coupler, and accordingly from the applicator, as disclosed herein.

The needle cover 132 may be configured to separate from the wearable housing 108 at a desired time, with the distal end of the needle cover 132 being removed from the wearable housing 108. The needle cover 132 when positioned in the cartridge 104, however, may be in a configuration as shown in FIG. 3 and coupled to the wearable housing 108.

Figure 5:
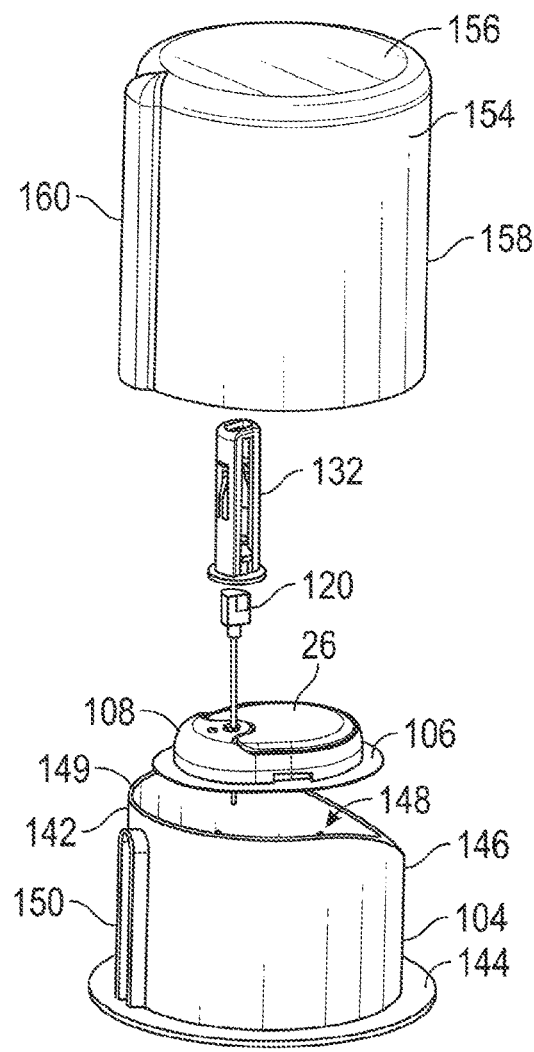
FIG. 5 illustrates an exploded view of components of a cartridge.

FIG. 5 shows an exploded view of an assembly of components of the cartridge 104. The cartridge 104 may include a body 142 having a base 144 and a wall 146. The body 142 may be configured to be coupled to the applicator housing. The base 144 may form a bottom of the cartridge 104 that the cartridge 104 may be positioned upon. As shown in FIG. 5, the base 144 may form a flange extending outward from the wall 146. The wall 146 may extend upward from the base 144, transverse to a direction that the base 144 extends in. The wall 146 may extend around and define a cavity 148 that may receive components of the cartridge including the transcutaneous analyte sensor 24 and the needle 120. The wall 146 may extend around at least a portion of the needle cover 132. The wall 146 may extend upward to an upper opening 149 that exposes the components retained by the body 142. The wall 146 may including an inner surface configured to face inward towards a central portion of the cartridge 104 and the transcutaneous analyte sensor 24 may include an outer surface facing opposite the inner surface. The outer surface of the wall may be configured to be positioned within at least a portion of an applicator. The outer surface of the wall may comprise a mating surface for a receiver of the applicator, and may be contoured to a shape of an inner surface of the receiver of the applicator.

The wall 146 may have a shape that is configured to be inserted into a receiver of an applicator, and may be shaped such that only certain orientations of the cartridge 104 relative to the receiver of the applicator may allow for coupling of the cartridge 104 to the applicator. For example, the outer surface of the wall 146 may have an asymmetric contour in at least one dimension, such as an ovoid shape, that only allows for mating in a single rotational orientation between the cartridge 104 and the applicator. In embodiments, for example, as shown in FIG. 5, a protrusion 150 may be positioned on the outer surface of the cartridge 104 and may extend in an axial direction. The protrusion 150 may be utilized to allow the cartridge 104 to align with the receiver of the applicator in the correct rotational orientation. The protrusion 150 may be configured to fit within a complementary shaped channel of the applicator. The shape of the cartridge or the protrusion may comprise a keyed portion of the cartridge configured to align the cartridge with the receiver in a single rotational orientation.

The body 142 may include a retainer 152 (marked in FIG. 21) that is configured to retain the transcutaneous analyte sensor 24, the wearable housing 108, and the patch 106, and the other components coupled thereto including the needle 120 and the needle cover 132. The retainer 152 may comprise a recess within the body 142 that the transcutaneous analyte sensor 24, the wearable housing 108, and the patch 106 are positioned within. The recess may be shaped to the outer contour shape of the patch 106 to prevent the patch 106 and wearable housing 108 from rotating within the body 142. In other embodiments, other forms of retainers 152 may be utilized, such as clasps, clips, pins, or other forms of retainers. The retainer 152 may at least retain the transcutaneous analyte sensor 24, the wearable housing 108, and the patch 106 such that the wall 146 extends around at least a portion of one or more of the transcutaneous analyte sensor 24, the wearable housing 108, the patch 106, the needle 120, and the cover 132. The inner surface of the wall may be configured to face inward towards the transcutaneous analyte sensor 24 and the outer surface of the wall may be configured to face opposite the transcutaneous analyte sensor 24.

Figure 21:
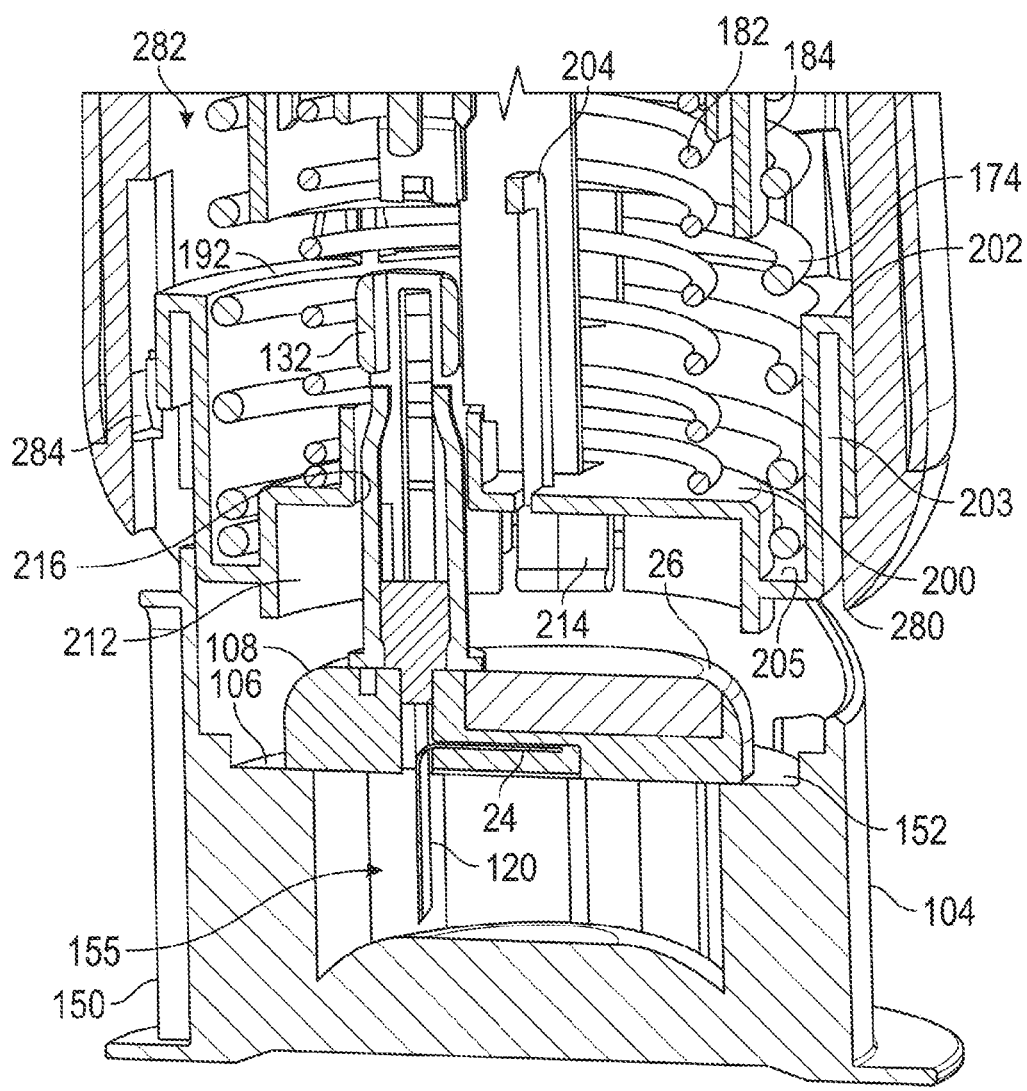
FIG. 21 illustrates a cross sectional view of the applicator shown in FIG. 2 along line I-I, with a cross section of a cartridge taken along the same line I-I.

Referring to FIG. 21, the body 142 of the cartridge 104 may include a central cavity 155 that is configured to receive the needle 120 when positioned within the body 142 of the cartridge 104 and retained by the retainer 152.

Referring back to FIG. 5, the cartridge 104 may include a removable cover 154 that extends over a portion of the body 142. The removable cover 154 covers the upper opening 149 and may block access to the components contained within the body 142. The cover 154 may have a cylindrical shape as shown in FIG. 5, with a top surface 156 and a side surface 158 extending axially downward from the top surface 156. The top surface 156 may be configured to be positioned over the upper opening 149 and the side surface 158 may be configured to be positioned over the outer surface of the wall 146 when the removable cover 154 is positioned over the body 142. The side surface 158 may have a contoured portion 160 that may be configured to extend over the protrusion 150 and may have a shape that is complementary to the shape of the protrusion 150.

The removable cover 154 may comprise a body, such as a canister body, having a height and a width and covers the needle cover 132. The side surface 158 of the removable cover 154 may be configured to have a height such that the needle cover 132 may extend upward from the wearable housing 108 without being undesirably compressed by the top surface 156 of the removable cover 154. The top surface 156 may have a width corresponding to the width of the cartridge 104.

The removable cover 154 may be configured to form a hermetic seal of the upper opening 149, to seal the contents of the body 142 and prevent microbes, or undesired human interaction with the interior of the body 142 and the components contained therein. Thus, components such as the needle 120 and the transcutaneous analyte sensor 24 that may be inserted into an individual's skin may remain sterile within the body 142. The removable cover 154 may cover the contents of the cartridge 104, including the transcutaneous analyte sensor 24 and the needle 120 within the cartridge 104.

The components of the transcutaneous analyte sensor system may be retained by the body 142 prior to deployment to the individual's skin. Such components may or may not include the electronics unit 26, which is shown in FIG. 5, which ultimately may be provided separately from the cartridge 104 and coupled to the wearable housing 108 after deployment of the wearable housing 108 to the individual's skin. The needle 120 and needle cover 132 may be retained by the body 142 and positioned under the removable cover 154. A variety of other components may be retained by the body 142 as desired.

Figure 6:
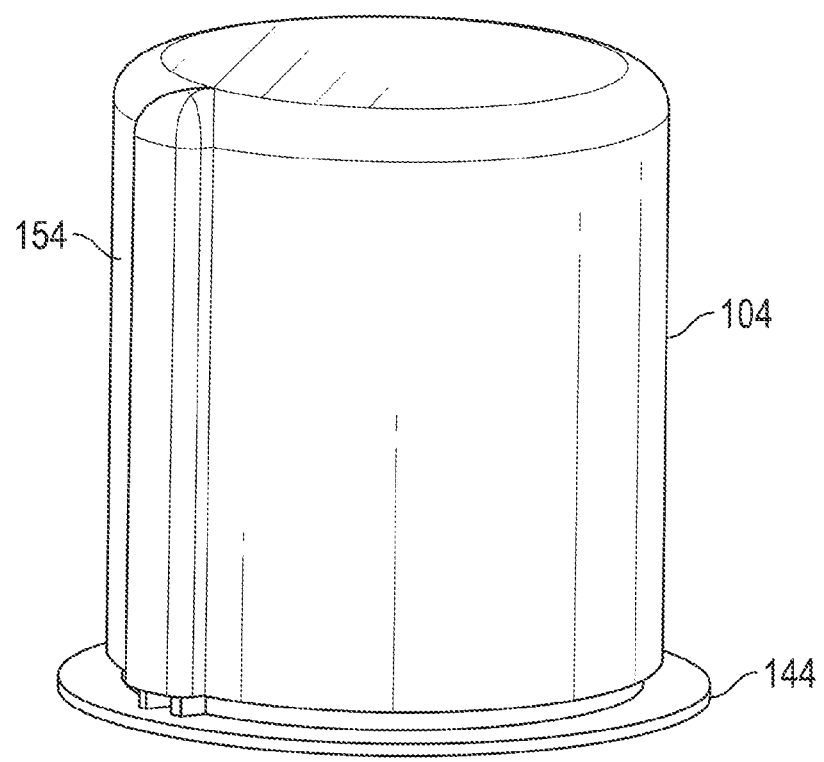
FIG. 6 illustrates a perspective view of a cartridge.

FIG. 6 illustrates a perspective view of the cartridge 104 including the removable cover 154 in position. The cartridge 104 may be provided as a unit that is supplied to an individual for use with a transcutaneous analyte sensor applicator. The unit may comprise a sealed unit that retains the contents in a sterile condition prior to deployment of the transcutaneous analyte sensor system. The removable cover 154 may be removed and then discarded. The body 142 of the cartridge 104 may be configured to be coupled to an applicator for the components of the transcutaneous analyte sensor system to be deployed to the individual's skin. The body 142 of the cartridge may be discarded, and if another transcutaneous analyte sensor system is desired to be deployed to the individual's skin, then another cartridge 104 may be utilized. As such, multiple cartridges may be utilized with the applicator, with components of the cartridges being discarded after use.

Figure 7:
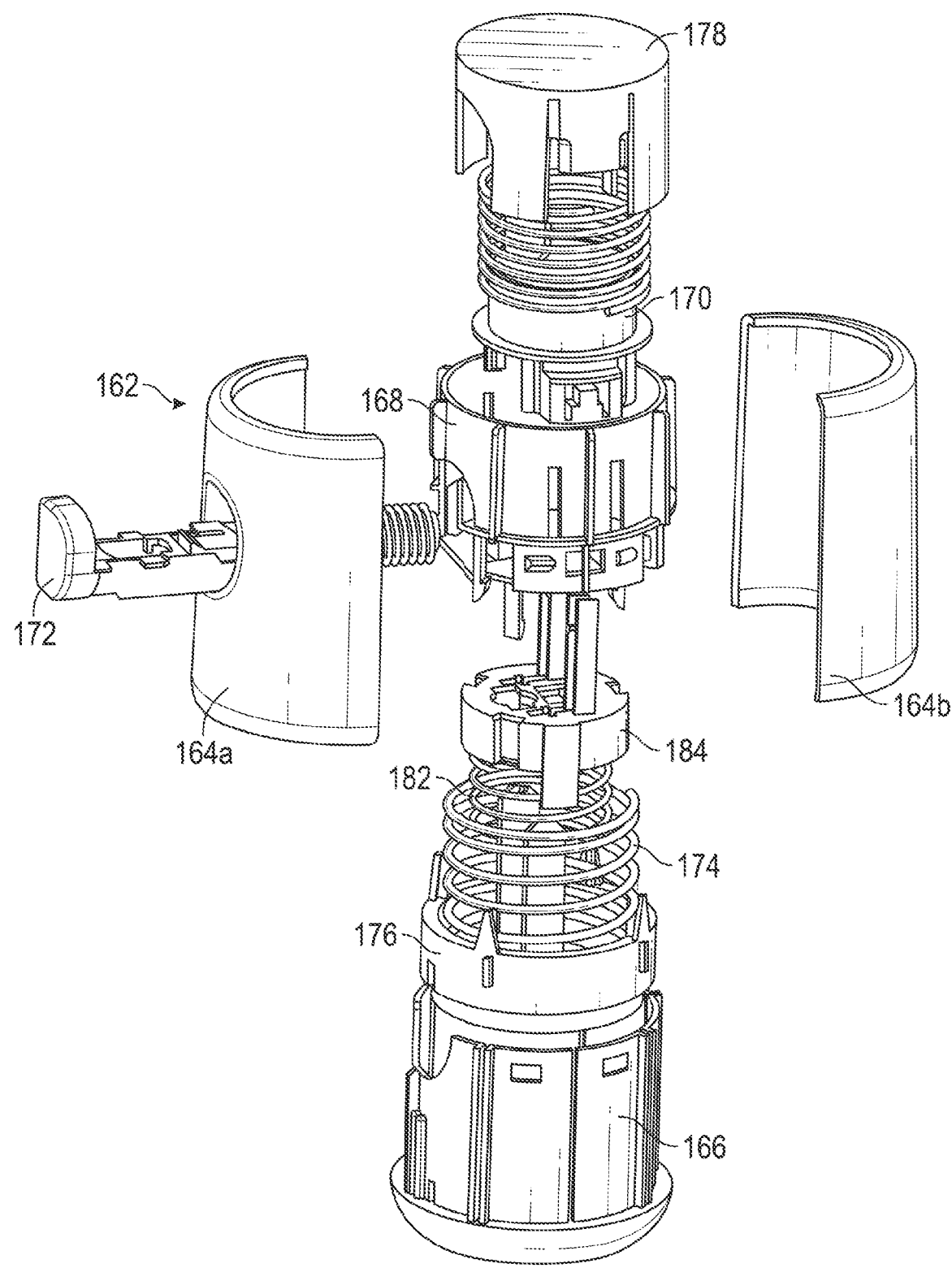
FIG. 7 illustrates an exploded perspective view of the applicator shown in FIG. 2.

FIG. 7 illustrates an exploded perspective view of the applicator 102 shown in FIG. 2. The applicator 102 comprises a transcutaneous analyte sensor applicator, and is configured to apply other components of the transcutaneous analyte sensor system to the skin of an individual including the wearable housing 108 and patch 106 of the transcutaneous analyte sensor system. The applicator may deploy all or a portion of components of an on-skin sensor assembly 12 to an individual's skin.

The applicator 102 comprises a reusable applicator, which may be repeatedly utilized for deployment of transcutaneous analyte sensor, as well as other components of a transcutaneous analyte sensor system. As such, the applicator 102 may not be intended to be discarded after a single use, and comprise a multi-use applicator. The applicator 102 however may be configured to deploy transcutaneous analyte sensors, as well as other components of a transcutaneous analyte sensor system that may be intended for a single use. The applicator 102 may be configured to be reloaded with multiple different transcutaneous analyte sensors, and other components of a transcutaneous analyte sensor systems, for repeated deployment of the multiple different components.

FIG. 7 illustrates components of the applicator 102. The applicator 102 may include an applicator housing 162, which may comprise a single component or multiple components. As shown in FIG. 7, the applicator housing 162 may include side cover bodies 164*a, b*, a lower body 166, an upper body 168, and a support body 170. The components of the applicator housing 162 may be coupled together to form a single applicator housing 162. The applicator housing 162 may be configured to be gripped by an individual to apply the transcutaneous analyte sensor into the individual's skin, to be held during deployment of the transcutaneous analyte sensor, as well as other components of a transcutaneous analyte sensor system. As shown in FIG. 2, for example, the applicator housing 162 may have a cylindrical shape with an outer surface configured to be gripped by an individual. Other shapes of the applicator housing 162 may be utilized as desired.

The applicator housing 162 may include a side portion (formed by the side cover bodies 164*a, b*), a top portion (formed by the control device 178) and a bottom portion including an opening 280 shown in FIG. 21 for the transcutaneous analyte sensor to be deployed from to be inserted into the individual's skin. The opening 280 may be configured for the needle 120 and the transcutaneous analyte sensor 24 to pass through to insert the transcutaneous analyte sensor 24 into the individual's skin.

FIG. 7 illustrates other components of the applicator 102. The components may include an actuator that may be coupled to the applicator housing 162 and is configured to insert the needle 120 into the individual's skin to deposit the transcutaneous analyte sensor 24 into the individual's skin. Such an actuator may be referred to as an insertion actuator. The insertion actuator may include components that may include a control device 172 and a driver 174, and may include a carriage 176. The insertion actuator may include other components (or fewer components) in other embodiments. The applicator 102 may include a release actuator that is configured to release the needle 120 from a releasable coupler. The release actuator may include components that may include a control device 178 and may include a pressing surface 180 (marked in FIG. 18) that is configured to apply a force to the releasable coupler to cause the needle 120 to release from the releasable coupler. The release actuator may be configured to release the needle 120 from the releasable coupler to allow the needle 120 to be passed through the opening 280 at the bottom portion of the applicator housing. The release actuator may include other components (or fewer components) in other embodiments. The applicator 102 may include a retraction actuator that is configured to retract the needle 120 from the individual's skin following insertion of the transcutaneous analyte sensor into the individual's skin. The retraction actuator may include components that may include a driver 182 and a carriage 184. The retraction actuator may include other components (or fewer components) in other embodiments. The configuration of components in the applicator 102 may be varied in other embodiments.

Figure 8:
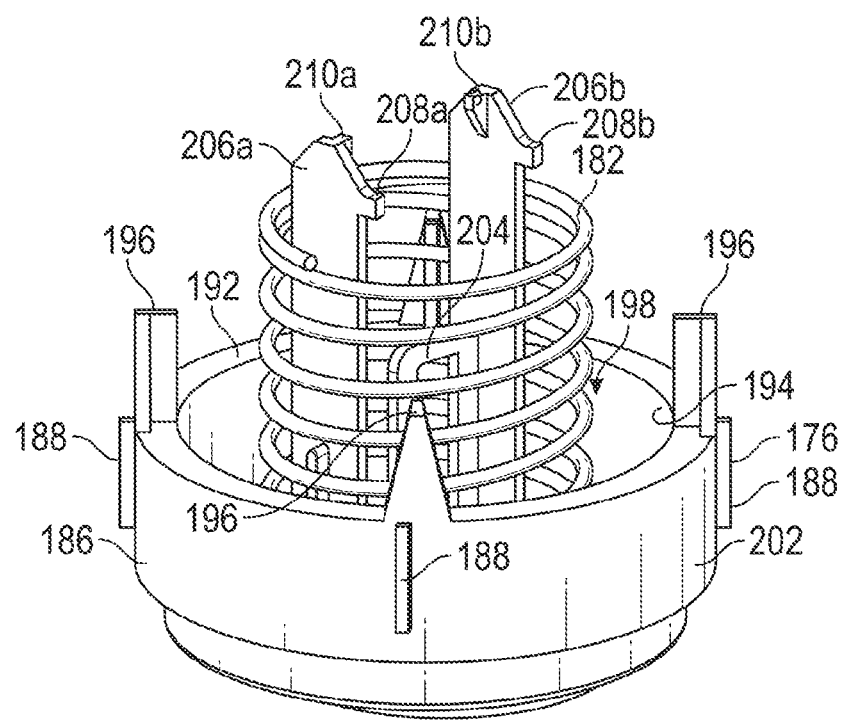
FIG. 8 illustrates a perspective assembly view of a carriage of the applicator shown in FIG. 2.

FIG. 8 illustrates a perspective view of the carriage 176 of the insertion actuator. The carriage 176 may comprise a body configured to slide within an interior cavity of the applicator 102 that may be defined by the applicator housing 162. The carriage 176 may be configured to slide relative to the applicator housing and be configured to be slid by the driver 174 of the insertion actuator. The carriage 176 may include an outer ring 202 having an outer surface 186 that may include protrusions 188 that slide along channels 190 (marked in FIG. 12) of the lower body 166 of the applicator housing 162. The position of the protrusions 188 within the channels 190 may prevent the carriage 176 from undesirably rotating axially within the applicator housing 162. The protrusions 188 may be spaced from each other on the outer surface 186 of the carriage 176.

The outer ring 202 of the carriage 176 may include an upper surface 192 that spans between the outer surface 186 of the carriage 176 and an inner surface 194 of the outer ring 202 of the carriage 176. Stops 196 may protrude upward from the upper surface 192 of the carriage 176 for contacting a portion of the release actuator and impeding movement of the portion of the release actuator.

The inner surface 194 may face opposite the outer surface 186 and may surround a cavity 198 of the carriage 176. The cavity 198 may be configured to receive the carriage 184 of the retraction actuator and may be configured to receive a driver 182 of the retraction actuator.

The carriage 176 may include a central body 200 (marked in FIG. 21) that spans the interior of the outer ring 202 (marked in FIG. 21) of the carriage 176. The outer ring 202 may include a channel 203 (marked in FIG. 21) configured to receive the wall 146 of the cartridge 104. A channel 205 (marked in FIG. 21) may extend circumferentially around the central body 200 between the central body 200 and the outer ring 202. The channel 205 may be configured to receive the driver 174 of the insertion actuator.

An upper surface of the central body 200 may include a releasable coupler 204 configured to couple to a coupling member of the insertion actuator. The releasable coupler 204 may comprise a U-shaped body having a central opening that the coupling member, which may be in the form of a ledge, is configured to extend into. The U-shaped body extends upward from the central body 200 and is configured to be deflectable to bend off of the ledge of the insertion actuator, to release the releasable coupler 204 from the ledge. In other embodiments, the releasable coupler 204 may have different forms.

Referring to FIG. 8, one or more arms 206a, b may extend upward from the central body 200 of the carriage 176 and may include releasable couplers 208a, b that are configured to couple with portions of the carriage 184 of the retraction actuator. The releasable couplers 208a, b may comprise protrusions as shown in FIG. 8, yet in other embodiments may have other configurations. Coupler releases in the form of deflectors 210a, b may be coupled to the respective arms 206a, b and may be configured to deflect the arms 206a, b in a direction transverse to the axial dimension of the applicator 102 to release the releasable couplers 208a, b in a manner disclosed herein.

Referring to FIG. 21, a lower surface of the central body 200 may include a receiver 212 that is configured to receive at least a portion of the transcutaneous analyte sensor system. The receiver 212 may comprise a cavity that is configured to receive the transcutaneous analyte sensor system. As shown in FIG. 21, the receiver 212 may include at least one releasable coupler 214 that is configured to couple to the wearable housing 108 of the transcutaneous analyte sensor system. The releasable coupler 214 may comprise a protrusion configured to enter into a cavity 123 (marked in FIG. 3) of the wearable housing 108 to couple to the wearable housing 108. In other embodiments, other forms of releasable couplers 214 may be utilized.

Referring to FIG. 21, an opening 216 may be positioned on the central body 200 and may extend through the lower surface of the central body 200 to the upper surface of the central body 200. The opening 216 may be configured for the needle cover 132 to pass through.

The configuration of the carriage 176 may be varied in other embodiments.

FIG. 8 represents an assembly view of the carriage 176, with the driver 182 of the retraction actuator shown in position within the cavity 198 of the carriage 176. The driver 182 may comprise a device for driving the carriage 184 and driving the retraction actuator, and may be configured to provide a motive force to cause the carriage 184 to slide within the applicator housing 162. The driver 182 may be configured to drive the needle 120 out of the individual's skin. The driver 182 may comprise a spring as shown in FIG. 8. The spring may be configured to be provided with energy that compresses the spring, upon which the spring exerts a responsive force that releases the energy and expands the spring. The spring may be a helical spring as shown in FIG. 8, or in other embodiments other configurations of springs or other drivers may be utilized as desired.

Figure 9:
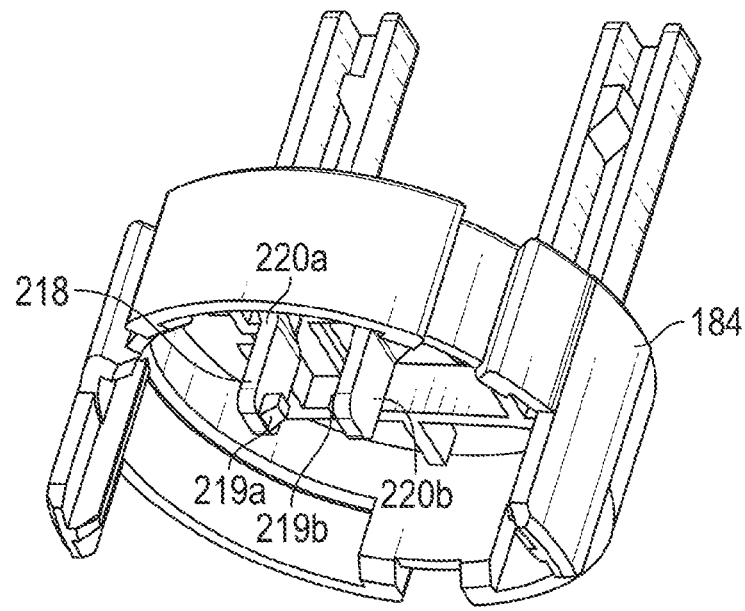
FIG. 9 illustrates a bottom perspective view of a carriage of the applicator shown in FIG. 2.

FIG. 9 illustrates a bottom perspective view of the carriage 184 of the retraction actuator. The carriage 184 may be configured to slide relative to the applicator housing and be configured to be slid by the driver 182 and driver 174. The lower surface of the carriage 184 may include a releasable coupler 218 that is configured to retain the needle 120 at least partially within the applicator housing 162 following insertion of the transcutaneous analyte sensor 24 into the individual's skin and removal of the applicator housing 162 from the transcutaneous analyte sensor 24, and configured to release the needle 120 from within the applicator housing 162 following insertion of the transcutaneous analyte sensor 24 into the individual's skin. As shown in FIG. 9, the releasable coupler 218 may include one or more protrusions 219a, b that are configured to releasably couple to the needle 120, particularly the coupling members 128 of the needle hub 124 shown in FIG. 3. The protrusions 219a, b may overlap the surfaces of the coupling members 128 to couple to the coupling members 128. The protrusions 219a, b may be angled such that the protrusions 219a, b slide over angled portions of the coupling members 128 to couple to the coupling members 128.

The releasable coupler 218 may include respective arms 220a, b coupled to the protrusions 219a, b and having the protrusions 219a, b at their distal ends. The arms 220a, b may be configured to be deflectable to allow the protrusions 219a, b to decouple from the needle 120 to release the needle 120. The arms 220a, b may be positioned on sides of a central channel that allows the needle cover 132 and the needle 120 to pass between the arms 220a, b. In other embodiments, other configurations of a releasable coupler 218 may be utilized.

Figure 10:
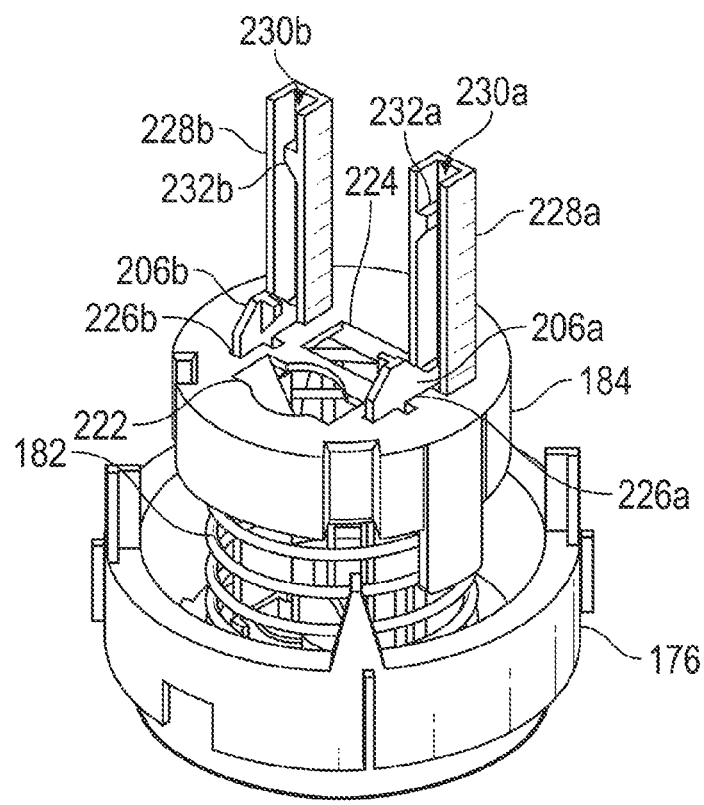
FIG. 10 illustrates a perspective assembly view of the carriage shown in FIG. 8 and the carriage shown in FIG. 9.

FIG. 10 illustrates a top perspective view of the carriage 184 of the retraction actuator, while being slid over the arms 206a, b of the carriage 176 of the insertion actuator. An upper surface of the carriage 184 is visible, showing an opening 222 surrounding the central channel that allows the needle cover 132 and the needle 120 to pass therethrough. An opening 224 is visible that allows the releasable coupler 204 of the insertion actuator to pass therethrough. Openings 226a, b allow the arms 206a, b of the carriage 176 of the insertion actuator to pass therethrough.

The carriage 184 is shown to include arms 228a, b that extend upward from the upper surface in the axial dimension. The arms 228a, b each include respective channels 230a, 230b that the releasable couplers 208a, 208b are configured to extend into. The arms 228a, b may include coupling members 232a, b within the respective channels 230a, 230b that couple to the respective releasable couplers 208a, 208b. The coupling members 232a, b may comprise ledges for the releasable couplers 208a, 208b to rest upon. The releasable couplers 208a, 208b may be configured to be deflected in a direction transverse to the axial dimension (e.g., each in a direction laterally outward from the center of the carriage 184) to release from the coupling members 232a, b.

Figure 11:
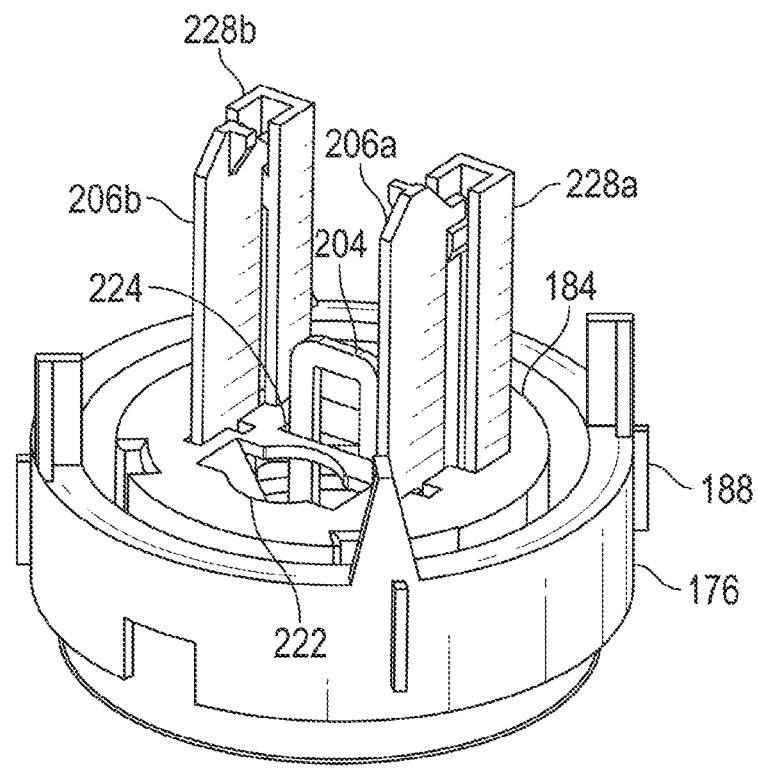
FIG. 11 illustrates a perspective assembly view of the carriage shown in FIG. 8 coupled with the carriage shown in FIG. 9.

FIG. 10 shows an assembly view of the carriage 184 of the retraction actuator being positioned upon the carriage 176 of the insertion actuator with the driver 182 of the retraction actuator being positioned between the lower surface of the carriage 184 and the upper surface of the carriage 176. The driver 182 may be compressed and energized between the carriages 184, 176. The carriages 184, 176 may be slid towards each other to cause the releasable couplers 208*a*, 208*b* of the arms 206*a*, *b* to couple to the respective coupling members 232*a*, *b* of the arms 228*a*, *b*. FIG. 11, for example, illustrates such a configuration, with the carriage 184 of the retraction actuator being releasably coupled to the carriage 176 of the insertion actuator.

Figure 12:
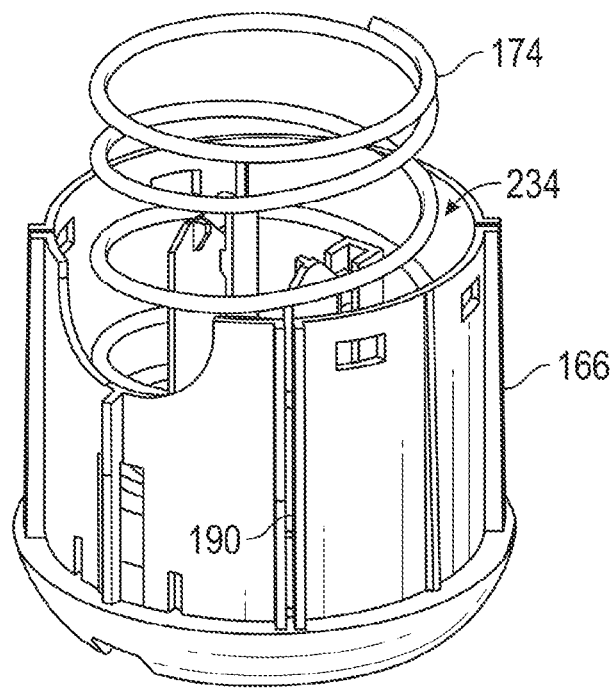
FIG. 12 illustrates a perspective assembly view of the carriages shown in FIGS. 8 and 9 inserted into a housing of an applicator shown in FIG. 2.

Referring to FIG. 12, the coupled carriage 184 of the retraction actuator and carriage 176 of the insertion actuator may be inserted into a portion of the applicator housing, namely the lower body 166 of the applicator housing 162. The lower body 166 may include a cavity 234 that the carriages 184, 176 are positioned within. The protrusions 188 on the outer surface of the carriage 176 may slide within the channels 190 of the lower body 166.

The driver 174 of the insertion actuator may be positioned within the cavity 234 and placed within the channel 205 of the carriage 176 shown in FIG. 21. The driver 174 may be configured similarly as the driver 182 discussed in regard to the retraction actuator, and may comprise a device for driving the carriage 176 as well as the carriage 184 and driving the insertion actuator. The driver 174 may be configured to provide a motive force to cause both the carriages 176, 184 to slide within the applicator housing 162. The driver 174 may be configured to drive the needle 120 into the individual's skin to insert the transcutaneous analyte sensor into the individual's skin. The driver 174 may comprise a spring as shown in FIG. 12. The spring may be configured to be provided with energy to compress the spring, upon which the spring exerts a responsive force that releases the energy and expands the spring. The spring may be a helical spring as shown in FIG. 12, or in other embodiments other configurations of springs or drivers may be utilized as desired.

Figure 13:
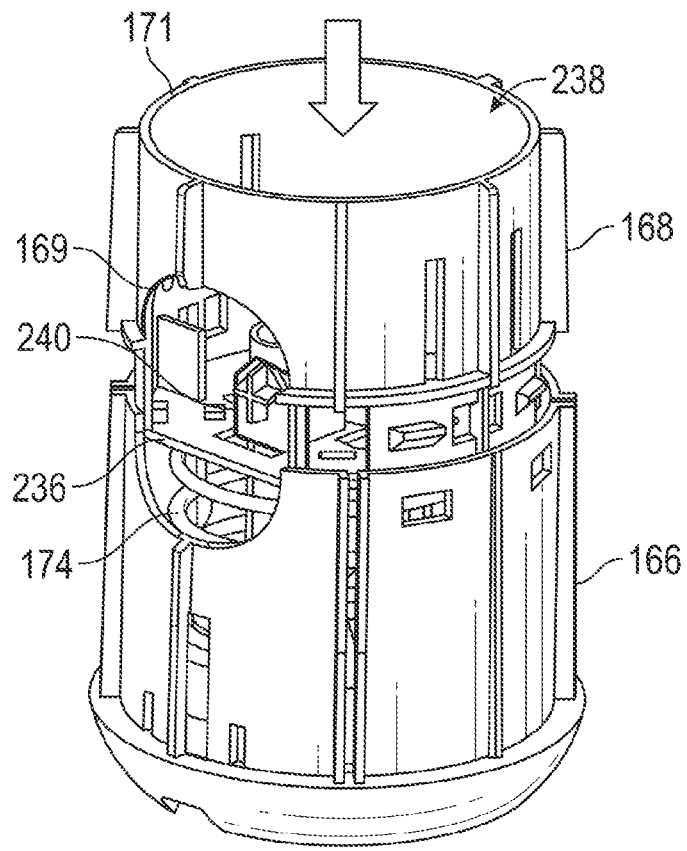
FIG. 13 illustrates a perspective assembly view the housing of the applicator shown in FIG. 2.

Referring to FIG. 13, the upper body 168 may be positioned over the lower body 166 and may include a spring support body 236 that serves to compress or provide an opposing force to the driver 174 as the driver 174 is compressed. The upper body 168 may be coupled to the lower body 166. The upper body 168 may define a cavity 238 configured to receive at least a portion of the release actuator. The upper body 168 may include a spring support body 240 configured to compress or provide an opposing force to a spring for biasing the control device 172 of the insertion actuator. The upper body 168 may include an opening 169 on the side of the applicator housing for the control device 172 to extend through. The upper body may include an upper opening 171 at the top of the applicator housing for receiving a control device of the release actuator.

Figure 14:
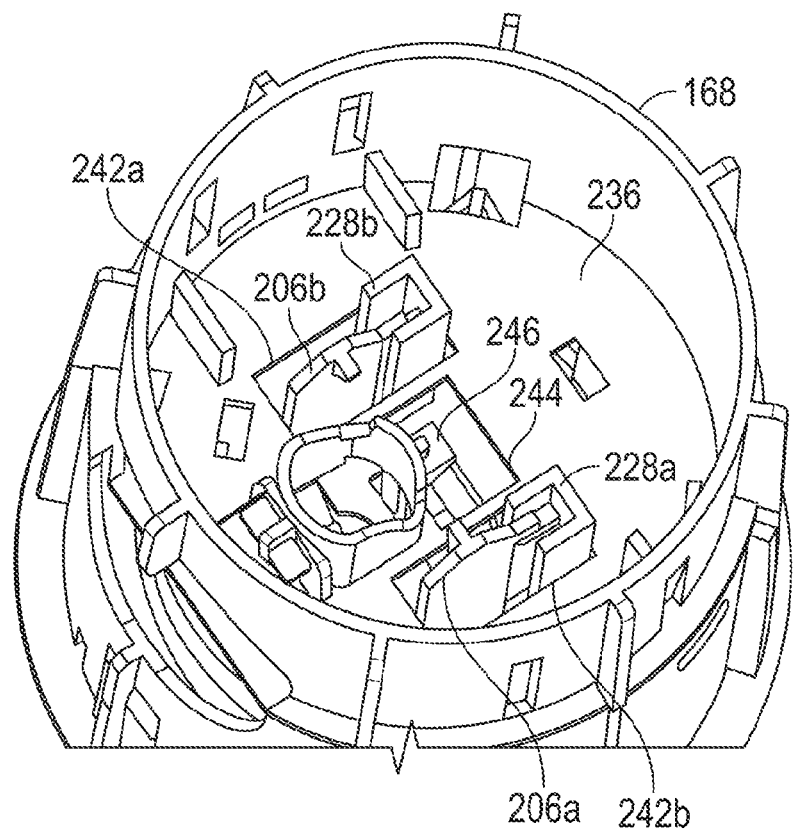
FIG. 14 illustrates a top perspective assembly view of the housing of the applicator shown in FIG. 2.

FIG. 14 illustrates a top perspective view of the upper body 168 coupled to the lower body 166. The arms 206*a*, *b*, and arms 228*a*, *b* extend through respective openings 242*a*, *b* in the spring support body 236. The spring support body 236 may include an opening 244 for the releasable coupler 204 of the insertion actuator to extend through, to couple to the ledge 246 of the upper body 168.

Figure 15:
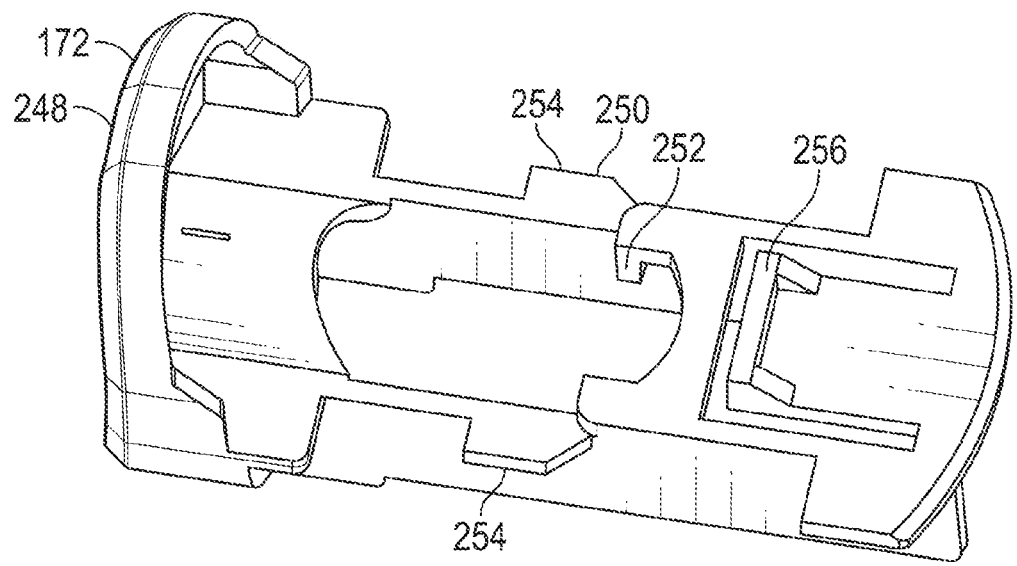
FIG. 15 illustrates a perspective view of a control device.

FIG. 15 illustrates a perspective view of the control device 172 of the insertion actuator. The control device 172 may be configured to be operated by an individual. The control device 172 may comprise a button or other form of body that may be moved to activate the insertion actuator. The control device 172 may include a button surface 248 and a control arm 250 that extends from the button surface 248. The control arm 250 may include a coupler release in the form of a contact surface 252 that is configured to contact the releasable coupler 204 of the insertion actuator, to release the releasable coupler 204 from the ledge 246. The control arm 250 may also include a coupler release in the form of a contact surface 254 that the deflectors 210*a*, *b* may contact at the desired time to release the releasable couplers 208*a*, *b* that couple the carriages 176, 184 together. The contact surface 252 may comprise a hook structure or downward extending surface, and the contact surface 254 may comprise one or more protrusions extending laterally from the control arm 250. The control arm 250 may further comprise a releasable coupler in the form of a lock 256 at a portion of the control arm 250 distal the button surface 248, configured to lock the control device 172 in position.

Figure 16:
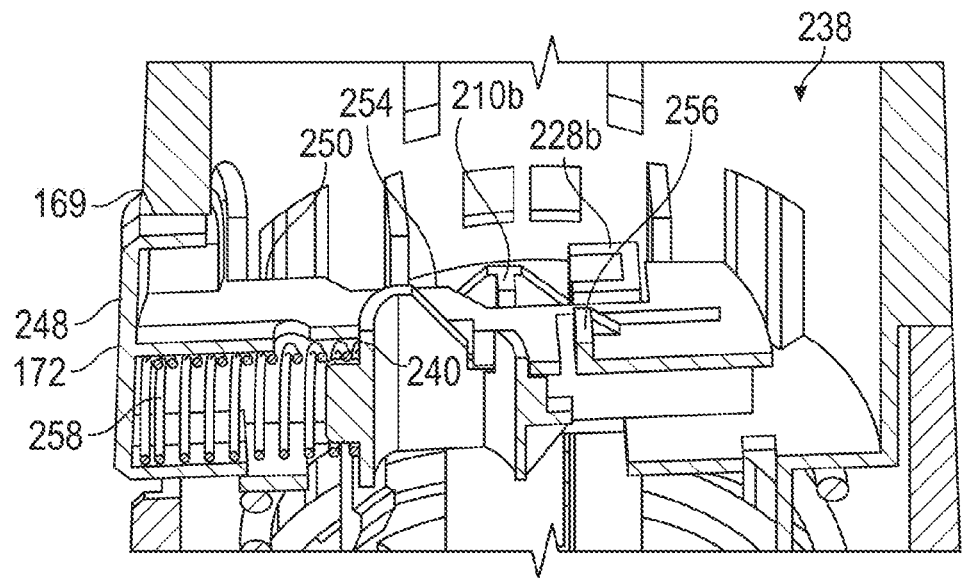
FIG. 16 illustrates a perspective assembly view of the control device of FIG. 15 inserted into the housing of the applicator shown in FIG. 2.

FIG. 16 illustrates an assembly view of the control device 172 being inserted through the opening 169 of the upper body 168. A portion of the control arm 250 distal the button surface 248 may extend distally past the arm 228*b*. The coupler release in the form of contact surface 254 does not yet contact the deflector 210*b*.

A biasing spring 258 may be provided that presses against the surface of the spring support body 240 and an inner surface of the button, to bias the control device 172 in a direction away from the surface of the spring support body 240.

Figure 17:
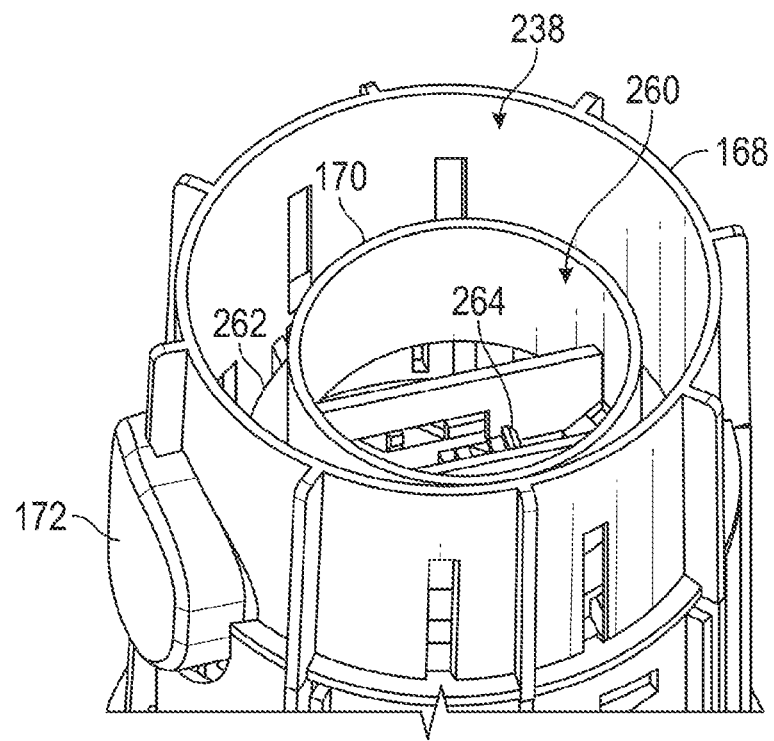
FIG. 17 illustrates a top perspective assembly view of the housing of the applicator shown in FIG. 2.

FIG. 17 illustrates a top perspective view of the support body 170 being positioned over the control device 172. The support body 170 may be positioned within the cavity 238 of the upper body 168 and may define a cavity 260 configured to receive at least a portion of the release actuator. The support body 170 may include a spring support surface 262 that is configured to support a biasing spring of the release actuator. The support body 170 may also include a locking surface 264 configured to engage the lock 256 of the control device 172.

Figure 18:
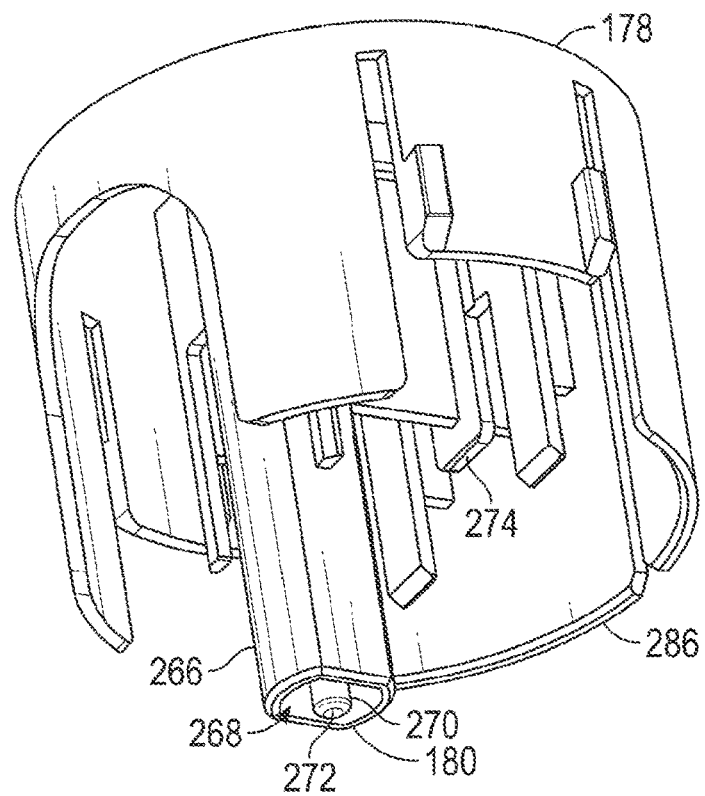
FIG. 18 illustrates a bottom perspective view of a release actuator.

FIG. 18 illustrates a bottom perspective view of the release actuator, showing the control device 178 and the pressing surface 180. The control device 178 may comprise a button or other form of body that may be moved by an individual to activate the release actuator. The control device 178 may be coupled to the pressing surface 180, which may be configured to press against the releasable coupler 218 shown in FIG. 9 to release the needle 120 from within the applicator housing 162. The pressing surface 180 as shown in FIG. 18 may comprise a distal surface of a column 266 that extends axially from a button surface of the control device 178. The column 266 may surround an interior cavity 268 that may be configured to receive a portion of the needle cover 132. The interior cavity 268 may include a rod 270 having a pressing surface 272 at the distal end of the rod 270, for pressing directly on the needle hub 124 of the needle 120, to cause the needle 120 to release from the applicator housing 162. The needle cover 132 accordingly may be positioned between the rod 270 and the column 266 as the release actuator moves axially downward toward the needle 120.

The release actuator may further include a coupler release in the form of a lock release surface 274, which may comprise a protrusion configured to release the lock 256 of the control device 172 from the locking surface 264.

Figure 19:
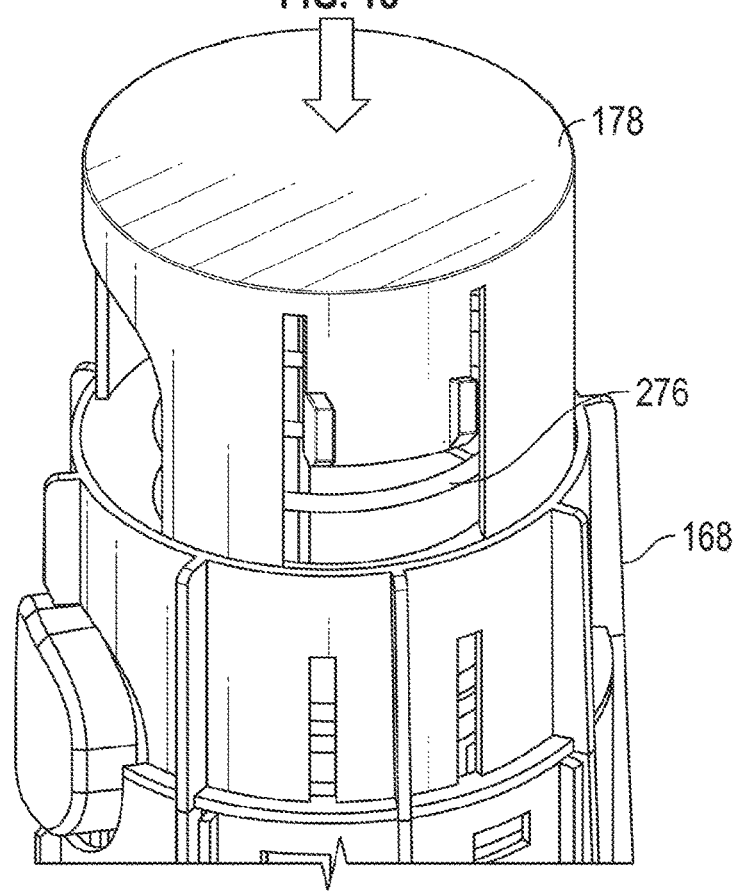
FIG. 19 illustrates a perspective assembly view of a release actuator of FIG. 18 inserted into the housing of the applicator shown in FIG. 2.

As shown in FIG. 19, the release actuator may be inserted into the cavity 238 of the upper body 168. A biasing spring 276 may be positioned between the control device 178 and the spring support surface 262 shown in FIG. 17 to provide a biasing force in an upward direction for the control device 178 and accordingly for the pressing surface 180.

Figure 20:
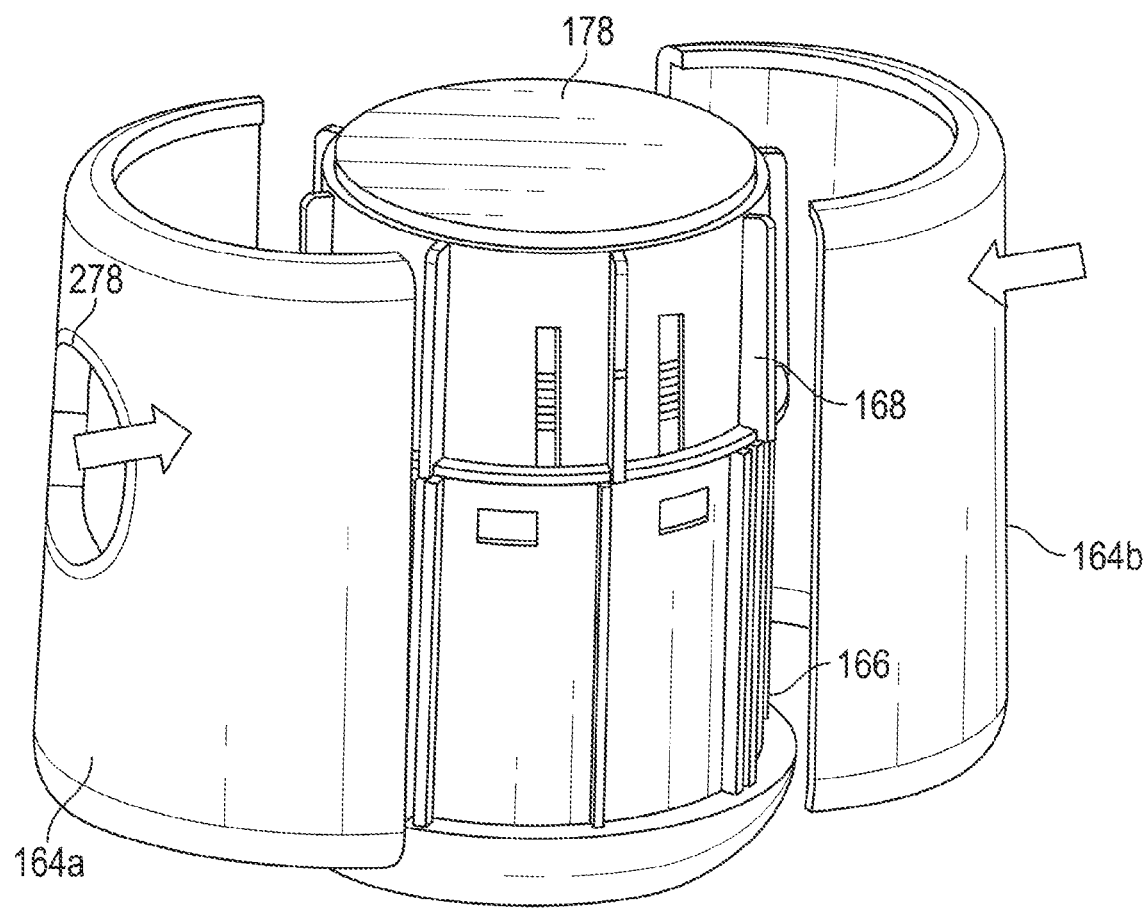
FIG. 20 illustrates a perspective assembly view of the housing of the applicator shown in FIG. 2.

FIG. 20 illustrates the side cover bodies 164*a*, *b* extending over the sides of the lower body 166 and the upper body 168 and forming the outer surface of the applicator housing 162. The side cover 164*a* may include an opening 278 for the control device 172, such that the control device 172 is accessible on a side surface of the applicator housing 162. The side covers 164a, b together may form an opening at the top of the applicator housing 162 such that the control device 178 is accessible at the top of the applicator housing, opposite an opening 280 (marked in FIG. 21) at the bottom of the applicator housing for receiving the cartridge 104 and for the transcutaneous analyte sensor 24 to be deployed from.

Referring to FIG. 21, the applicator housing 162 may include a receiver 282 for receiving the cartridge 104. The receiver may be configured for the cartridge 104 retaining the transcutaneous analyte sensor to be inserted into. The receiver 282 may comprise a cavity within the applicator housing 162 that receives the cartridge 104. The cartridge 104 may be inserted into the receiver 282 axially through the opening 280.

FIGS. 21-28 illustrate steps in a method of operating the system 100. FIG. 21 illustrates the applicator 102 in an initial state, in which the applicator 102 is configured to receive the cartridge 104 and components of the transcutaneous analyte sensor system including the transcutaneous analyte sensor 24, the wearable housing 108, and the patch 106. The electronics unit 26 is shown to be coupled to the wearable housing 108 upon insertion into the receiver 282 of the applicator 102, however the electronics unit 26 may be excluded and later coupled to the wearable housing 108 as desired.

The applicator 102 in the initial state has the carriage 176 of the insertion actuator in a lowered state, proximate the lower opening 280 of the applicator 102. The carriage 176 of the insertion actuator may be pressed to the lowered state by the force provided by the driver 174 of the insertion actuator. The carriage 184 of the retraction actuator may be in a raised state, pressed to the raised state by the force of the driver 182 of the retraction actuator. The releasable couplers 208a, b shown in FIG. 8 are not yet coupling the carriages 176, 184 together.

The cartridge 104 as shown in FIG. 21 has the removable cover 154 shown in FIG. 6, for example, removed to remove the hermetic seal of the contents contained therein. The cartridge 104 may then be inserted into the receiver 282 of the applicator housing 162 with the upper end of the needle cover 132 passing through the opening 216 of the carriage 176 of the insertion actuator. The body of the cartridge 104 may be inserted into the receiver 282 with the protrusion 150 fitting into a complementary shaped channel 284 of the applicator housing 162, to align the desired axial rotation of the cartridge 104 with the applicator 102.

Figure 22:
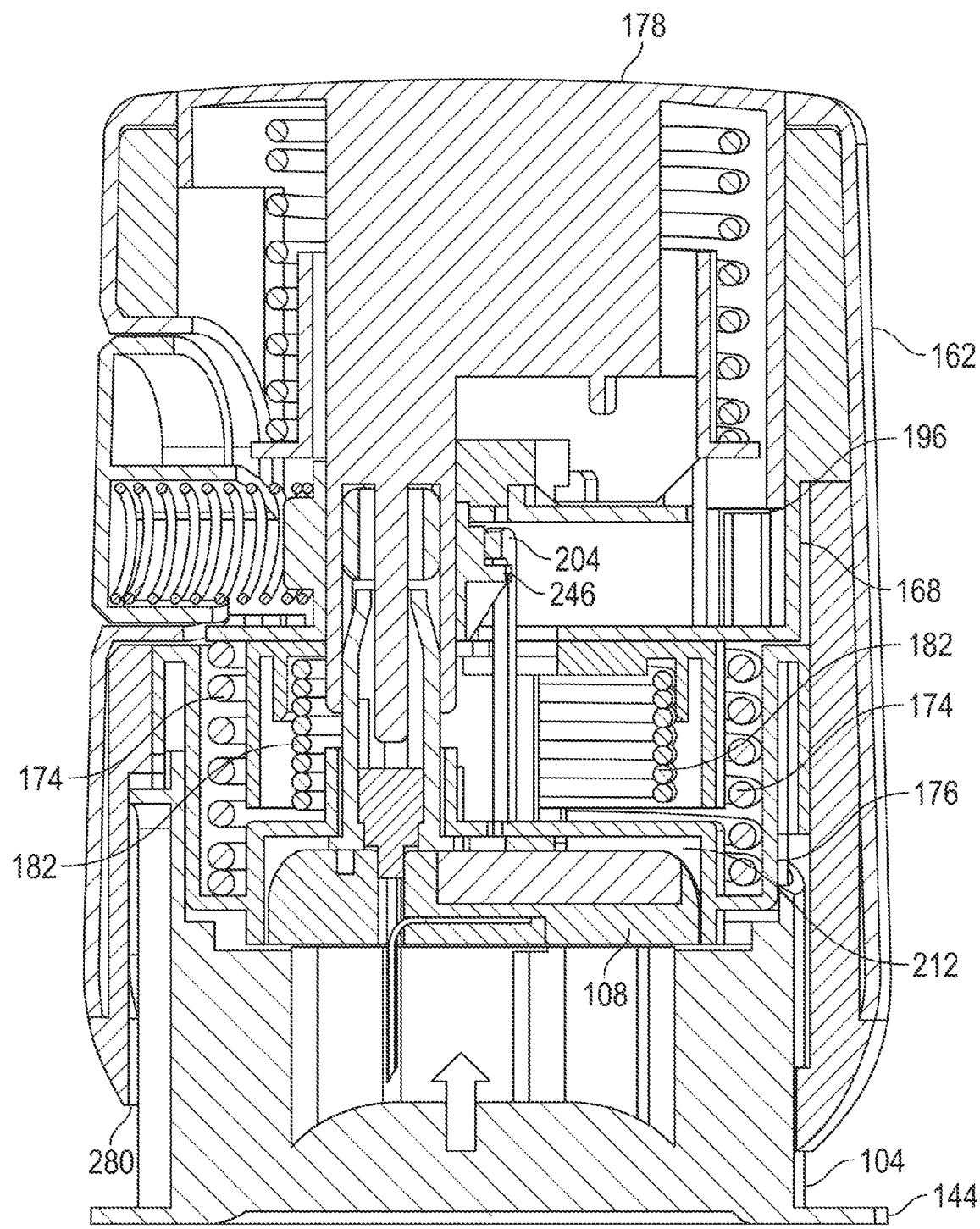
FIG. 22 illustrates a cross sectional view of the applicator shown in FIG. 2 along line I-I, with a cross section of a cartridge taken along the same line I-I.

FIG. 22 illustrates the cartridge 104 fully inserted into the receiver 282 of the applicator housing 162. The cartridge 104 may be inserted in the axial dimension of the applicator housing 162, which is the same dimension that the transcutaneous analyte sensor 24 as well as other components of the transcutaneous analyte sensor system will be deployed from the applicator housing 162 (although in an opposite axial direction that the cartridge 104 is inserted into the receiver 282). The insertion of the cartridge 104 and the transcutaneous analyte sensor 24 into the receiver 282 of the applicator housing 162 may compress and thus provide energy to both the driver 174 of the insertion actuator and the driver 182 of the retraction actuator. Both drivers 174, 182 are shown to be compressed in FIG. 22. In an embodiment in which the drivers 174, 182 are springs, the springs may be compressed by the insertion of the cartridge 104 and the transcutaneous analyte sensor 24 into the receiver. The cartridge 104 may include a pressing surface upon an upper surface of the cartridge 104 to press against the carriage 176 of the insertion actuator to provide energy to the insertion actuator.

The insertion of the cartridge 104 into the receiver 282 of the applicator housing 162 also causes the releasable coupler 204 of the insertion actuator to engage the coupling member, in the form of a ledge 246, of the upper body 168. The engagement of the releasable coupler 204 holds the carriage 176 of the insertion actuator in position and prevents the driver 174 from pressing the carriage 176 in an axial direction towards the lower opening 280 of the applicator housing 162. The releasable couplers 208a, b shown in FIG. 8 engage the coupling members 232a, b of the carriage 184 of the retraction actuator to couple the carriages 176, 184 together, producing a configuration as shown in FIG. 11.

The stops 196 protruding upward from the upper surface 192 of the carriage 176 may contact a contact surface 286 of the release actuator (marked in FIG. 18) to impede downward movement and activation of the release actuator. As such, the release actuator may be prevented from operating prematurely.

The wearable housing 108 of the transcutaneous analyte sensor system may be positioned in the receiver 212 of the lower surface of the carriage 176. The releasable coupler 214 shown in FIG. 21 may couple to the cavity 123 shown in FIG. 3 to grip the wearable housing 108 to the lower surface of the carriage. Thus, as the cartridge 104 is withdrawn from the applicator housing 162, the wearable housing 108 remains coupled to the receiver 212.

Figure 23:
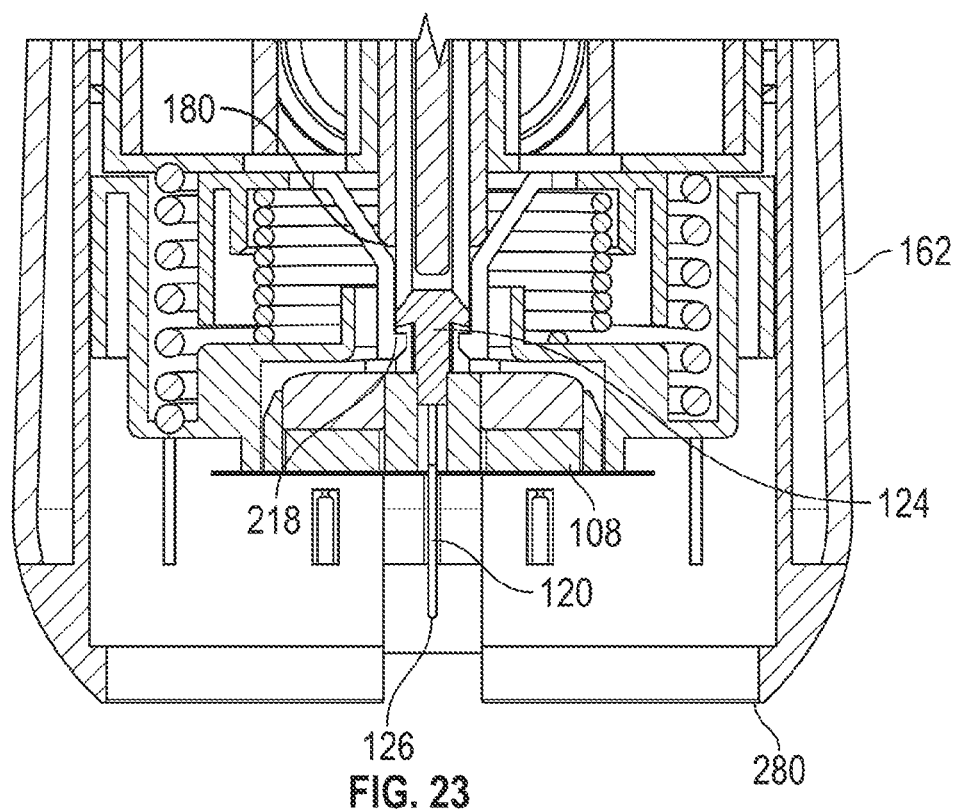
FIG. 23 illustrates a cross sectional view of the applicator shown in FIG. 2 along line II-II, which is orthogonal to the view of line I-I.

FIG. 23, for example, illustrates a front cross sectional view of the applicator housing 162 in which the cartridge 104 has been removed from the applicator housing 162. The cartridge 104 may be gripped by the flange at the base 144 of the cartridge body, to pull the cartridge 104 out of the applicator housing 162 in an opposite direction in which the cartridge 104 was inserted into the applicator housing 162.

The releasable coupler 218 is shown coupled to the needle 120, particularly with the protrusions 219a, b of the releasable coupler 218 shown in FIG. 9 engaging the coupling members 128 of the needle hub 124 shown in FIG. 3. The needle 120 is shown to extend downward from the wearable housing 108 of the transcutaneous analyte sensor system, extending for insertion of the penetrating tip 126 of the needle 120 into the individual's skin.

Figure 24:
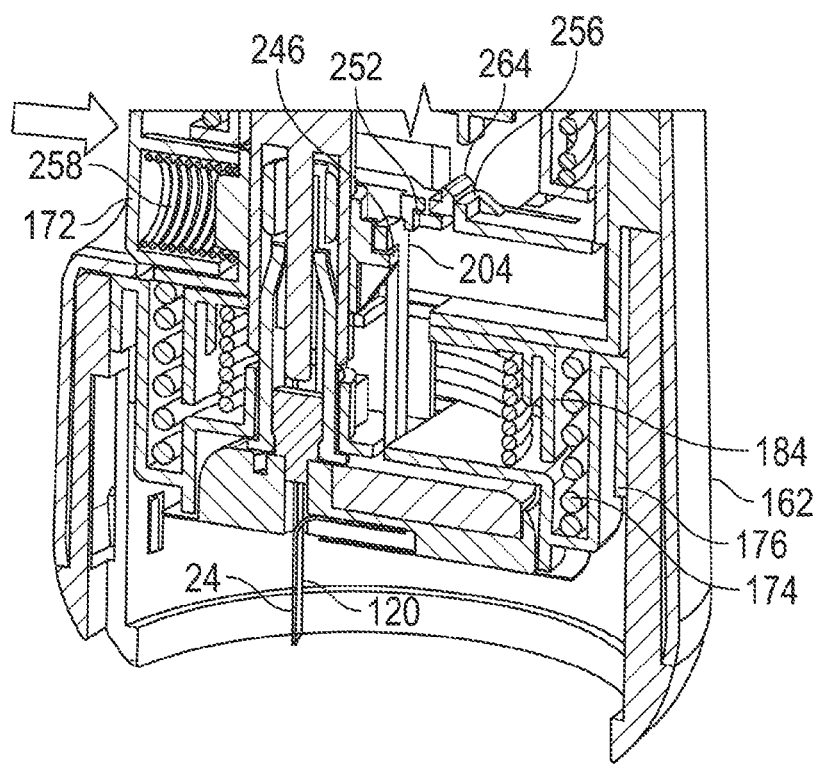
FIG. 24 illustrates a cross sectional view of the applicator shown in FIG. 2 along line I-I.

FIG. 24, for example, shows the needle 120 may extend axially along with the sensing portion of the transcutaneous analyte sensor 24, such that the needle 120 upon insertion into the individual's skin may guide or insert the sensing portion of the transcutaneous analyte sensor 24 into the individual's skin.

Referring back to FIG. 23, the pressing surface 180 of the release actuator is shown to not yet be pressing against the releasable coupler 218.

Referring to FIG. 24, with the cartridge 104 withdrawn from the applicator housing 162, the transcutaneous analyte sensor system is in position for application to the individual's skin by the applicator 102. The transcutaneous analyte sensor system may be moved axially downward within the receiver of the applicator housing 162 to contact the individual's skin and be applied to the individual's skin.

The insertion actuator may operate to insert the needle 120 into the individual's skin to deposit the transcutaneous analyte sensor 24 into the individual's skin. FIG. 24 illustrates that the control device 172 of the insertion actuator may be pressed in a lateral direction, or a direction transverse to the axial dimension of the applicator housing 162. The movement of the control device 172 may compress the biasing spring 258. The control device 172 may disengage the releasable coupler 204 from the ledge 246, to allow the coupled carriages 176, 184 to slide axially downward within the applicator housing 162. The contact surface 252 shown in FIG. 15 for instance may press against the upper "U" portion of the releasable coupler 204 to push the upper "U" portion off of the ledge 246. The force of the driver 174 upon the carriage 176 causes the coupled carriages 176, 184 to descend rapidly with sufficient force to drive the needle 120 into the individual's skin and insert the transcutaneous analyte sensor 24 into the individual's skin.

Further as shown in FIG. 24, upon the control device 172 of the insertion actuator being pressed in a lateral direction, the locking surface 264 of the support body 170 may engage the lock 256 of the control device 172. The lock 256 may include an angled surface that slides under the locking surface 264 to allow the lock 256 to be positioned distal of the locking surface 264 and thus lock the lock 256 in position. The lock 256 may prevent the control device 172 from undesirably moving after the control device 172 has been pressed.

Figure 25:
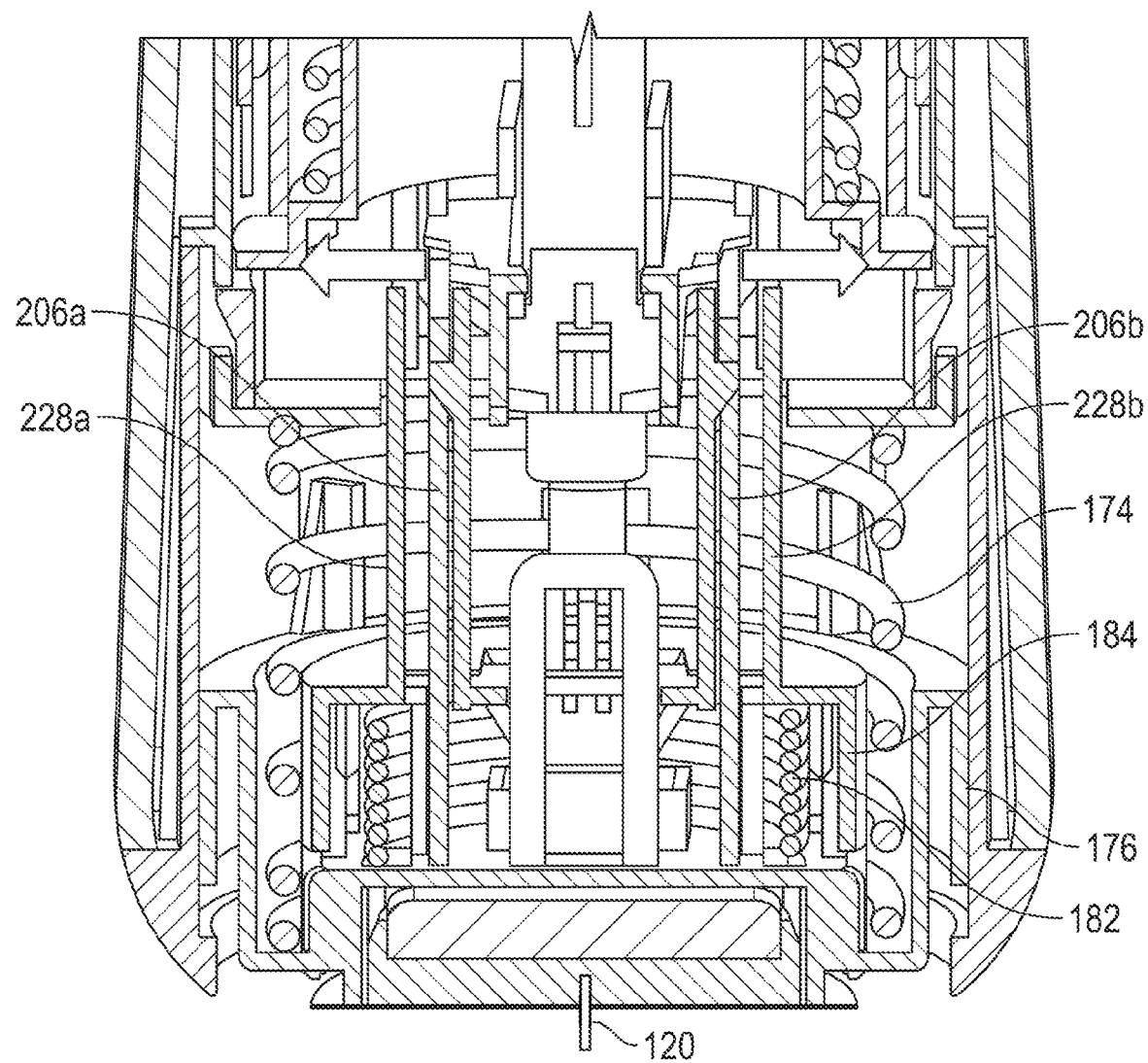
FIG. 25 illustrates a perspective cross sectional view of the applicator shown in FIG. 2 along line which is orthogonal to the view of line I-I.

FIG. 25 illustrate the configuration of the coupled carriages 176, 184 after the carriage 176 of the insertion actuator has been slid within the applicator housing 162 in a downward direction. The movement of the carriage 176 has inserted the needle 120 into the individual's skin and has inserted the transcutaneous analyte sensor 24 into the individual's skin. Further, the movement of the carriage 176 has pressed the patch 106 to the individual's skin, allowing the patch 106 to adhere to the individual's skin and providing an adhesive force to the skin for the transcutaneous analyte sensor system. The lower portion of the applicator housing may be applied to and contact the individual's skin during deployment of the transcutaneous analyte sensor system.

Further, with the carriages 176, 184 both being slid downward within the applicator housing 162, the deflectors 210a, b coupled to the arms 206a, b may contact the contact surfaces 254 shown in FIG. 15. Such contact may apply a force to the deflectors 210a, b in lateral directions that causes the releasable couplers 208a, b on the arms 206a, b to disengage from the coupling members 232a, b of the arms 228a, b and be able to slide within the channels 230a, b of the arms 228a, b (marked in FIG. 10). Accordingly, the carriages 176, 184 may be decoupled from each other and able to slide relative to each other. The retraction actuator accordingly may be configured to automatically operate upon the needle 120 inserting the transcutaneous analyte sensor into the individual's skin. The releasable couplers 208a, b may be configured to automatically release upon contact with the coupler release in the form of contact surfaces 254 shown in FIG. 15.

With the carriages 176, 184 decoupled from each other, the driver 182 of the retraction actuator may apply an upward force to the carriage 184 of the retraction actuator to move the carriage 184 upward.

Figure 26:
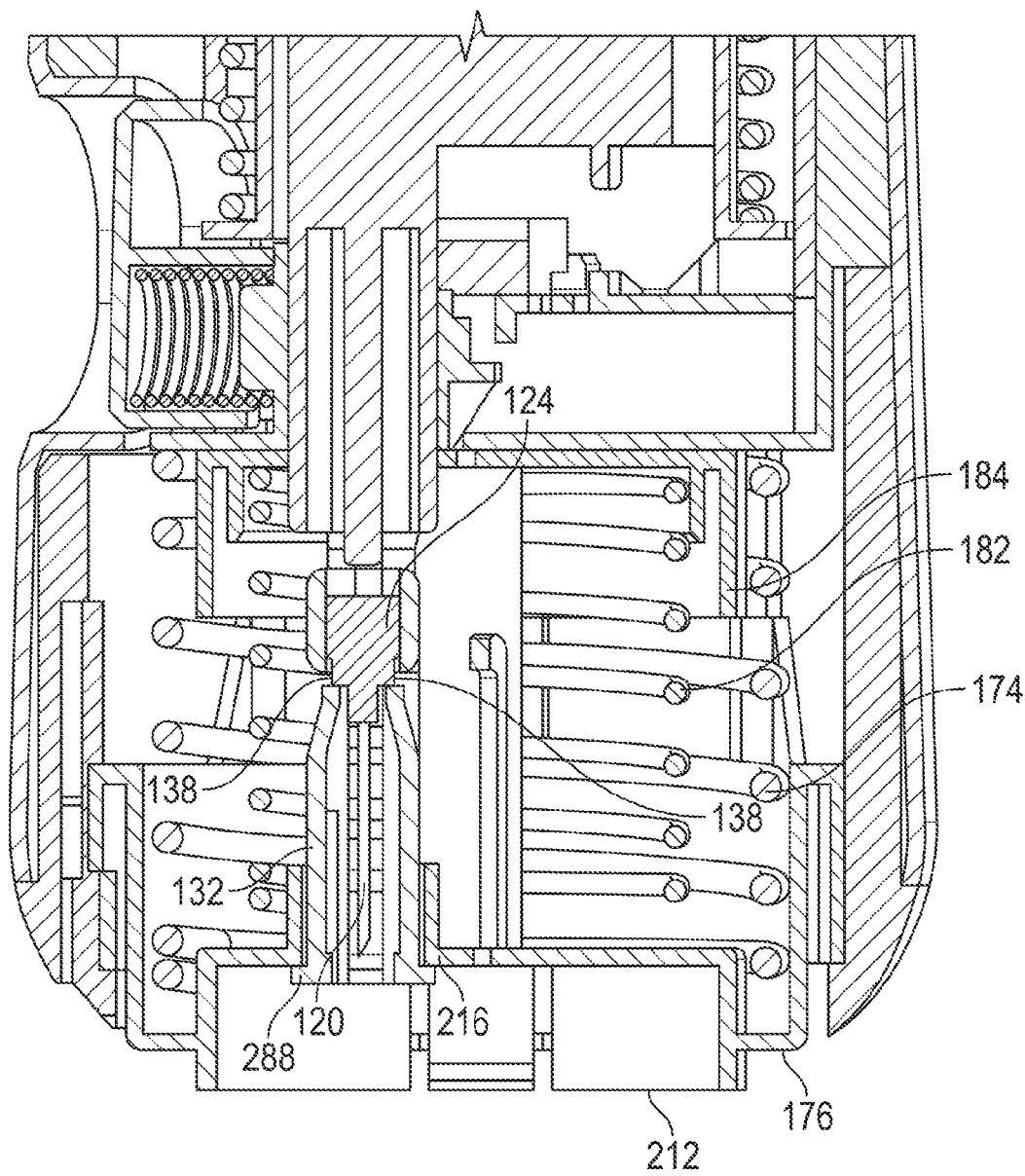
FIG. 26 illustrates a perspective cross sectional view of the applicator shown in FIG. 2 along line I-I.

Referring to FIG. 26, the upward movement of the retraction actuator carriage 184 may cause the needle 120 that is coupled to the releasable coupler 218 to retract out of the individual's skin, due to the upward movement of the releasable coupler 218. The releasable coupler 218 may cause the needle 120 to retract into the needle cover 132, to be sheathed within the needle cover 132. The retraction actuator may position the needle 120 into the needle cover 132. The releasable coupler 218 may retract the needle 120 such that the needle 120 retracts so that the locks 136 shown in FIG. 3 engage the locking members 138 of the needle hub 124 and retain the needle 120 in position within the needle cover 132. A flange 288 shown in FIG. 26 at an end of the needle cover 132 that extends through the opening 216 may impede further upward movement of the needle 120 and the needle cover 132 due to the upward movement of the releasable coupler 218.

Further, as shown in FIG. 26, the transcutaneous analyte sensor system in the form of an on-skin sensor assembly may remain on the individual's skin as the applicator 102 is withdrawn from the individual's skin and removed and withdrawn from the transcutaneous analyte sensor 24. The transcutaneous analyte sensor system accordingly is no longer present within the receiver 212. The releasable coupler 218 retains the needle 120 to the applicator housing 162 following insertion of the transcutaneous analyte sensor 24 into the individual's skin and removal from the applicator housing from the transcutaneous analyte sensor 24. The transcutaneous analyte sensor 24 remains within the individual's skin as the applicator housing is removed from the transcutaneous analyte sensor 24.

With the applicator housing removed from the transcutaneous analyte sensor 24, the release actuator may be operated to release the needle 120 from within the releasable coupler 218.

Figure 27:
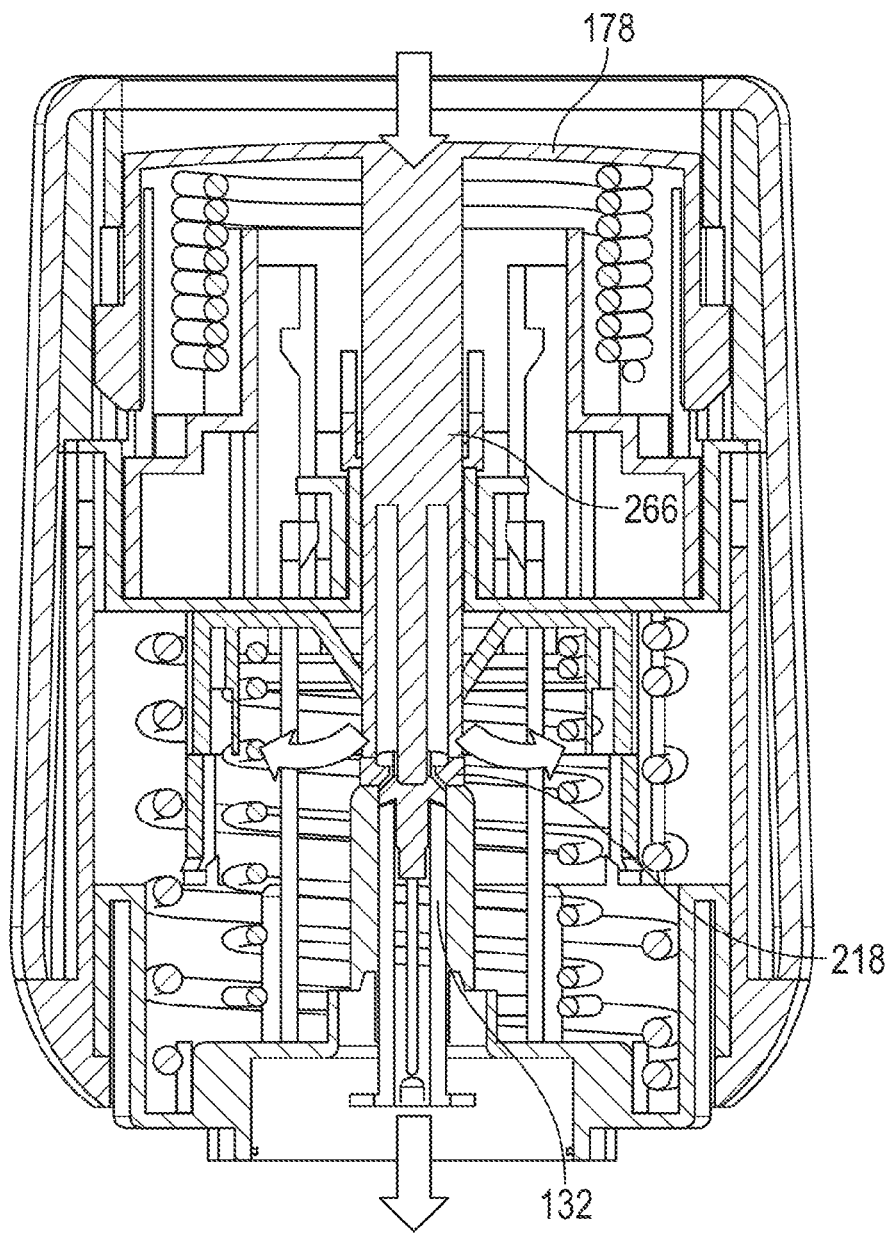
FIG. 27 illustrates a perspective cross sectional view of the applicator shown in FIG. 2 along line II-II.

FIG. 27, for example, illustrates the control device 178 of the release actuator having been pressed axially downward, causing the column 266 of the release actuator to similarly move axially downward. The pressing surface 180 of the release actuator accordingly may be moved axially downward to press against the releasable coupler 218 and particularly press against the deflectable arms 220a, b shown in FIG. 9. The pressure of the pressing surface 180 against the deflectable arms 220a, b causes the protrusions 219a, b (marked in FIG. 9) to release from the coupling members 128 of the needle hub 124. Accordingly, the releasable coupler 218 may be released from the needle 120. Further, the pressing surface 272 of the rod 270 shown in FIG. 18 may press against the needle 120 (particularly the needle hub 124) to cause the needle 120 to release from the applicator housing 162. The needle 120 may remain sheathed within the needle cover 132 during this process.

Figure 28:
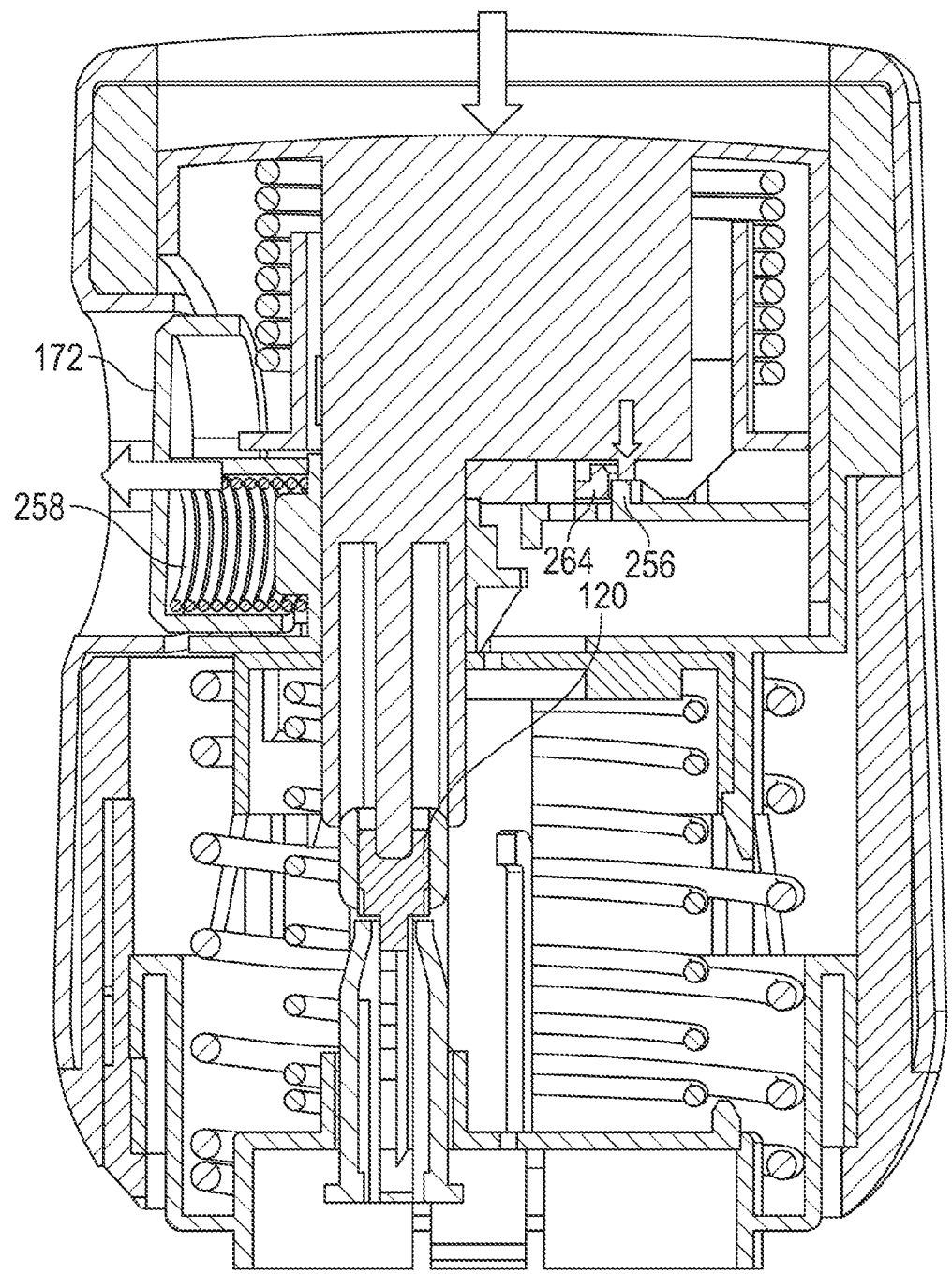
FIG. 28 illustrates a perspective cross sectional view of the applicator shown in FIG. 2 along line I-I.

Further, as shown in FIG. 28, which is a side cross sectional view of FIG. 27, the lock release surface 274 (marked in FIG. 18) may contact the lock 256 of the control device 172, to press the lock 256 under the locking surface 264. As such, the control device 172 may be free to move in the opposite lateral direction than shown in FIG. 24 and may be moved back to the position shown in FIG. 22 due to the force applied by the biasing spring 258.

The release actuator may be configured to release the needle 120 covered by the needle cover 132 from the applicator housing 162 following insertion of the needle into the individual's skin. The releasable coupler 218 configured to retain the needle 120 is configured to release the needle 120 positioned within the needle cover 132 from within the applicator housing. The release actuator may eject the needle 120 and the needle cover 132 together as a unit that is configured for discard. The force of the pressing surface 272 of the rod 270 may eject the unit together from the applicator housing 162 (i.e., release from the applicator housing with velocity).

The needle 120 may be released from the applicator housing 162 for discard, as the needle 120 may have been contaminated through the process of insertion within the individual's skin. The needle 120 accordingly may be a single use needle that is configured to discard within a sharps container or other disposal area. The needle 120 may remain sheathed within the needle cover 132 such that an individual does not contact the used needle 120 and be subject to the contamination of the needle 120 or otherwise be injured by the penetrating tip of the needle 120. The needle 120 may remain locked in position within the needle cover 132 such that an individual cannot access the contaminated portion of the needle 120. The needle 120 and needle cover 132 together may form a unit for disposal following insertion into an individual's skin and separation from the applicator housing.

Referring to FIG. 28, upon release of the needle 120 and needle cover 132 from the applicator housing 162 and following the return of the control device 172 to the position shown in FIG. 24, the applicator is in a configuration for deployment of another transcutaneous analyte sensor 24 and other components of a transcutaneous analyte sensor system. As such, the applicator 102 is configured for multiple uses, and is not intended to be discarded. The applicator 102 returns to a configuration shown in FIG. 21 for repeat of the steps shown in FIGS. 21-28. The applicator 102 may be loaded with another cartridge 104 and the steps shown in FIGS. 21-28 may repeat as desired.

Figure 29:
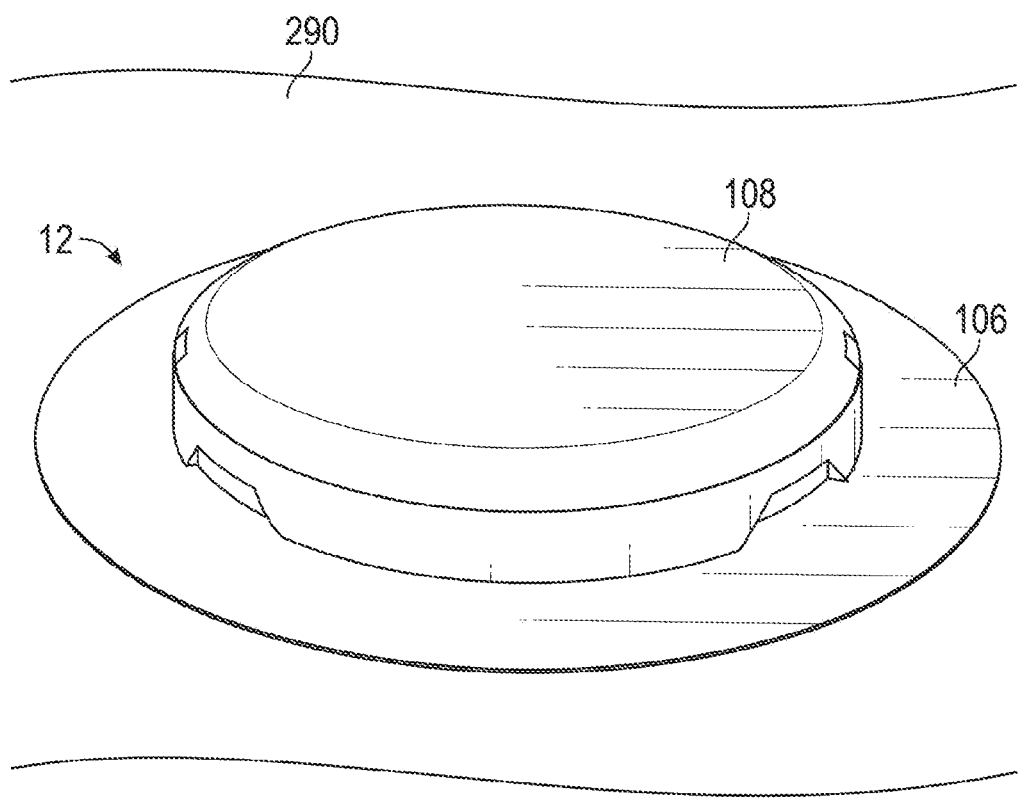
FIG. 29 illustrates a perspective view of an on-skin sensor assembly positioned on an individual's skin.

FIG. 29 illustrates a side perspective view of a transcutaneous analyte sensor system that may be deployed to an individual's skin with the applicator 102. The transcutaneous analyte sensor system is in the form of an on-skin sensor assembly 12. The transcutaneous analyte sensor 24 is inserted into the skin of an individual. The patch 106 and wearable housing 108 are visible, and an electronics unit may be incorporated within the wearable housing 108. As discussed the electronics unit may be integral with the wearable housing 108, or may be separable. All or a portion of the transcutaneous analyte sensor system may be configured for single use, and may be disposable. For example, as discussed, all components of the transcutaneous analyte sensor system except the electronics unit may be configured for single use, whereas in other embodiments the entirety of the transcutaneous analyte sensor system may be configured for single use. Other components of the transcutaneous analyte sensor system may be configured to be reusable other than the electronics unit.

Variations of the system 100 may be provided.

Figure 30:
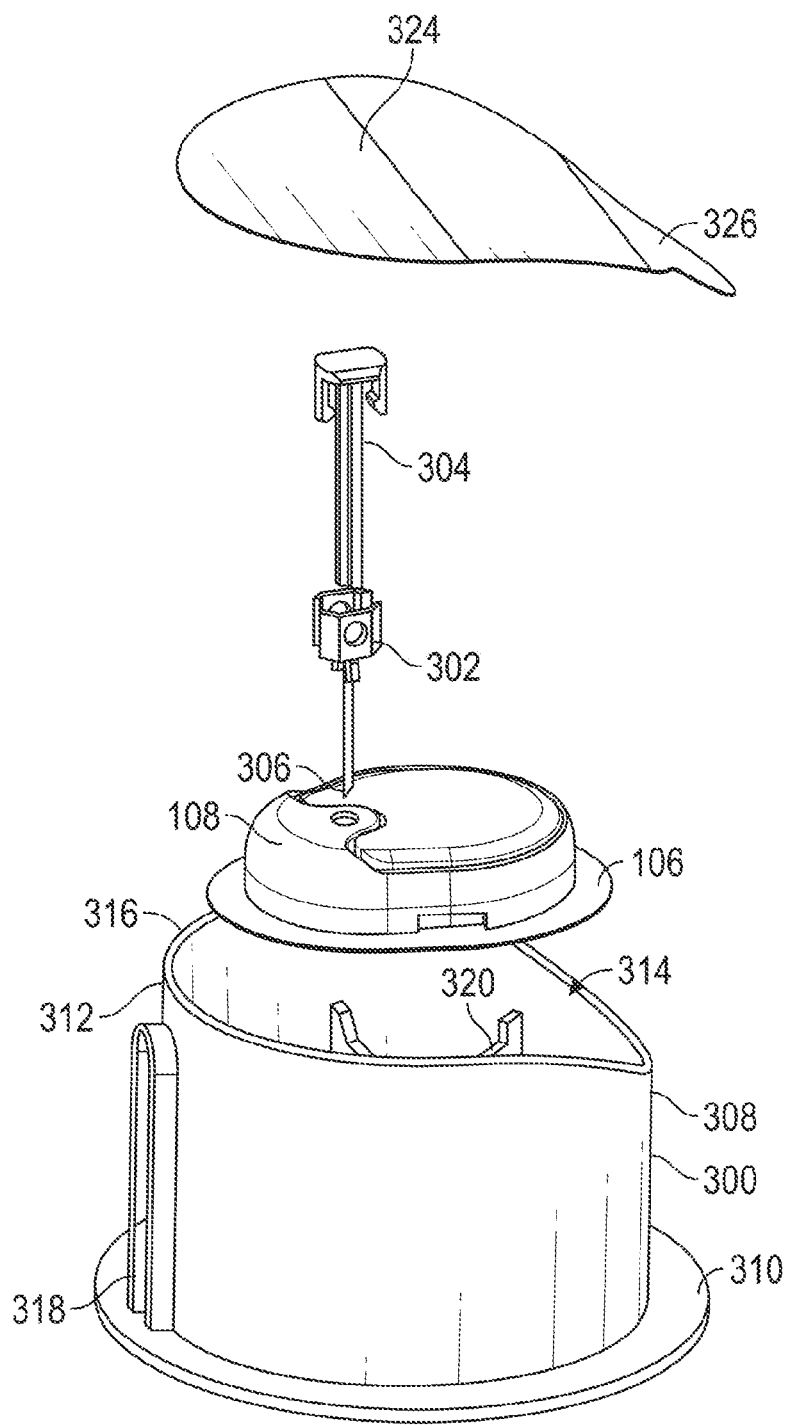
FIG. 30 illustrates an exploded view of components of a cartridge.

FIG. 30 illustrates an embodiment of a cartridge 300 that includes a needle 302 having a needle cover 304 that is configured to slide to uncover a portion of the needle 302 as the needle 302 is inserted into the individual's skin. The needle cover 304 may be configured to slide axially away from the penetrating tip 306 of the needle 302 to uncover the penetrating portion of the needle 302 as it is being inserted. The needle cover 304 may then be configured to slide axially towards the penetrating tip 306 of the needle 302 to cover the needle 302 as the needle 302 is retracted from the individual's skin. The needle 302 may be configured to be moved relative to the needle cover 304 to be positioned into the needle cover 304. The cover 304 accordingly may provide reciprocating axial motion along the needle 302.

As shown in FIG. 30, the cartridge 300 may be configured similarly as the cartridge 104 shown in FIG. 5. The cartridge 300 may include a body 308 having a base 310 and a wall 312. The base 310 may form a bottom of the cartridge 300 that the cartridge 300 may be positioned upon. The base 310 may form a flange extending outward from the wall 312. The wall 312 may extend upward from the base 310, transverse to a direction that the base 310 extends in. The wall 312 may extend around and define a cavity 314 that may receive components of the cartridge including the transcutaneous analyte sensor 24 and the needle 302 among other components disclosed herein. The wall 312 may extend around at least a portion of the needle cover 304. The wall 312 may extend upward to an upper opening 316 that exposes the components retained by the body 308. The wall 312 may including an inner surface configured to face inward towards a central portion of the cartridge 300 and the transcutaneous analyte sensor 24 and an outer surface facing opposite the inner surface. The outer surface of the wall may be configured to be positioned within at least a portion of an applicator. The outer surface of the wall may comprise a mating surface for a receiver of the applicator, and may be contoured to a shape of an inner surface of the receiver.

The wall 312 may be shaped similarly as the wall 146 discussed in regard to the cartridge 104 shown in FIG. 5. A protrusion 318 may be positioned on the outer surface of the cartridge 300 and may extend in an axial direction. The protrusion 318 may be configured to align the cartridge 300 with the receiver of the applicator.

The body 308 may include a retainer 320 that may operate and be structured similarly as the retainer 152 discussed in regard to the cartridge 104.

Figure 34:
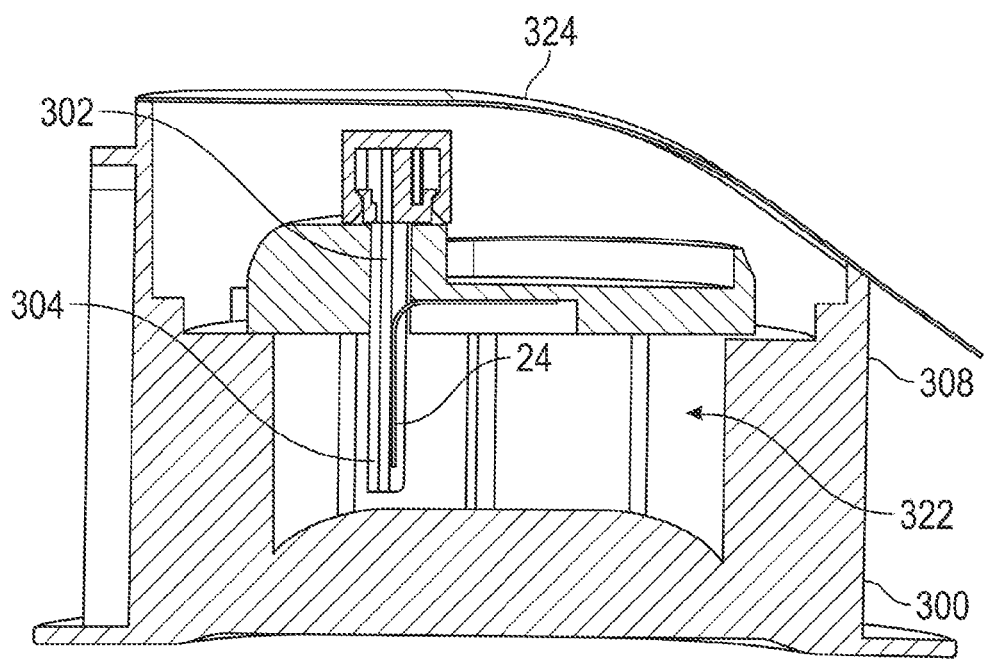
FIG. 34 illustrates a cross sectional view of the cartridge shown in FIG. 33 along line V-V.

Referring to FIG. 34, the body 308 of the cartridge 300 may include a central cavity 322 that is configured to receive the needle 302 when positioned within the body 308 of the cartridge 300.

Referring back to FIG. 30, the cartridge 300 may include a removable cover 324 that extends over a portion of the body 308. The removable cover 324 covers the upper opening 316 and may block access to the components contained within the body 308. The removable cover 324 may cover the contents of the cartridge 300, including the transcutaneous analyte sensor 24 and the needle 302 within the cartridge 300. The removable cover 324 may comprise a flap that extends over the upper opening 316, and may have an adhesive that couples the cover 324 to the body 308. The cover 324 may include a tab 326 for an individual to grasp to peel the cover 324 from the body 308. The removable cover 324 may be configured to form a hermetic seal of the upper opening 316, in a similar manner as the removable cover 154.

The components of the transcutaneous analyte sensor system may be retained by the body 308 in a similar manner as discussed in regard to the cartridge 104, and the cartridge 300 may be utilized in a similar manner as the cartridge 104.

Figures 31, 32:
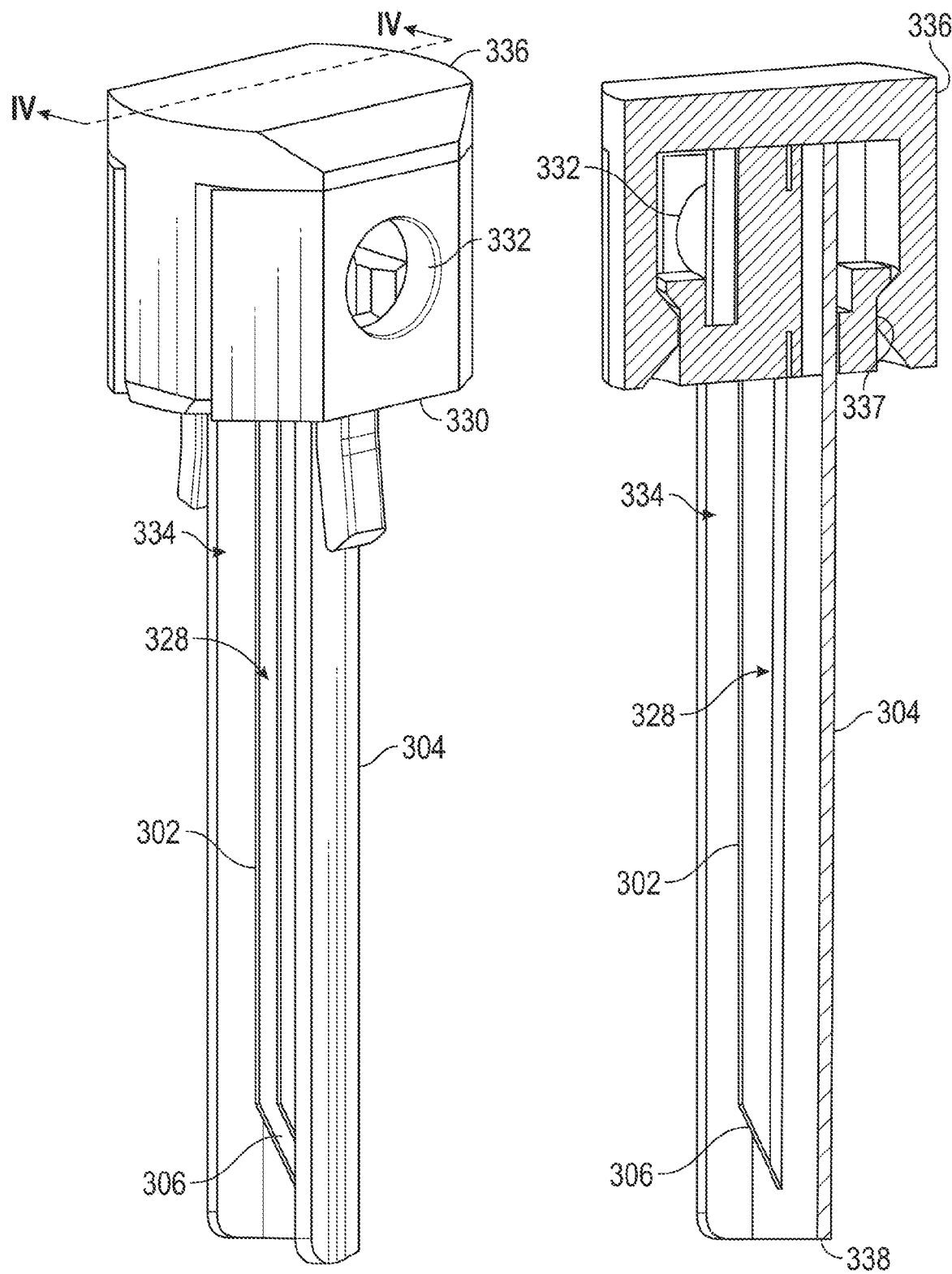
FIG. 31 illustrates a perspective view of a needle and needle cover.
FIG. 32 illustrates a perspective cross sectional view of the needle and needle cover shown in FIG. 31 along line IV-IV.

FIG. 31 illustrates a perspective view of the needle 302 with the needle cover 304 extending over the length of the needle 302. The needle cover 304 extends over the penetrating tip 306 of the needle 302.

The needle 302 may have a "C" shape with a fold of needle material extending on two sides of a needle channel 328. The needle channel 328 may be configured for the transcutaneous analyte sensor 24 to extend in, such that the needle 302 upon insertion into the skin may guide and deposit the transcutaneous analyte sensor 24 within the individual's skin. FIG. 34, for example, illustrates the transcutaneous analyte sensor 24 positioned within the needle channel 328 prior to insertion of the needle 302. A needle hub 330 may be positioned at a proximal end of the needle shaft and may include coupling members 332 that may be configured to engage a releasable coupler. The coupling members 332 as shown in FIG. 31 may comprise cavities within the needle hub 330.

The needle cover 304 may comprise a sheath configured to extend over at least a portion of the needle 302 and similarly may have a "C" shape with a fold of needle cover material extending on two sides of a needle cover channel 334. The needle 302 may be positioned within the needle cover channel 334 and the "C" shape may expose the needle channel 328 such that the transcutaneous analyte sensor 24 may be positioned within the needle channel 328. The needle cover 304 may include a needle cover hub 336 at a proximal end of the needle cover 304 and a contact surface 338 at a distal end of the needle cover 304 for contacting a portion of an individual's skin to retract the needle cover 304 relative to the needle 302. The needle cover hub 336 may be configured to slide within a channel of the applicator.

Figure 33:
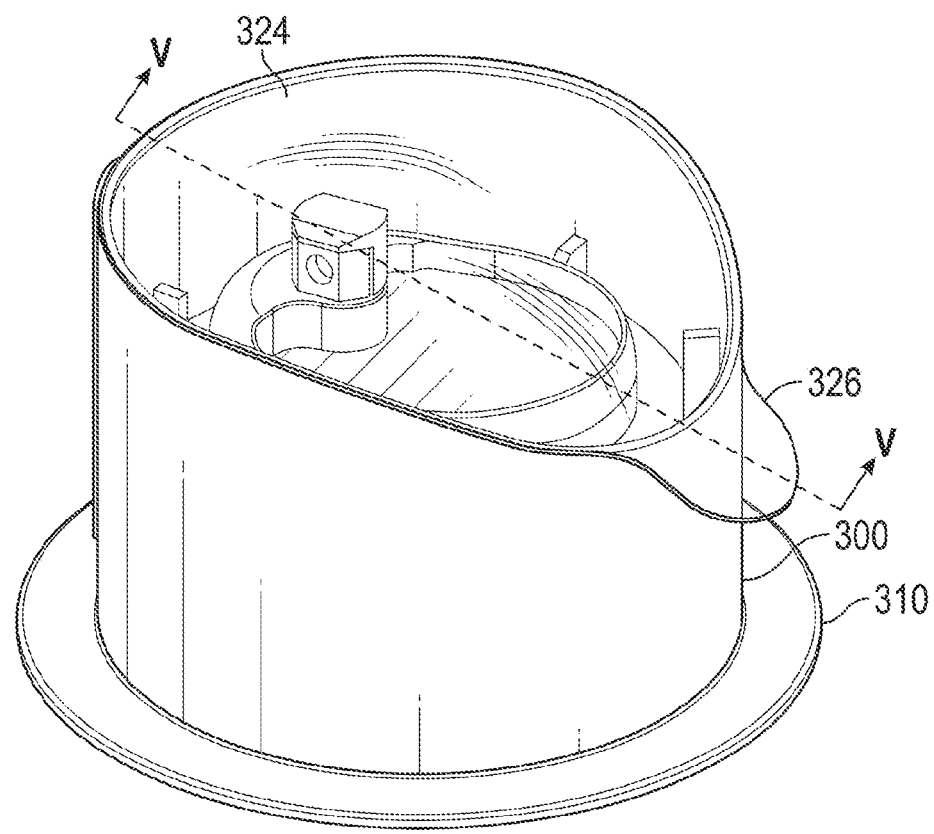
FIG. 33 illustrates a top perspective view of the cartridge shown in FIG. 30.

FIG. 33 illustrates a perspective view of the cartridge 300 including the cover 324 in position on the cartridge body 308. Similar to the cartridge 104 shown in FIG. 5, the cartridge 300 may comprise a unit that is coupled to an applicator for the transcutaneous analyte sensor contained therein.

FIG. 34 illustrates a cross sectional view of the cartridge 300 including the cover 324 in position on the cartridge body 308. The needle cover 304 is shown to extend over the needle 302, with the transcutaneous analyte sensor 24 in position within the needle 302.

Figure 35:
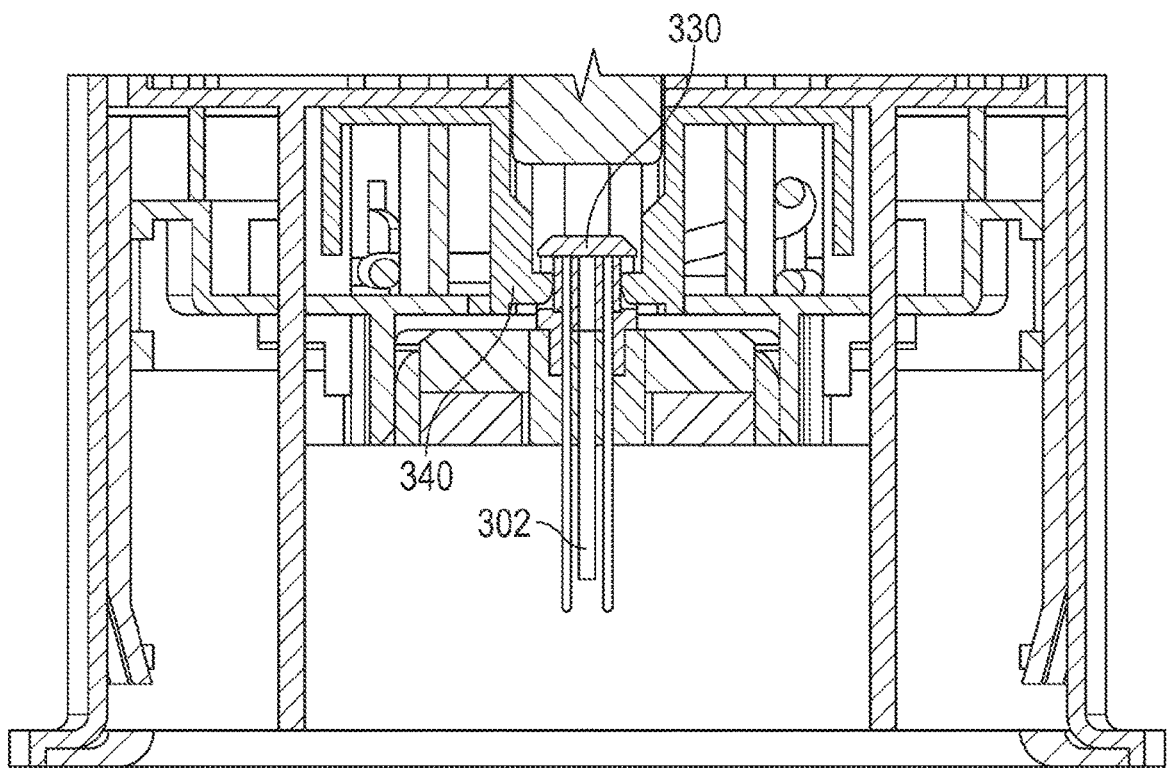
FIG. 35 illustrates a cross sectional view of an applicator along a line II-II as shown in FIG. 2.

The cartridge 300 may be utilized with an applicator that is configured similarly as the applicator 102 shown in FIG. 2. The applicator 102 may be modified to accommodate the configuration of the needle 302 and needle cover 304. For example as shown in FIG. 35, a releasable coupler 340 may operate and be configured similarly as the releasable coupler 218 shown in FIG. 9. The releasable coupler 340 however may be modified to include protrusions (similar to the protrusions 219a, b shown in FIG. 9) that fit within the coupling members 332 (shown in FIG. 31) of the needle hub 330. Further, the carriage of the insertion actuator may be configured to include a channel 342 (marked in FIG. 36) for the needle cover hub 336 to slide along as the needle 302 is inserted into the individual's skin.

FIG. 35 illustrates an embodiment of such an applicator in which the steps of FIGS. 21 and 22 have been performed. The releasable coupler 340 is coupled to the needle 302. Upon the step shown in FIG. 24 being performed, the needle 302 and the needle cover 304 may both be moved axially downward by the insertion actuator (which may operate similarly as with the applicator 102).

Figure 36:
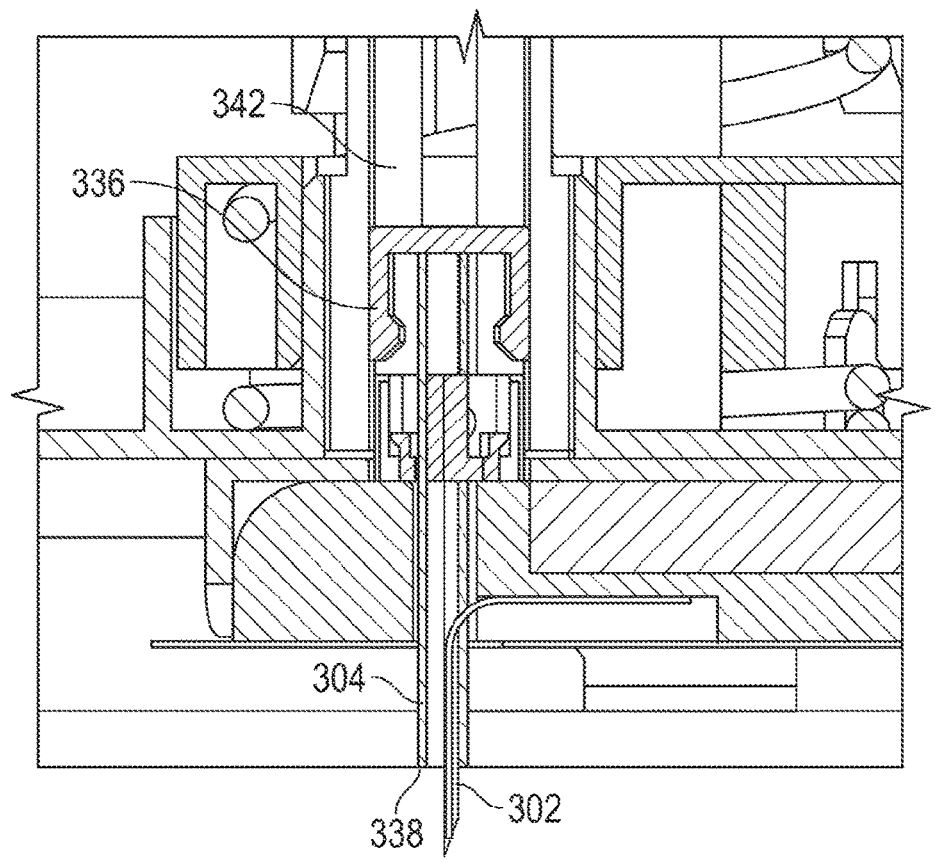
FIG. 36 illustrates a cross sectional view of an applicator along a line I-I as shown in FIG. 2.

FIG. 36 illustrates the needle 302 and the needle cover 304 both being moved axially downward by the insertion actuator, with the needle 302 being inserted into the skin of the individual. The contact surface 338 of the needle cover 304 may contact the individual's skin yet be too dull to penetrate the skin. As such, the needle cover 304 may be slid axially upward relative to the needle 302 as the needle 302 moves axially downward into the individual's skin. The needle cover hub 336 may include a releasable coupler 337 (marked in FIG. 32) that couples to a coupling member on the needle hub 330, yet the force against the individual's skin may be strong enough to release the releasable coupler 337. The force against the needle cover 304 may cause the needle cover 304 to slide and uncover a portion of the needle 302 that is inserted into the individual's skin. The needle cover 304 and particularly the needle cover hub 336 may slide within the channel 342 of the insertion actuator.

Figure 37:
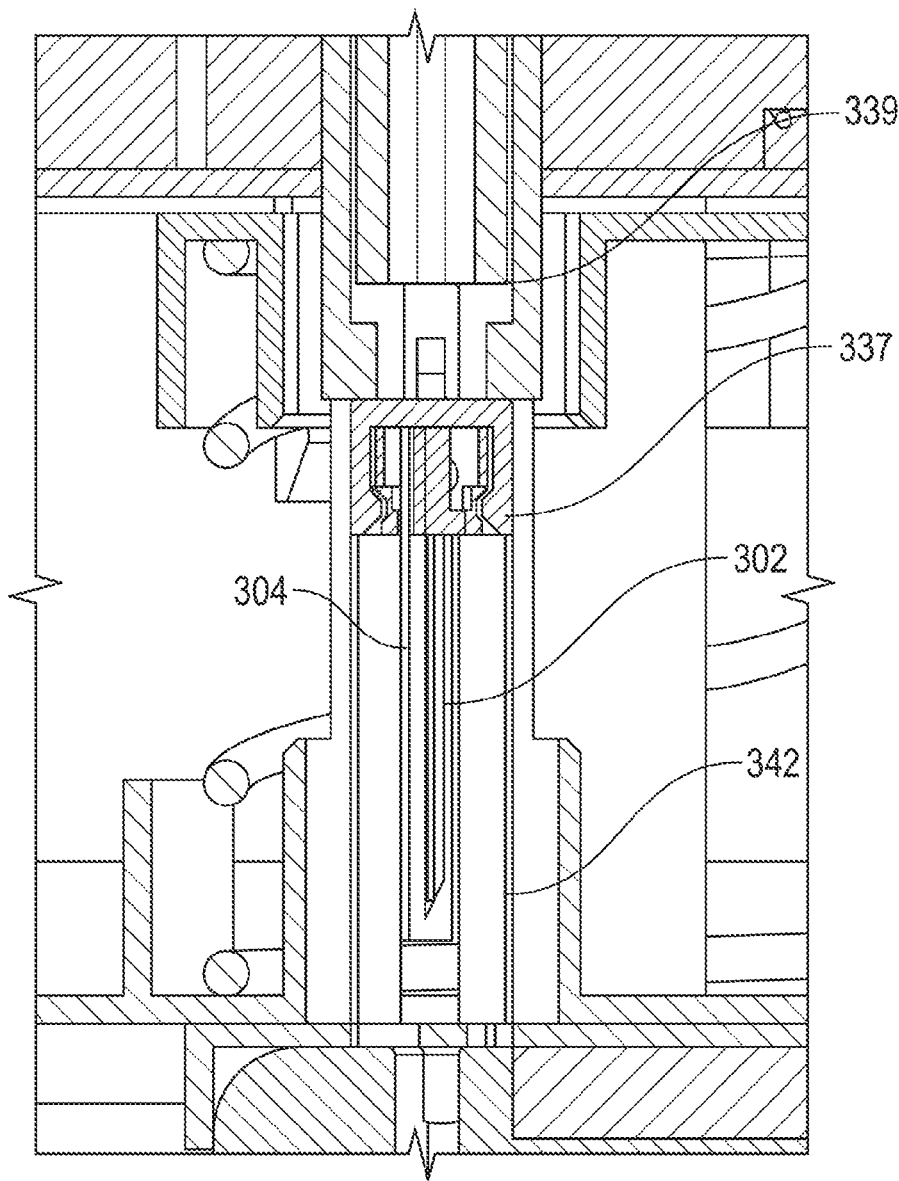
FIG. 37 illustrates a cross sectional view of an applicator along a line I-I as shown in FIG. 2.

Upon the retraction actuator operating (which may operate similarly as the retraction actuator of the applicator 102), the needle 302 may be retracted out of the individual's skin and resheathed within the needle cover 304. Referring to FIG. 37, the needle 302 and the needle cover 304 are both shown in a retracted position after the retraction actuator has operated. The needle 302 is coupled to the needle cover 304 by way of the releasable coupler 337. The release actuator (which may operate similarly as the release actuator of the applicator 102) may then operate to apply the pressing surface 339 to the releasable coupler 340 shown in FIG. 35 and release the needle 302 from within the releasable coupler 340. The pressing surface 339 may deflect the arms of the releasable coupler 340 in a similar manner as the operation of the release actuator of the applicator 102. The pressing surface 339 may further press the needle (sheathed within the needle cover 304) axially downward out of the channel 342 of the insertion actuator and out of the applicator housing. The force of the pressing surface 339 may be sufficient to eject the sheathed needle 302.

The embodiment referenced in FIGS. 30-37 may beneficially keep the needle 302 sheathed by the needle cover 304 prior to insertion of the needle 302 into the individual's skin. As such, an individual may be blocked from access to the needle 302 and particularly the penetrating tip of the needle prior to insertion of the needle 302 into the individual's skin. The needle cover 304 may then be resheathed over the needle 302 at the time the needle 302 is released from the applicator housing and comprises a unit for discard. The needle cover 304 provides a similar purpose as the needle cover 132 shown in FIG. 3, namely to block access to the needle 302 after use of the needle 302.

Figure 38:
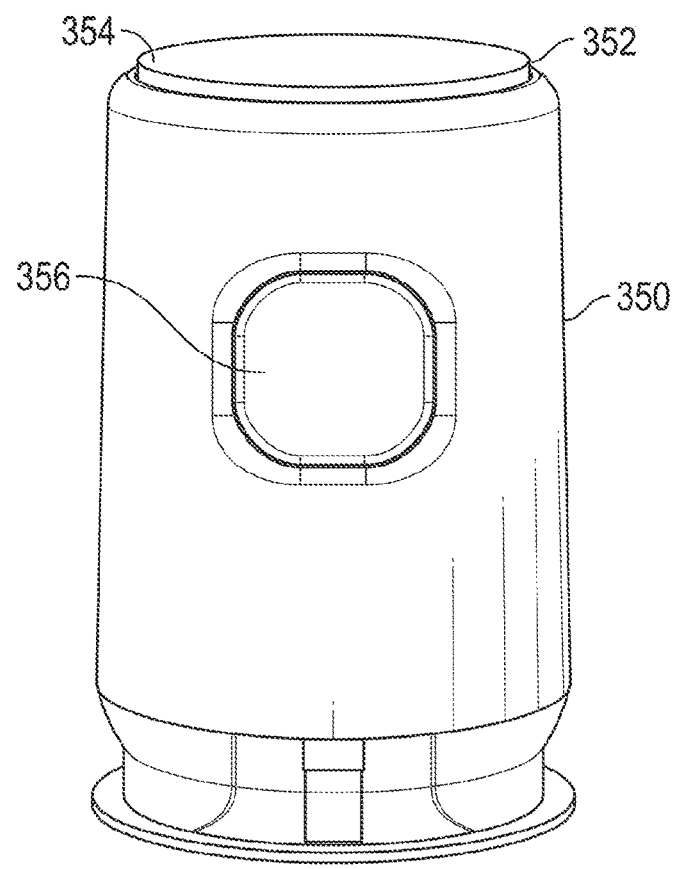
FIG. 38 illustrates a perspective view of an applicator.

FIG. 38 illustrates an embodiment of an applicator 350 that is configured similarly as the applicator 102, yet includes an indicator 352 indicating when the release actuator is to be operated. The indicator 352 may comprise a visual indicator, which may comprise a surface, a color, or a combination thereof as shown in FIG. 38, or other forms of visual indicators. As shown in FIG. 38, the indicator 352 may comprise a surface of the release actuator that moves upward at a time the release actuator is to be activated. The surface may be colored to provide a greater visual impact to an individual. The indicator 352 may comprise all or a portion of a control device 354 for the release actuator, which may operate similarly as the control device 178 shown in FIG. 22. The indicator 352 may be activated by the control device 356 for the insertion actuator being pressed in a similar manner as shown in FIG. 24. The control device 354 may include a portion or activate a mechanism or assembly that causes the indicator 352 to move upward, to indicate that the control device 354 may be pressed and the needle must be released from the applicator housing. The user may then press the control device 354 to activate the release actuator.

Various other forms of indicators may be utilized in other embodiments, including but not limited to visual, auditory, tactile, or other forms of indicators. The indicator may be provided on a display screen or the like and may be provided in an electronic format in certain embodiments.

Figure 39:
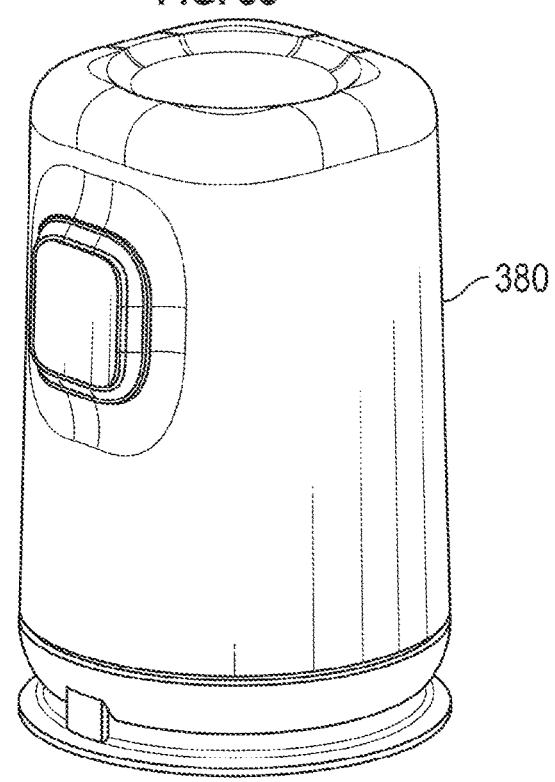
FIG. 39 illustrates a perspective view of an applicator and a cartridge.

FIG. 39 illustrates an embodiment in which an applicator 380 may be configured similarly as the applicator 102, yet has a rectangular or square outer shape of the applicator housing. Such a shape may improve grip upon the applicator housing. Other shapes or configurations may be utilized such as triangular, pentagonal, oval, or other shapes as desired.

Figure 40:
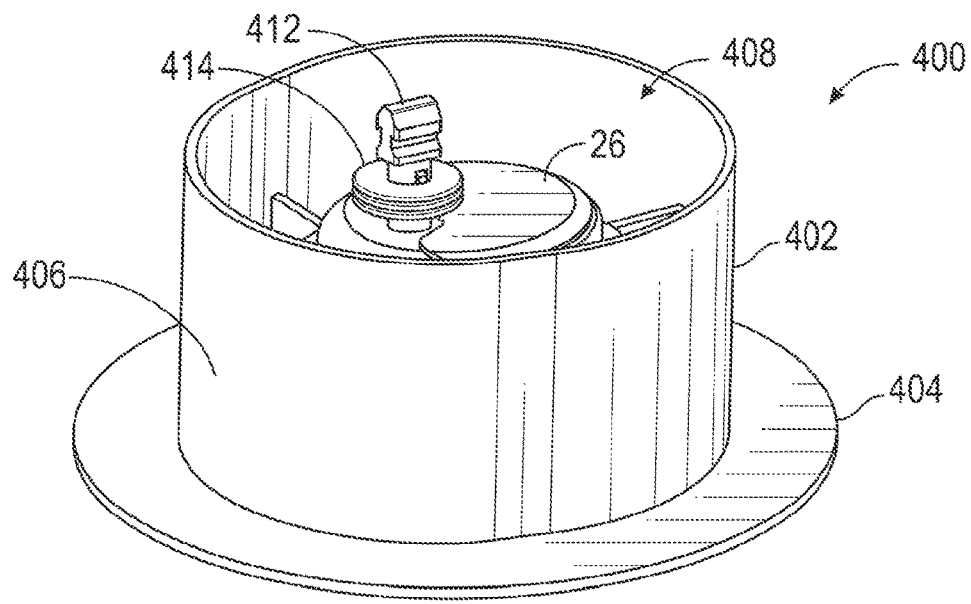
FIG. 40 illustrates a perspective view of a cartridge.

FIG. 40 illustrates an embodiment of a cartridge 400 that may be configured similarly as the cartridge 104 shown in FIG. 5, for example, or similarly as the cartridge 300 shown in FIG. 30. The cartridge 400, for example, may include a body 402 having a base 404 and a wall 406. The base 404 may form a bottom of the cartridge 400 that the cartridge 400 may be positioned upon. The base 404 may form a flange extending outward from the wall 406. The wall 406 may extend upward from the base 404, transverse to a direction that the base 404 extends in. The wall 406 may extend around and define a cavity 408 that may receive components of the cartridge including the transcutaneous analyte sensor and the needle 410 (marked in FIG. 41).

Figure 41:
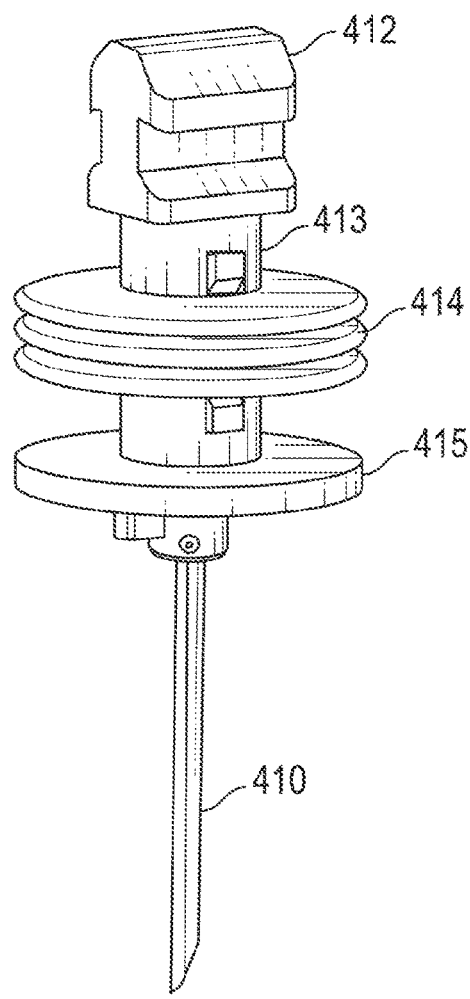
FIG. 41 illustrates a perspective view of a needle and a needle cover.

Referring to FIG. 41, the needle 410 may include a needle hub 412 at a proximal end of the needle 410. The needle hub 412 may couple to a proximal end 413 of a needle cover 414, with the needle cover 414 configured to expand and contract axially along the length of the needle 410. The distal end 415 of the needle cover 414 may be configured to slide along the shaft of the needle 410. The needle cover 414, for example, may comprise an accordion structure that allows for expansion and contraction.

Figure 42:
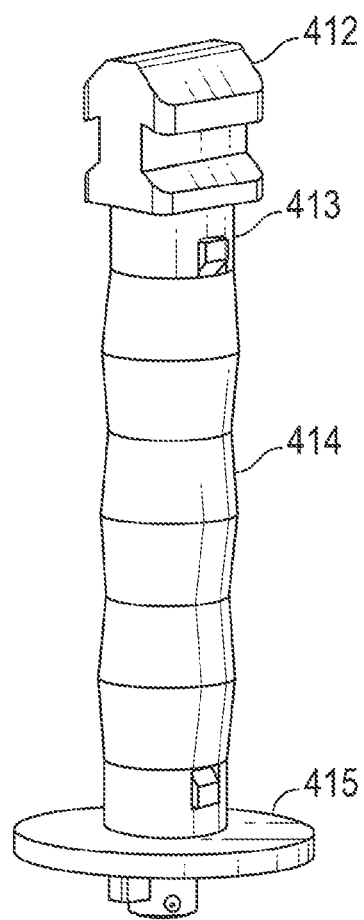
FIG. 42 illustrates a perspective view of the needle cover of FIG. 41 extending over the needle of FIG. 41.

In a configuration in which the needle 410 is held in the cartridge 400 prior to insertion of the needle 410, the needle cover 414 may be in the compressed state as shown in FIG. 41. Thus, the shaft of the needle 410 may be positioned for insertion into the individual's skin. When the needle 410 is withdrawn from the individual's skin, the needle cover 414 may expand axially along the shaft of the needle 410 to cover the needle shaft. FIG. 42, for example, illustrates such a configuration.

The retraction of the needle 410 may occur by any method disclosed herein. For example, a releasable coupler may engage the needle hub 412 and retract the needle hub 412 according to embodiments herein. The needle cover 414 may extend over the retracted needle upon retraction of the needle 410.

Figure 43:
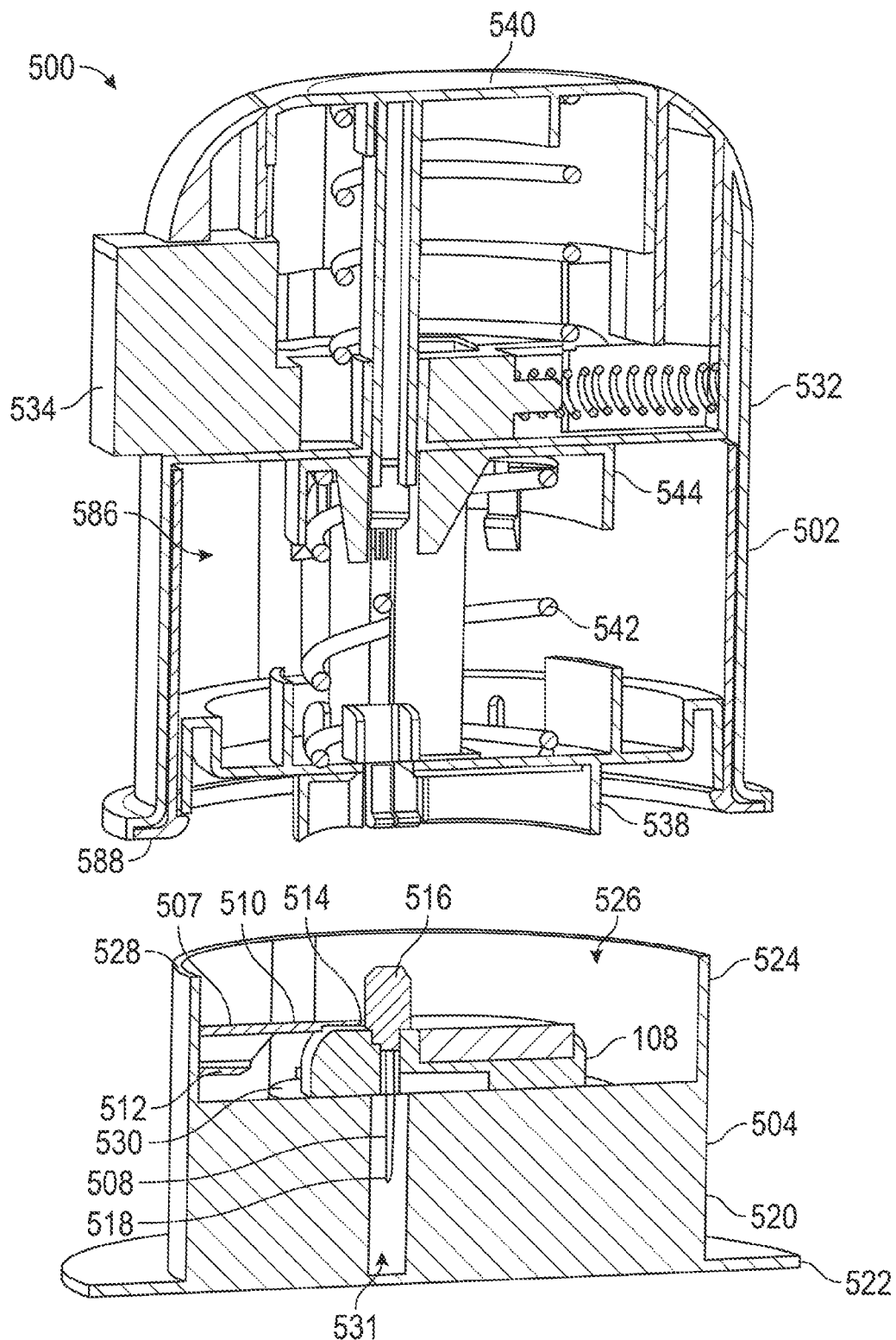
FIG. 43 illustrates a cross sectional view of an applicator and a cartridge along a mid-line of the applicator and cartridge.

FIGS. 43-51 illustrate an embodiment of a variation of a system 500 for inserting a transcutaneous analyte sensor into an individual's skin, including an applicator 502 and a cartridge 504. FIG. 43 illustrates a cross sectional view of the applicator 502 and the cartridge 504. Referring first to the cartridge 504, the cartridge 504 may be configured similarly as the cartridge 300 shown in FIG. 30, yet may include a needle cover 507 that is configured to rotate relative to the needle 508 to extend over at least a portion of the needle 508. The needle cover 507 may be configured to cover at least a portion of the needle 508 following the needle 508 guiding the transcutaneous analyte sensor into the skin of the individual. The needle 508 may be configured to be moved relative to the needle cover 507 to be positioned into the needle cover 507. The needle cover 507 as shown in FIG. 43 includes an arm 510 coupled to a sheath 512. The arm 510 couples to a pivot 514 that couples to a needle hub 516 positioned at a proximal end of the needle shaft. The pivot 514 allows the arm 510 to rotate to position the sheath 512 over the penetrating tip 518 of the needle 508 at the desired time. The sheath 512 may be configured to extend over at least a portion of the needle 508. The needle cover 507 may be coupled to the wearable housing 108 and configured to be separable from the wearable housing 108.

Figure 51:
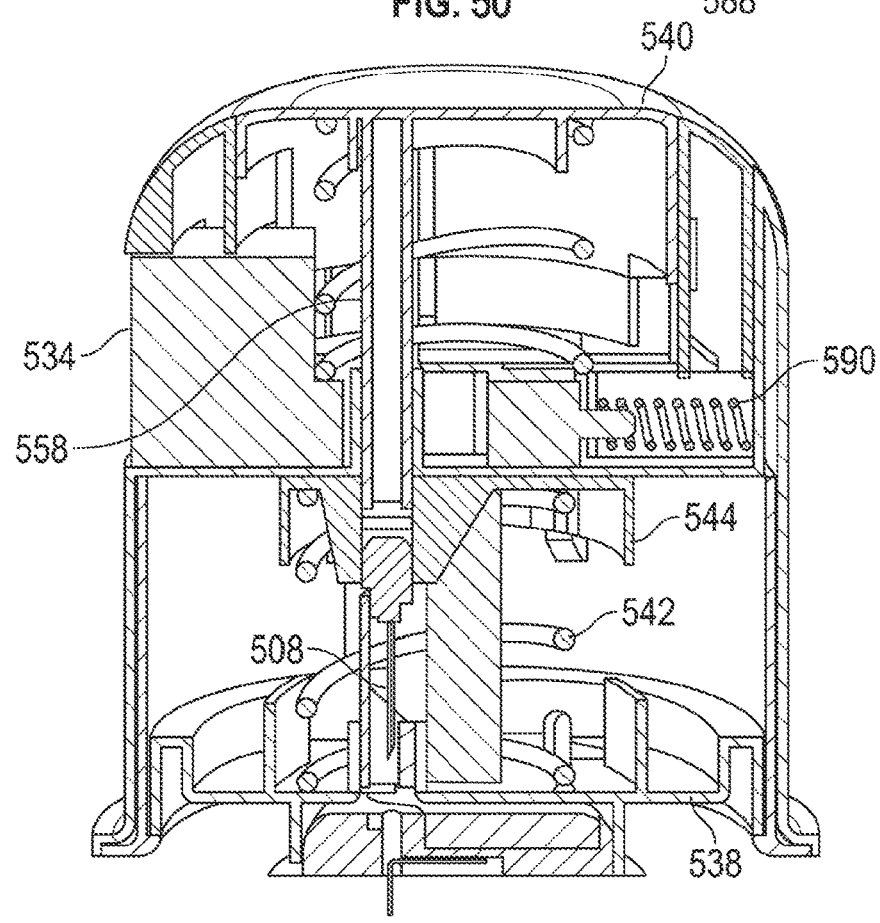
FIG. 51 illustrates a cross sectional view of an applicator and a cartridge along the mid-line of the applicator and cartridge shown in FIG. 43.

As shown in FIG. 43, the arm 510 may rest upon a surface of the wearable housing 108, and then as the needle 508 is retracted from the wearable housing 108, the arm 510 may swing downward towards the penetrating tip 518 to cover the tip 518 in a manner shown in FIG. 51.

The cartridge 504 may include a body 520 having a base 522 and a wall 524. The base 522 may form a bottom of the cartridge 504 that the cartridge 504 may be positioned upon. The base 522 may form a flange extending outward from the wall 524. The wall 524 may extend upward from the base 522, transverse to a direction that the base 522 extends in. The wall 524 may extend around and define a cavity 526 that may receive components of the cartridge including the transcutaneous analyte sensor 24 and the needle 508. The wall 524 may extend around at least a portion of the needle cover 507. The wall 524 may extend upward to an upper opening 528 that exposes the components retained by the body 520. The wall 524 may including an inner surface configured to face inward towards a central portion of the cartridge 504 and the transcutaneous analyte sensor 24 and an outer surface facing opposite the inner surface. The outer surface of the wall may be configured to be positioned within at least a portion of an applicator. The outer surface of the wall may comprise a mating surface for a receiver of the applicator, and may be contoured to a shape of an inner surface of the receiver.

The wall 524 may be shaped similarly as the wall 146 discussed in regard to the cartridge 104 shown in FIG. 5. The body 520 may include a retainer 530 that may operate and be structured similarly as the retainer 152 discussed in regard to the cartridge 104.

Referring to FIG. 43, the body 520 of the cartridge 504 may include a central cavity 531 that is configured to receive the needle 508 when positioned within the body 520 of the cartridge 504. The cartridge 504 may include a removable cover that operates similarly as the cover 324 shown in FIG. 30. The components of the transcutaneous analyte sensor system may be retained by the body 520 in a similar manner as discussed in regard to the cartridge 104, and the cartridge 504 may be utilized in a similar manner as the cartridge 104.

The applicator 502 comprises a transcutaneous analyte sensor applicator, and is configured to apply other components of the transcutaneous analyte sensor system to the skin of an individual including the wearable housing 108 and patch 106 of the transcutaneous analyte sensor system. The applicator may deploy all or a portion of components of an on-skin sensor assembly 12 to an individual's skin.

The applicator 502 comprises a reusable applicator, and may provide reusable functionality in a similar manner as the applicator 102.

FIG. 43 illustrates components of the applicator 502. The applicator 502 may include an applicator housing 532, which may comprise a single component or multiple components, similar to the housing of the applicator 102. The applicator housing may have a cylindrical shape with an outer surface configured to be gripped by an individual. The applicator housing 532 may be configured to be gripped to apply the transcutaneous analyte sensor into the individual's skin. Other shapes of the applicator housing 532 may be utilized as desired.

The applicator housing 532 may include a top portion (formed by the control device 540) and a bottom portion including an opening 588 for the transcutaneous analyte sensor to be deployed from to be inserted into the individual's skin. A side portion may be positioned between the top portion and the bottom portion. The opening 588 may be configured for the needle 508 and the transcutaneous analyte sensor 24 to pass through to insert the transcutaneous analyte sensor 24 into the individual's skin.

FIG. 43 illustrates other components of the applicator 502. The components may include an actuator that may be coupled to the applicator housing 532 and that is configured to insert the needle 508 into the individual's skin to deposit the transcutaneous analyte sensor 24 into the individual's skin. Such an actuator may be referred to as an insertion actuator. The insertion actuator may include components that may include a control device 534 and a driver 536 (marked in FIG. 49), and may include a carriage 538. The insertion actuator may include other components (or fewer components) in other embodiments. The applicator 502 may include a release actuator that is configured to release the needle 508 from within a releasable coupler. The release actuator may include components that may include a control device 540 and may include a pressing surface 543 (marked in FIG. 48) that is configured to apply a force to the releasable coupler to cause the needle 508 to release from the releasable coupler. The release actuator may be configured to release the needle 508 from the releasable coupler to allow the needle 508 to be passed through the opening 588 at the bottom portion of the applicator housing. The release actuator may include other components (or fewer components) in other embodiments. The applicator 502 may include a retraction actuator that is configured to retract the needle 508 from the individual's skin following insertion of the transcutaneous analyte sensor into the individual's skin. The retraction actuator may include components that may include a driver 542 and a carriage 544. The retraction actuator may include other components (or fewer components) in other embodiments. The configuration of components in the applicator 502 may be varied in other embodiments.

Figure 44:
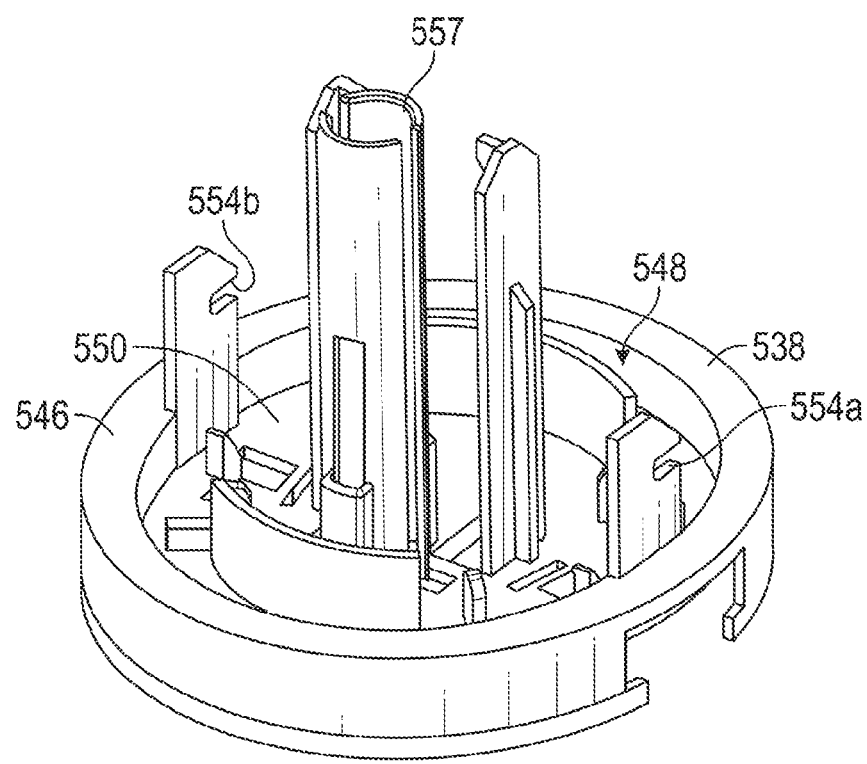
FIG. 44 illustrates a perspective view of a carriage of the applicator shown in FIG. 43.

FIG. 44 illustrates a perspective view of the carriage 538 of the insertion actuator. The carriage 538 may comprise a body configured to slide within an interior cavity of the applicator 502 that may be defined by the applicator housing 532. The carriage 538 may be configured to slide relative to the applicator housing and be configured to be slid by the driver 536. The carriage 538 may include an outer ring 546. The outer ring 546 may surround a cavity 548 of the carriage 538. The cavity 548 may be configured to receive the carriage 544 of the retraction actuator and may be configured to receive a driver 542 (marked in FIG. 43) of the retraction actuator. The driver 542 may be configured to drive the needle 508 out of the individual's skin.

The carriage 538 may include a central body 550 that spans the interior of the outer ring 546 of the carriage 538. The outer ring 546 may include a channel 552 (marked in FIG. 45) configured to receive the wall 524 of the cartridge 504.

Figure 47:
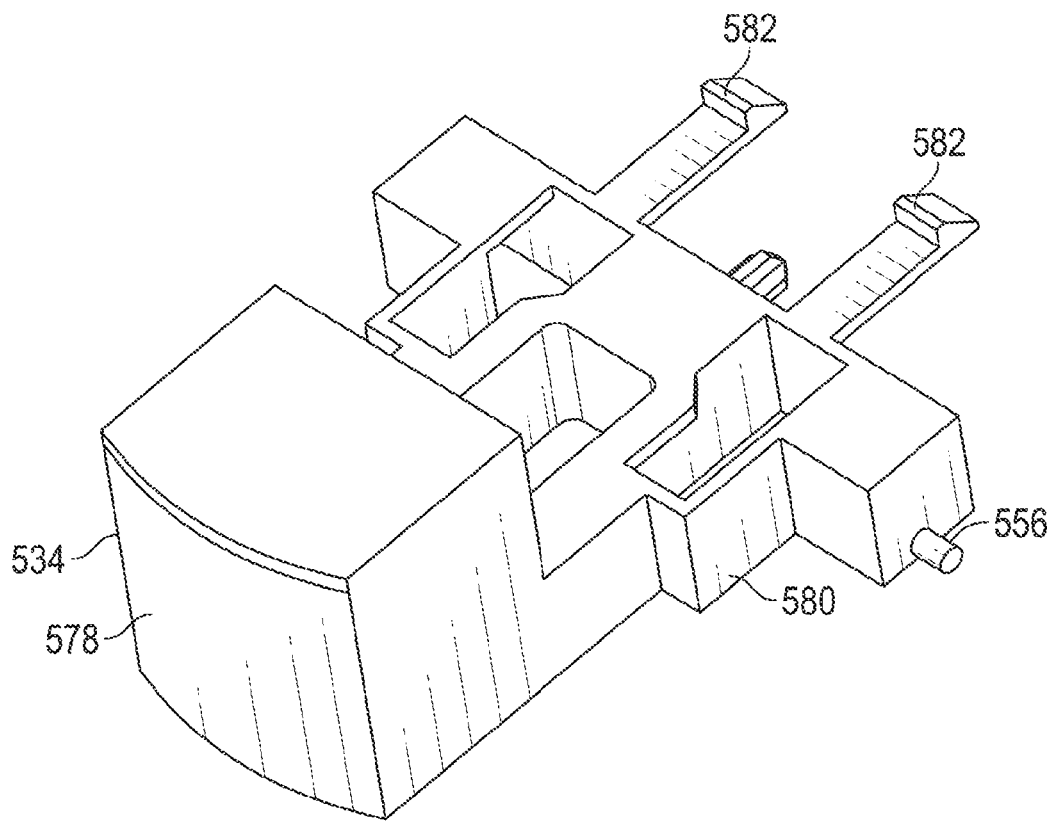
FIG. 47 illustrates a perspective view of a control device of the applicator shown in FIG. 43.

An upper surface of the carriage 538 may include a releasable coupler 554a, b configured to couple to a coupling member 556 of the insertion actuator as shown in FIG. 47 (a similar coupling member 556 is on the opposite side of the control device 534). The releasable coupler 554a, b may comprise arms having openings configured for the coupling member 556 of the insertion actuator to engage. The coupling member 556 may comprise protrusions that enter into the openings of the releasable coupler 554a, b. In other embodiments, the releasable coupler 554 may have different forms.

Figure 50:
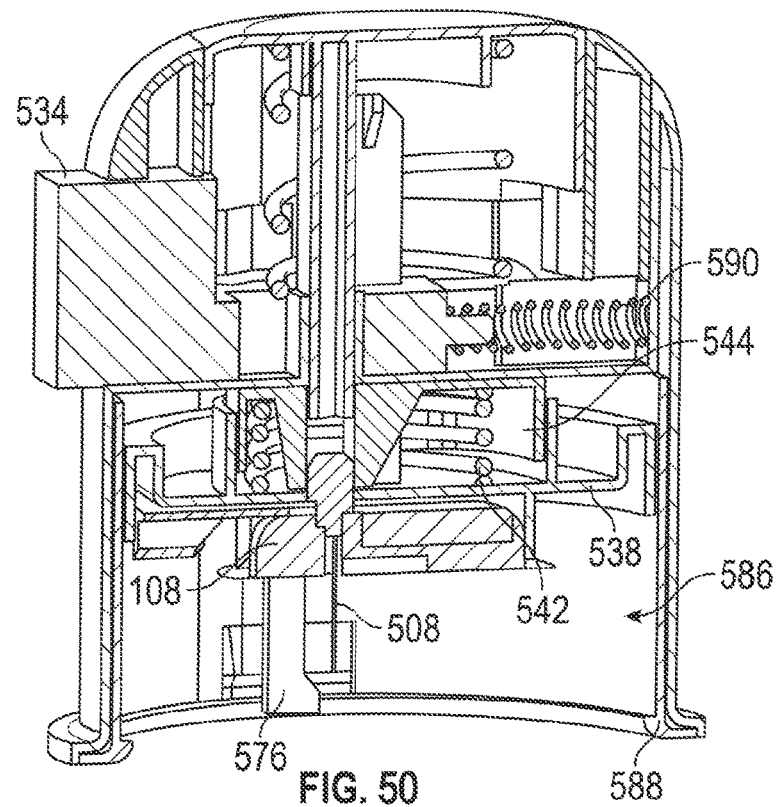
FIG. 50 illustrates a cross sectional view of an applicator and a cartridge along the mid-line of the applicator and cartridge shown in FIG. 43.

FIG. 44 illustrates a central channel 557 may be provided (excluded from view in FIGS. 43, 50, and 51). The central channel 557 may be configured for the needle 508 to be retracted into upon operation of the retraction actuator and may provide a guide path for a column 558 (marked in FIG. 48) of the retraction actuator to extend in.

Figure 45:
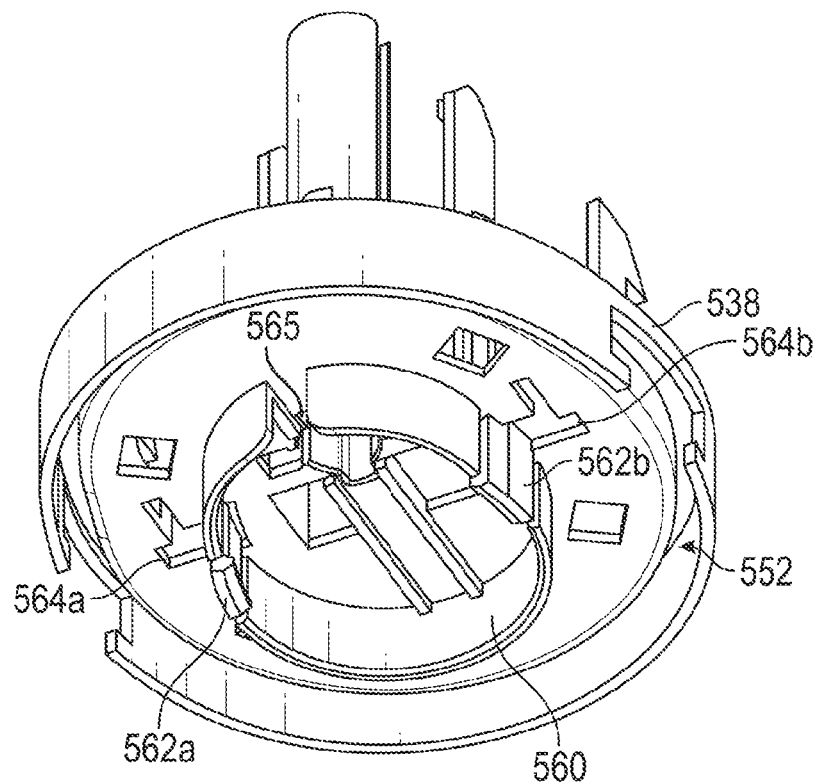
FIG. 45 illustrates a bottom perspective view of the carriage shown in FIG. 44.

FIG. 45 illustrates a perspective view of a lower surface of the carriage 538. The lower surface of the carriage may include a receiver 560 that is configured to receive at least a portion of the transcutaneous analyte sensor system. The receiver 560 may comprise a cavity that is configured to receive the transcutaneous analyte sensor system. The receiver 560 may include at least one releasable coupler 562a, b that is configured to couple to the wearable housing 108 of the transcutaneous analyte sensor system. The releasable coupler 562a, b may comprise a protrusion configured to enter into a cavity 123 (marked in FIG. 3) of the wearable housing 108 to couple to the wearable housing 108. In other embodiments, other forms of releasable couplers 562a, b may be utilized.

An opening 565 may be positioned on the carriage 538 and may extend through the lower surface of the central body 550 to the upper surface of the central body 550. The opening 565 may be configured for the needle 508 to pass through.

The carriage 538 may include openings 564a, b configured for releasable couplers of the carriage 544 of the retraction actuator to extend through, to couple the carriages 538, 544 together.

Figure 46:
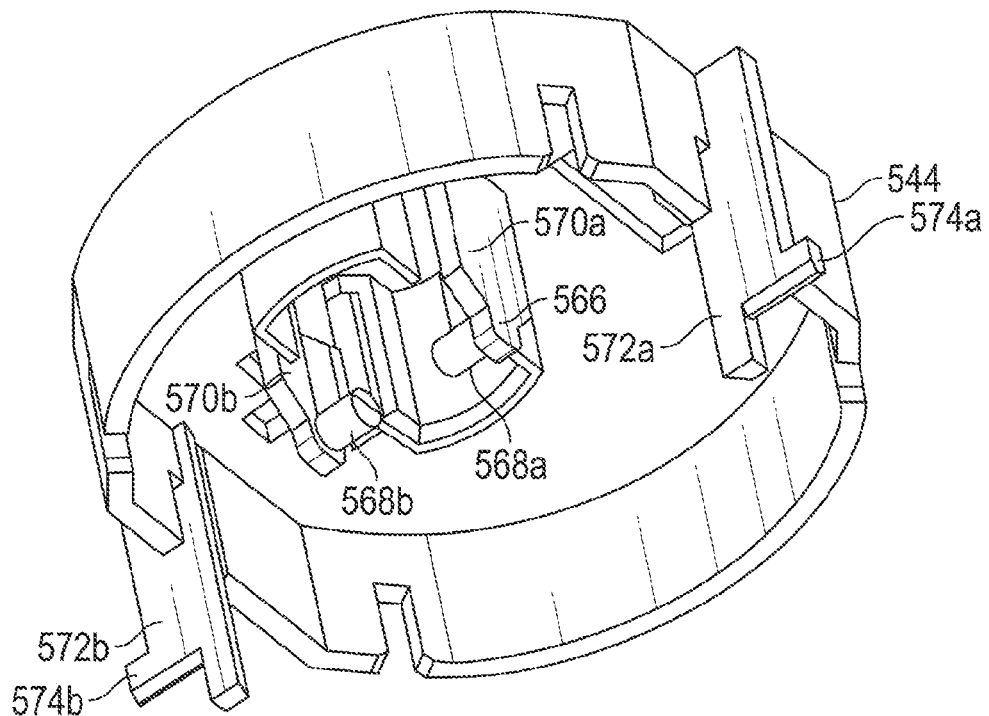
FIG. 46 illustrates a perspective view of a carriage of the applicator shown in FIG. 43.

FIG. 46 illustrates a bottom perspective view of the carriage 544 of the release actuator. The carriage 544 may be configured to slide relative to the applicator housing and be configured to be slid by the drivers 542 and 536. The carriage may include a releasable coupler 566 that is configured to releasably couple to the needle 508. The releasable coupler 566 may include protrusions 568a, b that are configured to engage coupling members of the needle hub 516 to releasably couple to the needle 508. The protrusions 568a, b may be movable upon a pressing surface pressing upon arms 570a, b coupled to the protrusions 568a, b. The releasable coupler 566 may be configured to retain the needle 508 at least partially within the applicator housing 532 following insertion of the transcutaneous analyte sensor 24 into the individual's skin and removal of the applicator housing 532 from the transcutaneous analyte sensor 24, and configured to release the needle 508 from within the applicator housing 532 following insertion of the transcutaneous analyte sensor 24 into the individual's skin.

The carriage 544 of the retraction actuator may include deflectable arms 572a, b having releasable couplers 574a, b at their ends for coupling to the openings 564a, b of the carriage 538 of the insertion actuator shown in FIG. 45. The releasable couplers 574a, b may be configured to release from the openings 564a, b of the carriage 538 upon contact with coupler releases in the form of deflectors 576 of the applicator housing, with one such deflector being shown in FIG. 50 along an inner sidewall of the applicator housing.

The configuration of the carriage 544 may be varied in other embodiments.

FIG. 47 illustrates a perspective view of the control device 534 of the insertion actuator. The control device 534 may comprise a button that may be pressed or other device that may be moved to activate the insertion actuator. The control device 534 may be configured to be slid laterally to activate the insertion actuator. The control device 534 may include a button surface 578 and a control arm 580 that extends from the button surface 578. The control arm 580 may include a coupling member 556 in the form of a protrusion extending laterally outward from the control arm 580. A similar coupling member 556 is on the opposite side of the control device 534. The control arm 580 may further comprise a releasable coupler in the form of a lock 582 at a portion of the control arm 580 distal the button surface 578, configured to lock the control device 534 in position. The lock 582 may comprise a deflectable hook structure as shown in FIG. 47.

Figure 48:
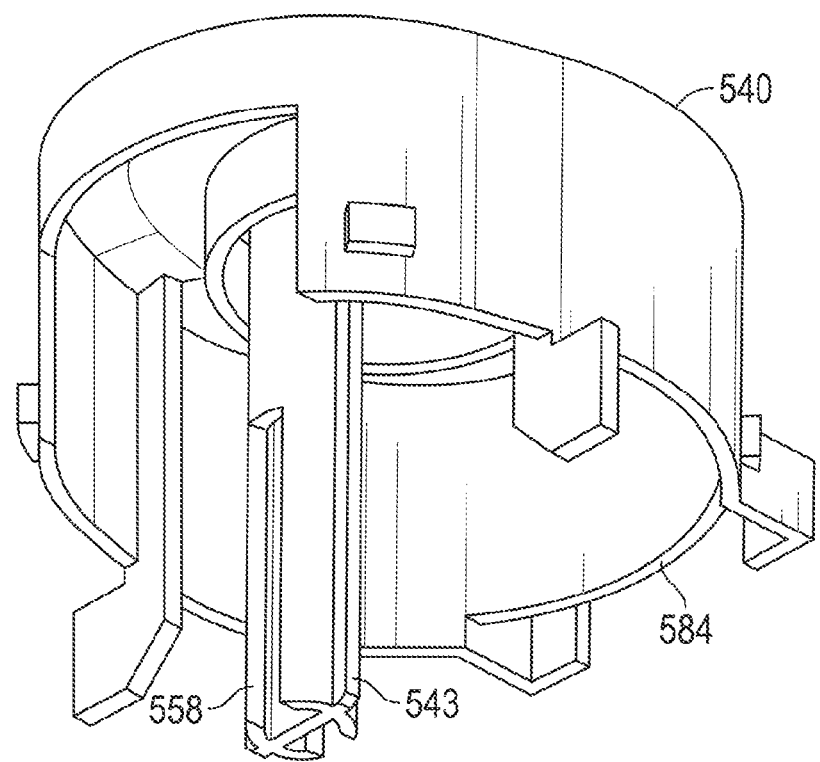
FIG. 48 illustrates a bottom perspective view of a release actuator of the applicator shown in FIG. 43.

FIG. 48 illustrates a bottom perspective view of the release actuator, showing the control device 540 and the pressing surface 543. The control device 540 may comprise a button that may be pressed by an individual to activate the release actuator. The control device 540 may be coupled to the pressing surface 543, which may be configured to press against the releasable coupler 566 to release the needle 508 from within the applicator housing 532. The pressing surface 543 as shown in FIG. 48 may comprise a distal surface of a column 558 that extends axially from the control device 540. The column 558 may include outward extending ridges comprising the pressing surface 543.

The release actuator may further include a lock release 584, which may comprise a surface configured to release the lock 582 of the control device 534 from a locking surface of the applicator housing.

Figure 49:
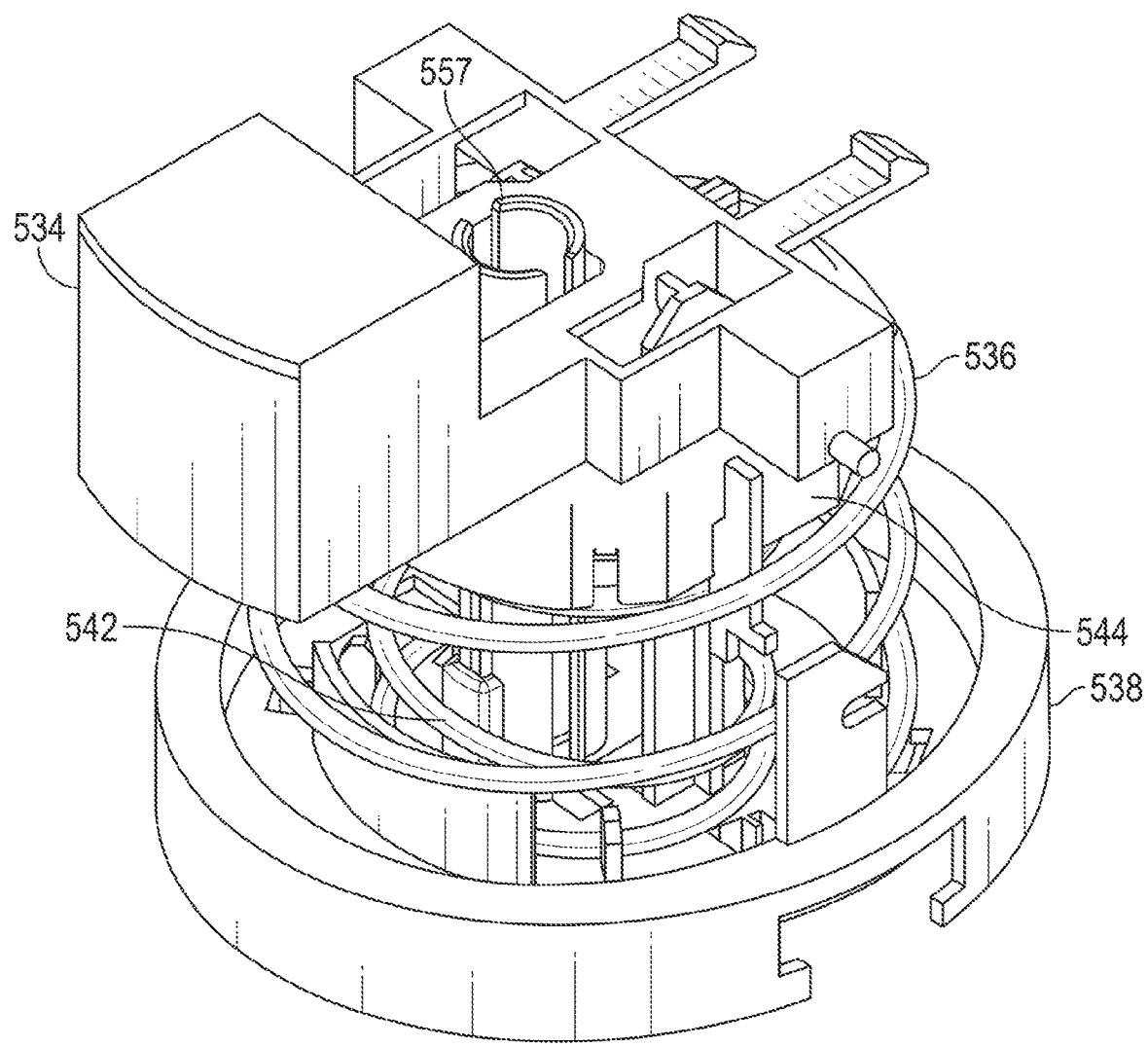
FIG. 49 illustrates a perspective assembly view of the carriages shown in FIGS. 44 and 46 and the control device shown in FIG. 47.

FIG. 49 illustrates a perspective assembly view of the carriage 538 of the insertion actuator with the carriage 544 of the release actuator positioned over the carriage 538. The driver 542 of the retraction actuator is positioned between the carriages 538, 544 for compression by the carriages 538, 544. The driver 536 of the insertion actuator may be positioned upon the carriage 538 of the insertion actuator and configured to be compressed between the carriage 538 and a portion of the applicator housing 532. The control device 534 may be positioned above the carriage 544 with the central channel 557 extending through an opening in the control arm 580 of the control device 534.

FIG. 50 illustrates a perspective cross sectional view of the applicator 502 showing that the applicator housing 532 includes a receiver 586 for receiving the cartridge 504. The receiver 586 may be configured for the cartridge 504 retaining the transcutaneous analyte sensor to be inserted into. The receiver 586 may comprise a cavity within the applicator housing 532 that receives the cartridge 504. The cartridge 504 may be inserted into the receiver 586 axially through an opening 588 at a bottom of the applicator housing 532.

The applicator 502 may operate in a manner shown in FIGS. 43, 50 and 51. FIG. 43 illustrates the applicator 502 in an initial state, in which the applicator 502 is configured to receive the cartridge 504 and components of the transcutaneous analyte sensor system including the transcutaneous analyte sensor 24, the wearable housing 108, and the patch 106. The electronics unit 26 is shown to be coupled to the wearable housing 108 upon insertion into the receiver 586 of the applicator 502, however the electronics unit 26 may be excluded and later coupled to the wearable housing 108 as desired.

The applicator 502 in the initial state has the carriage 538 of the insertion actuator in a lowered state, proximate the lower opening 588 of the applicator 502. The carriage 538 of the insertion actuator may be pressed to the lowered state by the force provided by the driver 536 of the insertion actuator. The driver 536 may be configured to drive the needle 508 into the individual's skin to insert the transcutaneous analyte sensor into the individual's skin. The carriage 544 of the retraction actuator may be in a raised state, pressed to the raised state by the force of the driver 542 of the retraction actuator. The releasable couplers 574a, b shown in FIG. 46 are not yet coupling the carriages 538, 544 together.

The cartridge 504 may be inserted into the receiver 586 of the applicator housing 532 to allow the releasable coupler 562a, b of the carriage 538 of the insertion actuator to engage the wearable housing 108 of the on-skin sensor assembly. A removable cover of the cartridge 504 may previously have been removed by an individual.

FIG. 50 illustrates after the cartridge 504 has been fully inserted into the receiver 586 of the applicator housing 532. The cartridge 504 may be inserted in the axial dimension of the applicator housing 532, which is the same dimension that the transcutaneous analyte sensor 24 as well as other components of the transcutaneous analyte sensor system will be deployed from the applicator housing 532 (although in an opposite axial direction that the cartridge 504 is inserted into the receiver 586). The insertion of the cartridge 504 and the transcutaneous analyte sensor 24 into the receiver 586 of the applicator housing 532 may compress and thus provide energy to both the driver 536 of the insertion actuator (shown in FIG. 49 and not shown in FIG. 50) and the driver 542 of the retraction actuator. Both drivers 536, 542 are compressed in the configuration shown in FIG. 50. In an embodiment in which the drivers 536, 542 are springs, the springs may be compressed by the insertion of the cartridge 504 and the transcutaneous analyte sensor 24 into the receiver. The cartridge 504 may include a pressing surface upon an upper surface of the cartridge 504 to press against the carriage of the insertion actuator to provide energy to the insertion actuator.

The insertion of the cartridge 504 fully into the receiver 586 of the applicator housing 532 also causes the releasable coupler 554a, b (marked in FIG. 44) of the insertion actuator to engage the coupling member 556 (marked in FIG. 47) of the control device 534. The engagement of the releasable coupler 554a, b holds the carriage 538 of the insertion actuator in position and prevents the driver 536 from pressing the carriage 538 in an axial direction towards the lower opening 588 of the applicator housing 532. The releasable couplers 574a, b shown in FIG. 46 engage the openings 564a, b of the carriage 538 of the insertion actuator shown in FIG. 45 to couple the carriages 538, 544.

As shown in FIG. 50, the wearable housing 108 of the transcutaneous analyte sensor system may be positioned in the receiver 586 of the lower surface of the carriage 538. The releasable coupler 562a, b shown in FIG. 45 may couple to the cavity 123 shown in FIG. 3 to grip the wearable housing 108 to the lower surface of the carriage. Thus, as the cartridge 504 is withdrawn from the applicator housing 532, the wearable housing 108 remains coupled to the receiver 560.

The releasable coupler 566 couples to the needle 508, particularly with the protrusions 568a, b of the releasable coupler 566 engaging coupling members of the needle hub 516. The needle 508 is shown to extend downward from the wearable housing 108 of the transcutaneous analyte sensor system, extending for insertion of the penetrating tip of the needle 508 into the individual's skin.

With the cartridge 504 withdrawn from the applicator housing 532 as shown in FIG. 50, the transcutaneous analyte sensor system is in position for application to the individual's skin by the applicator 502. The transcutaneous analyte sensor system may be moved axially downward within the receiver 586 of the applicator housing 532 to contact the individual's skin and be applied to the individual's skin.

The insertion actuator may operate to insert the needle 508 into the individual's skin to deposit the transcutaneous analyte sensor 24 into the individual's skin. The control device 534 of the insertion actuator may be pressed in a lateral direction, or a direction transverse to the axial dimension of the applicator housing 532. The movement of the control device 534 may compress a biasing spring 590 that is configured to apply a biasing force to the control device 534. The movement of the control device 534 may disengage the coupling member 556 shown in FIG. 47 from the releasable coupler 554a, b, by moving the coupling member 556 laterally out of the openings of the releasable coupler 554a, b. The force of the driver 536 shown in FIG. 49 upon the carriage 538 causes the coupled carriages 544, 538 to descend rapidly with sufficient force to drive the needle 508 into the individual's skin.

Further as shown in FIG. 51, upon the control device 534 of the insertion actuator being pressed in a lateral direction, the lock 582 shown in FIG. 47 may engage a locking surface of the applicator housing 532. The lock 582 may prevent the control device 534 from undesirably moving after the control device 534 has been pressed.

After the control device 534 has been pressed and the insertion actuator has been activated, the movement of the carriage 538 has inserted the needle 508 into the individual's skin and has inserted the transcutaneous analyte sensor 24 into the individual's skin. Further, the movement of the carriage 538 has pressed the patch 106 to the individual's skin, allowing the patch 106 to adhere to the individual's skin and providing an adhesive force to the skin for the transcutaneous analyte sensor system.

Further, with the carriages 544, 538 both being slid downward within the applicator housing 532, the releasable couplers 574a, b may contact the coupler release in the form of deflectors 576 shown in FIG. 50. Such contact may apply a force to the releasable couplers 574a, b in lateral directions that causes the releasable couplers 574a, b to disengage from the openings 564a, b. Accordingly, the carriages 538, 544 may be decoupled from each other and able to slide relative to each other. The releasable couplers 574a, b may be configured to automatically release upon contact with the coupler release in the form of the deflectors 576 shown in FIG. 50. The retraction actuator accordingly may be configured to automatically operate upon the needle 508 guiding the transcutaneous analyte sensor into the individual's skin.

Referring to FIG. 51, with the carriages 538, 544 decoupled from each other, the driver 542 of the retraction actuator may apply an upward force to the carriage 544 of the retraction actuator to move the carriage 544 upward.

The upward movement of the retraction actuator carriage 544 may cause the needle 508 that is coupled to the releasable coupler 566 (shown in FIG. 46) to retract out of the individual's skin, due to the upward movement of the releasable coupler 566. The releasable coupler 566 may cause the needle 508 to slide upwards, with the arm 510 of the needle cover 507 (marked in FIG. 43) contacting the opening 565 shown in FIG. 45, to cause the arm 510 to pivot and rotate towards the needle 508. The sheath 512 of the needle cover 507 extends over the penetrating tip of the needle 508 as shown in FIG. 51. The needle cover 507 accordingly may extend over at least a portion of the needle 508. The retraction actuator may position the needle 508 into the needle cover 507.

The releasable coupler 566 retains the needle 508 to the applicator housing 532 following insertion of the transcutaneous analyte sensor 24 into the individual's skin and removal from the applicator housing from the transcutaneous analyte sensor 24. The transcutaneous analyte sensor 24 remains within the individual's skin as the applicator housing is removed from the transcutaneous analyte sensor 24.

With the applicator housing removed from the transcutaneous analyte sensor 24, the release actuator may be operated to release the needle 508 from the releasable coupler 566.

The control device 540 of the release actuator may be pressed axially downward, causing the column 558 of the release actuator to similarly move axially downward. The pressing surface 543 (marked in FIG. 48) of the release actuator accordingly may be moved axially downward to press against the releasable coupler 566 shown in FIG. 46 and particularly press against the deflectable arms 570a, b shown in FIG. 46. The pressure of the pressing surface 543 against the deflectable arms 570a, b causes the protrusions 568a, b (marked in FIG. 46) to release from the coupling members of the needle hub 516. Accordingly, the releasable coupler 566 may be released from the needle 508. The needle 508 and needle cover 507 may be released from the applicator housing 532 with the needle cover 507 covering the penetrating tip of the needle 508.

The release actuator may be configured to release the needle 508 covered by the needle cover 507 from within the applicator housing 532 following insertion of the needle 508 into the individual's skin. The releasable coupler 566 configured to retain the needle 508 is configured to release the needle 508 positioned within the needle cover 507 from the applicator housing. The force of the column 558 of the release actuator may eject the needle 508 and the needle cover 507 together as a unit from the applicator housing 532 for discard (i.e., release from the applicator housing with velocity).

Further, lock release 584 (marked in FIG. 48) may contact the lock 582 of the control device 534, to press the lock 582 under a locking surface of the applicator housing. As such, the control device 534 may be free to move in the opposite lateral direction than shown in FIG. 51 and may be moved back to the position shown in FIG. 50 due to the force applied by the biasing spring 590.

The needle 508 may be released from the applicator housing 532 for discard, as the needle 508 may have been contaminated through the process of insertion within the individual's skin. The needle 508 accordingly may be a single use needle that is configured to discard within a sharps container or other disposal area. The needle 508 may remain sheathed within the needle cover 507 such that an individual does not contact the used needle 508 and be subject to the contamination of the needle 508 or otherwise be injured by the penetrating tip of the needle 508. The needle 508 may remain locked in position within the needle cover 507 such that an individual cannot access the contaminated portion of the needle 508. The needle 508 and needle cover 507 together may form a unit for disposal following insertion into an individual's skin and separation from the applicator housing.

Upon release of the needle 508 and needle cover 507 from the applicator housing 532, and following the return of the control device 534 to the position shown in FIG. 43, the applicator is in a configuration for deployment of another transcutaneous analyte sensor 24 and other components of a transcutaneous analyte sensor system. As such, the applicator 502 is configured for multiple uses, and is not intended to be discarded. The applicator 502 returns to a configuration shown in FIG. 43 for repeat of the steps shown in FIGS. 50 and 51. The applicator 502 may be loaded with another cartridge 504 and the steps disclosed herein may repeat as desired.

Figure 52:
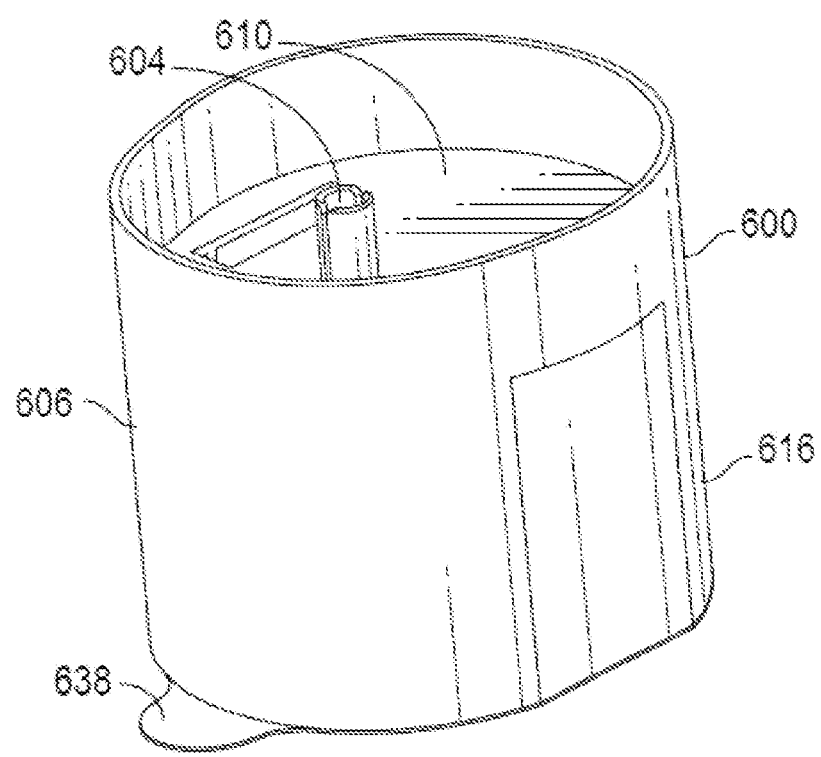
FIG. 52 illustrates a perspective view of a cartridge.

FIG. 52 illustrates an embodiment of a cartridge 600 that may be utilized with an applicator 602 (marked in FIG. 53) that may be configured similarly as the applicator 502 shown in FIGS. 43-51. The cartridge 600, however, may be configured to remove a used needle from the applicator 602 through use of a needle coupler 604 that is configured to engage a used needle that is coupled to the applicator housing and retain the used needle when the body 606 of the applicator is withdrawn from the applicator housing 608.

Figure 53:
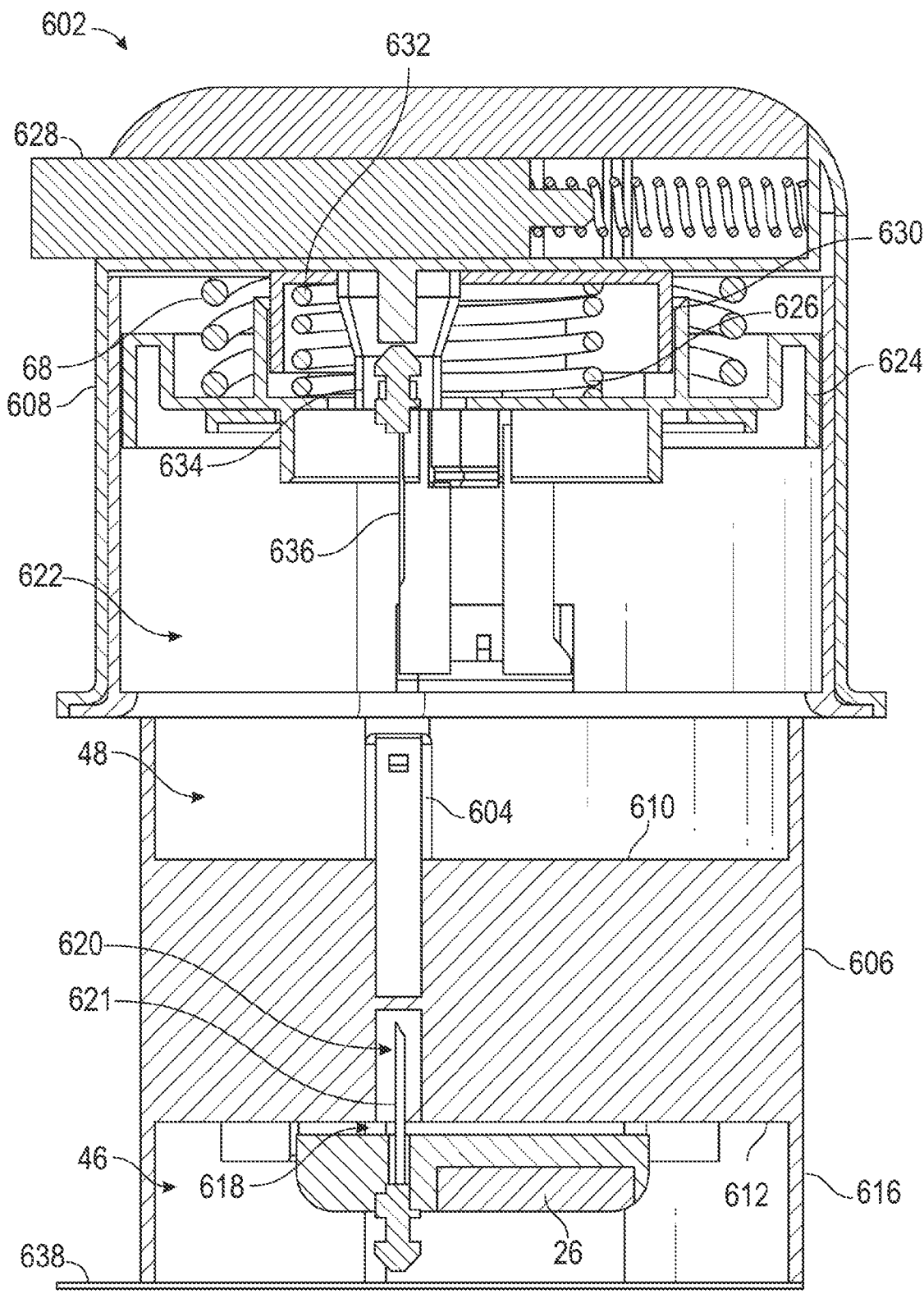
FIG. 53 illustrates a cross sectional view of an applicator and the cartridge shown in FIG. 52.

The cartridge 600 may include a lower surface 610 and an upper surface 612 (marked in FIG. 53) that faces opposite the lower surface 610. The lower surface 610 accordingly faces opposite the upper surface 612. Referring to FIG. 53, the cartridge 600 may include a retainer 618 that is configured to retain a transcutaneous analyte sensor to the body 606, and may include a receiver 620 that is configured to receive an unused needle 621 that is coupled to the transcutaneous analyte sensor. Thus, in embodiments, the needle coupler 604 may be positioned on an opposite side of the cartridge 600 (lower surface 610) from the retainer 618 (upper surface 612), the transcutaneous analyte sensor, unused needle 621, and the housing for the transcutaneous analyte sensor. The transcutaneous analyte sensor may be coupled to the retainer 618 and the unused needle 621 may be positioned within the receiver 620 and coupled to the transcutaneous analyte sensor.

Referring to FIG. 53, the applicator 602 may be configured similarly as the applicator 502 shown in FIGS. 43-51, and may include an insertion actuator (including carriage 624, driver 626, and control device 628), a retraction actuator (including carriage 630, driver 632) and a releasable coupler 634 for a needle. The insertion actuator and retraction actuator may operate in a similar manner as the respective actuators discussed in regard to the applicator 502 shown in FIGS. 43-51. The needle coupler 604 of the cartridge 600, however, may be utilized to remove the used needle 636 from the applicator 602. The needle 636 may be used because it has already been inserted into the skin of an individual.

The body 606 of the cartridge 600 may be configured to couple to the applicator housing 608 and may include a wall 616 that extends around at least a portion of the transcutaneous analyte sensor. The body 606 may be configured to be inserted into a receiver 622 of the applicator 602 with the upper surface 612 facing towards the applicator housing 608 and alternatively with the lower surface 610 facing towards the applicator housing 608.

Figure 54:
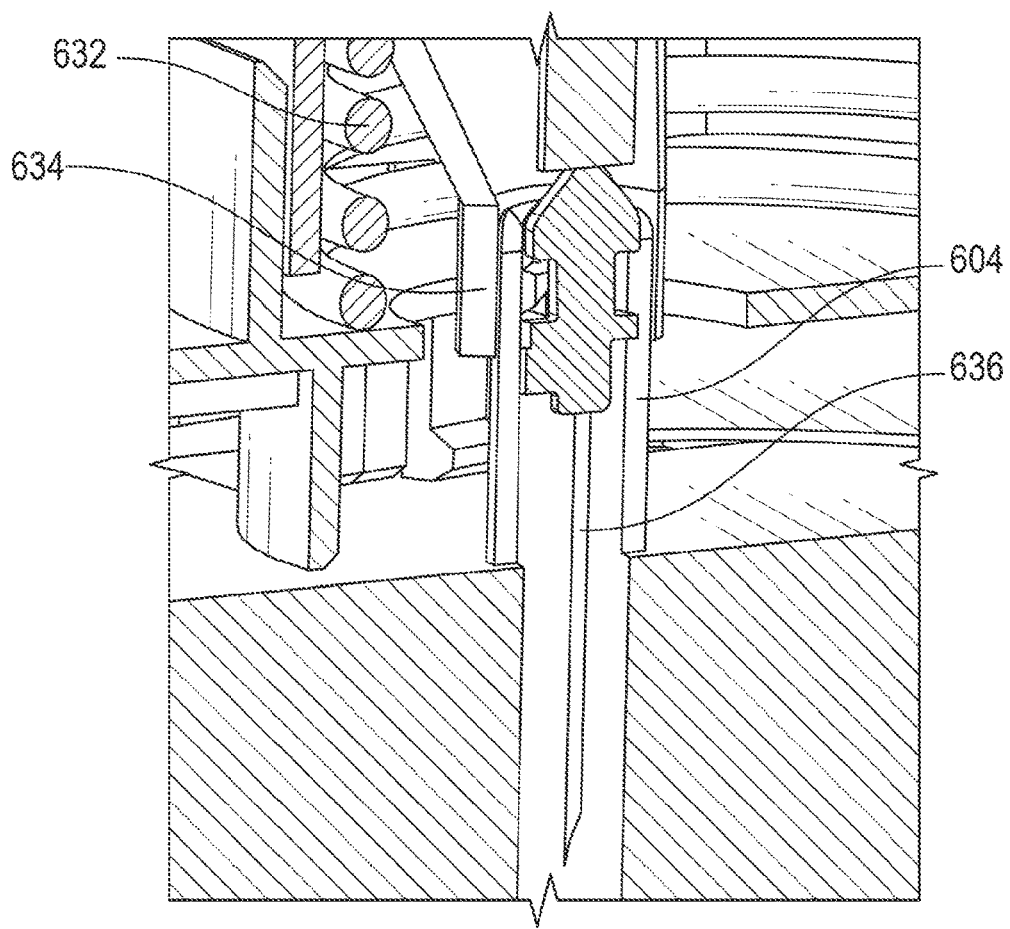
FIG. 54 illustrates a close up perspective cross sectional view of a used needle engaging a needle coupler.
Figure 55:
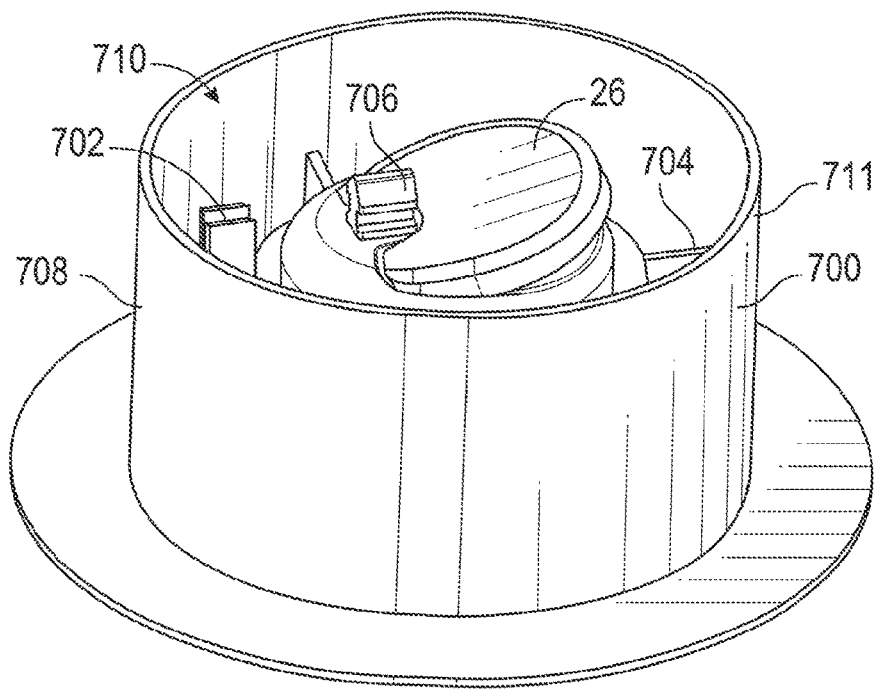
FIG. 55 illustrates a perspective view of a cartridge.

Thus, as the cartridge 600 is inserted into the receiver 622 and coupled to the applicator housing 602 with the needle coupler 604 and lower surface 610 facing the used needle 636, the needle coupler 604 may engage the used needle 636. FIG. 54, for example, illustrates such engagement. The cartridge 600 may then be withdrawn from the applicator housing 602, with the used needle 636 being carried with the cartridge 600 away from the applicator housing 602. As such, the used needle 636 is coupled to the needle coupler 604 and away from the releasable coupler 634. The used needle 636 may be retained to the cartridge 600 with the needle coupler 604 when the cartridge 600 is withdrawn from the applicator housing 602. The used needle 636 may remain coupled to the cartridge 600 for a time that the cartridge 600 is eventually discarded, to keep the used needle 636 separate and sheathed within the body 606 of the cartridge 600.

With the cartridge 600 removed from the applicator housing 602, the cartridge 600 may be rotated so that the upper surface 612 faces the applicator housing 602. For example, a cover 638 or lid as marked in FIG. 53 may be removed to expose the wearable within the cartridge 600. The cartridge 600 may be inserted into the receiver 622 of the applicator housing 602 with the upper surface 612 facing the applicator housing 602 to couple the unused needle 621 to the releasable coupler 634. Upon the unused needle 621 being inserted into the individual's skin, the process may be repeated to remove such needle 621 from the applicator housing 602.

Variations in the process of removing a needle with a cartridge, and other processes, may be provided. FIGS. 55-59, for example, illustrate an embodiment in which the cartridge 700 may include a needle coupler 702 that is positioned on the same upper surface 704 or upper side of the cartridge 700 (as opposed to the lower surface or side) as the retainer, the wearable housing, unused needle 706, the transcutaneous analyte sensor, and the electronics unit 26. The needle coupler 702 may be configured to engage a used needle that is coupled to the applicator housing and retain the used needle when the body is withdrawn from the applicator housing. The cartridge 700 otherwise may be configured similarly as the cartridge 104 shown in FIG. 5, for example, or similarly as the cartridge 300 shown in FIG. 30. For example, the cartridge 700 may include a body 708 configured to be coupled to an applicator housing, a retainer 710 configured to retain a transcutaneous analyte sensor to the body 708, a receiver 712 marked in FIG. 56 configured to receive the unused needle 706 that is coupled to the transcutaneous analyte sensor. The body 708 may include a wall 711 extending around at least a portion of the transcutaneous analyte sensor.

Figure 56:
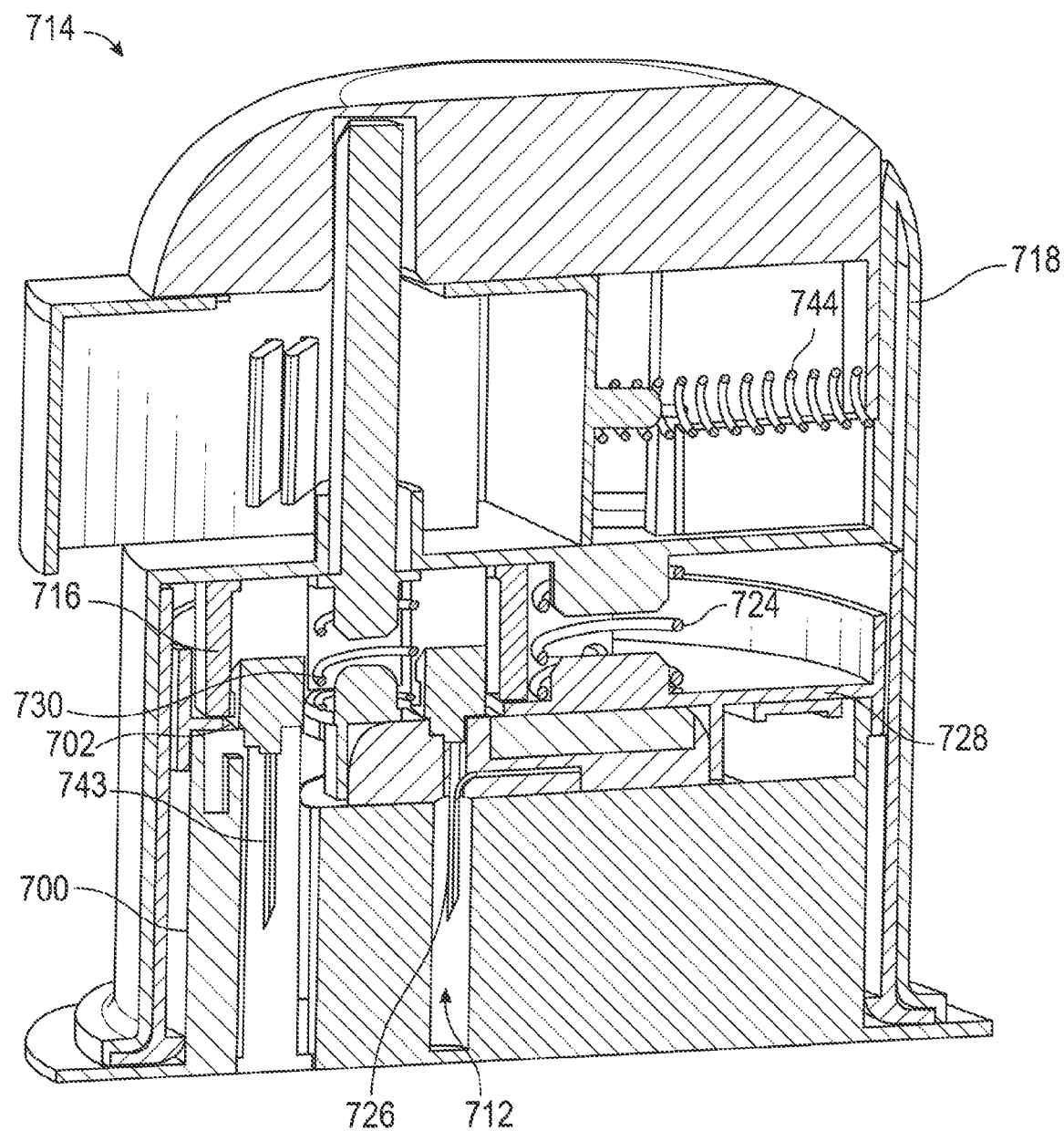
FIG. 56 illustrates a perspective cross sectional view of an applicator and the cartridge shown in FIG. 55.

The cartridge 700 may be utilized in combination with an applicator 714 (marked in FIG. 56). The applicator 714 may be configured similarly as the applicators 502, 602, yet may include a needle carriage 716 that may be configured to retain a needle after insertion into the individual's skin. The applicator 714 may include an applicator housing 718 that may be configured to be gripped to apply the transcutaneous analyte sensor into the individual's skin and may include an opening 720 (marked in FIG. 59) at a bottom surface 722 (marked in FIG. 59) of the applicator housing 718 for the transcutaneous analyte sensor to be deployed from. The applicator 714 may include a driver 724 for inserting a needle 726 into an individual's skin to guide the transcutaneous analyte sensor into the individual's skin. The driver 724, for example, may drive a carriage 728 that is coupled to the needle carriage 716, and drives both the wearable housing, the needle 726, and the needle carriage 716 downward towards the individual's skin to insert the needle 726 into the individual's skin.

The needle carriage 716 may comprise a portion of a retraction actuator, including a driver 730 that drives the needle carriage 716 upward with respect to the carriage 728 to retract the needle 726 following insertion into the individual's skin. The needle carriage 716 may be configured to rotate about an axis that is vertical with respect to the opening 720. The rotation of the needle carriage 716 may reposition the used needle to be aligned with and engaged with the needle coupler 702 when a subsequent cartridge is inserted into the applicator housing 718.

FIG. 56, for example, illustrates a cross sectional view of the cartridge 700 inserted into the receiver of the applicator housing 718. The insertion may provide energy to the drivers 724, 730. The needle carriage 716 may include two releasable couplers 732, 734 that rotate about an axis of a central shaft 736, as marked in FIG. 57. The central shaft 736 of the needle carriage 716 may include a gear, with gear teeth 738 that engage a gear, with gear teeth 740 that is coupled to the control device 742. The gear of the control device 742 may be configured to rotate the needle carriage 716 about the axis of the central shaft 736 that is vertical with respect to the opening 720. As such, movement of the control device 742 causes rotation of the needle carriage 716 due to engagement of the gears.

In embodiments, the gear teeth 740 may be angled such that pressing the control device 742 does not rotate the central shaft 736, and retraction of the control device 742 due to the driver 744 (shown in FIG. 56) causes the central shaft 736 to rotate. As such, the gears may operate as a one-way gear for causing the needle carriage 716 to rotate only upon release of the control device 742 following insertion of the needle into the individual's skin.

The rotation of the used needle may position the used needle to engage the needle coupler 702 of the cartridge 700, to withdraw the used needle from the needle carriage 716.

FIGS. 56-59, for example, illustrate a method of operation of the applicator 714 and cartridge. In FIG. 56, the cartridge 700 may be inserted to the receiver of the applicator housing 718 to couple the cartridge 700 to the applicator housing 718. The used needle 743 may be engaged with the needle coupler 702 upon insertion of the cartridge 700. Further, the unused needle 726 may be engaged with the releasable coupler 732. The cartridge 700 may then be withdrawn from the applicator housing 718 to retain the used needle 743 to the cartridge 700 with the needle coupler 702.

Figure 57:
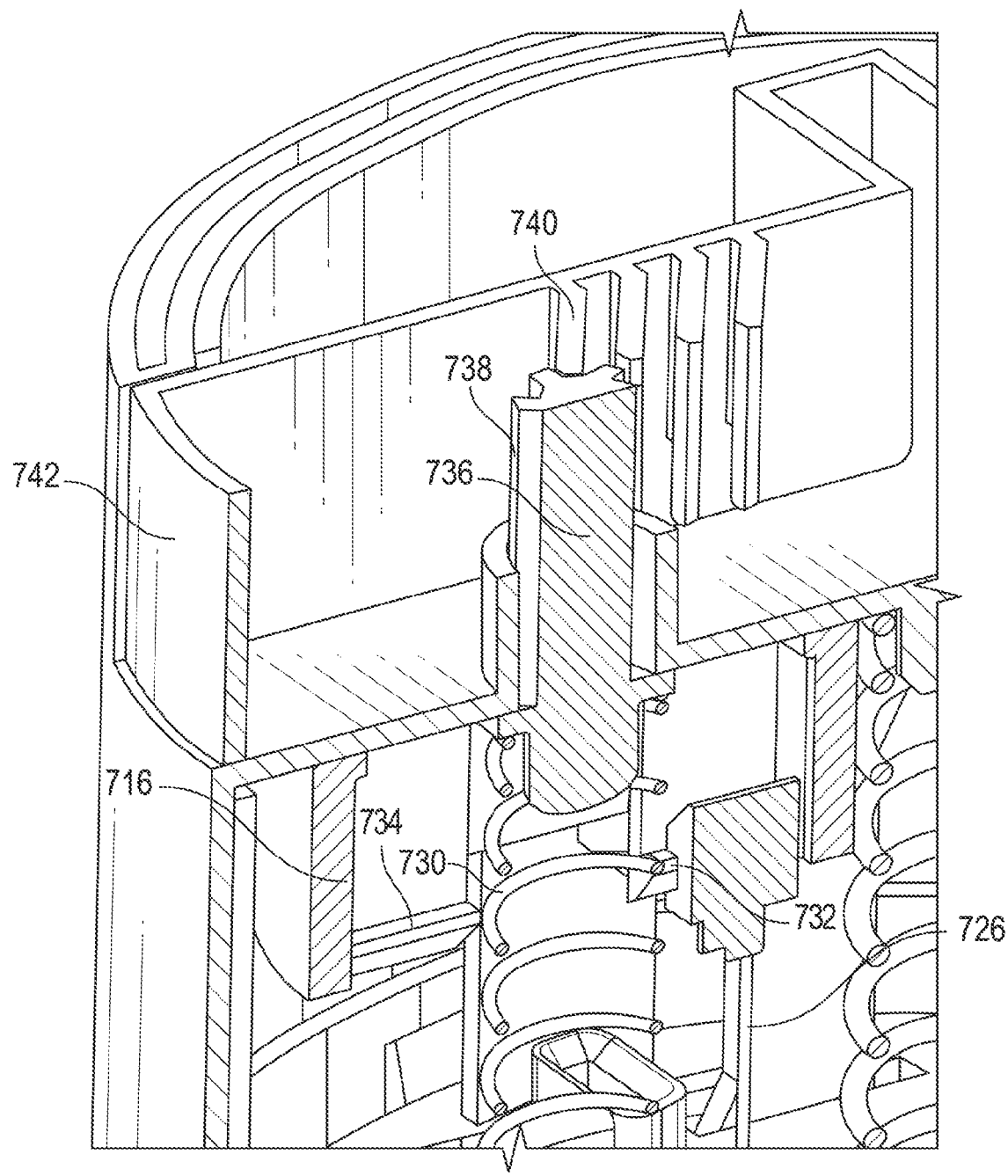
FIG. 57 illustrates a close up perspective cross sectional view of a needle carriage of the applicator shown in FIG. 56.

The control device 742 may be pressed to cause the needle carriage 716 and the carriage 728 to move towards the individual's skin. The needle carriage 716 may retract according to methods disclosed herein to withdraw the needle 726 from the individual's skin. The resulting position of the needle carriage 716 is shown in FIG. 57.

Figure 58:
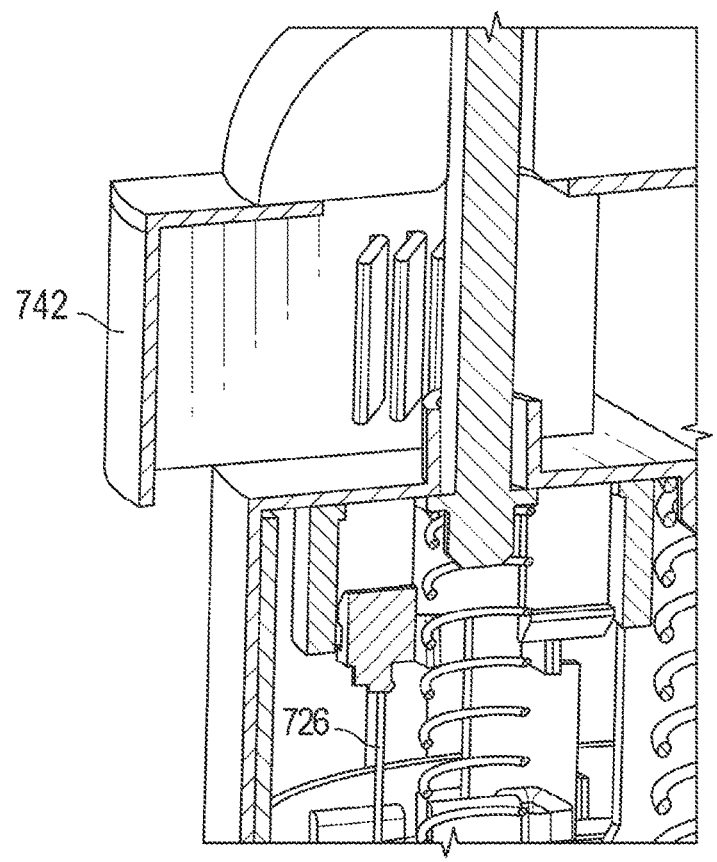
FIG. 58 illustrates a close up perspective cross sectional view of a needle carriage of the applicator shown in FIG. 56.
Figure 59:
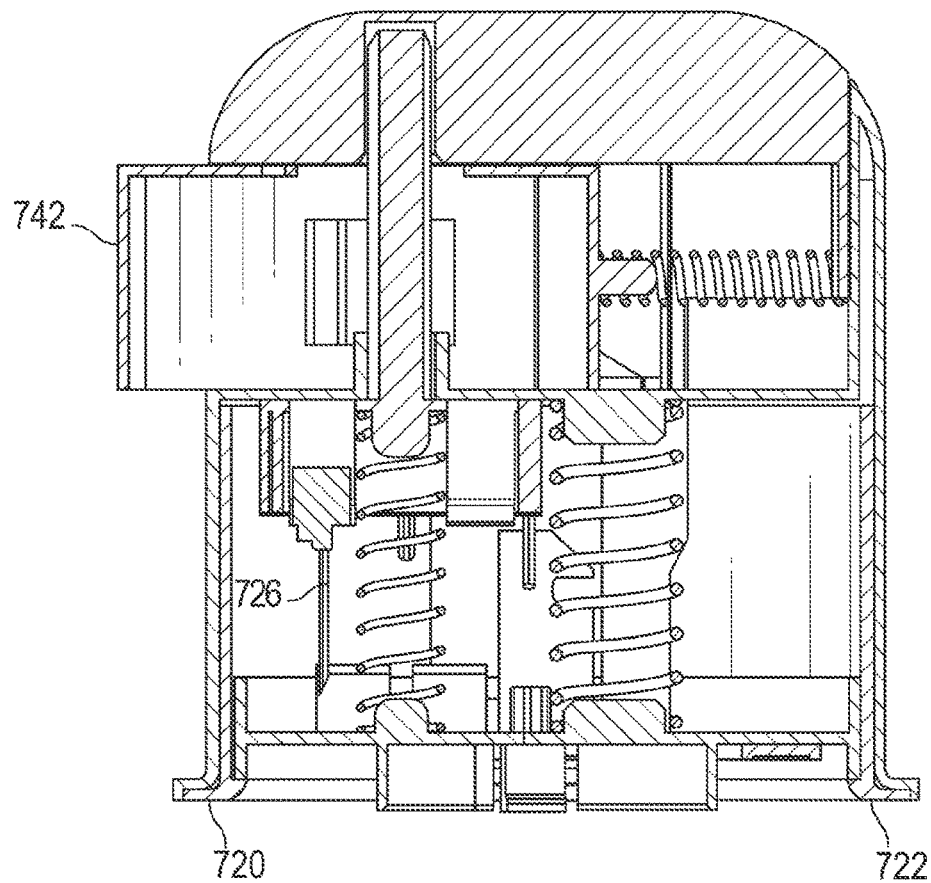
FIG. 59 illustrates a cross sectional view of the applicator shown in FIG. 56.

The control device 742 may then be released, to cause the gear to engage the central shaft 736 and rotate the needle 726 about the axis of the shaft 736 and to align with the needle coupler 702. The needle carriage 716 may be rotated within the applicator housing to position the used needle 726 for alignment with the needle coupler 702. FIGS. 58 and 59, for example, illustrate the position of the needle 726.

A next cartridge, configured similarly as cartridge 700, may then be inserted into the receiver of the applicator housing 718 to engage the needle coupler 702 with the used needle 726.

The processes and structures disclosed herein may be varied in embodiments.

Figure 60:
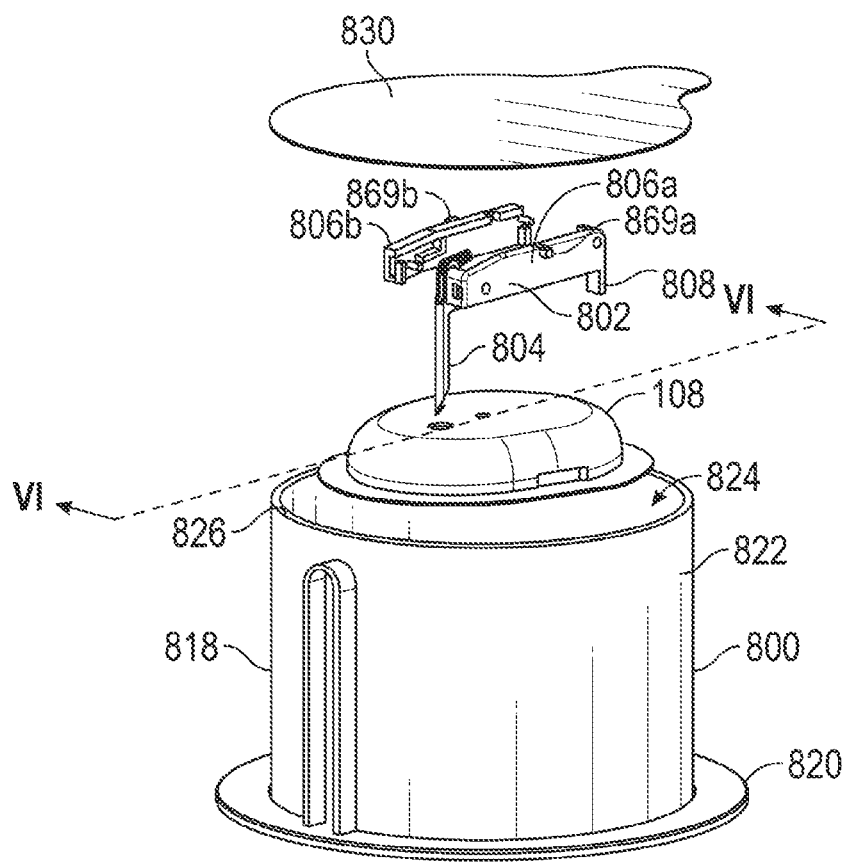
FIG. 60 illustrates an exploded perspective view of a cartridge.

FIG. 60 illustrates an embodiment of a cartridge 800 that may be configured similarly as the cartridge 300 shown in FIG. 30, yet may include a needle cover 802 also serving as a needle hub that is configured to rotate relative to the needle 804 to extend over at least a portion of the needle 804. The cartridge 800 may be utilized in a system for inserting a transcutaneous analyte sensor into an individual's skin. The needle cover 802 as shown in FIG. 60 includes two sheath bodies 806a, b that couple together to form a sheath configured to extend over at least a portion of the needle 804. The needle 804 may be configured to be moved relative to the needle cover 802 to be positioned into the needle cover 802. The needle cover 802 is configured to cover at least a portion of the needle 804 following the needle 804 inserting the transcutaneous analyte sensor into the skin of the individual. The needle cover 802 may include a releasable coupler 808 that is configured to couple to a coupling member of the wearable housing 108. The releasable coupler 808 may comprise a latch that extends into a coupling member in the form of a cavity in the wearable housing 108. The releasable coupler 808 may be positioned at an end of the needle cover 802 that covers the penetrating tip of the needle 804 when the needle cover 802 covers the needle 804. An opposite end of the needle cover 802 may include a pivot 810 (marked in FIG. 61) that the needle 804 is configured to pivot about, to rotate into a cavity of the needle cover 802. The needle cover 802 may be coupled to the wearable housing 108 and configured to be separable from the wearable housing 108.

Figure 61:
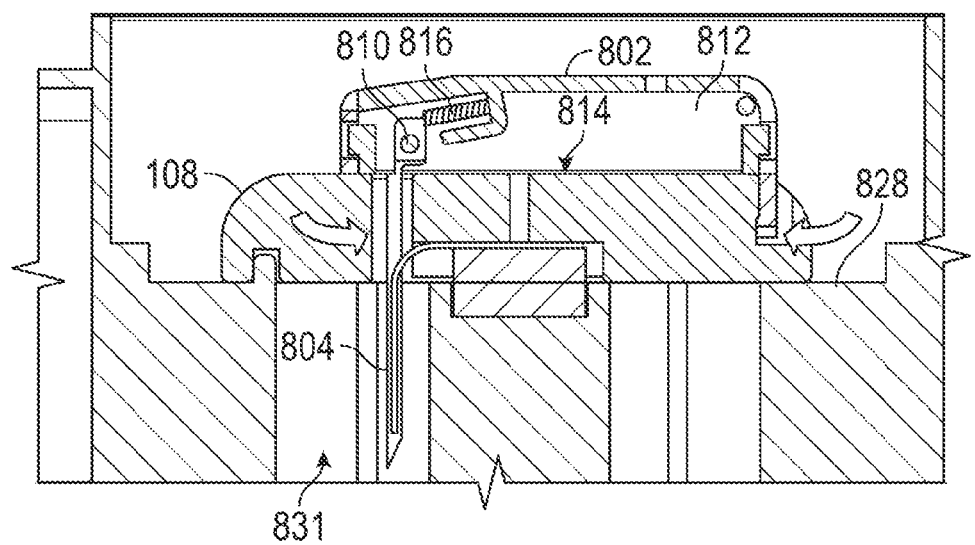
FIG. 61 illustrates a cross-sectional perspective view of an assembled cartridge along line VI-VI shown in FIG. 60.

Referring to FIG. 61, the two sheath bodies 806a, b may enclose a cavity 812 that the needle 804 may be rotated into upon release from the wearable housing 108. The two sheath bodies 806a, b may be separated from each other to define an opening 814 that the needle 804 may pass through to enter the cavity 812. A spring 816 may be provided in the needle cover 802 that applies a force to bias the needle 804 towards the cavity 812. The needle 804 may couple to the pivot 810 at a proximal end of the needle 804 opposite the penetrating tip of the needle 804.

Referring back to FIG. 60, the cartridge 800 may include a body 818 having a base 820 and a wall 822. The base 820 may form a bottom of the cartridge 800 that the cartridge 800 may be positioned upon. The base 820 may form a flange extending outward from the wall 822. The wall 822 may extend upward from the base 820, transverse to a direction that the base 820 extends in. The wall 822 may extend around and define a cavity 824 that may receive components of the cartridge including the transcutaneous analyte sensor 24 and the needle 804. The wall 822 may extend around at least a portion of the needle cover 802. The wall 822 may extend upward to an upper opening 826 that exposes the components retained by the body 818. The wall 822 may including an inner surface configured to face inward towards a central portion of the cartridge 800 and the transcutaneous analyte sensor 24 and an outer surface facing opposite the inner surface. The outer surface of the wall may be configured to be positioned within at least a portion of an applicator. The outer surface of the wall may comprise a mating surface for a receiver of the applicator, and may be contoured to a shape of an inner surface of the receiver.

The wall 822 may be shaped similarly as the wall 146 discussed in regard to the cartridge 104 shown in FIG. 5. The body 818 may include a retainer 828 (marked in FIG. 61) that may operate and be structured similarly as the retainer 152 discussed in regard to the cartridge 104.

Referring to FIG. 61, the body 818 of the cartridge 800 may include a central cavity 831 that is configured to receive the needle 804 when positioned within the body 818 of the cartridge 800. Referring back to FIG. 60, the cartridge 800 may include a removable cover 830 that operates similarly as the cover 324 shown in FIG. 30. The components of the transcutaneous analyte sensor system may be retained by the body 818 in a similar manner as discussed in regard to the cartridge 104, and the cartridge 800 may be utilized in a similar manner as the cartridge 104.

Figure 62:
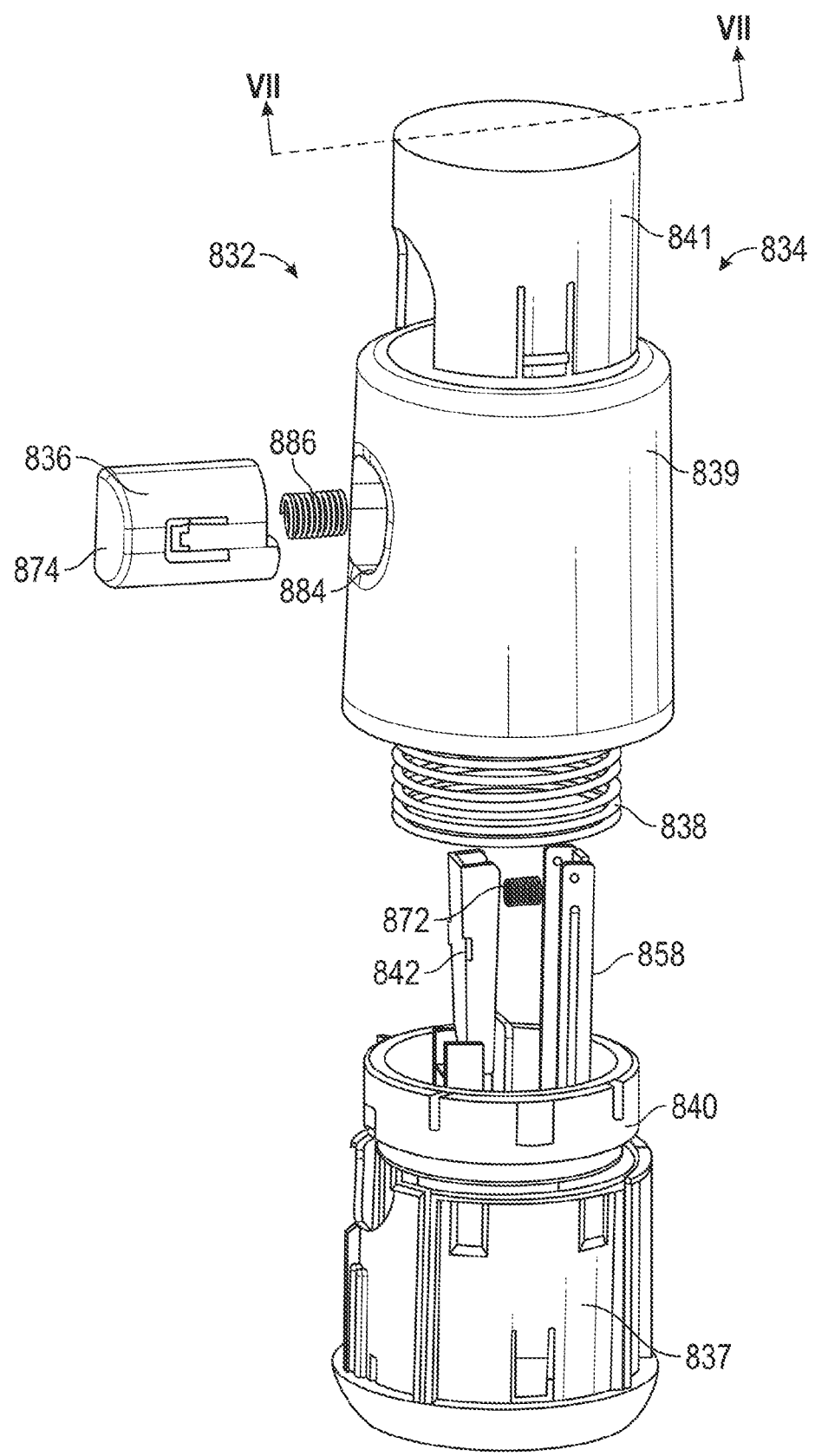
FIG. 62 illustrates a perspective exploded view of an applicator.

The cartridge 800 may be utilized with an applicator 832 as shown in an exploded view in FIG. 62. The applicator 832 comprises a transcutaneous analyte sensor applicator, and is configured to apply other components of the transcutaneous analyte sensor system to the skin of an individual including the wearable housing 108 and patch 106 of the transcutaneous analyte sensor system. The applicator may deploy all or a portion of components of an on-skin sensor assembly 12 to an individual's skin.

The applicator 832 comprises a reusable applicator, and may provide reusable functionality in a similar manner as the applicator 102.

FIG. 62 illustrates components of the applicator 832. The applicator 832 may include an applicator housing 834, which may comprise a single component or multiple components. As shown in FIG. 62, the applicator housing 834 may include a side cover body 839, a lower body 837, and an upper cap 841. The components of the applicator housing 834 may be coupled together to form a single applicator housing 834. The applicator housing 834 may be configured to be gripped by an individual to apply the transcutaneous analyte sensor into the individual's skin, to be held during deployment of the transcutaneous analyte sensor, as well as other components of a transcutaneous analyte sensor system. The applicator housing 834 may have a cylindrical shape with an outer surface configured to be gripped by an individual. Other shapes of the applicator housing 834 may be utilized as desired.

Figure 67:
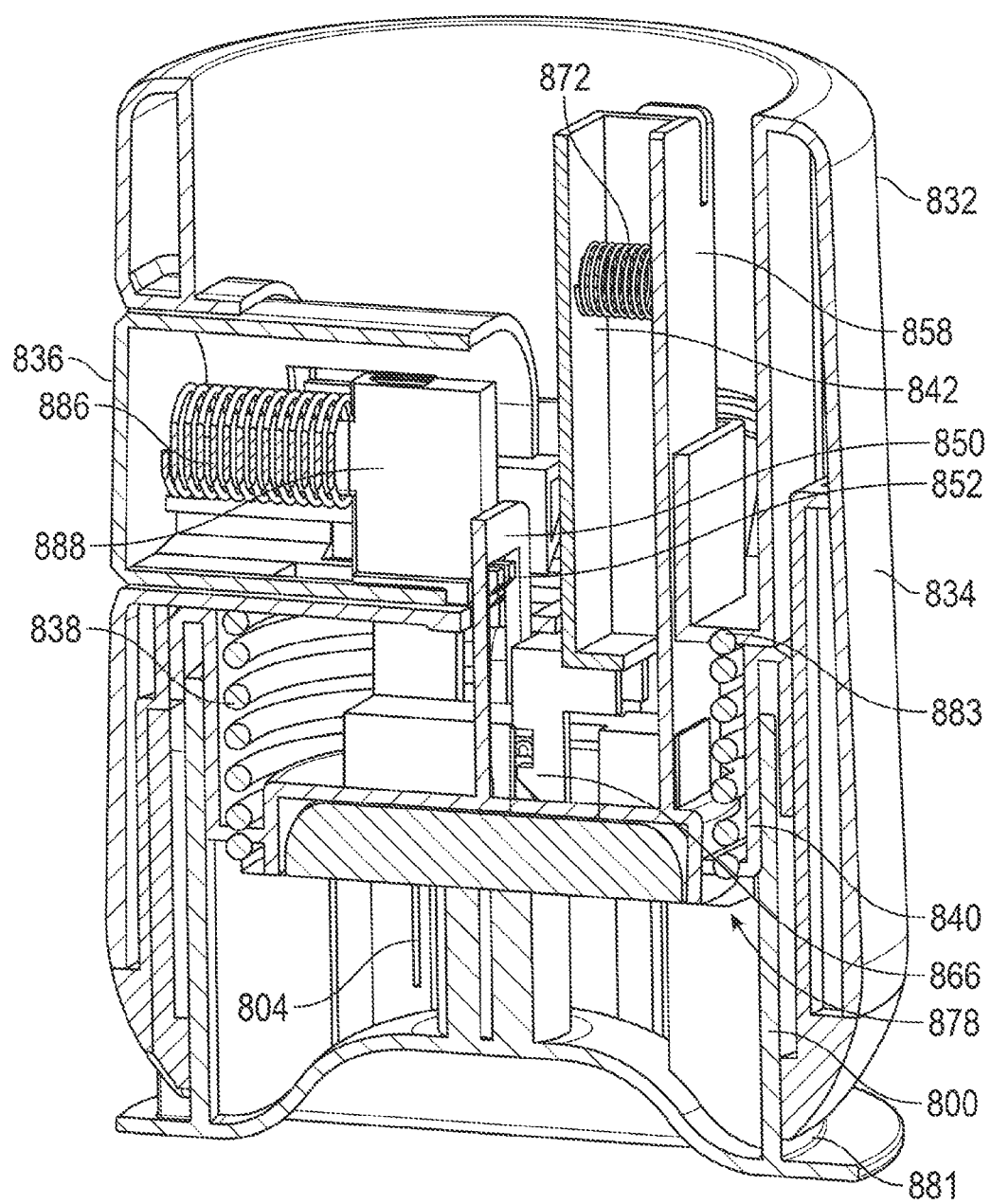
FIG. 67 illustrates a cross-sectional perspective view of the applicator of FIG. 62 along line VII-VII.

The applicator housing 834 may include a side portion (formed by the side cover body 839), a top portion (formed by the upper cap 841) and a bottom portion including an opening 881 shown in FIG. 67 for the transcutaneous analyte sensor to be deployed from to be inserted into the individual's skin. The opening 881 may be configured for the needle 804 and the transcutaneous analyte sensor 24 to pass through to insert the transcutaneous analyte sensor 24 into the individual's skin.

FIG. 62 illustrates other components of the applicator 832. The components may include an actuator that may be coupled to the applicator housing 834 and that is configured to insert the needle 804 into the individual's skin to deposit the transcutaneous analyte sensor 24 into the individual's skin. Such an actuator may be referred to as an insertion actuator. The insertion actuator may include components that may include a control device 836 and a driver 838, and may include a carriage 840. The insertion actuator may include other components (or fewer components) in other embodiments. The applicator 832 may include a release actuator that is configured to release the needle 804 from a releasable coupler. The release actuator may include components that may include the control device 836 and may include a lever arm 842 that is configured to move the releasable coupler to cause the needle 804 to release from the releasable coupler. The release actuator may be configured to release the needle 804 from the releasable coupler to allow the needle 804 to be passed through the opening 881 at the bottom portion of the applicator housing 834. The release actuator may include other components (or fewer components) in other embodiments. The configuration of components in the applicator 834 may be varied in other embodiments.

Figure 63:
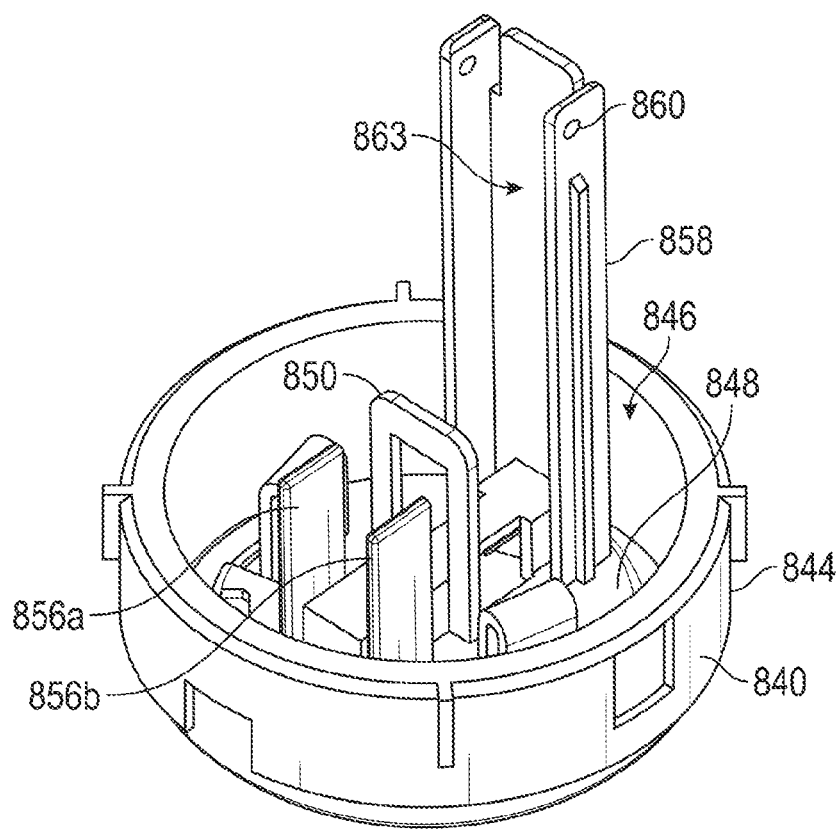
FIG. 63 illustrates a perspective view of a carriage of the applicator.

FIG. 63 illustrates a perspective view of the carriage 840 of the insertion actuator. The carriage 840 may comprise a body configured to slide within an interior cavity of the applicator 832 that may be defined by the applicator housing 834. The carriage 840 may be configured to slide relative to the applicator housing and be configured to be slid by the driver 838. The carriage 840 may include an outer ring 844. The outer ring 844 may surround a cavity 846 of the carriage 840. The cavity 846 may be configured to receive a driver 838 (marked in FIG. 62) of the insertion actuator.

The carriage 840 may include a central body 848 that spans the interior of the outer ring 844 of the carriage 840. An upper surface of central body 848 of the carriage 840 may include a releasable coupler 850 configured to couple to a coupling member 852 of the insertion actuator as shown in FIG. 67. The releasable coupler 850 may comprise a U-shaped body having a central opening that the coupling member 852, which may be in the form of a ledge, is configured to extend into. The U-shaped body extends upward from the central body 848 and is configured to be deflectable to bend off of the ledge of the insertion actuator, to release the releasable coupler 850 from the ledge. The releasable coupler 850 may also be configured to engage and be released from a coupling member 854 of the control device 836 (marked in FIG. 68). In other embodiments, the releasable coupler 850 may have different forms.

An upper surface of central body 848 of the carriage 840 may include stops 856a, b that extend upward from the central body 848 to contact a portion of the control device 836 to impede movement of the control device 836 at a desired time. The upper surface of the central body 848 may include a column 858 having a pivot 860 at an upper portion of the column 858. The column 858 may include a cavity 863 for receiving the lever arm 842. The pivot 860 may be configured to couple to the lever arm 842 for the lever arm 842 to pivot about.

Figure 64:
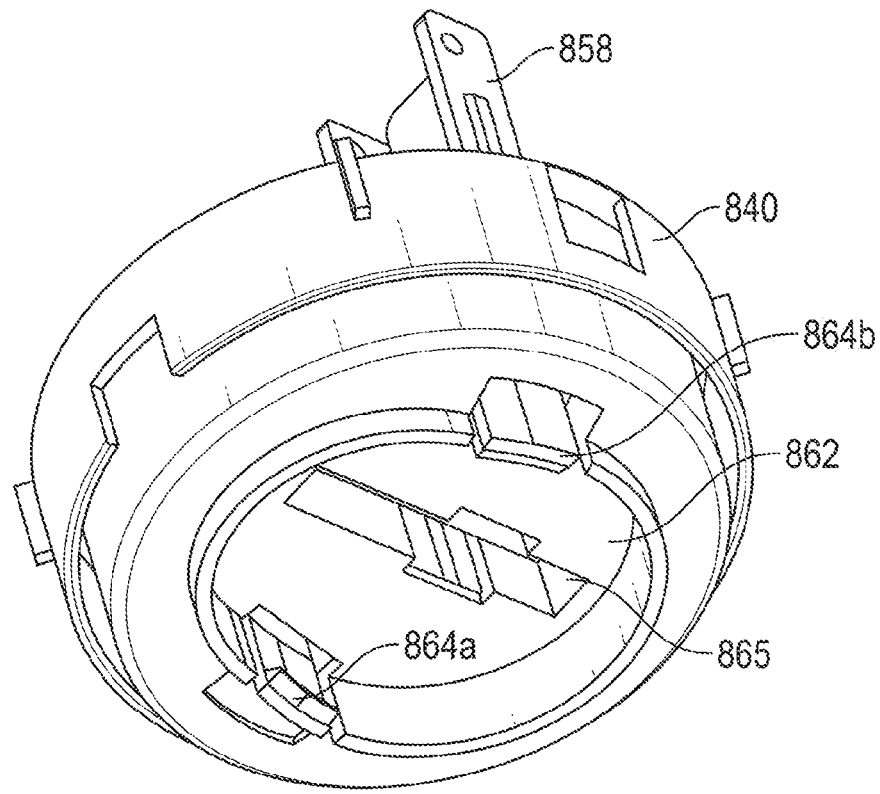
FIG. 64 illustrates a bottom perspective view of the carriage of the applicator shown in FIG. 62.

FIG. 64 illustrates a perspective view of a lower surface of the carriage 840. The lower surface of the carriage 840 may include a receiver 862 that is configured to receive at least a portion of the transcutaneous analyte sensor system. The receiver 862 may comprise a cavity that is configured to receive the transcutaneous analyte sensor system. The receiver 862 may include at least one releasable coupler 864a, b that is configured to couple to the wearable housing 108 of the transcutaneous analyte sensor system. The releasable coupler 864a, b may comprise a protrusion configured to enter into a cavity 123 (marked in FIG. 3) of the housing 108 to couple to the housing 108. In other embodiments, other forms of releasable couplers 864a, b may be utilized.

An opening 865 may be positioned on the carriage 840 and may extend through the lower surface of the central body 848. The opening 865 may be configured for the needle cover 802 to be positioned in when the housing 108 is positioned within the receiver 862.

Figure 65:
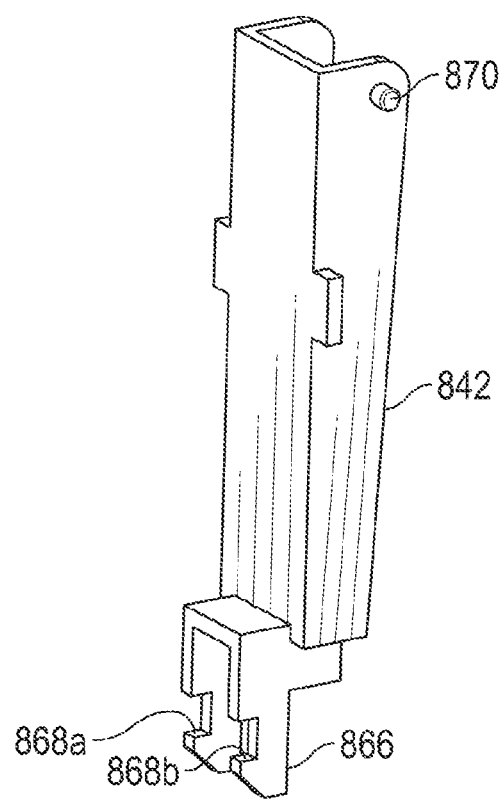
FIG. 65 illustrates a perspective view of the lever arm of the applicator shown in FIG. 62.

FIG. 65 illustrates a perspective view of the lever arm 842 of the release actuator. The lever arm 842 may include a releasable coupler 866 that is configured to releasably couple to the needle 804. The releasable coupler 866 may include hooks 868a, b that are configured to engage coupling members 869a, b (marked in FIG. 60) of the needle cover 802 to releasably couple to the needle 804. The coupling members 869a, b may comprise protrusions that extend outward from the sides of the needle cover 802. The releasable coupler 866 may be configured to retain the needle 804 at least partially within the applicator housing 834 following insertion of the transcutaneous analyte sensor 24 into the individual's skin and removal of the applicator housing 834 from the transcutaneous analyte sensor 24, and configured to release the needle 804 from within the applicator housing 834 following insertion of the transcutaneous analyte sensor 24 into the individual's skin.

The lever arm 842 may include pivot pins 870 that engage the pivot 860 of the column 858 and allow the lever arm 842 to rotate about the pivot. A biasing spring 872 (marked in FIG. 67) may bias the lever arm 842 in a direction away from the column 858. The configuration of the lever arm 842 may be varied in other embodiments.

Figure 66:
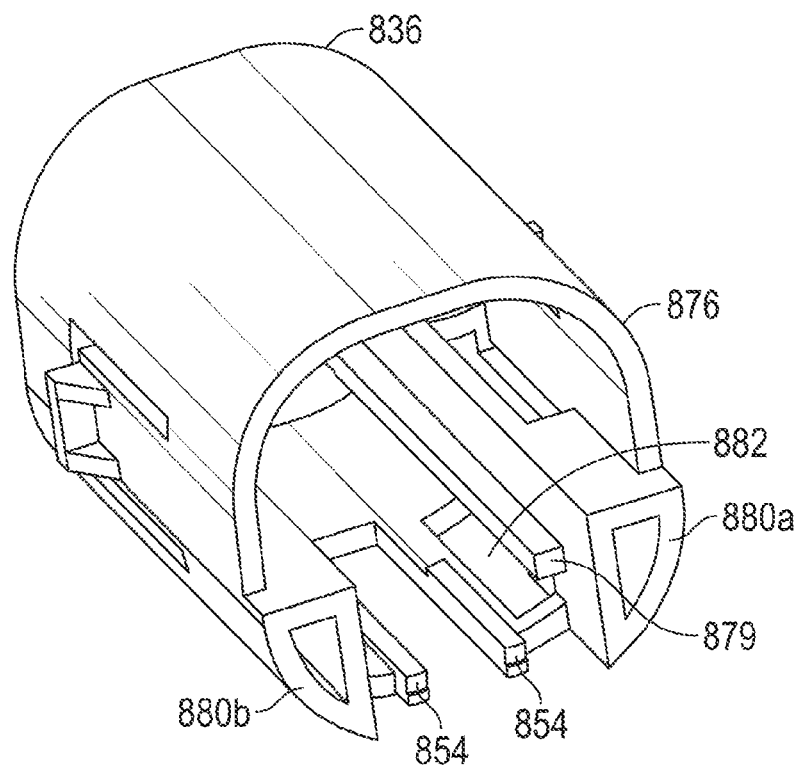
FIG. 66 illustrates a rear perspective view of a control device of the applicator shown in FIG. 62.

FIG. 66 illustrates a rear perspective view of the control device 836 of the insertion actuator and the release actuator. The control device 836 may comprise a button that may be pressed or other body that may be moved to activate the insertion actuator and activate the release actuator. The control device 836 may be configured to be slid laterally to activate the insertion actuator and activate the release actuator. The control device 836 may include a button surface 874 (marked in FIG. 62) and a control arm 876 that extends from the button surface 874. The control arm 876 may include coupling members 854 in the form of protrusions extending in a parallel direction with the control arm 876. The control arm 876 may further include pressing surfaces 879 that are configured to press the releasable coupler 850 of the carriage 840 shown in FIG. 63. The control arm 876 may include further pressing surfaces 880a, b that are configured to press against the lever arm 842. The control arm 876 may include openings 882 configured to receive the stops 856a, b of the carriage 840, to impede movement of the control device 836.

FIG. 67 illustrates a perspective cross sectional view of the applicator 832 showing that the applicator housing 834 includes a receiver 878 for receiving the cartridge 800. The receiver 878 may be configured for the cartridge 800 retaining the transcutaneous analyte sensor to be inserted into. The receiver 878 may comprise a cavity within the applicator housing 834 that receives the cartridge 800. The cartridge 800 may be inserted into the receiver 878 axially through an opening 881 at a bottom of the applicator housing 834.

FIG. 67 illustrates an assembled view of the components of the applicator 832, showing the carriage 840 of the insertion actuator within the applicator housing 834. The driver 838 of the insertion actuator may be positioned above the carriage 840 and between a spring support body 883 of the applicator housing 834. The driver 838 may be configured to drive the needle 804 into the individual's skin to insert the transcutaneous analyte sensor into the individual's skin. The lever arm 842 of the release actuator may be coupled to the pivot 860 shown in FIG. 63. The control device 836 may be inserted into an opening 884 (marked in FIG. 62) of the side wall of the applicator housing 834. The control device 836 may be biased by a biasing spring 886 in a direction away from a spring support surface 888 of the applicator housing.

The applicator 832 may operate in a manner shown in FIGS. 67-72. FIG. 67 illustrates the cartridge 800 having been inserted into the receiver 878 of the applicator housing 834. The releasable coupler 864a, b of the carriage 840 of the insertion actuator engages the wearable housing 108 of the on-skin sensor assembly. A removable cover of the cartridge 800 may previously have been removed by an individual.

FIG. 67 illustrates the applicator 832 after the cartridge 800 has been fully inserted into the receiver 878 of the applicator housing 834. The cartridge 800 may be inserted in the axial dimension of the applicator housing 834, which is the same dimension that the transcutaneous analyte sensor 24 as well as other components of the transcutaneous analyte sensor system will be deployed from the applicator housing 834 (although in an opposite axial direction that the cartridge 800 is inserted into the receiver 878). The insertion of the cartridge 800 and the transcutaneous analyte sensor 24 into the receiver 878 of the applicator housing 834 may compress and thus provide energy to the driver 838 of the insertion actuator. The driver 838 is compressed in the configuration shown in FIG. 67. In an embodiment in which the driver 838 is a spring, the spring may be compressed by the insertion of the cartridge 800 and the transcutaneous analyte sensor 24 into the receiver. The cartridge 800 may include a pressing surface on an upper surface of the cartridge 800 to press against the carriage of the insertion actuator to provide energy to the insertion actuator.

The insertion of the cartridge 800 fully into the receiver 878 of the applicator housing 834 also causes the releasable coupler 850 of the insertion actuator to engage the coupling member 852 of the insertion actuator. The engagement of the releasable coupler 850 holds the carriage 840 of the insertion actuator in position and prevents the driver 838 from pressing the carriage 840 in an axial direction towards the lower opening 881 of the applicator housing 834.

As shown in FIG. 67, the wearable housing 108 of the transcutaneous analyte sensor system may be positioned in the receiver 862 of the lower surface of the carriage 840. The releasable coupler 864a, b shown in FIG. 64 may couple to the cavity 123 shown in FIG. 3 to grip the wearable housing 108 to the lower surface of the carriage. Thus, as the cartridge 800 is withdrawn from the applicator housing 834, the wearable housing 108 remains coupled to the receiver 862.

The releasable coupler 866 couples to the needle 804, particularly with the hooks 868a, b of the releasable coupler 866 engaging the coupling members 869a, b (marked in FIG. 60) of the needle cover 802.

The needle 804 is shown to extend downward from the wearable housing 108 of the transcutaneous analyte sensor system, extending for insertion of the penetrating tip of the needle 804 into the individual's skin.

The cartridge 800 may be withdrawn from the applicator housing 834 to leave the transcutaneous analyte sensor system in position for application to the individual's skin by the applicator 832. The transcutaneous analyte sensor system may be moved axially downward within the receiver 878 of the applicator housing 834 to contact the individual's skin and be applied to the individual's skin.

The insertion actuator may operate to insert the needle 804 into the individual's skin to deposit the transcutaneous analyte sensor 24 into the individual's skin. The control device 836 of the insertion actuator may be pressed in a lateral direction, or a direction transverse to the axial dimension of the applicator housing 834. The movement of the control device 836 may compress the biasing spring 886 that is configured to apply a biasing force to the control device 836. The movement of the control device 836 may disengage the releasable coupler 850 from the coupling member 852, by the pressing surface 879 marked in FIG. 66 pressing against the upper "U" portion of the releasable coupler 850.

Figure 68:
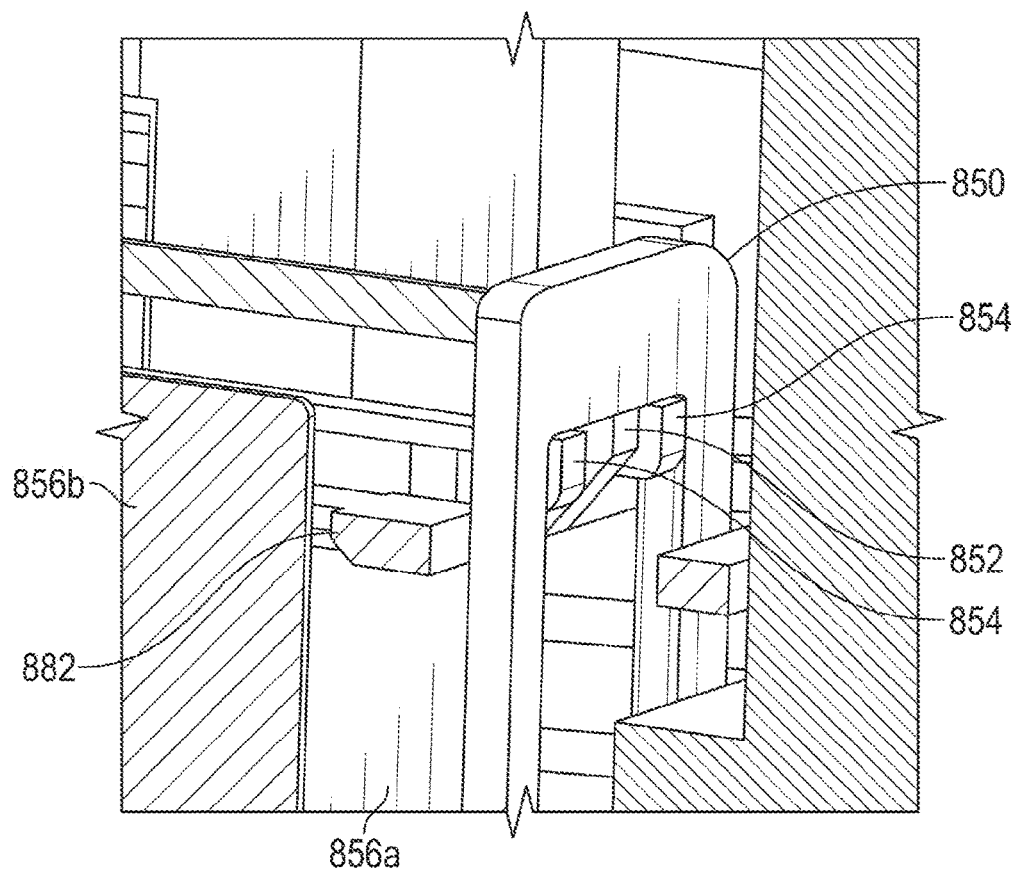
FIG. 68 illustrates a close up perspective view of a portion of the applicator shown in FIG. 62.

Referring to FIG. 68, upon the pressing surface 879 marked in FIG. 66 pressing against the upper "U" portion of the releasable coupler 850, the releasable coupler 850 may be pushed onto the coupling member 854 at the end of the control arm 876. The releasable coupler 850 may rest upon the coupling member 854. The stops 856a, b of the carriage 840 of the insertion actuator may insert into the openings 882 of the control device 836 to impede movement of the control device 836 such that the lever arm 842 is not pressed enough to cause the release actuator to activate or such that the lever arm 842 is not pressed at all.

Figure 69:
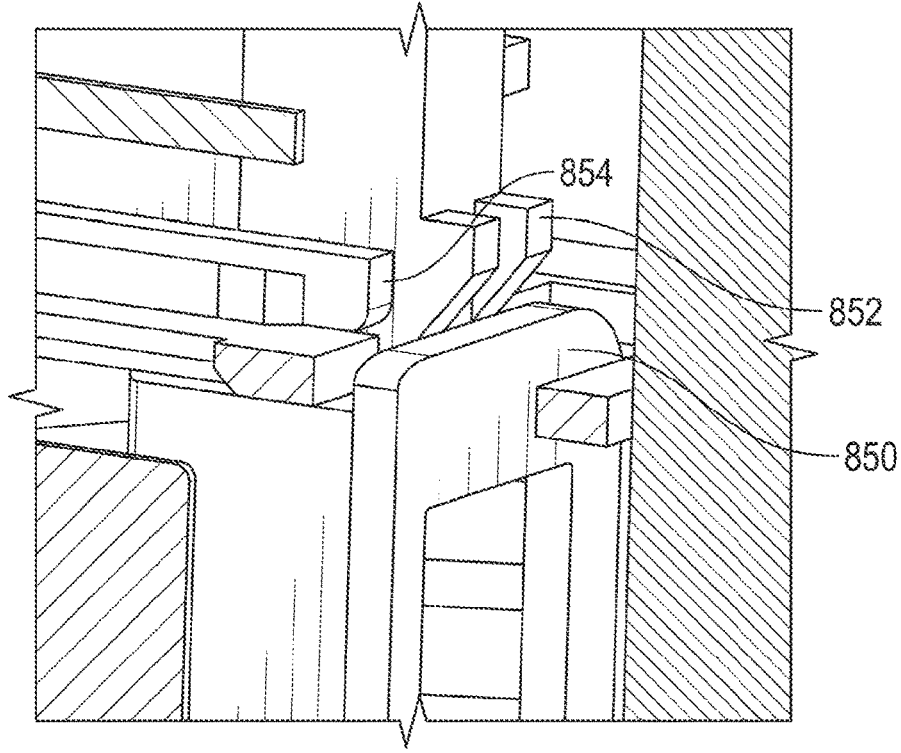
FIG. 69 illustrates a close up perspective view of a portion of the applicator shown in FIG. 62.

FIG. 69 illustrates the releasable coupler 850 supported upon the coupling member 854 at the end of the control arm 876.

The control device 836 may be released in order to release the coupler 850 from the coupling member 854 at the end of the control arm 876. An individual may release pressure on the button surface of the control device 836 to cause the biasing spring 886 (marked in FIG. 67) to move the control device 836 in the opposite direction from which the control device 836 was pushed. Such an operation slides the coupling member 854 at the end of the control arm 876 laterally, away from the coupler 850, and allows the coupler 850 to drop. FIG. 69 illustrates the coupling member 854 at the end of the control arm 876 being slid away from the coupler 850 to allow the coupler 850 to drop. The stops 856a, b of the carriage 840 of the insertion actuator also drop from the openings 882 in the control arm 876.

Figure 70:
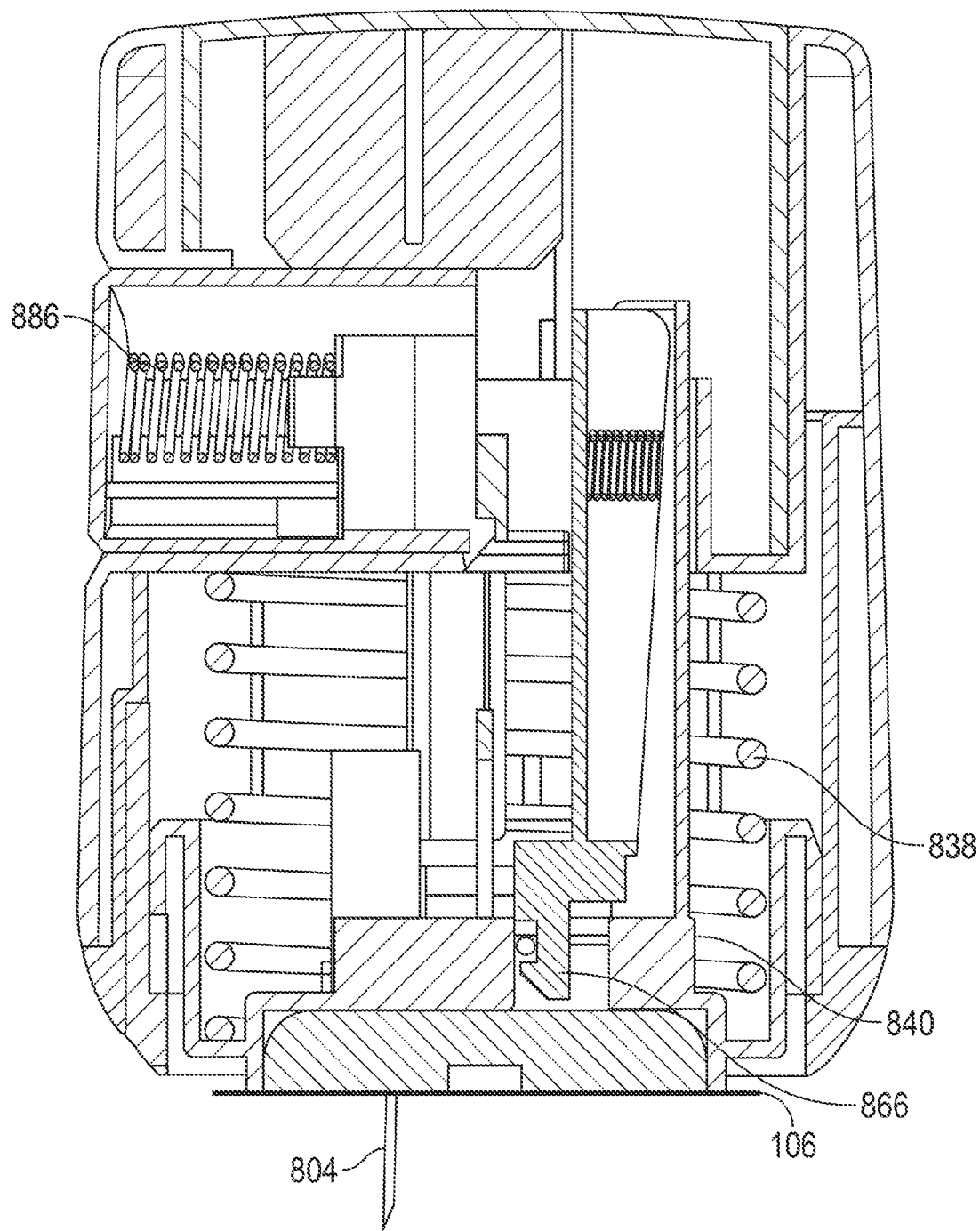
FIG. 70 illustrates a cross-sectional perspective view of the applicator of FIG. 62 along line VII-VII.

FIG. 70 illustrates the carriage 840 of the insertion actuator having been driven downward by the force from the driver 838. The force of the driver 838 upon the carriage 840 causes the carriage 840 to descend rapidly with sufficient force to drive the needle 804 into the individual's skin. Further, the movement of the carriage 840 has pressed the patch 106 to the individual's skin, allowing the patch 106 to adhere to the individual's skin and providing an adhesive force to the skin for the transcutaneous analyte sensor system.

Figure 71:
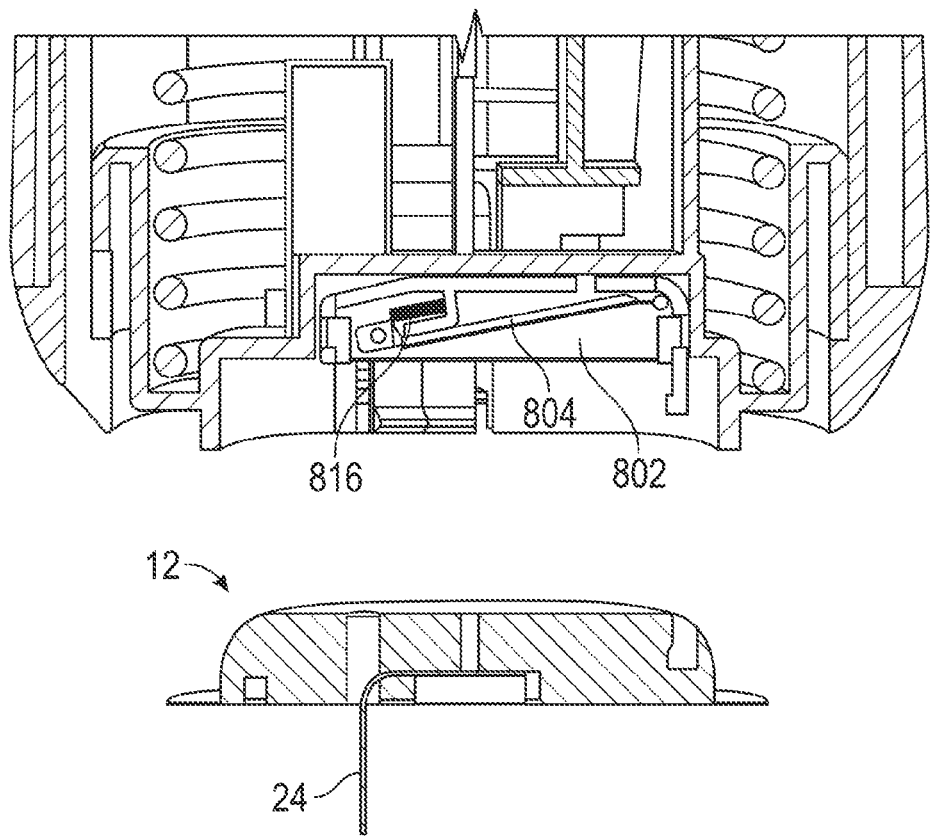
FIG. 71 illustrates a cross-sectional perspective view of the applicator of FIG. 62 along line VII-VII.

With the needle 804 and the transcutaneous analyte sensor 24 inserted into the individual's skin, the applicator housing 834 may be pulled away from the individual's skin to withdraw the needle 804 from the skin. FIG. 71, for example, illustrates the applicator housing 834 having been withdrawn from the individual's skin, with the on-skin sensor assembly 12 remaining positioned on the individual's skin. The releasable coupler 866 shown in FIG. 65 retains the needle 804 to the applicator housing 834 following insertion of the transcutaneous analyte sensor 24 into the individual's skin and removal from the applicator housing from the transcutaneous analyte sensor 24. The transcutaneous analyte sensor 24 remains within the individual's skin as the applicator housing is removed from the transcutaneous analyte sensor 24.

With the applicator housing removed from the transcutaneous analyte sensor 24, the spring 816 operates to rotate the needle 804 such that the needle enters the cavity 812 of the needle cover 802. The needle 804 may rotate such that the needle cover 802 covers the used needle 804 and particularly the penetrating tip of the needle 804.

With the needle 804 positioned within the needle cover 802, the release actuator may be operated to release the needle 804 from the releasable coupler 866 marked in FIG. 70.

Figure 72:
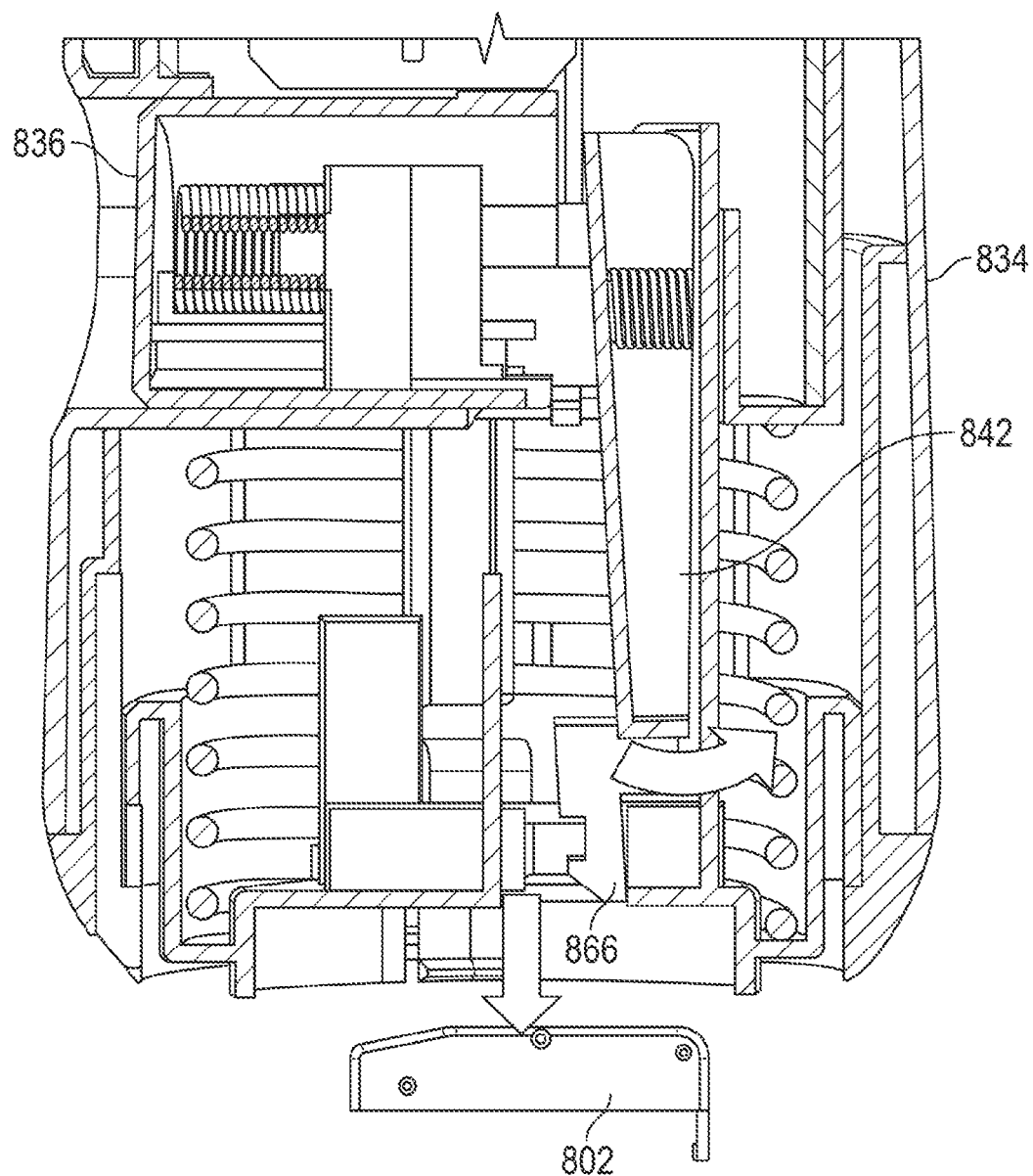
FIG. 72 illustrates a cross-sectional perspective view of the applicator of FIG. 62 along line VII-VII.

Referring to FIG. 72, the control device 836 of the release actuator may be pressed laterally, in a direction transverse to the axial dimension of the applicator housing 834, causing the pressing surface 880a, b of the control device 836 shown in FIG. 66 to be moved in the lateral direction. The pressing surface 880a, b may press against the lever arm 842 of the release actuator, causing the lever arm 842 to rotate about the pivot 860 marked in FIG. 63. The movement of the lever arm 842 may cause the releasable coupler 866 to release the needle 804. The needle 804 may drop from the applicator housing 834 as shown in FIG. 72. The needle 804 and needle cover 802 may be released from the applicator housing 834 with the needle cover 802 covering the penetrating tip of the needle 804. Accordingly, the same control device 836 may be operated twice to first operate the insertion actuator and then second to operate the release actuator. The control device 836 may be operated in a first operation to activate the insertion actuator, and may be configured to be operated in a second operation following the first operation to activate the release actuator. In an embodiment in which the control device 836 is a button, the first operation may comprise pressing the control device 836 and the second operation may comprise pressing the control device 836 a second time. The same control device 836 accordingly may be pressed twice to operate both the insertion actuator and the release actuator.

The release actuator may be configured to release the needle 804 covered by the needle cover 802 from the applicator housing 834 following insertion of the needle into the individual's skin. The releasable coupler 866 configured to retain the needle 804 is configured to release the needle 804 positioned within the needle cover 802 from the applicator housing. The needle 804 covered by the needle cover 802 may form a unit that is released together from the applicator housing for discard.

The needle 804 may be released from the applicator housing 834 for discard, as the needle 804 may have been contaminated through the process of insertion within the individual's skin. The needle 804 accordingly may be a single use needle that is configured to discard within a sharps container or other disposal area. The needle 804 may remain sheathed within the needle cover 802 such that an individual does not contact the used needle 804 and be subject to the contamination of the needle 804 or otherwise be injured by the penetrating tip of the needle 804. The needle 804 may remain locked in position within the needle cover 802 such that an individual cannot access the contaminated portion of the needle 804. The needle 804 and needle cover 802 together may form a unit for disposal following insertion into an individual's skin and separation from the applicator housing.

Upon release of the needle 804 and needle cover 802 from the applicator housing 834, the applicator is in a configuration for deployment of another transcutaneous analyte sensor 24 and other components of a transcutaneous analyte sensor system. As such, the applicator 832 is configured for multiple uses, and is not intended to be discarded. The applicator 832 may be loaded with another cartridge 800 and the steps disclosed herein may repeat as desired.

Figure 73:
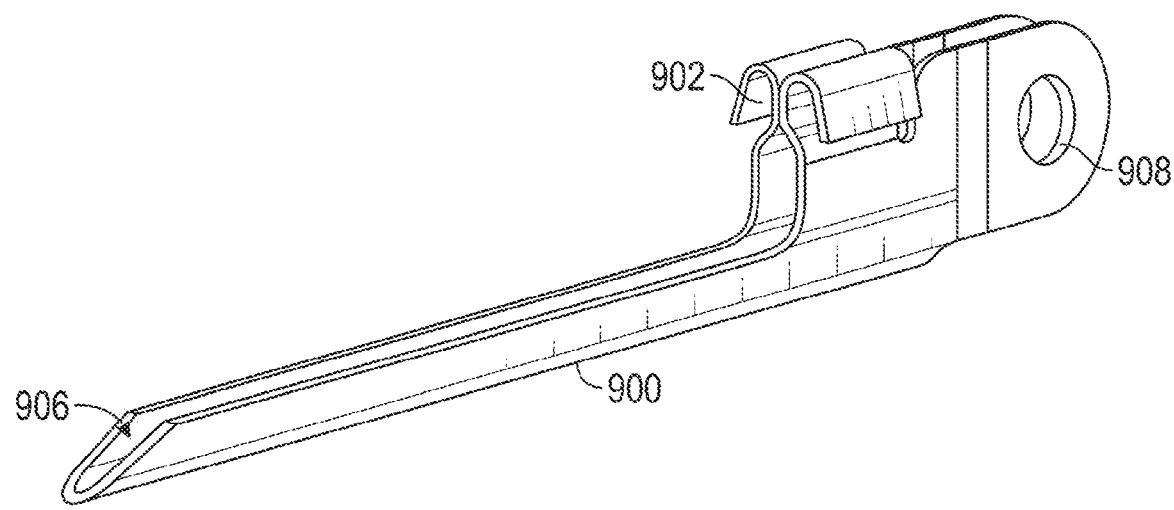
FIG. 73 illustrates a perspective view of a needle.

FIG. 73 illustrates an embodiment of a needle 900 that may be configured similarly as the needle 804 shown in FIG. 60. The needle 900, however, may include a lock 902 at a proximal end of the needle 900 that may lock the needle 900 in position within the needle cover 904 also serving as a needle hub shown in FIG. 74. The needle 900 may be utilized in a system for inserting a transcutaneous analyte sensor into an individual's skin. The needle 900 may include a "C" shaped body having a central channel 906 for the transcutaneous analyte sensor 24 to extend along upon insertion into the individual's skin. The needle 900 may include a pivot 908 at a proximal end of the needle 900 that the needle 900 is configured to pivot about, to rotate into a cavity 910 of the needle cover 904.

Figure 74:
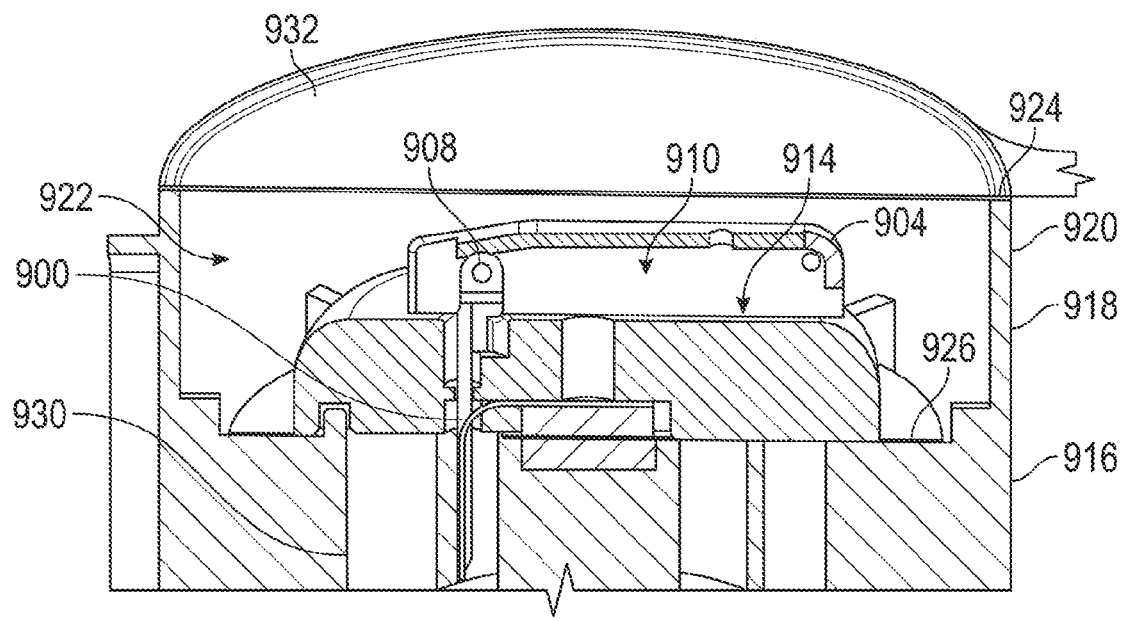
FIG. 74 illustrates a cross sectional view of a cartridge along a mid line of the cartridge.

Referring to FIG. 74, the needle cover 904 may include two sheath bodies that couple together to form a sheath configured to extend over at least a portion of the needle 900, similar to the needle cover 802 shown in FIG. 60. The needle cover 904 may be configured to rotate relative to the needle 900 to extend over at least a portion of the needle 900. The needle 900 may be configured to be moved relative to the needle cover 904 to be positioned into the needle cover 904. The needle cover 904 is configured to cover at least a portion of the needle 900 following the needle 900 inserting the transcutaneous analyte sensor into the skin of the individual. The needle cover 904 may include a coupling member 912 (marked in FIG. 86) that is configured to couple to a releasable coupler of an applicator. The coupling member 912 may comprise protrusions that extend outward from the body of the needle cover 904, similar to the coupling members 869a, b shown in FIG. 60 that extend outward from the sides of the needle cover 802. The needle cover 904 may be coupled to the wearable housing 108 and configured to be separable from the wearable housing 108.

The two sheath bodies of the needle cover 904 may enclose the cavity 910 that the needle 900 may be rotated into upon release from the wearable housing 108. The two sheath bodies may be separated from each other to define an opening 914 that the needle 900 may pass through to enter the cavity 910.

The needle 900 and needle cover 904 may be enclosed in a cartridge 916. The cartridge 916 be configured similarly as the cartridge 800 shown in FIG. 60. The cartridge 916 may include a body 918 having a base and a wall 920. The base may form a bottom of the cartridge 916 that the cartridge 916 may be positioned upon. The base may form a flange extending outward from the wall 920. The wall 920 may extend upward from the base, transverse to a direction that the base extends in. The wall 920 may extend around and define a cavity 922 that may receive components of the cartridge including the transcutaneous analyte sensor 24 and the needle 900. The wall 920 may extend around at least a portion of the needle cover 904. The wall 920 may extend upward to an upper opening 924 that exposes the components retained by the body 918. The wall 920 may including an inner surface configured to face inward towards a central portion of the cartridge 916 and the transcutaneous analyte sensor 24 and an outer surface facing opposite the inner surface. The outer surface of the wall may be configured to be positioned within at least a portion of an applicator. The outer surface of the wall may comprise a mating surface for a receiver of the applicator, and may be contoured to a shape of an inner surface of the receiver.

The wall 920 may be shaped similarly as the wall 146 discussed in regard to the cartridge 104 shown in FIG. 5. The body 918 may include a retainer 926 that may operate and be structured similarly as the retainer 152 discussed in regard to the cartridge 104.

The body 918 of the cartridge 916 may include a central cavity 930 that is configured to receive the needle 900 when positioned within the body 918 of the cartridge 916. The cartridge 916 may include a removable cover 932 that operates similarly as the cover 324 shown in FIG. 30. The components of the transcutaneous analyte sensor system may be retained by the body 918 in a similar manner as discussed in regard to the cartridge 104, and the cartridge 916 may be utilized in a similar manner as the cartridge 104.

Figure 75:
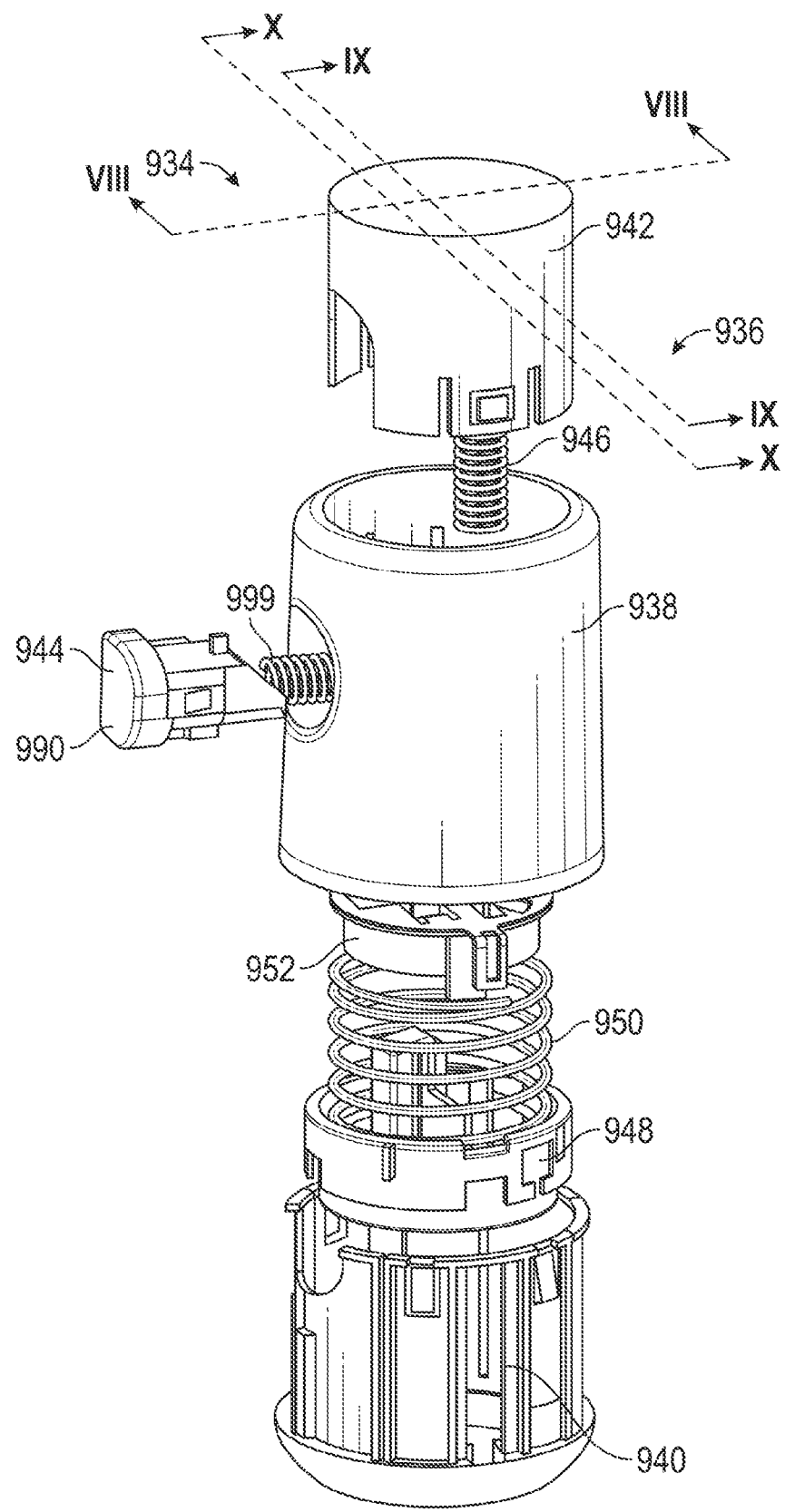
FIG. 75 illustrates a perspective exploded view of an applicator.

The cartridge 916 may be utilized with an applicator 934 as shown in an exploded view in FIG. 75. The applicator 934 comprises a transcutaneous analyte sensor applicator, and is configured to apply other components of the transcutaneous analyte sensor system to the skin of an individual including the wearable housing 108 and patch 106 of the transcutaneous analyte sensor system. The applicator may deploy all or a portion of components of an on-skin sensor assembly 12 to an individual's skin.

The applicator 934 comprises a reusable applicator, and may provide reusable functionality in a similar manner as the applicator 102.

FIG. 75 illustrates components of the applicator 934. The applicator 934 may include an applicator housing 936, which may comprise a single component or multiple components, similar to the housing of the applicator 102. As shown in FIG. 75, the applicator housing 936 may include a side cover body 938, a lower body 940, and an upper cap 942. The components of the applicator housing 936 may be coupled together to form a single applicator housing 936. The applicator housing 936 may be configured to be gripped by an individual to apply the transcutaneous analyte sensor into the individual's skin, to be held during deployment of the transcutaneous analyte sensor, as well as other components of a transcutaneous analyte sensor system. The applicator housing 936 may have a cylindrical shape with an outer surface configured to be gripped by an individual. Other shapes of the applicator housing 936 may be utilized as desired.

Figure 81:
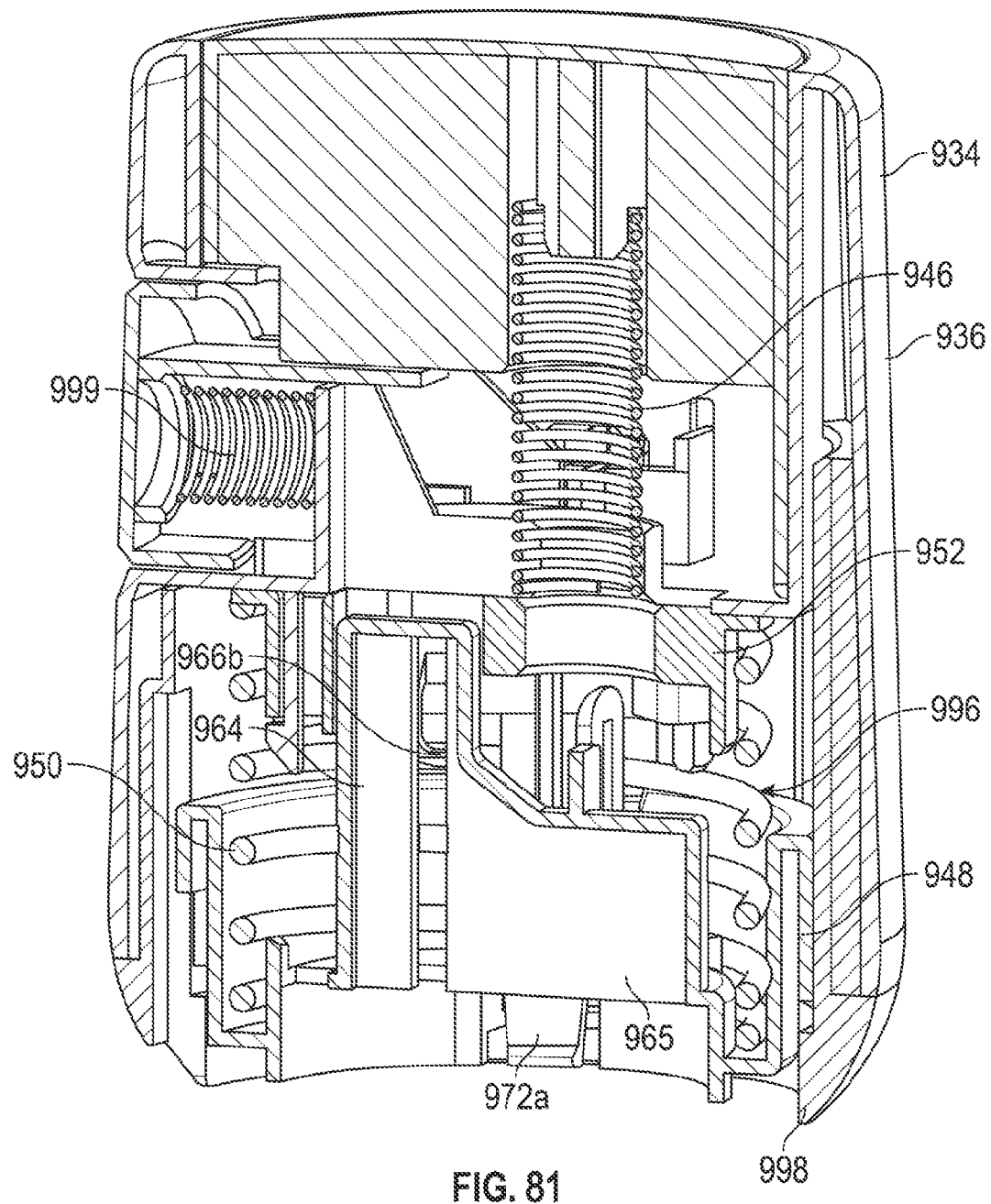
FIG. 81 illustrates a cross sectional view of the applicator along line VIII-VIII of FIG. 75.

The applicator housing 936 may include a side portion (formed by the side cover body 938), a top portion (formed by the upper cap 942) and a bottom portion including an opening 998 shown in FIG. 81 for the transcutaneous analyte sensor to be deployed from to be inserted into the individual's skin. The opening 998 may be configured for the needle 900 and the transcutaneous analyte sensor 24 to pass through to insert the transcutaneous analyte sensor 24 into the individual's skin.

FIG. 75 illustrates other components of the applicator 934. The components may include an actuator that may be coupled to the applicator housing 936 and that is configured to insert the needle 900 into the individual's skin to deposit the transcutaneous analyte sensor 24 into the individual's skin. Such an actuator may be referred to as an insertion actuator. The insertion actuator may include components that may include a control device 944 and a driver 946, and may include a carriage 948. The insertion actuator may include other components (or fewer components) in other embodiments.

The applicator 934 may include a release actuator that is configured to release the needle 900 from a releasable coupler. The release actuator may include components that may include a control device 944 and may include a pressing surface 951 (marked in FIG. 80) that is configured to apply a force to a releasable coupler to cause the needle 900 to release from the releasable coupler. The release actuator may be configured to release the needle 900 from the releasable coupler to allow the needle 900 to be passed through the opening 998 at the bottom portion of the applicator housing. The release actuator may include other components (or fewer components) in other embodiments. The applicator 934 may include a retraction actuator that is configured to retract the needle 900 from the individual's skin following insertion of the transcutaneous analyte sensor into the individual's skin. The retraction actuator may include components that may include a driver 950 and a carriage 952. The retraction actuator may include other components (or fewer components) in other embodiments. The configuration of components in the applicator 934 may be varied in other embodiments.

Figure 76:
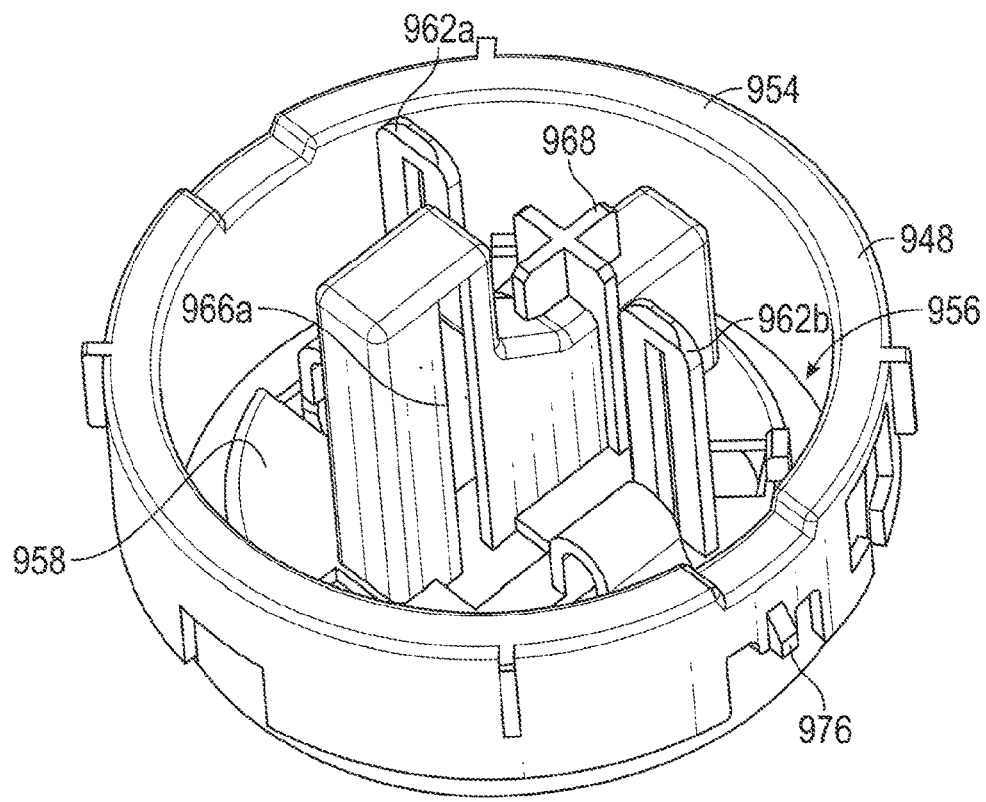
FIG. 76 illustrates a perspective view of a carriage of the applicator shown in FIG. 75.

FIG. 76 illustrates a perspective view of the carriage 948 of the insertion actuator. The carriage 948 may comprise a body configured to slide within an interior cavity of the applicator 934 that may be defined by the applicator housing 936. The carriage 948 may be configured to slide relative to the applicator housing and be configured to be slid by the driver 946 of the insertion actuator. The carriage 948 may include an outer ring 954. The outer ring 954 may surround a cavity 956 of the carriage 948. The cavity 956 may be configured to receive the carriage 952 (marked in FIG. 78) of the retraction actuator and may be configured to receive a driver 950 (marked in FIG. 75) of the retraction actuator.

The carriage 948 may include a central body 958 that spans the interior of the outer ring 954 of the carriage 948. The outer ring 954 may include a channel 960 (marked in FIG. 77) configured to receive the wall 920 of the cartridge 916.

Figure 84:
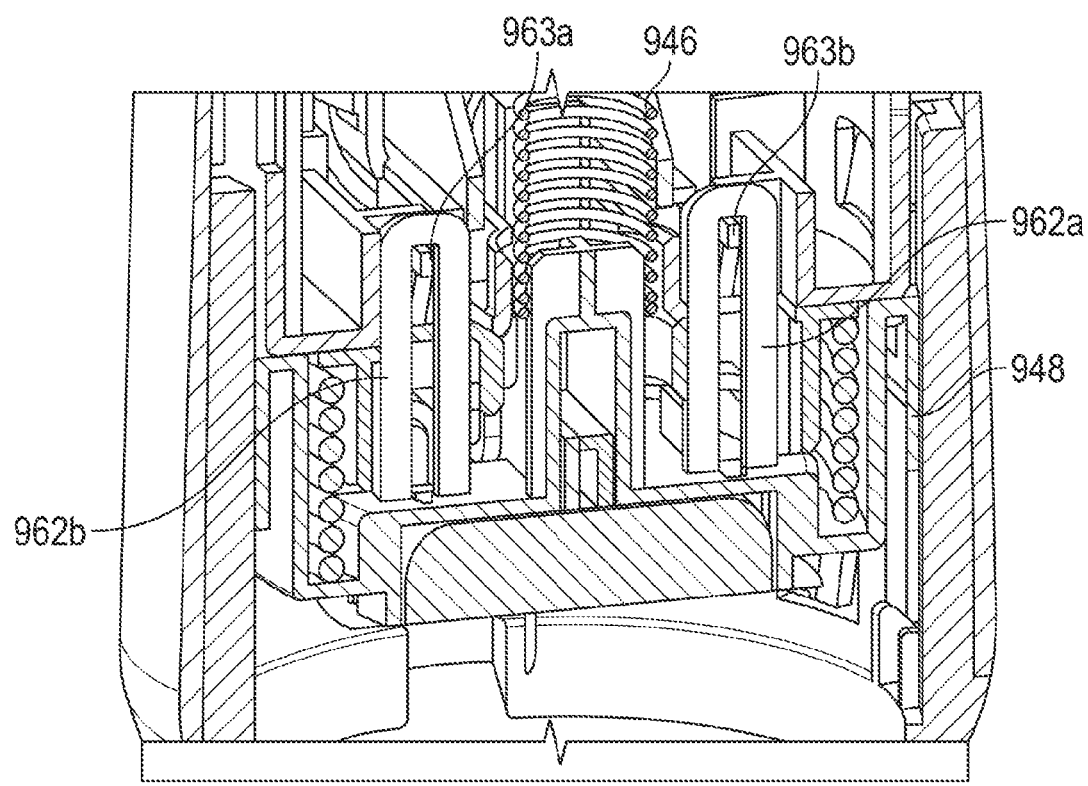
FIG. 84 illustrates a cross sectional view of the applicator along line X-X of FIG. 75, which is orthogonal to line VIII-VIII.

An upper surface of the carriage 948 may include a releasable coupler 962a, b configured to couple to a coupling member 963a, b of the insertion actuator as shown in FIG. 84. The releasable coupler 962a, b may comprise "U" shaped bodies having openings configured for the coupling member 963a, b of the insertion actuator to engage. The coupling member 963a, b may comprise protrusions that enter into the openings of the releasable coupler 962a, b. In other embodiments, the releasable coupler 962a, b may have different forms.

A central channel 964 (marked in FIG. 81) may be provided that may be configured for the needle 900 and the needle cover 904 to be positioned in. The central channel 964 may be configured for the needle 900 to be retracted into upon operation of the retraction actuator. Guide channels 966a, b (marked in FIGS. 81 and 76) may be provided on sides of the central channel 964 for the coupling member 912 (marked in FIG. 86) of the needle cover 904 to slide in upon retraction of the needle 900.

Referring to FIG. 81, the carriage 948 may include a deflection surface 965 that is configured for the needle cover 904 to contact to cause the needle cover 904 to rotate onto the needle 900 when the needle is retracted. The deflection surface 965 may have an angled shape as desired.

Referring back to FIG. 76, the upper surface of the carriage 948 may include a support 968 for supporting the driver 946 of the insertion actuator.

Figure 77:
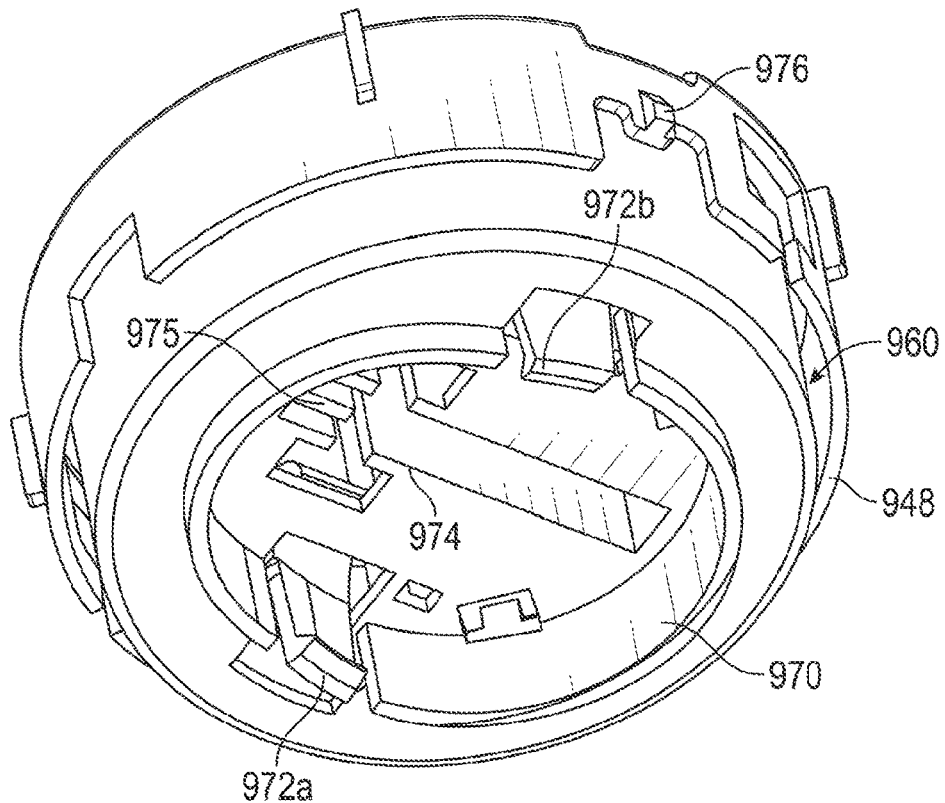
FIG. 77 illustrates a bottom perspective view of a carriage of the applicator shown in FIG. 75.

FIG. 77 illustrates a perspective view of a lower surface of the carriage 948. The lower surface of the carriage may include a receiver 970 that is configured to receive at least a portion of the transcutaneous analyte sensor system. The receiver 970 may comprise a cavity that is configured to receive the transcutaneous analyte sensor system. The receiver 970 may include at least one releasable coupler 972a, b that is configured to couple to the wearable housing 108 of the transcutaneous analyte sensor system. The releasable coupler 972a, b may comprise a protrusion configured to enter into a cavity 123 (marked in FIG. 3) of the wearable housing 108 to couple to the wearable housing 108. In other embodiments, other forms of releasable couplers 972a, b may be utilized.

An opening 974 may be positioned on the carriage 948 and may be configured to allow the needle 900 and needle cover 904 to be retracted into the central channel 964. Further, the carriage 948 may include an alignment rail 975 that is configured for the needle 900 to slide against to maintain a rotational orientation of the needle 900 as the needle is retracted into the central channel 964. The needle 900 may be positioned in axial alignment with the applicator 934 as the needle is retracted into the central channel 964. The alignment rail 975 may be configured to extend between portions of the needle cover 904 proximate the needle 900.

The outer ring 954 of the carriage 948 may include coupling members 976 for releasable couplers of the carriage 952 of the retraction actuator to engage. The coupling members 976 may be positioned on the outer surface of the carriage 948 and may be in the form of protrusions as shown in FIG. 77.

Figure 78:
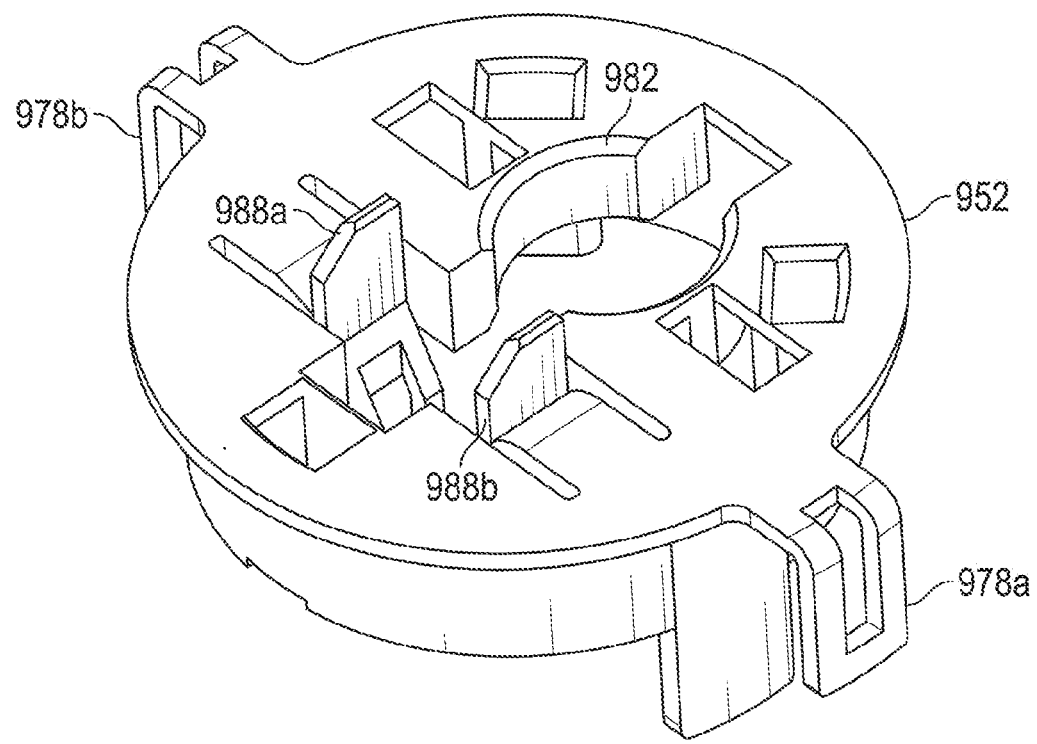
FIG. 78 illustrates a perspective view of a carriage of the applicator shown in FIG. 75.
Figure 87:
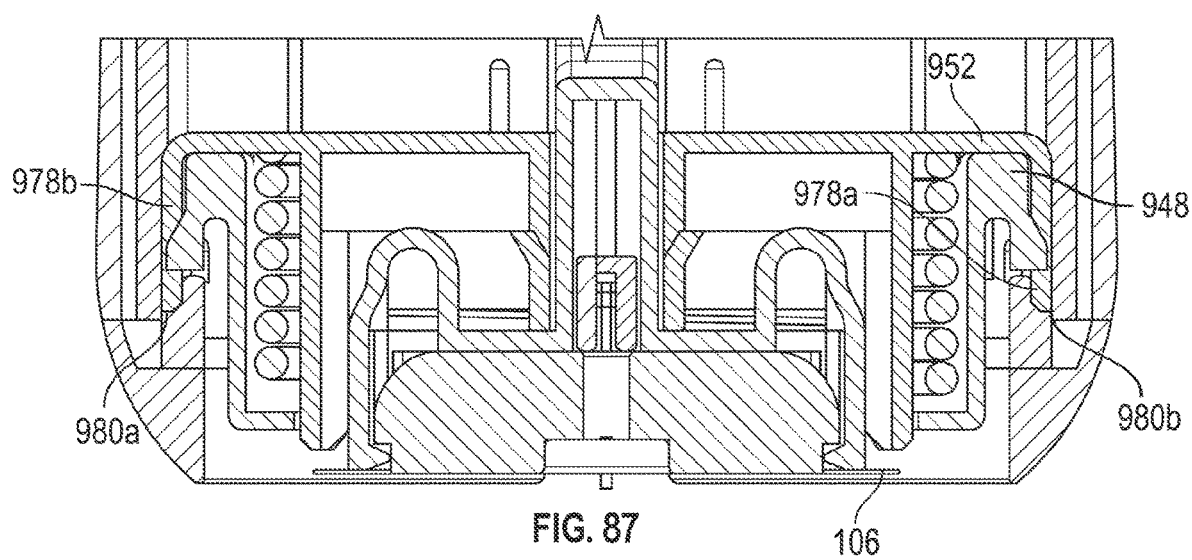
FIG. 87 illustrates a close up cross sectional view of the applicator in a view that is orthogonal to line VIII-VIII of FIG. 75.

FIG. 78 illustrates a top perspective view of the carriage 952 of the release actuator. The carriage 952 may be configured to slide relative to the applicator housing and be configured to be slid by the driver 950 of the retraction actuator and the driver 946 of the insertion actuator. The carriage 952 may include releasable couplers 978a, b for coupling to the coupling members 976 of the carriage 948 of the insertion actuator. The releasable couplers 978a, b may comprise deflectable arms configured to extend over the coupling members 976 to engage with the coupling members 976. The releasable couplers 978a, b may be configured to automatically release from the coupling members 976 of the carriage 948 upon contact with a coupler release in the form of deflectors 980a, b of the applicator housing, as shown in FIG. 87 along an inner sidewall of the applicator housing. The carriage 952 may include an opening 982 configured for the support 968 and the driver 946 of the insertion actuator to extend through.

Figure 79:
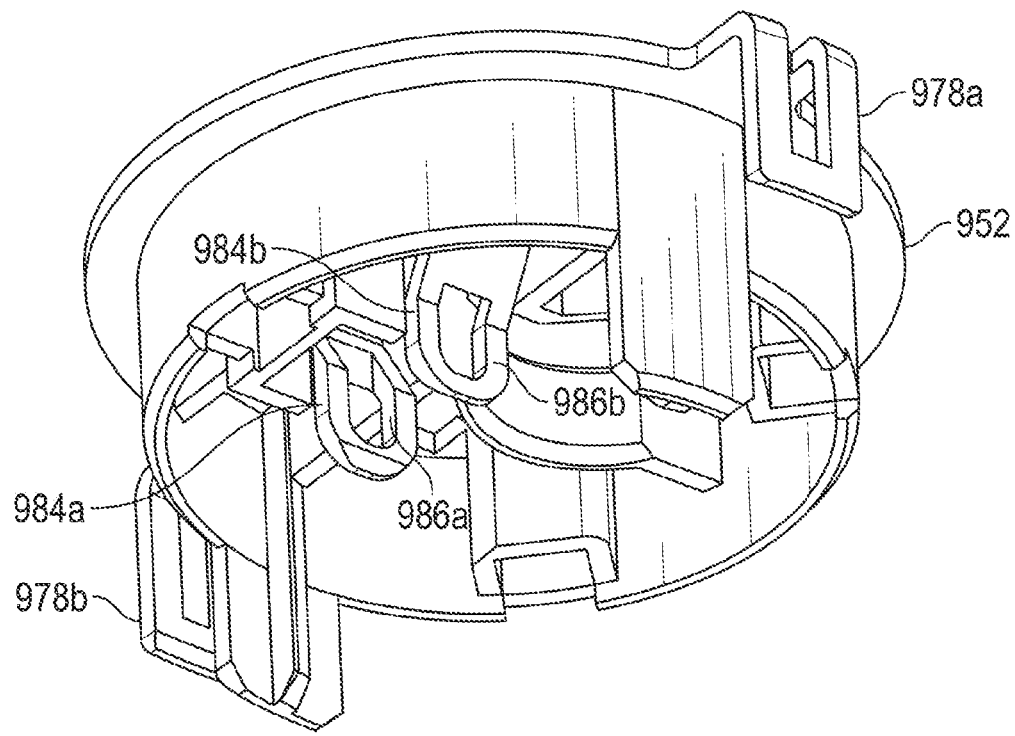
FIG. 79 illustrates a bottom perspective view of a carriage of the applicator shown in FIG. 75.

FIG. 79 illustrates a perspective view of a bottom surface of the carriage 952 of the release actuator. The carriage 952 may include a releasable coupler 984a, b that is configured to releasably couple to the needle 900. The releasable coupler 984a, b may include openings 986a, b that are configured to engage the coupling members 912 of the needle cover 904 marked in FIG. 86 to releasably couple to the needle 900. The openings 986a, b may be movable upon a pressing surface pressing upon arms 988a, b (marked in FIG. 78) coupled to the openings 986a, b. The releasable coupler 984a, b may be configured to retain the needle 900 at least partially within the applicator housing 936 following insertion of the transcutaneous analyte sensor 24 into the individual's skin and removal of the applicator housing 936 from the transcutaneous analyte sensor 24, and configured to release the needle 900 from within the applicator housing 936 following insertion of the transcutaneous analyte sensor 24 into the individual's skin. The configuration of the carriage 952 may be varied in other embodiments.

Figure 80:
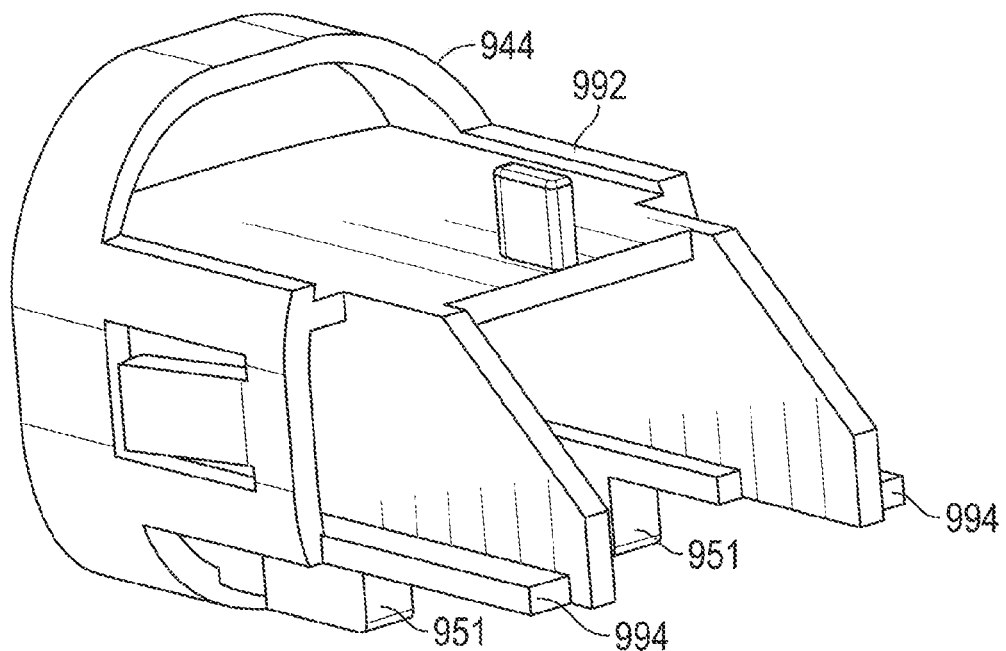
FIG. 80 illustrates a rear perspective view of a control device of the applicator shown in FIG. 75.

FIG. 80 illustrates a perspective view of the control device 944 of both the insertion actuator and the release actuator. The control device 944 may comprise a button that may be pressed or another form of movable body to activate the insertion actuator and to activate the release actuator. The control device 944 may be configured to be slid laterally to activate the insertion actuator and to activate the release actuator. The control device 944 may include a button surface 990 (marked in FIG. 75) and a control arm 992 that extends from the button surface 990. The control arm 992 may include a coupler release in the form of a pressing surface 994 configured to be pressed against the releasable coupler 962a, b of the carriage 948 shown in FIG. 76 to release the releasable coupler 962a, b from the coupling member 963a, b shown in FIG. 84. The control arm 992 may also include a coupler release in the form of pressing surface 951 for pressing the arms 988a, b shown in FIG. 78 to release the releasable coupler 984a, b. The pressing surfaces 994 may extend further distally from the button surface 990 (marked in FIG. 75) than the pressing surface 951, and are staggered from the pressing surface 951.

FIG. 81 illustrates a perspective cross sectional view of the applicator 934 showing that the applicator housing 936 includes a receiver 996 for receiving the cartridge 916. The receiver 996 may be configured for the cartridge 916 retaining the transcutaneous analyte sensor to be inserted into. The receiver 996 may comprise a cavity within the applicator housing 936 that receives the cartridge 916. The cartridge 916 may be inserted into the receiver 996 axially through an opening 998 at a bottom of the applicator housing 936.

The applicator 934 may operate in a manner shown in FIGS. 81-92. FIG. 81 illustrates the applicator 934 in an initial state, in which the applicator 934 is configured to receive the cartridge 916 and components of the transcutaneous analyte sensor system including the transcutaneous analyte sensor 24, the wearable housing 108, and the patch 106.

The applicator 934 in the initial state has the carriage 948 of the insertion actuator in a lowered state, proximate the lower opening 998 of the applicator 934. The carriage 948 of the insertion actuator may be pressed to the lowered state by the force provided by the driver 946 of the insertion actuator. The driver 946 may be configured to drive the needle 900 into the individual's skin to insert the transcutaneous analyte sensor into the individual's skin. The carriage 952 of the retraction actuator may be in a raised state, pressed to the raised state by the force of the driver 950 of the retraction actuator. The driver 950 may be configured to drive the needle 900 out of the individual's skin. The releasable couplers 978a, b shown in FIG. 78 are not yet coupling the carriages 948, 952 together.

The cartridge 916 may be inserted into the receiver 996 of the applicator housing 936 to allow the releasable coupler 972a, b of the carriage 948 of the insertion actuator to engage the wearable housing 108 of the on-skin sensor assembly. A removable cover 932 of the cartridge 916 may previously have been removed by an individual.

Figure 82:
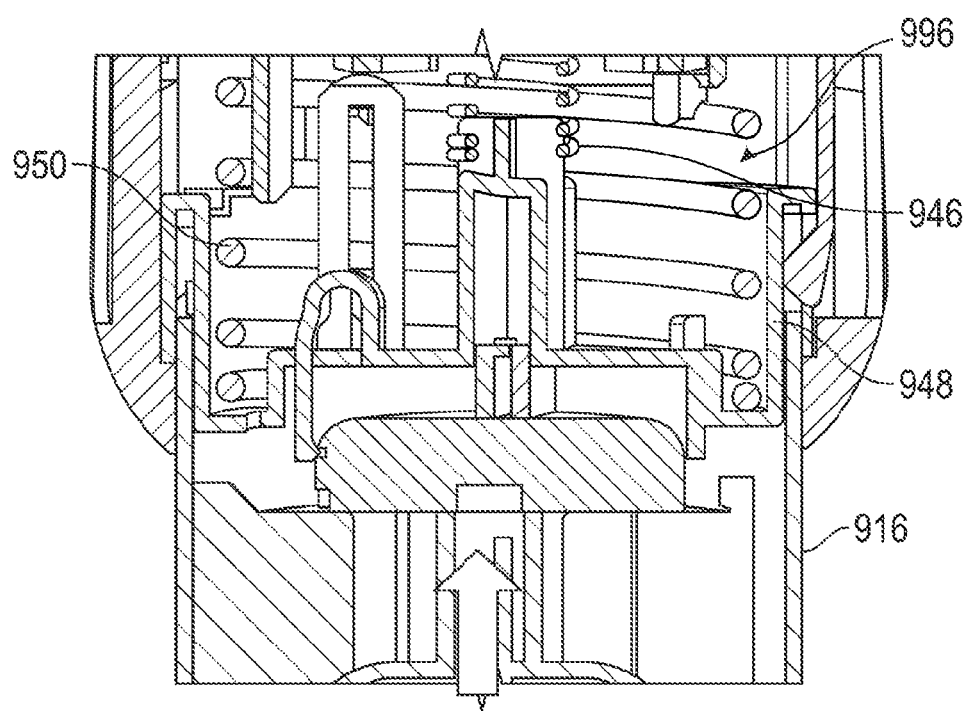
FIG. 82 illustrates a cross sectional view of the applicator along line IX-IX of FIG. 75, which is orthogonal to line VIII-VIII.

FIG. 82 illustrates the cartridge 916 being inserted into the receiver 996 of the applicator housing 936. The cartridge 916 may be inserted in the axial dimension of the applicator housing 936, which is the same dimension that the transcutaneous analyte sensor 24 as well as other components of the transcutaneous analyte sensor system will be deployed from the applicator housing 936 (although in an opposite axial direction that the cartridge 916 is inserted into the receiver 996). The insertion of the cartridge 916 and the transcutaneous analyte sensor 24 into the receiver 996 of the applicator housing 936 may compress and thus provide energy to both the driver 946 of the insertion actuator and the driver 950 of the retraction actuator. Both drivers 946, 950 may be compressed for example as shown in FIG. 84. In an embodiment in which the drivers 946, 950 are springs, the springs may be compressed by the insertion of the cartridge 916 and the transcutaneous analyte sensor 24 into the receiver. The cartridge 916 may include a pressing surface on an upper surface of the cartridge 916 to press against the carriage of the insertion actuator to provide energy to the insertion actuator.

Figure 83:
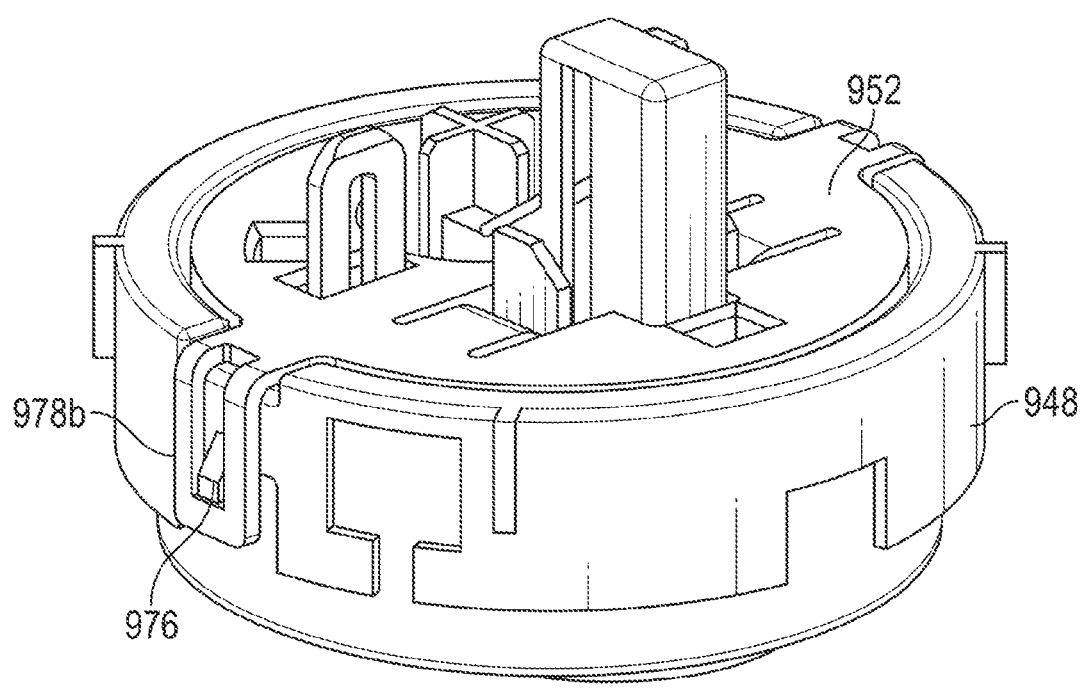
FIG. 83 illustrates a perspective view of coupled carriages of the applicator shown in FIG. 75.

The insertion of the cartridge 916 fully into the receiver 996 of the applicator housing 936 causes the releasable couplers 978a, b of the retraction actuator carriage 952 to engage the coupling members 976 of the insertion actuator carriage 948. FIG. 83, for example, illustrates a perspective view of the carriages 952, 948 coupled together.

The insertion of the cartridge 916 fully into the receiver 996 of the applicator housing 936 also causes the releasable coupler 962a, b of the insertion actuator to engage the coupling member 963a, b as shown in FIG. 84. The engagement of the releasable coupler 962a, b holds the carriage 948 of the insertion actuator in position and prevents the driver 946 from pressing the carriage 948 in an axial direction towards the lower opening 998 of the applicator housing 936.

Figure 85:
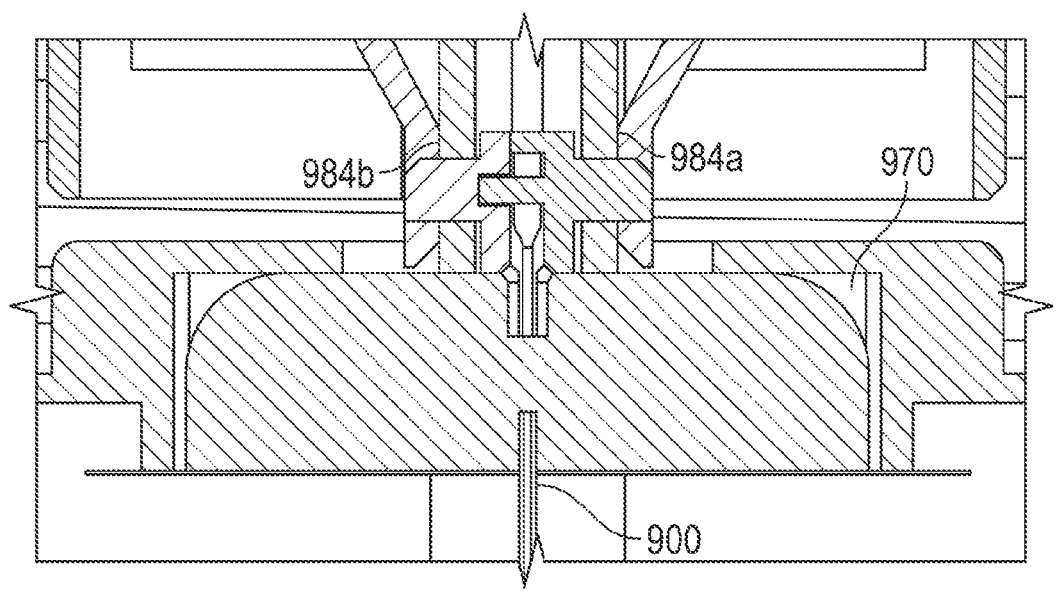
FIG. 85 illustrates a close up cross sectional view of a releasable coupler for the applicator in a view that is orthogonal to line VIII-VIII.

As shown in FIG. 85, the releasable coupler 984a, b couples to the needle 900, particularly with the openings 986a, b of the releasable coupler 984a, b engaging coupling members of the needle cover 904. The needle 900 extends downward from the wearable housing 108 of the transcutaneous analyte sensor system, extending for insertion of the penetrating tip of the needle 900 into the individual's skin.

As shown in FIG. 85, the wearable housing 108 of the transcutaneous analyte sensor system may be positioned in the receiver 970 of the lower surface of the carriage 948. The releasable coupler 972a, b shown in FIG. 77 may couple to the cavity 123 shown in FIG. 3 to grip the wearable housing 108 to the lower surface of the carriage. Thus, as the cartridge 916 is withdrawn from the applicator housing 936, the wearable housing 108 remains coupled to the receiver 970.

With the cartridge 916 withdrawn from the applicator housing 936, the transcutaneous analyte sensor system is in position for application to the individual's skin by the applicator 934. The transcutaneous analyte sensor system may be moved axially downward within the receiver 996 of the applicator housing 936 to contact the individual's skin and be applied to the individual's skin.

The insertion actuator may operate to insert the needle 900 into the individual's skin to deposit the transcutaneous analyte sensor 24 into the individual's skin. The control device 944 of the insertion actuator may be pressed in a lateral direction, or a direction transverse to the axial dimension of the applicator housing 936. The movement of the control device 944 may compress a biasing spring 999 (marked in FIG. 75) that is configured to apply a biasing force to the control device 944.

Figure 86:
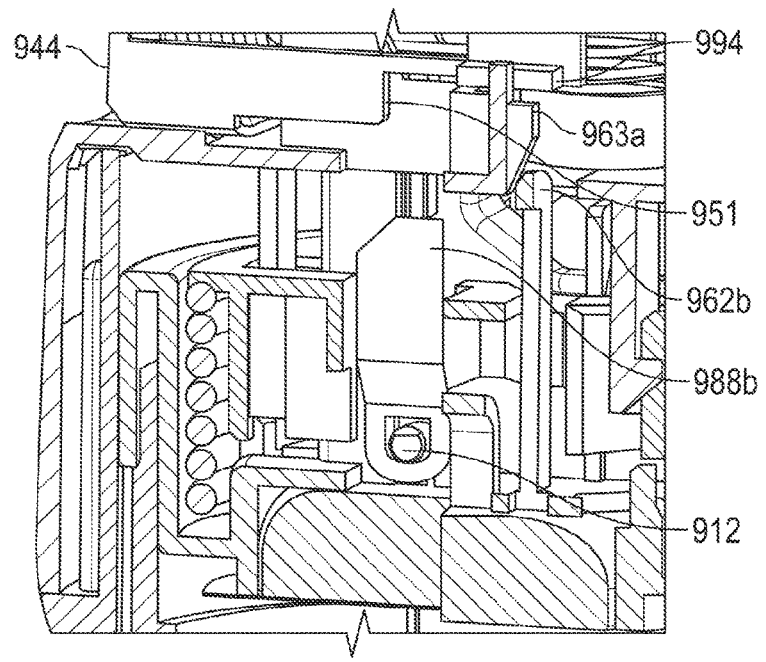
FIG. 86 illustrates a close up cross sectional view of the applicator along line VIII-VIII of FIG. 75.

Referring to FIG. 86, the movement of the control device 944 may disengage the coupling member 963a, b from the releasable coupler 962a, b by the pressing surface 994 pressing the releasable coupler 962a, b off of the coupling member 963a, b. The force of the driver 946 of the insertion actuator upon the carriage 948 causes the coupled carriages 948, 952 to descend rapidly with sufficient force to drive the needle 900 into the individual's skin. The descent of the coupled carriages 948, 952 is rapid enough such that the pressing surface 951 does not contact the arms 988a, b.

Referring to FIG. 87, after the control device 944 has been pressed and the insertion actuator has been activated, the movement of the carriage 948 has inserted the needle 900 into the individual's skin and has inserted the transcutaneous analyte sensor 24 into the individual's skin. Further, the movement of the carriage 948 has pressed the patch 106 to the individual's skin, allowing the patch 106 to adhere to the individual's skin and providing an adhesive force to the skin for the transcutaneous analyte sensor system.

Further, with the carriages 948, 952 both being slid downward within the applicator housing 936, the releasable couplers 978a, b of the retraction actuator carriage 952 may contact the coupler release in the form of deflectors 980a, b of the applicator housing 936. Such contact may apply a force to the releasable couplers 978a, b in lateral directions that causes the releasable couplers 978a, b to disengage from the protrusions of the coupling members 976. Accordingly, the carriages 948, 952 may be decoupled from each other and able to slide relative to each other. The retraction actuator accordingly may be configured to automatically operate upon the needle 900 inserting the transcutaneous analyte sensor into the individual's skin.

Figure 88:
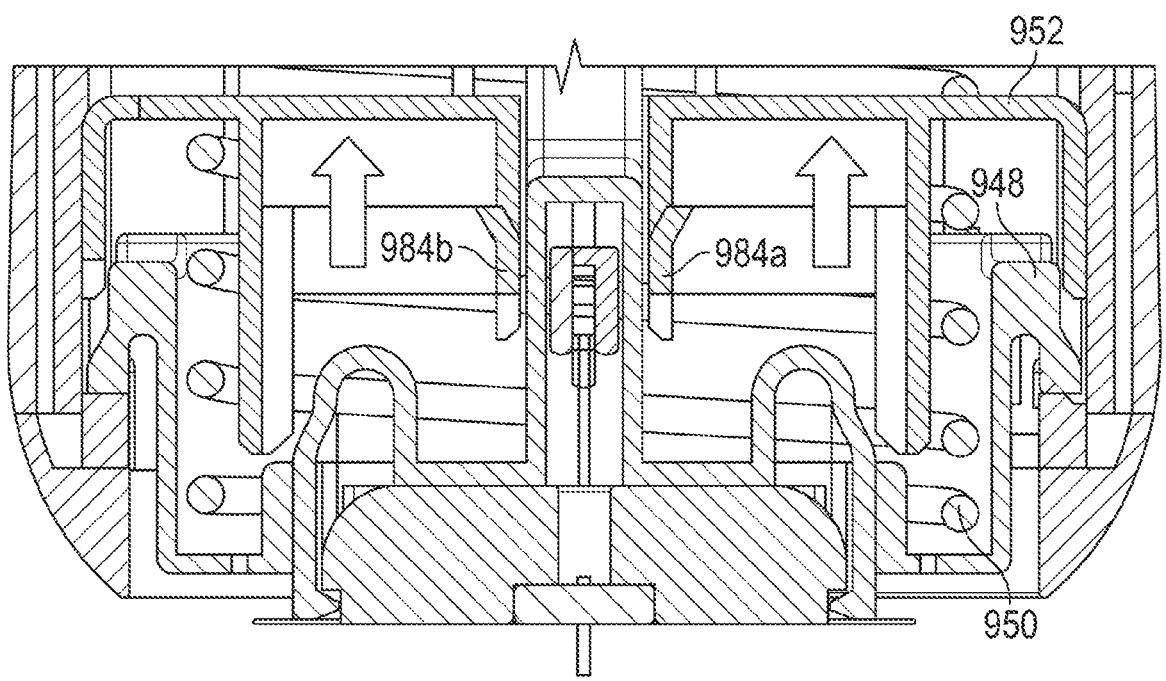
FIG. 88 illustrates a close up cross sectional view of the applicator in the view of FIG. 87.

Referring to FIG. 88, with the carriages 948, 952 decoupled from each other, the driver 950 of the retraction actuator may apply an upward force to the carriage 952 of the retraction actuator to move the carriage 952 upward.

The upward movement of the retraction actuator carriage 952 may cause the needle 900 that is coupled to the releasable coupler 984a, b to retract out of the individual's skin, due to the upward movement of the releasable coupler 984a, b. The releasable coupler 984a, b may cause the needle 900 to slide upwards.

Figure 89:
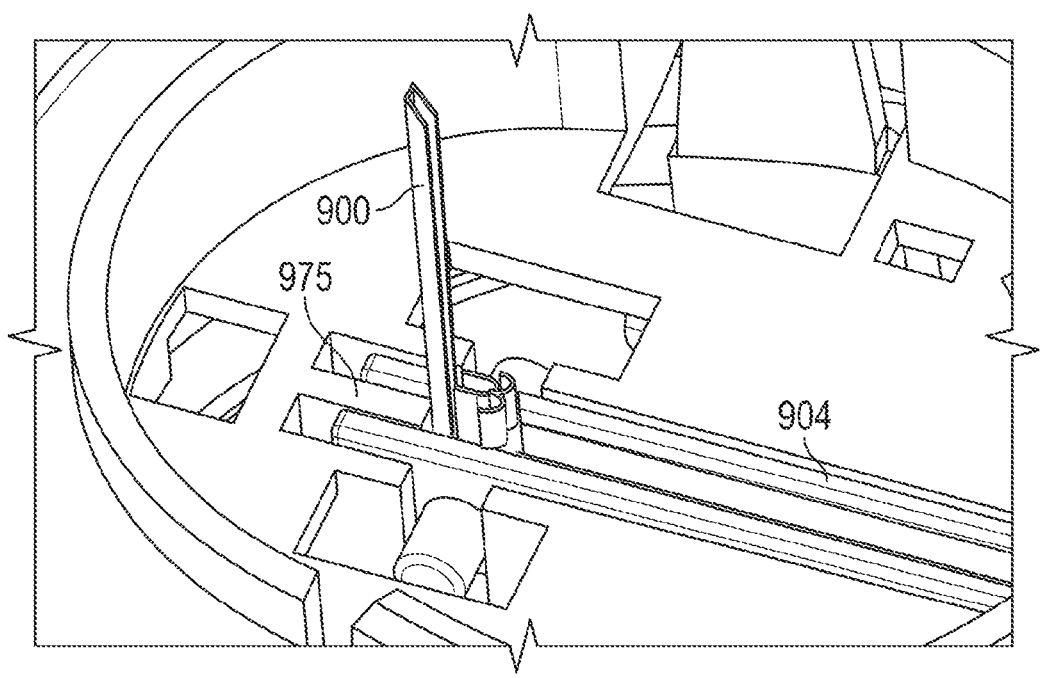
FIG. 89 illustrates a perspective view of a needle extending from a carriage of the applicator shown in FIG. 75.

Referring to FIG. 89, the needle 900 may slide upwards against the alignment rail 975, which extends between portions of the needle cover 904 proximate the needle 900. The alignment rail 975 may allow the needle 900 to stay in an axially vertical position as the needle is retracted upwards in the applicator housing 936. The needle cover 904, however, may be able to pivot relative to the needle 900.

Figure 90:
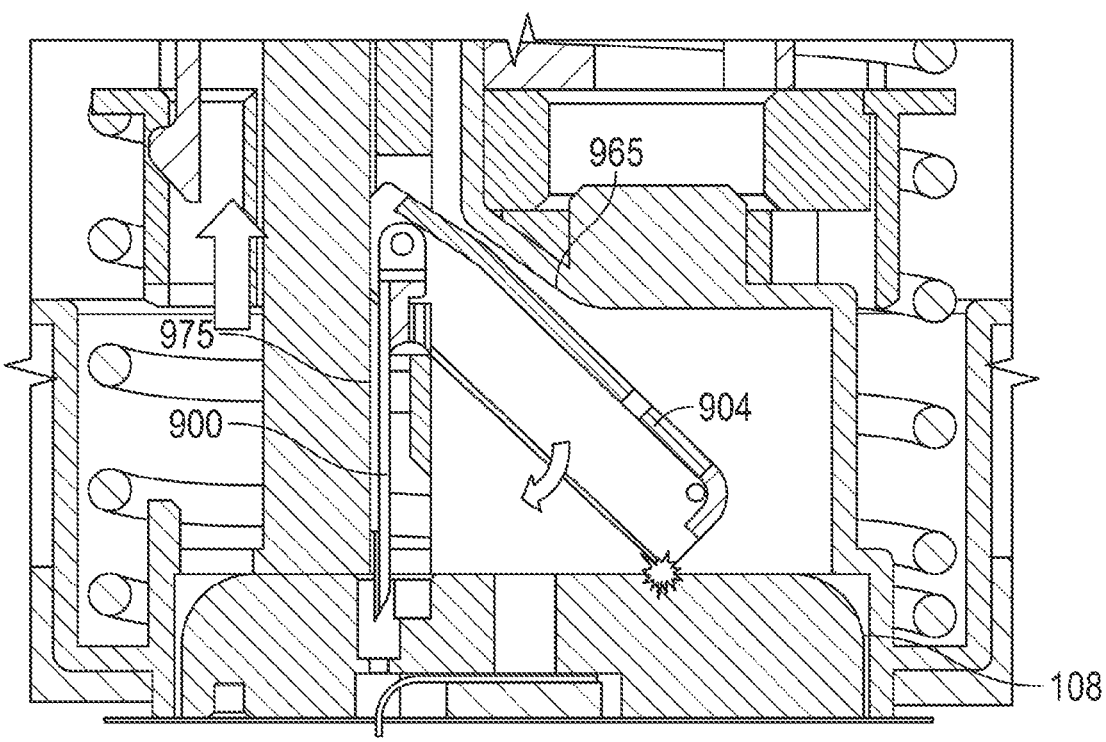
FIG. 90 illustrates a cross sectional view of the applicator along line VIII-VIII of FIG. 75.
Figure 92:
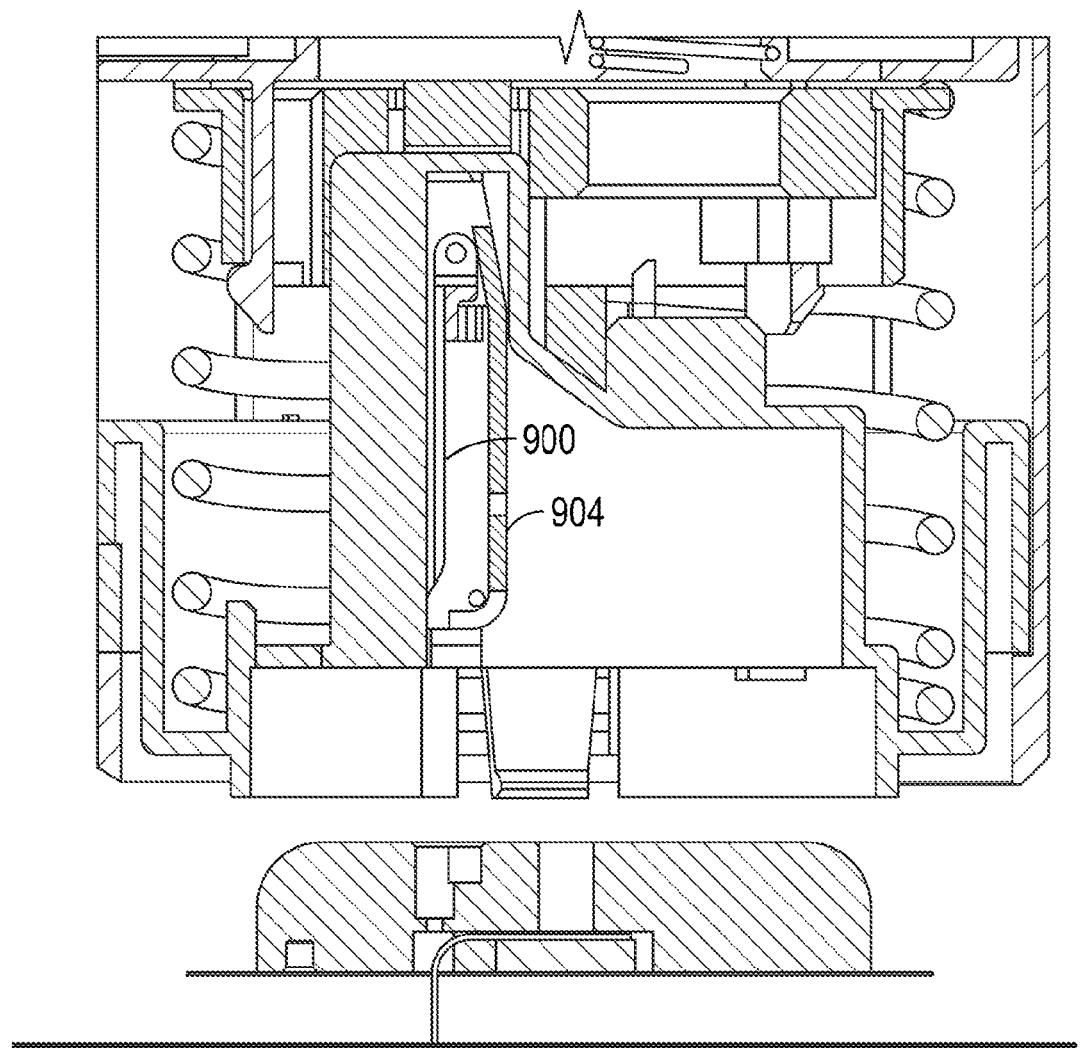
FIG. 92 illustrates a cross sectional view of the applicator along line VIII-VIII of FIG. 75.

FIG. 90, for example, illustrates the needle 900 being slid upward along the alignment rail 975, with the needle cover 904 contacting the deflection surface 955. The needle cover 904 may rotate towards the penetrating tip of the needle 900, yet may contact the wearable housing 108 of the on-skin sensor assembly. This may stall the rotation of the needle cover 904 until the applicator housing 936 is removed from the wearable housing 108 of the on-skin sensor assembly. With the applicator housing 936 removed from the wearable housing 108, the needle 900 may continue to slide upward in the central channel 964 and the needle cover 904 may fully cover the needle 900. The needle 900 and needle cover 904 may both be aligned axially within the central channel 964, as shown in FIG. 92. The retraction actuator may position the needle 900 into the needle cover 904.

The lock 902 shown in FIG. 73 may lock with the needle cover 904, to prevent the needle cover 904 from rotating away from the needle 900.

The releasable coupler 984a, b shown in FIG. 79 retains the needle 900 to the applicator housing 936 following insertion of the transcutaneous analyte sensor 24 into the individual's skin and removal from the applicator housing from the transcutaneous analyte sensor 24. The transcutaneous analyte sensor 24 remains within the individual's skin as the applicator housing is removed from the transcutaneous analyte sensor 24.

With the applicator housing removed from the transcutaneous analyte sensor 24, the release actuator may be operated to release the needle 900 from the releasable coupler 984a, b.

Figure 91:
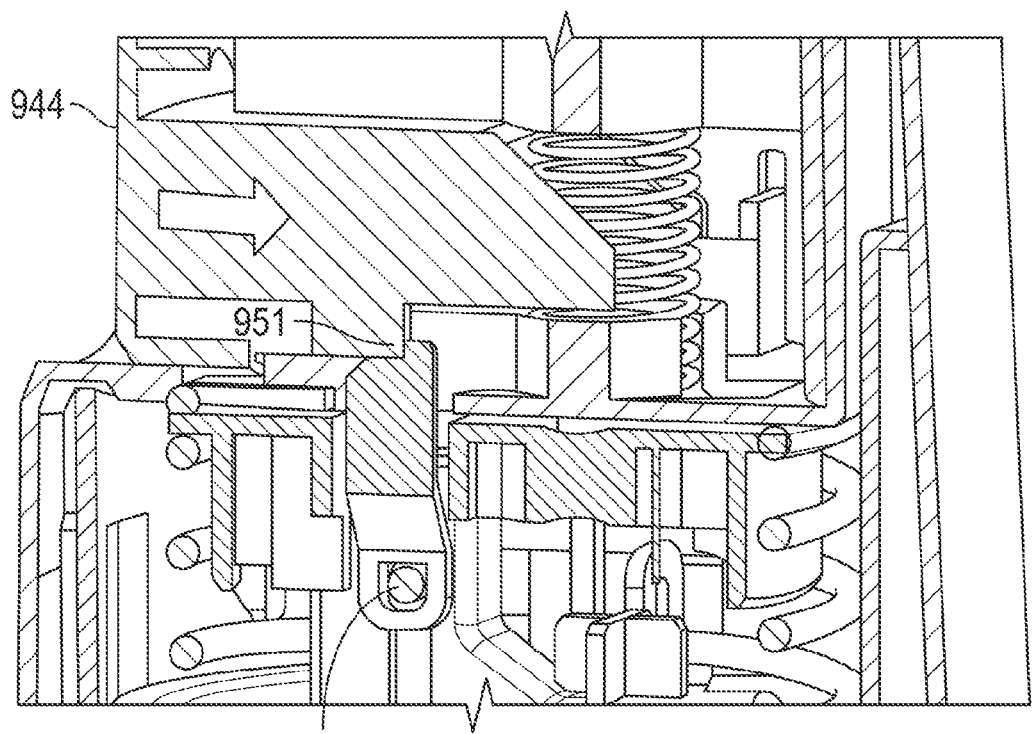
FIG. 91 illustrates a cross sectional perspective view of the applicator along line VIII-VIII of FIG. 75.

Referring to FIG. 91, the control device 944 of the release actuator may be pressed laterally, causing the pressing surface 951 to apply a force against the arms 988a, b of the releasable couplers 984a, b. The force against the arms 988a, b may cause the openings 986a, b to release from the coupling members 912 of the needle cover 904. Accordingly, the releasable coupler 984a, b may be released from the needle 900. The needle 900 and needle cover 904 may be released from the applicator housing 936 with the needle cover 904 covering the penetrating tip of the needle 900. The releasable coupler 984a, b configured to retain the needle 900 is configured to release the needle 900 positioned within the needle cover 904 from the applicator housing. The needle 900 covered by the needle cover 904 may drop from the applicator housing 936.

Accordingly, the same control device 944 may be operated twice to first operate the insertion actuator and then second to operate the release actuator. The control device 944 may be operated in a first operation to activate the insertion actuator, and may be configured to be operated in a second operation following the first operation to activate the release actuator. In an embodiment in which the control device 944 is a button, the first operation may comprise pressing the control device 944 and the second operation may comprise pressing the control device 944 a second time. The same control device 944 accordingly may be pressed twice to operate both the insertion actuator and the release actuator.

The needle 900 may be released from the applicator housing 936 for discard, as the needle 900 may have been contaminated through the process of insertion within the individual's skin. The needle 900 accordingly may be a single use needle that is configured to discard within a sharps container or other disposal area. The needle 900 may remain sheathed within the needle cover 904 such that an individual does not contact the used needle 900 and be subject to the contamination of the needle 900 or otherwise be injured by the penetrating tip of the needle 900. The needle 900 may remain locked in position within the needle cover 904 such that an individual cannot access the contaminated portion of the needle 900. The needle 900 and needle cover 904 together may form a unit for disposal following insertion into an individual's skin and separation from the applicator housing.

Upon release of the needle 900 and needle cover 904 from the applicator housing 936, and following the return of the control device 944 to the position shown in FIG. 81, the applicator is in a configuration for deployment of another transcutaneous analyte sensor 24 and other components of a transcutaneous analyte sensor system. As such, the applicator 934 is configured for multiple uses, and is not intended to be discarded. The applicator 934 returns to a configuration shown in FIG. 81 for repeat of the steps shown in FIGS. 81-92. The applicator 934 may be loaded with another cartridge 916 and the steps disclosed herein may repeat as desired.

FIGS. 93-106 illustrate a variation of the embodiment of FIGS. 73-92. In the embodiment of FIGS. 93-106, a pull tab or the like may be utilized to release the used needle from the releasable coupler, although in some embodiments a release actuator, similar to other release actuators disclosed herein may be utilized.

Figure 93:
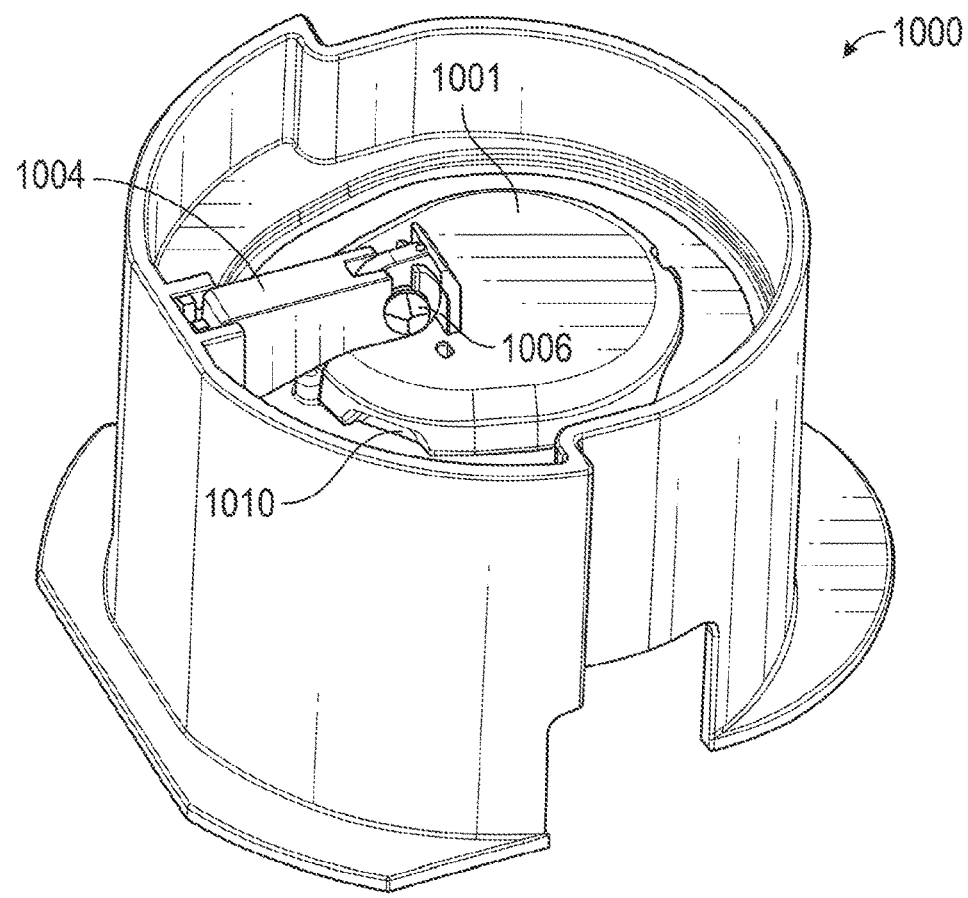
FIG. 93 illustrates a perspective view of a cartridge.

Referring to FIG. 93, a perspective view of a cartridge 1000 that may be configured similarly as the cartridge 916 shown in FIG. 74. The cartridge 1000 may be configured to be inserted into an applicator housing and may retain a transcutaneous analyte sensor. The cartridge 1000 may include a body configured to be coupled to an applicator housing and may include a retainer retaining the transcutaneous analyte sensor and a wall extending around at least a portion of the transcutaneous analyte sensor. The wearable housing 1001, including the transcutaneous analyte sensor may be positioned within and retained by the cartridge 1000, as well as the needle 1002 and the needle cover 1004. The needle 1002 may be coupled to the needle cover 1004 at a pivot, at which a coupling member 1006 may be positioned for engagement with a releasable coupler of an applicator. The coupling member 1006 may comprise protrusions that extend outward from the body of the needle cover 1004.

Figure 94:
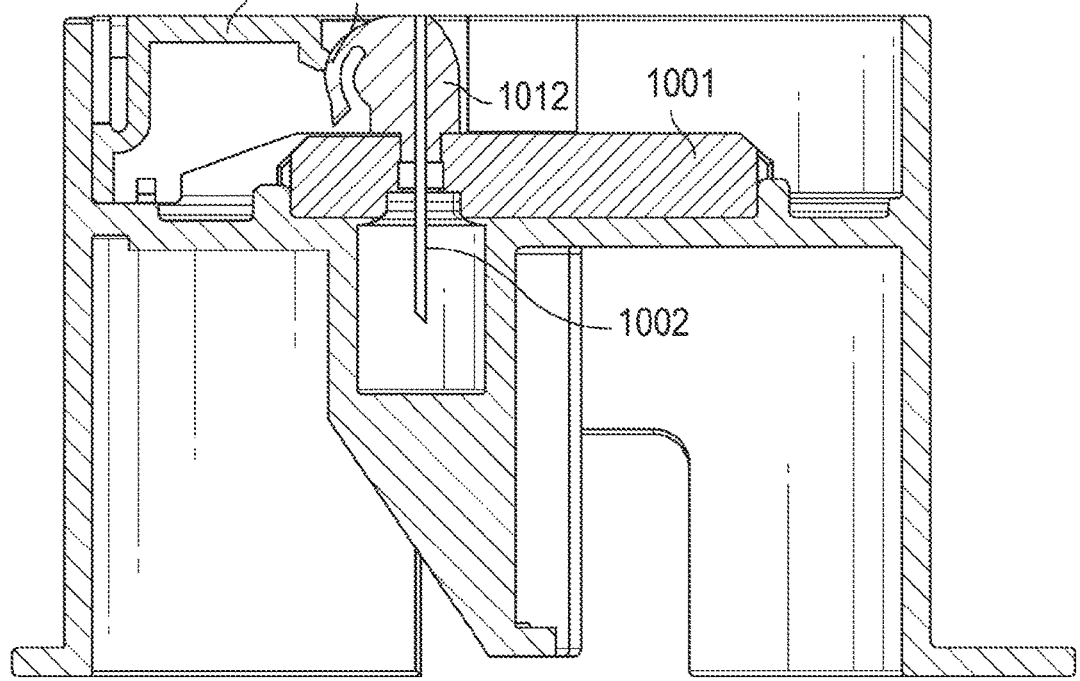
FIG. 94 illustrates a cross sectional view of the cartridge of FIG. 93.

The needle cover 1004, referring to FIG. 94, may include a lock 1008 that is configured to lock the needle 1002 in position within the needle cover 1004 upon rotation of the needle cover 1004 relative to the needle 1002. The needle cover 1004 may be configured to rotate relative to the needle 1002 to extend over at least the portion of the needle 1002. The needle cover 1004 may be configured to cover at least a portion of the needle 1002 following the needle 1002 inserting the transcutaneous analyte sensor into the skin of an individual.

The wearable housing 1001 may include indentations 1010 for engagement with a releasable coupler of an actuator, for retaining the wearable housing 1001 to the releasable coupler upon the cartridge 1000 being removed from an applicator.

In the cross sectional view of FIG. 94, the needle 1002 extends at an angle (e.g., a perpendicular angle) with respect to the needle cover 1004. The needle hub 1012 coupled to the proximal portion of the needle 1002 may include the lock 1008 and may be configured to rotate relative to the needle cover 1004.

Figure 95:
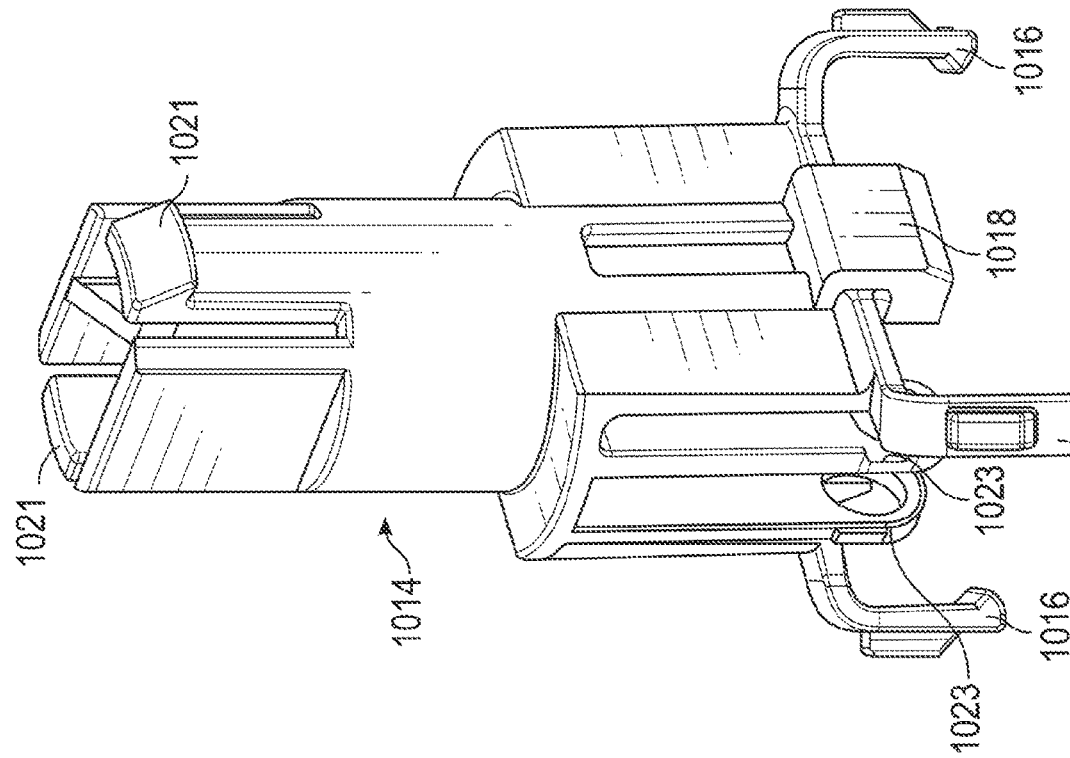
FIG. 95 illustrates a perspective view of a carriage.

FIG. 95 illustrates a perspective view of a first carriage 1014 that may comprise a retraction carriage for retracting the needle 1002 from the individual's skin following insertion of the needle 1002. The carriage 1014 may include releasable couplers 1016 that engage the wearable housing 1001 to retain the wearable housing 1001 to the releasable coupler 1016 upon the cartridge 1000 being removed from an applicator. The carriage 1014 may further include coupler releases in the form of deflectors 1018 configured to release a coupler to allow the carriage 1014 to move relative to the insertion carriage 1020. The releasable couplers 1022 may couple the insertion carriage 1020 to the carriage 1014. The deflectors 1018, for example, may be configured to deflect the releasable couplers 1022 of the insertion carriage 1020 shown in FIG. 97 to release the carriages 1014, 1020 from each other. The releasable couplers 1022 may be configured to automatically release upon contact with the deflectors 1018. The releasable couplers 1022 may release the carriages to allow the driver 1050 to move the carriage 1020 in a direction away from the carriage 1014. The first carriage 1014 may further include protrusions 1021 that retain the first carriage 1014 to the second carriage 1025.

The first carriage 1014 may further include releasable couplers 1023 for coupling to the coupling member 1006 of the needle 1002, to withdraw the needle 1002 from the individual's skin following insertion into the individual's skin. One or more of the releasable couplers 1023 may be configured to retain a needle to the applicator housing following insertion of the transcutaneous analyte sensor into the individual's skin and removal of the applicator housing from the transcutaneous analyte sensor, and release the needle from within the applicator housing following insertion of the transcutaneous analyte sensor into the individual's skin. The one or more releasable couplers 1023 may be configured to couple to a needle hub 1012 of the needle.

Figure 96:
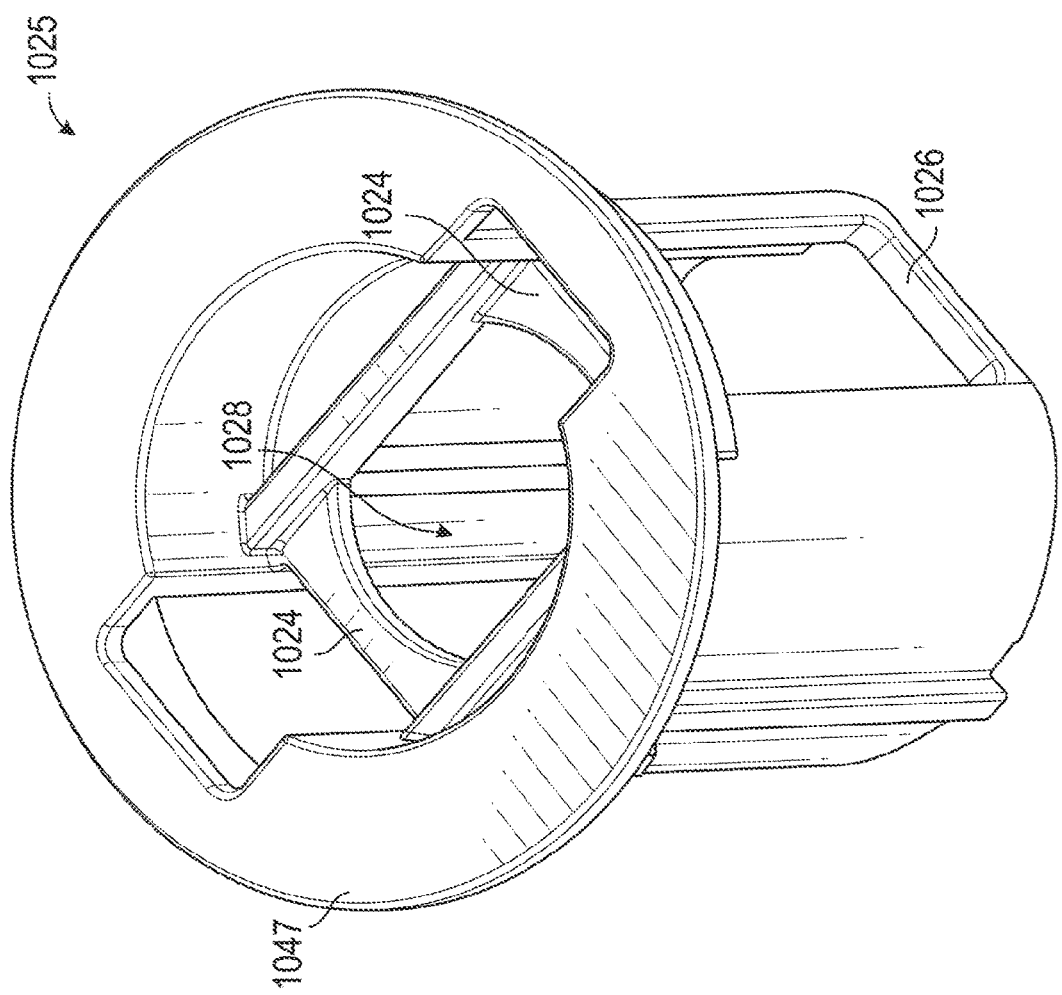
FIG. 96 illustrates a perspective view of a carriage.

FIG. 96 illustrates a perspective view of a second carriage 1025 that may include support surfaces 1024 for the protrusions 1021 to contact to keep the carriages 1014, 1025 engaged with each other. The second carriage 1025 may further include support surfaces 1026 for the releasable couplers 1022 shown in FIG. 97 to engage with. The second carriage 1025 may further include a central channel 1028 for the first carriage 1014 to be positioned within.

Figure 97:
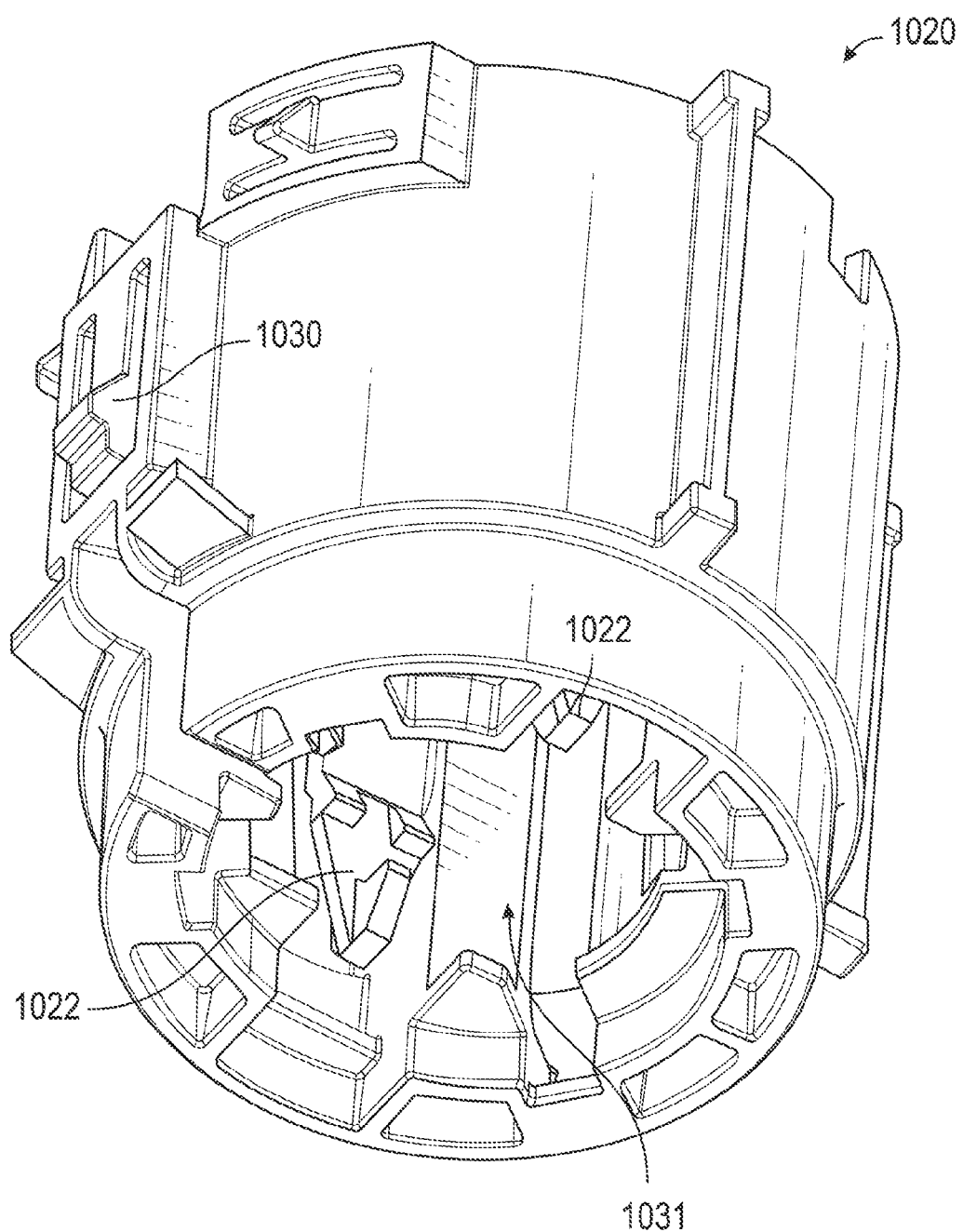
FIG. 97 illustrates a perspective view of a carriage.

FIG. 97 illustrates a bottom perspective view of the insertion carriage 1020. The insertion carriage 1020 may include the releasable couplers 1022 for engaging with the support surface 1026 of the second carriage 1025. The insertion carriage 1020 may further include a releasable coupler 1030 for engaging with the interior housing 1032 of the applicator, and particularly with an aperture 1034 of the interior housing 1032. The insertion carriage 1020 may comprise a component of an actuator or insertion actuator that may be coupled to the applicator housing and configured to insert a needle and the transcutaneous analyte sensor into the individual's skin. The insertion carriage 1020 may be configured to slide relative to the applicator housing and configured to be slid by the driver 1048.

In assembly, the first carriage 1014 may be positioned within the channel 1028 of the second carriage 1025, and the carriages 1014, 1025 may be positioned within the central channel 1031 of the insertion carriage 1020. The assembly may be positioned within the interior housing 1032 shown in FIG. 98.

Figure 98:
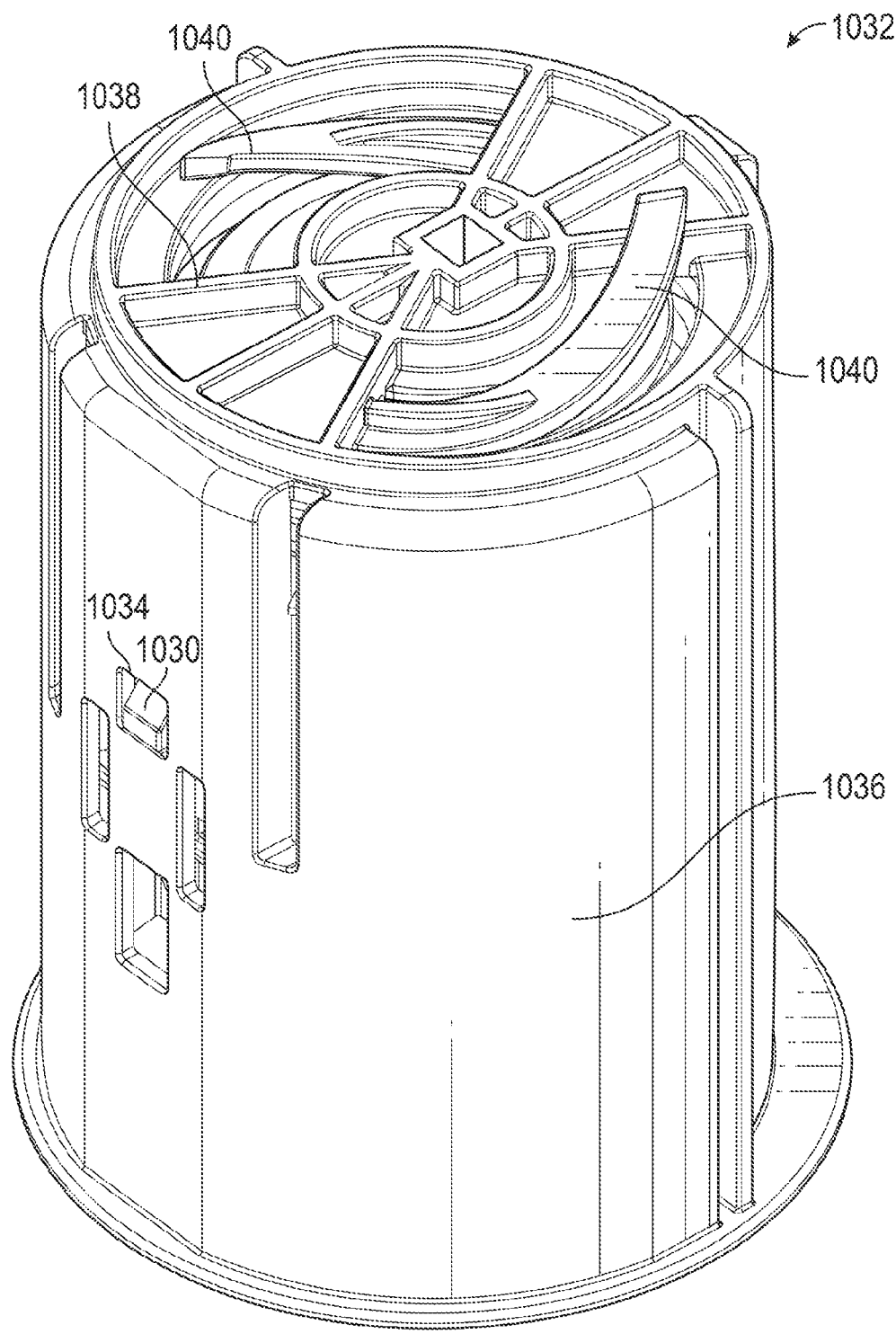
FIG. 98 illustrates a perspective view of an interior housing for an applicator.

FIG. 98 illustrates a perspective view of the interior housing 1032. The interior housing may include a central cavity for the assembly of the carriages 1014, 1025, 1020 to be positioned within. The interior housing 1032 may include an outer surface 1036 including the aperture 1034 for the releasable coupler 1030 to pass through, to hold the assemblies in position relative to the interior housing 1032. The interior housing 1032 may further include an upper surface 1038 having biasing members 1040 in the form of springs, and particularly leaf springs configured to bias the interior housing 1032 downward with respect to an outer housing of the applicator. The interior housing 1032 may include a lower opening at a bottom surface of the interior housing 1032 for the transcutaneous analyte sensor, and the needle 1002 and housing 1001 to be deployed from.

Figure 99:
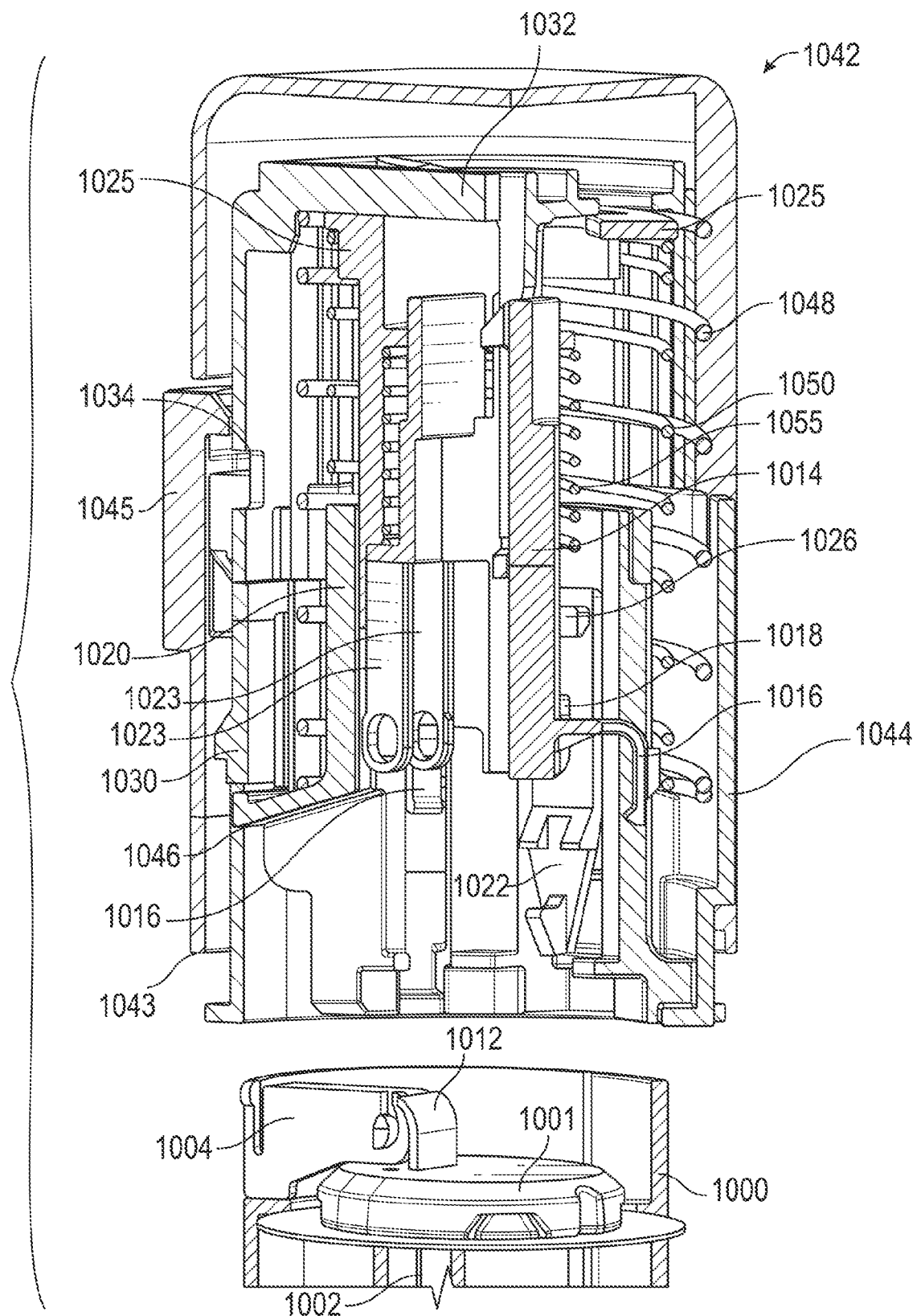
FIG. 99 illustrates a three quarters cross section perspective view of an applicator and the cartridge of FIG. 93.

FIG. 99 illustrates a three-quarters cross sectional perspective view of the applicator 1042, including carriages 1014, 1025, 1020 assembled and positioned within the interior housing 1032 of the applicator housing. The applicator housing may be configured to be gripped by an individual to apply the transcutaneous analyte sensor into the individual's skin. The applicator housing may include a side portion, a top portion and a bottom portion including an opening for the transcutaneous analyte sensor to be deployed from to be inserted into the individual's skin. The receiver of the applicator housing may be configured to receive the cartridge 1000 through the opening of the bottom portion. The interior housing 1032 may be positioned within an outer housing 1044 and may be configured to slide within the outer housing 1044. The biasing members 1040, for example, may press against the interior surface of the top of the outer housing 1044 to bias the interior housing 1032 towards the bottom opening 1043. A force applied upwards against the interior housing 1032, by the skin of an individual, for example, may move the interior housing 1032 upwards within the outer housing 1044.

The outer housing 1044 may comprise an outer surface of the applicator 1042, and may include a control device 1045 that may be activated to cause the transcutaneous analyte sensor to be inserted into the individual's skin. For example, the control device 1045 may comprise a button that is pressed to remove the releasable coupler 1030 of the carriage 1020 from the aperture 1034 of the interior housing 1032.

The insertion carriage 1020 is shown to further include a deflection surface 1046 that may be utilized to deflect the needle cover 1004 upon retraction of the needle 1002 from the housing 1001.

A driver 1048 may comprise a spring and may be configured to drive the needle into the individual's skin to insert the transcutaneous analyte sensor into the individual's skin. The driver 1048 may be configured to drive the entire assembly downward towards the individual's skin to insert the needle 1002 into the individual's skin. A driver 1050 may comprise a component of a retraction actuator and may be configured to drive the needle out of the individual's skin. A driver 1050 may comprise a spring, and may be configured to press against a surface 1047 of the second carriage 1025, as shown in FIG. 96, to retract the carriages 1025, 1014, to retract the needle from the individual's skin. A driver 1055 may comprise a spring, and further may be utilized to bias the first carriage 1014 and the second carriage 1025 from each other.

FIGS. 99-106 illustrate steps of a method that may utilize the applicator 1042. In the initial configuration, the interior housing 1032 may be biased downward with respect to the outer housing 1044 via the biasing members 1040 shown in FIG. 98. Further, the releasable coupler 1030 may be disengaged with the aperture 1034, and the driver 1048 may drive the carriage 1020 to be positioned downward at this point. The releasable coupler 1022 may not yet be engaged with the support surface 1026 at this point.

Figure 100:
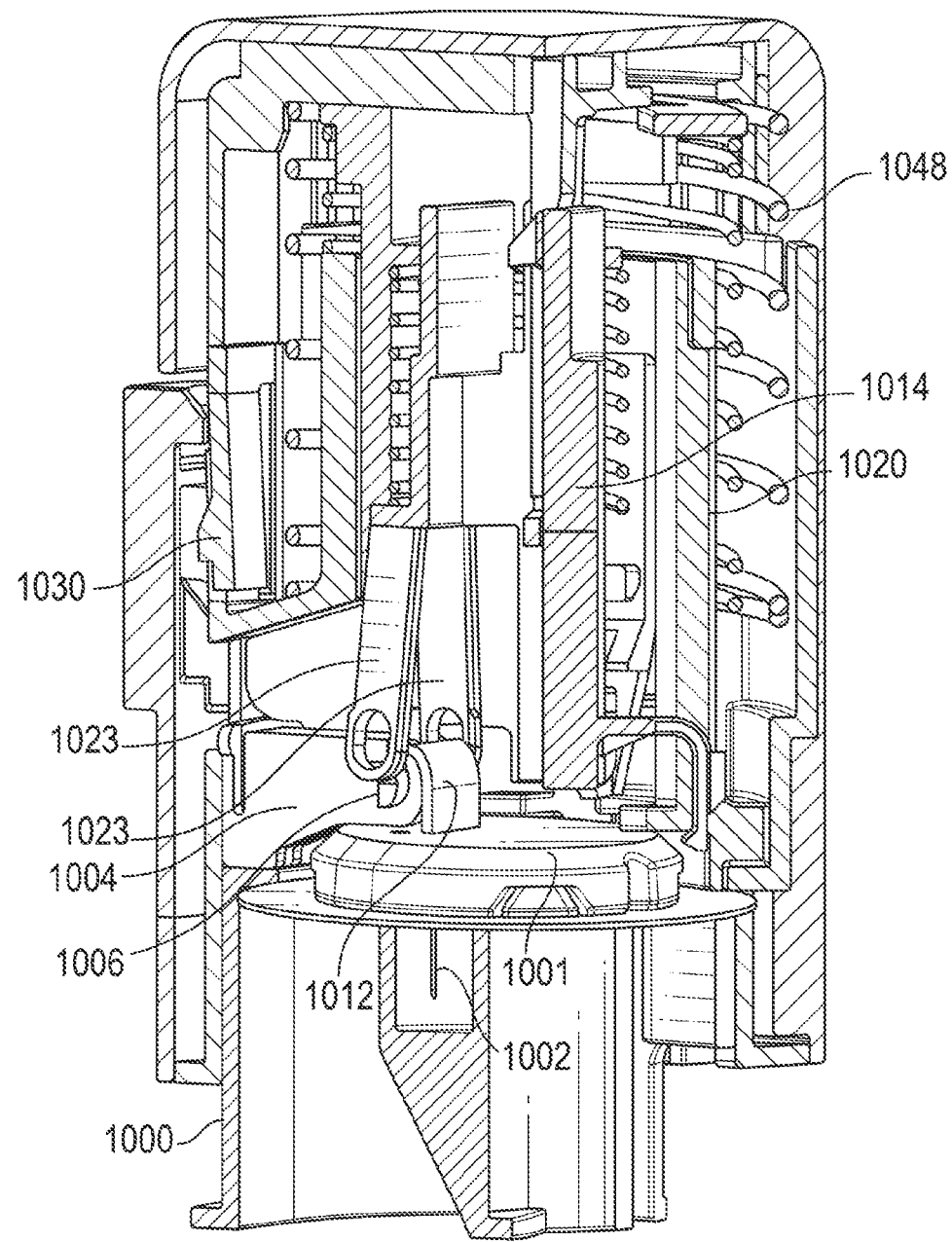
FIG. 100 illustrates a three quarters cross section perspective view of the applicator and the cartridge of FIG. 99.

The cartridge 1000 may be inserted into the receiver of the applicator 1042 by being inserted into the receiver. Upon insertion, a configuration as shown in FIG. 100 may result. The cartridge 1000 may be inserted into the applicator housing to provide energy to the insertion actuator and the retraction actuator. The insertion of the cartridge 1000 may provide energy to the drivers 1048, 1050, 1055. In an embodiment in which the drivers 1048, 1050, 1055 comprise springs, the insertion of the cartridge into the receiver may compress the springs. A force applied by the cartridge 1000 to the insertion and retraction actuators may provide energy to the respective actuators. The cartridge 1000 for example may include a pressing surface for pressing against an actuator to provide energy to the actuator.

The cartridge 1000 may be inserted to contact the insertion carriage 1020 and drive the insertion carriage 1020 upward. The driver 1048 may be compressed. The releasable coupler 1030 may move to engage the aperture 1034 of the interior housing 1032 marked in FIG. 99. The releasable couplers 1023 of the carriage 1014 may start to engage the coupling members 1006 of the needle 1002.

Figure 101:
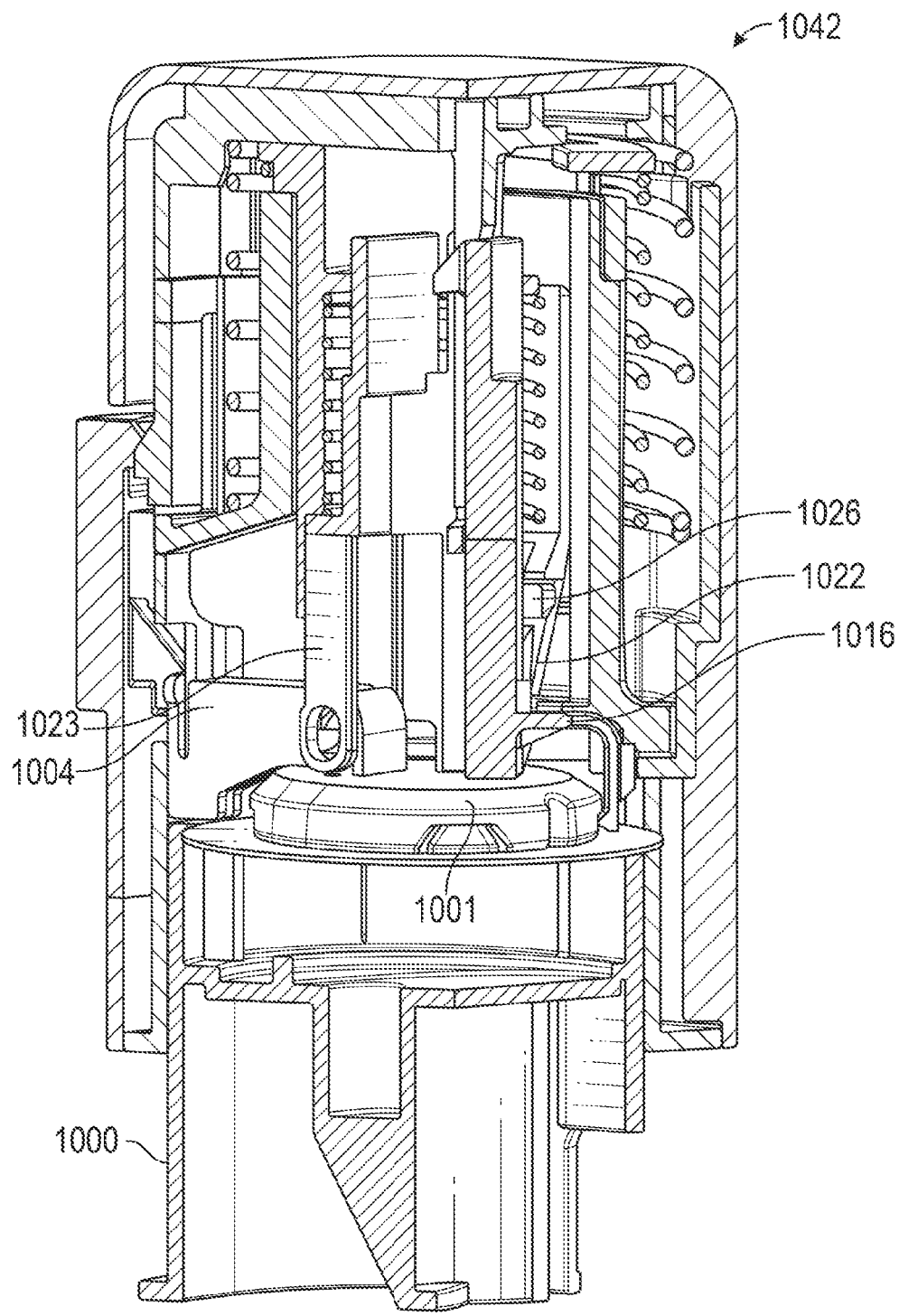
FIG. 101 illustrates a three quarters cross section perspective view of the applicator and the cartridge of FIG. 99.

The cartridge 1000 may continue to be inserted until the releasable couplers 1023 of the carriage 1014 fully engages the coupling members 1006 of the needle 1002. FIG. 101, for example, illustrates full engagement, at which point the cartridge 1000 may be withdrawn from the receiver of the applicator 1042. The cartridge 1000 may be removed from the applicator housing prior to the needle being inserted into the individual's skin to insert the transcutaneous analyte sensor into the individual's skin. The releasable coupler 1030 may fully engage the aperture 1034 of the interior housing 1032. The releasable coupler 1022 may further engage the support surface 1026 of the second carriage 1025 to couple the insertion carriage 1020 to the first and second carriages 1014, 1025.

The releasable coupler 1016 may further engage the indentations 1010 on the housing 1001 to retain the housing 1001 when cartridge 1000 is withdrawn.

Figure 102:
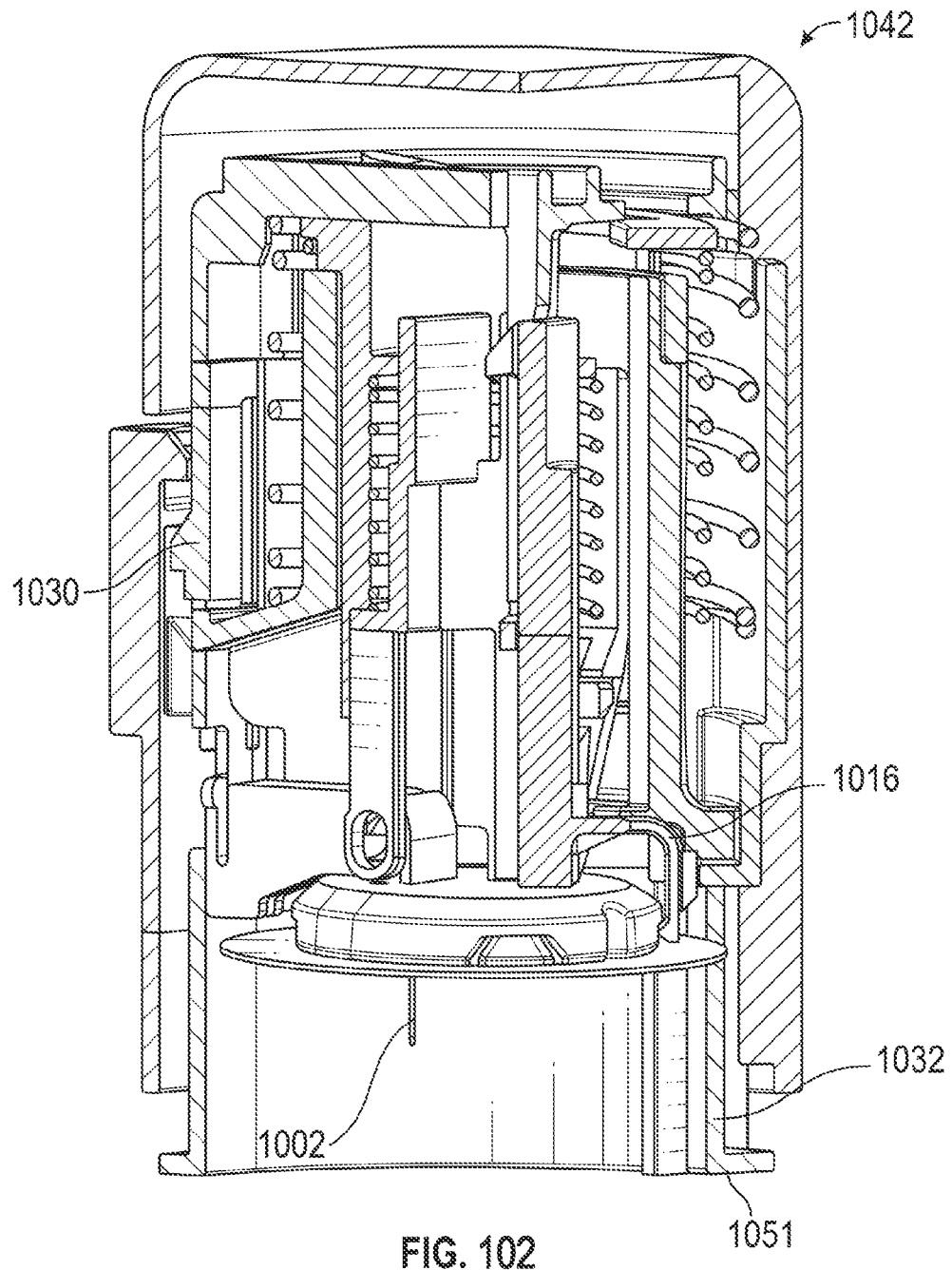
FIG. 102 illustrates a three quarters cross section perspective view of the applicator and the cartridge of FIG. 99.

With the cartridge 1000 withdrawn, the applicator 1042 may have a configuration as shown in FIG. 102. The interior housing 1032 may continue to be biased downward away from the top of the outer housing 1044. In such a configuration, the releasable coupler 1030 of the insertion carriage 1020 may be offset from the position of the control device 1045, such that pressing the control device 1045 does not actuate insertion of the needle 1002. Such a feature may serve as a safety feature to reduce the possibility of inadvertent actuation of the needle 1002 prior to a desired time (at which the bottom surface 1051 of the interior housing 1032 does not yet contact the individual's skin).

Figure 103:
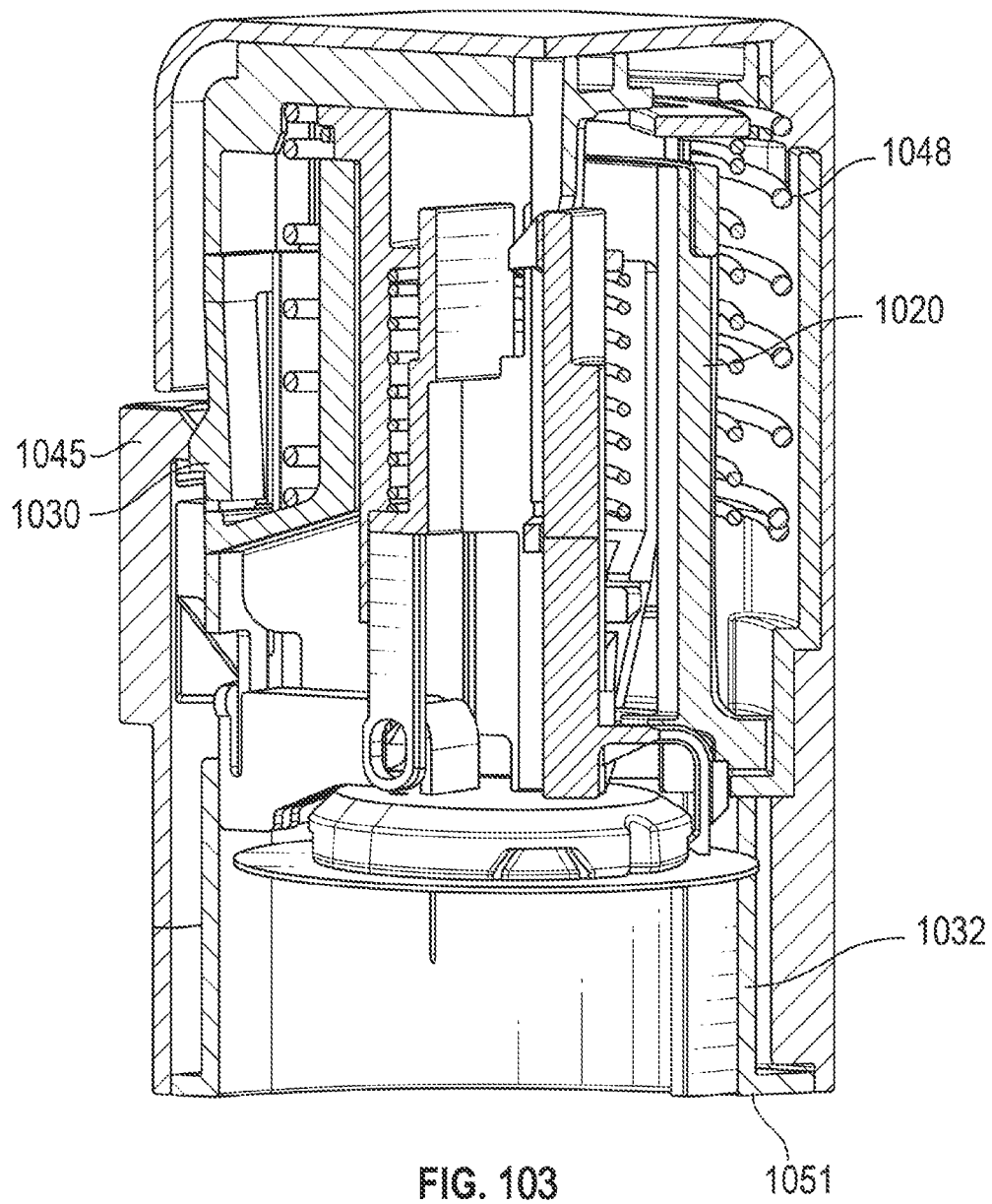
FIG. 103 illustrates a three quarters cross section perspective view of the applicator and the cartridge of FIG. 99.

FIG. 103 illustrates the bottom surface 1051 of the interior housing 1032 in contact with the individual's skin to overcome the bias of the biasing members 1040. In such a configuration, the position of the releasable coupler 1030 may be moved upwards to align with the control device 1045. As such, movement of the control device 1045 may result in the releasable coupler 1030 being pressed to release the insertion carriage 1020 from the interior housing 1032 and allow the driver 1048 to drive the carriages 1014, 1025, 1020 downward.

Figure 104:
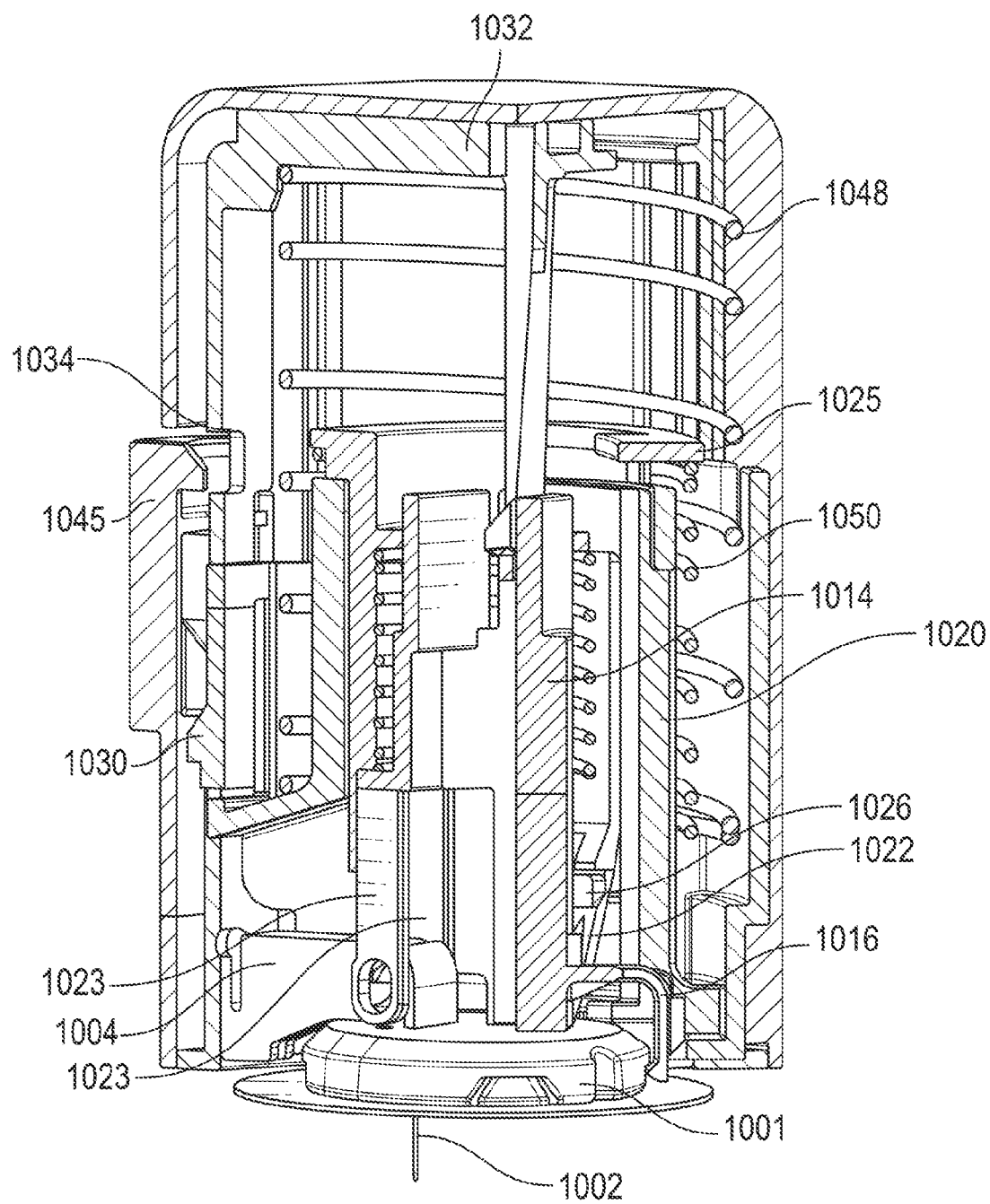
FIG. 104 illustrates a three quarters cross section perspective view of the applicator and the cartridge of FIG. 99.

FIG. 104, for example, illustrates the control device 1045 having been pressed to release the releasable coupler 1030 from the aperture 1034 of the interior housing 1032. The driver 1048 drives the carriages 1014, 1025, 1020 downward to press the needle 1002 into the individual's skin to deploy the transcutaneous analyte sensor into the individual's skin. The insertion carriage 1020 may remain coupled to the carriages 1014, 1025 by the releasable coupler 1022 remaining coupled to the support surfaces 1026.

At this point, the releasable coupler 1022 may move relative to the carriage 1014, and particularly the deflection surfaces 1018 of the carriage 1014 to push the releasable coupler 1022 outward away from the support surfaces 1026 and off of the support surfaces 1026. As such, the driver 1050 may drive the carriages 1014, 1025 upward relative to the insertion carriage 1020 and may pull the needle 1002 upward by way of the coupling of the coupling member 1006 of the needle cover 1004 with the releasable couplers 1023.

Figure 105:
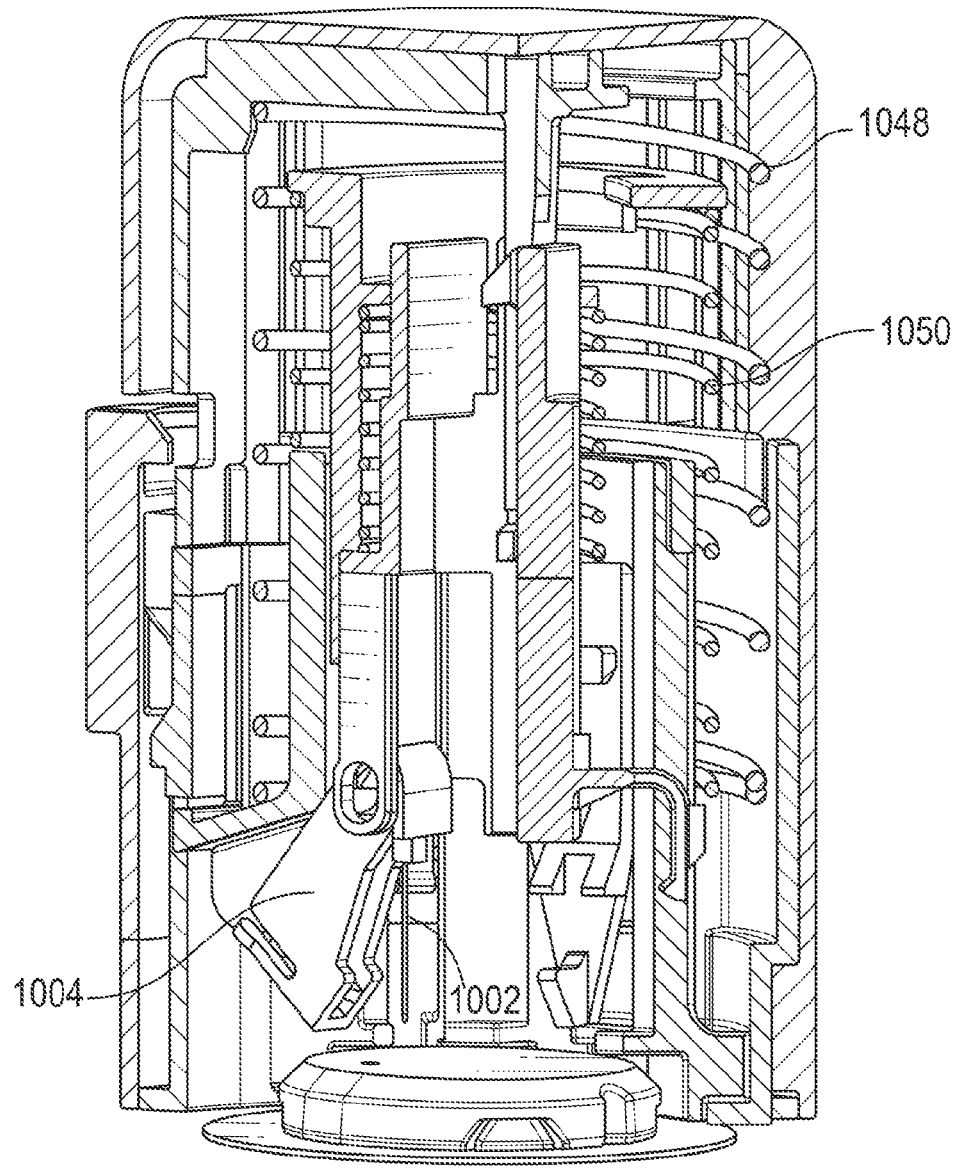
FIG. 105 illustrates a three quarters cross section perspective view of the applicator and the cartridge of FIG. 99.

FIG. 105, for example, illustrates the carriages 1014, 1025 being pressed upward by the driver 1050, and away from the insertion carriage 1020. The needle cover 1004 may contact the deflection surface 1046, such that the retraction actuator comprising the carriages 1014, 1025 and the driver 1050 rotates the needle 1002 into the needle cover 1004. The driver 1050 may slide the carriages 1014, 1025 relative to the applicator housing. The retraction actuator may retract the needle from the individual's skin following insertion of the transcutaneous analyte sensor into the individual's skin. The retraction actuator may be configured to automatically operate upon the needle inserting the transcutaneous analyte sensor into the individual's skin. The retraction actuator may position the needle 1002 into the needle cover 1004, and may rotate the needle 1002 into the needle cover 1004. The lock 1008 shown in FIG. 94 may lock the needle 1002 into the needle cover 1004.

Figure 106:
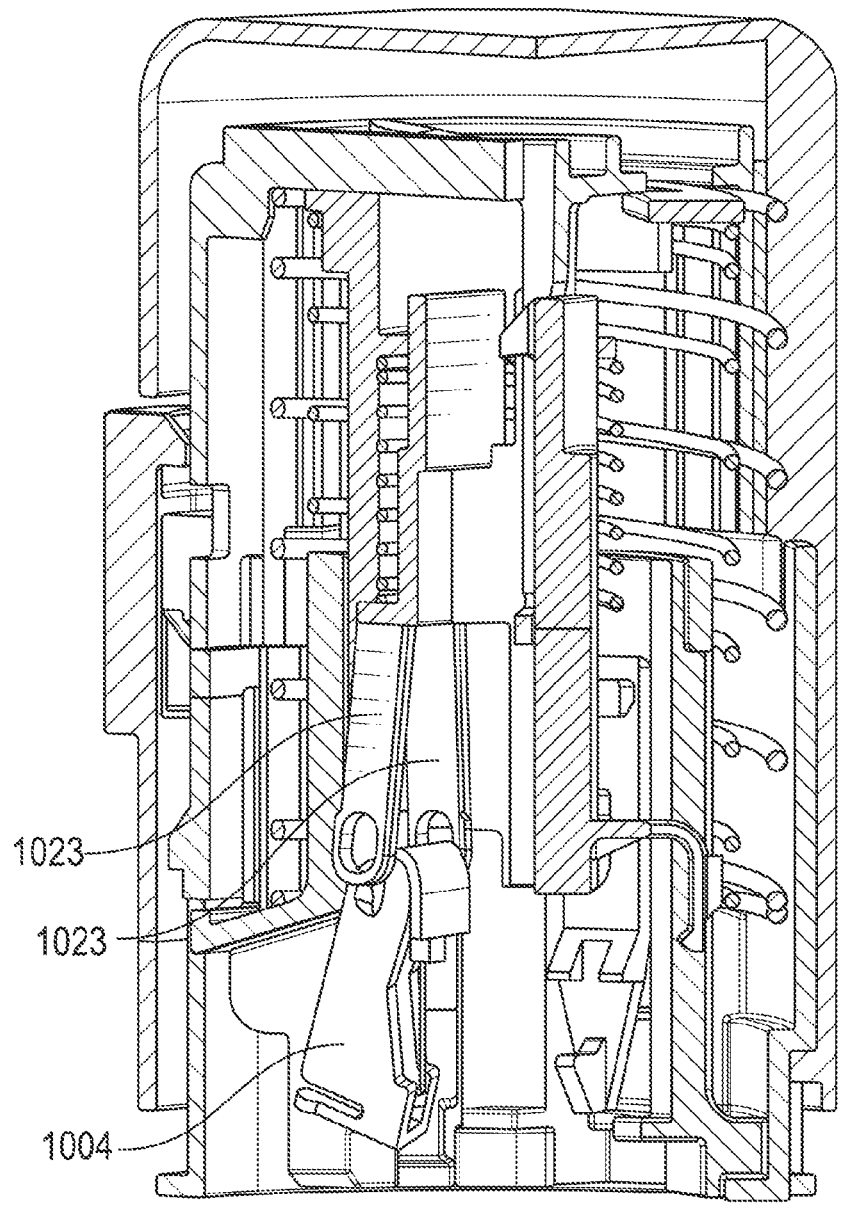
FIG. 106 illustrates a three quarters cross section perspective view of the applicator and the cartridge of FIG. 99.
Figure 107:
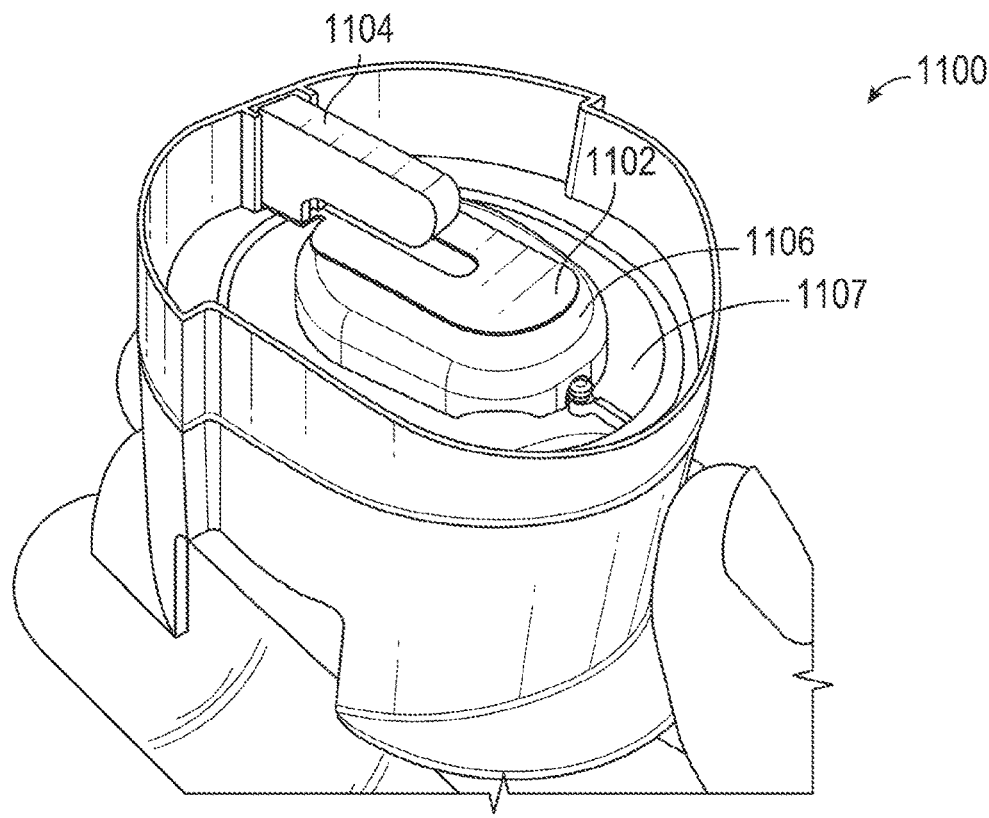
FIG. 107 illustrates a perspective view of a cartridge.
Figure 108:
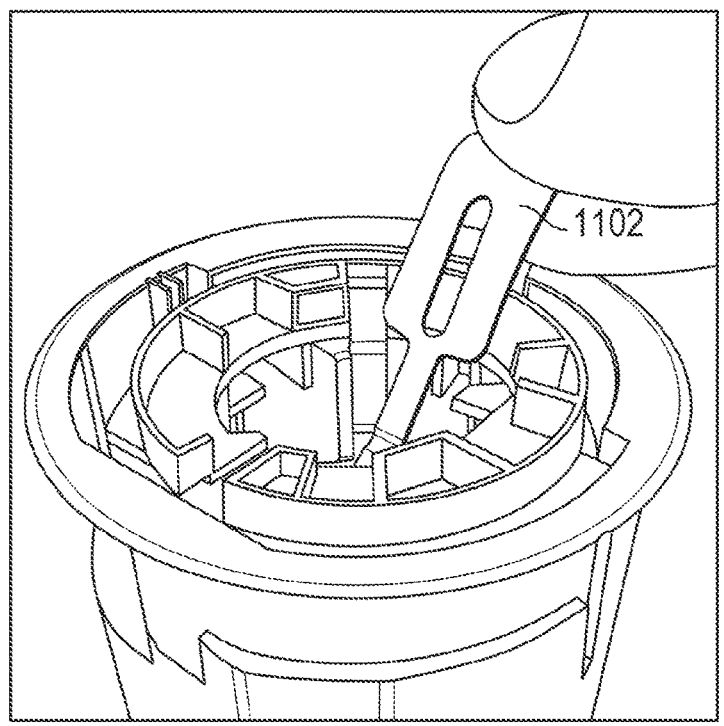
FIG. 108 illustrates a perspective view of a pull tab extending from an applicator.

Referring to FIG. 106, with the needle 1002 covered by the needle cover 1004, the unit of the needle 1002 and needle cover 1004 may be released from the releasable coupler 1023. The releasable coupler 1023 may release the needle 1002 positioned within the needle cover 1004 from the applicator housing. The needle 1002 may be separated from the applicator housing. The release may occur in a variety of manners. In embodiments, a pull tab as shown in FIGS. 107 and 108, for example, may be utilized to pull on the needle cover 1004 and release the needle 1002 from the releasable coupler 1023. In embodiments, a release actuator may be utilized, as disclosed herein. For example, a separate button may be utilized to release the unit of the needle 1002 and needle cover 1004 may be released from the releasable coupler 1023.

The embodiments disclosed in regard to FIGS. 93-106 may be varied and combined with other embodiments disclosed herein as desired.

FIG. 107 illustrates an embodiment of a cartridge 1100 that may include a pull tab 1102 that is configured to be pulled to release a needle from a releasable coupler. For example, the needle may be configured similarly as the needle 1002 shown in FIGS. 93-106, and the releasable coupler may be configured similarly as any of the releasable couplers for a needle disclosed herein. The needle, for example, may be positioned within a needle cover 1104 following insertion of the needle into an individual's skin. The pull tab 1102 may be pulled to release the needle from the releasable coupler of the applicator.

The pull tab 1102 may be positioned within the cartridge 1100 prior to insertion into the actuator, and may be packaged with the wearable housing 1106, the needle, a patch 1107, and a transcutaneous analyte sensor for implantation. The pull tab 1102, for example, may be positioned upon the wearable housing 1106 as shown in FIG. 107, or may be in another location such as surrounding the wearable housing 1106. The pull tab 1102 may be coupled to the needle cover 1104 or needle hub such that the pull tab 1102 descends from the needle cover 1104 with the needle positioned therein, and is accessible to be pulled to release the needle from a releasable coupler.

FIG. 108, for example, illustrates the pull tab 1102 after the needle has been inserted into the individual's skin. The pull tab 1102 is accessible for a user to grip (as shown) and pull to release the needle from the releasable coupler.

Any embodiment disclosed herein may utilize a pull tab.

Figure 109:
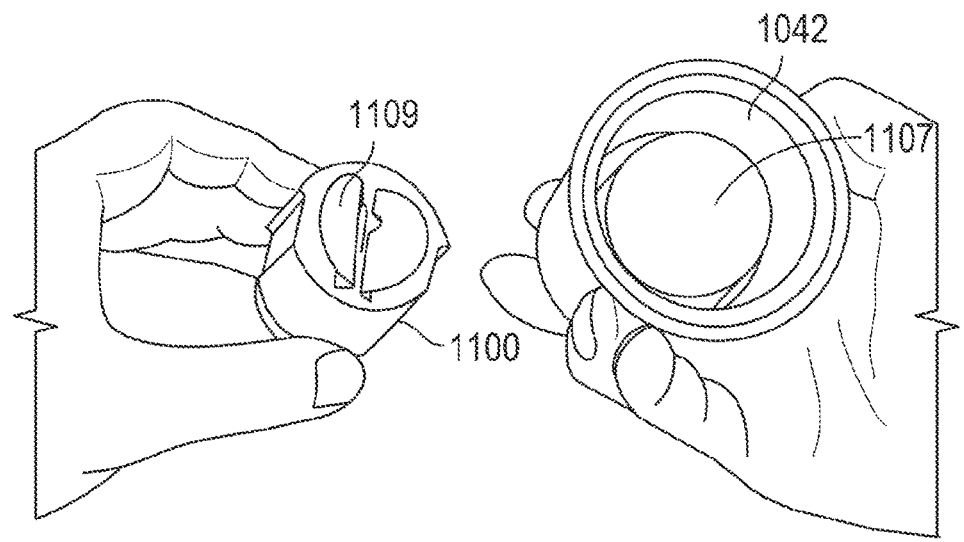
FIG. 109 illustrates a liner and cartridge being pulled from a patch.

The patch 1107 for the wearable housing 1106 may include a liner, and in embodiments, the cartridge 1100 may be coupled to the patch 1107 such that withdrawal of the cartridge from the wearable housing 1106 removes the liner from the patch 1107. FIG. 109 for example, illustrates such a configuration, including a liner 1109 that is coupled to the cartridge 1100. The liner 1109 may remain attached to the cartridge 1100 such that following withdrawal of the cartridge 1100 from the applicator and wearable housing 1106, the liner 1109 is removed from the patch 1107 along with the cartridge 1100. For example, a step as shown in FIG. 101 may result in the liner 1109 being removed. An adhesive layer of the patch 1107 may remain for application to the individual's skin.

Such a feature may reduce the number of application steps of the individual, as the liner 1109 would be automatically removed with the removal of the cartridge 1100 from the applicator. Any embodiment disclosed herein may utilize such a feature of a patch.

FIGS. 110-119 illustrate a variation of the embodiment of FIGS. 73-92. In the embodiment of FIGS. 110-119, a pull tab or the like may be utilized to release the used needle from the releasable coupler, although in some embodiments a release actuator, similar to other release actuators disclosed herein may be utilized.

Figure 110:
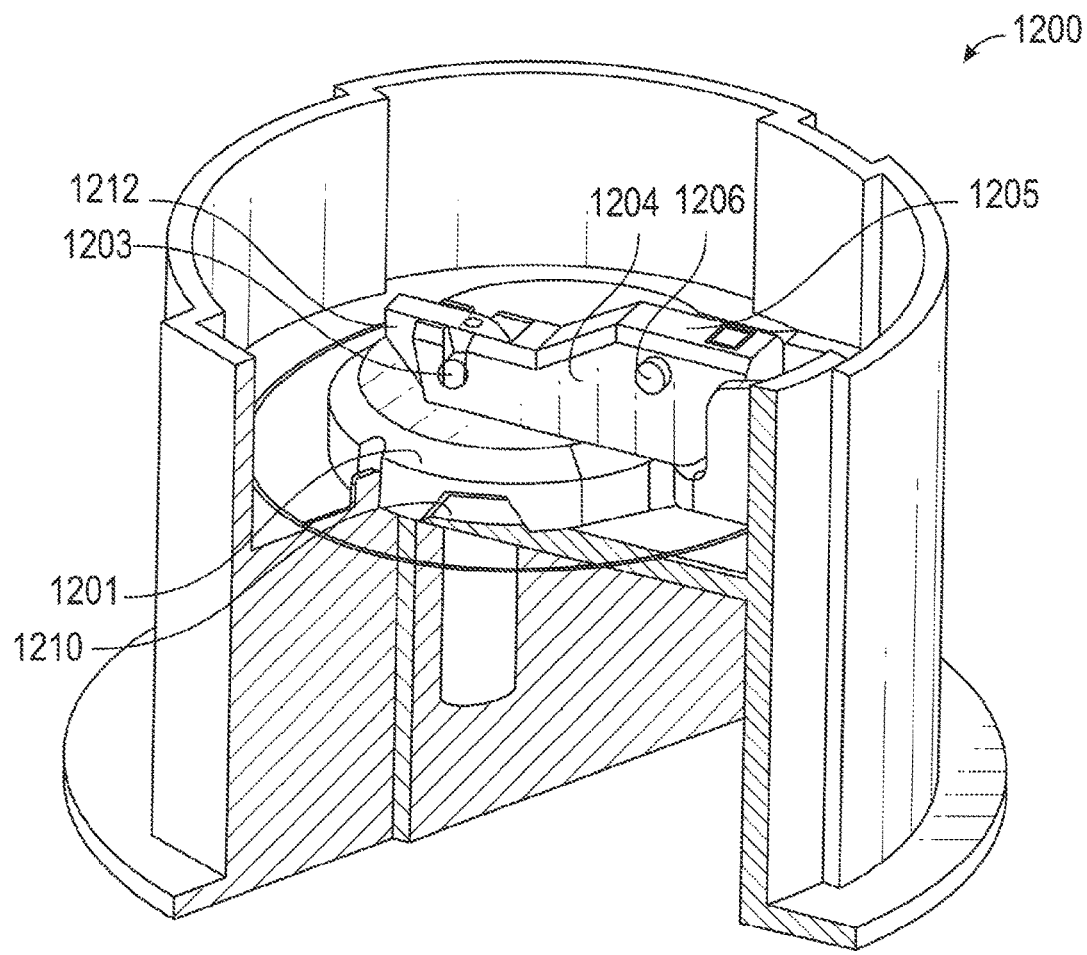
FIG. 110 illustrates a perspective view of a needle and needle cover positioned within a cartridge shown in three quarters cross section view.

Referring to FIG. 110, a perspective view of a cartridge 1200 that may be configured similarly as the cartridge 916 shown in FIG. 74. The cartridge 1200 may be configured to be inserted into an applicator housing and may retain a transcutaneous analyte sensor. The cartridge 1000 may include a body configured to be coupled to an applicator housing and may include a retainer retaining the transcutaneous analyte sensor and a wall extending around at least a portion of the transcutaneous analyte sensor. The wearable housing 1201, including the transcutaneous analyte sensor may be positioned within and retained by the cartridge 1200, as well as the needle 1202 (marked in FIG. 115) and the needle cover 1204. The needle 1202 may be coupled to the needle cover 1204 at a pivot 1203. A coupling member 1206 may be positioned spaced from the pivot 1203 for engagement with a releasable coupler of an applicator. The coupling member 1206 may comprise protrusions that extend outward from the body of the needle cover 1204.

The needle cover 1204 may include a lock that may be configured similarly as the lock shown in FIG. 94 and may be configured to lock the needle 1202 in position within the needle cover 1204 upon rotation of the needle cover 1204 relative to the needle 1202. The needle cover 1204 may further include a contact surface 1205 that may be contacted to cause the needle cover 1204 to pivot about the coupling member 1206. The needle cover 1204 may be configured to rotate relative to the needle 1202 to extend over at least the portion of the needle 1202. The needle cover 1204 may be configured to cover at least a portion of the needle 1202 following the needle 1202 guiding the transcutaneous analyte sensor into the skin of an individual.

The wearable housing 1201 may include indentations 1210 for engagement with a releasable coupler of an actuator, for retaining the wearable housing 1201 to the releasable coupler upon the cartridge 1200 being removed from an applicator.

The needle 1202 extends at an angle (e.g., a perpendicular angle) with respect to the needle cover 1204. The needle hub 1212 coupled to the proximal portion of the needle 1202 may include the lock and may be configured to rotate relative to the needle cover 1204.

FIG. 111 illustrates a perspective view of a first carriage 1214 that may be an insertion carriage configured to drive the needle 1202 downward to insert the needle 1202 into the individual's skin. The first carriage 1214 may comprise a component of an actuator or insertion actuator that may be coupled to the applicator housing and configured to insert a needle and the transcutaneous analyte sensor into the individual's skin. The first carriage 1214 may be configured to slide relative to the applicator housing and configured to be slid by the driver 1237.

The carriage 1214 may include releasable couplers 1216 that engage the coupling member 1206 to drive the needle 1212 downward and allow the needle cover 1204 to pivot with respect to the releasable couplers 1216. The carriage 1214 may further include a central channel 1218 for supports to extend through. The central channel 1218 may run through a central shaft 1219. The first carriage 1214 may further include a deflection surface 1217 configured to deflect the needle cover 1204 about the pivot 1203 and into the needle cover 1204.

One or more of the releasable couplers 1216 may be configured to retain a needle to the applicator housing following insertion of the transcutaneous analyte sensor into the individual's skin and removal of the applicator housing from the transcutaneous analyte sensor, and release the needle from within the applicator housing following insertion of the transcutaneous analyte sensor into the individual's skin. The one or more releasable couplers 1216 may be configured to couple to a needle hub 1212 of the needle.

The first carriage 1214 may further include releasable couplers 1213 for engaging the indentations 1210 on the wearable housing 1201.

FIG. 112 illustrates a perspective view of a second carriage 1220 that may be a retraction carriage configured to retract the needle 1202 from the individual's skin. The second carriage 1220 may include a releasable coupler 1222 and a pressing or contact surface 1224 configured to press against the needle cover 1204 to retract the needle 1202. The second carriage 1220 may comprise a portion of a retraction actuator for retracting the needle 1202 and rotating the needle 1202 into the needle cover 1204. The retraction actuator may retract the needle 1202 from the individual's skin following insertion of the transcutaneous analyte sensor into the individual's skin.

The second carriage 1220 may further include a central channel 1226 for the central shaft 1219 to pass through. The releasable coupler 1222 may be configured to couple to a portion of the applicator housing to retain the carriages 1220, 1214 in position. The releasable coupler 1222 may be configured to be pressed to release the carriage 1220. The second carriage 1220 may include a cavity 1228 for the first carriage 1214 to be positioned in.

Figure 113:
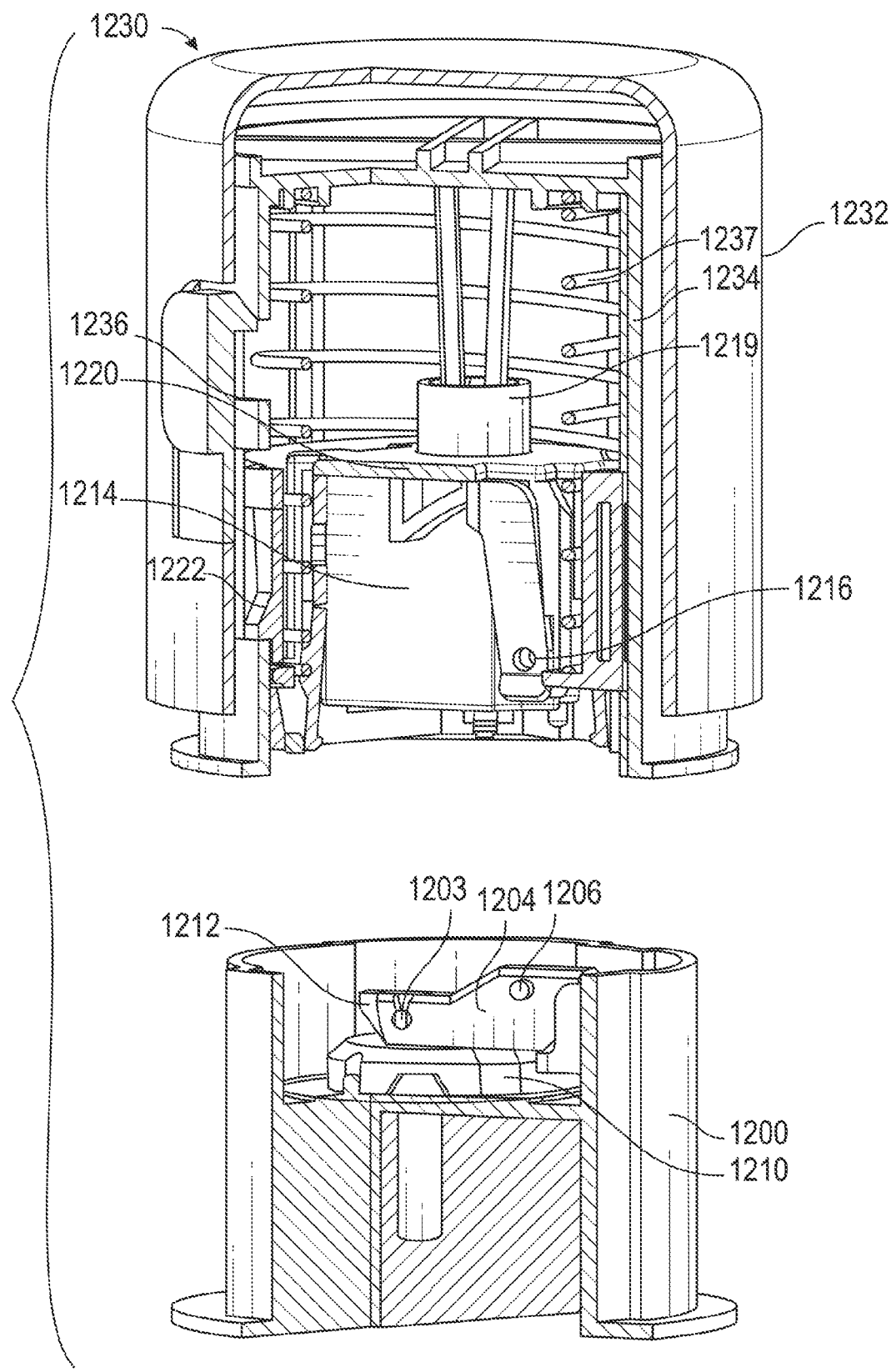
FIG. 113 illustrates a three quarters cross section perspective view of the cartridge of FIG. 110 and an applicator.

FIG. 113, for example, illustrates a three-quarters cross sectional perspective view of an assembly of the carriages 1220, 1214 within the housing of the applicator 1230. The applicator 1230 may include an applicator housing having an outer housing 1232 and an interior housing 1234, with the interior housing 1234 configured to slide relative to the outer housing 1232, similar to the embodiment shown in FIGS. 93-106. The applicator housing may be configured to be gripped by an individual to apply the transcutaneous analyte sensor into the individual's skin. The applicator housing may include a side portion, a top portion and a bottom portion including an opening for the transcutaneous analyte sensor to be deployed from to be inserted into the individual's skin. The receiver of the applicator housing may be configured to receive the cartridge 1000 through the opening of the bottom portion.

The interior housing 1234 for example, may be biased to extend downward relative to the outer housing 1232 as discussed regarding the biasing members 1040 (which may comprise springs or the like). The interior housing 1234 may include an aperture 1236 for engaging with the releasable coupler 1222.

The outer housing 1232 may include a control device 1221 configured to be actuated to insert the needle 1202 and operated by an individual.

The carriages 1220, 1214 may be positioned within the cavity of the interior housing 1234. The carriage 1214 may be positioned within the central cavity of the carriage 1220.

A driver 1237, which may comprise a spring, may be positioned to drive the carriages 1220, 1214 downward to insert the needle and the transcutaneous analyte sensor into the individual's skin. A driver 1238 (marked in FIG. 115), which may comprise a spring, may be positioned to bias the carriages 1220, 1214 away from each other.

FIGS. 113-119 illustrate steps of a method that may utilize the applicator 1230. In the initial configuration, the interior housing 1234 may be biased downward with respect to the outer housing 1232 via biasing members. Further, the releasable coupler 1222 may be disengaged with the aperture 1236, and the driver 1237 may drive the carriage 1220 to be positioned downward at this point.

Figure 114:
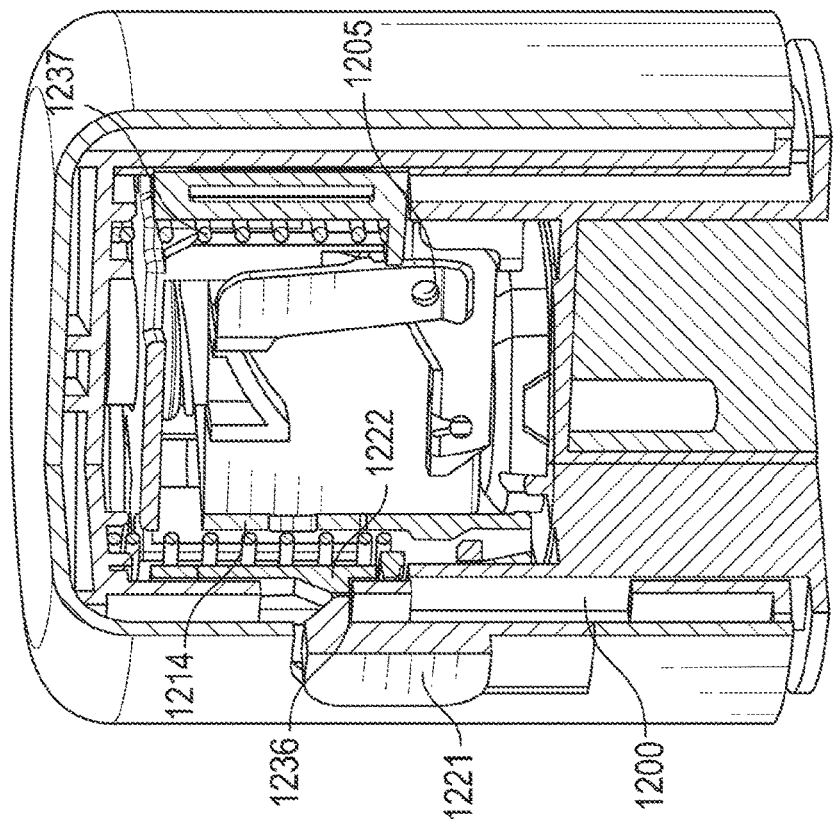
FIG. 114 illustrates a three quarters cross section perspective view of the cartridge of FIG. 110 and an applicator of FIG. 113.

The cartridge 1200 may be inserted into the receiver of the applicator 1230 by being inserted into the receiver. Upon insertion, a configuration as shown in FIG. 114 may result. The cartridge 1200 may be inserted into the applicator housing to provide energy to the insertion actuator. The force applied by the cartridge 1200 to the actuator may provide energy to the actuator. The insertion of the cartridge 1200 may provide energy to the driver 1237. In an embodiment in which the driver 1237 comprises a spring, the insertion of the cartridge into the receiver may compress the spring.

The cartridge 1200 may be inserted to contact the contact surface 1224 of the carriage 1220 and drive the carriages 1220, 1214 upward. The cartridge 1200 may include a pressing surface for pressing against the insertion actuator for providing energy to the actuator. The driver 1237 may be compressed. The releasable coupler 1222 may move to engage the aperture 1236 of the interior housing 1234. The releasable couplers 1216 of the carriage 1214 may engage the coupling members 1206 of the needle 1202.

The releasable couplers 1213 may further engage the indentations 1210 on the housing 1201 to retain the housing 1201 when cartridge 1200 is withdrawn.

The cartridge 1200 may be removed from the applicator housing prior to the needle being inserted into the individual's skin to guide the transcutaneous analyte sensor into the individual's skin.

Figure 115:
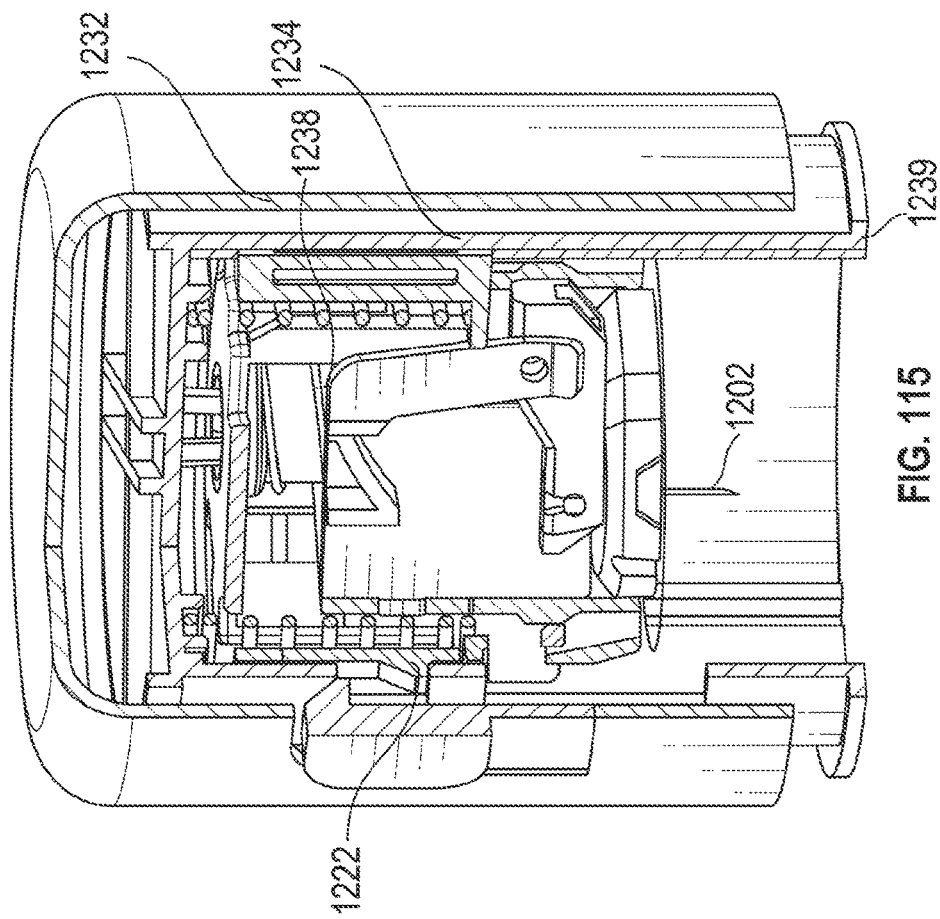
FIG. 115 illustrates a three quarters cross section perspective view of the applicator of FIG. 113.

With the cartridge 1200 withdrawn, the applicator 1230 may have a configuration as shown in FIG. 115. The interior housing 1234 may continue to be biased downward away from the top of the outer housing 1232. In such a configuration, the releasable coupler 1222 of the carriage 1220 may be offset from the position of the control device 1221, such that pressing the control device 1221 does not actuate insertion of the needle 1202. Such a feature may serve as a safety feature to reduce the possibility of inadvertent actuation of the needle 1202 prior to a desired time (at which the bottom surface 1239 of the interior housing 1234 does not yet contact the individual's skin).

Figure 116:
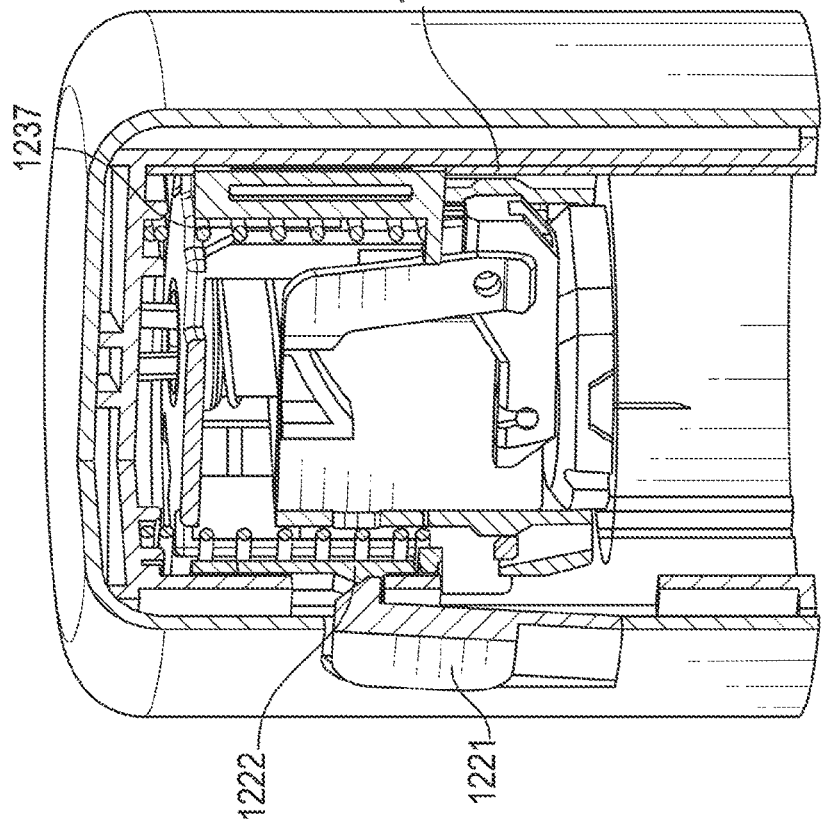
FIG. 116 illustrates a three quarters cross section perspective view of the applicator of FIG. 113.

FIG. 116 illustrates the bottom surface 1239 of the interior housing 1234 in contact with the individual's skin to overcome the bias of the biasing members. In such a configuration, the position of the releasable coupler 1222 may be moved upwards to align with the control device 1221. As such, movement of the control device 1221 may result in the releasable coupler 1222 being pressed to release the carriages 1220, 1214 from the interior housing 1234 and allow the driver 1237 to drive the carriages 1220, 1214 downward.

Figure 117:
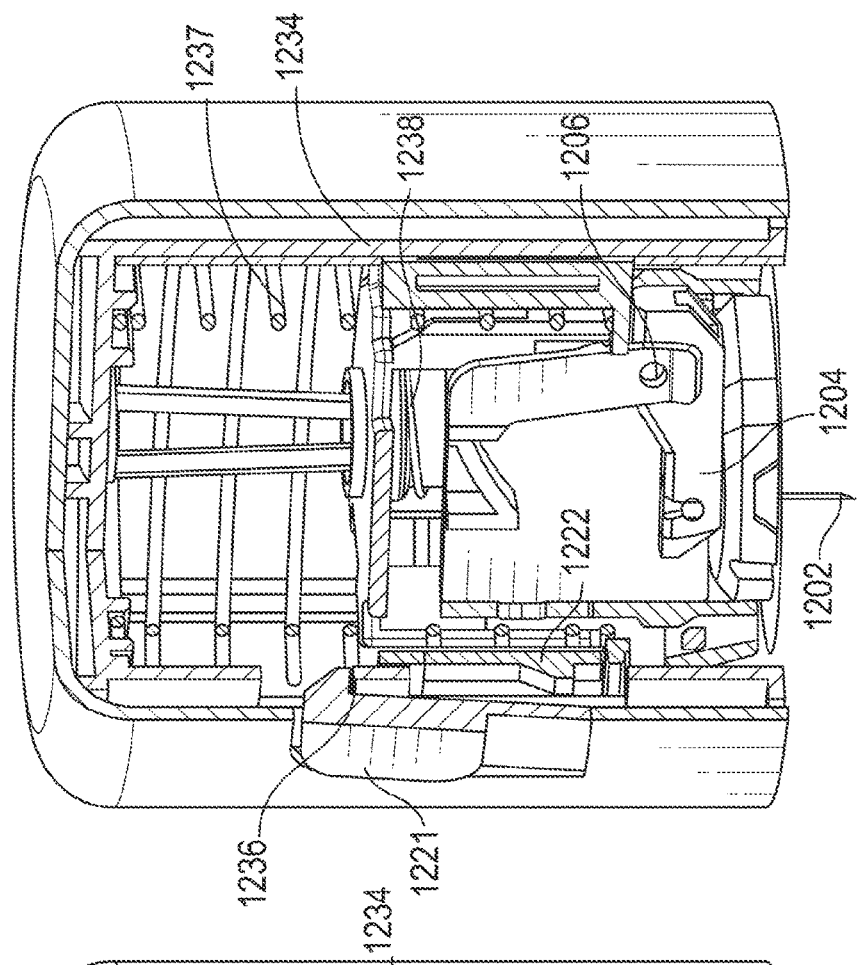
FIG. 117 illustrates a three quarters cross section perspective view of the applicator of FIG. 113.

FIG. 117, for example, illustrates the control device 1221 having been pressed to release the releasable coupler 1222 from the aperture 1236 of the interior housing 1234. The driver 1237 drives the carriages 1220, 1214 downward to press the needle 1202 into the individual's skin to deploy the transcutaneous analyte sensor into the individual's skin.

At this point, the second carriage or retraction carriage 1220 may continue to be driven downward by the driver 1237. The second carriage or retraction carriage 1220 may move downward relative to the first carriage or the insertion carriage 1214. The force of the driver 1237 may overcome the biasing force of the driver 1238. The contact surface 1224 shown in FIG. 112 for example, may press against the contact surface 1205 of the needle cover 1204 shown in FIG. 110, to cause the needle cover 1204 to rotate. As such, the second carriage 1220 may serve as a retraction actuator configured to rotate the needle 1202 into the needle cover 1204. The needle cover 1204 may pivot about the coupling member 1206 and withdraw the needle 1202 from the individual's skin. The retraction actuator may be configured to automatically operate upon the needle 1202 inserting the transcutaneous analyte sensor into the individual's skin.

Figure 118:
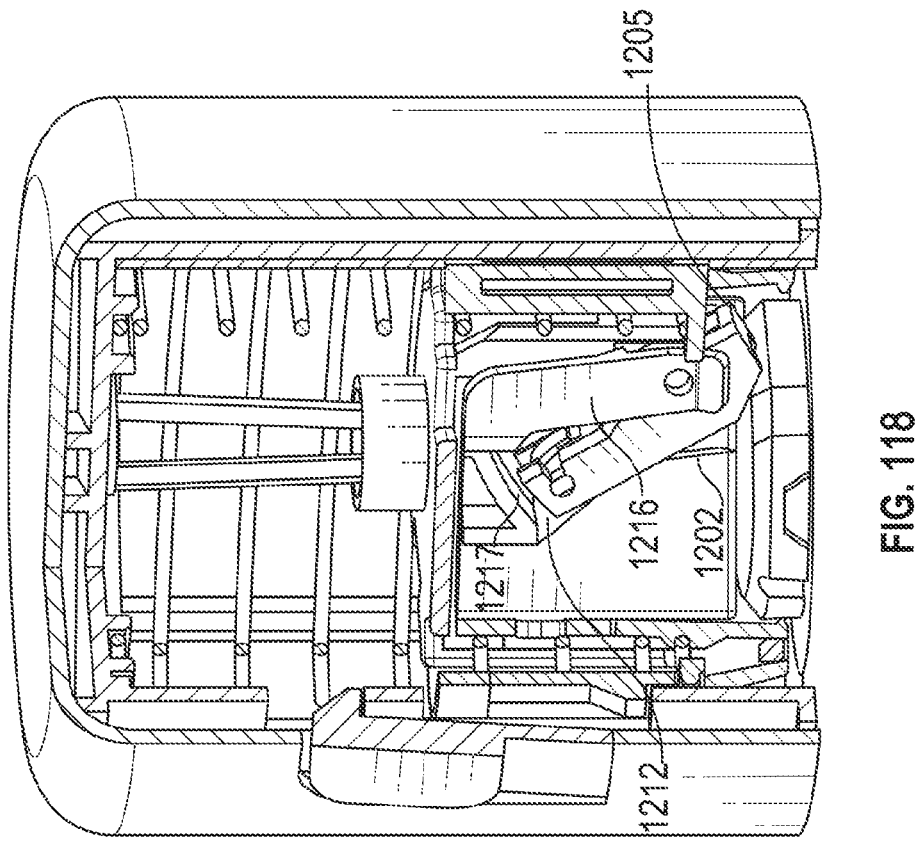
FIG. 118 illustrates a three quarters cross section perspective view of the applicator of FIG. 113.

The needle cover 1204 may pivot and contact the deflection surface 1217, to contact the needle hub 1212 and lock the needle 1202 into the needle cover 1204. FIG. 118, for example, illustrates the needle 1202 being rotated into the needle cover 1204 due to the contact with the contact surface 1205 of the needle cover 1204 and the contact of the needle hub 1212 with the deflection surface 1217. The retraction actuator may position the needle 1202 into the needle cover 1204 and rotate the needle 1202 into the needle cover 1204.

Figure 119:
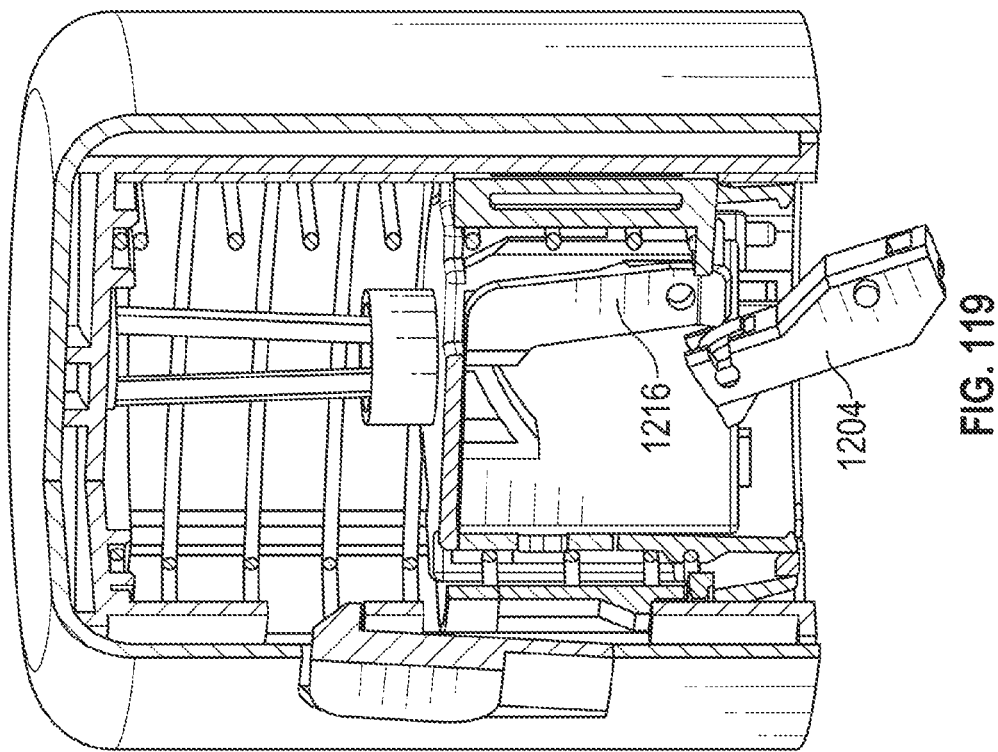

With the needle 1202 covered by the needle cover 1204, the unit of the needle 1202 and needle cover 1204 may be released from the releasable coupler 1216. The releasable coupler 1216 configured to retain the needle 1202 may be configured to release the needle 1202 positioned within the needle cover 1204 from the applicator housing. The needle 1202 may be separated from the applicator housing. The release may occur in a variety of manners. In embodiments, a pull tab as shown in FIGS. 107 and 108, for example, may be utilized to pull on the needle cover 1204 and release the needle 1202 from the releasable coupler 1216. In embodiments, a release actuator may be utilized, as disclosed herein. For example, a separate button may be utilized to release the unit of the needle 1202 and needle cover 1204 may be released from the releasable coupler 1223. FIG. 119, for example, illustrates the release of the unit of the needle 1202 and needle cover 1204 may be released from the releasable coupler 1216.

The embodiments disclosed in regard to FIGS. 110-119 may be varied and combined with other embodiments disclosed herein as desired.

Figure 120:
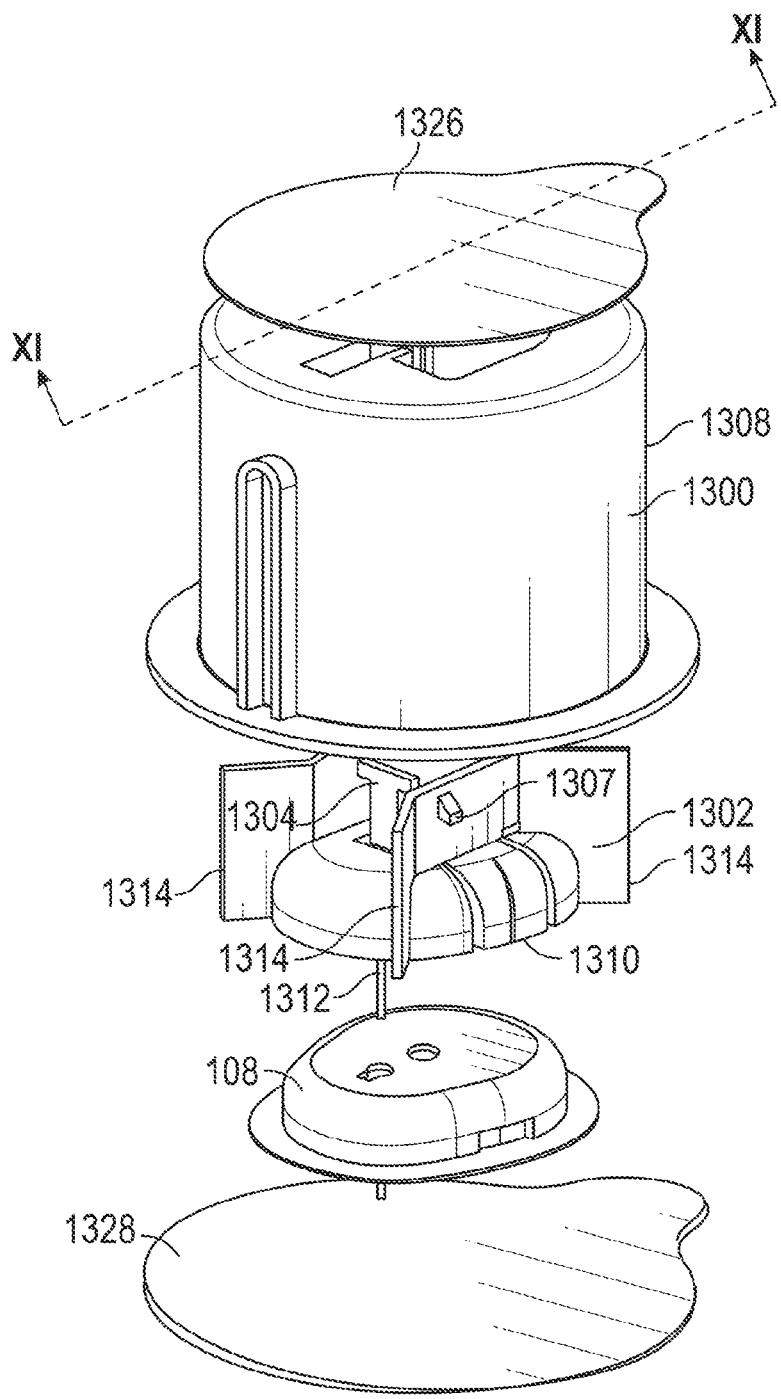

FIG. 120 illustrates an embodiment of a cartridge 1300 that may be configured similarly as the cartridge 300 shown in FIG. 30, yet may include a needle hub 1302 that includes a releasable coupler 1304 that is configured to couple to a coupling member 1306 (marked in FIG. 122) of the body 1308 of the cartridge 1300. The needle hub 1302 may further include coupling members 1307 configured to engage a releasable coupler 1309 of the retraction actuator (marked in FIG. 125). The needle hub 1302 may include a housing 1310 that is configured to extend over the wearable housing 108 of the on-skin sensor assembly. The cartridge 1300 may be utilized in a system for inserting a transcutaneous analyte sensor into an individual's skin.

Figure 121:
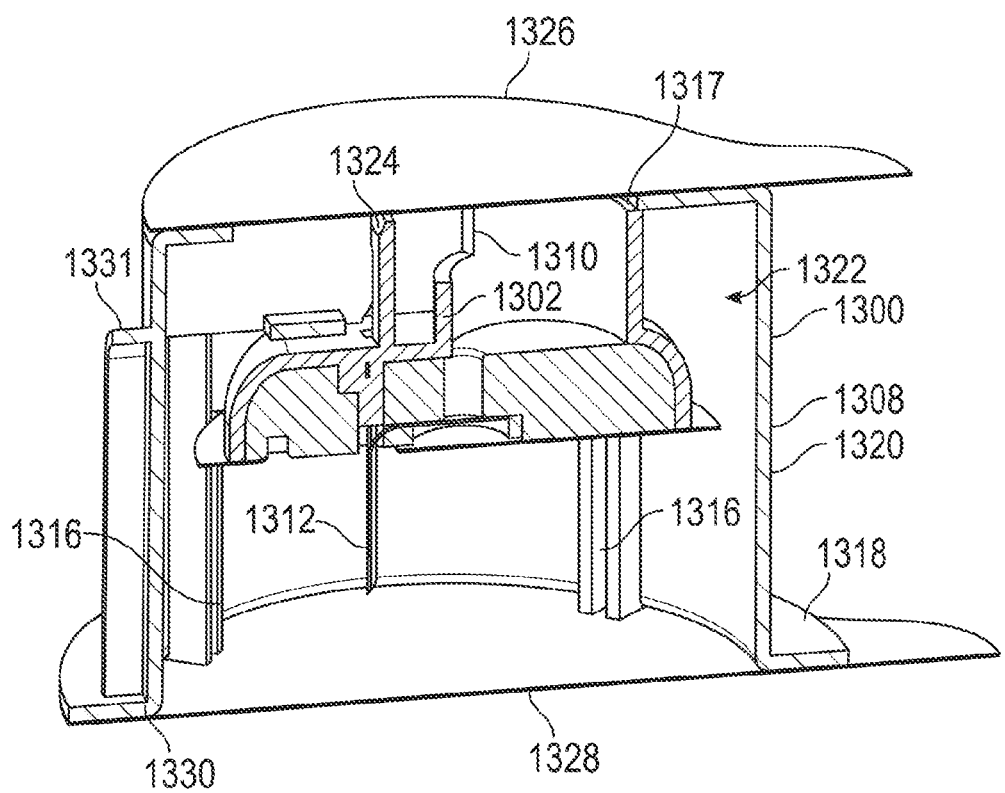

Referring to FIGS. 120 and 121, a needle 1312 may have a proximal end coupled to the needle hub housing 1310 and may extend from the needle hub housing 1310. The needle hub housing 1310 may include rails 1314 that extend outward from the needle hub housing 1310. The rails 1314 may be configured to slide along channels 1316 on the inner surface of the cartridge body 1308 to guide the needle hub 1302 as it slides axially relative to the cartridge body 1308. The needle hub 1302 may include an opening 1317 configured to receive a carriage of the insertion actuator.

Referring to FIG. 121, the cartridge 1300 may include a body 1308 having a base 1318 and a wall 1320. The base 1318 may form a bottom of the cartridge 1300 that the cartridge 1300 may be positioned upon. The base 1318 may form a flange extending outward from the wall 1320. The wall 1320 may extend upward from the base 1318, transverse to a direction that the base 1318 extends in. The wall 1320 may extend around and define a cavity 1322 that may receive components of the cartridge including the transcutaneous analyte sensor 24 and the needle 1312. The wall 1320 may extend upward to an upper opening 1324 that exposes the components retained by the body 1308. The wall 1320 may including an inner surface configured to face inward towards a central portion of the cartridge 1300 and the transcutaneous analyte sensor 24 and an outer surface facing opposite the inner surface. The outer surface of the wall may be configured to be positioned within at least a portion of an applicator. The outer surface of the wall may comprise a mating surface for a receiver of the applicator, and may be contoured to a shape of an inner surface of the receiver. The wall 1320 may be shaped similarly as the wall 146 discussed in regard to the cartridge 104 shown in FIG. 5.

The cartridge 1300 may include an upper removable cover 1326 that operates similarly as the cover 324 shown in FIG. 30. The upper removable cover 1326 may cover the upper opening 1324 of the cartridge 1300. The cartridge 1300 may include a lower removable cover 1328. The lower removable cover 1328 may be coupled to the base 1318 of the cartridge 1300 and may cover a lower opening 1330 of the cartridge 1300. The transcutaneous analyte sensor system 24 and the on-skin sensor assembly 12 may be configured to be deployed through the lower opening 1330 of the cartridge. The lower removable cover 1328 may be configured similarly as the upper removable cover 1326.

The body 1308 of the cartridge 1300 may include a protrusion 1331 that is configured to align with a channel of the applicator housing to align the cartridge 1300 with the receiver of the applicator housing.

Figure 122:
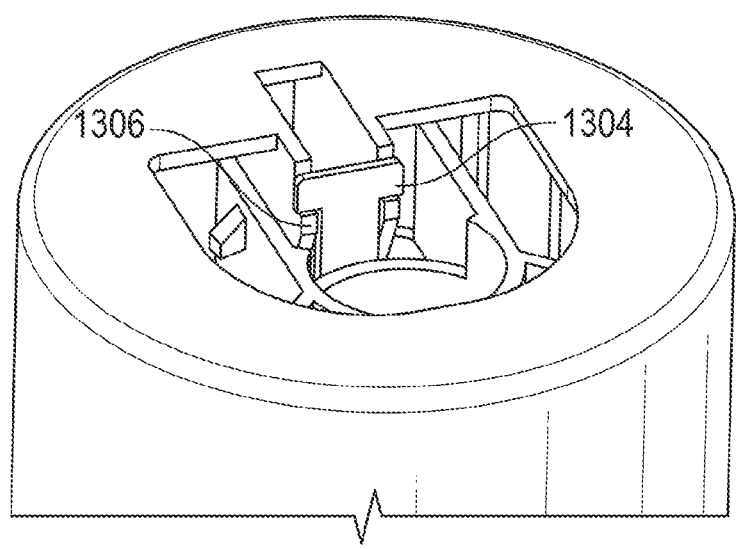

FIG. 122 illustrates a top perspective view of the cartridge 1300 with the releasable coupler 1304 shown coupled to the coupling member 1306.

The cartridge 1300 may be utilized with an applicator 1332 as shown in an exploded view in FIG. 123. The applicator 1332 comprises a transcutaneous analyte sensor applicator, and is configured to apply other components of the transcutaneous analyte sensor system to the skin of an individual including the wearable housing 108 and patch 106 of the transcutaneous analyte sensor system. The applicator may deploy all or a portion of components of an on-skin sensor assembly 12 to an individual's skin.

The applicator 1332 comprises a reusable applicator, and may provide reusable functionality in a similar manner as the applicator 102.

FIG. 123 illustrates components of the applicator 1332. The applicator 1332 may include an applicator housing 1334, which may comprise a single component or multiple components, similar to the housing of the applicator 102. As shown in FIG. 123, the applicator housing 1334 may include a side cover body 1336, a lower body 1338, and an upper cap 1340. The components of the applicator housing 1334 may be coupled together to form a single applicator housing 1334.

The applicator housing 1334 may be configured to be gripped by an individual to apply the transcutaneous analyte sensor into the individual's skin, to be held during deployment of the transcutaneous analyte sensor, as well as other components of a transcutaneous analyte sensor system. The applicator housing 1334 may have a cylindrical shape with an outer surface configured to be gripped by an individual. Other shapes of the applicator housing 1334 may be utilized as desired.

Figure 127:
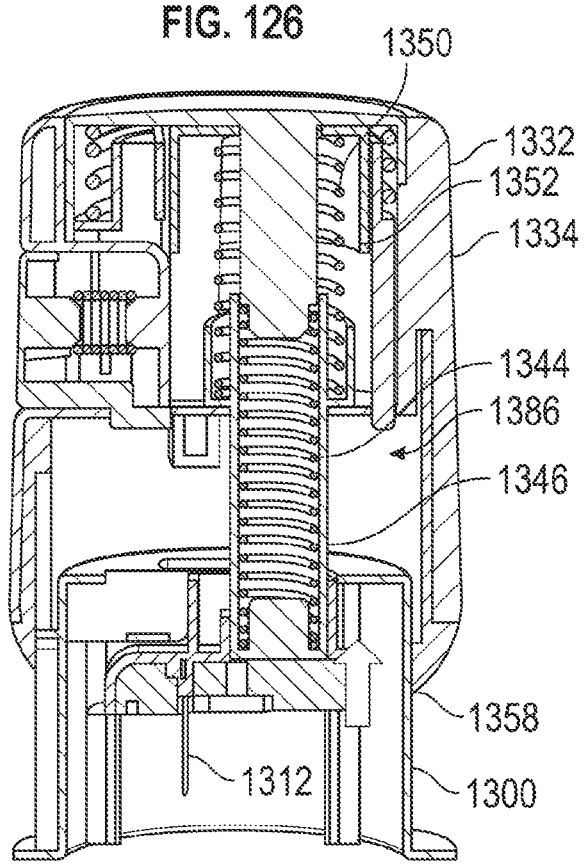

The applicator housing 1334 may include a side portion (formed by the side cover body 1336), a top portion (formed by the upper cap 1340) and a bottom portion including an opening 1358 shown in FIG. 127 for the transcutaneous analyte sensor to be deployed from to be inserted into the individual's skin. The opening 1358 may be configured for the needle 1312 and the transcutaneous analyte sensor 24 to pass through to insert the transcutaneous analyte sensor 24 into the individual's skin.

FIG. 123 illustrates other components of the applicator 1332. The components may include an actuator that may be coupled to the applicator housing 1334 and that is configured to insert the needle 1312 into the individual's skin to deposit the transcutaneous analyte sensor 24 into the individual's skin. Such an actuator may be referred to as an insertion actuator. The insertion actuator may include components that may include a control device 1342 and a driver 1344, and may include a carriage 1346. The insertion actuator may include other components (or fewer components) in other embodiments. The insertion actuator may be configured to insert the needle 1312 into the individual's skin with the cartridge 1300 positioned in the receiver 1386 of the applicator housing and remaining coupled to the applicator housing 1334. An individual may leave the cartridge 1300 in the receiver during insertion of the needle and transcutaneous analyte sensor 24. The receiver 1386 may be configured to release the cartridge 1300 from the applicator housing.

Figure 125:
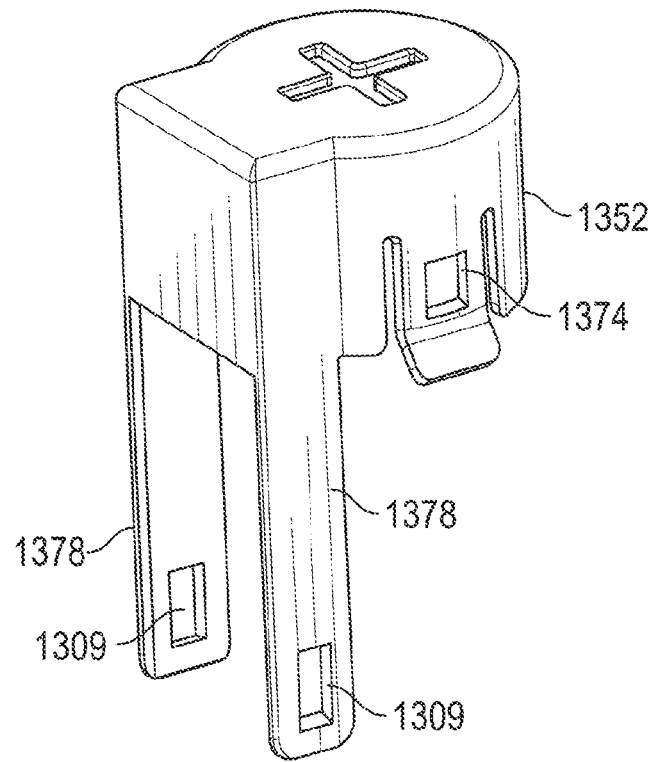

The applicator 1332 may include a release actuator that is configured to release the needle 1312 from a releasable coupler 1309 shown in FIG. 125. The release actuator may include components that may include the control device 1342 and may include a pressing surface 1348 (marked in FIG. 126) that is configured to apply a force to a releasable coupler to cause the needle 1312 to release from the releasable coupler 1309. The releasable coupler 1309 may be configured to retain the needle 1312 at least partially within the applicator housing 1334 following insertion of the transcutaneous analyte sensor 24 into the individual's skin and removal of the applicator housing 1334 from the transcutaneous analyte sensor 24, and configured to release the needle 1312 from within the applicator housing 1334 following insertion of the transcutaneous analyte sensor 24 into the individual's skin. The release actuator may include other components (or fewer components) in other embodiments.

The applicator 1332 may include a retraction actuator that is configured to retract the needle 1312 from the individual's skin following insertion of the transcutaneous analyte sensor into the individual's skin. The retraction actuator may include components that may include a driver 1350 and a carriage 1352. The retraction actuator may include other components (or fewer components) in other embodiments.

The applicator 1332 may further comprise a biasing carriage 1354 including a biasing surface 1356 configured to bias the cartridge 1300 towards a lower opening 1358 of the applicator 1332. The biasing carriage 1354 may be biased towards the lower opening 1358 of the applicator 1332 by way of a biasing spring 1360 that presses against a surface 1361 of the biasing carriage 1354. The biasing carriage 1354 may include stops 1362 that may be configured to impede movement of the control device 1342.

Figure 124:
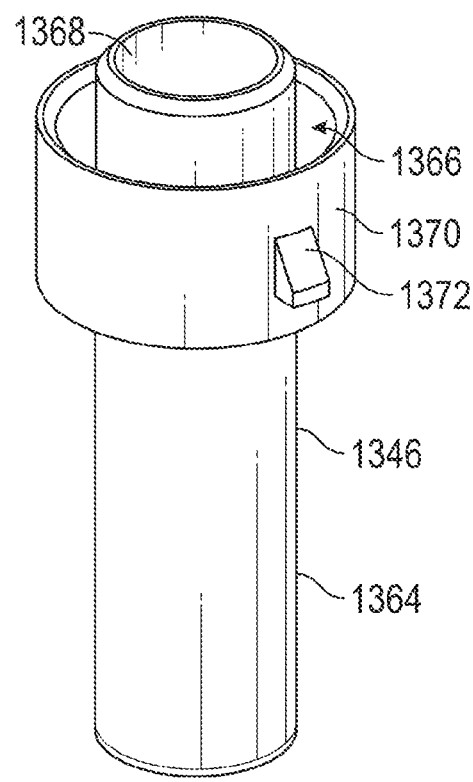

FIG. 124 illustrates a perspective view of the carriage 1346 of the insertion actuator. The carriage 1346 may comprise a body configured to slide within an interior cavity of the applicator 1332 that may be defined by the applicator housing 1334. The carriage 1346 may be configured to slide relative to the applicator housing and be configured to be slid by the driver 1344. The carriage 1346 may include a pressing body 1364 that may be in the shape of a column and is configured to press against the needle hub 1302 shown in FIG. 121. The pressing body 1364 may be configured to enter the opening 1317 of the needle hub 1302. An upper portion of the carriage 1346 may include a channel 1366 that is configured to receive the driver 1350 of the retraction actuator. The upper portion of the carriage 1346 may include an opening 1368 that is configured to receive the driver 1344 of the insertion actuator.

An outer surface 1370 of the upper portion of the carriage 1346 may include coupling members 1372 configured to couple to releasable couplers 1374 of the carriage 1352 of the retraction actuator. The coupling members 1372 may be in the form of protrusions or another form of coupling member.

FIG. 125 illustrates a perspective view of the carriage 1352 of the retraction actuator. The carriage 1352 may be configured to slide relative to the applicator housing and be configured to be slid by the driver 1350. The driver 1350 may be configured to drive the needle 1312 out of the individual's skin. The carriage 1352 may include releasable couplers 1374 for coupling to the coupling members 1372 of the carriage 1346 of the insertion actuator. The releasable couplers 1374 may comprise deflectable arms configured to extend over the coupling members 1372 to engage with the coupling members 1372. The releasable couplers 1374 may be configured to automatically release from the coupling members 1372 of the carriage 1346 upon contact with a coupler release in the form of deflectors 1376 of the applicator housing, as shown in FIG. 132. The retraction actuator accordingly may be configured to automatically operate upon the needle 1312 inserting the transcutaneous analyte sensor into the individual's skin.

The carriage 1352 may include a releasable coupler 1309 that is configured to releasably couple to the needle 1312. The releasable coupler 1309 may include openings that are configured to engage the coupling members 1307 of the needle hub 1302 to releasably couple to the needle 1312. The openings of the releasable coupler 1309 may be movable upon a coupler release in the form of pressing surface 1348 of the control device 1342 (marked in FIG. 126) pressing upon arms 1378 of the releasable coupler 1309.

Figure 126:
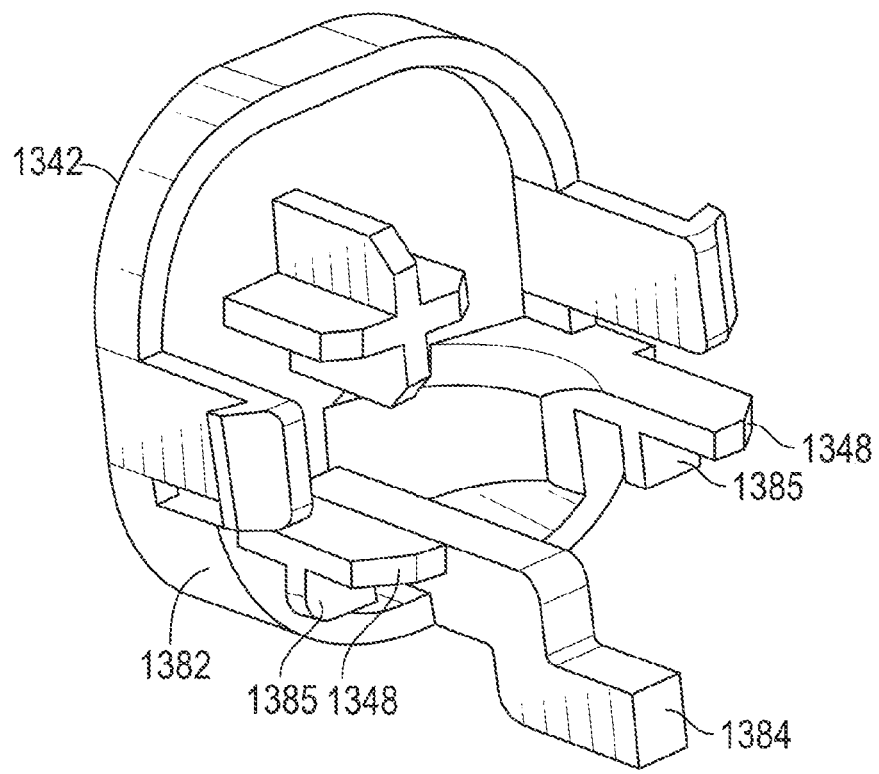

FIG. 126 illustrates a perspective view of the control device 1342 of both the insertion actuator and the release actuator. The control device 1342 may comprise a button that may be pressed or another body that may be moved to activate the insertion actuator and to activate the release actuator. The control device 1342 may be configured to be slid laterally to activate the insertion actuator and to activate the release actuator. The control device 1342 may include a button surface 1380 (marked in FIG. 123) and a control arm 1382 that extends from the button surface 1380. The control arm 1382 may include a coupler release in the form of pressing surface 1384 configured to be pressed against the releasable coupler 1304 of the needle hub 1302 (marked in FIG. 122) to release the releasable coupler 1304 from the coupling member 1306 shown in FIG. 122. The control arm 1382 may also include a pressing surface 1348 for pressing the arms 1378 shown in FIG. 125 to release the releasable coupler 1309 (marked in FIG. 125). The control arm 1382 may further include a stop surface 1385 for contacting the stops 1362 of the biasing carriage 1354 shown in FIG. 123.

FIG. 127 illustrates a perspective cross sectional view of the applicator 1332 showing that the applicator housing 1334 includes a receiver 1386 for receiving the cartridge 1300. The receiver 1386 may be configured for the cartridge 1300 retaining the transcutaneous analyte sensor to be inserted into. The cartridge 1300 may be coupled to the applicator housing 1334 by being inserted into the receiver 1386. The receiver 1386 may comprise a cavity within the applicator housing 1334 that receives the cartridge 1300. The cartridge 1300 may be inserted into the receiver 1386 axially through the opening 1358 at the bottom of the applicator housing 1334.

The applicator 1332 may operate in a manner shown in FIGS. 127-136. FIG. 127 illustrates the applicator 1332 in an initial state, in which the applicator 1332 is configured to receive, and is receiving, the cartridge 1300 and components of the transcutaneous analyte sensor system including the transcutaneous analyte sensor 24, the wearable housing 108, and the patch 106.

The applicator 1332 in the initial state has the carriage 1346 of the insertion actuator in a lowered state, proximate the lower opening 1358 of the applicator 1332. The carriage 1346 of the insertion actuator may be pressed to the lowered state by the force provided by the driver 1344 of the insertion actuator. The driver 1344 may be configured to drive the needle 1312 into the individual's skin to insert the transcutaneous analyte sensor into the individual's skin.

The carriage 1352 of the retraction actuator may be in a raised state, pressed to the raised state by the force of the driver 1350 of the retraction actuator. The releasable couplers 1374 shown in FIG. 125 are not yet coupling the carriages 1352, 1346 together.

The cartridge 1300 may be inserted into the receiver 1386 of the applicator housing 1334, with the removable covers 1326, 1328 of the cartridge 1300 having been previously removed by an individual. The cartridge 1300 may be inserted in the axial dimension of the applicator housing 1334, which is the same dimension that the transcutaneous analyte sensor 24 as well as other components of the transcutaneous analyte sensor system will be deployed from the applicator housing 1334 (although in an opposite axial direction that the cartridge 1300 is inserted into the receiver 1386). The insertion of the cartridge 1300 and the transcutaneous analyte sensor 24 into the receiver 1386 of the applicator housing 1334 may compress and thus provide energy to both the driver 1344 of the insertion actuator and the driver 1350 of the retraction actuator. Both drivers 1344, 1350 may be compressed for example as shown in FIG. 131. In an embodiment in which the drivers 1344, 1350 are springs, the springs may be compressed by the insertion of the cartridge 1300 and the transcutaneous analyte sensor 24 into the receiver.

Figure 129:
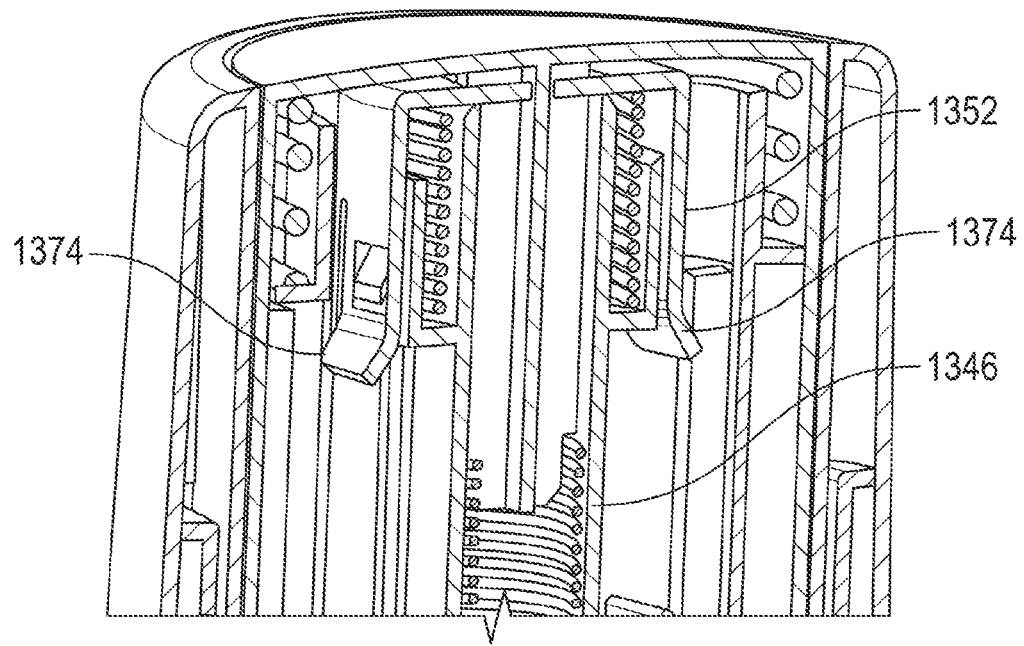

The insertion of the cartridge 1300 fully into the receiver 1386 of the applicator housing 1334 causes the releasable couplers 1374 of the retraction actuator carriage 1352 (marked in FIG. 125) to engage the coupling members 1372 of the insertion actuator carriage 1346. FIG. 129, for example, illustrates a perspective view of the carriages 1346, 1352 coupled together.

Figure 128:
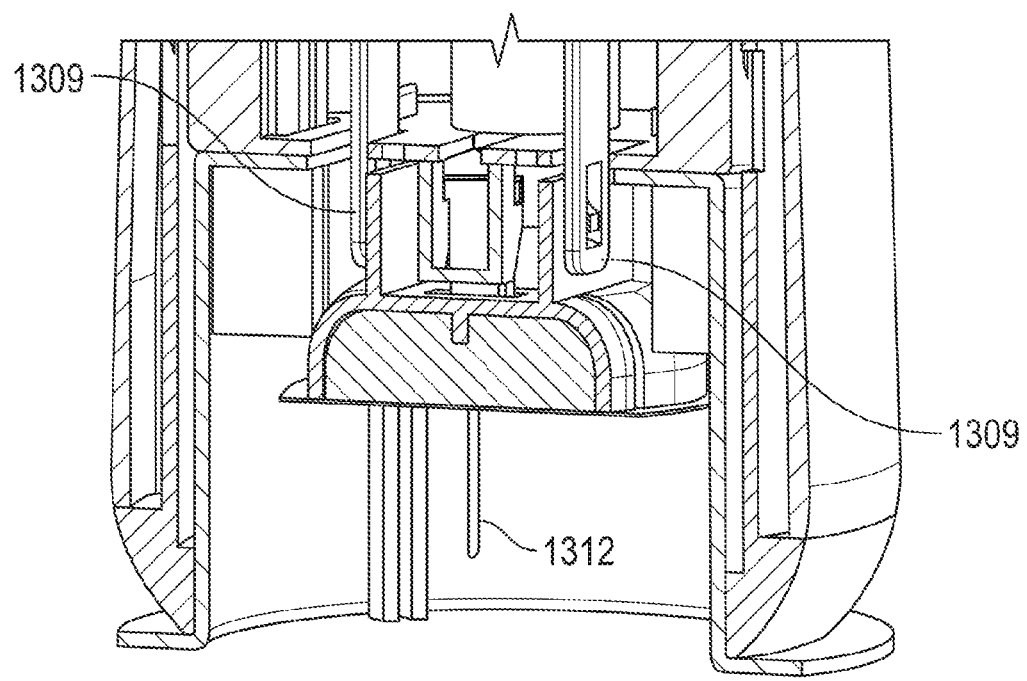

As shown in FIG. 128, the releasable coupler 1309 of the retraction actuator couples to the needle 1312, particularly with the openings of the releasable coupler 1309 engaging coupling members of the needle hub 1302. The needle 1312 extends downward from the wearable housing 108 of the transcutaneous analyte sensor system, extending for insertion of the penetrating tip of the needle 1312 into the individual's skin.

The cartridge 1300 notably may remain within the receiver 1386 of the applicator housing 1334 during insertion of the needle 1312 and insertion of the transcutaneous analyte sensor 24 into the individual's skin, as well as deployment of the on-skin sensor assembly 12 to the individual's skin.

Figure 130:
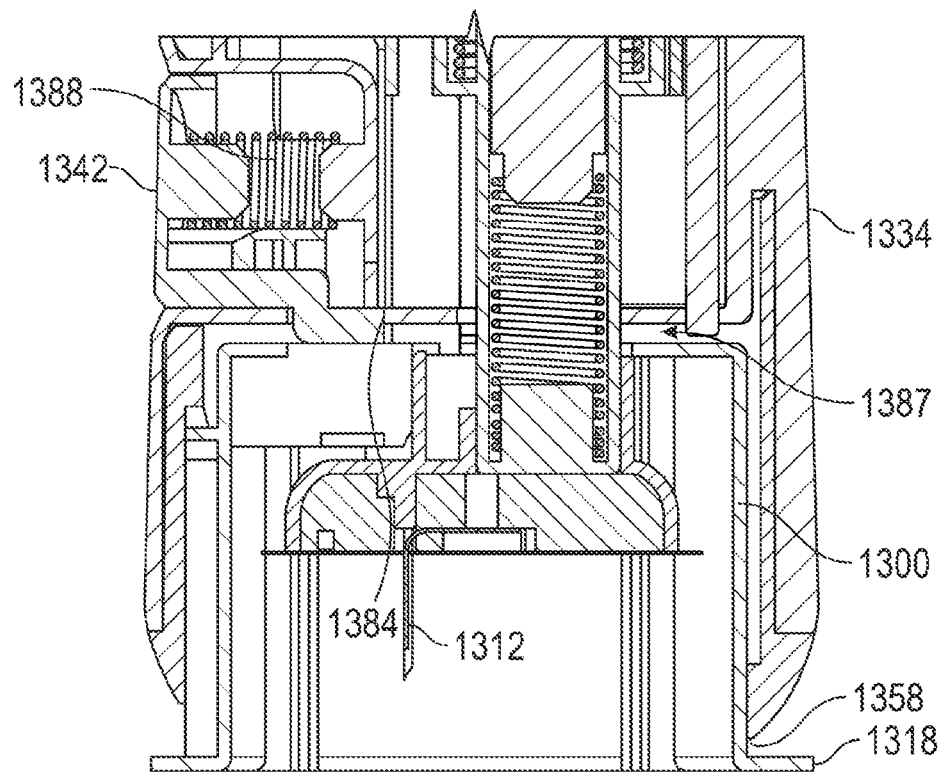

Referring to FIG. 130, upon the cartridge 1300 being inserted into the receiver 1386, the biasing surface 1356 of the biasing carriage 1354 may press against the cartridge 1300 to bias the cartridge 1300 towards the lower opening 1358 of the applicator housing 1334. The biasing operation of the biasing carriage 1354 may keep the releasable coupler 1304 shown in FIG. 122 in a lowered position, beneath the range of motion of the pressing surface 1384 of the control device 1342 shown in FIG. 126. Such an operation may prevent the applicator 1332 from deploying the needle 1312 until a time that the base 1318 of the cartridge 1300 contacts the individual's skin. As shown in FIG. 130, a gap 1387 may be positioned between an upper surface of the cartridge 1300 and a surface of the applicator housing. The base 1318 of the cartridge 1300 may contact the individual's skin and then be pressed upward to overcome the biasing force of the biasing spring 1360 and be inserted further into the receiver 1386 to close the gap 1387. Such a configuration may be shown in FIG. 131.

Further, as shown in FIG. 134, upon the cartridge 1300 being pressed further upward to overcome the biasing force of the biasing spring 1360 and be inserted further into the receiver 1386, the stops 1362 of the biasing carriage 1354 may be raised to impede undesired lateral movement of the control device 1342, such that the control device 1342 does not contact the arms 1378 of the carriage 1352 of the retraction actuator and undesirably release the needle 1312 from the releasable coupler 1309 at this time. As such, the biasing carriage 1354 may act as a safety mechanism to prevent the needle 1312 from being deployed until a desired time, and prevent the needle 1312 to be released from the releasable coupler 1309 until a desired time.

Referring to FIG. 131, with the cartridge 1300 fully inserted into the receiver 1386, and with the base 1318 of the cartridge 1300 pressed against the individual's skin, the releasable coupler 1304 shown in FIG. 122 may be in a raised position, within the range of motion of the pressing surface 1384 of the control device 1342.

The control device 1342 may be pressed laterally, compressing a biasing spring 1388 of the control device 1342. The pressing surface 1384 of the control device 1342 may contact the releasable coupler 1304 of the needle hub 1302 shown in FIG. 122, to release the releasable coupler 1304 from the coupling member 1306. The force of the driver 1344 of the insertion actuator causes the carriage 1346 of the insertion actuator to press against the wearable housing 108 and insert the needle 1312 and the transcutaneous analyte sensor 24 into the individual's skin, and deploy the other components of the on-skin sensor assembly 12 to the individual's skin. The movement of the carriage 1346 has pressed the patch 106 to the individual's skin, allowing the patch 106 to adhere to the individual's skin and providing an adhesive force to the skin for the transcutaneous analyte sensor system.

The needle hub 1302 may slide within the body of the cartridge 1300, with the rails 1314 of the needle hub 1302 sliding along the channels 1316 on the inner surface of the cartridge body 1308.

Referring to FIG. 132, upon the carriages 1346, 1352 of the insertion actuator and the retraction actuator both descending within the applicator housing 1334, the coupler release in the form of deflectors 1376 of the applicator housing may contact the releasable couplers 1374, causing them to deflect and disengage from the coupling members 1372 of the insertion actuator carriage 1346. Accordingly, the carriages 1346, 1352 may be decoupled from each other and able to slide relative to each other. The force of the driver 1350 of the retraction actuator may cause the carriage 1352 of the retraction actuator to move upwards thus retracting the needle 1312 and the needle hub 1302 away from the individual's skin. Such a configuration is shown in FIG. 133.

The releasable coupler 1304 as shown in FIG. 122 may further be recoupled to the coupling member 1306 shown in FIG. 122 due to the movement of the retraction actuator.

The releasable coupler 1309 retains the needle 1312 to the applicator housing 1334 following insertion of the transcutaneous analyte sensor 24 into the individual's skin and removal from the applicator housing from the transcutaneous analyte sensor 24. The transcutaneous analyte sensor 24 remains within the individual's skin as the applicator housing is removed from the transcutaneous analyte sensor 24.

Referring to FIG. 134, notably, with the base 1318 of the cartridge 1300 continuing to be pressed against the individual's skin, the stops 1362 impede movement of the control device 1342 from contacting the arms 1378. Thus, the needle 1312 cannot be released from the applicator housing 1334. The cartridge 1300 must be removed from the individual's skin to allow the biasing carriage 1354 to press the cartridge 1300 in a direction towards the lower opening 1358 of the applicator housing 1334. With the cartridge 1300 pressed downward by the biasing carriage 1354, the gap 1387 is produced and the stop 1362 lowers beneath the stop surface 1385 of the control device 1342.

As shown in FIG. 135, with the stops 1362 lowered, the control device 1342 may be moved laterally to contact the arms 1378. As shown in FIG. 136, the pressing surface 1348 of the control device 1342 may press against the arms 1378, and release the releasable coupler 1309 shown in FIG. 125. The cartridge 1300, including the needle 1312 and needle hub 1302 may be released from the applicator housing 1334 with the needle 1312 positioned within the body 1308 of the cartridge.

The release actuator accordingly may operate to allow the cartridge 1300 to be removed from the receiver of the applicator housing. The release actuator may unlock the cartridge 1300 from the applicator housing by the releasable coupler 1309 releasing the cartridge 1300, and thereby releasing the needle 1312 from the applicator housing. The needle 1312 may be separated from the applicator housing by separating the cartridge from the applicator housing.

The same control device 1342 may be operated twice to first operate the insertion actuator and then second to operate the release actuator. The control device 1342 may be operated in a first operation to activate the insertion actuator, and may be configured to be operated in a second operation following the first operation to activate the release actuator. In an embodiment in which the control device 1342 is a button, the first operation may comprise pressing the control device 1342 and the second operation may comprise pressing the control device 1342 a second time. The same control device 1342 accordingly may be pressed twice to operate both the insertion actuator and the release actuator.

The needle 1312 may be released from the applicator housing 1334 for discard, as the needle 1312 may have been contaminated through the process of insertion within the individual's skin. The needle 1312 accordingly may be a single use needle that is configured to discard within a sharps container or other disposal area. The needle 1312 may remain positioned within the body 1308 of the cartridge 1300 such that an individual does not contact the used needle 1312 and be subject to the contamination of the needle 1312 or otherwise be injured by the penetrating tip of the needle 1312. For example, the wall 1320 of the cartridge 1300 may block access to the needle 1312. The cartridge 1300 is configured to retain the needle after the cartridge 1300 has been separated from the receiver and the needle has been inserted into the individual's skin. The needle 1312 may remain locked in position within the cartridge 1300 such that an individual cannot access the contaminated portion of the needle 1312. The needle 1312 and other portions of the cartridge 1300 together may form a unit for disposal following insertion into an individual's skin and separation from the applicator housing.

Upon release of the cartridge 1300 from the applicator housing 1334, and following the return of the control device 1342 to the position shown in FIG. 133, the applicator is in a configuration for deployment of another transcutaneous analyte sensor 24 and other components of a transcutaneous analyte sensor system. As such, the applicator 1332 is configured for multiple uses, and is not intended to be discarded. The applicator 1332 returns to an initial configuration for repeat of the steps shown in FIGS. 127-136. The applicator 1332 may be loaded with another cartridge 1300 and the steps disclosed herein may repeat as desired.

Variations of the applicator 1332 and cartridge 1300 may be provided. FIGS. 137-145 for example illustrate a variation of the applicator 1332 and cartridge 1300 including the features disclosed herein.

Referring to FIG. 137, a cartridge 1400 may be provided that is similar to the cartridge 1300 shown in FIGS. 120-122, yet includes a needle cover 1402 over the needle 1404. The needle cover 1402 may be coupled to the body 1406 of the cartridge 1400 and may extend through an opening in the wearable housing 108 to cover the needle 1404. A wall of the cartridge 1400 may extend around at least a portion of the needle cover 1402. The needle cover 1402 may cover all or a portion of the needle 1404 (as shown in FIG. 137) and may comprise a sheath configured to extend axially along at least a portion of the needle shaft 1408. The needle cover 1402 may be configured to slide relative to the needle 1404 as the needle 1404 penetrates the individual's skin. The needle 1404 may thus be configured to be moved relative to the needle cover 1402 to be positioned into the needle cover 1402.

Beneficially, the needle cover 1402 may prevent an individual from contacting the penetrating tip of the needle 1404 prior to insertion into the individual's skin, and following insertion into the individual's skin. The needle cover 1402 is configured to cover at least a portion of the needle 1404 following the needle 1404 inserting the transcutaneous analyte sensor into the skin of the individual. The needle cover 1402 may be coupled to the wearable housing 108 and configured to be separable from the wearable housing 108.

The cartridge 1400 may include a coupling member 1407 on an outer surface of the cartridge 1400 for coupling with a releasable coupler 1412 of the applicator 1410 as shown in FIG. 141.

FIG. 138 illustrates a perspective view of variations of the applicator 1332. The applicator 1410 may be configured similarly as the applicator 1332. The insertion actuator of the applicator 1410 may be configured to insert the needle 1404 into the individual's skin with the cartridge 1400 positioned in the receiver 1435 (marked in FIG. 140) of the applicator housing. The applicator 1410, however, may include a releasable coupler 1412 in the form of a cartridge catch that retains the cartridge 1400 to the applicator housing 1413. The receiver 1435 may be configured to release the cartridge 1400 from the applicator housing.

The releasable coupler 1412 may be pressed by a biasing spring 1414. The applicator 1410 may further include a coupler release in the form of a slide arm 1416 that may be slid to press against the releasable coupler 1412 to overcome the biasing spring 1414 and release the releasable coupler 1412.

The applicator 1410 may further include additional biasing surfaces 1418 that may be pressed by biasing springs 1420. The biasing surfaces 1418 may be coupled to bodies 1419 configured to slide axially within the applicator housing 1413. The biasing surfaces 1418 may be configured to press against upper surfaces of the cartridge 1400, to apply a downward force to the cartridge 1400.

The carriage 1424 of the insertion actuator may include stops 1426 extending outward from arms 1428 of the carriage 1424. The stops 1426 may be configured to contact portions of the biasing carriage 1430, to impede movement of the biasing carriage 1430 at a desired time.

Referring to FIG. 139, in operation, the applicator 1410 may operate in a similar manner as the applicator 1332. The applicator 1410, however, may include a stop 1432 on the biasing carriage 1430 that contacts the control device 1434 to impede lateral movement of the control device 1434 such that the control device 1434 does not contact a releasable coupler 1436 (marked in FIG. 142) configured similarly as the releasable coupler 1304 shown in FIG. 122. The stop 1432 accordingly blocks movement of the control device 1434 until the cartridge 1400 contacts and is pressed against the individual's skin to cause the cartridge 1400 to fully insert into the receiver 1435 of the applicator housing 1413. Upon full insertion of the cartridge 1400 into the receiver 1435 of the applicator housing 1413, the biasing carriage 1430 may be pressed upward (in a similar manner as discussed regarding the biasing carriage 1354). The upward movement of the biasing carriage 1430 may move the stop 1432 upward, to remove contact between the stop 1432 and the control device 1434, and to allow the control device 1434 to be slid laterally to contact the releasable coupler 1436 (marked in FIG. 142).

FIG. 140 illustrates the cartridge 1400 positioned within the receiver 1435 of the applicator housing 1413, with the biasing carriage 1430 pressing against the cartridge 1400. The biasing spring 1438 presses the biasing carriage 1430 pressing against the cartridge 1400.

FIG. 141 illustrates the cartridge 1400 fully inserted within the receiver 1435 of the applicator housing 1413. The releasable coupler 1412 couples to the coupling member 1407 of the cartridge 1400 to retain the cartridge 1400 within the receiver of the applicator housing 1413.

Further, as shown in FIG. 141, with the cartridge 1400 fully inserted within the receiver 1435 of the applicator housing 1413, the stop 1432 of the biasing carriage 1430 is lifted to allow for lateral movement of the control device 1434. As shown in FIG. 142, the control device 1434 may be pressed laterally, to contact and release the releasable coupler 1436. A stop 1441 on the cartridge 1400 may contact the control device 1434 to impede further lateral movement of the control device 1434. As such, the control device 1434 may be blocked from contacting an end of the slide arm 1416 and may be blocked from contacting the arms of the carriage 1440 of the retraction actuator that are coupled to the releasable coupler 1436.

The operation of the insertion actuator to insert the needle 1404 and the transcutaneous analyte sensor 24 into the individual's skin may be the same as with the applicator 1332. Similarly, the operation of the retraction actuator to retract the needle 1404 may be the same as with the applicator 1332. Further, as shown in FIG. 144, the releasable coupler 1436 couples to the coupling member 1444, which is configured similarly as the coupling member 1306 shown in FIG. 122.

However, as shown in FIG. 143, with the carriage 1424 of the insertion actuator in a lowered position, the stops 1426 of the carriage 1424 contact and press against surfaces of the biasing carriage 1430. As such, the biasing carriage 1430 is blocked from moving downward upon the applicator housing 1413 being withdrawn from the individual's skin. The biasing surfaces 1418 of the bodies 1419, however, continue to apply a downward biasing force against the cartridge 1400 as the cartridge 1400 is withdrawn from the individual's skin (as shown in FIG. 144). As such, the stop 1441 on the cartridge 1400 shown in FIG. 142 lowers with the cartridge 1400, while the stop 1432 shown in FIG. 139 remains in a raised positioned.

Referring to FIG. 145, in such a configuration of stops 1441, 1432, the control device 1434 may freely move laterally to contact the arms 1446 (marked in FIG. 144) of the retraction actuator to release the releasable coupler 1442 from the needle hub 1448. Further, the control device 1434 may contact an end of the slide arm 1416 to press the slide arm 1416 laterally and press against the releasable coupler 1412. As such, the cartridge 1400 may be free to release from the receiver 1435 of the applicator housing 1413, with the releasable coupler 1442 released from the needle hub 1448 and with the needle cover 1402 covering the needle 1404. The retraction actuator may position the needle 1404 into the needle cover 1402. The cartridge 1400 is configured to retain the needle after the cartridge 1400 has been separated from the receiver and the needle has been inserted into the individual's skin.

The release actuator accordingly may operate to allow the cartridge 1400 to be removed from the receiver of the applicator housing. The release actuator may unlock the cartridge 1400 from the applicator housing by the releasable coupler 1442 releasing the cartridge 1400, and thereby releasing the needle 1404 from the applicator housing 1413. Further, the release actuator may operate the releasable coupler 1412 to unlock the cartridge 1400.

In a similar manner as discussed in regard to the applicator 1332, the applicator 1410 may be in a configuration for receiving another cartridge 1400 for deployment of an on-skin sensor assembly.

FIGS. 146-151 illustrate a further variation in which the cartridge includes the retraction actuator for retracting the needle from the individual's skin following insertion of the transcutaneous analyte sensor into the individual's skin. The retraction actuator may be configured to automatically operate upon the needle inserting the transcutaneous analyte sensor into the individual's skin. FIG. 146, for example, illustrates a construction of a cartridge 1500 including a retraction actuator 1502 positioned within the cartridge 1500. The cartridge 1500 may otherwise be configured similarly as the cartridge 1300 shown in FIG. 120, and may include an upper removable cover 1504, a lower removable cover 1506, a body 1508 and may include the wearable housing 1510, transcutaneous analyte sensor, and the needle 1512. A patch 1513 may be coupled to the wearable housing 1510 and positioned within the cartridge 1500. A retraction carriage 1514 and driver 1516 may be positioned within the cartridge 1500.

The retraction carriage 1514 may couple to a needle hub 1518 of the needle 1512 and may include arms 1520 extending outward from the needle hub 1518 and configured to contact interior portions of the cartridge 1500. The connection of the retraction carriage 1514 to the needle hub 1518 may include a beveled surface 1522 that the driver 1516 may abut.

The cartridge 1500 may further include a carriage 1524 for pressing the needle 1512 into the individual's body and pressing the patch 1513 and the housing 1510 against the individual's skin. The carriage 1524 may include a releasable coupler 1531 for coupling with a portion of the control device 1523.

Further features such as locks 1526 (shown in FIG. 147) may be included with the cartridge 1500 for locking the cartridge 1500 to the applicator housing 1528. The locks 1526 may comprise a releasable coupler configured to retain the needle 1512 at least partially within the applicator housing 1528 following insertion of the transcutaneous analyte sensor 24 into the individual's skin and removal of the applicator housing 1528 from the transcutaneous analyte sensor 24, and configured to release the needle 1512 from within the applicator housing 1528 following insertion of the transcutaneous analyte sensor 24 into the individual's skin. The releasable coupler may release the needle via the cartridge 1500 being separated from the applicator housing 1528. The releasable coupler may be configured to release the cartridge 1500 from the applicator housing 1528 to release the needle from within the applicator housing 1528.

FIG. 147 illustrates a three-quarters cross sectional view of the applicator 1530 and the cartridge 1500. The applicator 1530 may be configured similarly as the applicator 1334 shown in FIGS. 123-136, with the control device 1523 corresponding to the control device 1342, the biasing carriage 1534 corresponding to the biasing carriage 1354, the insertion carriage 1536 corresponding to the carriage 1346, and the driver 1538 corresponding to driver 1344. The biasing spring 1540 corresponds to biasing spring 1360. The applicator 1530 operates in a similar manner as the application 1334, however, the retraction actuator is within the cartridge 1500.

FIG. 147, for example, illustrates the retraction actuator in an undeployed state within the cartridge 1500. The driver 1516 of the retraction actuator that is configured to drive the needle out of the individual's skin is compressed between the wearable housing 1510 and support arms 1542 extending upward from the carriage 1524. The carriage 1514 may be configured to slide relative to the applicator housing and may be configured to be slid by the driver 1516 of the retraction actuator. The support arms 1542 may be positioned between the driver 1516 and the needle hub 1518, and may have ends positioned above the beveled surface 1522 of the needle hub 1518. The support arms 1542 may hold against the driver 1516 to prevent the driver 1516 from contacting the arms 1520 of the retraction carriage 1514 until the desired time. The support arms 1542 may comprise releasable couplers that couple the carriage 1524 to the retraction carriage 1514. The support arms 1542 may release the carriage 1524 from the retraction carriage 1514 to allow the driver 1516 to move the retraction carriage 1514 in a direction away from the carriage 1524.

The interior portions of the cartridge 1500 may include stops 1544 that the arms 1520 may be configured to contact to impede downward movement of the retraction carriage 1514. During downward movement of the retraction carriage 1514 and the carriage 1524, the arms 1520 may contact the stops 1544 to offset the position of the carriage 1524 relative to the retraction carriage 1514 and cause the support arms 1542 to slide relative to the beveled surface 1522. The sliding motion moves the arms 1542 below the beveled surface 1522 and causes the arms 1542 to move radially inward towards the needle hub 1518, thus releasing the driver 1516 to press against the arms 1542 and retract the needle 1512.

FIG. 148, for example, illustrates the cartridge 1500 inserted into the receiver of the applicator 1530. The biasing carriage 1534 is compressed to allow the control device 1523 to move in a similar manner as described in regard to FIG. 131 for example. Upward pressure against the cartridge 1500 by the individual's skin presses the biasing carriage 1534 upward, to move the stop 1533, and allow the control device 1523 to move inward to be pressed.

The insertion of the cartridge 1500 and the transcutaneous analyte sensor 24 into the receiver of the applicator housing 1528 may compress and thus provide energy to the driver 1538 of the insertion actuator. The driver 1538 may be compressed. In an embodiment in which the driver 1538 includes a spring, the spring may be compressed by the insertion of the cartridge 1500 and the transcutaneous analyte sensor 24 into the receiver.

The insertion carriage 1536 is compressed in a similar manner as the insertion carriage 1346 and may be in contact with the carriage 1524 to drive the carriage 1524 downward.

The cartridge 1500 may remain within the receiver of the applicator housing 1528 during insertion of the needle 1512 and insertion of the transcutaneous analyte sensor 24 into the individual's skin, as well as deployment of the on-skin sensor assembly 12 to the individual's skin.

The control device 1523 may contact the releasable coupler 1531 to release the releasable coupler 1531 in a similar manner as described in regard to FIG. 131 for example. The control device 1523 may press against the releasable coupler 1531 to disengage the coupler 1531 from a surface and allow the insertion carriage 1536 to drive the carriage 1524 downward.

FIG. 149 illustrates the descent of the carriage 1524. The carriage 1524 may move downward to insert the needle 1512 into the individual's skin to insert the transcutaneous analyte sensor into the individual's skin. Further, the patch 1513 may be applied to the individual's skin with an adhesive. The retraction carriage 1514 may slide along with the carriage 1524 due to an interference fit between the arms 1542 and the needle hub 1518.

Referring to FIG. 150, with the needle 1512 inserted and the patch 1513 applied, the arms 1520 may contact the stops 1544 to move the retraction carriage 1514 upward with respect to the carriage 1524. The arms 1542 may then move downward with respect to the beveled surface 1522, which allows the arms 1542 to move radially inward with respect to the needle hub 1518. The inward movement of the arms 1542 may release the driver 1516, which allows the retraction carriage 1514 to move upward due to the force of the driver 1516.

The cartridge 1500 may be configured to retain the needle 1512 after the cartridge 1500 has been separated from the receiver and the needle 1512 has been inserted into the individual's skin.

FIG. 151, for example, illustrates such a configuration, in which the retraction carriage 1514 has moved upward to withdraw the needle 1512 from the individual's skin. The housing 1510 is excluded from view in FIG. 151.

The cartridge 1500 may then be withdrawn and discarded, to discard the used needle 1512. The actuator 1530 may return to the state shown in FIG. 147, for insertion of another cartridge.

Variations in the configuration of the cartridge may be provided. FIGS. 152-158 for example, illustrate embodiments in which the cartridges include a bottom surface with an opening for the transcutaneous analyte sensor to be deployed from and a patch for the transcutaneous analyte sensor coupled to the bottom surface and covering the opening. In such embodiments, the transcutaneous analyte sensor may be configured to slide within the cartridge relative to the patch. The cartridge may be configured to allow the needle to slide within the cartridge relative to the patch. The patch may be configured to be deployed to the individual's skin from the bottom surface of the cartridge.

FIG. 152, for example, illustrates an embodiment of a patch 1600 that may be utilized. The patch 1600 may include an adhesive layer 1602 and a liner 1604 coupled to the adhesive layer 1602. The patch 1600 may include a window 1607 such as a relatively thin portion, or an opening in the patch 1600 for the needle and transcutaneous analyte sensor to pass through.

FIG. 153 illustrates a bottom view of the patch 1600. The liner 1604 may include multiple portions, including a first portion 1606 and a second portion 1608 each configured to be separately removable from the adhesive layer 1602 prior to application of the adhesive layer 1602. Each portion 1606, 1608 may include a respective tab 1610, 1612 that may be gripped and pulled to remove the respective portion of the liner 1604 to expose the adhesive portion of the adhesive layer 1602.

The patch 1600 may be sized to be positioned at the bottom of a cartridge. FIG. 154, for example, illustrates such a configuration. The cartridge 1614 may include a body 1616 configured to be coupled to an applicator housing and including a bottom surface 1618 with an opening 1620 (marked in FIG. 156) for the transcutaneous analyte sensor to be deployed from. The patch 1600 spans the opening 1620 and covers the opening 1620. The patch 1600 is coupled to the bottom surface 1618 with an adhesive or other means of attaching the patch 1600 to the bottom surface 1618. The liner layer 1604 may be removed prior to application of the patch 1600 to the individual's skin.

In embodiments, a retraction actuator may be positioned within the cartridge 1614 for retracting the needle from the skin of an individual following insertion of the transcutaneous analyte sensor into the individual's skin. The retraction actuator may be configured to automatically operate upon the needle inserting the transcutaneous analyte sensor into the individual's skin. FIG. 155, for example, illustrates a retraction actuator including a carriage 1617 and a retraction carriage 1621. The carriage 1621 may be configured to slide relative to the applicator housing and may be configured to be slid by the driver 1636 of the retraction actuator.

The retraction carriage 1621 may include arms 1622 that engage releasable couplers 1624. The releasable couplers 1624 may couple the carriage 1617 to the retraction carriage 1621. The releasable couplers 1624 may release the carriage 1617 from the retraction carriage 1621 to allow the driver 1636 to move the retraction carriage 1621 in a direction away from the carriage 1617. The retraction carriage 1621 may couple to a needle 1626 that is configured to insert the transcutaneous analyte sensor into skin of an individual.

Referring to FIG. 156, a cross sectional view of the cartridge 1614 is shown. The cartridge 1614 is shown to include an interior surface including coupler releases 1628 that are configured to contact the arms 1622 upon downward sliding movement of the carriage 1617. The coupler releases 1628 deflect the arms 1622 upon contact, to release the arms 1622 from the releasable couplers 1624. The arms 1622 may then slide upward to retract the needle 1626 away from the individual's skin.

As such, in operation, the cartridge 1614 may be in a configuration as shown in FIG. 156. The housing 1630, needle 1626, and transcutaneous analyte sensor 1632 are spaced from the patch 1600. Upon an insertion carriage passing downward through the opening 1619 of the cartridge 1614 and pressing the carriage 1617 downward, the housing 1630, sensor 1632, and needle 1626 may be driven downward towards the patch 1600 and may slide relative to the patch 1600. The adhesive layer of the patch 1600 may be exposed and in contact with the individual's skin.

The cartridge 1614 may remain within the receiver of the applicator housing 1528 during insertion of the needle 1626 and insertion of the transcutaneous analyte sensor 24 into the individual's skin, as well as deployment of the on-skin sensor assembly 12 to the individual's skin.

The needle 1626 may penetrate through the patch 1600, or may pass through an opening in the patch 1600. The needle 1626 may slide relative to the patch 1600 to insert the sensor 1632 into the skin of an individual. The needle 1626 may insert the sensor 1632 into the individual's skin. The housing 1630 may be applied to the patch 1600 and may adhere to the patch 1600 with an adhesive or other means of connection.

The retraction actuator may then engage, with the retraction carriage 1621 being released due to the movement of the arms 1622, and the driver 1636 driving the retraction carriage 1621 upwards to drive the needle 1626 out of the individual's skin.

The cartridge 1600 may be configured to retain the needle 1626 after the cartridge 1600 has been separated from the receiver and the needle 1626 has been inserted into the individual's skin.

FIGS. 157 and 158 illustrate an alternate configuration of the retraction carriage 1640 and the carriage 1642. The retraction carriage 1640 in such an embodiment may include arms 1644 that are configured to be pressed inward to disengage from releasable couplers 1646 to retract the needle 1648. The arms 1644 may press against coupler releases 1650 that may be positioned on the interior surface of the cartridge 1614 upon the carriage 1621 sliding downwards towards the patch 1600. The spring 1652 may press the retraction carriage 1640 upward relative to the carriage 1642 to retract the needle 1648. FIG. 158, for example, illustrates a configuration of a deployed housing 1654 with the needle 1648 retracted.

Various modifications of the embodiments of cartridges shown in FIGS. 155-158 may be provided. For example, in embodiments, a separate retraction actuator may be provided outside of the cartridge, such as in an embodiment of FIGS. 120-145. In embodiments, certain components of the sensor system may be positioned directly on the patch. For example, in embodiments, the wearable housing may be positioned directly on the patch, and the needle may comprise the only component sliding with respect to the patch. In embodiments, other retraction methods of the needle may be provided, such as rotation of the needle.

The embodiments of cartridges having a patch at a bottom surface may beneficially reduce the possibility of the skin of the individual entering the cavity 1660 (marked in FIG. 156) of the cartridge. Such a feature may reduce variation in the angle of entry of the needle into the individual's skin, and may space the individual's skin at a desired distance from the needle prior to actuation of the needle. For example, if a certain speed of entry of the needle into the individual's skin is needed, then spacing the needle from the skin will beneficially reduce the possibility of the skin being undesirably close to the needle such that the needle does not gain enough speed to properly penetrate the skin. Various other benefits may result. Any embodiment as disclosed herein may utilize patches at a bottom surface of a cartridge or applicator.

In the embodiments discussed in regard to FIGS. 2-158, the electronics unit 26 may be coupled to the wearable housing 108 of the on-skin sensor assembly after the on-skin sensor assembly is deployed to the individual's skin. Further, in other embodiments, the electronics unit 26 may be integral with the wearable housing 108 and deployed to the individual's skin along with the wearable housing 108. In other embodiments, the electronics unit 26 may be coupled to the housing 108 prior to deployment of the wearable housing 108 to the individual's skin. The electronics unit 26 may include a communication device for the transcutaneous analyte sensor 24.

FIGS. 159 and 160 illustrate features of an embodiment in which the electronics unit 26 is coupled to the wearable housing 108 prior to deployment of the wearable housing 108 to the individual's skin. FIGS. 159 and 160 illustrate a system for inserting a transcutaneous analyte sensor into an individual's skin. The wearable housing 108 may be positioned in a receiver 1800 of an applicator 1802, which may be configured similarly as any of the applicators disclosed herein. The receiver 1800 may be of an applicator housing configured to be gripped to apply the transcutaneous analyte sensor into the individual's skin, or may be a receiver of a cartridge, for instance in an embodiment as shown in FIGS. 120-158.

The wearable housing 108 may include a coupler 1804 that is positioned on a bottom surface of the wearable housing 108. Thus, the electronics unit 26 may be coupled to the wearable housing 108 via insertion on a bottom surface of the wearable housing 108 to couple to the coupler 1804.

A mounting base 1806 may be provided that is configured to retain the electronics unit 26. The electronics unit 26 may be provided on the mounting base 1806. The mounting base 1806 may be configured to apply the electronics unit 26 to the coupler 1804 for the transcutaneous analyte sensor 24 when the transcutaneous analyte sensor is retained by the receiver 1800, to couple the electronics unit 26 to the transcutaneous analyte sensor 24.

The mounting base 1806 may include a receiver 1808 on an upper surface 1810 of the mounting base 1806 that is configured to retain the electronics unit 26. The mounting base 1806 may include one or more side surfaces 1812 that may be shaped to mate with an inner surface 1814 of the receiver 1800. The one or more side surfaces 1812 may extend between the upper surface and a lower surface of the mounting base 1806. The one or more side surfaces 1812 may be shaped to mate with an inner surface of the receiver 1800 of the applicator 1802. Protrusions 1807 may be positioned on the one or more side surfaces 1812 that are configured to align the mounting base 1806 with the receiver 1800.

The wearable housing 108 may be positioned in the receiver 1800 of the applicator 1802, and the mounting base 1806 may be inserted into the receiver 1800 of the applicator 1802 retaining the transcutaneous analyte sensor 24 to couple the electronics unit 26 to the wearable housing 108.

The receiver 1800 of the applicator may comprise a cavity or other form of receiver. The receiver 1800 may be configured to retain the transcutaneous analyte sensor within the cavity. The receiver 1800 may include an inner surface 1805 extending between the lower portion of the receiver 1800 and the upper portion of the receiver 1800 and surrounding the cavity. As shown in FIG. 159, the applicator housing may include an opening 1803 for the mounting base 1806 to be passed through to enter the cavity. The opening 1803 may be positioned at a bottom portion of the applicator housing.

The mounting base 1806 may be configured to be inserted into the receiver 1800 of the applicator housing to apply the electronics unit 26 to the coupler 1804 for the transcutaneous analyte sensor. The electronics unit 26 may be pressed into the coupler 1804 of the wearable housing 108 or may be coupled to the wearable housing 108 via another method. The electronics unit 26 may be coupled to the transcutaneous analyte sensor 24 and may be in electrical connection with the transcutaneous analyte sensor 24.

The mounting base 1806 may then be removed from the applicator housing prior to the needle inserting the transcutaneous analyte sensor into the individual's skin, with the electronics unit 26 remaining coupled to the wearable housing 108. The mounting base 1806 may be separated from the electronics unit 26. The wearable housing 108 and electronics unit 26 together may then be deployed to the individual's skin in a manner disclosed herein. The transcutaneous analyte sensor 24 may be inserted into the individual's skin while coupled to the electronics unit 26.

In one embodiment, the receiver of the applicator may comprise a receiver 212 as shown in FIG. 21 for example. The receiver of the applicator may be positioned on a carriage of an insertion actuator for example that is configured to insert a needle and a transcutaneous analyte sensor into an individual's skin as represented in FIG. 21.

FIG. 160 illustrates a side view of an embodiment in which the receiver 1800 forms at least a portion of a cartridge 1816 configured for insertion into the applicator housing (for example, in an embodiment shown in FIGS. 120-158). The mounting base 1806 is configured to be inserted into the cartridge 1816 to apply the electronics unit to the coupler 1804 for the transcutaneous analyte sensor. The mounting base 1806 may be removed from the cartridge 1816 prior to the needle inserting the transcutaneous analyte sensor into the individual's skin and deployment of the wearable housing 108 to the individual's skin.

The features of the embodiments of FIGS. 159 and 160 may be utilized with any embodiment of applicator system disclosed herein.

FIGS. 161-166 illustrate an embodiment of an applicator system in which a cartridge 1900 may be inserted into a side of the applicator 1902. FIG. 161 illustrates a system for inserting a transcutaneous analyte sensor into an individual's skin. Referring to FIG. 161, the cartridge 1900 may retain the needle 1904, the transcutaneous analyte sensor 24, and the housing of the on-skin sensor assembly. The cartridge 1900 may include an inner cartridge body 1906 and an outer cartridge body 1908 that the inner cartridge body 1906 may slide relative to. The inner cartridge body 1906 may retain the needle 1904, the transcutaneous analyte sensor 24, and the wearable housing of the on-skin sensor assembly.

The inner cartridge body 1906 may further include a needle retainer 1909 for retaining the needle 1904 after the needle 1904 has been inserted into the individual's skin.

The outer cartridge body 1908 may include a cocking surface 1910 that may be configured to press against a carriage 1912 of an insertion actuator to cock the insertion actuator and provide energy to the driver 1914 (marked in FIG. 163) of the insertion actuator and the driver 1916 (marked in FIG. 163) of a retraction actuator configured to retract the needle 1904 following insertion of the transcutaneous analyte sensor into the individual's skin. The outer cartridge body 1908 may further include protrusions in the form of rails 1918 configured to slide along channels 1920 of an applicator housing 1922 and align the cartridge 1900 with the receiver of the housing.

FIG. 162 illustrates a top perspective view of the cartridge 1900 showing the needle 1904 and the wearable housing 108 coupled to the body of the cartridge. The wearable housing 108 may be coupled to the inner cartridge body 1906 such that the electronics unit 26 may be coupled to the wearable housing 108 while the wearable housing 108 remains coupled to the inner cartridge body 1906. The body of the cartridge, for example, may include a slot 1926 for the electronics unit 26 to be passed into to couple to the wearable housing 108.

Referring back to FIG. 161, the applicator 1902 may include the applicator housing 1922, which may contain the contents of the applicator 1902 therein. The applicator housing 1922 may be configured to be gripped to apply the transcutaneous analyte sensor into the individual's skin.

The applicator housing 1922 may include a side portion (formed by one or more side surfaces 1936), a top portion (formed by a top surface 1934) and a bottom portion including a bottom opening 1928 for the transcutaneous analyte sensor to be deployed from to be inserted into the individual's skin. The opening 1928 may be configured for the needle 1904 and the transcutaneous analyte sensor 24 to pass through to insert the transcutaneous analyte sensor 24 into the individual's skin. The applicator housing 1922 may include the top surface 1934 and one or more side surfaces 1936 defining sides of the applicator housing 1922. The bottom opening 1928 may define the opening 1928 that the transcutaneous analyte sensor 24 and needle 1904 are inserted into the individual's body from, and that other components of the on-skin sensor assembly are deployed from.

The applicator housing 1922 may include a side opening 1930 for the transcutaneous analyte sensor 24 to be inserted into. The side opening 1930 may define an entry to a receiver 1932 of the applicator housing 1922 for receiving the cartridge 1900 through the side opening 1930. The receiver 1932 may be configured for the cartridge 1900 retaining the transcutaneous analyte sensor to be inserted into. The receiver 1932 may include a cavity for receiving the cartridge 1900 retaining the transcutaneous analyte sensor. The side opening 1930 may be positioned transverse to the axial dimension defined by the bottom opening 1928.

The applicator 1902 may include an insertion actuator, which may include the carriage 1912 and the driver 1914 (marked in FIG. 163). The insertion actuator may further include a control device 1925 for activating the insertion actuator. The insertion actuator may be coupled to the applicator housing 1922 and may be configured to insert a needle into the individual's skin to insert a transcutaneous analyte sensor into the individual's skin. The insertion actuator may be configured to insert the needle 1904 into the individual's skin with the cartridge 1900 positioned in the receiver 1932 of the applicator housing and remaining coupled to the applicator housing. The cartridge 1900 may be left within the receiver 1932 during insertion of the needle 1904. The receiver 1932 may be configured to release the cartridge 1900 from the applicator housing. The control device 1925 may comprise a button that may be pressed by an individual or another form of movable body for releasing the carriage 1912. The control device 1925 may include a button surface 1939 and a control arm 1941 extending from the button surface 1939.

The applicator 1902 may include a retraction actuator for retracting the needle 1904 from the individual's skin. The retraction actuator may include the driver 1916 and a carriage 1924 (marked in FIG. 163). The driver 1916 may be configured to drive the needle 1904 out of the individual's skin.

Referring to FIG. 163, the carriage 1912 of the insertion actuator may include a releasable coupler 1938 that is configured to couple to a coupling member of the applicator housing 1922. The releasable coupler 1938 may be positioned such that lateral movement of the control device 1925 causes the control arm 1941 to press against the releasable coupler 1938 to release the releasable coupler 1938. The carriage 1912 may be configured to slide relative to the applicator housing and be configured to be slid by the driver 1914.

The carriage 1924 of the retraction actuator may include a releasable coupler 1944 that is configured to couple to the carriage 1912 of the insertion actuator. The releasable coupler 1944 may be configured to contact a coupler release 1946 that may be positioned on the cartridge 1900 to automatically release the coupler 1944. The carriage 1924 may be configured to slide relative to the applicator housing and be configured to be slid by the drivers 1916 and 1914. A releasable coupler 1948 may be coupled to a portion of the carriage 1924 of the retraction actuator. The releasable coupler 1948 may be configured to couple to the needle 1904. The releasable coupler 1948 may be configured such that sliding lateral movement of the needle 1904 may release the needle 1904 from the releasable coupler 1948. The releasable coupler 1948 may be configured to retain the needle 1904 at least partially within the applicator housing 1922 following insertion of the transcutaneous analyte sensor 24 into the individual's skin and removal of the applicator housing 1922 from the transcutaneous analyte sensor 24, and configured to release the needle 1904 from within the applicator housing 1922 following insertion of the transcutaneous analyte sensor 24 into the individual's skin.

The operation of the applicator 1902 may be illustrated in FIGS. 163-166. Referring to FIG. 163, the cartridge 1900 may be inserted into the receiver 1932 of the applicator housing 1922. The cartridge 1900 may be coupled to the applicator housing 1922 by being inserted into the receiver 1932. The cartridge 1900 may be inserted into the side of the applicator housing 1922, through the side opening 1930 of the applicator housing 1922. The rails 1918 may slide along the channels 1920 of the applicator housing 1922.

As the cartridge 1900 is slid laterally into the applicator housing 1922, the cocking surface 1910 of the cartridge 1900 may contact a surface of the insertion actuator carriage 1912 to compress the drivers 1914, 1916 and raise the carriage 1912 to the position shown in FIG. 163. Further, the carriage 1924 of the retraction actuator may be raised such that the releasable coupler 1944 of the retraction actuator couples to the coupling member of the insertion actuator carriage 1912. The carriages 1912, 1924 of the insertion actuator and retraction actuator may be in the position shown in FIG. 163. The insertion of the cartridge 1900 and the transcutaneous analyte sensor 24 into the receiver 1932 through the side opening of the applicator housing 1922 may compress and thus provide energy to both the driver 1914 of the insertion actuator and the driver 1916 of the retraction actuator. Both drivers 1914, 1916 are shown to be compressed in FIG. 163. In an embodiment in which the drivers 1914, 1916 are springs, the springs may be compressed by the insertion of the cartridge 1900 and the transcutaneous analyte sensor 24 into the receiver. The cocking surface 1910 may comprise a pressing surface to press against the carriage of the insertion actuator to provide energy to the insertion actuator.

Referring to FIG. 164, the control device 1925 may be pressed to apply a pressing force to the releasable coupler 1938 of the insertion actuator carriage 1912. The driver 1914 may press the insertion actuator carriage 1912 axially downward and may press against the inner cartridge body 1906 of the cartridge 1900. The driver 1914 may be configured to drive the needle 1904 into the individual's skin to insert the transcutaneous analyte sensor into the individual's skin.

Referring to FIG. 165, the insertion actuator carriage 1912 may be driven axially downward to insert the needle 1904 and the transcutaneous analyte sensor 24 into the individual's skin. The insertion actuator carriage 1912 may further press the wearable housing 108 against the individual's skin to deploy a patch 106 or the like to the individual's skin.

The releasable coupler 1948 may be pressed downward to couple to a needle hub 1950 of the needle 1904. The releasable coupler 1948 may include arms that are drawn together as the releasable coupler 1948 descends, to cause the releasable coupler 1948 to couple to the needle hub 1950. The arms, however, may include openings that allow the needle hub 1950 to be slid out from the arms to release the needle hub 1950.

Further as shown in FIG. 165, the releasable coupler 1944 of the retraction actuator carriage 1924 may contact the coupler release 1946 to disengage from the insertion actuator carriage 1912. As shown in FIG. 166, the driver 1916 of the retraction actuator may drive the retraction actuator carriage 1924 upwards to retract the needle 1904 from the individual's skin. The needle 1904 may then be drawn upwards to couple to the needle retainer 1909 shown in FIG. 161. The retraction actuator accordingly may be configured to automatically operate upon the needle 1904 inserting the transcutaneous analyte sensor into the individual's skin.

The applicator housing 1922 may then be lifted upward to leave the on-skin sensor assembly in position. The cartridge 1900, with the needle 1904 coupled to the needle retainer 1909, may then be slid back out of the receiver 1932 through the opening 1930 in the side wall. The needle 1904 may be separated from the applicator housing by separating the cartridge from the applicator housing. The needle hub 1950 may slide out from the releasable coupler 1948 to release from the releasable coupler 1948. The cartridge 1900 is configured to be withdrawn from the receiver 1932 through the side opening 1930 to release the needle 1904 from the releasable coupler 1948. The cartridge 1900 is configured to retain the needle after the cartridge 1900 has been separated from the receiver and the needle has been inserted into the individual's skin.

The applicator 1902 may return to a state as shown in FIG. 161, to receive another cartridge 1900. The applicator 1902 accordingly may comprise a reusable applicator for receipt of multiple different cartridges 1900. The used cartridge 1900 and needle 1904 may be discarded.

FIGS. 167-173 illustrate an embodiment of an applicator system in which a cartridge 2000 may be inserted into side of the applicator 2002. FIG. 167 illustrates a system for inserting a transcutaneous analyte sensor into an individual's skin. A view of the cartridge 2000 is shown in FIG. 168. The cartridge 2000 may include an inner cartridge body 2004 and an outer cartridge body 2006 extending over the inner housing or inner cartridge body 2004. A removable cover 2008 may seal an opening of the outer cartridge body 2006. The opening 2010 may be on a side of the outer cartridge body 2006 as shown in FIG. 169. Referring to FIG. 167, the outer housing or outer cartridge body 2006 may include a grip 2012 for an individual to grip to control movement of the cartridge 2004.

An outer surface of the cartridge 2004 may include protrusions in the form of rails 2014 configured to slide along channels 2016 of the applicator housing 2018 to align the cartridge 2004 with the receiver of the applicator housing.

Referring to FIG. 169, the cartridge 2000 may retain the needle 2019 (marked in FIG. 172), the transcutaneous analyte sensor 24, and the wearable housing 108 of the on-skin sensor assembly. The inner cartridge body 2004 may retain the needle 2019, the transcutaneous analyte sensor 24, and the housing of the on-skin sensor assembly.

The inner cartridge body 2004 may further include a needle retainer that may be configured similarly as the needle retainer 1909 shown in FIG. 161, for retaining the needle 2019 after the needle 2019 has been inserted into the individual's skin.

The inner cartridge body 2004 may further include a slot 2020 for the electronics unit 26 to be inserted into, to couple to the wearable housing 108 while the wearable housing 108 remains coupled to the inner cartridge body 2004. The inner cartridge body 2004 may further include a receiver 2022 for receiving a portion of an insertion actuator carriage 2025 (marked in FIG. 170).

Referring back to FIG. 167, the applicator 2002 may include the applicator housing 2018, which may contain the contents of the applicator 2002 therein. The applicator housing 2018 may be configured to be gripped to apply the transcutaneous analyte sensor into the individual's skin. The applicator housing 2018 may include a side portion (formed by one or more side surfaces 2032 of the applicator housing), a top portion (formed by a top surface 2030) and a bottom portion including a bottom opening 2024 for the transcutaneous analyte sensor to be deployed from to be inserted into the individual's skin. The opening 2024 may be configured for the needle 2019 and the transcutaneous analyte sensor 24 to pass through to insert the transcutaneous analyte sensor 24 into the individual's skin. The transcutaneous analyte sensor 24 and needle 2019 may be inserted into the individual's body from the bottom opening 2024.

The applicator housing 2018 may include a side opening 2026 defining an entry to a receiver 2028 (marked in FIG. 170) of the applicator housing 2018 for receiving the cartridge 2000. The receiver 2028 may be configured for the cartridge 2000 retaining the transcutaneous analyte sensor to be inserted into. The receiver 2028 may include a cavity for receiving the cartridge 2000 retaining the transcutaneous analyte sensor. The side opening 2026 may be positioned transverse to the axial dimension defined by the bottom opening 2024.

The applicator 2002 may include an insertion actuator, which may include a carriage 2033 and a driver 2034 (shown as a spring in FIG. 172). The carriage 2033 may be configured to slide relative to the applicator housing and be configured to be slid by the driver 2034. The insertion actuator may further include a control device 2036 for activating the insertion actuator. The insertion actuator may be coupled to the applicator housing 2018 and may be configured to insert a needle into the individual's skin to insert a transcutaneous analyte sensor into the individual's skin. The insertion actuator may be configured to insert the needle 2019 into the individual's skin with the cartridge 2000 positioned in the receiver 2028 of the applicator housing and remaining coupled to the applicator housing. The receiver 2028 may be configured to release the cartridge 2000 from the applicator housing.

The control device 2036 may comprise a button that may be pressed by an individual or other body configured to be moved to release the carriage 2033. The control device 2036 may include a button surface 2038 and a control arm 2041 (marked in FIG. 173) extending from the button surface 2038.

The applicator 2002 may include a retraction actuator for retracting the needle 2019 from the individual's skin following insertion of the transcutaneous analyte sensor into the individual's skin. The retraction actuator may be configured similarly as the retraction actuator shown in FIG. 163. The retraction actuator accordingly may be configured to automatically operate upon the needle 2019 inserting the transcutaneous analyte sensor into the individual's skin.

Further, the carriage 2025 of the insertion actuator may include a releasable coupler 2040 (marked in FIG. 172) that is configured to couple to a coupling member 2042 of the applicator housing 2018. The releasable coupler 2040 may be positioned such that lateral movement of the control device 2036 causes the control arm 2041 to press against the releasable coupler 2040 to release the releasable coupler 2040.

A releasable coupler 2044 (marked in FIG. 172) may be coupled to a portion of the carriage of the retraction actuator. The releasable coupler 2044 may be configured to couple to the needle 2019. The releasable coupler 2044 may be configured such that sliding lateral movement of the needle 2019 may release the needle 2019 from the releasable coupler 2044, in a similar manner as discussed in regard to the releasable coupler 1948. The releasable coupler 2044 may be configured to retain the needle 2019 to the applicator housing 2018 following insertion of the transcutaneous analyte sensor 24 into the individual's skin and removal of the applicator housing 2018 from the transcutaneous analyte sensor 24, and configured to release the needle 2019 from within the applicator housing 2018 following insertion of the transcutaneous analyte sensor 24 into the individual's skin.

Referring to FIG. 171, the insertion actuator carriage 2025 may be coupled to a cocking device 2046. The cocking device 2046 may comprise a lever or other form of cocking device that may be manually pressed or otherwise manually operated. The cocking device 2046 may be configured to be manually operated to cock the insertion actuator and to provide energy to the actuator which may include providing energy to the driver 2034. The cocking device 2046 may compress the spring in an embodiment in which the driver 2034 is a spring. The cocking device 2046 may be coupled to the carriage 2025 of the insertion actuator and the cocking device 2046 may be configured to lift or otherwise move the carriage 2025 to compress the driver 2034. As shown in FIG. 171, the cocking device 2046 may extend along a slot on the side surface of the applicator housing 2018 and may protrude and extend outward from the applicator housing 2018.

The cocking device 2046 may be in an initial uncocked state as shown in FIG. 171 and may be manually moved to a cocked state as shown in FIG. 172 in which the cocking device 2046 cocks the actuator. The control device 2036 may be configured such that operation of the control device 2036 returns the cocking device 2046 to an uncocked state.

The operation of the applicator 2002 may be illustrated in FIGS. 169-173. Referring to FIG. 169, the cartridge 2000 may have the removable cover 2008 removed, and the electronics unit 26 may be inserted into the slot 2020 to couple with the wearable housing 108. The cartridge may then be inserted into the receiver 2028 of the applicator housing 2018 as shown in FIG. 170, with the rails 2014 of the cartridge 2000 sliding along the channels 2016 of the applicator housing 2018. The insertion actuator carriage 2025 may insert into the receiver 2022 of the inner cartridge body 2004. The cartridge 2000 may be coupled to the applicator housing 2018 by being inserted into the receiver 2028.

Referring to FIG. 171, with the cartridge 2000 positioned within the receiver 2028 of the applicator housing 2018, the cocking device 2046 may be manually moved to cock the insertion actuator. The insertion actuator may be manually cocked. Such cocking action may include compressing the driver 2034, and coupling the releasable coupler 2040 to the coupling member 2042 of the applicator housing 2018 as shown in FIG. 172. Further, such cocking action may compress a spring of a retraction actuator or otherwise provide energy to a driver of the retraction actuator, with the retraction actuator configured to retract the needle from the individual's skin.

Referring to FIG. 172, upon insertion of the cartridge 2000 into the receiver 2028, the releasable coupler 2044 may be coupled to the needle 2019 in a similar manner as shown in FIG. 164. An angled pressing surface 2048 within the inner cartridge body 2004 may press the releasable coupler 2044 downward upon the cartridge 2000 being inserted into the receiver 2028, to cause the releasable coupler 2044 to couple to the needle 2019.

The outer cartridge body 2006 is configured to be separated from the inner cartridge body 2004 prior to the actuator inserting the needle 2019 into the individual's skin. The outer cartridge body 2006 may be removed from the inner cartridge body 2004 and the receiver 2028 by being slid out of the receiver 2028 in an opposite direction from which the body 2006 was inserted. With the outer cartridge body 2006 removed, the needle 2019 and the on-skin applicator assembly is exposed to the bottom opening 2024 of the applicator housing 2018 for deployment to the individual's skin.

The control device 2036 may be activated by the individual to activate the insertion actuator. Referring to FIG. 173, the driver 2034 of the insertion actuator may drive the insertion actuator carriage 2025 downward to insert the needle 2019 and the transcutaneous analyte sensor 24 into the individual's skin. The driver 2034 may be configured to drive the needle 2019 into the individual's skin to insert the transcutaneous analyte sensor into the individual's skin with the cartridge remaining coupled to the applicator housing. An individual may leave the cartridge in the receiver of the applicator housing during such operation.

The retraction actuator, which may be configured similarly as the retraction actuator discussed in regard to the applicator 1902, may retract the needle 2019 from the individual's skin. The needle 2019 may remain coupled to the releasable coupler 2044 upon withdrawal of the applicator 2002 from the on-skin sensor assembly.

In a similar manner as discussed in regard to FIG. 166, the inner cartridge body 2004 may be removed from the receiver 2028 to withdraw the used needle 2019 from the applicator housing 2018. For instance, a needle hub of the needle 2019 may slide out from the releasable coupler 2044 to release from the releasable coupler 2044. The cartridge 2004 is configured to be withdrawn from the receiver 2028 through the side opening 2026 to release the needle 2019 from the releasable coupler 2044. The needle 2019 may be separated from the applicator housing by separating the cartridge 2004 from the applicator housing.

The cartridge 2000 is configured to retain the needle after the cartridge 2000 has been separated from the receiver and the needle has been inserted into the individual's skin.

The applicator 2002 may return to a state as shown in FIG. 170, to receive another cartridge 2000. The applicator 2002 accordingly may comprise a reusable applicator for receipt of multiple different cartridges 2000. The used cartridge 2000 and needle 2019 may be discarded.

In embodiments disclosed herein, the electronics unit 26 may be coupled to the wearable housing 108 of the on-skin sensor assembly either prior to deployment of the on-skin sensor assembly to the individual's skin or after deployment to the individual's skin. A variety of methods may be utilized to couple the electronics unit 26 to the wearable housing 108. FIGS. 174-187 illustrate methods that may be utilized.

FIG. 174 illustrates an embodiment of a wearable assembly 2100 in which the electronics unit 26 includes a coupler in the form of a clip 2102 at an end of the electronics unit 26. The wearable housing 108 of the wearable assembly 2100 includes a coupling member in the form of a post 2104 for coupling to the clip 2102. The electronics unit 26, with the clip 2102 coupled to the post 2104 may be configured to rotate about the post 2104 to have an opposite end of the electronics unit 26 couple to a latch 2106. Each of the couplers may be releasable as desired to allow the electronics unit 26 to be released from the wearable housing 108.

FIG. 175 illustrates an embodiment of a wearable assembly 2200 in which the electronics unit 26 includes a coupler in the form of a magnet 2202 and an opening 2204 at an end of the electronics unit 26. The wearable housing 108 of the wearable assembly 2200 includes a coupling member in the form of a magnet 2206 and a post 2208 for coupling to the magnet 2202 and opening 2204 respectively. The electronics unit 26, with the opening 2204 coupled to the post 2208 may be configured to rotate about the post 2208 to have an opposite end of the electronics unit 26 couple to a coupler in the form of a latch 2210. Each of the couplers may be releasable as desired to allow the electronics unit 26 to be released from the wearable housing 108.

FIG. 176 illustrates an embodiment of a wearable assembly 2300 in which the electronics unit 26 includes a coupler in the form of a magnet 2302 surrounding an opening 2304 at an end of the electronics unit 26. The wearable housing 108 of the wearable assembly 2300 includes a coupling member in the form of a magnet 2306 surrounding a post 2308 for coupling to the magnet 2302 and opening 2304 respectively. The electronics unit 26, with the opening 2304 coupled to the post 2308 may be configured to rotate about the post 2308 to have an opposite end of the electronics unit 26 couple to a coupler in the form of a latch 2310. Each of the couplers may be releasable as desired to allow the electronics unit 26 to be released from the wearable housing 108.

FIG. 177 illustrates an embodiment of a wearable assembly 2400 in which the electronics unit 26 includes a coupler in the form of an opening 2402 at an end of the electronics unit 26. The wearable housing 108 of the wearable assembly 2400 includes a coupling member in the form of a post 2404 for coupling to opening 2402. The electronics unit 26, with the opening 2402 coupled to the post 2404 may be configured to rotate about the post 2404 to have an opposite end of the electronics unit 26 couple to a coupler in the form of a latch 2406. Each of the couplers may be releasable as desired to allow the electronics unit 26 to be released from the wearable housing 108.

FIG. 178 illustrates an embodiment of a wearable assembly 2500 in which the electronics unit 26 includes a coupler in the form of a magnet at a central location in the electronics unit 26. The wearable housing 108 of the wearable assembly 2500 includes a coupling member in the form of a magnet 2502 for coupling to the magnet of the electronics unit 26. The electronics unit 26, may be configured to slide upon the wearable housing 108 to have the electronics unit 26 couple to a coupler in the form of a latch 2504. The electronics unit 26 may slide until contacting a wall 2506 of the wearable housing 108. Each of the couplers may be releasable as desired to allow the electronics unit 26 to be released from the wearable housing 108.

FIG. 179 illustrates an embodiment of a wearable assembly 2600 in which the electronics unit 26 includes a coupler in the form of an opening 2602 magnet at an end of the electronics unit 26. The wearable housing 108 of the wearable assembly 2600 includes a coupling member in the form of a tapered pin 2604 for coupling to the opening 2602 of the electronics unit 26. The electronics unit 26, may be configured to rotate upon the wearable housing 108 to have an opposite end of the electronics unit 26 couple to a coupler in the form of a latch 2606. Each of the couplers may be releasable as desired to allow the electronics unit 26 to be released from the wearable housing 108.

FIG. 180 illustrates an embodiment of a wearable assembly 2700 in which the electronics unit 26 includes a coupler in the form of an opening 2702 and a magnet 2704 at an end of the electronics unit 26. The wearable housing 108 of the wearable assembly 2700 includes a coupling member in the form of a magnet 2706 and a post 2708 for coupling to the magnet 2704 and opening 2702 of the electronics unit 26. The electronics unit 26, may be configured to rotate upon the wearable housing 108 to have an opposite end of the electronics unit 26 couple to a coupler in the form of a latch 2710. The latch 2710 may be a releasable latch 2710, operable by pressing the lever 2712. Each of the couplers may be releasable as desired to allow the electronics unit 26 to be released from the wearable housing 108.

FIG. 181 illustrates an embodiment of a wearable assembly 2800 in which the electronics unit 26 includes a coupler in the form of an opening 2802 at an end of the electronics unit 26. The wearable housing 108 of the wearable assembly 2800 includes a coupling member in the form of a post 2804 for coupling to the opening 2802 of the electronics unit 26. The electronics unit 26, may be configured to rotate upon the wearable housing 108 to have an opposite end of the electronics unit 26 couple to a coupler in the form of a latch 2806. The latch 2806 may be a releasable latch 2806, operable by pressing a lever that is similar to lever 2712. Each of the couplers may be releasable as desired to allow the electronics unit 26 to be released from the wearable housing 108.

FIG. 182 illustrates an embodiment of a wearable assembly 2900 in which the electronics unit 26 includes a coupler in the form of a plurality of magnets 2902, 2904 in a central portion of the electronics unit 26. The wearable housing 108 of the wearable assembly 2900 may include a coupling member in the form of magnets of correspondingly opposite polarity for coupling with the magnets 2902, 2904. The electronics unit 26 may be configured lock to the wearable housing 108 by way of a coupler in the form of a lock arm 2906 that pivots to cover a portion of the electronics unit 26. Each of the couplers may be releasable as desired to allow the electronics unit 26 to be released from the wearable housing 108.

FIG. 183 illustrates an embodiment of a wearable assembly 3000 in which the electronics unit 26 includes a coupler in the form of a magnet 3002 in a central portion of the electronics unit 26. The wearable housing 108 of the wearable assembly 3000 may include a coupling member in the form of a magnet of correspondingly opposite polarity for coupling with the magnet 3002. The electronics unit 26 may be configured lock to the wearable housing 108 by way of a coupler in the form of two lips 3004, 3006 that extend over a portion of the wearable housing 108 as the wearable housing 108 rotates to couple to the electronics unit 26. Each of the couplers may be releasable as desired to allow the electronics unit 26 to be released from the housing 108.

FIG. 184 illustrates an embodiment of a wearable assembly 3100 in which the electronics unit 26 includes a coupler in the form of a magnet 3102 in a central portion of the electronics unit 26. The wearable housing 108 of the wearable assembly 3100 may include a coupling member in the form of a magnet of correspondingly opposite polarity for coupling with the magnet 3102. The electronics unit 26 may be configured lock to the wearable housing 108 by way of a coupler in the form of a lips 3104 that extend over a portion of the wearable housing 108 as the electronics unit 26 slides to couple to the electronics unit 26. Each of the couplers may be releasable as desired to allow the electronics unit 26 to be released from the wearable housing 108.

FIG. 185 illustrates an embodiment of a wearable assembly 3200 in which the electronics unit 26 includes a coupler in the form of a plurality of magnets 3202, 3204 at ends of the electronics unit 26. The wearable housing 108 of the wearable assembly 3200 may include a coupling member in the form of a plurality of magnets of correspondingly opposite polarity for coupling with the magnets 3202, 3204 and for aligning the electronics unit 26 in the desired orientation on the wearable housing 108. The electronics unit 26 may be configured to lock to the wearable housing 108 by way of a coupler in the form of a rail, which as shown in FIGS. 186 and 187 may include a dove tail shaped rail 3206a and a t-slot shaped rail 3206b, inserted into correspondingly shaped channels in the electronic unit 26. Each of the couplers may be releasable as desired to allow the electronics unit 26 to be released from the wearable housing 108.

FIG. 188 illustrates an embodiment of a cartridge 3300 having a body 3302 configured to be coupled to an applicator housing of a transcutaneous analyte sensor applicator. The body 3302 may include a bottom cavity 3304 marked in FIG. 189 that is configured to receive another body 3306 (marked in FIG. 190) that has a same shape as the body 3302 to stack the body 3302 upon the body 3306.

The cartridge 3300 may include a cover 3308 comprising a lid or seal of the body 3302. The cover 3308 may cover an upper opening 3310 of the body 3302 and cover the contents of the upper cavity 3312 (marked in FIG. 189) of the body 3302 retaining the transcutaneous analyte sensor, the needle configured to insert the transcutaneous analyte sensor into the skin of an individual, and may include a wearable housing and patch as disclosed herein.

Referring to FIG. 189, the body 3302 may have a bottom surface 3314 that is wider than an upper surface 3316 of the body 3302. The body 3302 may have a trapezoidal shape in embodiments, or may have another shape as desired. The bottom cavity 3304 may be shaped to receive another cartridge, which may be similarly shaped as the cartridge 3300. For example, referring to FIG. 190, the cartridge 3300 may stack upon the other cartridge 3307, with the body 3306 of the other cartridge 3307 fitting into the bottom cavity 3304. Thus, space saving may be realized, as the cartridges 3300, 3307 may be stacked to reduce the total size of the combination. Multiple other cartridges may be stacked as well.

Any embodiment of cartridge disclosed herein may comprise a stackable cartridge as desired.

FIG. 191 illustrates an embodiment of a kit or system 3400 that may be utilized for storage or transport of a transcutaneous analyte sensor applicator and cartridges according to embodiments herein. A case 3402 may be utilized including an area 3404 for receiving an applicator housing 3406, which may comprise any form of applicator housing as disclosed herein. The area 3404 may comprise a cavity or other receiving area in embodiments. The case 3402 may include an area 3408 for receiving another component of the applicator system, such as a sharps container 3410 for retaining used needles. The sharps container 3410 may comprise a convenient receptacle for used needles. In embodiments, a cover 3412 may be provided for the case 3402.

Other components may be stored, including cartridges 3414 that may be utilized with the applicator housing 3406. The cartridges 3414 in embodiments may be stackable, as disclosed herein and/or may be configured to fit into a case 3416 for the cartridges 3414. The case 3416 may include areas 3418 for receiving the cartridges 3414. In embodiments, a single case may be provided for all components.

FIGS. 192-195 illustrate embodiments of covers for cartridges that may be utilized in embodiments herein. FIG. 192, for example, illustrates a container 3500 for a cartridge 3502, in which the container 3500 includes a removable cover 3504 or lid. The cover 3504 may be removed to access the cartridge 3502 within the container 3500.

FIG. 193, for example illustrates a cartridge 3510 having a cover 3512 with two sides connected. An upper cover 3514 may cover an upper opening of the cartridge 3510 and a lower cover 3516 may cover a lower opening of the cartridge 3510. A connecting portion 3518 may couple the upper cover 3515 to the lower cover 3516 such that removal of one of the covers 3514, 3516 removes both covers 3514, 3516 at the same time. Thus, an ease of use and time saving may be realized.

FIGS. 194-195 illustrate an embodiment of a cartridge 3520 including a cover 3522 in the form of a puncturable layer. The cartridge 3520 may be inserted into a receiver of an applicator housing and the cover 3522 may be punctured upon insertion. As such, no cover 3522 is manually removed by the individual. Rather, the cover 3522 is automatically punctured upon insertion into a receiver.

The embodiments of covers may be utilized with any embodiment of cartridge herein.

FIG. 196 illustrates an embodiment of an applicator 3600 that may be utilized according to embodiments of applicators herein. A cover 3602 may be provided for the bottom surface of the applicator 3600 that covers the bottom opening of the applicator 3600. As such, access to the receiver of the applicator 3600 may be blocked in embodiments. For use, the cover 3602 may be removed by an individual.

Any embodiment of applicator disclosed herein may utilize a cover over a portion of the applicator.

FIG. 197 illustrates an embodiment of an applicator 3700 and an embodiment of a cartridge 3702 that may be utilized according to embodiments herein. The applicator 3700 may include a tactile indictor 3704 on an outer surface of the applicator 3700 that may be configured to indicate a position of a feature or component of the applicator 3700. The tactile indicator 3704, for example, may indicate a position of a control device 3706 that may be operated to perform a function of the applicator 3700, for example, an insertion or release operation of the applicator 3700, among others. The tactile indicator 3704 may allow the user to feel the indicator 3704 to determine the location of the feature or component of the applicator 3700, such as a control device 3706. The tactile indicator 3704 may have a variety of forms, for example, the tactile indicator 3704 may comprise a roughened outer surface of the applicator housing as shown in FIG. 197. The roughened outer surface may indicate a position of the control device 3706. The tactile indicator 3704 may have other forms such as a slick portion of the applicator housing, or a series of raised characters on the applicator housing, among other forms.

The cartridge 3702 may include a tactile indicator 3708 that may have a similar configuration as the tactile indicator 3704 of the applicator 3700, or may have a different configuration. The tactile indicator 3708 may be positioned on an outer surface of the cartridge 3702 and may indicate a feature or component of the cartridge, such as a keyed portion of the cartridge used to align with a receiver of the applicator (a keyed portion of a cartridge being shown in FIG. 198 for example).

The tactile indicator 3708 may indicate other features or components of the cartridge 3702 as desired, and may be felt by a user to determine the location of such features or components. The tactile indicator 3708 may have a variety of forms, for example, the tactile indicator 3708 may comprise a roughened outer surface of the cartridge as shown in FIG. 197, or may have other forms as discussed in regard to the applicator 3700, for example. Any embodiment of applicator or cartridge, or other feature of a system, disclosed herein may include a tactile indicator.

FIGS. 198-214 illustrates a variation of the embodiments of FIGS. 93-106. In the embodiments of FIGS. 198-214, a release actuator may be utilized in the applicator system. Other modifications of the embodiments of FIGS. 93-106 may be provided.

FIG. 198 illustrates an assembly view of a cartridge 3800 that may be utilized. The cartridge 3800 may be configured similarly as other cartridges disclosed herein, and may include a body 3802 having a base 3804 and a wall 3806 surrounding a cavity 3808 for receiving the on-skin sensor assembly 3810. The cartridge 3800 may be configured to be inserted into an applicator housing and may retain a transcutaneous analyte sensor. The cartridge 3800 may include a body configured to be coupled to an applicator housing and may include a retainer retaining the transcutaneous analyte sensor and a wall extending around at least a portion of the transcutaneous analyte sensor.

The cartridge 3800 may include one or more coupling members in the form of coupling surfaces 3812 that may be configured to couple to one or more coupling members 3814 of the needle hub 3816. The coupling surfaces 3812, for example, may engage the coupling members 3814 of the needle hub 3816 by forming a ledge that the coupling members 3814 are positioned under.

The cartridge 3800 may include a keyed portion 3818, similar to other embodiments of cartridges disclosed herein. The keyed portion 3818 may be configured to align the cartridge 3800 with a receiver of the applicator housing in a single rotational orientation. For example, the keyed portion 3818 may comprise one or more of a protrusion 3820 or a flattened portion 3822 that may be utilized to align with a corresponding shape of a receiver. The use of the keyed portion 3818 may reduce the possibility of misinsertion of the cartridge into the receiver of the applicator housing. Any embodiment of cartridge 3800 disclosed herein may include a keyed portion.

The needle hub 3816 may include multiple components including a needle cover 3824 and a rotating body 3826. The rotating body 3826 may couple to the proximal portion of the needle 3828 and may couple to the needle cover 3824 at the proximal portion of the needle 3828. The rotating body 3826 may include a pivot 3830 that couples to the needle cover 3824 and allows the rotating body 3826 to rotate with respect to the needle cover 3824. The rotating body 3826 may include a locking surface 3832 that is configured to engage a lock 3834 (marked in FIG. 212) of the needle cover 3824 upon rotation of the rotating body 3826 and the needle 3828 relative to the needle cover 3824. The lock 3834 may lock the needle 3828 in position within the needle cover 3824.

The needle cover 3824 may be configured to rotate relative to the needle 3828 to extend over at least the portion of the needle 3828. The needle 3828 is configured to be moved relative to the needle cover 3824 to be positioned into the needle cover 3824. The needle cover 3824 may include a channel 3836 (marked in FIG. 212) that is configured to receive the needle 3828 upon the needle 3828 rotating into the needle cover 3824. The channel 3836 may extend along the length of the body of the needle cover 3824. Further, the needle cover 3824 may include a channel 3838 that is configured for a deflection surface 3840 (marked in FIG. 210) to pass through to rotate the needle 3828. The channel 3838 may extend vertically or transverse with respect to the horizonal length of the needle cover 3824. The channel 3838 for the deflection surface 3840 may extend perpendicular with respect to the needle channel 3836. An insertion carriage 3900 shown in FIG. 203 may include the deflection surface 3840 that may be utilized to deflect the rotating body 3826 upon retraction of the needle 3828.

The needle cover 3824 may be configured to extend along the plane of the patch 3842 and along the plane of the wearable housing 3844 when positioned within the cartridge 3800. The length of the needle cover 3824 may extend along the plane of the opening 3847 (marked in FIG. 204) of the applicator housing. The needle 3828 may be configured to extend at an angle, transverse and perpendicular, with respect to the needle cover 3824 when positioned within the cartridge 3800. The needle 3828, for example, may extend within a cavity 3846 (marked in FIG. 198) of the cartridge 3800 for receiving the needle 3828.

The needle cover 3824 may include opposite ends having coupling members 3814. Each of the coupling member 3814 may be configured to engage the coupling surfaces 3812 of the cartridge 3800 to retain the needle cover 3824 and the on-skin sensor assembly 3810 within the cartridge 3800 prior to insertion of the cartridge 3800 into the applicator housing. The coupling members 3814 may comprise deflectable arms configured to deflect inward with respect to the needle cover 3824 to allow the coupling members 3814 to disengage from the coupling surfaces 3812 of the cartridge 3800. Each of the coupling members 3814 may be biased to deflect outward with respect to the needle cover 3824 to retain engagement between the coupling member 3814 and the coupling surfaces 3812 of the cartridge 3800. Each of the coupling members 3814 may include one or more protrusions 3849 that may be configured to engage a releasable coupler of an applicator.

A pull tab 3848 may be positioned within the cartridge 3800 and may be configured to couple to the needle hub 3816 of the needle 3828. The pull tab 3848 may be configured to be pulled to release the needle 3828 from the releasable couplers 3890, 3892 shown in FIG. 203.

The pull tab 3848 may have a ring configuration and may be configured to extend circumferentially about the wearable housing 3844 of the on-skin sensor assembly 3810. The pull tab 3848 may be positioned upon the patch 3842, although other locations may be provided in embodiments. The pull tab 3848 may have a folded configuration, with a first portion 3850 folded upon a second portion 3852 to form a crescent shape as shown in FIG. 198. The pull tab 3848 may be configured to unfold at a desired time to form a ring for grasping by a user. The pull tab 3848 may include a coupling portion 3845 for a screw 3851 or other form of coupler to pass through, for the pull tab 3848 to couple to the needle hub 3816.

FIG. 199 illustrates the on-skin sensor assembly 3810 positioned within the cartridge 3800. The coupling members 3814 of the needle cover 3824 engage the coupling surfaces 3812 of the cartridge 3800. The pull tab 3848 is in a folded configuration positioned circumferentially about the applicator housing 3844.

Referring to FIG. 200, in embodiments, the needle hub and needle cover may include one or more releasable couplers 3854 that may be configured to engage the wearable housing 3844 to retain the wearable housing 3844 to the needle hub 3816. FIG. 200, for example, illustrates a configuration of a needle hub 3856 including such releasable couplers 3854. In embodiments, the releasable couplers 3854 may be included or excluded as desired.

FIG. 200 illustrates an embodiment of a pull tab 3858 that may be configured similarly as the pull tab 3848 yet including a looped coupling portion 3861 that may be configured to hook onto a coupler 3859 of the needle hub 3856. FIG. 201 illustrates the coupling of the pull tab 3858 to the needle hub 3856. FIG. 202 illustrates an assembly step in which the pull tab 3858 may be folded to form a crescent shape. The first portion 3860 may be folded upon the second portion 3862 with the first portion 3860 and second portion 3862 positioned on opposite sides of the coupling member 3814. The rotating body 3826 of the needle hub 3856 may be inserted into the needle cover 3824, with the pivot 3830 inserting into the aperture 3863 shown in FIG. 202. The needle hub 3856 coupled to the pull tab 3858 may be inserted into the cartridge 3800 over the wearable housing 3844 of the on-skin sensor assembly 3810, in a configuration shown in FIG. 199, for example.

In embodiments, a cover may be positioned over the upper opening 3864 (marked in FIG. 199) of the cartridge 3800 to seal the contents of the cartridge, similar to other embodiments of cartridges disclosed herein.

FIG. 203 illustrates components of an applicator 3870 that may be utilized. The applicator 3870 may include an applicator housing 3872 that may have an outer housing 3874 and an interior housing 3876. The applicator housing 3872 may be configured to be gripped by an individual to apply the transcutaneous analyte sensor into the individual's skin. The applicator housing may include a side portion, a top portion and a bottom portion including an opening 3847 (marked in FIG. 204) for the transcutaneous analyte sensor to be deployed from to be inserted into the individual's skin. The receiver of the applicator housing may be configured to receive the cartridge 3800 through the opening of the bottom portion.

The outer housing 3874 may comprise an outer surface of the applicator 3870, and may include a control device 3878 that may be activated to cause the transcutaneous analyte sensor of the on-skin sensor assembly 3810 to be inserted into the individual's skin. The control device 3878 may be operated by an individual. For example, the control device 3878 may comprise a button that is pressed to activate an insertion actuator of the applicator 3870.

The interior housing 3876 may be positioned within the outer housing 3874 and may include a central cavity 3880 (marked in FIG. 204) for components of the applicator 3870 to be positioned within. The interior housing 3876 may include an outer surface 3881 including an aperture 3882 for a releasable coupler 3884 to pass through, to hold the assemblies in position relative to the interior housing 3876. The interior housing 3876 may further include an upper surface 3883 configured for biasing members 3886 in the form of springs, and particularly coil springs configured to bias the interior housing 3876 downward with respect to the outer housing 3874 of the applicator. The interior housing 3876 may include the lower opening 3847 at a bottom surface of the interior housing 3876 for the transcutaneous analyte sensor, and the needle 3828 and wearable housing 3844 to be deployed from.

FIG. 203 illustrates a perspective view of a first carriage 3888 that may comprise a retraction carriage for retracting the needle 3828 from the individual's skin following insertion of the needle 3828. The carriage 3888 may include releasable couplers 3890, 3892 that engage the needle hub of the needle, to withdraw the needle from the individual's skin following insertion into the individual's skin. The releasable couplers 3890, 3892, for example, may be configured to engage the protrusions 3849 of the coupling members 3814 shown in FIGS. 198 and 200 to couple to the needle hub and the needle.

One or more of the releasable couplers 3890, 3892 may be configured to retain a needle to the applicator housing following insertion of the transcutaneous analyte sensor into the individual's skin and removal of the applicator housing from the transcutaneous analyte sensor, and release the needle from within the applicator housing following insertion of the transcutaneous analyte sensor into the individual's skin. The one or more releasable couplers 3890, 3892 may be configured to couple to the needle hub of the needle.

The releasable coupler 3890 may be a static or non-rotating releasable coupler 3890 and the releasable coupler 3892 may be configured to rotate to couple or uncouple from the needle hub. The releasable coupler 3892 may be configured to rotate to hook onto or release from the needle hub of the needle. The releasable coupler 3892, for example, may be pivotally coupled to the carriage 3888. The releasable coupler 3892 may include one or more hooks 3894 for coupling to the needle hub and may include one or more deflection surfaces 3896 configured to be contacted to rotate the releasable coupler 3892 into a desired position. The insertion carriage may include a guide channel 3898 (marked in FIG. 210) that the deflection surface 3896 slides along to deflect the deflection surface 3896 and rotate the releasable coupler 3892 into a desired position.

The guide channel 3898 and deflection surfaces 3896 may comprise a release actuator configured to release the needle and the needle cover 3824 from the releasable coupler 3892. The release actuator may release the needle from the releasable coupler 3892 to allow the needle to be passed through the opening 3847 marked in FIG. 204. The release actuator may be configured to release the needle covered by the needle cover 3824 from the applicator housing following insertion of the needle into the individual's skin.

Referring to FIG. 203, the first carriage 3888 may further include coupler releases in the form of deflectors 3899 configured to release a coupler to allow the first carriage 3888 to move relative to the insertion carriage 3900. The deflectors 3899, for example, may be configured to deflect the releasable couplers 3902 of the insertion carriage 3900 shown in FIG. 204 to release the carriages 3888, 3900 from each other. The releasable couplers 3902 may release to allow the driver 3918 to move the carriages 3888, 3900 away from each other. The releasable couplers 3902 may be configured to resist the force of the driver 3918. The releasable couplers 3902 may be configured to automatically release upon contact with the coupler release. The first carriage 3888 may further include protrusions 3904 that retain the first carriage 3888 to the second carriage 3910.

The second carriage 3910 may include support surfaces 3912 for the protrusions 3904 to contact to keep the carriages 3888, 3910 engaged with each other. The second carriage 3910 may further include support surfaces 3914 for the releasable couplers 3902 shown in FIG. 204 to engage with. The second carriage 3910 may further include a central channel 3915 for the first carriage 3888 to be positioned within.

The insertion carriage 3900 may include the releasable couplers 3902 for engaging with the support surface 3914 of the second carriage 3910. The insertion carriage 3900 may comprise a component of an actuator or insertion actuator that may be coupled to the applicator housing and configured to insert a needle and the transcutaneous analyte sensor into the individual's skin. The insertion carriage 3900 may be configured to slide relative to the applicator housing and configured to be slid by the driver 3916.

The insertion carriage 3900 may further include a releasable coupler 3884 for engaging with the interior housing 3876 of the applicator, and particularly with an aperture 3882 of the interior housing 3876. The insertion carriage 3900 may include a central channel 3919 (marked in FIG. 204) for the carriages 3888, 3910 to be positioned within.

The applicator 3870 may further include a driver 3916 in the form of springs configured to drive the entire assembly of carriages, including the insertion carriage 3900 downward to drive the needle into the individual's skin to insert the transcutaneous analyte sensor into the individual's skin. The applicator 3870 may further include a driver 3918 in the form of springs configured to retract the carriages 3888, 3910 to retract the needle from the individual's skin following deployment. The applicator 3870 may further include a spring 3920 that biases the first carriage 3888 away from the second carriage 3910.

In assembly, the first carriage 3888 may be positioned within the channel 3915 of the second carriage 3910, and the carriages 3888, 3910 may be positioned within the central channel 3919 of the insertion carriage 3900. The assembly may be positioned within the interior housing 3876 shown in FIG. 204.

FIG. 204 illustrates a three-quarters cross sectional perspective view of the applicator 3870, including carriages 3900, 3888, 3910 assembled and positioned within the interior housing 3876. The interior housing 3876 may be positioned within the outer housing 3874 and may be configured to slide within the outer housing 3874. The biasing members 3886 (marked in FIG. 203), for example, may press against the interior surface of the top of the outer housing 3874 to bias the interior housing 3876 towards the lower opening 3847. A force applied upwards against the interior housing 3876, by the skin of an individual, for example, may move the interior housing 3876 upwards within the outer housing 3874.

FIGS. 204-214 illustrate steps of a method that may utilize the applicator 3870. Referring to FIG. 204, in the initial configuration, the interior housing 3876 may be biased downward with respect to the outer housing 3874 via the biasing members 3886 shown in FIG. 203. Further, the releasable coupler 3884 may be disengaged with the aperture 3882, and the driver 3916 may drive the carriage 3900 to be positioned downward at this point. The releasable coupler 3902 may not yet be engaged with the support surface 3914 at this point.

The releasable coupler 3892 may be rotated radially outward in the initial state shown in FIG. 204.

The cartridge 3800 may be inserted into the receiver of the applicator 3870. Upon initial insertion, a configuration as shown in FIG. 205 may result. The cartridge 3800 may be inserted to contact the insertion carriage 3900 and drive the insertion carriage 3900 upward. The driver 3916 may be compressed. The releasable coupler 3884 may move in a direction to engage the aperture 3882 of the interior housing 3876.

The cartridge 3800 may be inserted into the applicator housing to provide energy to the insertion actuator and the retraction actuator. The force applied by the cartridge 3800 to the insertion and retraction actuators may provide energy to the insertion and retraction actuators. The insertion of the cartridge 3800 may provide energy to the drivers 3916, 3918. In an embodiment in which the drivers 3916, 3918 comprise springs, the insertion of the cartridge into the receiver may compress the springs. The cartridge 3800 may include a pressing surface for pressing against the insertion and retraction actuators for providing energy to the actuators.

The releasable coupler 3892 may be rotated radially inward as shown in FIG. 205, such that the releasable coupler 3892 is oriented axially or vertically within the applicator. Referring to FIG. 210, such movement may be caused by the guide channel 3898 applying a force to the deflection surfaces 3896 of the releasable coupler 3892 to orient the releasable coupler 3892 axially or vertically. The upward movement of the insertion carriage 3900 may produce the rotation of the releasable coupler 3892 via contact between the guide channel 3898 and the deflection surfaces 3896 of the releasable coupler 3892.

Referring to FIG. 206, the cartridge 3800 may continue to be inserted until the releasable couplers 3890, 3892 (shown in FIG. 203) of the first carriage 3888 fully engage the coupling members 3814 of the needle and needle hub 3856 (marked in FIG. 200). The coupling members 3814 of the needle hub 3856 may deflect inward to allow the releasable couplers 3890, 3892 to couple to and hook around the protrusions 3849 of the coupling members 3814. Further, the inward deflection of the coupling members 3814 may decouple the coupling members 3814 from the coupling surfaces 3812 of the cartridge 3800 shown in FIG. 199. As such, the needle and needle hub 3856 may be released from the cartridge 3800 and coupled to the first carriage 3888. The coupling of the releasable couplers 3854 of the needle hub 3856 (marked in FIG. 200) to the wearable housing 3844 may retain the on-skin sensor assembly 3810 to the carriage 3888. The cartridge 3800 accordingly may be withdrawn from the receiver of the applicator 3870 with the on-skin sensor assembly 3810 retained by the first carriage 3888 as shown in FIG. 207.

Referring to FIG. 206, the releasable coupler 3884 may fully engage the aperture 3882 of the interior housing 3876. The releasable coupler 3902 of the insertion carriage 3900 may engage the support surface 3914 of the second carriage 3910 to couple the insertion carriage 3900 to the first and second carriages 3888, 3910.

The cartridge 3800 may be removed from the applicator housing prior to the needle being inserted into the individual's skin to insert the transcutaneous analyte sensor into the individual's skin.

With the cartridge 3800 withdrawn, the interior housing 3876 may be biased downward away from the top of the outer housing 3874. In such a configuration, the releasable coupler 3884 of the insertion carriage 3900 may be offset from the position of the control device 3878, such that pressing the control device 3878 does not actuate insertion of the needle 3828. Such a feature may serve as a safety feature to reduce the possibility of inadvertent actuation of the needle 3828 prior to a desired time (at which the bottom surface 3922 of the interior housing 3876 does not yet contact the individual's skin).

FIG. 207 illustrates a configuration of the applicator 3870 if the bottom surface 3922 of the interior housing 3876 were in contact with the individual's skin to overcome the bias of the biasing members 3886. In such a configuration, the position of the releasable coupler 3884 may be moved upwards to align with the control device 3878. As such, movement of the control device 3878 may result in the releasable coupler 3884 being pressed to release the insertion carriage 3900 from the interior housing 3876 and allow the driver 3916 to drive the carriages 3900, 3910, 3888 downward.

FIG. 208, for example, illustrates the control device 3878 having been pressed to release the releasable coupler 3884 from the aperture 3882 of the interior housing 3876. The driver 3916 drives the carriages 3900, 3910, 3888 downward to press the needle 3828 into the individual's skin to deploy the transcutaneous analyte sensor into the individual's skin. The insertion carriage 3900 may remain coupled to the carriages 3910, 3888 by the releasable coupler 3902 remaining coupled to the support surfaces 3914.

The carriages 3900, 3910, 3888 may continue to be driven downward until contact occurs between the on-skin sensor assembly 3810 and the individual's skin. FIG. 209, for example, illustrates a position representing contact between the on-skin sensor assembly 3810 and an individual's skin. FIG. 210 illustrates a cross sectional view of contact between the on-skin sensor assembly 3810 and the individual's skin.

Referring to FIG. 209, upon contact between the on-skin sensor assembly 3810 and the individual's skin, the first carriage 3888 may displace relative to the second carriage 3910, with the second carriage 3910 moving downward relative to the first carriage 3888. The releasable coupler 3902 may move relative to the first carriage 3888, and particularly the deflection surfaces 3899 of the first carriage 3888 may push the releasable coupler 3902 outward away from the support surfaces 3914 and off of the support surfaces 3914. The driver 3918 may drive the carriages 3910, 3888 upward relative to the insertion carriage 3900 and may pull the needle 3828 upward by way of the coupling of the coupling member 3814 of the needle hub 3856 with the releasable couplers 3890, 3892.

FIG. 211, for example, illustrates the carriages 3910, 3888 being pressed upward by the driver 3918, and away from the insertion carriage 3900.

Referring to FIG. 212, the rotating body 3826 of the needle hub 3856 may be contacted by the deflection surface 3840 of the insertion carriage 3900 to cause the rotating body 3826 to rotate the needle 3828 into the needle cover 3824. The needle cover 3824 may contact the deflection surface 3840, such that the retraction actuator comprising the carriages 3888, 3910 and the driver 3918 rotates the needle 3828 into the needle cover 3824. The driver 3918 may drive the needle out of the individual's skin. The driver 3918 may slide the carriages 3888, 3910 relative to the applicator housing. The retraction actuator may retract the needle from the individual's skin following insertion of the transcutaneous analyte sensor into the individual's skin. The retraction actuator may be configured to automatically operate upon the needle inserting the transcutaneous analyte sensor into the individual's skin. The retraction actuator may position the needle 3828 into the needle cover 3824, and may rotate the needle 3828 into the needle cover 3824.

The lock 3834 may lock the needle 3828 into the needle cover 3824.

The retraction actuator of the applicator 3870 may be configured to activate based on a force of contact with the individual's skin at a deployment site of the transcutaneous analyte sensor. The retraction actuator of the applicator 3870 may activate at the point of contact with the individual's skin. For example, if the individual's skin protrudes into the receiver of the applicator housing then the retraction actuator may activate at the position of the individual's skin rather than at a defined position relative to the applicator. This feature may be beneficial in a case where skin protrudes greatly into the receiver of the applicator, to allow for the retraction actuator to activate due to the force of contact with the individual's skin and thus at the position of the individual's skin.

The retraction actuator may operate based on the insertion carriage 3900 over traveling with respect to the first carriage 3888. The insertion carriage 3900 may displace relative to the first carriage 3888 based on contact with the individual's skin to operate the release actuator. The downward movement of the first carriage 3888 may be impeded by contact with the individual's skin, thus causing the insertion carriage 3900 to move downward relative to the first carriage 3888 and displacing relative to the first carriage 3888. Such displacement may cause the release of the releasable coupler 3902 and the retraction of the needle 3828, due to the release of the releasable couplers 3902.

The rotatable releasable coupler 3892 may be retracted relative to the insertion carriage 3900 and along the guide channel 3898 to a position of the guide channel 3898 that allows the rotatable releasable coupler 3892 to rotate outward with respect to the coupling member 3814 of the needle hub 3856. As such, the outward biasing force of the coupling member 3814 may push the rotatable releasable coupler 3892 outward to allow the releasable coupler 3892 to decouple from and unhook from the coupling member 3814. The releasable coupler 3892 may release the needle 3828 positioned within the needle cover 3824 from within the applicator housing. The needle 3828 may be separated from the applicator housing.

The pull tab (not shown in FIG. 212) may remain coupled to the needle hub 3856 and may descend or be otherwise be accessible by a user to pull on the needle hub 3856 with the needle 3828 locked therein.

FIG. 213, for example, illustrates the applicator 3870 having been withdrawn from the individual's skin with the pull tab 3858 dangling from the receiver of the applicator housing and accessible for a user to pull. The pull tab 3858 may unfold into a ring shape and may be positioned downward of the lower opening of the applicator housing. The rotatable releasable coupler 3892 may be decoupled from the needle hub 3856 to allow for a pull force on the pull tab 3858 to release the needle hub 3856 from the applicator 3870. The needle hub 3856 may rotate out of the applicator 3870, with the coupling member 3814 that was coupled to the rotatable releasable coupler 3892 releasing prior to the coupling member 3814 coupled to the opposite static releasable coupler 3890 shown in FIG. 203.

FIG. 214, for example, illustrates a user grasping the pull tab 3858 to pull the unit of the used needle, covered by the needle cover 3824 of the needle hub 3816, out of the applicator 3870.

In embodiments, the applicator system of FIGS. 198-214 may be modified to allow for a user to operate the release actuator with a control device. The control device may comprise a device such as a button that may be pushed by a user to operate the release actuator. In an embodiment as shown in FIGS. 215-223, the control device may be configured to be operated in a first operation to activate an insertion actuator configured to insert a needle into the individual's skin, and may be configured to be operated in a second operation following the first operation to activate the release actuator.

FIG. 215, for example, illustrates components of an applicator 4000 that may be utilized. The applicator 4000 may be configured similarly as the applicator 3870 of FIGS. 198-214 unless indicated or stated otherwise. The applicator 4000 may include an applicator housing 4002 that may have an outer housing 4004 with a top cover 4006 and may include an interior housing 4008.

The applicator housing 4002 may be configured to be gripped by an individual to apply the transcutaneous analyte sensor into the individual's skin. The applicator housing may include a side portion, a top portion and a bottom portion including an opening 4014 (marked in FIG. 216) for the transcutaneous analyte sensor to be deployed from to be inserted into the individual's skin. The receiver of the applicator housing may be configured to receive a cartridge through the opening of the bottom portion.

The outer housing 4004 may comprise an outer surface of the applicator 4000 and may include an aperture 4009 configured for a control device 4010 to pass through.

The interior housing 4008 may be positioned within the outer housing 4004 and may include a central cavity 4012 (marked in FIG. 216) for components of the applicator 4000 to be positioned within. The interior housing 4008 may be configured to be biased away from the outer housing 4004 via the force of biasing members such as leaf springs or coil springs that may press against the top cover 4006 and bias the interior housing 4008 downward.

The interior housing 4008 may include the lower opening 4014 at a bottom surface of the interior housing 4008 for the transcutaneous analyte sensor, and the needle and housing of the on-skin sensor assembly to be deployed from.

FIG. 215 illustrates a perspective view of a first carriage 4016 that may comprise a retraction carriage for retracting the needle from the individual's skin following insertion of the needle. The first carriage 4016 may be configured similarly as the first carriage 3888 shown in FIG. 203, including use of a static or non-rotating releasable coupler 4017 and a rotatable releasable coupler 4018. The static releasable coupler 4017 and the rotatable releasable coupler 4018 may be configured similarly as the respective releasable couplers 3890, 3892 shown in FIG. 203.

One or more of the releasable couplers 4017, 4018 may be configured to retain a needle to the applicator housing following insertion of the transcutaneous analyte sensor into the individual's skin and removal of the applicator housing from the transcutaneous analyte sensor, and release the needle from within the applicator housing following insertion of the transcutaneous analyte sensor into the individual's skin. The one or more releasable couplers 4017, 4018 may be configured to couple to the needle hub of the needle.

The first carriage 4016 may include a central channel 4020 that a slide body 4022 of a release actuator may be positioned within. The central channel 4020 may be configured to allow the slide body 4022 to slide therein to press against the needle hub of a used needle to eject the used needle from the applicator 4000.

The first carriage 4016 may further include coupler releases in the form of deflectors 4024 configured to release a coupler to allow the carriage 4016 to move relative to the insertion carriage 4026. The deflectors 4024, for example, may be configured to deflect the releasable couplers 4028 of the insertion carriage 4026 shown in FIG. 216 to release the carriages 4016, 4026 from each other. The releasable couplers 4028 may release to allow the driver 4048 to move the carriages 4026, 4032 away from each other. The releasable couplers 4028 may be configured to resist the force of the driver 4048. The releasable couplers 4028 may be configured to automatically release upon contact with the coupler release.

The first carriage 4016 may further include protrusions 4030 that retain the first carriage 4016 to the second carriage 4032.

The second carriage 4032 may include support surfaces 4034 for the protrusions 4030 to contact to keep the carriages 4032, 4016 engaged with each other. The second carriage 4032 may further include support surfaces 4036 for the releasable couplers 4028 shown in FIG. 216 to engage with. The second carriage 4032 may further include a central channel 4038 for the first carriage 4016 to be positioned within.

An insertion carriage 4026 may include the releasable couplers 4028 (shown in FIG. 216) for engaging with the support surface 4036 of the second carriage 4032. The insertion carriage 4026 may comprise a component of an actuator or insertion actuator that may be coupled to the applicator housing and configured to insert a needle and the transcutaneous analyte sensor into the individual's skin. The insertion carriage 4026 may be configured to slide relative to the applicator housing and configured to be slid by the driver 4046.

The insertion carriage 4026 may further include coupling members 4040 for engaging with a releasable coupler 4042 of the interior housing 4008 (as marked in FIG. 220). The insertion carriage 4026 may include a central channel 4044 for the carriages 4016, 4032 to be positioned within.

The applicator 4000 may further include a driver 4046 in the form of springs configured to drive the entire assembly of carriages, including the insertion carriage 4026 downward to drive the needle into the individual's skin to insert the transcutaneous analyte sensor into the individual's skin. The applicator 4000 may further include a driver 4048 in the form of springs configured to retract the carriages 4016, 4032 to retract the needle from the individual's skin following deployment.

The applicator 4000 may include a control device 4010 that may be activated to cause the transcutaneous analyte sensor of the on-skin sensor assembly to be inserted into the individual's skin. The control device 4010 may be operated by an individual. For example, the control device 4010 may comprise a button that is pressed to activate an insertion actuator of the applicator 4000. Referring to FIG. 219, the control device 4010 may include a pressing surface 4049 that may be configured to press against the coupling member 4040 of the insertion carriage 4026 to release the insertion carriage 4026 from the applicator housing 4002 and allow the insertion carriage 4026 to descend and insert the transcutaneous analyte sensor into the individual's skin. The control device 4010 may further include locking surfaces 4050 configured to engage locks 4052 of the insertion carriage 4026. Referring to FIG. 216, the control device 4010 may further include a locking surface 4054 configured to engage a lock 4056 of a slide lock 4058 or slide shuttle.

Referring to FIG. 215, the control device 4010 in embodiments may include a sub-control device 4060 that may be configured to extend from the control device 4010 to provide a different operation of the control device 4010. The sub-control device 4060 may comprise a protrusion that may be configured to extend from the control device 4010 inward with respect to the applicator 4000. Thus, the overall length of the control device 4010 may be increased upon deployment of the sub-control device 4060. The sub-control device 4060 may include a pressing surface 4061 (marked in FIG. 216) that may be configured to press against the slide body 4022. Referring to FIG. 217, the sub-control device 4060 may be positioned within a channel of the control device 4010 prior to extension of the sub-control device 4060. Upon extension of the sub-control device 4060, a lock 4062 may be released outward from the channel and may be configured to lock the extension of the sub-control device 4060 relative to the control device 4010 (as shown in FIG. 222 for example).

Referring to FIG. 215, the applicator 4000 may include a slide lock 4058 or slide shuttle that may be configured to slide to lock the control device 4010 in position. The slide lock 4058 may include one or more biasing members 4064 that may bias the slide lock 4058 downward to a locked position, which may be overcome with an upward movement of the insertion carriage 4026. The slide lock 4058 may include the lock 4056 for locking to the locking surface 4054 of the control device 4010. The slide lock 4058 may include a stop 4059 for impeding inward movement of the control device 4010.

The applicator 4000 may include the slide body 4022, which may have an angled contact surface 4066. The slide body 4022 may include a pressing surface 4068 (marked in FIG. 216) for pressing against a needle hub of the needle to release from the applicator 4000.

A cartridge that may be utilized with the applicator 4000 may be similar to the cartridge as discussed in regard to FIGS. 198-202 or may have another form.

In assembly, similar to the embodiment of FIGS. 198-214, the first carriage 4016 may be positioned within the channel 4038 of the second carriage 4032, and the carriages 4016, 4032 may be positioned within the central channel 4044 of the insertion carriage 4026. The assembly may be positioned within the interior housing 4008 shown in FIG. 215.

FIG. 216 illustrates a cross sectional view of the applicator 4000 with the carriages 4016, 4026, 4032 assembled and positioned within the interior housing 4008. The interior housing 4008 may be positioned within the outer housing 4004 and may be configured to slide within the outer housing 4004. A force applied upwards against the interior housing 4008, by the skin of an individual, for example, may move the interior housing 4008 upwards within the outer housing 4004.

FIGS. 216-223 illustrate steps of a method that may utilize the applicator 4000. Referring to FIG. 216, in the initial configuration, the control device 4010 may be locked in a retracted position by the slide lock 4058. The slide lock 4058 may be held in a lowered position. The lock 4056 of the slide lock 4058, for example, may engage the locking surface 4054 of the control device 4010 to hold the control device 4010 in the retracted position. The stop 4059 may impede inward pressing movement of the control device 4010.

The control device 4010 may be held flush with the outer surface of the applicator housing 4002. As such, the position of the control device 4010 may serve as a tactile and visual indicator that the applicator 4000 is not in a configuration to deploy a transcutaneous analyte sensor to the individual's skin. The position of the control device 4010 may indicate that the control device 4010 should not be pressed by the user at this point to perform an operation.

FIG. 217 illustrates an upper cross sectional view of the applicator 4000 in the configuration shown in FIG. 216. The control device 4010 is shown flush with the outer surface of the applicator housing 4002 and the sub-control device 4060 is shown in a retracted configuration positioned within the control device 4010.

A cartridge, such as cartridge 3800 shown in FIGS. 198-202, may be inserted into the receiver of the applicator 4000. Upon initial insertion, the first carriage 4016 may couple to the needle hub 3856 in a similar manner as the first carriage 3888 discussed in regard to the embodiments of FIGS. 198-214.

The cartridge 3800 may be inserted into the applicator housing to provide energy to the insertion actuator and the retraction actuator. The force applied by the cartridge 3800 to the insertion and retraction actuators may provide energy to the insertion and retraction actuators. The insertion of the cartridge 3800 may provide energy to the drivers 4046, 4048. In an embodiment in which the drivers 4046, 4048 comprise springs, the insertion of the cartridge into the receiver may compress the springs. The cartridge 3800 may include a pressing surface for pressing against the insertion and retraction actuators for providing energy to the actuators.

An upward movement of the insertion carriage 4026 may raise the position of the slide lock 4058. FIG. 218, for example, illustrates the cartridge 3800 after it has been withdrawn from the receiver of the applicator housing 4002, with the needle hub 3856 remaining coupled to the releasable couplers 4018, 4017. The insertion carriage 4026 has been raised by the insertion of the cartridge 3800. The insertion carriage 4026 has pressed against the slide lock 4058 to raise the slide lock 4058 and release the lock 4056 from the locking surface 4054 of the control device 4010. As such, the control device 4010 may protrude from the outer surface of the applicator housing 4002 to a distance.

FIG. 219 illustrates an upper cross sectional view of the applicator 4000 in the configuration shown in FIG. 218. The protrusion of the control device 4010 may be limited by the locking surfaces 4050 contacting the locks 4052 of the insertion carriage 4026. Further, the sub-control device 4060 may not yet be fully extended from the control device 4010 and the lock 4062 may not yet be deployed.

FIG. 220 illustrates a cross sectional view of the configuration shown in FIG. 219, with the pressing surface 4049 of the control device 4010 shown to be in position to decouple the coupling members 4040 of the insertion carriage 4026 from the releasable coupler 4042 of the applicator housing 4002.

The cartridge 3800 may be removed from the applicator housing prior to the needle being inserted into the individual's skin to insert the transcutaneous analyte sensor into the individual's skin.

The control device 4010 may be pressed to release the coupling members 4040 of the insertion carriage 4026 from the releasable coupler 4042 of the applicator housing 4002 to allow the needle and transcutaneous analyte sensor to be deployed in a similar manner as discussed in regard to the embodiments of FIGS. 198-214.

FIG. 221 illustrates the configuration of the carriages 4016, 4026, 4032 after insertion of the transcutaneous analyte sensor and retraction of the needle. The needle is not shown in FIG. 221 for clarity, yet would be rotated into the needle cover via a deflection surface of the insertion carriage 4026, in a similar manner as discussed in regard to the embodiments of FIGS. 198-214. The needle cover may contact the deflection surface, such that the retraction actuator comprising the carriages 4032, 4016 and the driver 4048 rotates the needle into the needle cover. The driver 4048 may drive the needle out of the individual's skin. The driver 4048 may slide the carriage 4032, 4016 relative to the applicator housing. The retraction actuator may retract the needle from the individual's skin following insertion of the transcutaneous analyte sensor into the individual's skin. The retraction actuator may be configured to automatically operate upon the needle inserting the transcutaneous analyte sensor into the individual's skin. The retraction actuator may position the needle into the needle cover, and may rotate the needle into the needle cover.

The retraction actuator of the applicator 4000 may be configured to activate based on a force of contact with the individual's skin at a deployment site of the transcutaneous analyte sensor. The retraction actuator of the applicator 4000 may activate at the point of contact with the individual's skin. For example, if the individual's skin protrudes into the receiver of the applicator housing then the retraction actuator may activate at the position of the individual's skin rather than at a defined position relative to the applicator. This feature may be beneficial in a case where skin protrudes greatly into the receiver of the applicator, to allow for the retraction actuator to activate due to the force of contact with the individual's skin and thus at the position of the individual's skin.

The retraction actuator may operate based on the insertion carriage 4026 over traveling with respect to the first carriage 4016. The insertion carriage 4026 may displace relative to the first carriage 4016 based on contact with the individual's skin to operate the release actuator. The downward movement of the first carriage 4016 may be impeded by contact with the individual's skin, thus causing the insertion carriage 4026 to move downward relative to the first carriage 4016 and displacing relative to the first carriage 4016. Such displacement may cause the release of the releasable coupler 4028 and the retraction of the needle.

Following deployment of the transcutaneous analyte sensor, the insertion carriage 4026 may be in a lowered position, which lowers the locks 4052 shown in FIG. 219. As such, referring to the upper cross sectional view of the applicator 4000 shown in FIG. 222, the control device 4010 may protrude to a distance that is further than the position shown in FIGS. 218 and 219 due to the locks 4052 shown in FIG. 219 being lowered. The locking surfaces 4050 may engage the outer housing 4004 to impede further outward movement of the control device 4010.

The control device 4010 may protrude to a distance that allows the sub-control device 4060 to extend inward from the control device 4010 and have the lock 4062 deploy. The lock 4062 may extend outward from the channel of the control device 4010 to contact an interior surface of the control device 4010, and lock the position of the sub-control device 4060 relative to the control device 4010 upon an inward pressing movement of the control device 4010.

The pressing surface 4061 of the sub-control device 4060 may further be aligned with the angled contact surface 4066 of the slide body 4022 in a configuration as shown in FIG. 222.

Referring to FIG. 223, the release actuator may include components comprising the control device 4010 and sub-control device 4060 and the slide body 4022. The release actuator may be configured to release the needle from the releasable coupler 4018. The control device 4010 and sub-control device 4060 may be operated by an individual to cause the needle to release from the releasable coupler 4018. The control device 4010 may be pressed inward to move the sub-control device 4060 inward and press against the slide body 4022. The force applied by the sub-control device 4060 inward may be against the angled contact surface 4066, thus causing the release actuator in the form of the slide body 4022 to move downward.

The pressing surface 4068 of the slide body 4022 may contact the needle hub 3816 to cause the needle hub to release from the applicator 4000. The release actuator may release the needle from the releasable coupler to allow the needle to be passed through the opening. The needle may be released while covered with the needle cover. The needle and needle cover may form a unit for ejection from the applicator housing by the release actuator following insertion of the needle into the individual's skin. The pressing surface 4068 may apply a force to the needle to eject the needle from the needle from the applicator housing 4002. The slide body 4022 may eject the needle and needle hub 3816 from the applicator housing 4002.

The control device 4010 accordingly may be operated in a first operation to activate the insertion actuator, and is configured to be operated in a second operation following the first operation to activate the release actuator. The first operation may comprise pressing the control device 4010 and the second operation may comprise pressing the control device 4010. The control device 4010 may protrude from the applicator housing 4002 to a different distance for the first operation than for the second operation.

The releasable coupler 4018 may release the needle positioned within the needle cover from the applicator housing. The needle may be separated from the applicator housing.

The slide lock 4058 may descend and the lock 4056 may lock with the locking surface 4054 of the control device 4010. The sub-control device 4060 may slide back within the channel of the control device 4010 and the applicator 4000 may return back to a configuration shown in FIG. 216.

FIGS. 224-232 illustrate a variation of cartridges as shown in FIGS. 146-158, in which the cartridge includes the retraction actuator for retracting the needle from the individual's skin following insertion of the transcutaneous analyte sensor into the individual's skin. The retraction actuator may be configured to automatically operate upon the needle inserting the transcutaneous analyte sensor into the individual's skin. In an embodiment of FIGS. 224-232, however, the retraction actuator may be configured to activate based on a force of contact with the individual's skin at a deployment site of the transcutaneous analyte sensor.

FIG. 224, for example, illustrates a construction of a cartridge 4100 including a retraction actuator 4102 positioned within the cartridge 4100. The cartridge 4100 may have features similar as the cartridge 1500 shown in FIG. 146, and may include an upper removable cover 4104, a lower removable cover 4106, a body 4108 and may include the wearable housing 4109, transcutaneous analyte sensor, and the needle. A patch 4111 may be coupled to the wearable housing 4109 and positioned within the cartridge 4100. A first retraction carriage 4110, a second retraction carriage 4112 and a driver 4114 may be positioned within the cartridge 4100.

The first retraction carriage 4110 may couple to a needle hub 4116 of the needle 4117 (marked in FIG. 226) and may include arms 4118 extending outward from the needle hub 4116 and configured to contact interior portions of the cartridge 4100 to rotationally orient the first retraction carriage 4110 within the cartridge 4100. The first retraction carriage 4110 may include coupling members 4120 in the form of protrusions for coupling to releasable couplers of the insertion carriage 4122.

The second retraction carriage 4112 may include a releasable coupler 4124 for coupling with a portion of the control device 1523 shown in FIG. 147 for example. Referring to FIG. 225, the second retraction carriage 4112 may include a channel 4125 for receiving a portion of the insertion carriage 4122 and for the needle hub 4116 to pass through. The second retraction carriage 4112 may include support surfaces 4132 for abutting releasable couplers 4130 of the insertion carriage 4122 to prevent deflection of the releasable couplers 4130 until a desired time.

Referring to FIG. 224, the second retraction carriage 4112 may include pressing surfaces 4133 for pressing against releasable couplers 4134 of the insertion carriage 4122.

The second retraction carriage 4112 may further include one or more locks 4126 protruding from the second retraction carriage 4112 and configured to engage an interior portion of the cartridge 4100 to prevent upward or inward pushing of the second retraction carriage 4112 following insertion of the needle 4117. The second retraction carriage 4112 may be configured to be pushed by the insertion actuator of the applicator (for example, an insertion carriage 1536 as shown in FIG. 147) to insert the needle 4117 and transcutaneous analyte sensor into the individual's skin. The second retraction carriage 4112 in embodiments may comprise an over travel carriage that is configured to over travel a position of the insertion carriage 4122 upon insertion of the needle 4117 and transcutaneous analyte sensor into the individual's skin. The over travel may cause the first retraction carriage 4110 to release and retract from the insertion carriage 4122. The insertion carriage 4122 may displace relative to the second retraction carriage 4112 based on contact with the individual's skin to operate the release actuator.

The cartridge 4100 may further include the insertion carriage 4122 for retaining the wearable housing 4109. The insertion carriage 4122 may be configured to be moved downward via the motion of the second retraction carriage 4112 to insert the needle and transcutaneous analyte sensor into the individual's skin. The insertion carriage 4122 may include an internal cavity 4128 for receiving the second retraction carriage 4112.

The insertion carriage 4122 may include one or more releasable couplers 4130 for coupling to the coupling members 4120 of the first retraction carriage 4110. The releasable couplers 4130 may be configured as support arms extending upward for coupling with the coupling members 4120 of the first retraction carriage 4110. The support arms may be configured to deflect outward from the coupling members 4120 to release from the coupling members 4120. The support arms may be biased to deflect outward with the support surfaces 4132 (marked in FIG. 225) of the second retraction carriage 4112 moved out of position relative to the support arms.

The releasable couplers 4130 that couple the insertion carriage 4122 to the first retraction carriage 4110 may release the first retraction carriage 4110 from the insertion carriage 4122 to allow the driver 4114 to move the first retraction carriage 4110 in a direction away from the insertion carriage 4122.

The insertion carriage 4122 may include releasable couplers 4134 that may be configured to engage the wearable housing 4109 and retain the wearable housing 4109 to the insertion carriage 4122. The releasable couplers 4134 may comprise deflectable arms that may be biased to engage the wearable housing 4109 and may be deflectable outward to disengage and release from the wearable housing 4109.

Referring to FIG. 227, the releasable couplers 4134 may include upper contact surfaces 4137 that may be configured to contact the pressing surfaces 4133 of the second retraction carriage 4112. The contact between the pressing surfaces 4133 and the upper contact surfaces 4137 may press the insertion carriage 4122 away from the second retraction carriage 4112 during use. The force required to deflect the releasable couplers 4134 outward may comprise a force that must be overcome for deployment of the wearable housing and retraction of the needle upon contact with the individual's skin.

The insertion carriage 4122 may further include stops 4136 for contacting an interior portion of the cartridge 4100 to impede downward movement of the insertion carriage 4122 upon release of the releasable coupler 4124 from the portion of the control device 1523.

The driver 4114 of the retraction actuator may be configured to drive the needle out of the individual's skin. The first retraction carriage 4110 may be configured to slide relative to the applicator housing and may be configured to be slid by the driver 4114 of the retraction actuator. The driver 4114 may be configured as a spring configured to apply an upward force from the insertion carriage 4122 towards the first retraction carriage 4110. The driver 4114 may be configured to be compressed between the insertion carriage 4122 and the coupling members 4120 of the first retraction carriage 4110, as shown in FIG. 226 for example.

FIG. 225 illustrates a perspective view of the second retraction carriage 4112 positioned within the insertion carriage 4122. The needle 4117 and needle hub 4116 may pass through a central channel of the insertion carriage 4122 in assembly, such that the coupling members 4120 may engage with the releasable couplers 4130 of the insertion carriage 4122.

FIG. 226, for example, illustrates a cross sectional view of the first retraction carriage 4110 coupled with the releasable couplers 4130 of the insertion carriage 4122. The releasable couplers 4130 may be deflected inward to engage with the coupling members 4120 of the first retraction carriage 4110 by way of the support surfaces 4132 backing the releasable couplers 4130 to prevent their outward deflection. The driver 4114 may be compressed between the insertion carriage 4122 and the coupling members 4120 of the first retraction carriage 4110. The engagement of the releasable couplers 4130 and the coupling members 4120 may prevent the release of the driver 4114 until the desired time.

Referring to FIG. 227, the insertion carriage 4122 may be held within the cartridge 4100 such that an interior surface 4135 of the cartridge 4100 may press against the releasable couplers 4134 that may be configured to engage the wearable housing 4109. Such contact between the interior surface 4135 and the releasable couplers 4134 may reduce the possibility of the releasable couplers 4134 releasing prematurely and producing dislodgement of the wearable housing 4109 during transport or otherwise prior to use.

An applicator that may be utilized with the cartridge 4100 may comprise an applicator 1530 as shown in FIG. 147. The cartridge 4100 may insert into the receiver of the applicator 1530 in a similar manner as the cartridge 1500 shown in FIG. 147. The applicator operates in a similar manner as the applicator 1530.

The insertion of the cartridge 4100 and the transcutaneous analyte sensor 24 into the receiver of the applicator housing 1528 may compress and thus provide energy to the driver 1538 of the insertion actuator. The driver 1538 may be compressed. In an embodiment in which the driver 1538 includes a spring, the spring may be compressed by the insertion of the cartridge 4100 and the transcutaneous analyte sensor 24 into the receiver.

With the cartridge 4100 inserted into the receiver of the applicator 1530 shown in FIG. 147, the biasing carriage 1534 shown in FIG. 147 may be compressed to allow the control device 1523 to move in a similar manner as described in regard to FIG. 131 for example. Upward pressure against the cartridge 4100 by the individual's skin presses the biasing carriage 1534 shown in FIG. 147 upward, to move the stop 1533 marked in FIG. 148, and allow the control device 1523 to move inward to be pressed.

The insertion carriage 1536 may be in contact with the second retraction carriage 4112 to drive the assembly of carriages 4110, 4112, 4122 downward at the desired time.

The control device 1523 shown in FIG. 147 may contact the releasable coupler 4124 shown in FIG. 224 to release the releasable coupler 4124 in a similar manner as described in regard to FIG. 131 for example. The control device 1523 may press against the releasable coupler 4124 to disengage the coupler 4124 from a surface and allow the insertion carriage 1536 to drive the assembly of carriages 4110, 4112, 4122 downward.

FIG. 228 illustrates the carriage 1536 having descended. The insertion carriage 4122 may move downward to insert the needle 4117 into the individual's skin to insert the transcutaneous analyte sensor into the individual's skin. Further, the patch 4111 may be applied to the individual's skin with an adhesive.

The releasable couplers 4134 that may be configured to engage the wearable housing 4109 may displace relative to the interior surface 4135 shown in FIG. 227 and may be able to deflect outward from the wearable housing 4109 at a desired time.

The cartridge 4100 may remain within the receiver of the applicator housing 1528 during insertion of the needle 4117 and insertion of the transcutaneous analyte sensor into the individual's skin, as well as deployment of the on-skin sensor assembly to the individual's skin.

The retraction actuator of the cartridge 4100 may be configured to activate based on a force of contact with the individual's skin at a deployment site of the transcutaneous analyte sensor. Such a feature may differ from a cartridge 1500 as shown in FIG. 147, for example, which may have a retraction actuator that retracts based on a position or displacement of the actuator relative to the cartridge 1500 (e.g., contact between the arms 1520 and the stops 1544). The retraction actuator of the cartridge 4100 may activate at the point of contact with the individual's skin. For example, as shown in FIG. 228, if the individual's skin 4138 protrudes into the receiver of the cartridge 4100 then the retraction actuator may activate at the position of the individual's skin 4138 rather than at a defined position relative to the cartridge (as shown in FIG. 151 for example). This feature may be beneficial in a case where skin protrudes greatly into the receiver of the cartridge 4100, to allow for the retraction actuator to activate due to the force of contact with the individual's skin and thus at the position of the individual's skin.

The retraction actuator may operate utilizing a carriage that over travels with respect to another carriage based on contact with the individual's skin at a deployment site of the transcutaneous analyte sensor. For example, the second retraction carriage 4112 may be configured to over travel with respect to the insertion carriage 4122 upon deployment. Upon deployment, the downward motion of the insertion carriage 4122 may be impeded based on contact with the individual's skin. The insertion carriage 4122 may thus cease downward movement along with the wearable housing 4109 upon the individual's skin applying a resistive force to the insertion carriage 4122 upon deployment. The second retraction carriage 4112, however, may continue to be pressed by the insertion carriage 1536 and may continue to travel, or over travel, with respect to the insertion carriage 4122. The insertion carriage 4122 may displace relative to the second retraction carriage 4112 based on contact with the individual's skin to operate the release actuator. The over travel may cause a displacement of the second retraction carriage 4112 downward with respect to the insertion carriage 4122 and accordingly a displacement of the support surfaces 4132 of the second retraction carriage 4112 relative to the releasable couplers 4130 of the insertion carriage 4122. FIG. 228, for example, illustrates the relative displacement of the support surfaces 4132 relative to the releasable couplers 4130.

With the support surfaces 4132 of the second retraction carriage 4112 released from the releasable couplers 4130 of the insertion carriage 4122, the releasable couplers 4130 may be able to decouple from the coupling members 4120 of the first retraction carriage 4110. Referring to FIG. 229, the releasable couplers 4130 may deflect outward from the coupling members 4120 to allow the driver 4114 to expand and retract the needle 4117 from the individual's skin.

FIG. 230 illustrates that upon the over travel of the second retraction carriage 4112 with respect to the insertion carriage 4122, the pressing surfaces 4133 of the second retraction carriage 4112 may press against the releasable couplers 4134. The pressing surfaces 4133 may deflect the releasable couplers 4134 away from the wearable housing 4109 and may disengage the releasable couplers 4134 from the wearable housing 4109 to allow the wearable housing 4109 to remain on the individual's skin upon deployment.

The cartridge 4100 may be configured to retain the needle 4117 after the cartridge 4100 has been separated from the receiver and the needle 4117 has been inserted into the individual's skin.

FIG. 231 illustrates that the locks 4126 of the second retraction carriage 4112 may engage an interior portion of the cartridge 4100 to prevent upward or inward pushing of the second retraction carriage 4112 following insertion of the needle 4117. Such a feature may reduce the possibility of access by a user of the used needle within the cartridge 4100.

In the event that no skin is contacted by the assembly of carriages 4110, 4112, 4122, the retraction actuator may yet activate. Referring to FIG. 232, the stops 4136 of the insertion carriage 4122 may contact an interior portion of the cartridge 4100 to impede downward movement of the insertion carriage 4122. Thus, a position or displacement based activation may occur if no skin is contacted. The second retraction carriage 4112 may continue to over travel or displace with respect to the insertion carriage 4122 and cause the needle 4117 to be retracted from the individual's skin. Such a feature may reduce the possibility of the needle 4117 remaining extended from the cartridge 4100 if no skin is contacted upon activation of the insertion actuator.

With the needle 4117 retracted, the cartridge 4100 may then be withdrawn and discarded, to discard the used needle 4117. The applicator may return to the state shown in FIG. 147, for example, for insertion of another cartridge.

Variations in the configuration of the cartridge may be provided. FIGS. 233-237 illustrate a variation of the cartridge as shown in FIGS. 224-232. The cartridge 4200 may include a retraction actuator for retracting the needle from the individual's skin following insertion of the transcutaneous analyte sensor into the individual's skin. The retraction actuator may be configured to automatically operate upon the needle inserting the transcutaneous analyte sensor into the individual's skin. The retraction actuator may be configured to activate based on a force of contact with the individual's skin at a deployment site of the transcutaneous analyte sensor. The retraction actuator may include a driver 4202 such as a spring that biases carriages 4204, 4206 away from each other.

FIG. 233 illustrates a construction of the cartridge 4200 including a retraction actuator 4208 positioned within the cartridge 4200. The cartridge 4200 may have features similar as the cartridge 4100 shown in FIG. 224, and may include an upper removable cover 4210, a lower removable cover 4212, a body 4214 and may include the wearable housing 4216, transcutaneous analyte sensor, and the needle. A patch 4218 may be coupled to the wearable housing 4216 and positioned within the cartridge 4200. A first retraction carriage 4220, a second retraction carriage 4204 and a driver 4202 may be positioned within the cartridge 4200.

The first retraction carriage 4220 may couple to a needle hub 4222 of the needle 4224 (marked in FIG. 235) and may include arms 4226 extending outward from the needle hub 4222 and configured to contact interior portions of the cartridge 4200 to rotationally orient the first retraction carriage 4220 within the cartridge 4200.

The first retraction carriage 4220 may include coupling members 4228 in the form of support arms having protrusions for coupling to releasable couplers 4229 of the insertion carriage 4206 (marked in FIG. 235). The coupling members 4228 in the form of support arms may be biased to deflect outward.

The first retraction carriage 4220 may include apertures 4230 for receiving releasable couplers 4231 of the second retraction carriage 4204. Support surfaces 4235 (marked in FIG. 234) may form sides of the apertures 4230 for contacting the releasable couplers 4231 of the second retraction carriage 4204.

The second retraction carriage 4204 may include a releasable coupler 4233 for coupling with a portion of the control device 1523 shown in FIG. 147 for example. Referring to FIG. 234, the second retraction carriage 4204 may include a channel 4234 for receiving a portion of the insertion carriage 4206 and for the needle hub 4222 to pass through.

Referring to FIG. 235, the second retraction carriage 4204 may include support surfaces 4236 for abutting the coupling members 4228 of the first retraction carriage 4220. The releasable couplers 4231 of the second retraction carriage 4204 may couple to the driver 4202 to retain the driver 4202 in a compressed state. The releasable couplers 4231 may be in the form of support arms biased to deflect outward upon release from the apertures 4230 of the first retraction carriage 4220.

Referring to FIG. 234, the second retraction carriage 4204 may further include one or more locks 4238 protruding from the second retraction carriage 4204 and configured to engage an interior portion of the cartridge 4200 to prevent upward or inward pushing of the second retraction carriage 4204 following insertion of the needle 4224.

The second retraction carriage 4204 may be configured to be pushed by the insertion actuator of the applicator (for example, an insertion carriage 1536 as shown in FIG. 147) to insert the needle 4224 and transcutaneous analyte sensor into the individual's skin. The second retraction carriage 4204 in embodiments may comprise an over travel carriage that is configured to over travel a position of the insertion carriage 4206 upon insertion of the needle 4224 and transcutaneous analyte sensor into the individual's skin. The second retraction carriage 4204 may displace relative to the insertion carriage 4206 based on contact with the individual's skin to operate the release actuator. The over travel may cause the first retraction carriage 4220 to release and retract from the insertion carriage 4206.

The cartridge 4200 may further include an insertion carriage 4206 for retaining the wearable housing 4216. The insertion carriage 4206 may be configured to be moved downward via the motion of the second retraction carriage 4204 to insert the needle and transcutaneous analyte sensor into the individual's skin. The insertion carriage 4206 may include an internal cavity 4243 for receiving the second retraction carriage 4204.

Referring to FIG. 235, the insertion carriage 4206 may include one or more releasable couplers 4229 for coupling to the coupling members 4228 of the first retraction carriage 4220. The releasable couplers 4229 may be configured to be static and support the coupling members 4228 of the first retraction carriage 4220 against the support surfaces 4236.

The releasable couplers 4229 that couple the insertion carriage 4206 to the first retraction carriage 4220 may release the first retraction carriage 4220 from the insertion carriage 4206 to allow the driver 4202 to move the first retraction carriage 4220 in a direction away from the insertion carriage 4206.

Referring to FIG. 234, the insertion carriage 4206 may include releasable couplers 4240 that may be configured to engage the wearable housing 4216 and retain the wearable housing 4216 to the insertion carriage 4206. The releasable couplers 4240 may comprise deflectable arms that may be biased to deflect outward from the wearable housing 4216 and may be deflectable inward to engage the wearable housing 4216.

The insertion carriage 4206 may further include stops 4242 for contacting an interior portion of the cartridge 4200 to impede downward movement of the insertion carriage 4206 upon release of the releasable coupler 4233 from the portion of the control device 1523.

The driver 4202 of the retraction actuator may be configured to drive the needle out of the individual's skin. The first retraction carriage 4220 may be configured to slide relative to the applicator housing and may be configured to be slid by the driver 4202 of the retraction actuator.

The driver 4202 may be configured as a spring configured to apply an upward force from the insertion carriage 4206 towards the second retraction carriage 4204 and the first retraction carriage 4220. The spring may be configured to be compressed between the insertion carriage 4206 and the releasable couplers 4231 of the second retraction carriage 4204, as shown in FIG. 235 for example. The spring may bias the insertion carriage 4206 away from the second retraction carriage 4204. The spring force may define a force that must be overcome by the contact with the individual's skin to activate the retraction actuator. The spring force may be set based on a desired level of the force of contact with the individual's skin. As such, a greater spring force may result in a greater force of contact being required to activate the retraction actuator. A lesser spring force may result in a lesser force of contact being required to activate the retraction actuator. The spring constant of the spring, or other configuration of the spring, may be set as desired to define the force that must be overcome by the contact with the individual's skin.

FIG. 234 illustrates a perspective view of second retraction carriage 4204 positioned within the insertion carriage 4206. In assembly, the needle 4224 and needle hub 4222 may pass through a central channel of the insertion carriage 4206. FIG. 235 illustrates a cross sectional view of the assembled cartridge 4200 with the releasable couplers 4229 of the insertion carriage 4206 coupled to the coupling members 4228 of the first retraction carriage 4220. The releasable couplers 4231 of the second retraction carriage 4204 may be coupled to the driver 4202, and may be supported by the support surfaces 4235 of the first retraction carriage 4220. The support surfaces 4236 of the second retraction carriage 4204 may support the coupling members 4228 against the releasable couplers 4229 of the insertion carriage 4206. As such, the support surfaces 4236 may prevent the releasable couplers 4231 from deflecting away from the driver 4202 until a desired time, and the support surfaces 4236 may prevent the coupling members 4228 from deflecting away from the releasable couplers 4229 until a desired time.

The insertion carriage 4206 may be held within the cartridge 4200 such that an interior surface of the cartridge 4200 may press against the releasable couplers 4240 that may be configured to engage the wearable housing 4216. Such contact between the interior surface and the releasable couplers 4240 may reduce the possibility of the releasable couplers 4240 releasing prematurely and producing dislodgement of the wearable housing 4216 during transport or otherwise prior to use.

An applicator that may be utilized with the cartridge 4200 may comprise an applicator 1530 as shown in FIG. 147. The cartridge 4200 may insert into the receiver of the applicator 1530 in a similar manner as the cartridge 1500 shown in FIG. 147. The applicator operates in a similar manner as the applicator 1530.

The insertion of the cartridge 4200 and the transcutaneous analyte sensor 24 into the receiver of the applicator housing 1528 may compress and thus provide energy to the driver 1538 of the insertion actuator. The driver 1538 may be compressed. In an embodiment in which the driver 1538 includes a spring, the spring may be compressed by the insertion of the cartridge 4200 and the transcutaneous analyte sensor 24 into the receiver.

With the cartridge 4200 inserted into the receiver of the applicator 1530 shown in FIG. 147, the biasing carriage 1534 shown in FIG. 147 may be compressed to allow the control device 1523 to move in a similar manner as described in regard to FIG. 131 for example. Upward pressure against the cartridge 4200 by the individual's skin presses the biasing carriage 1534 shown in FIG. 147 upward, to move the stop 1533 marked in FIG. 148, and allow the control device 1523 to move inward to be pressed.

The insertion carriage 1536 may be in contact with the second retraction carriage 4204 to drive the assembly of carriages 4206, 4204, 4220 downward.

The control device 1523 shown in FIG. 147 may contact the releasable coupler 4233 shown in FIG. 233 to release the releasable coupler 4233 in a similar manner as described in regard to FIG. 131 for example. The control device 1523 may press against the releasable coupler 4233 to disengage the coupler 4233 from a surface and allow the insertion carriage 1536 to drive the assembly of carriages 4206, 4204, 4220 downward.

FIG. 236 illustrates the carriage 1536 having descended. The insertion carriage 4206 may move downward to insert the needle 4224 into the individual's skin to insert the transcutaneous analyte sensor into the individual's skin. Further, the patch 4218 may be applied to the individual's skin with an adhesive.

The cartridge 4200 may remain within the receiver of the applicator housing 1528 during insertion of the needle 4117 and insertion of the transcutaneous analyte sensor 24 into the individual's skin, as well as deployment of the on-skin sensor assembly 12 to the individual's skin.

The retraction actuator of the cartridge 4200 may be configured to activate based on a force of contact with the individual's skin at a deployment site of the transcutaneous analyte sensor. The retraction actuator of the cartridge 4200 may activate at the point of contact with the individual's skin, in a similar manner as the cartridge 4100 shown in FIG. 224.

The retraction actuator may operate utilizing a carriage that over travels with respect to another carriage based on contact with the individual's skin at a deployment site of the transcutaneous analyte sensor. For example, the second retraction carriage 4204 may be configured to over travel with respect to the insertion carriage 4206 upon deployment. Upon deployment, the downward motion of the insertion carriage 4206 may be impeded based on contact with the individual's skin. The insertion carriage 4206 may thus cease downward movement along with the wearable housing 4216 upon the individual's skin applying a resistive force to the insertion carriage 4206 upon deployment. The second retraction carriage 4204, however, may continue to be pressed by the insertion carriage 1536 and may continue to travel, or over travel, with respect to the insertion carriage 4206. The over travel may cause a displacement of the second retraction carriage 4204 downward with respect to the insertion carriage 4206. The force to be overcome by the force of contact with the individual's skin may be the spring force of the driver 4202.

With the spring force of the driver 4202 overcome, the support surfaces 4236 may displace downward relative to the coupling members 4228 of the first retraction carriage 4220 and may allow the coupling members 4228 to deflect inward to decouple from the releasable couplers 4229 of the insertion carriage 4206. The support surfaces 4235 of the first retraction carriage 4220 may displace upward relative to the releasable couplers 4231 of the second retraction carriage 4204 to allow the releasable couplers 4231 to deflect outward. The outward deflection of the releasable couplers 4231 of the second retraction carriage 4204 may allow the driver 4202 to be released and expand to apply an upward force to the first retraction carriage 4220. The upward force of the driver 4202 upon the first retraction carriage 4220 may retract the needle 4224 from the individual's skin.

The cartridge 4200 may be configured to retain the needle 4224 after the cartridge 4200 has been separated from the receiver and the needle 4224 has been inserted into the individual's skin.

Referring to FIG. 237, the releasable couplers 4240 that may be configured to engage the wearable housing 4216 may displace relative to the interior surface of the cartridge 4200 and may deflect outward from the wearable housing 4216 to release from the wearable housing 4216.

The locks 4238 of the second retraction carriage 4204 may operate in a similar manner as the locks 4126 shown in FIG. 231. The stops 4242 of the carriage 4204 may operate in a similar manner as the stops 4136 shown in FIG. 232.

With the needle 4224 retracted, the cartridge 4200 may then be withdrawn and discarded, to discard the used needle 4224. The applicator may return to the state shown in FIG. 147, for example, for insertion of another cartridge.

Variations in the configuration of the cartridge may be provided.

FIG. 238-240 illustrate an embodiment in which a needle hub 4301 may be integrated with a retraction carriage 4302. The retraction carriage 4302 may be configured as a ring that extends circumferentially about an insertion carriage 4304. A driver 4305 may be configured as a spring that extends in a ring circumferentially about the outer periphery of the insertion carriage 4304. The driver 4305 may be configured to apply an upward force against the retraction carriage 4302 to retract the needle hub 4301 and needle coupled thereto.

FIG. 239 illustrates the retraction carriage 4302 separate from the insertion carriage 4304. The retraction carriage 4302 may include first releasable couplers 4306 that may be configured to engage a wearable housing 4307. The retraction carriage 4302 may further include second releasable couplers 4308 that may be configured to couple to the insertion carriage 4304. For example, the second releasable couplers 4308 may be in the form of deflectable support arms that may pass through openings 4310 in the insertion carriage 4304 shown in FIG. 240. The retraction carriage 4302 may include support surfaces 4312 for supporting releasable couplers 4314 of the insertion carriage 4304 shown in FIG. 240.

FIG. 240 illustrates the insertion carriage 4304 with the retraction carriage 4302 shown removed from the upper surface of the insertion carriage 4304. The insertion carriage 4304 may include the releasable couplers 4314 configured to retain the driver 4305 in a compressed configuration and configured to deflect inward from the driver 4305 to release the driver 4305.

In operation, the retraction carriage 4302 may be configured to activate based on a force of contact with the individual's skin at a deployment site of the transcutaneous analyte sensor, similar to the operation of the cartridges 4200, 4100. The insertion carriage 4304 may over travel with respect to the retraction carriage 4302 based on contact with the individual's skin at a deployment site of the transcutaneous analyte sensor. The insertion carriage 4304 may displace relative to the retraction carriage 4302 based on contact with the individual's skin to operate the release actuator. For example, the carriages 4304, 4302 may be advanced downward until the wearable housing 4307 contacts the individual's skin. The upward force applied to the first releasable couplers 4306 of the retraction carriage 4302 may cause the second releasable couplers 4308 of the retraction carriage 4302 to release from the openings 4310 shown in FIG. 240.

The relative displacement of the retraction carriage 4302 from the insertion carriage 4304 may cause the support surfaces 4312 to displace from the releasable couplers 4314 of the insertion carriage 4304. The releasable couplers 4314 of the insertion carriage 4304 accordingly may move inward to release the driver 4305, which may press upward against the retraction carriage 4302 to retract the needle hub 4301 and the needle.

Variations in the configuration of the cartridge may be provided.

In embodiments, the applicators and cartridges utilized herein may utilize a releasable coupler 4400 as shown in FIGS. 241-244. The releasable coupler 4400 may be utilized to couple to a cartridge 4402 that may be configured similarly as any cartridge disclosed herein, including the cartridges disclosed in regard to FIGS. 146-158 and 198-240. The cartridge, for example, may be a cartridge that retains a used needle following insertion of the needle, and may be a cartridge including a retraction actuator. Other cartridges may be utilized with the releasable coupler 4400. An applicator that may utilize the releasable coupler 4400 may include an applicator 1530 as described in regard to FIG. 147, or another form of applicator as desired.

The releasable coupler 4400 that may be utilized with embodiment herein, including the cartridges disclosed in regard to FIGS. 146-158 and 198-240, may be configured to retain the needle at least partially within the applicator housing following insertion of a transcutaneous analyte sensor into the individual's skin and removal of the applicator housing from the transcutaneous analyte sensor, and configured to release the needle from within the applicator housing following insertion of the transcutaneous analyte sensor into the individual's skin. The releasable coupler 4400 may comprise a cartridge catch that retains the cartridge to the applicator housing. The releasable coupler 4400 may be configured to release the cartridge from the applicator housing.

The releasable coupler 4400 may be released via operation of a release actuator, which may include a lever arm 4404 coupled to the releasable coupler 4400. The lever arm 4404 may further include a detent 4406. The lever arm 4404 may further include a contact surface 4408 that may be angled for contact with an angled pressing surface 4409 of an insertion carriage 4410, which may be configured similarly as the insertion carriage 1536 discussed in regard to FIG. 147.

A biasing spring 4412, such as a leaf spring, may be configured to bias the lever arm 4404 inward towards the insertion carriage 4410 and the cartridge 4402.

The lever arm 4404 may have a lower portion 4414 and an upper portion 4416, with the lower portion 4414 configured to couple to the applicator housing 4413 with a pivot to cause the upper portion 4416 to rotate about the pivot within the applicator housing 4413. The rotation of the lever arm 4404 may cause the releasable coupler 4400 and the detent 4406 to rotate towards the cartridge 4402 and away from the cartridge 4402 as desired.

The cartridge 4402 may include an outer surface with features for engaging with the releasable coupler 4400 and the detent 4406. The cartridge 4402, for example, may include a coupling member in the form of a ledge surface 4418 for the releasable coupler 4400 to insert into and lock to. The ledge surface 4418, for example, may comprise a flattened surface that a corresponding flattened surface 4420 of the releasable coupler 4400 may contact to maintain a lock between the releasable coupler 4400 and the ledge surface 4418.

Referring to FIG. 243, the cartridge 4402 may include a receiving recess 4423 for receiving the detent 4406 of the lever arm 4404.

Referring to FIG. 241, prior to insertion of the cartridge 4402 into the receiver of the applicator housing 4413, the insertion carriage 4410 may be in a lowered position. The pressing surface 4409 of the insertion carriage 4410 may press against the contact surface 4408 to push the lever arm 4404 outward. The lever arm 4404 pressed outward may clear a path for the cartridge 4402 to be inserted into the receiver of the applicator housing 4413.

The cartridge 4402 may be inserted into the receiver, as shown in FIG. 241, for example. The upward movement of the cartridge 4402 may press the insertion carriage 4410 upward, which may cause the pressing surface 4409 of the insertion carriage 4410 to move upward. The detent 4406 may be configured to slide along the outer surface of the cartridge 4402 to allow for insertion of the cartridge 4402 into the receiver.

FIG. 242, for example, illustrates further insertion of the cartridge 4402 into the receiver of the applicator housing 4413. The pressing surface 4409 of the insertion carriage 4410 may separate from the contact surface 4408 of the lever arm 4404. The detent 4406, however, may press against the outer surface of the cartridge 4402 to retain the outward position of the lever arm 4404.

FIG. 243 illustrates the cartridge fully inserted into the receiver of the applicator housing 4413. The detent 4406 may slide into the receiving recess 4423 and may move inward towards the cartridge 4402. The biasing spring 4412, for example, may press the detent 4406 into the receiving recess 4423. The releasable coupler 4400 may insert into the coupling member of the cartridge 4402 and may rest upon the ledge surface 4418 of the cartridge 4402. The releasable coupler 4400 may prevent the cartridge 4402 from being released from the applicator until a desired time.

The applicator may be operated to insert the needle and transcutaneous analyte sensor into the individual's skin. The insertion carriage 4410 may be released and may move downward. The downward motion of the insertion carriage 4410 may cause the pressing surface 4409 to contact the angled contact surface 4408 and deflect the lever arm 4404 outward. The releasable coupler 4400 may decouple from the ledge surface 4418 to unlock the cartridge 4402 from the applicator.

Referring to FIG. 244, the detent 4406 may be positioned to slide along the outer surface of the cartridge 4402 to provide frictional engagement with the cartridge 4402. Such frictional engagement may reduce the possibility of the cartridge 4402 dropping from the receiver of the applicator housing 4413, yet able to be pulled from the receiver at a desired time by the user. The pressing surface 4409 of the insertion carriage 4410 may press against the contact surface 4408 to keep the detent 4406 and the releasable coupler 4400 disengaged from the ledge surface 4418 and the receiving recess 4423 of the cartridge 4402.

With the cartridge 4402 removed, the applicator may be in a configuration to receive another cartridge for deployment of another needle and transcutaneous analyte sensor to the individual's skin.

Variations in the configuration of the cartridge may be provided.

FIG. 245 illustrates an embodiment of a cartridge 4500 in which the cartridge body 4501 may include a removable body 4502 configured to retain a used needle and to be removable from the cartridge body 4501 to separate the used needle from the cartridge body 4501.

The cartridge 4500 may be configured to retain components that other cartridges disclosed herein may retain, including a needle or unused needle, a transcutaneous analyte sensor, and/or a wearable housing for the transcutaneous analyte sensor.

The cartridge 4500 may be configured as a cartridge that may retain the used needle following insertion, or may be configured as another form of cartridge. The cartridge 4500 may include a retraction actuator or may be configured as another form of cartridge as desired.

The removable body 4502 may be removed by a user following insertion of the used needle. The removable body 4502, for example, may comprise an insert positioned within the cartridge body 4501. A pull body 4506 such as a ring may be coupled to the removable body 4502. The pull body 4506 may be configured to be gripped by a user and pulled to remove the removable body 4502 from the portion of the cartridge body 4504 remaining after the removable body 4502 is removed from the cartridge body 4504. The removable body 4502 may comprise a needle cover for covering the used needle.

In embodiments, the removable body 4502 may have a smaller volume than the portion of the cartridge body 4504 remaining after the removable body 4502 is removed from the cartridge body 4504. The removable body 4502 may thus comprise less material to be disposed of in a biological waste container than the entire cartridge 4500. As such, reduced material may be provided in a biological waste container, with the remaining cartridge body 4504 comprising a larger volume to be placed in a standard waste or recyclable material container. Further, a user may desirably be able to separate biological waste from materials that may be recycled by a recycling facility, such as the remaining cartridge body 4504.

Variations in the cartridge may be provided. FIGS. 246A-B for example, illustrate a removable body 4602 comprising an insert configured to be surrounded by the remaining cartridge body 4604 in the form of a shell about the removable body 4602. The removable body 4602 may be pulled from the remaining cartridge body 4604 and disposed in a biological waste container, separate from the remaining cartridge body 4604.

FIGS. 247A-B illustrate a removable body 4702 forming an outer surface of the cartridge 4700. The removable body 4702 may comprise an upper portion of the cartridge 4700, with an outer surface that is gripped to separate from the remaining cartridge body 4704.

FIGS. 248A-B illustrate a removable body 4802 forming an outer surface of the cartridge 4800. The removable body 4802 may configured to be surrounded by the remaining cartridge body 4804 in the form of a shell about the removable body 4802. The remaining cartridge body 4804 may be split apart to release the removable body 4802 from the cartridge body 4804, as represented by the arrows in FIG. 248B.

The embodiments disclosed herein may each be configured to perform methods disclosed herein. Such methods may include utilizing an actuator coupled to an applicator housing to insert a needle into the individual's skin to insert the transcutaneous analyte sensor into the individual's skin, the needle being coupled to the applicator housing. Such methods may include withdrawing the applicator housing from the individual's skin with the needle coupled to the applicator housing after the needle has inserted the transcutaneous analyte sensor into the individual's skin. Such methods may include separating the needle from the applicator housing. The actuators disclosed herein may be reloadable actuators configured to insert multiple different needles into the individual's skin. The actuator may comprise a reusable actuator.

The various components disclosed herein may be varied as desired. For example, the actuators, couplers, coupler releases, control devices, drivers, housings, and other components may be provided in a variety of forms as desired. In a non-limiting manner, the actuators may comprise assemblies or mechanisms for performing the defined operations. The actuators may be electrically actuated in certain embodiments. The couplers, releasable couplers, and coupler releases may include a variety of forms of bodies and openings, including protrusions, latches, ledges, locks, clips, snaps, pressing surfaces or other forms. The couplers, releasable couplers, and coupler releases may be magnetic as desired and may be electrically controlled (electromagnetic control). The control devices may be manually operated, or may be remotely operated via electrical control which may include transmission of wireless control signals. Other forms of electrical control devices (switches, motion sensors, or other electrical control devices) may be utilized. The drivers may comprise springs as disclosed herein, or may comprise other forms of drivers including solenoids, magnetic rail actuation, gas springs, compressed gas (for expansion to provide driving movement), among other forms of drivers. The housings may have a variety of forms as desired. Each component disclosed herein may comprise an assembly or mechanism for performing the defined operation of that component. Components across embodiments may be substituted, varied, modified, or added to as desired across embodiments.

The above description presents the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention. While the disclosure has been illustrated and described in detail in the drawings and foregoing description, such illustration and description are to be considered illustrative or exemplary and not restrictive.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article 'a' or 'an' does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases 'at least one' and 'one or more' to introduce claim recitations. However, the use of such phrases should not be construed to imply that the introduction of a claim recitation by the indefinite articles 'a' or 'an' limits any particular claim containing such introduced claim recitation to embodiments containing only one such recitation, even when the same claim includes the introductory phrases 'one or more' or 'at least one' and indefinite articles such as 'a' or 'an' (e.g., 'a' and/or 'an' should typically be interpreted to mean 'at least one' or 'one or more'); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of 'two recitations,' without other modifiers, typically means at least two recitations, or two or more recitations). Furthermore, in those instances where a convention analogous to 'at least one of A, B, and C, etc.' is used, in general such a construction is intended in the sense one having skill in the art would understand the convention (e.g., 'a system having at least one of A, B, and C' would include but not be limited to systems that have A alone, B alone, C alone, A and B together, A and C together, B and C together, and/or A, B, and C together, etc.). In those instances where a convention analogous to 'at least one of A, B, or C, etc.' is used, in general such a construction is intended in the sense one having skill in the art would understand the convention (e.g., 'a system having at least one of A, B, or C' would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase 'A or B' will be understood to include the possibilities of 'A' or 'B' or 'A and B.'

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A system for inserting a transcutaneous analyte sensor into an individual's skin, the system comprising:
   an applicator housing configured to be gripped to apply the transcutaneous analyte sensor into the individual's skin, the applicator housing including a top portion, a side portion, and a bottom portion including an opening for the transcutaneous analyte sensor to be deployed from to be inserted into the individual's skin, the side portion including an opening for receiving a cartridge retaining the transcutaneous analyte sensor;
   an actuator coupled to the applicator housing and configured to insert a needle into the individual's skin to guide the transcutaneous analyte sensor into the individual's skin; and
   a cocking device configured to be manually operated to cock the actuator for insertion of the needle into the individual's skin, the cocking device configured to move at least a portion of the cartridge upon being manually operated.

2. The system of claim 1, wherein the cocking device includes a lever configured to be manually pressed.

3. The system of claim 1, wherein the cocking device is configured to be manually operated to provide energy to the actuator.

4. The system of claim 1, wherein the actuator includes a driver configured to drive the needle into the individual's skin to guide the transcutaneous analyte sensor into the individual's skin, and the cocking device is configured to provide energy to the driver.

5. The system of claim 4, wherein the driver includes a spring configured to drive the needle into the individual's skin to guide the transcutaneous analyte sensor into the individual's skin, and the cocking device is configured to compress the spring.

6. The system of claim 5, wherein the actuator includes a carriage configured to slide relative to the applicator housing and configured to be slid by the spring, and the cocking device is configured to move the carriage to compress the spring.

7. The system of claim 6, wherein the cocking device is coupled to the carriage.

8. The system of claim 1, wherein the actuator includes a control device configured to be manually operated to activate the actuator.

9. The system of claim 8, wherein the cocking device is configured to be in an initial uncocked state and manually moved to a cocked state in which the cocking device cocks the actuator, and the control device is configured such that operation of the control device returns the cocking device to an uncocked state.

10. The system of claim 1, wherein the cocking device protrudes from the applicator housing.

11. The system of claim 1, further comprising a releasable coupler configured to retain the needle at least partially within the applicator housing following insertion of the transcutaneous analyte sensor into the individual's skin, and release the needle from within the applicator housing.

12. The system of claim 11, further comprising a retraction actuator for retracting the needle from the individual's skin following insertion of the transcutaneous analyte sensor into the individual's skin.

13. A method of applying a transcutaneous analyte sensor into an individual's skin, the method comprising:
manually cocking an insertion actuator of a reusable applicator for the transcutaneous analyte sensor, wherein the reusable applicator includes a housing having a top portion, a side portion, and a bottom portion including an opening for the transcutaneous analyte sensor to be deployed from to be inserted into the individual's skin, the side portion including an opening for receiving a cartridge retaining the transcutaneous analyte sensor, and manually cocking the insertion actuator includes moving at least a portion of the cartridge; and
utilizing the insertion actuator to insert a needle into the individual's skin to guide the transcutaneous analyte sensor into the individual's skin.

14. The method of claim 13, wherein manually cocking the insertion actuator includes manually operating a cocking device extending from the housing.

15. The method of claim 14, wherein the cocking device includes a lever configured to be manually pressed.

16. The method of claim 13, wherein manually cocking the insertion actuator includes compressing a spring of the insertion actuator.

17. The method of claim 16, wherein manually cocking the insertion actuator includes compressing a spring of a retraction actuator for retracting the needle from the individual's skin.

* * * * *